(12) United States Patent
O'Connor et al.

(10) Patent No.: US 7,166,586 B2
(45) Date of Patent: Jan. 23, 2007

(54) SULFONAMIDE LACTAM INHIBITORS OF FXA AND METHOD

(75) Inventors: Stephen P. O'Connor, Newtown, PA (US); Michael Lawrence, Yardley, PA (US); Yan Shi, Flourtown, PA (US); Philip D. Stein, Pennington, NJ (US)

(73) Assignee: Bristol Myers Squibb Co., Princeton, NJ (US)

( * ) Notice: Subject to any disclaimer, the term of this patent is extended or adjusted under 35 U.S.C. 154(b) by 393 days.

(21) Appl. No.: 10/374,299

(22) Filed: Feb. 26, 2003

(65) Prior Publication Data

US 2004/0186134 A1  Sep. 23, 2004

Related U.S. Application Data

(62) Division of application No. 10/059,621, filed on Jan. 29, 2002, now Pat. No. 6,555,542.

(60) Provisional application No. 60/264,964, filed on Jan. 30, 2001.

(51) Int. Cl.
*C07D 41/02* (2006.01)
*A61K 31/454* (2006.01)
*A61K 31/445* (2006.01)

(52) U.S. Cl. .................. 514/183; 514/349; 514/326; 546/207; 546/218

(58) Field of Classification Search ............. 514/183, 514/349, 326; 546/207, 218
See application file for complete search history.

(56) References Cited

U.S. PATENT DOCUMENTS

| | | | |
|---|---|---|---|
| 5,164,388 A | 11/1992 | De et al. | |
| 5,489,583 A * | 2/1996 | Mack et al. | 514/183 |
| 5,502,032 A | 3/1996 | Haupt et al. | |
| 5,541,343 A | 7/1996 | Himmelsbach et al. | |
| 5,591,769 A | 1/1997 | Himmelsbach et al. | |
| 5,612,353 A | 3/1997 | Ewing et al. | |
| 5,714,499 A | 2/1998 | Semple et al. | |
| 5,719,296 A | 2/1998 | Acton, III et al. | |
| 5,932,733 A * | 8/1999 | Semple et al. | 546/188 |
| 5,981,490 A | 11/1999 | Baxter et al. | |
| 6,034,215 A | 3/2000 | Semple et al. | |
| 6,136,834 A | 10/2000 | Ohmoto et al. | |
| 6,281,227 B1 | 8/2001 | Choi-Sledeski et al. | |

FOREIGN PATENT DOCUMENTS

| | | |
|---|---|---|
| EP | 0519433 | 6/1992 |
| JP | 09165370 | 6/1997 |
| WO | WO89/10961 | 11/1989 |
| WO | WO90/04917 | 5/1990 |
| WO | WO90/05531 | 5/1990 |
| WO | WO92/10509 | 6/1992 |
| WO | WO92/10510 | 6/1992 |
| WO | WO93/01208 | 1/1993 |
| WO | WO95/35311 | 12/1995 |
| WO | WO95/35313 | 12/1995 |
| WO | WO96/40679 | 12/1996 |
| WO | WO97/14417 | 4/1997 |
| WO | WO97/30073 | 8/1997 |
| WO | WO97/31937 | 9/1997 |
| WO | WO97/31939 | 9/1997 |
| WO | WO98/00401 | 1/1998 |
| WO | WO98/08840 | 3/1998 |
| WO | WO98/16523 | 4/1998 |
| WO | WO98/46220 | 10/1998 |
| WO | WO98/47876 | 10/1998 |
| WO | WO98/50420 | 11/1998 |
| WO | WO00/05243 | 3/2000 |
| WO | WO00/44733 | 8/2000 |
| WO | WO01/19795 | 3/2001 |

OTHER PUBLICATIONS

Biochemistry, 1998, 37(35), 12094-12103.*
J. Med. Chem. 1993, 36, 300-303.*
Goodman and Gilman's "The Pharmacological Basis of Therapeutics", 10th Ed., 1996, pp. 54-57.*
Siev, et al. (2000) Organic Letters vol. 2, No. 1, pp. 19-22.
Ewing et al., (1999) J. Med. Chem. vol. 42, pp. 3557-3571.
Reiner et al., (1999) Bioorganic & Medicinal Chemistry Letters 9, pp. 895-900.
Owens et al., (1998) Bioorganic & Medicinal Chemistry Letters 8, pp. 3683-3688.
Semple, J. Edward (1998) Bioorganic & Medicinal Chemistry Letters 8, pp. 2501-2506.
Nutt, et al., (1996) Peptides, pp. 71-74.
Semple, J. Edward (1998) Tetrahedron Letters 39, pp. 6645-6648.
Krishnan, et al. (1998) Biochemistry, vol. 37, pp. 12094-12103.
Semple et al., (1997) Bioorganic & Medicinal Chemistry Letters, vol. 7, No. 18, pp. 2421-2426.

(Continued)

*Primary Examiner*—Shaojia Jiang
*Assistant Examiner*—Ganapathy Krishnan
(74) *Attorney, Agent, or Firm*—Ronald S. Hermenau; Stephen B. Davis; Jing G. Sun

(57) ABSTRACT

Sulfonamide lactams of the following formula

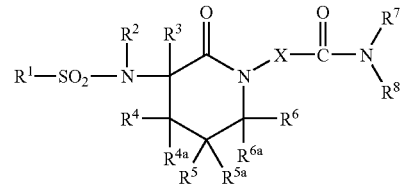

wherein X, $R^1$, $R^2$, $R^3$, $R^4$, $R^{4a}$, $R^5$, $R^{5a}$, $R^6$, $R^{6a}$, $R^7$ and $R^8$ are as described herein, are provided which inhibitors of Factor Xa and are useful as anticoagulants in the treatment of cardiovascular diseases associated with thromboses.

15 Claims, No Drawings

OTHER PUBLICATIONS

Klingler et al., (1997) Biophysical Journal, vol. 73, pp. 2195-2200.
Levy et al., (1996) Journal of Medicinal Chemistry, vol. 39, No. 23, pp. 4527-4530.
Semple et al., (1996) J. Med. Chem., vol. 39, pp. 4531-4536.
Okayama et al., (1995) Chem. Pharm. Bull., vol. 43, No. 10, pp. 1683-1691.
Mack et al., (1995) J. Enzyme Inhibition, vol. 9, pp. 73-86.
Tamura et al., (1997) Bioorganic & Medicinal Chemistry Letters, vol. 7, No. 3, pp. 331-336.
Semple et al., (1998) Bioorganic & Medicinal Chemistry Letters 8, pp. 3525-3530.
Semple et al. (2000) Organic Letters, vol. 2, No. 18, pp. 2769-2772.

* cited by examiner

SULFONAMIDE LACTAM INHIBITORS OF FXA AND METHOD

This application is a divisional of U.S. Ser. No. 10/059,621, filed Jan. 29, 2002, now U.S. Pat. No. 6,555,542, which claims priority to U.S. Provisional Application Ser. No. 60/264,964, filed Jan. 30, 2001, the entirety of which is incorporated herein by reference.

FIELD OF THE INVENTION

The present invention relates to sulfonamide lactam inhibitors of the enzyme Factor Xa which are useful as anticoagulants in the treatment of cardiovascular diseases associated with thromboses.

BRIEF DESCRIPTION OF THE INVENTION

In accordance with the present invention, novel lactam derivatives are provided which are inhibitors of the enzyme Factor Xa and have the structure I

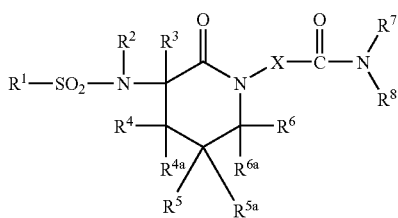

including pharmaceutically acceptable salts thereof and all stereoisomers thereof, and prodrugs thereof, wherein X is defined as:

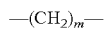

where m is an integer between 1 and 3 and which may be optionally mono- or di-substituted on 1 to 3 of the methylenes with oxo, lower alkyl, and aryl;

$R^1$ is selected from alkyl, alkenyl, alkynyl, substituted alkyl, substituted alkenyl, substituted alkynyl, cycloalkyl, substituted cycloalkyl, aryl, substituted aryl, cycloheteroalkyl, substituted cycloheteroalkyl, heteroaryl and substituted cycloheteroalkyl;

$R^2$ and $R^3$ are independently selected from hydrogen, alkyl, alkenyl, alkynyl, substituted alkyl, substituted alkenyl, substituted alkynyl, cycloalkyl, substituted cycloalkyl, aryl, substituted aryl, cycloheteroalkyl, substituted cycloheteroalkyl, heteroaryl, or substituted heteroaryl;

$R^4$, $R^{4a}$, $R^5$, and $R^{5a}$ are independently selected from hydrogen, alkyl, substituted alkyl, alkenyl, substituted alkenyl, alkynyl, substituted alkynyl, cycloalkyl, substituted cycloalkyl, aryl, heteroaryl, cycloheteroalkyl, hydroxy, alkoxy,

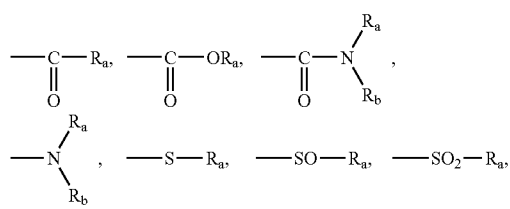

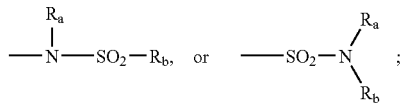

$R^6$ and $R^{6a}$ are independently selected from hydrogen, alkyl, substituted alkyl, alkenyl, substituted alkenyl, alkynyl, substituted alkynyl, cycloalkyl, substituted cycloalkyl, aryl, heteroaryl, cycloheteroalkyl;

$R^7$ and $R^8$ are independently chosen from

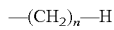

where n is an integer between 1 and 4 and which may be optionally mono- or di-substituted on 1 to 4 of the methylenes with alkyl, substituted alkyl, alkenyl, substituted alkenyl, alkynyl, substituted alkynyl, aryl, and heteroaryl, and which may be optionally substituted with 1 to 4 halogens except on a carbon that is directly bonded to a nitrogen;

or $R^7$ and $R^8$ together with the nitrogen atom to which they are attached may form an optionally substituted cycloheteroalkyl group;

$R^a$ and $R^b$ are the same or different and are independently selected from hydrogen, alkyl, substituted alkyl, alkenyl, substituted alkenyl, alkynyl, substituted alkynyl, aryl, heteroaryl, cycloheteroalkyl, cycloalkyl, substituted cycloalkyl, alkylcarbonyl, arylcarbonyl, cycloalkylcarbonyl, substituted alkyl-carbonyl, cycloheteroalkylcarbonyl, heteroarylcarbonyl, aminocarbonyl, alkylaminocarbonyl, substituted alkylaminocarbonyl, dialkylaminocarbonyl, and substituted dialkylaminocarbonyl.

Compounds within the scope of the present invention include compounds of the following formula II

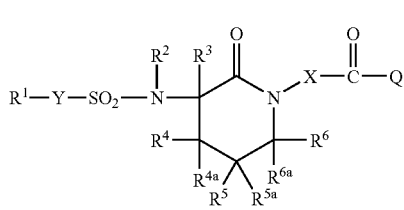

including pharmaceutically acceptable salts thereof and all stereoisomers thereof, and prodrugs thereof, wherein Y and $Y^a$ are independently a bond, alkyl, alkenyl or alkynyl;

X and $X^a$ are independently

where m is an integer between 1 and 3 and where each methylene group of X may be optionally substituted with oxo, or mono- or di-substituted with lower alkyl or aryl;

Q is a group A or B

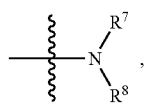

-continued

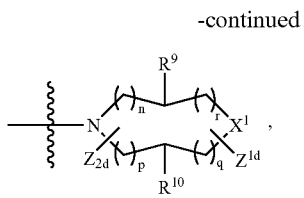
B where
(1) n, p, q and r are each independently 0 to 2, provided that at least one of n, p, q and r is other than zero;
(2) $X^1$ is —O—, $CR^{14}R^{15}$—, —$NR^{14}$—, or —$S(O)_t$— where t is 1 or 2;
(3) the group B ring system optionally contains one or more double bonds where valence allows; and
(4) optionally fused to the group B ring system is an optionally substituted cycloalkyl ring, an optionally substituted cycloheteroalkyl ring, an optionally substituted heteroaryl ring, or an optionally substituted aryl ring;

$R^1$ and $R^{1a}$ are independently aryl, heteroaryl, cycloalkyl or cycloheteroalkyl any of which may be optionally substituted with one or more groups $Z^1$, $Z^2$ or, $Z^3$;

$R^2$, $R^{2a}$, $R^3$ and $R^{3a}$ are independently selected from
(1) hydrogen, alkyl, alkenyl, alkynyl, cycloalkyl, aryl, cycloheteroalkyl, or heteroaryl any of which may be optionally substituted with one or more groups $Z^{1a}$, $Z^{2a}$ or $Z^{3a}$; or
(2) —$C(O)_tH$, or $C(O)_tZ^6$ where t is 1 or 2; or
(3) -$Z^4$-$NZ^7Z^8$;

$R^4$, $R^{4a}$, $R^{4b}$, $R^{4c}$, $R^5$, $R^{5a}$, $R^{5b}$ and $R^{5c}$ are independently selected from hydrogen, alkyl, alkenyl, alkynyl, cycloalkyl, aryl, heteroaryl, cycloheteroalkyl, hydroxy, alkoxy,

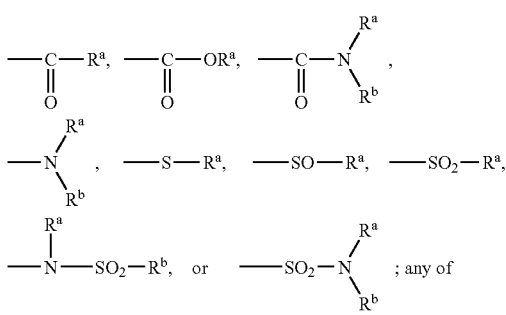

which may be optionally substituted with one or more groups $Z^{1b}$, $Z^{2b}$ or $Z^{3b}$;

$R^6$ and $R^{6a}$ are independently selected from hydrogen, alkyl, alkenyl, alkynyl, cycloalkyl, aryl, heteroaryl, or cycloheteroalkyl any of which may be optionally substituted with one or more groups $Z^{1c}$, $Z^{2c}$ or $Z^{3c}$;

$R^7$ and $R^8$ are independently chosen from optionally substituted cycloalkyl, optionally substituted cycloheteroalkyl or —$(CH_2)_n$—H where n is an integer between 1 and 4 and wherein 1 to 4 of the methylene groups may be optionally mono- or di-substituted with alkyl, substituted alkyl, alkenyl, substituted alkenyl, alkynyl, substituted alkynyl, aryl, and heteroaryl, and which may be optionally substituted with 1 to 4 halogens except on a carbon that is directly bonded to a nitrogen;

or $R^7$ and $R^8$ together with the nitrogen atom to which they are attached may form an optionally substituted cycloheteroalkyl group;

$R^a$ and $R^b$ are the same or different and are independently selected from hydrogen, alkyl, alkenyl, alkynyl, aryl, heteroaryl, cycloheteroalkyl, cycloalkyl, alkylcarbonyl, arylcarbonyl, cycloalkylcarbonyl, cycloheteroalkylcarbonyl, heteroarylcarbonyl, aminocarbonyl, alkylaminocarbonyl, and dialkylaminocarbonyl.

$R^9$ is H, $Z^{3d}$ or when a group $R^{11}$ is present $R^9$ combines with $R^{11}$ to form a bond;

$R^{10}$ is H, $Z^{1f}$, —$Y^2$—$R^{11}$, —$Y^2$—$N(R^{11})(Z^4$-$Z^{9a})$, —$Y^2$—$OR^{11}$, —$Y^2$—$C(O)OR^{11}$, $Y^2$—$OC(O)R^{11}$, —$Y^2$—$N(Z^4$-$Z^{9a})$-$C(O)R^{11}$, —$Y^2$—$N(Z^4$-$Z^{9a})$-$C(O)OR^{11}$, —$Y^2$—$S(O)_tR^{11}$ where t is 0 to 2, or —$Y^2$—$R^{12}$;

$Y^2$ is —$(CH_2)_u$—, —O—$(CH_2)_u$—, —$C(O)$—$(CH_2)_u$—, —$C(O)O$—$(CH_2)_u$—, —$OC(O)$—$(CH_2)_u$— where u is 0 to 3;

$R^{11}$ when present combines with $R^9$ to form a bond;

$R^{12}$ is

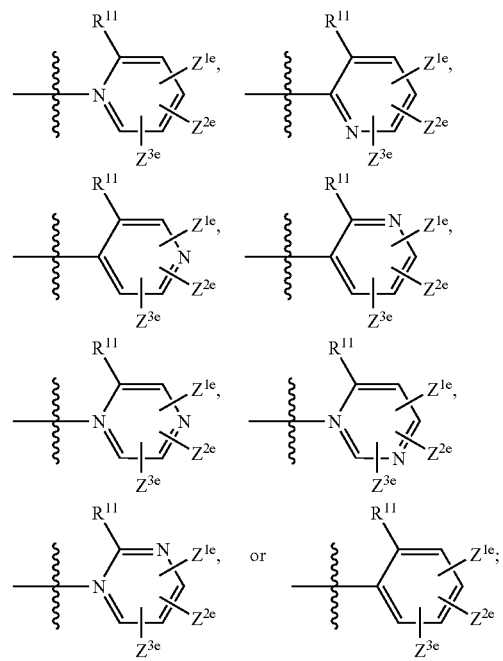

$R^{13}$ is H, $Z^{2f}$,
$R^{14}$ is H, $Z^{3f}$ or a group D

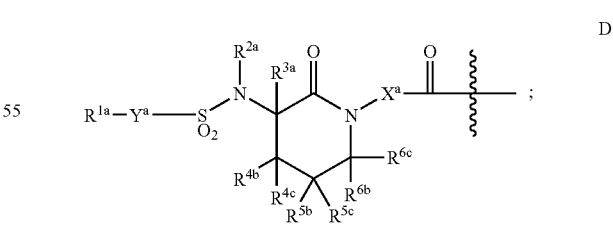
D or $R^{13}$ and $R^{14}$ combine to form =O or =S;

$Z^1$, $Z^{1a}$, $Z^{1b}$, $Z^{1c}$, $Z^{1d}$, $Z^{1e}$, $Z^{1f}$, $Z^2$, $Z^{2a}$, $Z^{2b}$, $Z^{2c}$, $Z^{2d}$, $Z^{2e}$, $Z^{2f}$, $Z^3$, $Z^{3a}$, $Z^{3b}$, $Z^{3c}$, $Z^{3d}$, $Z^{3e}$, $Z^{3f}$, $Z^{13}$ and $Z^{14}$ are each independently (1) hydrogen or $Z^6$, where $Z^6$ is
   (i) alkyl, hydroxyalkyl, alkoxyalkyl, alkenyl, alkynyl, cycloalkyl, cycloalkylalkyl, cycloalkenyl, cycloalkenylalkyl, aryl, arylalkyl, cycloheteroalkyl, cycloheteroalkylalkyl, heteroaryl or heteroarylalkyl;
  (ii) (ii) a group (i) which is itself substituted by one or more of the same or different groups (i); or
  (iii) (iii) a group (i) or (ii) which is independently substituted by one or more (preferably 1 to 3) of the following groups (2) to (13) of the definition of $Z^1$ through $Z^{3f}$,
  (2) —OH or —$OZ^6$,
  (3) —SH or —$SZ^6$,
  (4) —$C(O)_rH$, —$C(O)_rZ^6$, or —O—$C(O)Z^6$,
  (5) —$SO_3H$, —$S(O)_rZ^6$, or $S(O)_rN(Z^9)Z^6$,
  (6) halo,
  (7) cyano,
  (8) nitro,
  (9) -$Z^4$-$NZ^7Z^8$,
  (10) -$Z^4$-$N(Z^9)$-$Z^5$-$NZ^7Z^8$,
  (11) -$Z^4$-$N(Z^{10})$-$Z^5$-$Z^6$,
  (12) -$Z^4$-$N(Z^{10})$-$Z^5$-H,
  (13) oxo,
$Z^4$ and $Z^5$ are each independently
  (1) a single bond,
  (2) -$Z^{11}$-$S(O)_t$-$Z^{12}$-,
  (3) -$Z^{11}$-$C(O)$-$Z^{12}$-,
  (4) -$Z^{11}$-$C(S)$-$Z^{12}$-,
  (6) -$Z^{11}$-S-$Z^{12}$-,
  (7) -$Z^{11}$-O—$C(O)$-$Z^{12}$-,
  (8) -$Z^{11}$-$C(O)$—O-$Z^{12}$-,
  (9) -$Z^{11}$-$C(=NZ^{9a})$-$Z^{12}$-, or
  (10) -$Z^{11}$-$C(O)$—$C(O)$-$Z^{12}$-, $Z^7$, $Z^8$, $Z^9$, $Z^{9a}$ and $Z^{10}$
  (1) are each independently hydrogen or a group provided in the definition of $Z^6$,
  (2) $Z^7$ and $Z^8$ may together be alkylene or alkenylene, completing a 3- to 8-membered saturated or unsaturated ring together with the atoms to which they are attached, which ring is unsubstituted or substituted with one or more groups provided in the defintion of $Z^1$ through $Z^3$,
  (3) $Z^7$ or $Z^8$, together with $Z^9$, may be alkylene or alkenylene completing a 3- to 8-membered saturated or unsaturated ring together with the nitrogen atoms to which they are attached, which ring is unsubstituted or substituted with one or more groups provided in the defintion of $Z^1$ through $Z^3$, or
  (4) $Z^7$ and $Z^8$ or $Z^9$ and $Z^{10}$ together with the nitrogen atom to which they are attached may combine to form a group —$N=CZ^{13}Z^{14}$;
$Z^{11}$ and $Z^{12}$ are each independently
  (1) a single bond,
  (2) alkylene,
  (3) alkenylene, or
  (4) alkynylene.
In addition, in accordance with the present invention, a method for preventing, inhibiting or treating cardiovascular diseases associated with thromboses is provided, wherein a compound of formula I or II is administered in a therapeutically effective amount which inhibits Factor Xa.

DETAILED DESCRIPTION OF THE INVENTION

The following definitions apply to the terms as used throughout this specification, unless otherwise limited in specific instances.

The term "alkyl" or "alk" as employed herein alone or as part of another group includes both straight and branched chain hydrocarbons containing 1 to 20 carbons, preferably 1 to 12 carbons, more preferably 1 to 8 carbons in the normal chain. Examples include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the various additional branched chain isomers thereof. The term "lower alkyl" includes both straight and branched chain hydrocarbons containing 1 to 4 carbons.

The term "alkenyl" as employed herein alone or as part of another group includes both straight and branched hydrocarbons having one or more double bonds, preferably one or two, and being of 2 to 20 carbons, preferably 2 to 12 carbons, and more preferably 2 to 8 carbons in the normal chain. Examples include

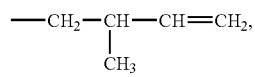

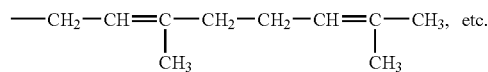

The term "alkynyl" as employed herein alone or as part of another group includes both straight and branched hydrocarbons having one or more triple bonds, preferably one or two, and being of 2 to 20 carbons, preferably 2 to 12 carbons, and more preferably 2 to 8 carbons in the normal chain. Examples include

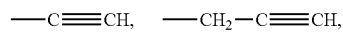

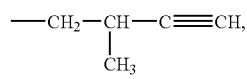

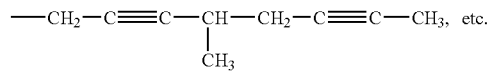

The terms "substituted alkyl", "substituted lower alkyl", "substituted alkenyl" and "substituted alkynyl" refer to such groups as defined above having one, two, or three substituents independently selected from the groups listed in the description of $T_1$, $T_2$ and $T_3$.

The term "halo" refers to chloro, bromo, fluoro and iodo.

The term "cycloallyl" as employed herein alone or as part of another group includes saturated or partially unsaturated (containing 1 or 2 double bonds and/or 1 or 2 triple bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons forming the rings. Also included within the definition of "cycloalkyl" are such rings fused to an aryl, cycloheteroalkyl, or heteroaryl ring and bridged multicyclic rings containing 5 to 20 carbons, preferably 6 to 12 carbons, and 1 or 2 bridges. Examples include cyclopropyl, cyclobutyl, cyclopentyl, cyclohexyl, cycloheptyl, cyclooctyl, cyclodecyl and cyclododecyl, cyclohexenyl,

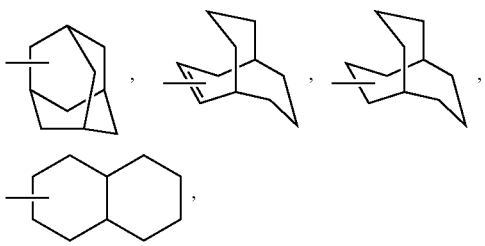

cyclopentenyl, cyclohexenyl, cycloheptenyl, cyclooctenyl, cyclohexadienyl, cycloheptadienyl, cyclopentynyl, cyclohexynyl, cycloheptynyl, cyclooctynyl, etc. Cycloalkyl groups may be optionally substituted with one, two or three substituents independently selected from the groups listed in the description of $T_1$, $T_2$ and $T_3$.

The term "aryl" or "ar" as employed herein alone or as part of another group refers to phenyl, 1-naphthyl, and 2-naphthyl as well as such rings fused to a cycloalkyl, aryl, cycloheteroalkyl, or heteroaryl ring.

Examples include

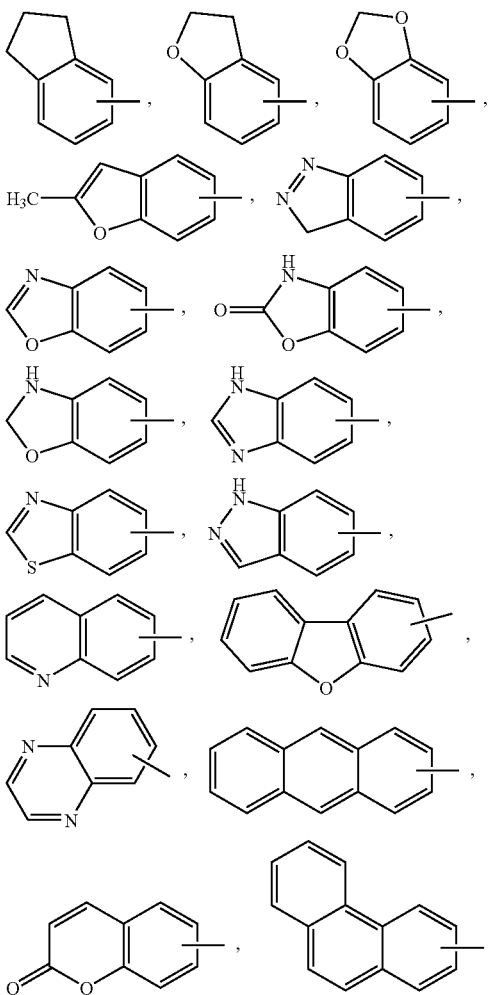

-continued

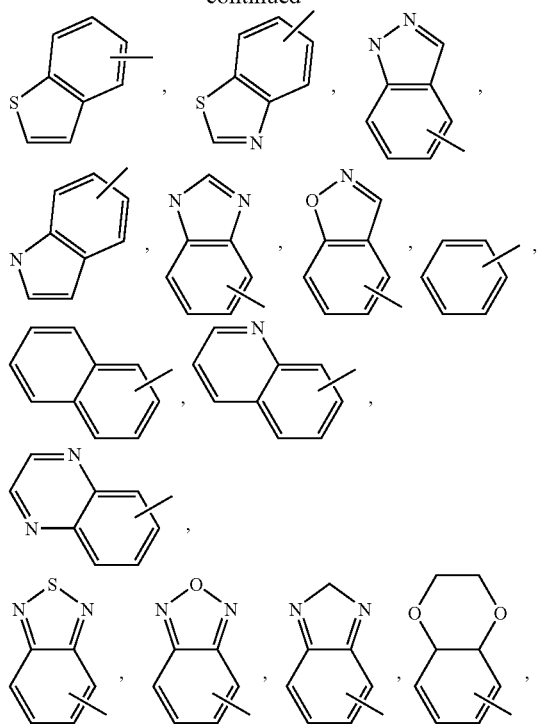

etc.

Aryl rings may be optionally substituted with one, two or three substituents independently selected from the groups listed in the description of $T_1$, $T_2$ and $T_3$.

The term "cycloheteroalkyl" as used herein alone or as part of another group refers to 3-, 4-, 5-, 6- or 7-membered saturated or partially unsaturated rings which includes 1 or more hetero atoms such as nitrogen, oxygen and/or sulfur (preferably 1 to 3 heteroatoms), linked through a carbon atom or an available nitrogen atom. Also included within the definition of cycloheteroalkyl are such rings fused to a cycloalkyl or aryl ring and spiro cycloheteroalkyl rings. One, two, or three available carbon or nitrogen atoms in the cycloheteroalkyl ring can be optionally substituted with substituents listed in the description of $T_1$, $T_2$ and $T_3$. Also, an available nitrogen or sulfur atom in the cycloheteroalkyl ring can be oxidized. Examples of cycloheteroalkyl rings include

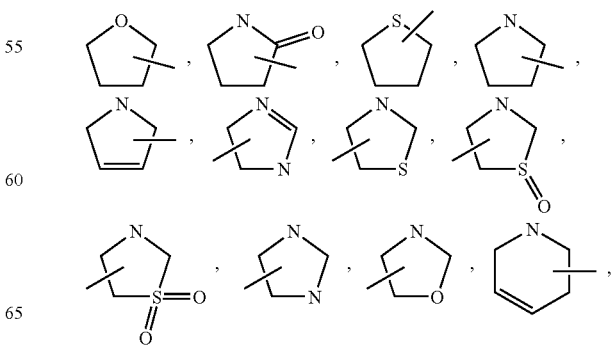

-continued

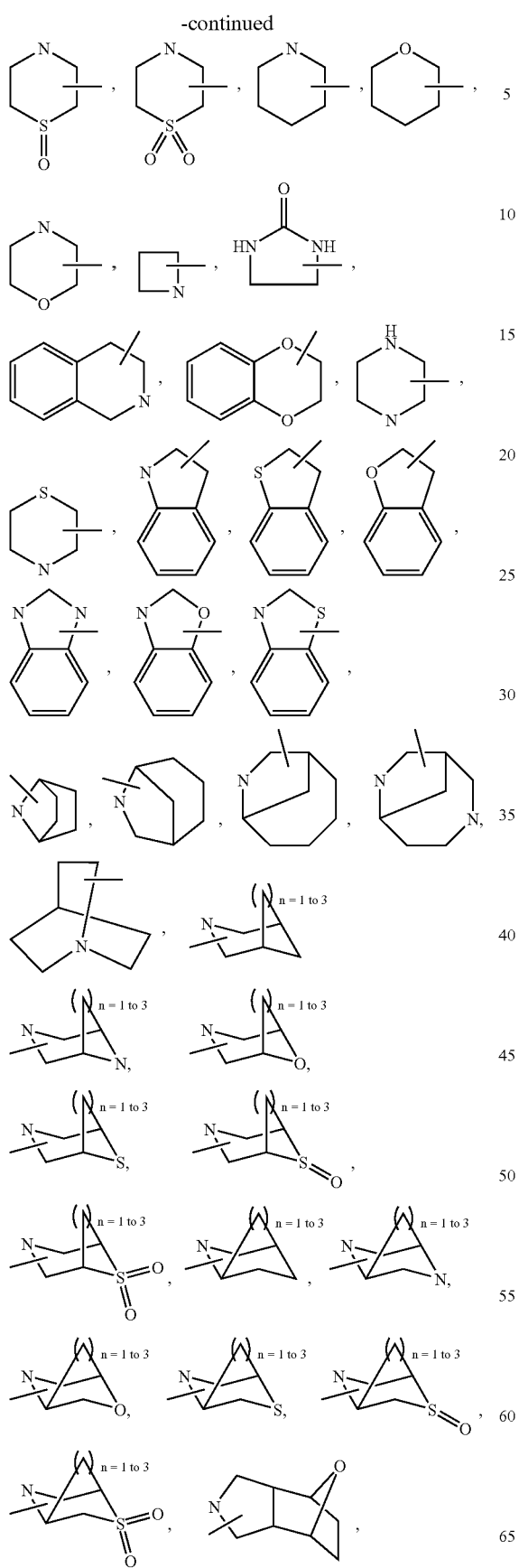

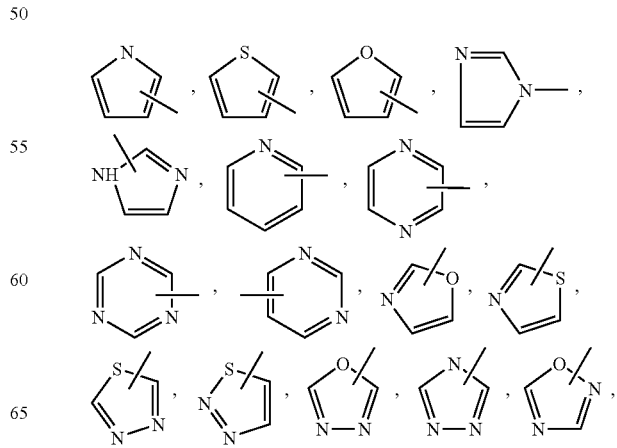

etc. Depending on the point of attachment, a hydrogen may be missing from the nitrogen atom in the above rings.

The term "heteroaryl" as used herein alone or as part of another group refers to a 5–6- or 7-membered aromatic rings containing from 1 to 4 nitrogen atoms and/or 1 or 2 oxygen or sulfur atoms provided that the ring contains at least 1 carbon atom and no more than 4 heteroatoms. The heteroaryl ring is linked through an available carbon or nitrogen atom. Also included within the definition of heteroaryl are, such rings fused to a cycloalkyl, aryl, cycloheteroalkyl, or another heteroaryl ring. One, two, or three available carbon or nitrogen atoms in the heteroaryl ring can be optionally substituted with substituents listed in the description of $T_1$, $T_2$ and $T_3$. Also an available nitrogen or sulfur atom in the heteroaryl ring can be oxidized. Examples of heteroaryl rings include -continued

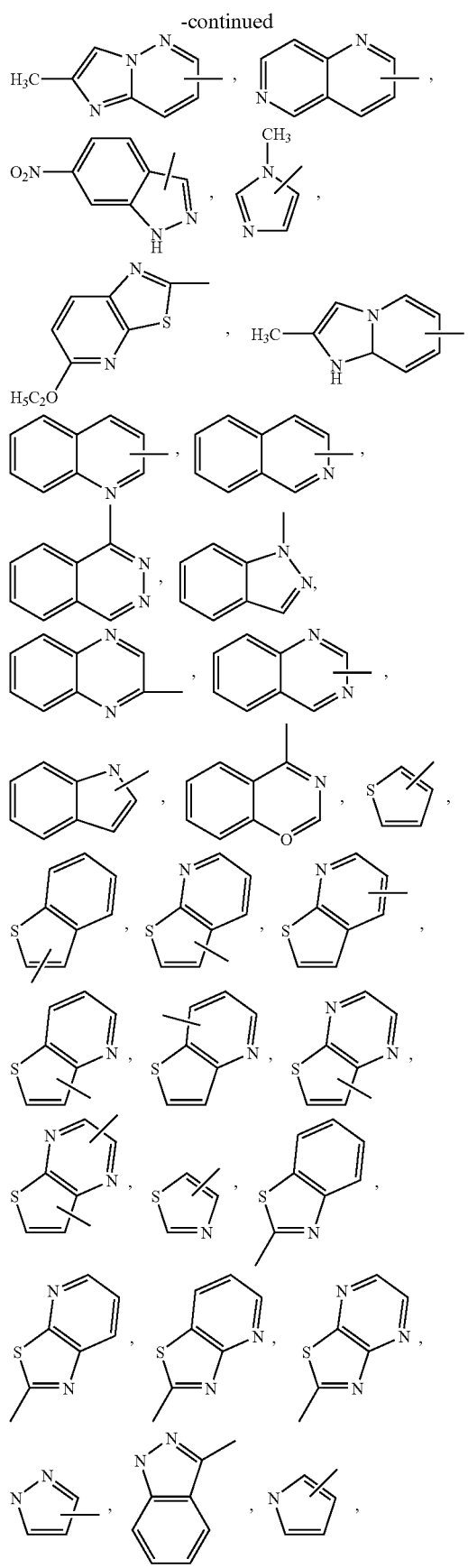

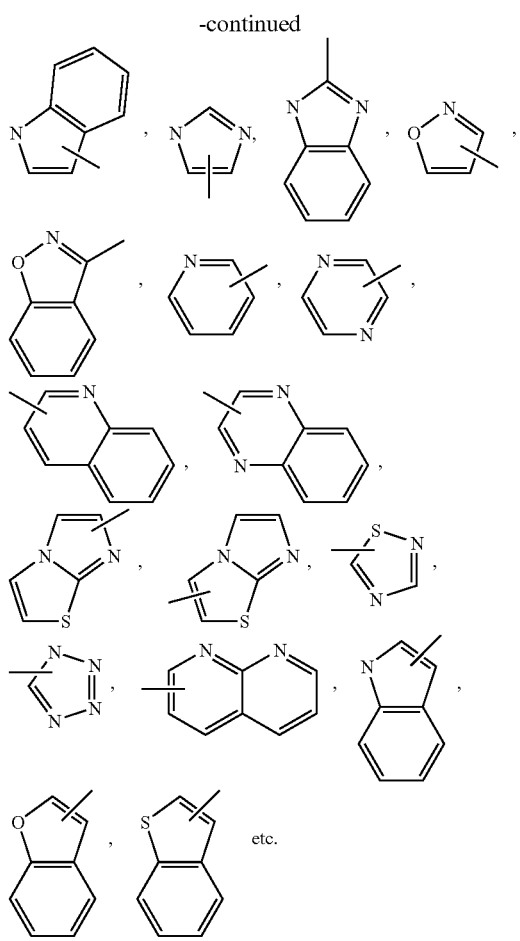

etc.

Again, depending on the point of attachment, a hydrogen may be missing from the nitrogen atom in the above rings.

The term "alkoxy" as employed herein alone or as part of another group includes "alkyl" groups as defined above bonded to an oxygen. Similarly, the term "alkylthio" as employed herein above or as part of another group includes "alkyl" groups as defined above bonded to a sulfur.

Unless otherwise indicated, the term "substituted amino" as employed herein alone or as part of another group refers to amino substituted with one or two substituents, which may be the same or different, such as alkyl (optionally substituted), aryl (optionally substituted), arylalkyl (optionally substituted), arylalkyl (optionally substituted), heteroaryl (optionally substituted), heteroarylalkyl (optionally substituted), cycloheteroalkyl (optionally substituted), (cycloheteroalkyl)alkyl (optionally substituted), cycloalkyl (optionally substituted), cycloalkylalkyl (optionally substituted), haloalkyl (optionally substituted), hydroxyalkyl (optionally substituted), alkoxyalkyl (optionally substituted) or thioalkyl (optionally substituted). In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, substituted alkyl, alkoxy, alkylthio, halo, trifluoromethyl, hydroxy, aryl or substituted aryl.

$T_1$, $T_2$ and $T_3$ are each independently
(1) hydrogen or $T_6$, where $T_6$ is
  (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, cycloheteroalkyl, (cylcloheteroalkyl)alkyl, heteroaryl, or (heteroaryl)alkyl;
  (ii) (ii) a group (i) which is itself substituted by one or more of the same or different groups (i); or
  (iii) (iii) a group (i) or (ii) which is independently substituted by one or more (preferably 1 to 3) of the following groups (2) to (13) of the definition of $T_1$, $T_2$ and $T_3$,
(2) —OH or $T_6$,
(3) —SH or $ST_6$,
(4) —C(O)$_t$H, —C(O)$_t T_6$, or —O—C(O)$T_6$,
(5) —SO$_3$H, —S(O)$_t T_6$, or S(O)$_t$N(T$_9$)T$_6$,
(6) halo,
(7) cyano,
(8) nitro,
(9) -T$_4$-NT$_7$T$_8$,
(10) -T$_4$-N(T$_9$)-T$_5$-NT$_7$T$_8$,
(11) -T$_4$-N(T$_{10}$)-T$_5$-T$_6$,
(12) -T$_4$-N(T$_{10}$)-T$_5$-H,
(13) oxo,
$T_4$ and $T_5$ are each independently
(1) a single bond,
(2) -T$_{11}$-S(O)$_t$-T$_{12}$-,
(3) -T$_{11}$-C(O)-T$_{12}$-,
(4) -T$_{11}$-C(S)-T$_{12}$-,
(5) -T$_{11}$-O-T$_{12}$-,
(6) -T$_{11}$-S-T$_{12}$-,
(7) -T$_{11}$-O—C(O)-T$_{12}$-,
(8) -T$_{11}$-C(O)—O-T$_{12}$-,
(9) -T$_{11}$-C(=NT$_{9a}$)-T$_{12}$-, or
(10) -T$_{11}$-C(O)—C(O)-T$_{12}$-,
$T_7$, $T_8$, $T_9$ and $T_{10}$
(1) are each independently hydrogen or a group provided in the definition of $T_6$, or
(2) $T_7$ and $T_8$ may together be alkylene or alkenylene, completing a 3- to 8-membered saturated or unsaturated ring together with the atoms to which they are attached, which ring is unsubstituted or substituted with one or more groups listed in the description of $T_1$, $T_2$ and $T_3$, or
(3) $T_7$ or $T_8$, together with $T_9$, may be alkylene or alkenylene completing a 3- to 8-membered saturated or unsaturated ring together with the nitrogen atoms to which they are attached, which ring is unsubstituted or substituted with one or more groups listed in the description of $T_1$, $T_2$ and $T_3$, or
(4) $T_7$ and $T_8$ or $T_9$ and $T_{10}$ together with the nitrogen atom to which they are attached may combine to form a group —N=CT$_{13}$T$_{14}$ where $T_{13}$ and $T_{14}$ are each independently H or a group provided in the definition of $T_6$;
$T_{11}$ and $T_{12}$ are each independently
(1) a single bond,
(2) alkylene,
(3) alkenylene, or
(4) alkynylene;

The compounds of formula I can be prepared as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, with saturated or unsaturated dicarboxylic acids, for example oxalic, malonic, succinic, maleic, fumaric, phthalic or terephthalic acid, with hydroxycarboxylic acids, for example ascorbic, glycolic, lactic, malic, tartaric or citric acid, with amino acids, (for example aspartic or glutamic acid or lysine or arginine), or benzoic acid, or with organic sulfonic acids, such as ($C_1$–$C_4$)-alkyl- or arylsulfonic acids which are unsubstituted or substituted, for example by halogen, for example methane- or p-toluene sulfonic acid. Corresponding acid addition salts can also be formed if the compounds of formula I have an additional basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I include monohydrochloride, hydrogensulfate, methanesulfonate, phosphate or nitrate.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When enantiomeric or diastereomeric products are prepared, they can be separated by conventional methods for example, chromatographic or fractional crystallization.

It should be understood that the present invention includes prodrug forms of the compounds of formula I such as alkylesters of acids or any known prodrugs for lactam derivatives.

The compounds of the instant invention may, for example, be in the free or hydrate form, and may be obtained by methods exemplified by the following descriptions.

The compounds of formula I may be prepared by the exemplary processes described in the following reaction schemes. Exemplary reagents and procedures for these reactions appear hereinafter and in the working Examples.

The compounds of formula I can be prepared using the reactions shown in the schemes below using techniques known to those skilled in the art of organic synthesis. Additional compounds within formula I can be generated from compounds disclosed in the schemes through conversion of the substituent groups to other functionality by the usual methods of chemical synthesis. In generating compounds of the present invention one skilled in the art will recognize that it may be necessary to protect reactive functionalilty such as hydroxy, amino, thio or carboxy groups, where these are desired in the final product, to avoid their unwanted participation in reactions. The introduction and removal of protecting groups are well known to those skilled in the art (for example see Green, T. W., "Protective Groups in Organic Synthesis", John Wiley and Sons 1991).

In one method, lactam II, the preparations of which are know in the literature to those skilled in the art, shall be protected on the nitrogen atom alpha to the carbonyl by the Cbz group to produce lactam III. The Boc and other protecting groups may also be used. Lactam III may then be derivatized by alkylation with appropriately substituted alpha-halo esters such as methyl bromoacetate, methyl 2-bromopropionate, or methyl 2-bromo-2-phenylacetate to yield lactam IV, where X is defined as in structure I. Hydrolysis of the ester with LiOH and the like will give the acid V.

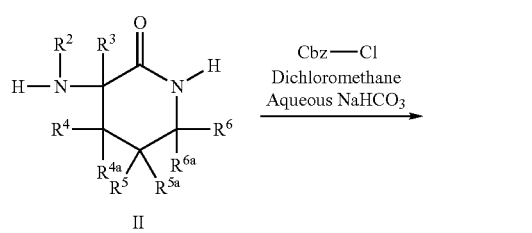

II

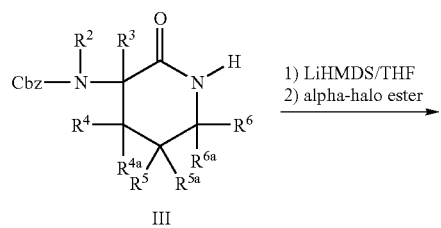

III

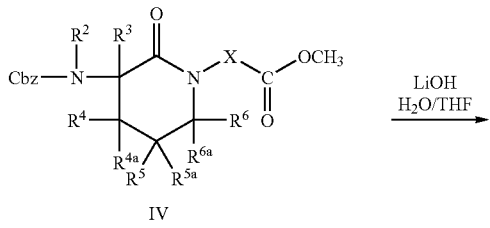

IV

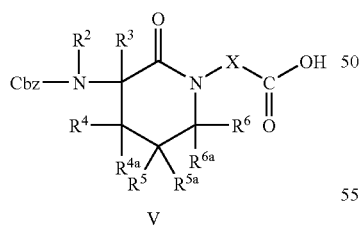

V

The coupling of V with various amines to produce product amides can be accomplished using numerous procedures known to those skilled in the art. A suitable example employs ethyl 3-(dimethylamino)propylcarbodiimide hydrochloride (WSC, EDCI) and 1-hydroxybenzotriazole hydrate (HOBt).

The Cbz protecting group can be removed, for example with hydrogen over palladium, to give amine compound VII. Reaction of VII with sulfonyl chlorides in the presence of triethylamine or other base will provide the product VIII.

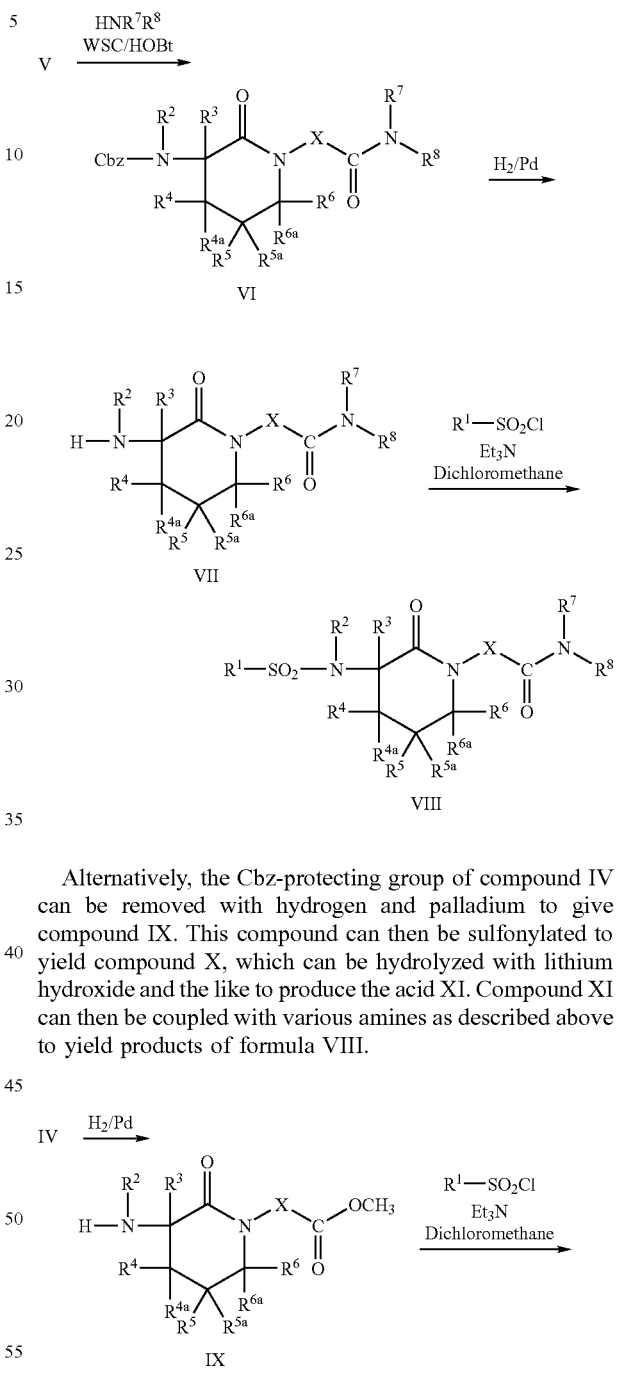

Alternatively, the Cbz-protecting group of compound IV can be removed with hydrogen and palladium to give compound IX. This compound can then be sulfonylated to yield compound X, which can be hydrolyzed with lithium hydroxide and the like to produce the acid XI. Compound XI can then be coupled with various amines as described above to yield products of formula VIII.

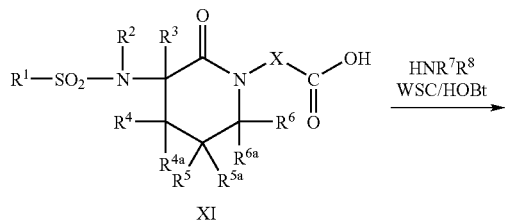

XI

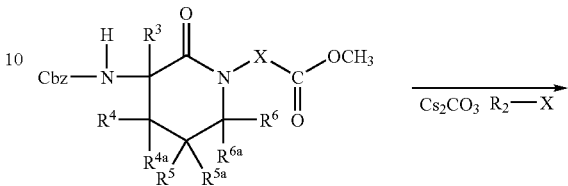

IVa

In a similar fashion, compounds of formula IVa are treated with a base (cesium carbonate and the like) and an alkylating agent such as methyl iodide to provide compounds of formula IV which are transformed using aformentioned procedures.

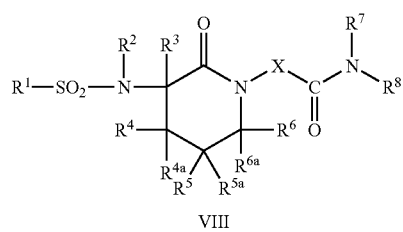

VIII

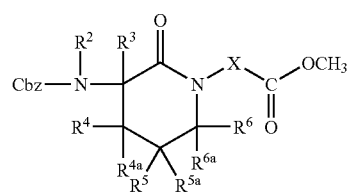

IV

In addition to the methods already described, compounds of formula I wherein $R_2$ is other than hydrogen can be prepared as shown in the following scheme. Compounds of formula VIIIa are sequentially treated with a base such as NaH or the like and then with an alkylating agent $R_2$-halogen (for example; methyl iodide, methyl bromoacetate, benzyl bromide and the like) to provide the title compounds. Similarly, compounds of formula VIIIa are treated with an acylating agent, for example methyl chloroformate, to provide the title compounds.

$R^2$ other then Hydrogen may also be introduced by reductive amination procedures. For example, compounds of formula IXa are treated with an aldehyde and a reducing agent such as sodium triacetoxyborohydride to produce compounds of the type IXb. The aldehyde may be attached to a polymer support to provide resin-bound intermediates which can be treated using the other described procedures. Resin cleavage techniques are well known to those skilled in the art.

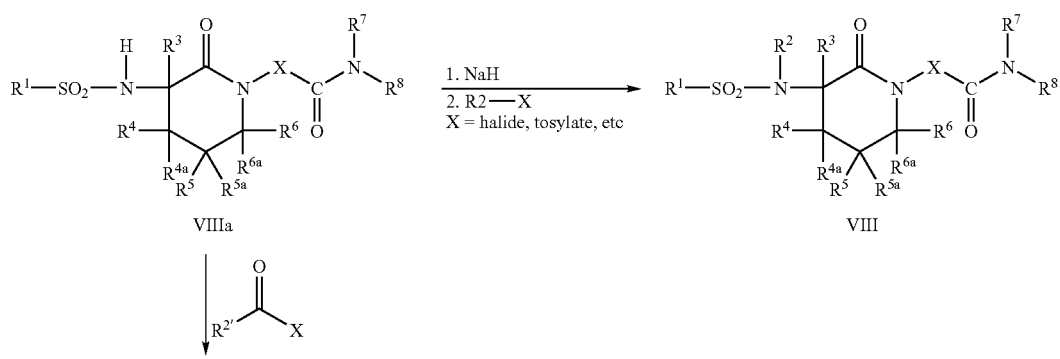

VIIIa

VIII

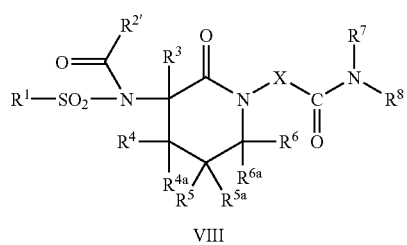

VIII

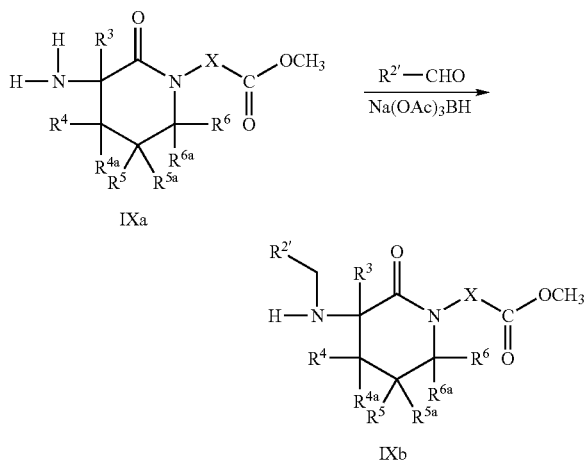

IXa

IXb

In a similar fashion compounds of formula VIIa may be resin bound or functionalized to produce compounds of formula VIIb.

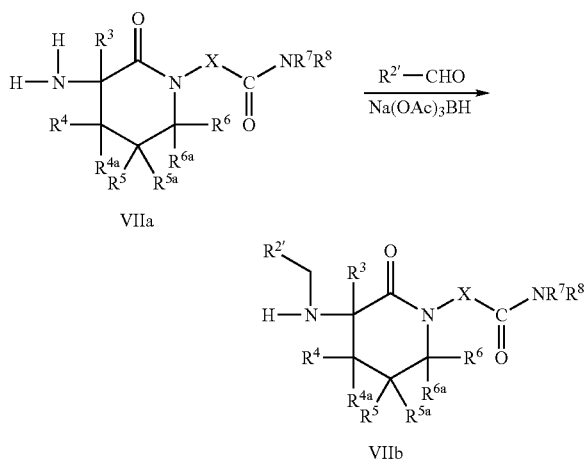

VIIa

VIIb

Preferred compounds of this invention are those of claim 1 including a pharmaceutically acceptable salt thereof wherein:

X is $CH_2$;

$R^1$ is selected from alkyl, alkenyl, alkynyl, substituted alkyl, substituted alkenyl, substituted alkynyl, cycloalkyl, substituted cycloalkyl, aryl, cycloheteroalkyl, and heteroaryl;

$R^2$ is H, alkyl or substituted alkyl;

$R^3$, $R^4$, $R^{4a}$, $R^5$, $R^{5a}$, $R^6$, and $R^{6a}$ are H or alkyl;

$R^7$ and $R^8$ are independently chosen from

—$(CH_2)_n$—H where n is an integer between 1 and 4 and which may be optionally mono- or di-substituted on 1 to 4 of the methylenes with alkyl, substituted alkyl, alkenyl, substituted alkenyl, alkynyl, substituted alkynyl, aryl, and heteroaryl, and which may be optionally substituted with 1 to 4 halogens except on a carbon that is directly bonded to a nitrogen;

or $R^7$ and $R^8$ together with the nitrogen atom to which they are attached form an optionally substituted cycloheteroalkyl group;

More preferred compounds of this invention are those of formula I or a pharmaceutically acceptable salt thereof wherein:

X is $CH_2$;

$R^1$ is selected from, substituted alkyl (especially (heteroaryl)alkyl or (aryl)alkyl), substituted alkenyl (especially (heteroaryl)alkenyl or (aryl)alkenyl), substituted alkynyl (especially (heteroaryl)alkynyl or arylalkynyl), substituted cycloalkyl, aryl, cycloheteroalkyl, and heteroaryl;

$R^2$ is H, alkyl or substituted alkyl;

$R^3$, $R^4$, $R^{4a}$, $R^5$, $R^{5a}$, $R^6$, and $R^{6a}$ are H.

$R^7$ and $R^8$ together with the nitrogen atom to which they are attached form an optionally substituted cycloheteroalkyl group (especially pyrolidine, piperadine, piperazine, morpholine, thiomorpholine or thiazolidine).

More preferred compounds include compounds of formula II wherein

X is $CH_2$;

Y is a bond or alkyenyl (when alkenyl, Y is preferably —CH=CH—, and more preferably,

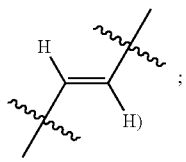

;

$R_1$ is aryl or heteroaryl, either of which may be optionally substituted with one or more groups $Z^1$, $Z^2$, $Z^3$ (especially where $Z^1$, $Z^2$ and $Z^3$ are independently halo, cyano, —OH, $OZ^6$, alkyl, aryl, heteroaryl, or -$Z^4$-$NZ^7Z^8$, any of which may be further substituted where valence allows as provided in the definition of $Z^1$, $Z^2$ and $Z^3$);

$R^2$ is H, alkyl, —C(O)$_r$H, —C(O)$_r$$Z^6$, -$Z^4$-$NZ^7Z^8$, -(alkyl)-C(O)$_r$H, -(alkyl)-C(O)$_r$$Z^6$, or -(alkyl)-$Z^4$-$NZ^7Z^8$;

$R^3$, $R^4$, $R^{4a}$, $R^5$, $R^{5a}$, $R^6$, and $R^{6a}$ are H;

Q is a group B;

$R^9$ is H, $Z^{3d}$ or when a group $R^{11}$ is present $R^9$ combines with $R^1$ to form a single bond;

$R^{10}$ is H, $Z^{1f}$, —$Y^2$—$R^{11}$, $Y^2$—$R^{12}$ or $Y^2$—$N(R^{11})$-$Z^4$-$Z^{9a}$;

$Y^2$ is —$(CH_2)_u$— or —C(O)—$(CH_2)$—;

$Z^{3d}$ and $Z^{1f}$ are each independently H, halo, oxo, alkyl, cycloalkyl, cycloheteroalkyl, aryl, heteroaryl, -(alkyl)-cycloalkyl, -(alkyl)-cycloheteroalkyl, -(alkyl)-aryl, -(alkyl)-heteroaryl, —OH, $OZ^6$, —C(O)$_r$H, —C(O)$_r$$Z^6$, —S(O)$_r$$Z^6$, -(alkyl)-OH, -(alkyl)-$OZ^6$, -(alkyl)-C(O)$_r$H, -(alkyl)-C(O)$_r$$Z^6$, -(alkyl)-S(O)$_r$$Z^6$, -$Z^4$-$NZ^7Z^8$, -$Z^4$-N$(Z^{10})$-$Z^5$-$Z^6$, -$Z^4$-N$(Z^{10})$-$Z^5$-H, -$Z^4$-N$(Z^9)$-$Z^5$-$NZ^7Z^8$, -(alkyl)-$Z^4$-$NZ^7Z^8$, -(alkyl)-$Z^4$-N$(Z^{10})$-$Z^5$-$Z^6$, -(alkyl)-$Z^4$-N$(Z^{10})$-$Z^5$-H, or -(alkyl)-$Z^4$-N$(Z^9)$-$Z^5$-$NZ^7Z^8$ any of which may be optionally further substituted where valence allows as provided in the respective definitions of $Z^{3d}$ and $Z^{1f}$;

$R^{14}$ is a group D or H, halo, oxo, alkyl, cycloalkyl, cycloheteroalkyl, aryl, heteroaryl, -(alkyl)-cycloalkyl, -(alkyl)-cycloheteroalkyl, -(alkyl)-aryl, -(alkyl)-heteroaryl, —OH, —$OZ^6$, —C(O)$_r$H, —C(O)$_r$$Z^6$, —S(O)$_r$$Z^6$, -(alkyl)-OH, -(alkyl)-$OZ^6$, -(alkyl)-C(O)$_r$H, -(alkyl)-C(O)$_r$$Z^6$, -(alkyl)-S(O)$_r$$Z^6$, -$Z^4$-$NZ^7Z^8$, -$Z^4$-N$(Z^{10})$ $Z^5$-$Z^6$, -$Z^4$-N$(Z^{10})$-$Z^5$-H, -$Z^4$-$NZ^7Z^8$-$NZ^7Z^8$, -(alkyl)-$Z^4$-$NZ^7Z^8$, -(alkyl)-$Z^4$-N$(Z^{10})$-$Z^5$-$Z^6$, -(alkyl)-$Z^4$-N$(Z^{10})$-$Z^5$-H, or -(alkyl)-$Z^4$-N$(Z^9)$-$Z^5$-$NZ^7Z^8$ any of which may be optionally further substituted where valence allows as provided in the definition of $R^{14}$;

$Z^4$ is a bond —C(O)—, —C(=NZ$^{9a}$)-, —C(O)—C(O)— or —C(O)O—; and
$Z^5$ is —C(O)— or —SO$_2$—.

The most preferred compounds are those of formula I or a pharmaceutically acceptable salt thereof wherein:
X is CH$_2$;
$R^1$ is selected from, optionally substituted heteroaryl, optionally substituted (heteroaryl)alkenyl, optionally substituted aryl or optionally substituted (aryl)alkenyl (especially where the aryl and heteroaryl groups are optionally substituted with one or more halogen, optionally substituted alkyl, optionally substituted aryl, or optionally substituted heteroaryl);
$R^2$ is H, alkyl or substituted alkyl;
$R^3$, $R^4$, $R^{4a}$, $R^5$, $R^{5a}$, $R^6$, and $R^{6a}$ are H;
$R^7$ and $R^8$ together with the nitrogen atom to which they are attached form a cycloheteroalkyl group (especially pyrrolidine) which may be optionally substituted (especially with one or more (amino)alkyl, or (substituted amino) alkyl.

Most preferred compounds include compounds of formula II wherein
X is CH$_2$;
Y is a bond or

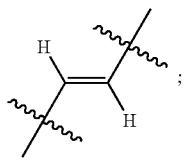

$R^1$ is aryl or heteroaryl, either of which may be optionally substituted with one or more halo, cyano, —OH, —OZ$^6$ (especially alkoxy), optionally substituted alkyl, optionally substituted aryl, optionally substituted heteroaryl, or -Z$^4$-NZ$^7$Z$^8$;
$R^2$ is H, alkyl, —C(O)$_t$H, —C(O)$_t$Z$^6$, -Z$^4$-NZ$^7$Z$^8$, -(alkyl)-C(O)$_t$H, -(alkyl)-C(O)$_t$Z$^6$, or -(alkyl)-Z$^4$-NZ$^7$Z$^8$;
$R^3$, $R^4$, $R^{4a}$, $R^5$, $R^{5a}$, $R^6$, and $R^{6a}$ are H;
Q is a group B;
$R^9$ is H, Z$^{3d}$ or, when a group $R^{11}$ is present $R^9$ combines with $R^{11}$ to form a single bond;
$R^{10}$ is H, Z$^{1f}$, —Y$^2$—$R^{11}$ or —Y$^2$—$R^2$;
$Y^2$ is —(CH$_2$)$_u$— or —C(O)—(CH$_2$)—;
$Z^{3d}$ and $Z^{1f}$ are each independently H, alkyl, heteroaryl, -(alkyl)-cycloheteroalkyl, -(alkyl)-Z$^4$-NZ$^7$Z$^8$, -Z$_4$-NZ$^7$Z$^8$, -(alkyl)-Z$^4$-N(Z$^{10}$)-Z$^5$-Z$_6$, -(alkyl)-Z$^4$-N(Z$^9$)-Z$^5$-NZ$^7$Z$^8$, —C(O)$_t$Z$^6$, -(alkyl)-C(O)$_t$Z$^6$, -(alkyl)-OH, -(alkyl)-OZ$^6$, or —S(O)$_t$Z$^6$;
$R^{14}$ is a group H, -(alkyl)-cycloheteroalkyl, -(alkyl)-Z$^4$-NZ$^7$Z$^8$, -Z$^4$-NZ$^7$Z$^8$, -(alkyl)-Z$^4$-N(Z$^{10}$)-Z$^5$-Z$^6$, -(alkyl)-Z$^4$-N(Z$^9$)-Z$^5$-NZ$^7$Z$^8$, —C(O)$_t$Z$^6$, -(alkyl)-C(O)$_t$Z$^6$, -(alkyl)-OH, -(alkyl)-OZ$^6$, —S(O)$_t$Z$^6$ or a group D;
$Z^4$ is a bond —C(O)—, —C(=NZ$^{9a}$)-, —C(O)—C(O)—, or —C(O)O—; and
$Z^5$ is —(O)— or —SO$_2$—.

Utility

The compounds of the present invention are inhibitors of the activated coagulation serine protease known as Factor Xa and thus are useful for the treatment or prophylaxis of those processes which involve activation of the coagulation cascade and especially those which involve the production and/or action of Factor Xa. Thus the compounds of the present invention are useful in the prevention and treatment of all Factor Xa-associated conditions. An "Factor Xa-associated condition" is a disorder which may be prevented, partially alleviated or cured by the administration of an inhibitor of Factor Xa. Such diseases include arterial thrombosis, coronary artery disease, acute coronary syndromes, myocardial infarction, unstable angina, ischemia resulting from vascular occlusion cerebral infarction, stroke and related cerebral vascular diseases (including cerebrovascular accident and transient ischemic attack). Additionally, the compounds are useful in treating or preventing formation of atherosclerotic plaques, transplant atherosclerosis, peripheral arterial disease and intermittent claudication. In addition, the compounds can be used to prevent restenosis following arterial injury induced endogenously (by rupture of an atherosclerotic plaque), or exogenously (by invasive cardiological procedures such as vessel wall injury resulting from angioplasty).

In addition, the inventive compounds are useful in preventing venous thrombosis, coagulation syndromes, deep vein thrombosis (DVT), disseminated intravascular coagulopathy, Kasabach-Merritt syndrome, pulmonary embolism, cerebral thrombosis, atrial fibrillation, and cerebral embolism. The compounds are useful in treating peripheral arterial occlusion, thromboembolic complications of surgery (such as hip replacement, endarterectomy, introduction of artificial heart valves, vascular grafts, and mechanical organs), implantation or transplantation of organ, tissue or cells, and thromboembolic complications of medications (such as oral contraceptives, hormone replacement, and heparin, e.g., for treating heparin-induced thrombocytopenia). The inventive compounds are useful in preventing thrombosis associated with artificial heart valves, stents, and ventricular enlargement including dilated cardiac myopathy and heart failure. The compounds are also useful in treating thrombosis due to confinement (i.e. immobilization, hospitalization, bed rest etc.).

These compounds are also useful in preventing thrombosis and complications in patients genetically predisposed to arterial thrombosis or venous thrombosis (including activated protein C resistance, FV$_{leiden}$, Prothrombin 20210 elevated coagulation factors FVII, FVIII, FIX, FX, FXI, prothrombin, TAFI and fibrinogen), elevated levels of homocystine, and deficient levels of antithrombin, protein C, and protein S. The inventive compounds may be used for treating heparin-intolerant patients, including those with congenital and acquired antithrombin III deficiencies, heparin-induced thrombocytopenia, and those with high levels of polymorphonuclear granulocyte elastase.

The present compounds may also be used to inhibit blood coagulation in connection with the preparation, storage, fractionation, or use of whole blood. For example, the compounds may be used to maintain whole and fractionated blood in the fluid phase such as required for analytical and biological testing, e.g., for ex vivo platelet and other cell function studies, bioanalytical procedures, and quantitation of blood-containing components. The compounds may be used as anticoagulants in extracorpeal blood circuits, such as those necessary in dialysis and surgery (such as coronary artery bypass surgery); for maintaining blood vessel patency in patients undergoing transluminal coronary angioplasty, vascular surgery including bypass grafting, arterial reconstruction, atherectomy, vascular graft and stent patency, tumor cell metastesis, and organ, tissue, or cell implantation and transplantation. The inventive compounds may also be inhibitors of the activated coagulation serine proteases known as Factor VIIa, Factor XIa, and thrombin and also inhibit other serine proteases, such as trypsin, tryptase, and urokinase. Thus, the compounds are useful for treating or preventing those processes, which involve the production or action of Factor VIIa, Factor XIa, thrombin, trypsin, and/or tryptase. Inventive compounds with urokinase inhibitory activity are useful as metastasis inhibitors in treating cancer. As used herein with reference to the utilities described below other than metastasis, the term "treating" or "treatment" encompasses prevention, partial alleviation, or cure of the disease or disorder.

In view of their above-referenced serine protease inhibitory activity, the inventive compounds are useful in treating consequences of atherosclerotic plaque rupture including cardiovascular diseases associated with the activation of the coagulation cascade in thrombotic or thrombophilic states.

The inventive compounds with tryptase inhibitory activity are useful as anti-inflammatory agents, in treating chronic asthma, allergic rhinitis, inflammatory bowel disease, psoriasis, conjunctivitis, atopic dermatitis, pancreatis, rheumatoid arthritis, osteoarthritis, septic shock, and chronic inflammatory joint diseases, diseases of joint cartilage destruction, and/or vascular damage due to bacterial and/or viral infections. Additionally, the inventive compounds may be useful for treating diabetic retinopathy or motor neuron diseases such as amyotrophic lateral sclerosis, progressive muscular atrophy, and primary lateral sclerosis. Additionally, the inventive compounds may be useful for tissue remodeling diseases and for treating plaque instability and sequelli. In addition, these compounds may be useful for treating fibrotic diseases and conditions, for example, fibrosis, scleroderma, pulmonary fibrosis, liver cirrhosis, myocardial fibrosis, neurofibromas, and hypertrophic scars.

In addition, the compounds of the present invention are useful in treating cancer and preventing the prothrombotic complications of cancer. In view of their metastasis inhibition activity, the compounds are useful in treating tumor growth, as an adjunct to chemotherapy, and for treating diseases involving metastases including, but not limited to cancer, more particularly, cancer of the lung, prostate, colon, breast, ovaries, and bone. These compounds may also be useful in preventing angiogenesis.

The inventive compounds may also be used in combination with other antithrombotic or anticoagulant drugs such as thrombin inhibitors, platelet aggregation inhibitors such as aspirin, clopidogrel, ticlopidine or CS-747, warfarin, low molecular weight heparins (such as LOVENOX), GPIIb/GPIIIa blockers, PAI-1 inhibitors such as XR-330 and T-686, inhibitors of α-2-antiplasmin such as anti-α-2-antiplasmin antibody and thromboxane receptor antagonists (such as ifetroban), prostacyclin mimetics, phosphodiesterase (PDE) inhibitors, such as dipyridamole or cilostazol, PDE inhibitors in combination with thromboxane receptor antagonists/thromboxane A synthetase inhibitors (such as picotamide), serotonin-2-receptor antagonists (such as ketanserin), fibrinogen receptor antagonists, hypolipidemic agents, such as HMG-CoA reductase inhibitors, e.g., pravastatin, simvastatin, atorvastatin, fluvastatin, cerivastatin, AZ4522, itavastatin (Nissan/Kowa), and compounds disclosed in U.S. provisional applications No. 60/211,594 filed Jun. 15, 2000, and No. 60/211,595 filed Jun. 15, 2000; microsomal triglyceride transport protein inhibitors (such as disclosed in U.S. Pat. Nos. 5,739,135, 5,712,279 and 5,760,246), antihypertensive agents such as angiotensin-converting enzyme inhibitors (e.g., captopril, lisinopril or fosinopril); angiotensin-II receptor antagonists (e.g., irbesartan, losartan or valsartan); and/or ACE/NEP inhibitors (e.g., omapatrilat and gemopatrilat); β-blockers (such as propranolol, nadolol and carvedilol), PDE inhibitors in combination with aspirin, ifetroban, picotamide, ketanserin, or clopidogrel and the like. The inventive compounds are also useful in combination with anti-arrhythmic agents such as for atrial fibrillation, for example, amiodarone or dofetilide.

The inventive compounds may be used in combination with prothrombolytic agents, such as tissue plasminogen activator (natural or recombinant), streptokinase, reteplase, activase, lanoteplase, urokinase, prourokinase, anisolated streptokinase plasminogen activator complex (ASPAC), animal salivary gland plasminogen activators, and the like. The inventive compounds may also be used in combination with β-adrenergic agonists such as albuterol, terbutaline, formoterol, salmeterol, bitolterol, pilbuterol, or fenoterol; anticholinergics such as ipratropium bromide; anti-inflammatory cortiocosteroids such as beclomethasone, triamcinolone, budesonide, fluticasone, flunisolide or dexamethasone; and anti-inflammatory agents such as cromolyn, nedocromil, theophylline, zileuton, zafirlukast, monteleukast and pranleukast.

The inventive compounds may also be useful in combination with other anticancer strategies and chemotherapies such as taxol and/or cisplatin.

The compounds may act synergistically with one or more of the above agents. For example, the inventive compounds may act synergistically with the above agents to prevent reocclusion following a successful thrombolytic therapy and/or reduce the time to reperfusion. Thus, reduced doses of thrombolytic agent(s) may be used, therefore minimizing potential hemorrhagic side effects.

The compounds of this invention may be administered by any means suitable for the condition to be treated, which may depend on the need for site-specific treatment or quantity of drug to be delivered. Systematic treatment is typically preferred for cancerous conditions, although other modes of delivery are contemplated. The compounds may be delivered orally, such as in the form of tablets, capsules, granules, powders, or liquid formulations including syrups; sublingually; bucally; transdermally; parenterally, such as by subcutaneous, intravenous, intramuscular or intrasternal injection or infusion (e.g., as sterile injectable aqueous or non-aqueous solutions or suspensions); nasally such as by inhalation spray; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ); and agents to control release such as polyacrylic copolymer (e.g., CARBOPOL 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art. The specific dose level and frequency of dosage for any particular subject may vary and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. An exemplary effective amount of compounds of formula I may be within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The ability of compounds of the present invention to inhibit Factor Xa can be determined using methods well known to those skilled in the art, such as methods that measure FXa amidolytic (Balasubramanian et al., J. Med. Chem. 36:300–303, 1993; Combrink et al., J. Med. Chem. 41:4854–4860, 1998), clotting time (Balasubramanian, N. et al., J. Med. Chem. 36:300–303, 1993) and in vivo models of arterial and venous thrombosis (Schumacher et al., Eur. J. Pharm. 259:165–171, 1994).

General Experimental and Definitions:

The following examples and preparations describe the manner and process of making and using the invention and are illustrative rather than limiting. It is to be understood that there may be other embodiments which fall within the spirit and scope of the invention as defined by the claims appended hereto. Abbreviations and terms employed herein are defined below.

brine=saturated aqueous sodium chloride

Dess-Martin periodinane=1,1,1-tris(acetyloxy)-1,1-dihydro-1,2-Benziodoxol-3(1H)-one DMF=N,N-dimethylformamide EDCI=1-[3-(dimethylamino)propyl]-3-ethylcarbodiimide hydrochloride.

PS-PB-CHO=1% Cross linked polystyrene with (4-formyl-3-methoxyphenoxy)methyl linker.

PyBOP=(T-4)-(1-hydroxy-1H-benzotriazolato-O)tri-1-pyrrolidinyl-phosphorus(1+) hexafluorophosphate(1−)=Benzotriazol-1-yloxytripyrrolidinophosphonium hexafluorophosphate TFA=trifluoroacetic acid TFFH=Tetramethylfluoroformamidinium hexafluorophosphate.

THF=tetrahydrofuran

WSC=1-[3-(dimethylamino)propyl]-3-ethylcarbodiimide hydrochloride.

Unless otherwise noted all mass spectral data are positive ion spectra.

The following conditions were used for HPLC:

Method 1: column-YMC S5 C18 ODS 4.6×50 mm; flow-4.0 mL/min.; detection at 220 nm; solvent-A=90:10/water:methanol+0.2% phosphoric acid, B=10:90/water:methanol+0.2% phosphoric acid; gradient-linear, 0% B to 100% B over 4 min and hold at 100% B for 1 min.

Method 2: column-YMC (ODS) S-5, 4.6 mm×33 mm; flow-5.0 mL/min.; detection at 220 nm; solvent-A=10% methanol/water+0.2% phosphoric acid, B=90% methanol/water+0.2% phosphoric acid; gradient-linear, 0% B to 100% B over 2 min and 100% B for 1 min.

Method 3: column-YMC A-ODS S-5, 4.6 mm×50 mm; flow-4 mL/min.; detection at 220 nm; solvent-A=90:10 water:methanol, solvent B=10:90 water:methanol (both containing 0.1% trifluoroacetic acid); 0% B to 100% B (4 min linear gradient) and 100% B for 1 min.

Method 4: column-YMC (ODS-A) S-5, 4.6 mm×33 mm; flow-5 mL/min.; detection at 220 nm; solvent-A=10% methanol/water+0.1% TFA, B=90% methanol/water+0.1% TFA; gradient-linear, 0% B to 100% B over 2 min and 100% B for 1 min.

Method 5: column-YMC (S3 ODS column) 3 mm×50 mm; detection at 220 nm; flow-5 mL/min; solvent-A=10% methanol/water+0.1% TFA, B=90% methanol/water+0.1% TFA; linear gradient, 0% B to 100% B over 2 min and 100% B for 1 min.

Method 6: column-Phenomenex (5 micron ODS column) 4.6 mm×30 mm; detection at 220 nm; flow-5 mL/min.; solvent-A=10% methanol/water+0.1% TFA, B=90% methanol/water+0.1% TFA; linear gradient, 0% B to 100% B over 2 min and 100% B for 1 min.

Method 7: column-Shimadzu VP-ODS, 4.6 mm×50 mm; flow-4 mL/min.; detection at 220 nm; solvent-A=10% methanol/water+0.1% TFA, B=90% methanol/water+0.1% TFA; linear gradient, 0% B to 100% B over 4 min and 100% B for 2 min.

Method 8: Luna (5 micron ODS column) 2×30 mm; flow-1 ml/min; detection at 220 nm; solvent-A=10 mM ammonium acetate in 98% water/acetonitrile; solvent B=10 mM ammonium acetate in 90% MeCN/water; 3 min linear gradient 0%–100% B and 0.4 min hold at 100% B.

Method 9: column-Waters Xterra, 4.6 mm×50 mm; flow-5.0 mL/min.; detection at 220 nm; solvent-A=10% methanol/water+0.2% phosphoric acid, B=90% methanol/water+0.2% phosphoric acid; gradient-linear, 0% B to 100% B over 2 min.

Method 10: column-YMC S5 C18 ODS 4.6×50 mm; flow-2.5 mL/min.; detection at 220 nm; solvent-A=90:10/water:methanol+0.2% phosphoric acid, B=10:90/water:methanol+0.2% phosphoric acid; gradient-linear, 40% B to 60% B over 10 min.

Intermediates used in the preparation of the example compounds are provided in Table 1, followed by a description of relevant procedures. The example compounds are provided in Table 2 followed by a description of relevant procedures.

TABLE 1

| # | Structure | Characterization | Method |
|---|---|---|---|
| INT1 | 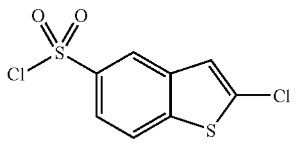 | | Title compound of Example INT1 |
| INT2 | 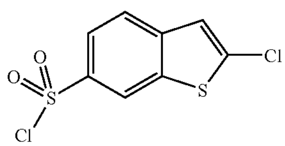 | | Title compound of Example INT2 |
| INT3 | 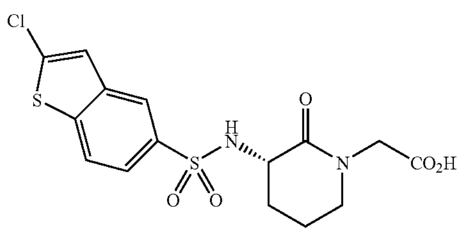 | HPLC (Method 2) $t_R$ = 2.0 min | Title compound of Example INT3 |
| INT4 | 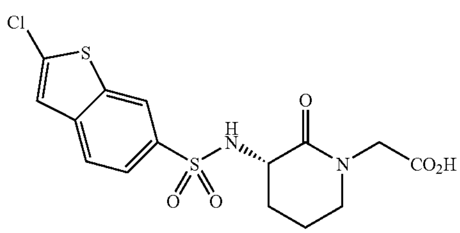 | HPLC (Method 2) $t_R$ = 2.0 min | Title compound of Example INT4 |
| INT5 | 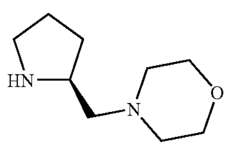 | | Title compound of Example INT5 |
| INT6 | 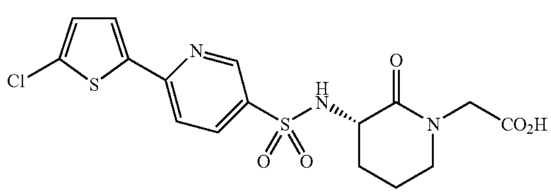 | HPLC (Method 2) $t_R$ = 2.0 min LCMS (ESI, pos. ion spectrum) m/z 430/432 (M + 1) | Title compound of Example INT6 |
| INT7 | 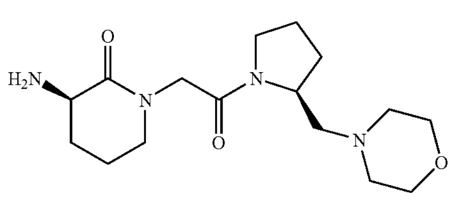 | | Title compound of Example INT7 |

TABLE 1-continued

| # | Structure | Characterization | Method |
|---|---|---|---|
| INT8 | 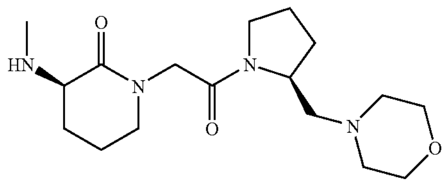 | HPLC (Method 2) $t_R$ = 0.12 min | Title compound of Example INT8 |
| INT9 | 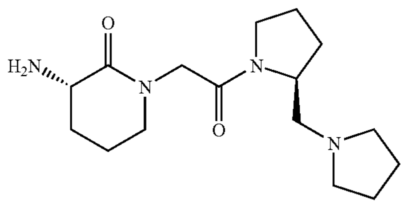 | | Title compound of Example INT9 |
| INT10 | 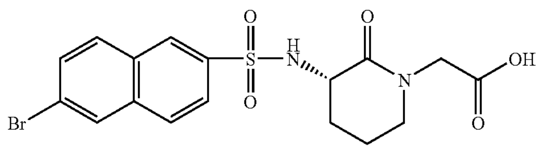 | LCMS (method 4) $t_R$ = 1.6 min (ESI, pos. ion spectrum) m/z 441/443 | Prepared using the methods described in Example INT3 |
| INT11 | 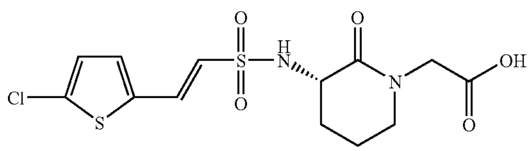 | LCMS (method 4) (ESI, pos. ion spectrum) m/z 379/381 (M + 1) | Prepared using the methods described in Example INT3 |
| INT12 | 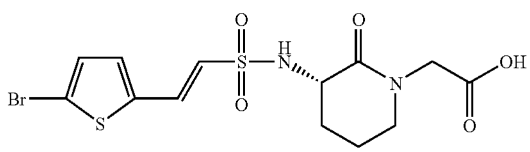 | LCMS (method 4) (ESI, pos. ion spectrum) m/z 424/426 (M + 1) | Prepared using the methods described in Exampl INT3 using INT28 |
| INT13 | 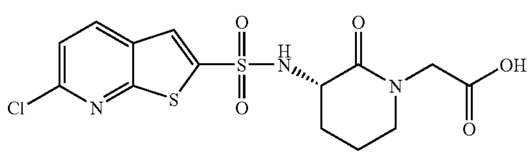 | LCMS (method 3) (ESI, pos. ion spectrum) m/z 404/406 (M + 1) | Prepared using the methods described in Example INT3 |
| INT14 | 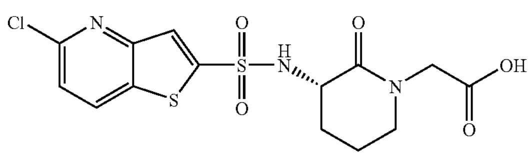 | LCMS (method 3) (ESI, pos. ion spectrum) m/z 404/406 (M + 1) | Prepared using the methods described in Example INT3 |
| INT15 | 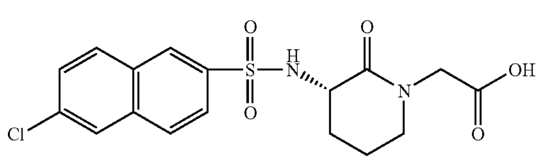 | LCMS (method 3) (ESI, pos. ion spectrum) m/z 397/399 (M + 1) | Prepared using the methods described in Example INT3 |
| INT16 | 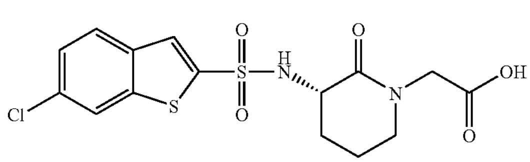 | LCMS (method 3) (ESI, pos. ion spectrum) m/z 403/405 (M + 1) | Prepared using the methods described in Example INT3 |

TABLE 1-continued

| # | Structure | Characterization | Method |
|---|---|---|---|
| INT17 | [5-chlorobenzothiophene-2-sulfonyl-NH-(piperidin-2-one)-N-CH2COOH] | LCMS (method 3) (ESI, pos. ion spectrum) m/z 403/405 (M + 1) | Prepared using the methods described in Example INT3 |
| INT18 | [5-chloro-bithiophene-sulfonyl-NH-(piperidin-2-one)-N-CH2COOH] | LCMS (method 3) (ESI, pos. ion spectrum) m/z 435/437 (M + 1) | Prepared using the methods described in Example INT3 |
| INT19 | [5-chlorobenzothiazole-2-sulfonyl-NH-(piperidin-2-one)-N-CH2CO2H] | LCMS (method 3) (ESI, pos. ion spectrum) m/z 404/406 (M + 1) | Prepared using the methods described in Example INT3 |
| INT20 | | LCMS (method 3) (ESI, pos. ion spectrum) m/z 516/518 (M + 1) | Title compound of Example INT20 |
| INT21 | [5-chlorothieno[3,2-b]pyridine-2-sulfonyl-NH-(piperidin-2-one)-N-CH2CO-pyrrolidine-2-CHO] | LCMS (method 4) (ESI, pos. ion spectrum) m/z 485/487 (M + 1) | Prepared using the methods described in Example INT20 using INT14 |
| INT22 | [(E)-2-(5-chlorothien-2-yl)vinylsulfonyl-NH-(piperidin-2-one)-N-CH2CO-pyrrolidine-2-CHO] | LCMS (method 3) (ESI, pos. ion spectrum) m/z 460/462 (M + 1) | Prepared using the methods described in Example INT20 using INT11 |
| INT23 | [5-chlorobenzothiophene-2-sulfonyl-NH-(piperidin-2-one)-N-CH2CO-pyrrolidine-2-CHO] | LCMS (method 3) (ESI, pos. ion spectrum) m/z 484/486 (M + 1) | Prepared using the methods described in Example INT20 using INT17 |
| INT24 | [5-chlorothiazol-2-yl-thiazole-5-SO2Cl] | | Title compound of Example INT24 |
| INT25 | [5-chlorobenzothiazole-2-SO2Cl] | | Title compound of Example INT25 |
| INT26 | [6-chlorobenzothiazole-2-SO2Cl] | | Title compound of Example INT26 |

TABLE 1-continued

| # | Structure | Characterization | Method |
|---|---|---|---|
| INT27 | 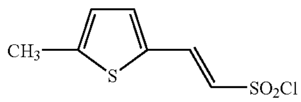 | | Title compound of Example INT27 |
| INT28 | 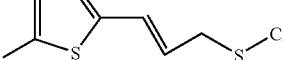 | | Prepared using the methods described in Example INT27 |
| INT29 | 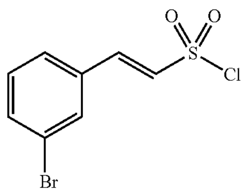 | | Title compound of Example INT29 |
| INT30 | 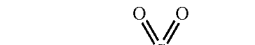 | | Prepared using the methods described in Example INT29 |
| INT31 | 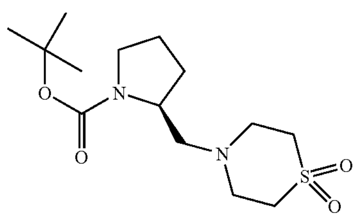 | | Title compound of Example INT31 |
| INT32 | 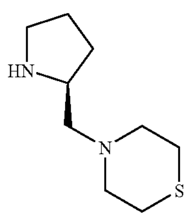 | | Prepared using the method described in Example INT5 |
| INT33 | 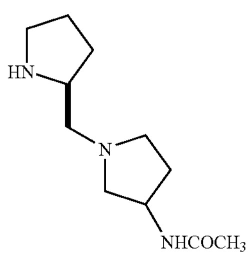 | | Prepared using the method described in Example INT5 |
| INT34 | 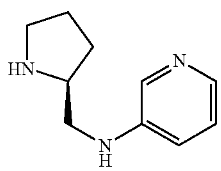 | | Prepared using the method described in Example INT5 |

TABLE 1-continued

| # | Structure | Characterization | Method |
|---|-----------|------------------|--------|
| INT35 | 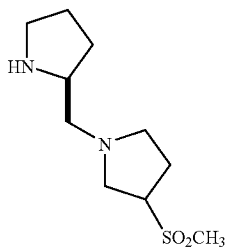 | | Prepared using the method described in Example INT5 |
| INT36 | 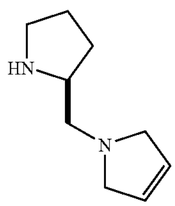 | | Prepared using the method described in Example INT5 |
| INT37 | 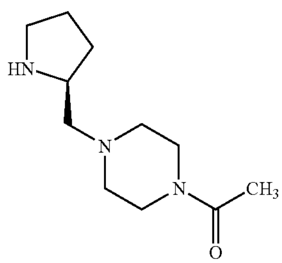 | | Prepared using the method described in Example INT5 |
| INT38 | 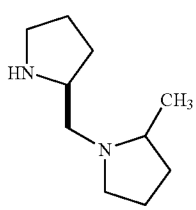 | | Prepared using the method described in Example INT5 |
| INT39 | 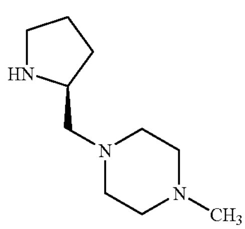 | | Prepared using the method described in Example INT5 |
| INT40 | 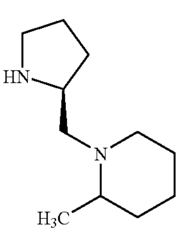 | | Prepared using the method described in Example INT5 |

TABLE 1-continued

| # | Structure | Characterization | Method |
|---|---|---|---|
| INT41 | 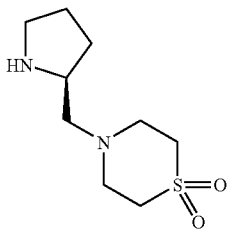 | | Prepared using the method described in Example INT5 |
| INT42 | 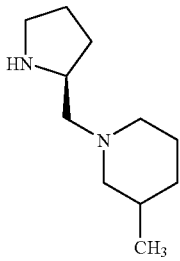 | | Prepared using the method described in Example INT5 |
| INT43 | 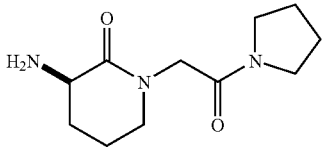 | | Prepared using the method described in Example INT7 parts C-D from INT60 |
| INT44 | 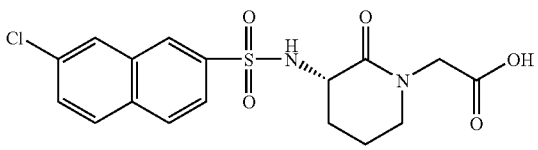 | | Prepared using the method described in Example INT3 |
| INT45 | 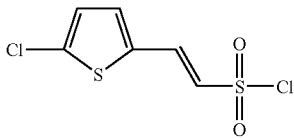 | | prepared using methods described in the literature |
| INT46 | 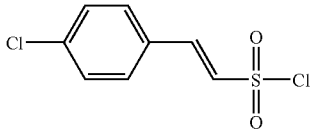 | | prepared using methods described in the literature |
| INT47 | 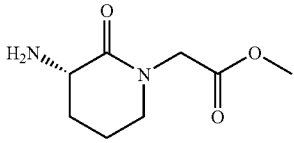 | | prepared using methods described in the literature |
| INT48 | 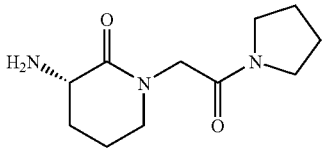 | | prepared using methods described in the literature |

TABLE 1-continued

| # | Structure | Characterization | Method |
|---|---|---|---|
| INT49 | 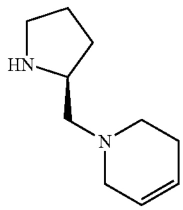 | | Prepared using methods described in: Tetrahedron: Asymmetry 1900, 1(12), 877. |
| INT50 | 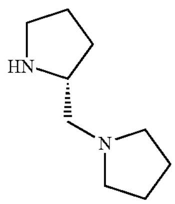 | | Prepared using methods described in: Tetrahedron: Asymmetry 1900, 1(12), 877. |
| INT51 | 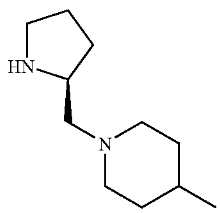 | | Prepared using methods described in: Tetrahedron: Asymmetry 1900, 1(12), 877. |
| INT52 | 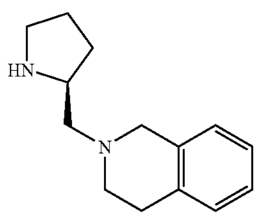 | | Prepared using methods described in: Tetrahedron: Asymmetry 1900, 1(12), 877. |
| INT53 | 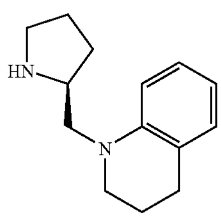 | | Prepared using methods described in: Tetrahedron: Asymmetry 1900, 1(12), 877. |
| INT54 | 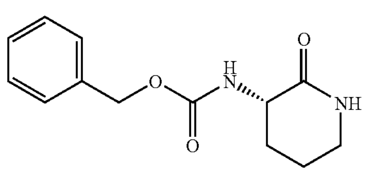 | | title compound of Example INT54 |
| INT55 | 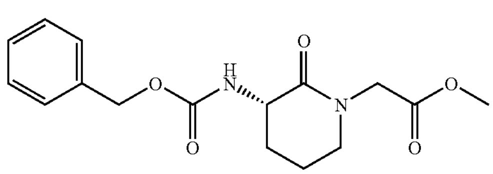 | | title compound of Example INT55 |
| INT56 | 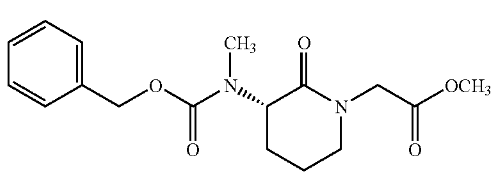 | HPLC (method 1) $t_R$ = 2.6 min LRMS (ESI, pos. ion spectrum) m/z 355 (M + H) | prepared using the method described in Example INT8 using INT55 |

TABLE 1-continued

| # | Structure | Characterization | Method |
|---|---|---|---|
| INT57 | 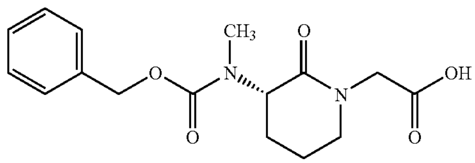 | HPLC (method 1) $t_R$ = 2.4 min LRMS (ESI, pos. ion spectrum) m/z 321 (M + H) | prepared using the method described in Example INT3 part B using INT56 |
| INT58 | 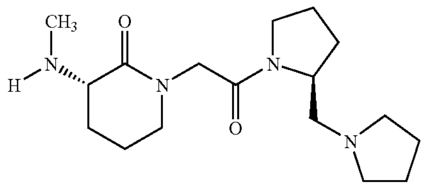 | HPLC (method 1) $t_R$ = 0.2 min LRMS (ESI, pos. ion spectrum) m/z 323 (M + H) | prepared using the method described in Example INT7 parts C and D using INT57 |
| INT59 | 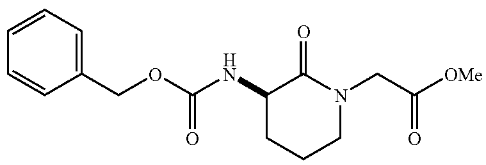 | | compound of Example INT7 part A |
| INT60 | 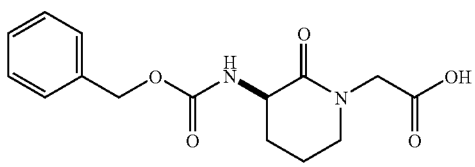 | | compound of Example INT7 part B |
| INT61 | 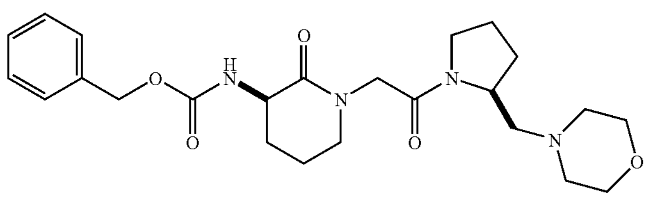 | | compound of Example INT7 part C |
| INT62 | 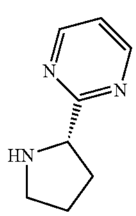 | | Title compound of Example INT62 |
| INT63 | 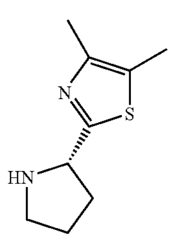 | | Title compound of Example INT63 |

TABLE 1-continued

| # | Structure | Characterization | Method |
|---|---|---|---|
| INT64 | 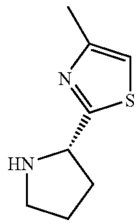 | | Title compound of Example INT64 |
| INT65 | 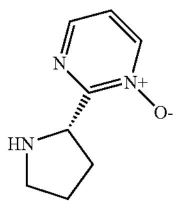 | | Title compound of Example INT65 |
| INT66 | 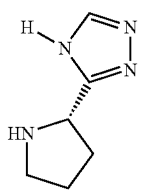 | | Title compound of Example INT66 |
| INT67 | 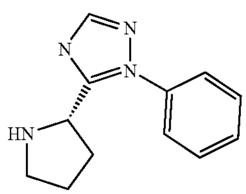 | | Title compound of Example INT67 |
| INT68 | 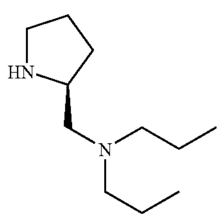 | | Prepared using the method described in Example INT5 |

EXAMPLE INT1 t-Butyl lithium (1.7 M in pentane, 0.78 mL, 1.3 mmol) was added over 5 min to a solution of 5-bromo-2-chlorobenzo[b]thiophene (0.17 g, 0.68 mmol) in ether (6 mL) stirring under nitrogen at −100° C. After stirring at −100° C. for 30 min, sulfur dioxide was bubbled into the reaction for about 3 min whereupon a white precipitate formed. After stirring at −100° C. for an additional 30 min, N-chlorosuccinimide (0.11 g, 0.84 mmol) in THF (1 ml) was added. The reaction was allowed to very slowly warm to ambient temperature. After stirring overnight the reaction was transferred to a separatory funnel with ether and water. Extraction with ether (2×15 mL), washing the combined organic layers with brine and drying over magnesium sulfate afforded 0.20 g of crude product. Purification over silica gel afforded 0.10 g (55%) of 2-chlorobenzo[b]thiophene-5-sulfonyl chloride. $^1$H-NMR (CDCl$_3$) δ 8.34 (1H, s), 8.05 (1H; d, J=7.5 Hz), 7.93 (1H, d, J=7.5 Hz), and 7.38 (1H, s).

EXAMPLE INT2

Part A: A suspension of 3-bromothiophenol (15.2 g, 81 mmol), bromoacetaldehyde dimethylacetal (9.5 mL, 81 mmol) and potassium carbonate (12.2 g, 88 mmol) in acetone (90 mL) was stirred at ambient temperature overnight. The solid was filtered and rinsed with ether. Evaporation of the filtrate afforded 23 g of 1-bromo-3-((2,2-dimethoxyethyl)thio)benzene which was carried forward without further purification.

Part B: A solution of 1-bromo-3-((2,2-dimethoxyethyl)thio)benzene (23 g, 81 mmol theory) in chlorobenzene (100 mL) was slowly added over 1 h to polyphosphoric acid (62 g) in chlorobenzene (500 mL) stirring vigorously at 140° C. under nitrogen. After refluxing for 4.5 h, the reaction was slowly poured into 1.5 L of ice water. Extraction with methylene chloride (2×700 mL) and washing the combined organic layers with water and saturated sodium bicarbonate solution and drying over magnesium sulfate afforded 17 g of crude product after evaporation of the solvent. Distillation (20 mm Hg) afforded 9.7 g (156–165° C., 55%) of a 50/50 mixture of 4-bromobenzo[b]thiophene and 6-bromobenzo[b]thiophene.

Part C: A portion of the part B product (2.1 g, 10 mmol) was slowly added over 20 min to a solution of LDA (2 M in THF/hexane, 5.5 mL, 11 mmol) stirring under argon at −78° C. After stirring at −78° C. for 40 min, this solution was transferred over 10 min via cannula to a solution of carbon tetrachloride (3.0 mL, 38 mmol) in THF (40 mL) stirring at −78° C. After stirring at −78° C. for 1.5 h, the reaction was quenched with sat. ammonium chloride and allowed to warm to room temperature and, transferred to a separatory funnel with methylene chloride/water. Extraction with methylene chloride (2×100 mL) and drying the combined organic layers over magnesium sulfate afforded 3.7 g of crude product after evaporation of the solvent. Purification over silica gel gave 2.1 g (87%) of a mixture of 4-bromo-2-chlorobenzo[b]thiophene and 6-bromo-2-chlorobenzo[b]thiophene.

Part D: t-Butyl lithium (1.7 M in pentane, 11 mL, 19 mmol) was slowly added over 30 min, to a solution of the part C product (2.1 g, 8.7 mmol) in ether (20 mL) stirring under nitrogen at −78° C. After stirring at −78° C. for 1 h, sulfur dioxide (150 drops, ~55 mmol) was added dropwise to the reaction by condensing the vapor onto a −78° C. cold finger and allowing it to drip into the reaction from the tip of the cold finger. The cold bath was removed after 1 h. After stirring an additional 2 h at ambient temperature, the reaction was evaporated in vacuo. Hexanes (22 mL) was added to the resultant residue and the reaction was cooled to 0° C. before adding sulfuryl chloride (0.83 mL, 10 mmol) over 10 min. The reaction was stirred at 0° C. for 30 min and then at ambient temperature overnight. The reaction was then purified over silica gel to afford 0.24 g (10%) of 2-chlorobenzo[b]thiophene-6-sulfonyl chloride: $^1$H-NMR (CDCl$_3$) δ 8.42 (1H, s), 7.98 (1H, d, J=7.6 Hz), 7.86 (1H, d, J=7.6 Hz), and 7.34 (1H, s).

EXAMPLE INT3

Preparation of [(3S)-3-(2-Chlorobenzo[b]thiophene-5-sulfonylamino)-2-oxo-piperidin-1-yl]acetic acid. Part A: Using the method described in Example 1 and using INT1 and methyl ((3S)-3-amino-2-oxopiperidin-1-yl)acetate, 0.18 g (73%) of methyl [(3S)-3-(2-chlorobenzo[b]thiophene-5-sulfonylamino)-2-oxo-piperidin-1-yl]acetate was prepared: $^1$H-NMR (CDCl$_3$) δ 8.13 (1H, s), 7.80 (2H, s), 7.18 (1H, s), 5.98 (1H, broad s), 4.02 (1H, d, J=15.3 Hz), 3.82 (1H, d, J=15.3 Hz), 3.61 (3H, s), 3.35 (1H, m), 3.32 (1H, m), 3.20 (1H, m), 1.90 (4H, m).

Part B: The compound of part A (0.44 mmol) was dissolved in THF (2.2 mL) and stirred at 0° C. Lithium hydroxide (2.0 N, 2.2 mL, 4.4 mmol) was then added. After stirring at 0° C. for 1 h, the reaction was quenched with 6 N HCl (0.7 mL) and transferred to a separatory funnel. Extraction with ethyl acetate (3×30 mL), washing the combined organic layers with brine, and drying over magnesium sulfate afforded 0.17 g (98%) of the title compound: HPLC (method 2) $t_R$=2.0 min.

EXAMPLE INT4

Preparation of [(3S)-3-(2-Chlorobenzo[b]thiophene-6-sulfonylamino)-2-oxo-piperidin=1-yl]acetic acid. Part A: Using the method described in Example 1 and using INT2 and methyl ((3S)-3-amino-2-oxopiperidin-1-yl)acetate, 0.26 g (100%) of methyl [(3S)-3-(2-chlorobenzo[b]thiophene-6-sulfonylamino)-2-oxo-piperidin-1-yl]acetate was prepared: $^1$H-NMR (CDCl$_3$) δ 8.27 (1H, s), 7.82 (1H, d, J=8.4 Hz), 7.74 (1H, d, J=8.4 Hz), 7.23 (1H, s), 6.20 (1H, broad s), 4.11 (1H, d, J=17.3 Hz), 3.90 (1H, d, J=17.3 Hz), 3.65 (3H, s), 3.60 (1H, m), 3.38 (1H, m), 3.28 (1H, m), 1.85 (4H, m).

Part B: Using the method of Example INT3 Part B, the compound of Part A (0.60 mmol) was converted to 0.24 g (100%) of the title compound: HPLC (method 2) $t_R$=2.0 min.

EXAMPLE INT5

Part A. Morpholine (7.1 g, 7.1 mL, 82 mmol) was added to a stirring solution of N-BOC-(S)-prolinal (3.3 g, 17 mmol) in methylene chloride (83 mL) followed by zinc chloride (0.5 M in THF, 100 mL, 50 mmol). After stirring at ambient temperature for 5 h, borane-pyridine (ca. 8 M, 2 mL, 16 mmol) was added. After stirring at ambient temperature overnight, the reaction was evaporated in vacuo. Methanol was added to the residue and the solids were filtered. Evaporation of the filtrate afforded 13 g of crude product. Purification over silica gel afforded 3.9 g (87%) of 1,1-dimethylethyl (S)-2-(4-morpholinylmethyl)-1-pyrrolidinecarboxylate: $^1$H-NMR (CDCl$_3$) δ 3.90 (1H, m), 3.69 (4H, m), 3.34 (2H, m), 2.57 (2H, m), 3.40 (2H, m), 2.18 (1H, m), 1.90 (4H, m), 1.74 (1H, m), 1.47 (9H, s).

Part B: A portion of Part A amine (14 mmol) was stirred in methylene chloride (44 mL) and TFA (22 mL). After stirring at ambient temperature for 2.5 h, the reaction was evaporated in vacuo. The residue was sequentially coevaporated twice with methylene chloride and once with methanol. The residue was loaded onto a column of AG 50W-X2 resin (160 g, prewashed with 480 mL of MeOH, 480 mL water, and 480 mL of 1/1 MeOH/water). The column was washed with MeOH (480 mL) and was then eluted with 2N ammonia in methanol to afford 2.0 g (82%) (S)-4-(2-pyrrolidinylmethyl)morpholine, the title compound: $^1$H-NMR (CDCl$_3$) δ 3.70 (4H, m), 3.46 (1H, s), 3.27 (1H, m), 2.96 (1H, m), 2.86 (1H, m), 2.53 (2H, m), 2.42 (2H, m), 2.30 (2H, m), 1.86 (1H, m), 1.74 (2H, m), 1.35 (1H, m).

EXAMPLE INT6

Preparation of ((3S)-3-[6-(5-Chlorothiophen-2-yl)pyridine-3-sulfonylamino]-2-oxopiperidin-1-yl)-acetic acid. Part A: Using the method described in Example 1 and using 2-chloro-5-pyridinesulfonyl chloride and methyl ((3S)-3-amino-2-oxopiperidin-1-yl)acetate, 0.16 g (83%) methyl [(3S)-3-(6-chloropyridine-3-sulfonylamino)-2-oxopiperidin-1-yl]acetate was prepared: HPLC (method 2) $t_R$=1.5 min; LCMS (ESI, pos. ion spectrum) m/z 362/364 (M+1).

Part B: Using the method described in Example 421, Part A compound was converted to 89 mg (45%) of methyl [(3S)-3-[6-(5-chlorothiophen-2-yl)pyridine-3-sulfonylamino]-2-oxopiperidin-1-yl]acetate: HPLC (method 2) $t_R$=2.10 min; LCMS (ESI, pos. ion spectrum) m/z 444/446 (M+1).

Part C: Using the method of Example INT3 Part B, Part B compound (0.20 mmol) was converted to 86 mg (100%) of the title compound: HPLC (method 2) $t_R$=2.0 min; LCMS (ESI, pos. ion spectrum) m/z 430/432 (M+1).

EXAMPLE INT7

Preparation of (3R)-3-amino-1-[((2S)-2-(4-morpholinylmethyl)-1-pyrrolidinyl)-2-oxoethyl]piperidin-2-one. Part A:

INT59 was prepared from D-ornithine using the procedures described in Example INT54 and Example INT55.

Part B. Using the procedures described in Example INT3 Part B and using Part A compound, INT60 was prepared Part C. Using the procedure described in Example 1 and using part B compound and INT5, INT61 was prepared: HPLC (method 2) $t_R$=1.4 min.

Part D. Part C compound (0.47 g, 1.0 mmol) was dissolved in methanol (14 mL) and 10% palladium on carbon (100 mg) was added. After stirring under hydrogen (50 psi) for 2 h, the reaction was filtered through CELITE. The pad was rinsed with methanol and the combined filtrates were concentrated to afford 0.33 g (100%) of (3R)-3-amino-1-[2-((2S)-2-(4-morpholinylmethyl)-1-pyrrolidinyl)-2-oxoethyl] piperidin-2-one after evaporation of the solvent: $^1$H-NMR (CDCl$_3$) δ 4.26 (1H, broad s), 4.07 (1H, d, J=13 Hz), 4.01 (1H, d, J=13 Hz), 3.69 (4H, m), 3.44 (2H, m), 2.60 (2H, m), 2.46 (2H, m), 2.27–1.92 (12H, m), 1.7 (2H, m).

EXAMPLE INT8

Preparation of (3R)-3-methylamino-1-[((2S)-2-(4-morpholinylmethyl)-1-pyrrolidinyl)-2-oxoethyl]piperidin-2-one (INT8). Part A: Cesium carbonate (1.9 g, 6.0 mmol) and tetrabutylammonium iodide (2.2 g, 6.0 mmol) were added to a stirring solution of INT59 (0.63 g, 2.0 mmol) in DMF (23 mL). After stirring at ambient temperature for 30 min, methyl iodide (filtered through basic alumina, 0.86 g, 0.38 mL, 6.0 mmol) was added. After stirring at ambient temperature for 3 d, the reaction was transferred to a separatory funnel with ethyl acetate/water. Extraction with ethyl acetate (3×140 mL), washing the combined organic layers with water (2×140 mL) and brine (140 mL), and drying over magnesium sulfate afforded 1.1 g of crude product. Purification over silica gel gave 0.33 g (50%) of methyl ((3R)-N-benzyloxycarbonyl-N-methylamino-2-oxopiperidin-1-yl) acetate. HPLC (method 2) $t_R$=1.8 min; LCMS (ESI, pos. ion specturm) m/z 335 (M+1); Chiral HPLC (Chiralcel OD; 4.6×250 mm; 2 mL/min; detection at 220 nm; isocratic, 15% isopropyl alcohol in hexane) $t_R$=11.0 min.

Part B: Part A compound was saponified using the procedure described in Example INT3 Part B using 2.0 equivalents of lithium hydroxide to afford ((3R)-N-benzyloxycarbonylmethylamino-2-oxopiperidin-1-yl)acetic acid.

Part C: Using the method described in Example 1 and using Part B compound and INT5 provided phenylmethyl R-methyl[1-[2-((2S)-2-(4-morpholinylmethyl)-1-pyrrolidinyl)-2-oxoethyl]-2-oxopiperidin-3-yl]carbamate. HPLC (method 2) $t_R$=1.6 min; LCMS (ESI, pos. ion specturm) m/z 474 (M+1); Chiral HPLC (Chiralcel AD; 4.6×250 mm; 2 mL/min; detection at 220 nm; isocratic,25% isopropyl alcohol in hexane) $t_R$=6.2 min.

Part D: Hydrogenation of Part C amine using the method described in Example INT7 Part D afforded the title compound: HPLC (method 2) $t_R$=0.12 min.
5

EXAMPLE INT9

Part A: To a suspension of (3S)-2-oxo-3-[[(phenylmethoxy)carbonyl]amino]-1-piperidineacetic acid (955 mg, 3.12 mmol) in acetonitrile (10 mL) was added WSC (899 mg, 4.68 mmol) and 1-hydroxy-7-azabenzotriazole (424 mg, 3.12 mmol) producing a homogeneous solution. After 10 minutes, 1-[(2S)-2-pyrrolidinylmethyl]pyrrolidine (721 mg, 4.68 mmol) was added. After an additional 20 minutes, the reaction was quenched with water (10 mL). This mixture was then added to a 10-g C-18 cartridge (Varian part no. 1425-6031). The cartridge was washed with water (100 mL). The product was then eluted with 60% acetonitrile in water (100 mL). Concentration of this solution provided phenylmethyl S-[2-Oxo-1-[2-oxo-2-((2S)-2-pyrrolidin-1-ylmethyl-pyrrolidin-1-yl)ethyl]piperidin-3-yl]carbamate (663 mg, 1.50 mmol, 48%) as a yellow foam: LCMS (method 3) m/z 443 (M+H), $t_R$=2.0 min.

Part B: To a solution of Part A compound (643 mg, 1.45 mmol) in methanol (20 mL) was added 10% palladium on carbon (200 mg). The mixture was stirred under an atmosphere of hydrogen (50 psi) for 17 hours. The reaction mixture was then filtered though CELITE (20 mm i.d.×10 mm). The pad was rinsed with methanol (20 mL). Concentration of the combined filtrates provided the title compound (430 mg, 1.40 mmol, 96%) as a light yellow foam.

EXAMPLE INT20

Part A: Using INT18 and (S)-2-hydroxymethylpyrrolidine and using the methods described in Example 130, N-([(S)-1-[2-[(S)-(2-hydroxymethyl)-1-pyrrolidinyl]-2-oxoethyl]-2-oxo-piperidin-3-yl]) 5'-Chloro-[2,2']bithienyl-5-sulfonamide was prepared: LCMS (method 4, ESI, pos. ion. spectrum), m/z 518/520).

Part B: The compound of part A (10.8 g, 20.9 mmol) was dissolved in 200 mL of "wet" methylene chloride. "Wet" methylene chloride is the lower layer produced by shaking equal amounts of methylene chloride and water in a separatory funnel. To this solution was added Dess-Martin periodinane (17.7 g, 41.8 mmol). After 80 minutes, the reaction was quenched with ether (100 mL) and 100 mL of a solution of 48 g of sodium thiosulfate in 80% saturated aqueous sodium bicarbonate/20% water. Some foaming occured, however after 10 minutes the layers separated. The upper organic layer was subsequently washed with saturated aqueous sodium bicarbonate (75 mL) followed by water (50 mL). The combined aqueous washes were backwashed with ether (100 mL) and the combined ether layers were dried over sodium sulfate. The filtrate was concentrated and purified by silica gel chromatography using 2% methanol in chloroform to provide N-[S-1-[2-[(S)-(2-formyl)-1-pyrrolidinyl]-2-oxoethyl]-2-oxo-piperidin-3-yl] 5'-Chloro-[2,2'] bithienyl-5-sulfonamide as a yellow foam (10.5 g): LCMS (method 3) (ESI, pos. ion. spectrum), m/z 516/518).

EXAMPLE INT24

Part A, Preparation of 5-Chloro-[2,2']bithiazole: To a solution of 2,2'-bithiazole (340 mg, 2.0 mmol) in THF (4 mL) at −78° C. was added n-butyllithium (0.85 mL, 2.5 M in hexanes). After 5 min, CCl$_4$ (310 mg, 2.0 mmol) was added and the mixture was brought to 0° C. After one hour, the reaction was quenched with saturated aqueous ammonium chloride (5 mL) and extracted with ether (20 mL+10 mL). The combined organic extracts were dried over magnesium sulfate and concentrated to yield 270 mg of crude material. This material was purified using preparative silica TLC (chloroform) to produce 5-Chloro-[2,2']bithiazole (76 mg, 0.37 mmol, 19%).

Part B, Preparation of 5'-Chloro-[2,2']bithiazole-5-sulfonyl chloride: To 5-Chloro-[2,2']bithiazole (76 mg, 0.37 mmol) in 2 mL of THF at −78° C. was added 1.6 M n-butyl lithium in hexane solution (0.25 mL, 0.41 mmol) dropwise. The reaction mixture was stirred at −78° C. for another 30 min. Sulfur dioxide gas was added at the surface of the reaction mixture for 30 min. The dry-ice cooling bath was removed and the reaction mixture was warmed to room temperature over 1 h. The reaction mixture was concentrated and 2 mL of hexanes was added. The reaction was cooled to 0° C. Sulfuryl chloride (56 mg, 0.41 mmol) was added and the mixture was stirred at room temperature overnight. The reaction mixture was loaded on a silica gel pad and eluted with 100 mL of a 1:1 mixture of hexanes and ethyl acetate to give the title compound as a yellow solid (110 mg, 98%) after concentration: $^1$H-NMR (CDCl$_3$) δ 7.83 (1H, s), 8.44 (1H, s).

EXAMPLE INT25

INT25 was prepared from 5-chlorobenzothiazole using the method described in the following reference: Vedejs, E., Kongkittingam, C. *J. Org. Chem.* 2000, 65, 2309. The crude product was used without purification.

EXAMPLE INT26

INT26 was prepared from 6-chlorobenzothiazole using the method described in the following reference: Vedejs, E., Kongkittingam, C. *J. Org. Chem.* 2000, 65, 2309. The crude product was used without purification.

EXAMPLE INT27

A. 2-(5-Methyl-thiophen-2-yl)-ethenesulfonic acid, ethyl ester.

n-Butyl lithium (1.6 mL of a 2.5 M solution in hexanes, 4.0 mmol) was added dropwise to a solution of ethyl diethylphosphorylmethanesulfonate (1.0 g, 3.8 mmol), prepared as described in *Tetrahedron*, 1987, 43(21), 5125, at −78° C. in THF (15 mL). The mixture was stirred for 20 min. then 5-methyl-2-thiophenecarboxaldehyde (460 mg, 4.2 mmol) was slowly added. The mixture was stirred at −78° C. for 1 h. then allowed to warm to room temperature overnight. The bulk of the solvents were evaporated and the residue was treated with water (2 mL) and extracted with CH$_2$CL$_2$. The organic layer was washed with brine, dried over MgSO$_4$, filtered and concentrated. The crude product was purified by column chromatography eluting with CH$_2$CL$_2$ to give the title compound.

B. 2-(5-Methyl-thiophen-2-yl)-ethenesulfonic acid, tetra-n-butylammonium salt.

2(5-Methyl-thiophen-2-yl)-ethenesulfonic acid, ethyl ester (0.92 g. 3.2 mmol) in acetone (16 mL) was treated with tetrabutylammonium iodide (1.3 g, 3.5 mmol) and heated to reflux for 19 h. The mixture was concentrated to dryness then diluted with CH$_2$CL$_2$ and washed with water and brine. The organic layer was dried over MgSO$_4$, filtered and concentrated to give the title compound which was taken on to the next step without further purification.

C. 2-(5-Methyl-thiophen-2-yl)-ethenesulfonyl chloride.

Sulfuryl chloride (0.61 mL, 7.6 mmol) was added to a solution of triphenylphosphine (1.8 g, 6.9 mmol) in CH$_2$CL$_2$ (8.6 mL) at 0° C. The ice bath was removed and part B compound (1.6 g, 3.4 mmol) in CH$_2$CL$_2$(17 mL) was added to the reaction mixture via cannula. The resulting solution was stirred for 1.5 h then hexane/ether (1:1 v/v, 200 mL) was added until the solution was no longer cloudy and two layers formed. The solution was decanted and the lower oily layer was discarded. The solution was concentrated to dryness and the product was purified by column chromatograph eluting with CH$_2$CL$_2$ to give the title compound; LRMS (ESI, pos. ion spectrum 223/225 (M+H).

EXAMPLE INT29

Sulfuryl chloride (2.87 mL, 35.7 mmol) was added dropwise to DMF (3.8 mL) at 0° C. The resulting mixture was stirred at room temperature for 50 min. To the mixture was added 3-bromostyrene (2.7 mL, 21 mmol). The mixture was then heated to 90° C. for 4 h, cooled to room temperature and poured into 50 mL of ice/water. The precipitate was collected by filtration, washed with water (2×), and dried by lyophilization to afford 3.54 g (60%) of the title compound: $^1$H-NMR (CD$_3$OD) δ 7.55–7.65 (3H, m), 7.38–7.44 (1H, d, m), 7.27 (1H, t, 7.9), 7.16 (1H, d, J=11.3 Hz).

EXAMPLE INT31

To a solution of 1,1-dimethylethyl (S)-2-thiomorpholin-4-ylmethyl-pyrrolidine-1-carboxylate (90 mg, 0.32 mmol) in dichloromethane (1.5 mL) was added 3-chloroperoxybenzoic acid (114 mg, 0.660 mmol). The mixture was stirred at room temperature until monitoring indicated that the oxidation was complete. The reaction was then diluted with dichloromethane and washed with saturated sodium bicarbonate aqueous solution and brine. The organic layer was dried over sodium sulfate and concentrated. The residue was purified over silica gel to afford 61 mg (61%) of the title compound.

EXAMPLE INT54

A suspension of L-Ornithine hydrochloride (102 g, 600 mmol) in MeOH (600 mL) was cooled to 0° C. Thionyl chloride (54.7 mL, 750 mmol) was added dropwise over 30 min maintaining an internal reaction temperature of <10° C. The cooling bath was removed and the reaction was stirred at room temperature overnight. The reaction mixture was concentrated in vacuo to afford a white solid (131 g). The solid was dissolved in water (600 mL) and 4N NaOH (160 mL, 640 mmol) was added to bring the pH to 8–9. After 4 h the reaction mixture was cooled to 0° C. and benzyl chloroformate (102 mL, 717 mmol) was added over 30 min. After the addition, the pH was maintained at ca. 8–9 by addition of 4N NaOH (160 mL, 640 mmol) until the pH stabilized. The reaction mixture was stirred an additional 30 min during which time the product began to precipitate as a sticky solid. Diethyl ether (500 mL) was added, and the resulting mixture was vigorously stirred for 30 min. The solid was filtered, washed with water and diethyl ether, then dried in vacuo. The title compound was obtained as a white solid (61.6 g, 41%): HPLC (method 1) $t_R$=2.7 min, >99% pure; (HPLC; Chiralcel AD, 4.6 mm×250 mm; 1 mL/min; 220 nm, 40% EtOH/hexanes, $t_R$(S)=9.9 min, $t_R$(R)=13.2 min)>99% ee; LRMS (ESI, pos. ion spectrum) m/z 249 (M+H).

EXAMPLE INT55

The title compound of Example INT54 (59.6 g, 240 mmol) was dissolved in anhydrous THF (672 mL) then cooled to −78° C. A solution of lithium bis(trimethylsilyl) amide (1.0 M in THF, 288 mL, 288 mmol) was added dropwise over 1 h. The reaction was stirred an additional 30 min, then methyl bromoacetate (27.3 mL, 288 mmol) was added dropwise over 15 min. The reaction mixture was stirred at −78° C. for 1 h before being quenched with aqueous saturated ammonium chloride solution (20 mL). The reaction mixture was warmed to room temperature then partitioned between aqueous 50% saturated ammonium chloride solution (400 mL) and ethyl acetate (200 mL). The organic phase was collected, and the aqueous phase extracted with ethyl acetate (200 mL). The organic layers were combined, dried (MgSO$_4$), and concentrated in vacuo to afford a semi-solid (78.9 g). This residue was triturated with ethyl acetate/hexanes (1:1, 100 mL) to afford a tan solid (65.4 g). This solid was triturated with ME (3×150 mL) to afford the title compound as an off-white solid (51.3 g, 67%): HPLC (method 1) $t_R$=2.9 min, 96% pure; HPLC (Chiralcel OD, 4.6 mm×250 mm; 2 mL/min; 220 nm, 20% isopropanol/hexanes, $t_r$(S)=14.7 min)>99% ee; LRMS (ESI, pos. ion spectrum) m/z 321 (M+H).

EXAMPLE INT62

Part A. Phosphorus trichloride (0.08 mL, 0.4 mmol) was added to a solution of part B compound of Example INT65 (58 mg, 0.19 mmol) in chloroform (1 mL). The reaction mixture was heated to 75° C. for 1 h and the solvents removed yielding benzyl (S)-2-pyrimidin-2-yl-pyrrolidine-1-carboxylate as an orange oil (55 mg, crude quantitative yield): HPLC (method 1) $t_R$=2.54 min, Purity 97%; LCMS (method 4) $t_R$=1.32 min, m/z 284 (M+H).

(S)-2-Pyrrolidin-2-yl-pyrimidine. Part B. Using the method described in Example INT66 part C, the bis HBr salt of (S)-2-pyrrolidin-2-ylpyrimidine isolated as a yellow solid (52 mg, 89% yield): $^1$H-NMR H (d4-MeOH) δ 2.2 (3H, m), 2.8 (1H, m), 3.8 (2H, m), 5.10 (1H, t, J=7.2 Hz), 7.55 (1H, t, J=4.0 Hz), 8.90 (2H, d, J=4.0 Hz).

EXAMPLE INT63

Part A. Lawesson's reagent (90 mg, 0.22 mmol) was added to a stirred slurry of benzyl (S)-2-carbamoyl-pyrrolidine-1-carboxylate (100 mg, 0.40 mmol) in toluene (3 mL) at ambient temperature. The reaction mixture was heated to 100° C. for 3 h then the solvents were removed. The residue was purified by flash silica gel chromatography yielding benzyl (S)-2-thiocarbamoylpyrrolidine-1-carboxylate as white solid (108 mg, crude quantitative yield): HPLC (method 1) $t_R$=2.55 min, Purity 100%; LCMS (method 4) $t_R$=1.34 min, m/z 287 (M+H).

Part B. to a solution of part A compound (108 mg, 0.41 mmol) in dry ethanol (1 mL) was added 3-bromo-2-butanone (68 mg, 0.45 mmol). The resulting solution was heated to reflux for 4 h then passed through a short silica gel pad then concentrated yielding benzyl (S)-2-(4,5-Dimethyl-thiazol-2-yl)-pyrrolidine-1-carboxylate as a colorless oil (130 mg, crude quantitative yield): HPLC (method 1) $t_R$=3.19 min, Purity 100%; LCMS (method 4) $t_R$=1.73 min, m/z 317 (M+H).

(S)-4,5-Dimethyl-2-pyrrolidin-2-ylthiazole. Part C. Using the method described in Example INT66 part C, the HBr salt of (S)-4,5-dimethyl-2-pyrrolidin-2-ylthiazole was isolated as a pale brown precipitate (85 mg, 79%): $^1$H-NMR (d4-MeOH) δ 2.3 (3H, m), 2.39 (3H, s), 2.44 (3H, s), 2.65 (1H, m), 3.49 (2H, m), 5.19 (1H, brs).

EXAMPLE INT64

Part A. Chloroacetone (36 mg, 0.37 mmol) was added to a solution of benzyl (S)-2-thiocarbamoyl-pyrrolidine-1-car-boxylate (90 mg, 0.34 mmol) in dry chloroform (2 mL). The resulting solution was heated to reflux for 24 h then purified by preparative HPLC yielding benzyl (S)-2-(4-methylthiazol-2-yl)-pyrrolidine-1-carboxylate as a colorless oil (55 mg, 54% yield): HPLC (method 1) $t_R$=3.11 min, Purity 100%; LCMS (method 4) $t_R$=1.57 min, m/z 303 (M+H).

(S)-4-Methyl-2-pyrrolidin-2-ylthiazole. Part B. Using the method described in Example INT66 part C, the HBr salt of (S)-4-methyl-2-pyrrolidin-2-ylthiazole isolated as an orange oil (45 mg, 100%): 1H-NMR(d4-MeOH) δ 2.2 (2H, m), 2.6 (1H, m), 3.36 (3H, s), 3.5 (2H, m), 5.20 (1H, t, J=7.2 Hz) 7.44 (1H, s).

EXAMPLE INT65

Part A. Benzyl (S)-2-cyanopyrrolidine-1-carboxylate (500 mg, 2.17 mmol) was dissolved in aqueous ethanol (3 m-L) and water (1 mL). Hydroxylamine hydrochloride (152 mg, 2.17 mmol) and Na$_2$CO$_3$ (115 mg, 1.08 mmol) were added and the reaction mixture heated to 100° C. for 1 h. The ethanol was removed and the aqueous residue was extracted with dichloromethane (3×25 mL), dried over Na$_2$SO$_4$ decanted and concentrated yielding benzyl (S)-2-(N-hydroxycarbamimidoyl)pyrrolidine-1-carboxylate as a pale yellow gum (428 mg, 75% yield): HPLC (method 1) $t_R$=1.40 min, Purity 76%; LCMS (method 4) $t_R$=0.81 min, m/z 264 (M+H).

Part B. Trifluoroacetic acid (0.24 mL) and tetramethoxypropane (400 mg, 2.43 mmol) were added to a solution of part A compound (428 mg, 1.63 mmol) in 2-propanol (5 mL). The resulting solution was heated to reflux for 13 h then concentrated and purified by preparative HPLC yielding benzyl (S)-2-(1-oxypyrimidin-2-yl)pyrrolidine-1-carboxylate as colorless oil (105 mg, 28%): HPLC (method 1) $t_R$=2.35 min, Purity 100%; LCMS (method 4) $t_R$=1.21 min, m/z 300 (M+H).

(S)-2-Pyrrolidin-2-yl-pyrimidine 1-oxide. Part C. Using the method described in Example INT66 part C, the HBr salt of (S)-2-pyrrolidin-2-ylpyrimidine 1-oxide isolated as a yellow oil (32 mg, 88% yield): $^1$H-NMR (d4-MeOH) δ 2.4 (2H, m), 2.6 (1H, m), 2.9 (1H, m), 3.8 (2H, m), 5.20 (1H, t, J=7.2 Hz), 7.95 (1H, dd, J=4.4 and 6.4 Hz), 8.76 (1H, d, J=4.4 Hz), 8.96 (1H, dd, J=6.4 Hz.

EXAMPLE INT66

Part A: N,N-Dimethylformamide dimethyl acetal (5 mL) was added to benzyl (2S)-2-carbamoyl-pyrrolidine-1-carboxylate (1.05 g, 4.23 mmol) at ambient temperature. The resulting slurry was heated to 120° C. for 2 h then allowed to cool and poured into hexane (50 mL). The solvents were removed under reduced pressure yielding benzyl (2S)-2-(dimethylaminomethylenecarbamoyl)pyrrolidine-1-carboxylate as a colorless oil (1.35 g, crude quantitative yield). HPLC (method 1) $t_R$=1.70 min, Purity 100%; LCMS (method 4) $t_R$=0.94 min, m/z 304 (M+1)

Part B. Part A compound (427 mg, 1.41 mmol) was dissolved in acetic acid (1.2 mL) and added to a solution of anhydrous hydrazine (52 mg, 1.6 mmol) in acetic acid (0.8 mL). The reaction mixture was heated to 90° C. for 1.5 h then poured into water (20 mL). The aqueous portion was extracted with chloroform (3×20 mL) and the combined organic portions washed with sat. NaHCO$_3$ (20 mL), dried over Na$_2$SO$_4$, and concentrated to provide benzyl (2S)-2-(4H-[1,2,4]triazol-3-yl)pyrrolidine-1-carboxylate was obtained as a colorless oil (351 mg, 92% crude yield): HPLC (method 1) t$_R$=2.76 min, Purity 100%; LCMS (method 4) t$_R$=1.15 min, m/z 273 (M+H).

(S)-3-Pyrrolidin-2-yl-4H-[1,2,4]triazole. Part C. To a portion of part B compound (76 mg, 0.28 mmol) was added HBr in acetic acid (30%, 1.0 mL). After 1 h, ether (70 mL) was added and the product precipitated as a white solid. The precipitate was filtered then washed from the frit with methanol (ca. 10 mL) and concentrated under reduced pressure yielding the HBr salt of (S)-3-pyrrolidin-2-yl-4H-[1,2,4]triazole as a pale yellow oil (55 mg, 90% yield): $^1$H-NMR (d4-MeOH) δ 2.24 (2H, m), 2.35 (1H, m), 2.61 (1H, m), 3.55 (2H, m), 5.10 (1H, t, J=7.2 Hz) 9.46 (1H, s).

EXAMPLE INT67

Part A. Using the methods described in Example INT66 parts A and B, benzyl (2S)-2-(2-phenyl-2H-[1,2,4]triazol-3-yl)pyrrolidine-1-carboxylate was obtained from phenylhydrazine as a pale yellow oil after purification by preparative HPLC (250 mg, 51% yield): HPLC (method 1) t$_R$=3.51 min, Purity 99%; LCMS (mehtod 4) t$_R$=1.24 min, m/z 349 (M+H).

(S)-1-Phenyl-5-pyrrolidin-2-yl-1H-[1,2,4]triazole. Part B. Using the method described in Example INT66 part C, the HBr salt of (S)-1-phenyl-5-pyrrolidin-2-yl-1H-[1,2,4]triazole was isolated as a white powder: 210 mg, 100% yield; HPLC (method 1) t$_R$=0.70 min, Purity 90%; LCMS (method 4) t$_R$=0.57 min, m/z 214 (M+H).

TABLE 2

| Ex # | Structure | characterization | method |
|---|---|---|---|
| 1 | 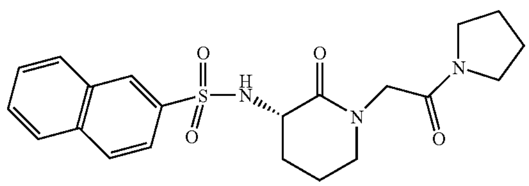 | HPLC (method 1) t$_R$ = 2.7 min LCMS (ESI, pos. ion spectrum) m/z 416 (M + H) | title compound of Example 1 |
| 2 | 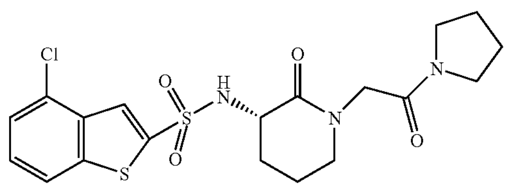 | HPLC (method 1) t$_R$ = 3.1 min LCMS (ESI, pos. ion spectrum) m/z 456/458 (M + H) | prepared using the method described in Example 1 |
| 3 | 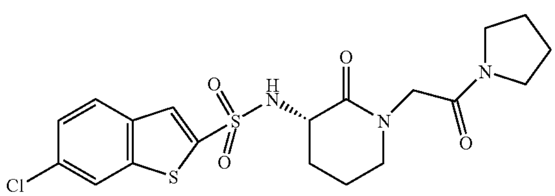 | HPLC (method 1) t$_R$ = 3.1 min LCMS (ESI, pos. ion spectrum) m/z 456/458 (M + H) | prepared using the method described in Example 1 |
| 4 | 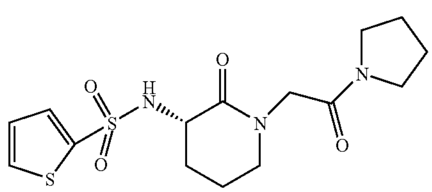 | HPLC (method 1) t$_R$ = 1.9 min LCMS (ESI, pos. ion spectrum) m/z 372 (M + H) | prepared using the method described in Example 1 |
| 5 | 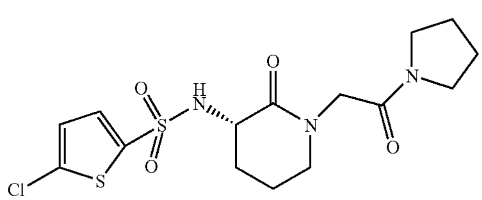 | HPLC (method 1) t$_R$ = 2.5 min LCMS (ESI, pos. ion spectrum) m/z 456/458 (M + H) | prepared using the method described in Example 1 |
| 6 | 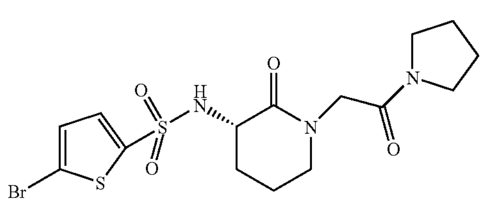 | HPLC (method 1) t$_R$ = 2.6 min LCMS (ESI, pos. ion spectrum) m/z 450/452 (M + H) | prepared using the method described in Example 1 |

TABLE 2-continued

| Ex # | Structure | characterization | method |
|---|---|---|---|
| 7 | 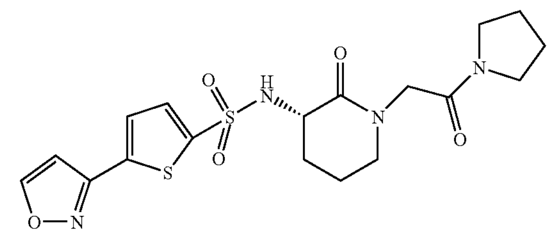 | HPLC (method 1) $t_R$ = 2.3 min LCMS (ESI, pos. ion spectrum) m/z 456/458 (M + H) | prepared using the method described in Example 1 |
| 8 | 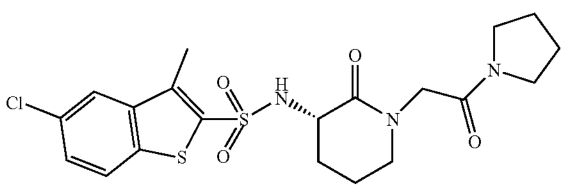 | HPLC (method 1) $t_R$ = 3.3 min LCMS (ESI, pos. ion spectrum) m/z 470/472 (M + H) | prepared using the method described in Example 1 |
| 9 | 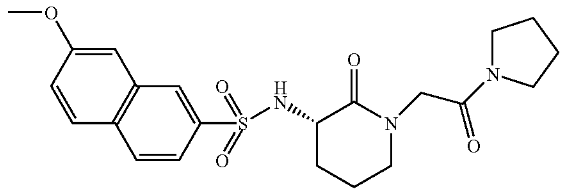 | HPLC (method 1) $t_R$ = 2.8 min LCMS (ESI, pos. ion spectrum) m/z 446 (M + H) | prepared using the method described in Example 1 |
| 10 | 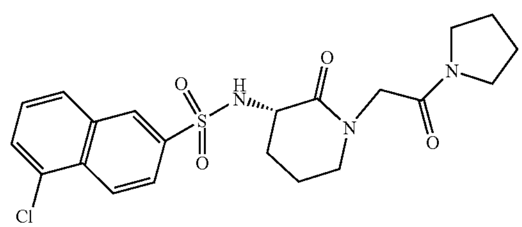 | HPLC (method 1) $t_R$ = 3.3 min LCMS (ESI, pos. ion spectrum) m/z 450/452 (M + H) | prepared using the method described in Example 1 |
| 11 | 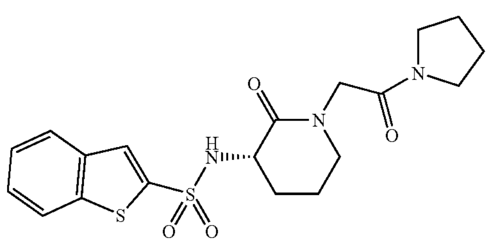 | HPLC (method 1) $t_R$ = 2.7 min LCMS (ESI, pos. ion spectrum) m/z 422 (M + H) | prepared using the method described in Example 1 |
| 12 | 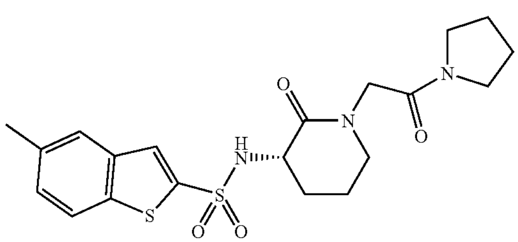 | HPLC (method 1) $t_R$ = 2.9 min LCMS (ESI, pos. ion spectrum) m/z 436 (M + H) | prepared using the method described in Example 1 |
| 13 | 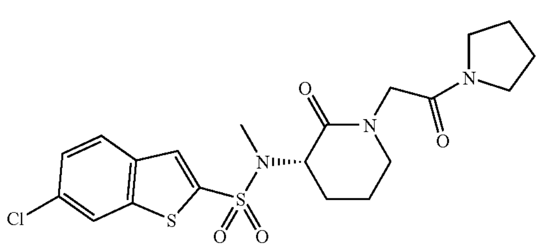 | HPLC (method 1) $t_R$ = 3.2 min LCMS (ESI, pos. ion spectrum) m/z 470/472 (M + H) | Title compound of Example 13 |

TABLE 2-continued

| Ex # | Structure | characterization | method |
|---|---|---|---|
| 14 | 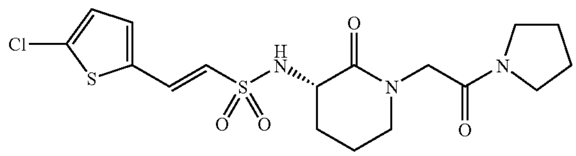 | HPLC (method 1) $t_R$ = 2.8 min LCMS (ESI, pos. ion spectrum) m/z 432/434 (M + H) | prepared using the method described in Example 1 |
| 15 | 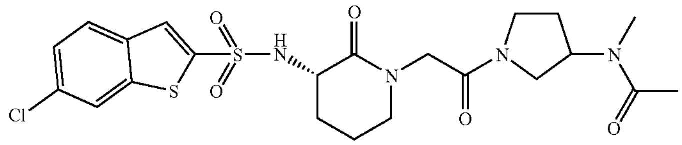 | HPLC (method 3) $t_R$ = 2.9 min LCMS (ESI, pos. ion spectrum) m/z 527/529 (M + 1) | prepared using the method described in Example 130 using INT16 |
| 16 | 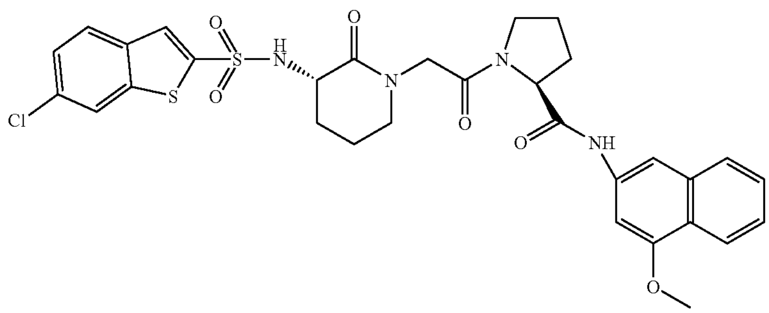 | HPLC (method 3) $t_R$ = 3.9 min LCMS (ESI, pos. ion spectrum) m/z 655/657 (M + 1) | prepared using the method described in Example 130 using INT16 |
| 17 | 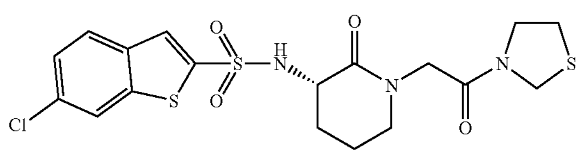 | HPLC (method 3) $t_R$ = 3.1 min LCMS (ESI, pos. ion spectrum) m/z 474/476 (M + 1) | prepared using the method described in Example 130 using INT16 |
| 18 | 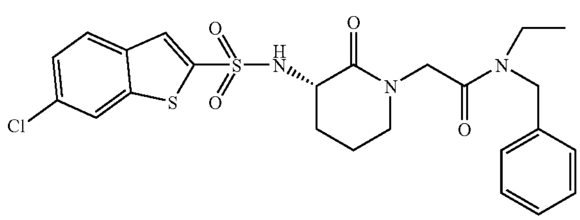 | HPLC (method 3) $t_R$ = 3.5 min LCMS (ESI, pos. ion spectrum) m/z 520/522 (M + 1) | prepared using the method described in Example 130 using INT16 |
| 19 | 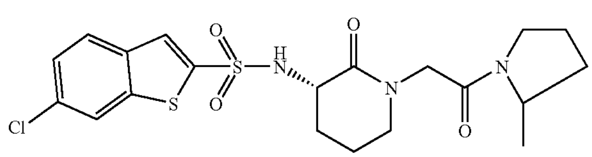 | HPLC (method 3) $t_R$ = 3.2 min LCMS (ESI, pos. ion spectrum) m/z 470/472 (M + 1) | prepared using the method described in Example 130 using INT16 |
| 20 | 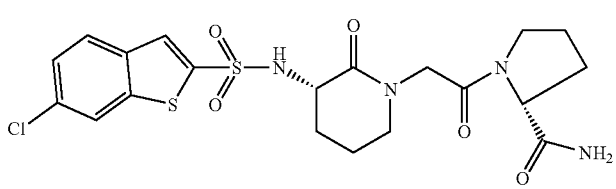 | HPLC (method 3) $t_R$ = 2.8 min LCMS (ESI, pos. ion spectrum) m/z 499/501 (M + 1) | prepared using the method described in Example 130 using INT16 |
| 21 | 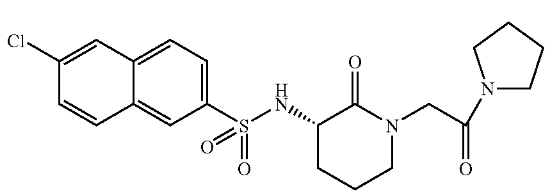 | HPLC (method 1) $t_R$ = 3.4 min LCMS (ESI, pos. ion spectrum) m/z 450/452 (M + 1) | Title compound of Example 21 |

TABLE 2-continued

| Ex # | Structure | characterization | method |
|---|---|---|---|
| 22 | 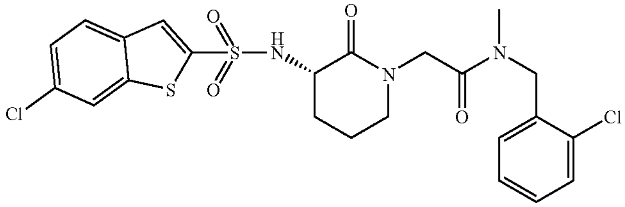 | HPLC (method 3) $t_R$ = 3.6 min LCMS (ESI, pos. ion spectrum) m/z 540/542 (M + 1) | prepared using the method described in Example 130 using INT16 |
| 23 | 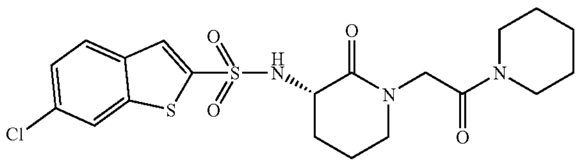 | HPLC (method 3) $t_R$ = 3.2 min LCMS (ESI, pos. ion spectrum) m/z 470/472 (M + 1) | prepared using the method described in Example 130 using INT16 |
| 24 | 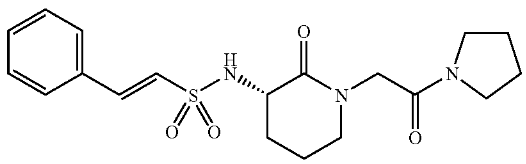 | HPLC (method 1) $t_R$ = 2.5 min LCMS (ESI, pos. ion spectrum) m/z 392 (M + H) | prepared using the method described in Example 1 |
| 25 | 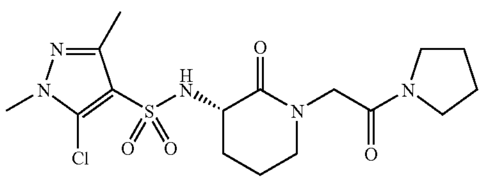 | HPLC (method 1) $t_R$ = 1.9 min LCMS (ESI, pos. ion spectrum) m/z 418/420 (M + H) | prepared using the method described in Example 1 |
| 26 | 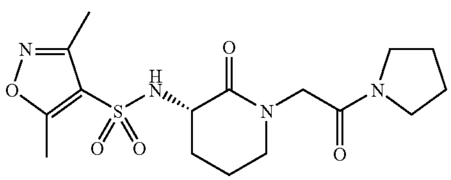 | HPLC (method 1) $t_R$ = 2.0 min LCMS (ESI, pos. ion spectrum) m/z 385 (M + H) | prepared using the method described in Example 1 |
| 27 | 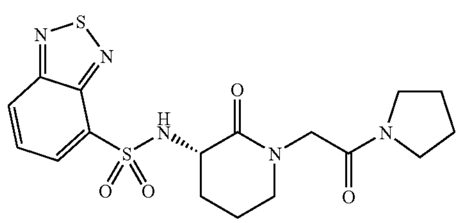 | HPLC (method 1) $t_R$ = 2.1 min LCMS (ESI, pos. ion spectrum) m/z 424 (M + H) | prepared using the method described in Example 1 |
| 28 | 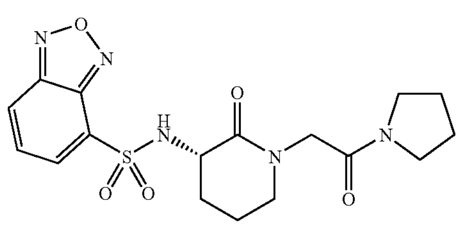 | HPLC (method 1) $t_R$ = 2.1 min LCMS (ESI, pos. ion spectrum) m/z 408 (M + H) | prepared using the method described in Example 1 |
| 29 | 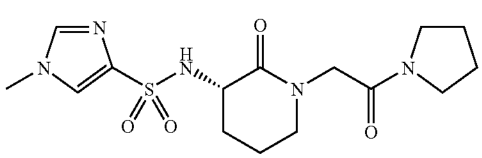 | HPLC (method 1) $t_R$ = 1.2 min LCMS (ESI, pos. ion spectrum) m/z 370 (M + H) | prepared using the method described in Example 1 |

TABLE 2-continued

| Ex # | Structure | characterization | method |
|---|---|---|---|
| 30 | 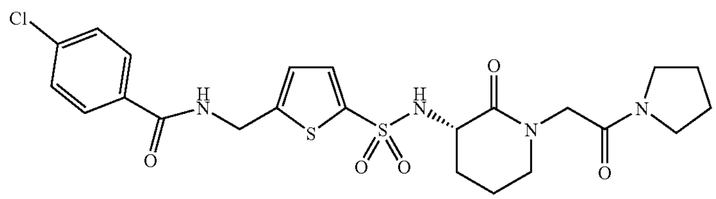 | HPLC (method 1) $t_R$ = 2.7 min LCMS (ESI, pos. ion spectrum) m/z 456/458 (M + H) | prepared using the method described in Example 1 |
| 31 | 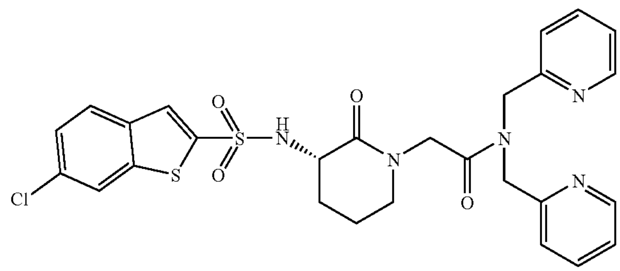 | HPLC (method 3) $t_R$ = 2.7 min LCMS (ESI, pos. ion spectrum) m/z 584/586 (M + H) | prepared using the method described in Example 130 using INT16 |
| 32 | 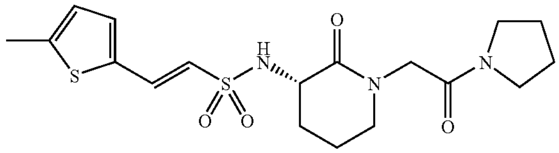 | HPLC (method 1) $t_R$ = 2.6 min LCMS (ESI, pos. ion spectrum) m/z 412 (M + H) | prepared using the method described in Example 1 using INT27 |
| 33 | 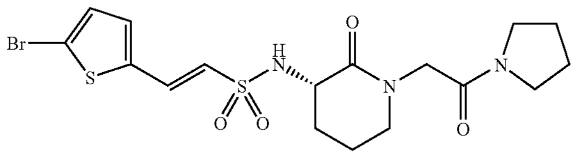 | HPLC (method 1) $t_R$ = 2.9 min LCMS (ESI, pos. ion spectrum) m/z 476/478 (M + H) | prepared using the method described in Example 1 using INT28 |
| 34 | 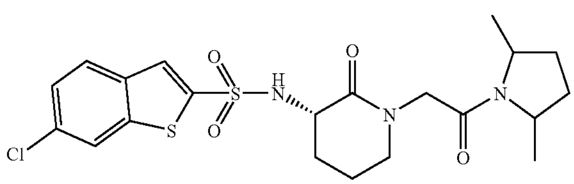 | HPLC (method 3) $t_R$ = 3.4 min LCMS (ESI, pos. ion spectrum) m/z 484/486 (M + H) | prepared using the method described in Example 130 using INT16 |
| 35 | 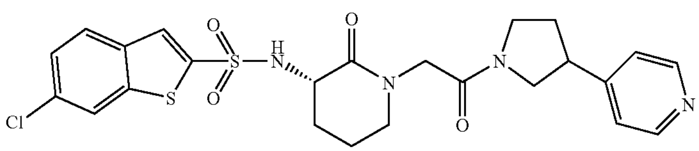 | HPLC (method 3) $t_R$ = 2.6 min LCMS (ESI, pos. ion spectrum) m/z 533/535 (M + 1) | prepared using the method described in Example 130 using INT16 |
| 36 | 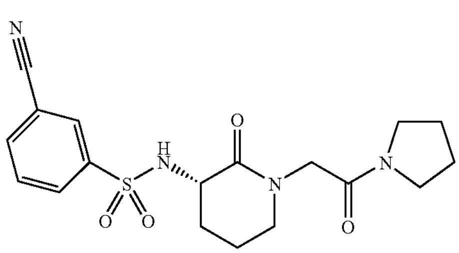 | HPLC (method 1) $t_R$ = 1.8 min LCMS (ESI, pos. ion spectrum) m/z 391 (M + H) | prepared using the method described in Example 1 |

TABLE 2-continued

| Ex # | Structure | characterization | method |
|---|---|---|---|
| 37 | 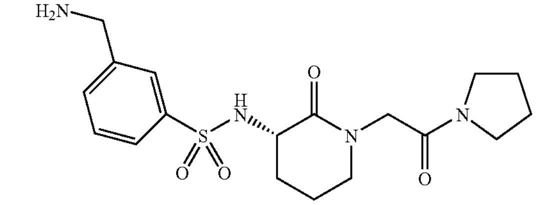 | HPLC (method 1) $t_R$ = 1.7 min LCMS (ESI, pos. ion spectrum) m/z 395 (M + H) | Title compound of example 37 |
| 38 | 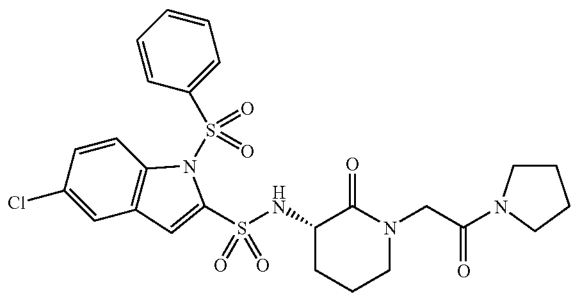 | HPLC (method 1) $t_R$ = 3.4 min LCMS (ESI, pos. ion spectrum) m/z 579/581 (M + H) | prepared using the method described in Example 1 |
| 39 | 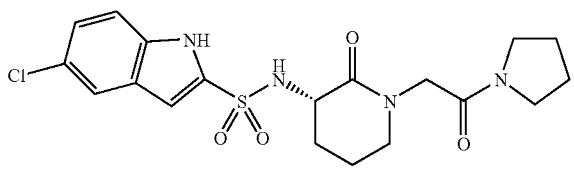 | HPLC (method 1) $t_R$ = 2.7 min LCMS (ESI, pos. ion spectrum) m/z 440/442 (M + H) | prepared using the method described in Example 1 |
| 40 | 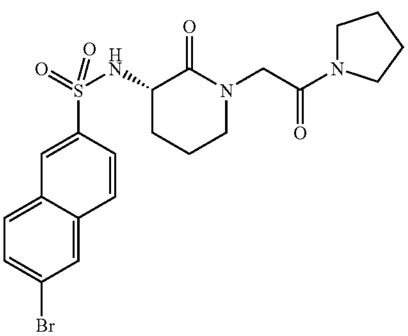 | HPLC (method 1) $t_R$ = 3.5 min LCMS (ESI, pos. ion spectrum) m/z 494/496 (M + 1) | Prepared using the method described in Example 21 |
| 41 | 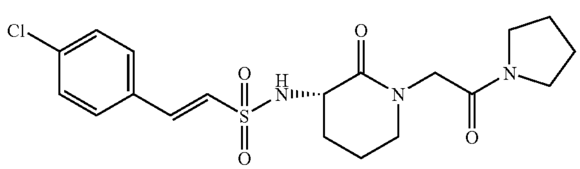 | HPLC (method 1) $t_R$ = 3.2 min LRMS (ESI, pos. ion spectrum) m/z 426/428 (M + H) | Title compound of Example 41 |
| 42 | 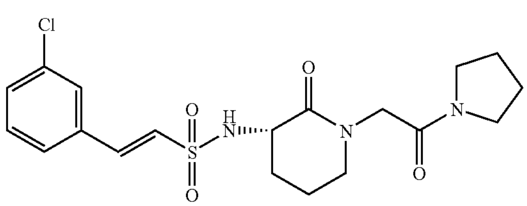 | HPLC (method 1) $t_R$ = 3.2 min LRMS (ESI, pos. ion spectrum) m/z 426/428 (M + H) | Prepared using the method described in Example 41 |
| 43 | 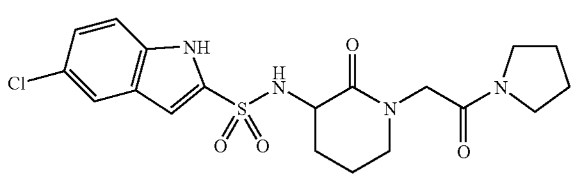 | HPLC (method 1) $t_R$ = 3.0 min LCMS (ESI, pos. ion spectrum) m/z 439/441 (M + H) | Title compound of Example 43 |

TABLE 2-continued

| Ex # | Structure | characterization | method |
|---|---|---|---|
| 44 | (6-chloro-1H-indol-2-yl)sulfonyl-NH-(2-oxo-1-(2-oxo-2-(pyrrolidin-1-yl)ethyl)piperidin-3-yl) | HPLC (method 1) t$_R$ = 2.9 min LCMS (ESI, pos. ion spectrum) m/z 439/441 (M + H) | prepared using the method described in Example 43 |
| 45 | (E)-2-(3-bromophenyl)ethenesulfonyl-NH-(2-oxo-1-(2-oxo-2-(pyrrolidin-1-yl)ethyl)piperidin-3-yl) | HPLC (method 1) t$_R$ = 3.3 min LRMS (ESI, pos. ion spectrum) m/z 470/472 (M + H) | Prepared using the method described in Example 41 and INT29 |
| 46 | (E)-2-(4-bromophenyl)ethenesulfonyl-NH-(2-oxo-1-(2-oxo-2-(pyrrolidin-1-yl)ethyl)piperidin-3-yl) | HPLC (method 1) t$_R$ = 3.3 min LRMS (ESI, pos. ion spectrum) m/z 470/472 (M + H) | Prepared using the method described in Example 41 and INT30 |
| 47 | (6-bromonaphthalen-2-yl)sulfonyl-N-methyl-(2-oxo-1-(2-oxo-2-(pyrrolidin-1-yl)ethyl)piperidin-3-yl) | HPLC (method 1) t$_R$ = 3.6 min LCMS (ESI, pos. ion spectrum) m/z 508/510 (M + 1) | Prepared using the method described in Example 13 using Example 40 title compound |
| 48 | (6-chloronaphthalen-2-yl)sulfonyl-NH-(2-oxo-1-(2-(thiomorpholin-4-yl)-2-oxoethyl)piperidin-3-yl) | HPLC (method 1) t$_R$ = 3.4 min LCMS (ESI, pos. ion spectrum) m/z 482/484 (M + 1) | Title compound of Example 48 |
| 49 | (6-chloronaphthalen-2-yl)sulfonyl-NH-(2-oxo-1-(2-(1-oxothiomorpholin-4-yl)-2-oxoethyl)piperidin-3-yl) | HPLC (method 1) t$_R$ = 3.2 min LCMS (ESI, pos. ion spectrum) m/z 498/500 (M + 1) | Title compound of Example 49 |
| 50 | (6-chloronaphthalen-2-yl)sulfonyl-NH-(2-oxo-1-(2-(1,1-dioxothiomorpholin-4-yl)-2-oxoethyl)piperidin-3-yl) | HPLC (method 1) t$_R$ = 3.2 min LCMS (ESI, pos. ion spectrum) m/z 514/516 (M + 1) | Title compound of Example 50 |

TABLE 2-continued

| Ex # | Structure | characterization | method |
|---|---|---|---|
| 51 | 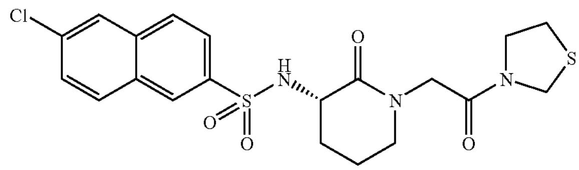 | HPLC (method 1) t_R = 3.4 min LCMS (ESI, pos. ion spectrum) m/z 468/470 (M + 1) | Prepared using the method described in Example 48 |
| 52 | 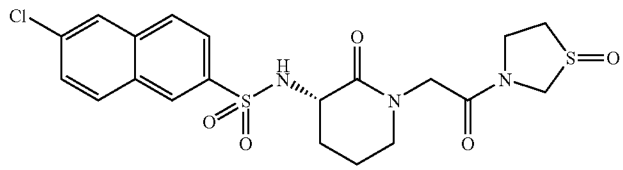 | HPLC (method 1) t_R = 3.2 min LCMS (ESI, pos. ion spectrum) m/z 484/486 (M + 1) | Prepared using the method described in Example 49 |
| 53 | 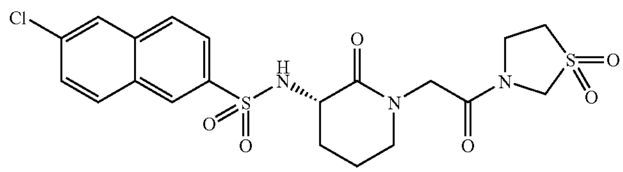 | HPLC (method 1) t_R = 3.2 min LCMS (ESI, pos. ion spectrum) m/z 500/502 (M + 1) | Prepared using the method described in Example 50 |
| 54 | 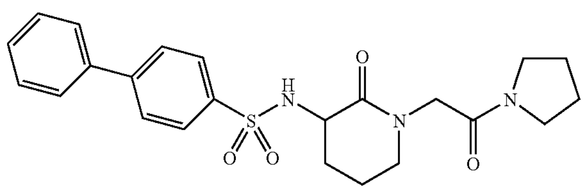 | HPLC (method 1) t_R = 3.0 min LCMS (ESI, pos. ion spectrum) m/z 442 (M + H) | prepared using the method described in Example 1 |
| 55 | 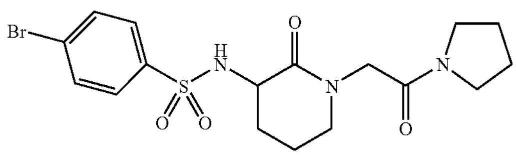 | HPLC (method 1) t_R = 2.6 min LCMS (ESI, pos. ion spectrum) m/z 444/446 (M + H) | prepared using the method described in Example 1 |
| 56 | 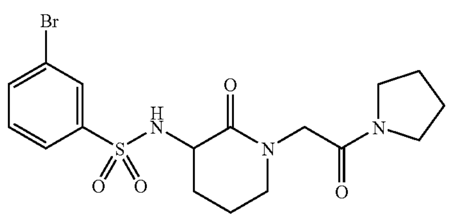 | HPLC (method 1) t_R = 2.6 min LCMS (ESI, pos. ion spectrum) m/z 444/446 (M + H) | prepared using the method described in Example 1 |
| 57 | 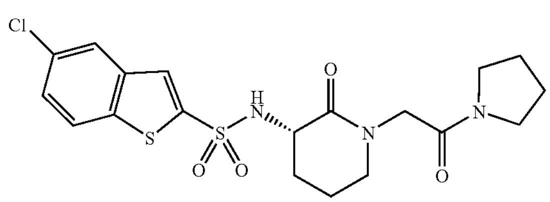 | HPLC (method 1) t_R = 3.1 min LCMS (ESI, pos. ion spectrum) m/z 456/458 (M + H) | prepared using the method described in Example 1 |
| 58 | 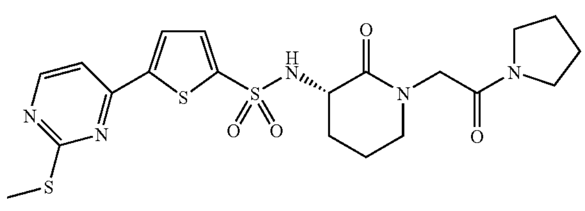 | HPLC (method 1) t_R = 2.8 min LCMS (ESI, pos. ion spectrum) m/z 496 (M + H) | prepared using the method described in Example 1 |

TABLE 2-continued

| Ex # | Structure | characterization | method |
|---|---|---|---|
| 59 | 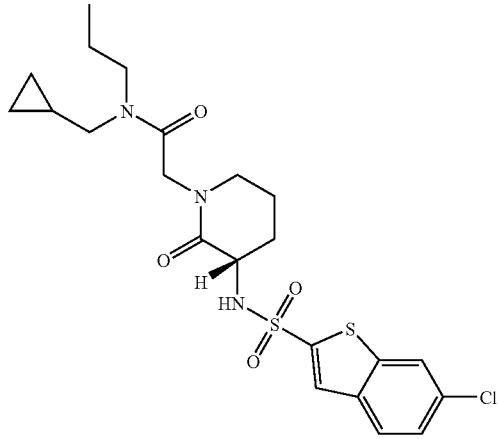 | HPLC (method 3) LCMS (ESI, pos. ion spectrum) m/z 498/500 (M + 1) | prepared using the method described in Example 130 using INT16 |
| 60 | 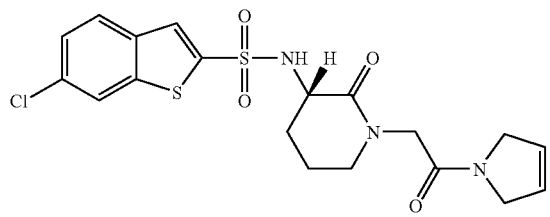 | HPLC (method 3) LCMS (ESI, pos. ion spectrum) m/z 454/456 (M + 1) | prepared using the method described in Example 130 using INT16 |
| 61 | 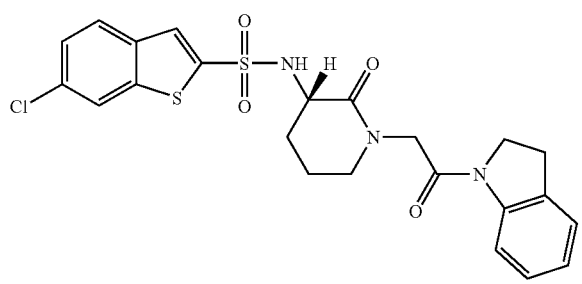 | HPLC (method 3) LCMS (ESI, pos. ion spectrum) m/z 503/505 (M + 1) | prepared using the method described in Example 130 using INT16 |
| 62 | 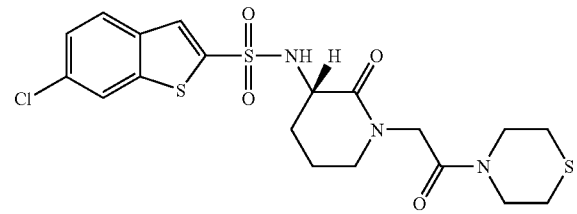 | HPLC (method 3) LCMS (ESI, pos. ion spectrum) m/z 488/490 (M + 1) | prepared using the method described in Example 130 using INT16 |
| 63 | 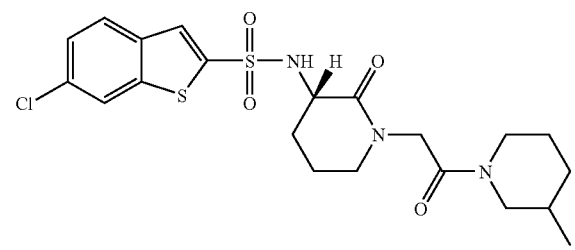 | HPLC (method 3) LCMS (ESI, pos. ion spectrum) m/z 484/486 (M + 1) | prepared using the method described in Example 130 using INT16 |

TABLE 2-continued

| Ex # | Structure | characterization | method |
|---|---|---|---|
| 64 | 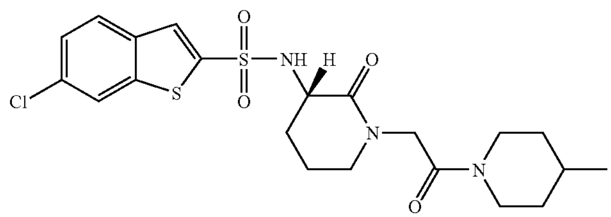 | HPLC (method 3) LCMS (ESI, pos. ion spectrum) m/z 484/486 (M + 1) | prepared using the method described in Example 130 using INT16 |
| 65 | 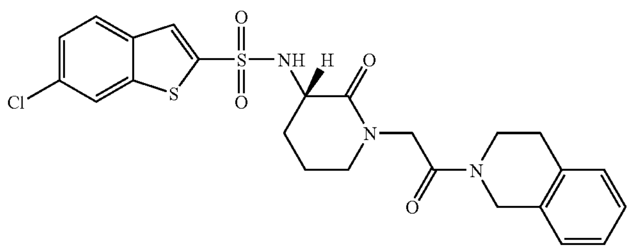 | HPLC (method 3) LCMS (ESI, pos. ion spectrum) m/z 518/520 (M + 1) | prepared using the method described in Example 130 using INT16 |
| 66 | 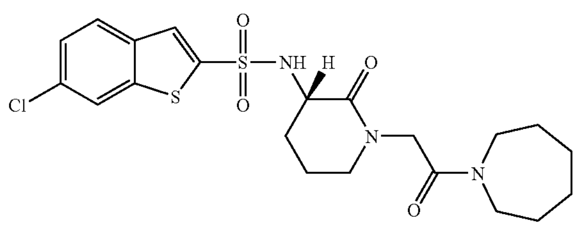 | HPLC (method 3) LCMS (ESI, pos. ion spectrum) m/z 484/486 (M + 1) | prepared using the method described in Example 130 using INT16 |
| 67 | 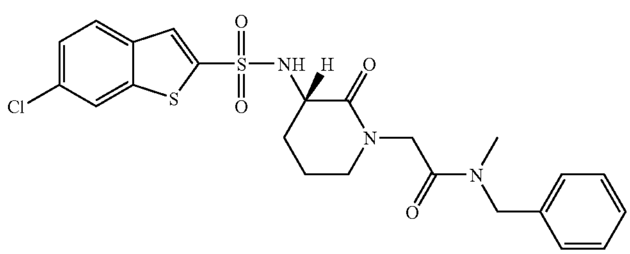 | HPLC (method 3) LCMS (ESI, pos. ion spectrum) m/z 506/508 (M + 1) | prepared using the method described in Example 130 using INT16 |
| 68 | 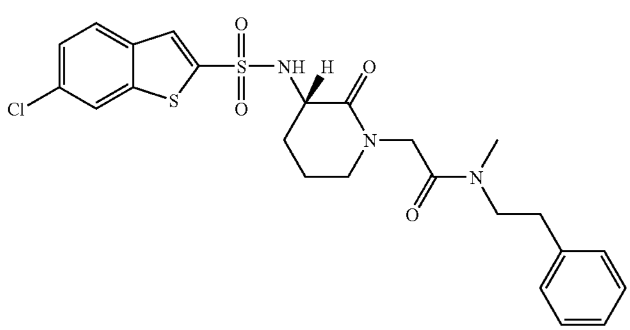 | HPLC (method 3) LCMS (ESI, pos. ion spectrum) m/z 519/521 (M + 1) | prepared using the method described in Example 130 using INT16 |
| 69 | 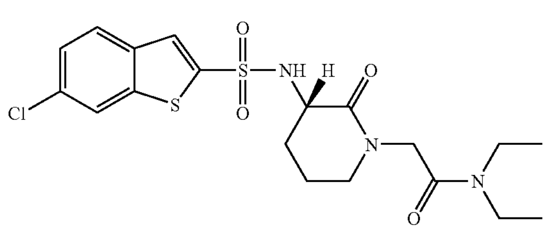 | HPLC (method 3) LCMS (ESI, pos. ion spectrum) m/z 458/460 (M + 1) | prepared using the method described in Example 130 using INT16 |

TABLE 2-continued

| Ex # | Structure | characterization | method |
|---|---|---|---|
| 70 | 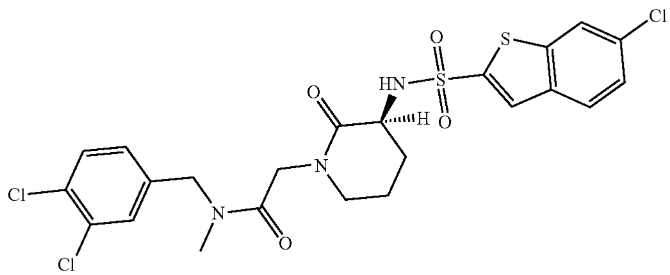 | HPLC (method 3) LCMS (ESI, pos. ion spectrum) m/z 574/576/578/580 (M + 1) | prepared using the method described in Example 130 using INT16 |
| 71 | 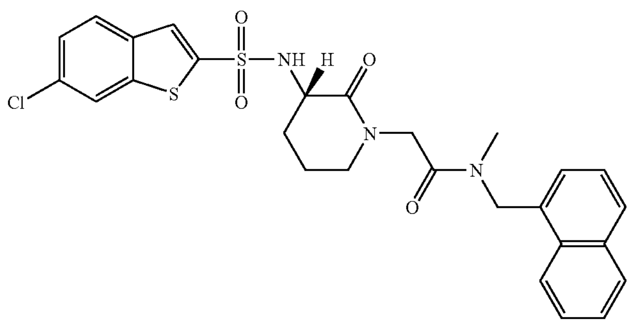 | HPLC (method 3) LCMS (ESI, pos. ion spectrum) m/z 556/558 (M + 1) | prepared using the method described in Example 130 using INT16 |
| 72 | 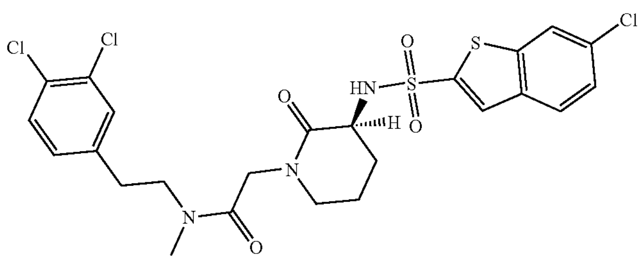 | HPLC (method 3) LCMS (ESI, pos. ion spectrum) m/z 589/591 (M + 1) | prepared using the method described in Example 130 using INT16 |
| 73 | 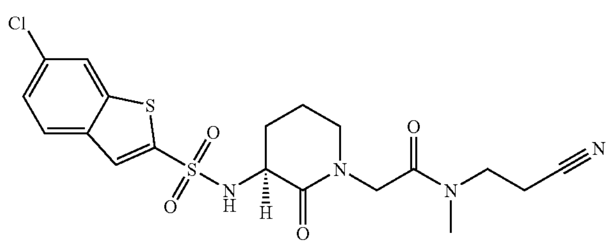 | HPLC (method 3) LCMS (ESI, pos. ion spectrum) m/z 469/471 (M + 1) | prepared using the method described in Example 130 using INT16 |
| 74 | 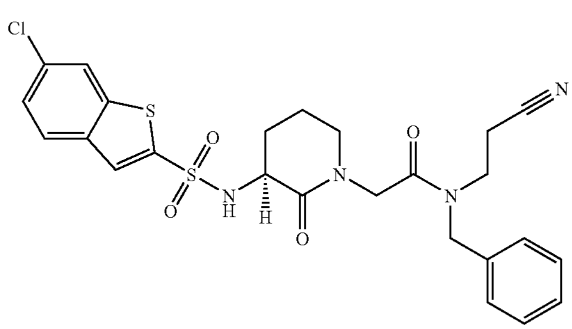 | HPLC (method 3) LCMS (ESI, pos. ion spectrum) m/z 544/546 (M + 1) | prepared using the method described in Example 130 using INT16 |

TABLE 2-continued

| Ex # | Structure | characterization | method |
|---|---|---|---|
| 75 | 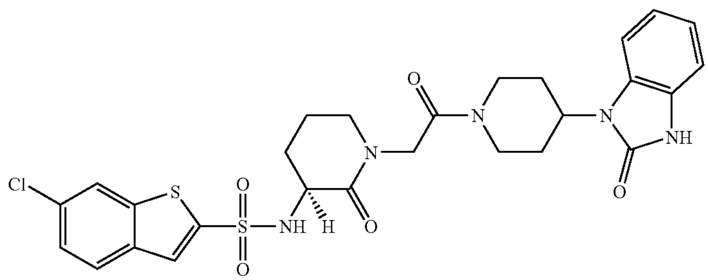 | HPLC (method 3) LCMS (ESI, pos. ion spectrum) m/z 602/604 (M + 1) | prepared using the method described in Example 130 using INT16 |
| 76 | 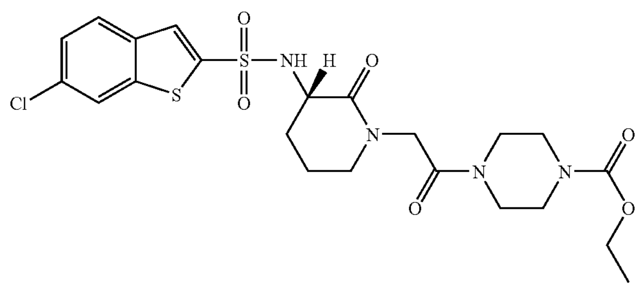 | HPLC (method 3) LCMS (ESI, pos. ion spectrum) m/z 543/545 (M + 1) | prepared using the method described in Example 130 using INT16 |
| 77 | 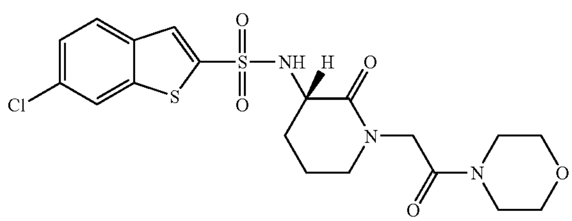 | HPLC (method 3) LCMS (ESI, pos. ion spectrum) m/z 472/474 (M + 1) | prepared using the method described in Example 130 using INT16 |
| 78 | 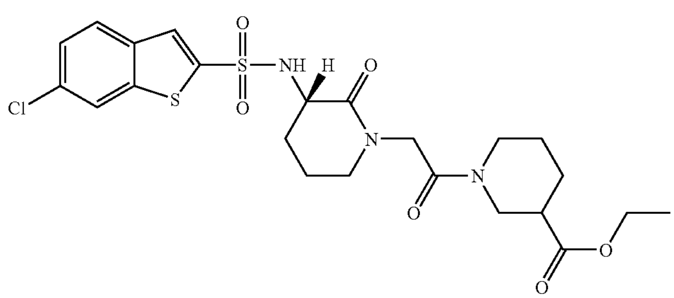 | HPLC (method 3) LCMS (ESI, pos. ion spectrum) m/z 542/544 (M + 1) | prepared using the method described in Example 130 using INT16 |
| 79 | 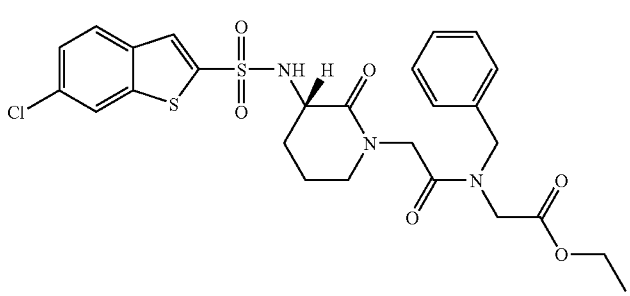 | HPLC (method 3) LCMS (ESI, pos. ion spectrum) m/z 578/580 (M + 1) | prepared using the method described in Example 130 using INT16 |

TABLE 2-continued

| Ex # | Structure | characterization | method |
|---|---|---|---|
| 80 | 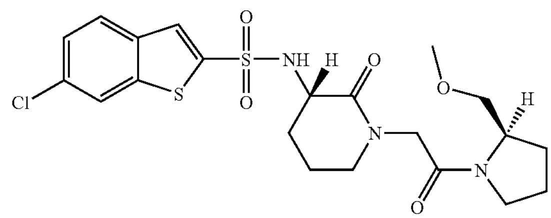 | HPLC (method 3) LCMS (ESI, pos. ion spectrum) m/z 500/502 (M + 1) | prepared using the method described in Example 130 using INT16 |
| 81 | 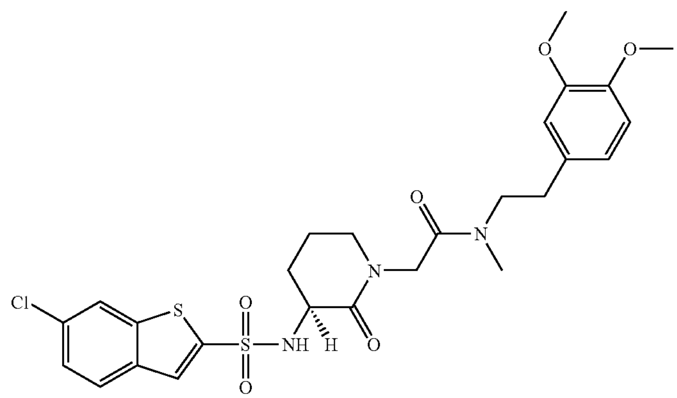 | HPLC (method 3) LCMS (ESI, pos. ion spectrum) m/z 580/582 (M + 1) | prepared using the method described in Example 130 using INT16 |
| 82 | 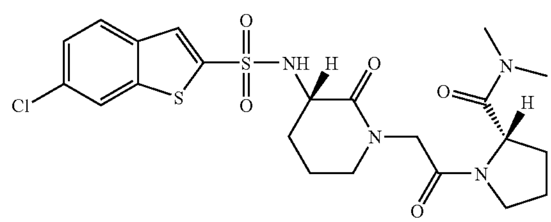 | HPLC (method 3) LCMS (ESI, pos. ion spectrum) m/z 527/529 (M + 1) | prepared using the method described in Example 130 using INT16 |
| 83 | 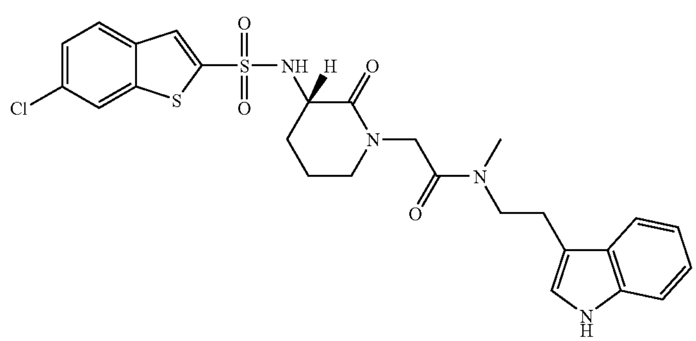 | HPLC (method 3) LCMS (ESI, pos. ion spectrum) m/z 559/561 (M + 1) | prepared using the method described in Example 130 using INT16 |
| 84 | 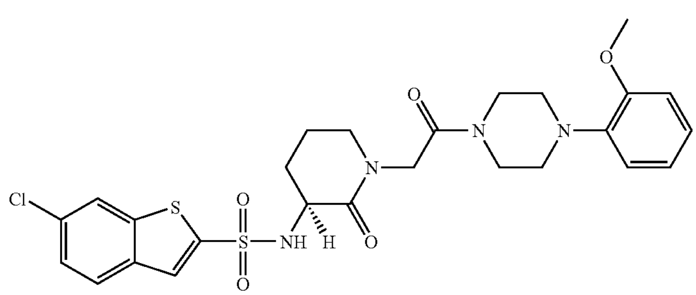 | HPLC (method 3) LCMS (ESI, pos. ion spectrum) m/z 577/579 (M + 1) | prepared using the method described in Example 130 using INT16 |

TABLE 2-continued

| Ex # | Structure | characterization | method |
|---|---|---|---|
| 85 | 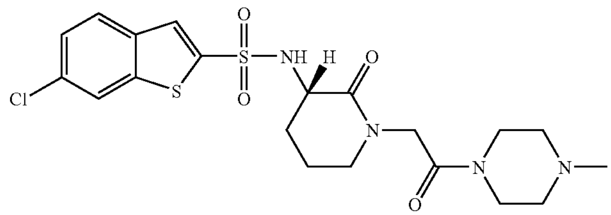 | HPLC (method 3) LCMS (ESI, pos. ion spectrum) m/z 485/487 (M + 1) | prepared using the method described in Example 130 using INT16 |
| 86 | 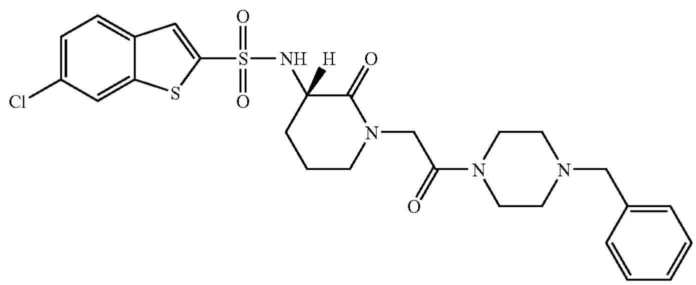 | HPLC (method 3) LCMS (ESI, pos. ion spectrum) m/z 561/563 (M + 1) | prepared using the method described in Example 130 using INT16 |
| 87 | 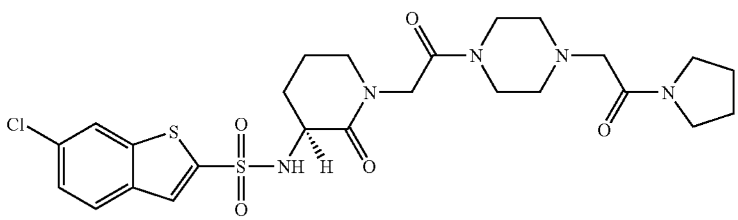 | HPLC (method 3) LCMS (ESI, pos. ion spectrum) m/z 582/584 (M + 1) | prepared using the method described in Example 130 using INT16 |
| 88 | 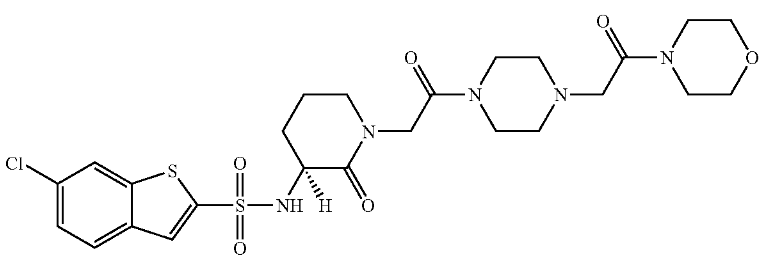 | HPLC (method 3) LCMS (ESI, pos. ion spectrum) m/z 598/600 (M + 1) | prepared using the method described in Example 130 using INT16 |
| 89 | 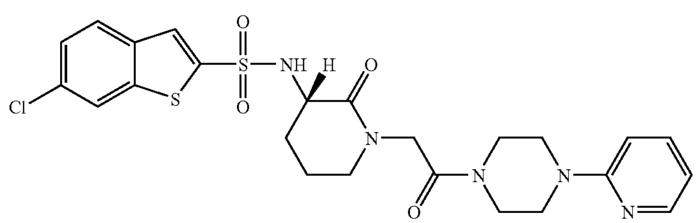 | HPLC (method 3) LCMS (ESI, pos. ion spectrum) m/z 548/550 (M + 1) | prepared using the method described in Example 130 using INT16 |
| 90 | 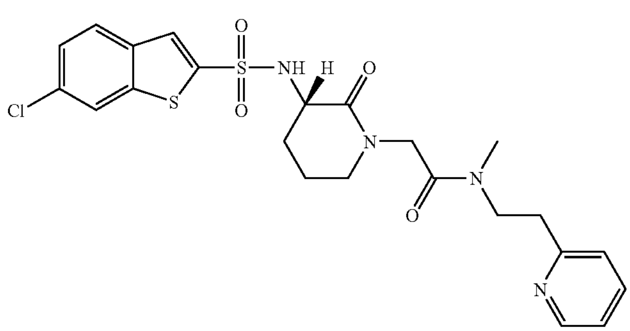 | HPLC (method 3) LCMS (ESI, pos. ion spectrum) m/z 521/523 (M + 1) | prepared using the method described in Example 130 using INT16 |

TABLE 2-continued

| Ex # | Structure | characterization | method |
|---|---|---|---|
| 91 | 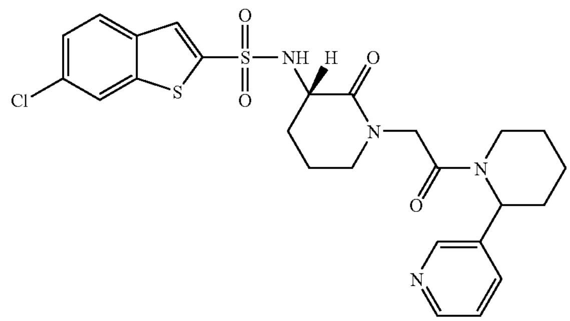 | HPLC (method 3) LCMS (ESI, pos. ion spectrum) m/z 547/549 (M + 1) | prepared using the method described in Example 130 using INT16 |
| 92 | 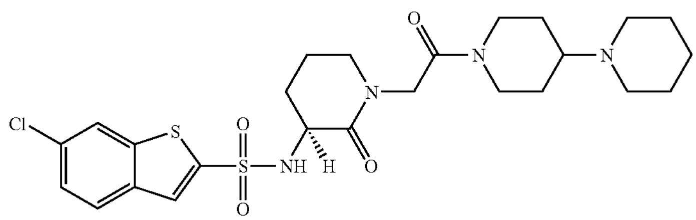 | HPLC (method 3) LCMS (ESI, pos. ion spectrum) m/z 553/555 (M + 1) | prepared using the method described in Example 130 using INT16 |
| 93 | 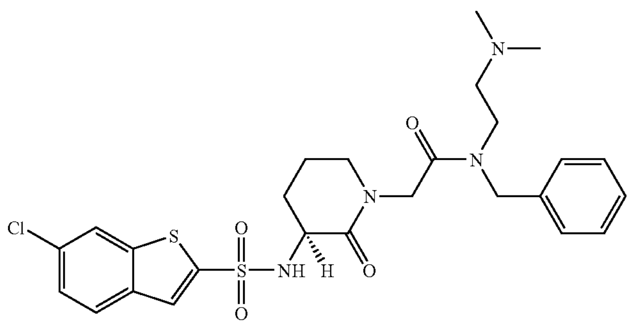 | HPLC (method 3) LCMS (ESI, pos. ion spectrum) m/z 563/565 (M + 1) | prepared using the method described in Example 130 using INT16 |
| 94 | 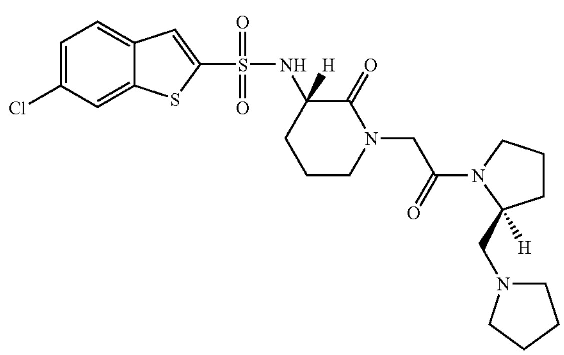 | HPLC (method 3) LCMS (ESI, pos. ion spectrum) m/z 539/541 (M + 1) | prepared using the method described in Example 130 using INT16 |
| 95 | 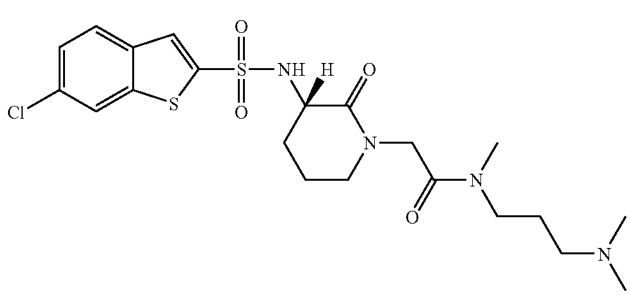 | HPLC (method 3) LCMS (ESI, pos. ion spectrum) m/z 501/503 (M + 1) | prepared using the method described in Example 130 using INT16 |

TABLE 2-continued

| Ex # | Structure | characterization | method |
|---|---|---|---|
| 96 | 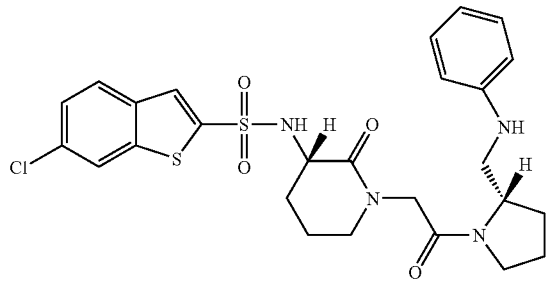 | HPLC (method 3) LCMS (ESI, pos. ion spectrum) m/z 561/563 (M + 1) | prepared using the method described in Example 130 using INT16 |
| 97 | 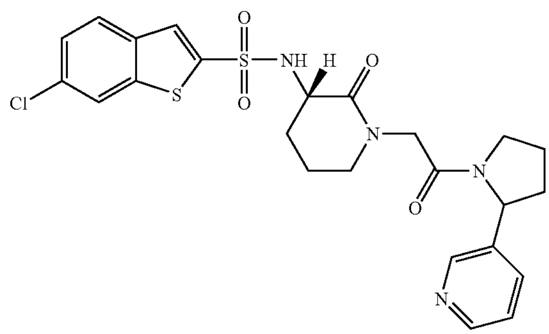 | HPLC (method 3) LCMS (ESI, pos. ion spectrum) m/z 533/535 (M + 1) | prepared using the method described in Example 130 using INT16 |
| 98 | 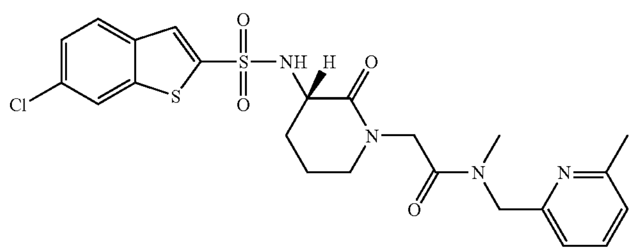 | HPLC (method 3) LCMS (ESI, pos. ion spectrum) m/z 521/523 (M + 1) | prepared using the method described in Example 130 using INT16 |
| 99 | 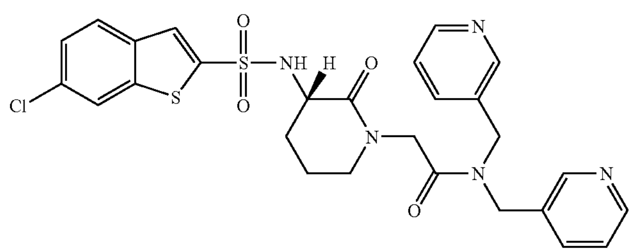 | HPLC (method 3) LCMS (ESI, pos. ion spectrum) m/z 584/586 (M + 1) | prepared using the method described in Example 130 using INT16 |
| 100 | 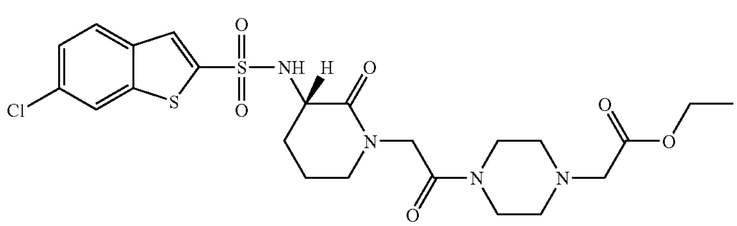 | HPLC (method 3) LCMS (ESI, pos. ion spectrum) m/z 557/559 (M + H) | prepared using the method described in Example 130 using INT16 |

TABLE 2-continued

| Ex # | Structure | characterization | method |
|---|---|---|---|
| 101 | 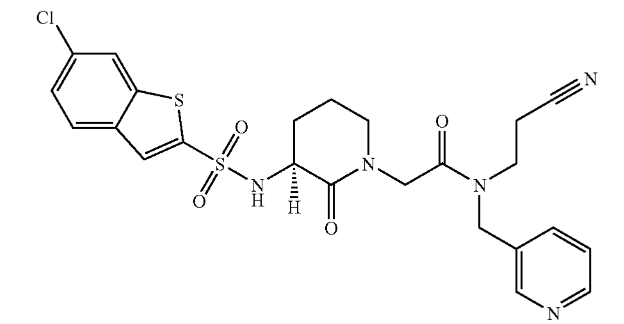 | HPLC (method 3) LCMS (ESI, pos. ion spectrum) m/z 546/548 (M + 1) | prepared using the method described in Example 130 using INT16 |
| 102 | 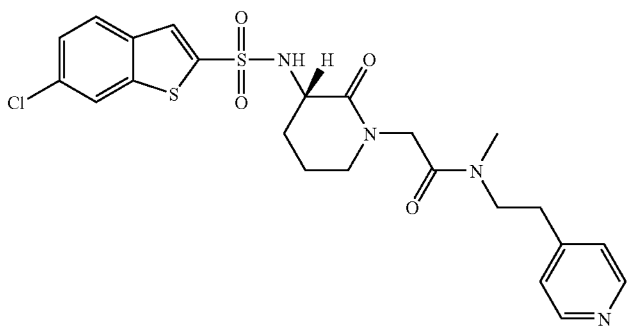 | HPLC (method 3) LCMS (ESI, pos. ion spectrum) m/z 521/523 (M + 1) | prepared using the method described in Example 130 using INT16 |
| 103 | 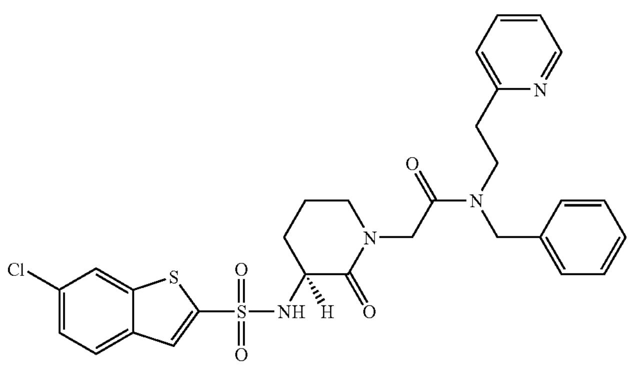 | HPLC (method 3) LCMS (ESI, pos. ion spectrum) m/z 597/599 (M + 1) | prepared using the method described in Example 130 using INT16 |
| 104 | 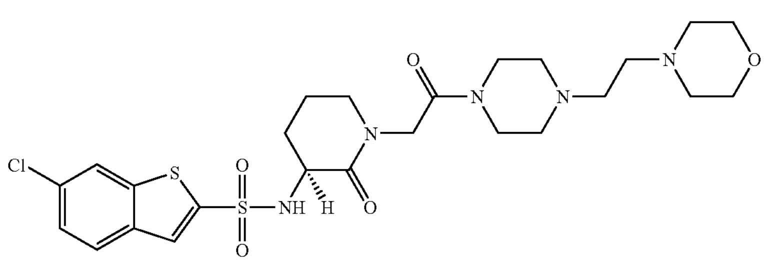 | HPLC (method 3) LCMS (ESI, pos. ion spectrum) m/z 584/586 (M + 1) | prepared using the method described in Example 130 using INT16 |
| 105 | 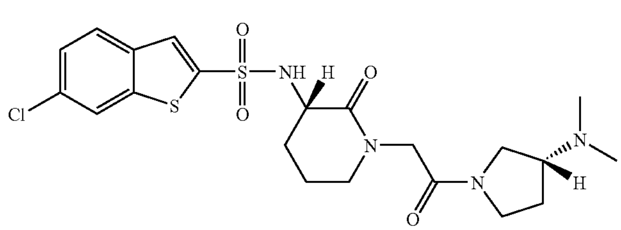 | HPLC (method 3) LCMS (ESI, pos. ion spectrum) m/z 499/501 (M + 1) | prepared using the method described in Example 130 using INT16 |

TABLE 2-continued

| Ex # | Structure | characterization | method |
|---|---|---|---|
| 106 | 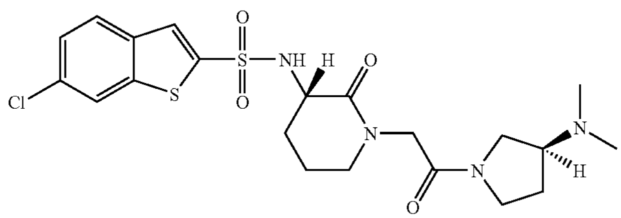 | HPLC (method 3) LCMS (ESI, pos. ion spectrum) m/z 499/501 (M + 1) | prepared using the method described in Example 130 using INT16 |
| 107 | 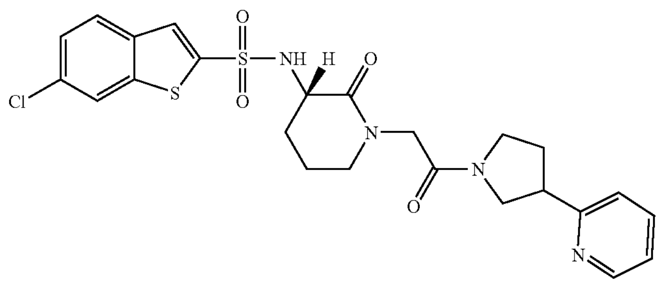 | HPLC (method 3) LCMS (ESI, pos. ion spectrum) m/z 533/535 (M + 1) | prepared using the method described in Example 130 using INT16 |
| 108 | 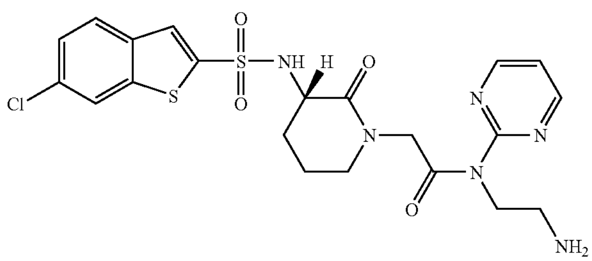 | HPLC (method 3) LCMS (ESI, pos. ion spectrum) m/z 523/525 (M + 1) | prepared using the method described in Example 130 using INT16 |
| 109 | 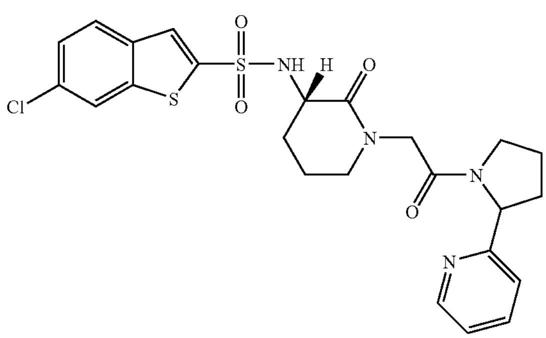 | HPLC (method 3) LCMS (ESI, pos. ion spectrum) m/z 533/535 (M + 1) | prepared using the method described in Example 130 using INT16 |
| 110 | 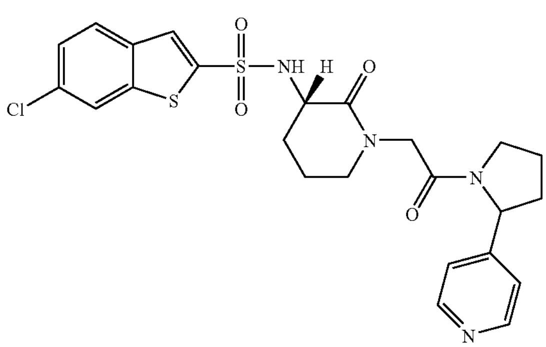 | HPLC (method 3) LCMS (ESI, pos. ion spectrum) m/z 533/535 (M + 1) | prepared using the method described in Example 130 using INT16 |

TABLE 2-continued

| Ex # | Structure | characterization | method |
|---|---|---|---|
| 111 | 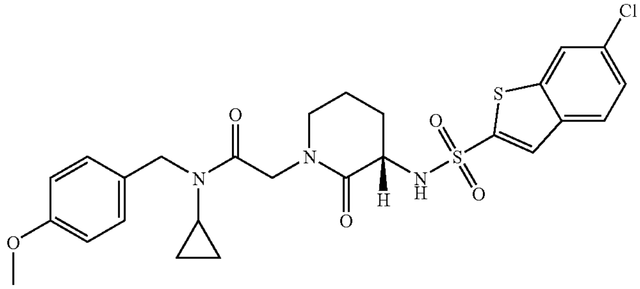 | HPLC (method 3) LCMS (ESI, pos. ion spectrum) m/z 562/564 (M + 1) | prepared using the method described in Example 130 using INT16 |
| 112 | 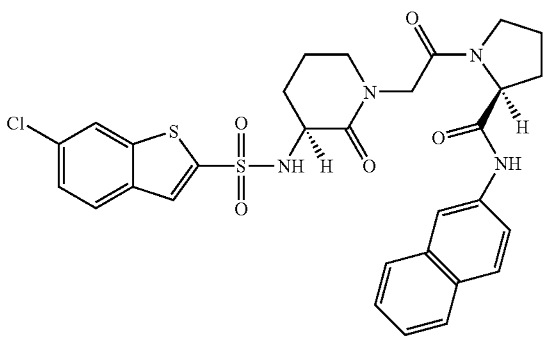 | HPLC (method 3) LCMS (ESI, pos. ion spectrum) m/z 625/627 (M + 1) | prepared using the method described in Example 130 using INT16 |
| 113 | 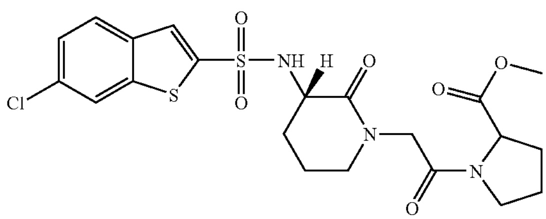 | HPLC (method 3) LCMS (ESI, pos. ion spectrum) m/z 514/516 (M + 1) | prepared using the method described in Example 130 using INT16 |
| 114 | 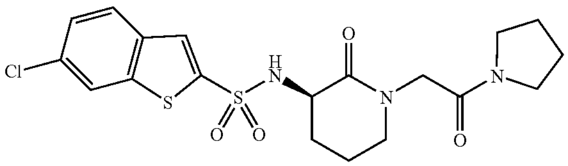 | HPLC (method 1) $t_R$ = 3.1 min LCMS (ESI, pos. ion spectrum) m/z 456/458 (M + H) | prepared using the method described in Example 1 using INT43 |
| 115 | 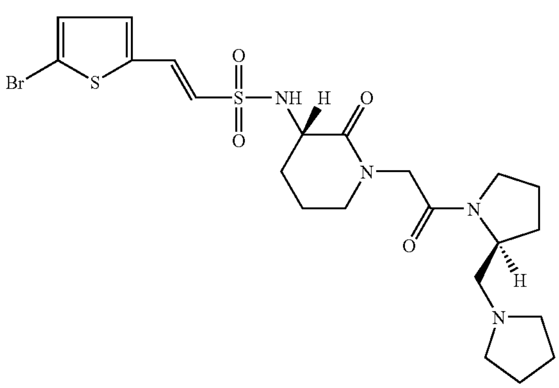 | HPLC (method 3) $t_R$ = 2.4 min LCMS (ESI, pos. ion spectrum) m/z 559/561 (M + 1) | prepared using the method described in Example 1 using INT9 and INT28 |

TABLE 2-continued

| Ex # | Structure | characterization | method |
|---|---|---|---|
| 116 | (6-chloronaphthalene-2-sulfonamide structure) | HPLC (method 3) t$_R$ = 2.7 min LCMS (ESI, pos. ion spectrum) m/z 533/535 (M + 1) | prepared using the method described in Example 1 using INT9 |
| 117 | (4-bromostyryl sulfonamide structure) | HPLC (method 4) t$_R$ = 1.4 min LCMS (ESI, pos. ion spectrum) m/z 553/555 (M + 1) | prepared using the method described in Example 1 using INT9 and INT30 |
| 118 | (4-chlorostyryl sulfonamide structure) | HPLC (method 4) t$_R$ = 1.4 min LCMS (ESI, pos. ion spectrum) m/z 509/511 (M + 1) | prepared using the method described in Example 1 using INT9 |
| 119 | (5-chlorobenzothiophene-2-sulfonamide structure) | HPLC (method 3) t$_R$ = 2.7 min LCMS (ESI, pos. ion spectrum) m/z 539/541 (M + 1) | prepared using the method described in Example 1 using INT9 |

TABLE 2-continued

| Ex # | Structure | characterization | method |
|---|---|---|---|
| 120 | 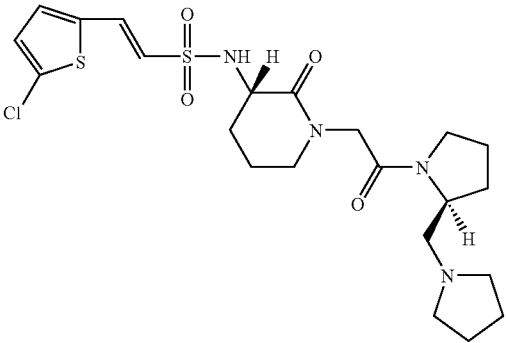 | HPLC (method 3) $t_R$ = 2.4 min LCMS (ESI, pos. ion spectrum) m/z 515/517 (M + 1) | prepared using the method described in Example 1 using INT9 |
| 121 | 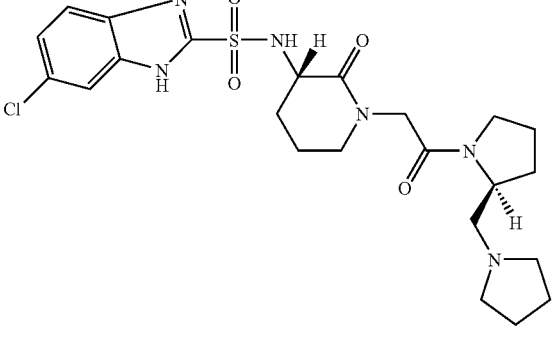 | HPLC (method 3) $t_R$ = 2.3 min LCMS (ESI, pos. ion spectrum) m/z 523/525 (M + 1) | prepared using the method described in Example 1 using INT9 |
| 122 | 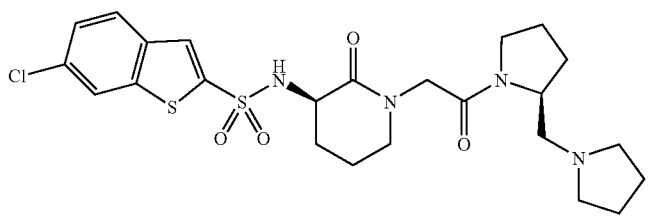 | HPLC (method 1) $t_R$ = 2.5 min LCMS (ESI, pos. ion spectrum) m/z 539/541 (M + H) | prepared using the method described in Example 1 using INT9 |
| 123 | 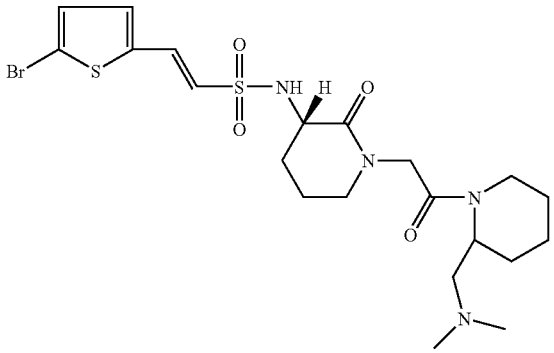 | HPLC (method 4) $t_R$ = 1.3 min LCMS (ESI, pos. ion spectrum) m/z 547/549 (M + 1) | prepared using the method described in Example 130 using INT12 |

TABLE 2-continued

| Ex # | Structure | characterization | method |
|---|---|---|---|
| 124 | 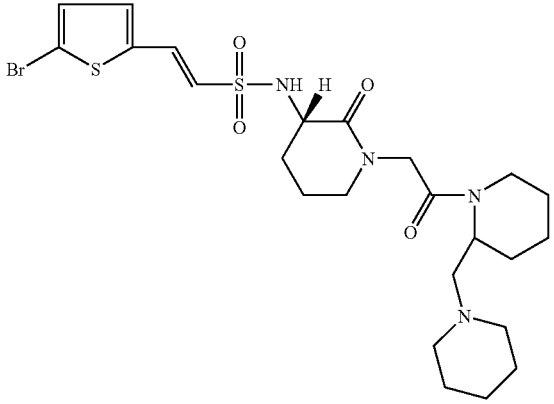 | HPLC (method 4) $t_R$ = 1.4 min LCMS (ESI, pos. ion spectrum) m/z 587/589 (M + 1) | prepared using the method described in Example 130 using INT12 |
| 125 | 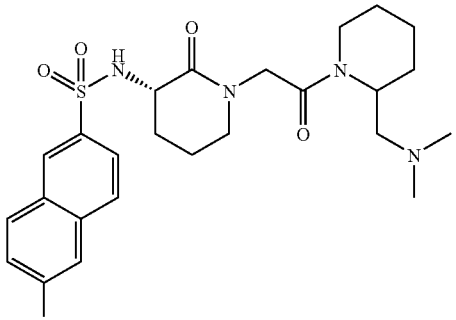 | HPLC (method 1) $t_R$ = 3.0 min (55%) and 3.27 (45%) LCMS (ESI, pos. ion spectrum) m/z 521/523 (M + 1) | Prepared using the method described in Example 48 |
| 126 | 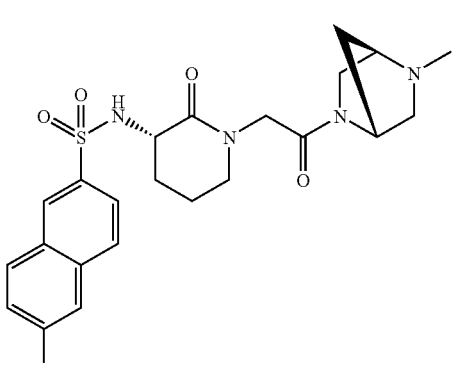 | HPLC (method 1) $t_R$ = 2.9 min LCMS (ESI, pos. ion spectrum) m/z 491/493 (M + 1) | Prepared using the method described in Example 48 |
| 127 | 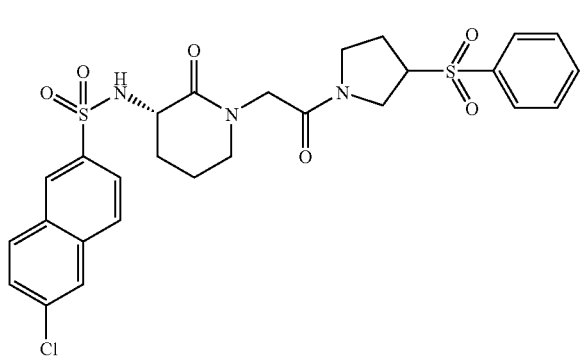 | HPLC (method 1) $t_R$ = 3.5 min LCMS (ESI, pos. ion spectrum) m/z 590/592 (M + 1) | Prepared using the method described in Example 48 |

TABLE 2-continued

| Ex # | Structure | characterization | method |
| --- | --- | --- | --- |
| 128 | 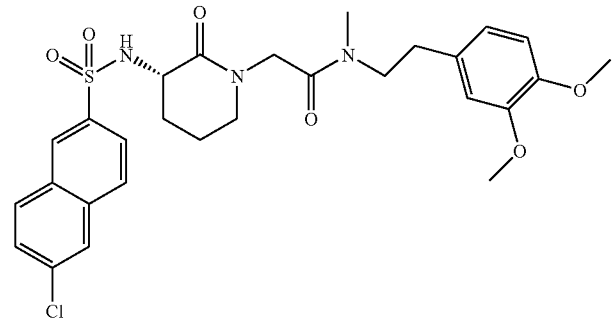 | HPLC (method 1) $t_R$ = 3.6 min LCMS (ESI, pos. ion spectrum) m/z 574/576 (M + 1) | Prepared using the method described in Example 48 |
| 129 | 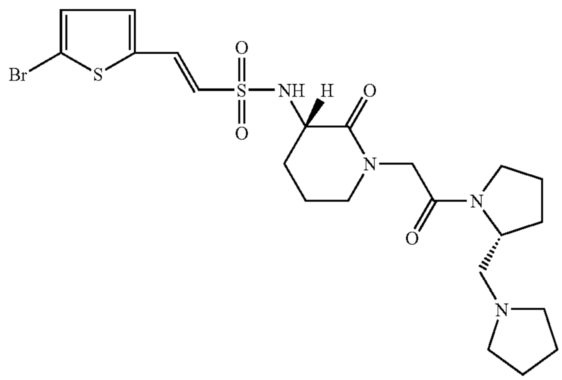 | HPLC (method 3) $t_R$ = 2.4 min LCMS (ESI, pos. ion spectrum) m/z 559/561 (M + 1) | prepared using the method described in Example 130 using INT12 and INT50 |
| 130 | 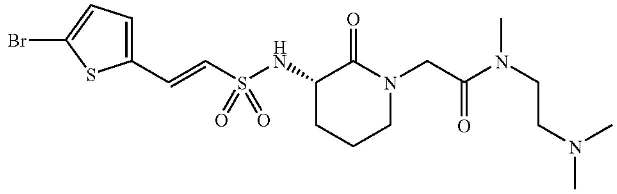 | HPLC (method 1) $t_R$ = 2.1 min LCMS (ESI, pos. ion spectrum) m/z 506/508 (M$^+$) | Title compound of Example 130 |
| 131 | 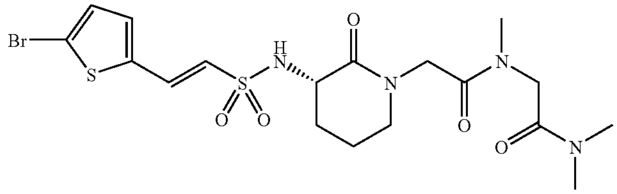 | HPLC (method 1) $t_R$ = 2.6 min LCMS (ESI, pos. ion spectrum) m/z 520/522 (M$^+$) | prepared using the method described in Example 130 using INT12 |
| 132 | 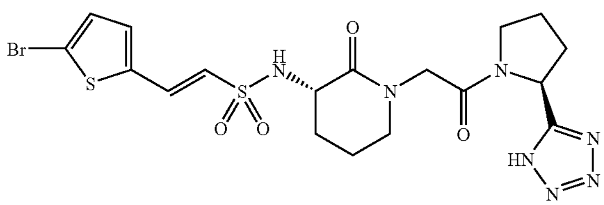 | HPLC (method 1) $t_R$ = 3.2 min LCMS (ESI, pos. ion spectrum) m/z 544/546 (M + H) | prepared using the method described in Example 130 using INT12 |
| 133 | 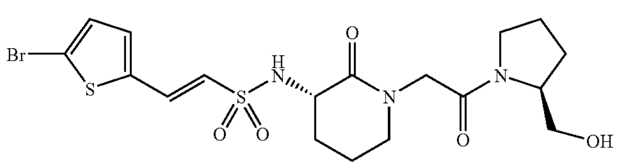 | HPLC (method 1) $t_R$ = 3.3 min LCMS (ESI, pos. ion spectrum) m/z 506/508 (M + H) | prepared using the method described in Example 130 using INT12 |

TABLE 2-continued

| Ex # | Structure | characterization | method |
|---|---|---|---|
| 134 | 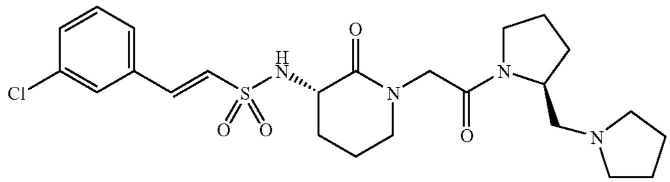 | HPLC (method 1) $t_R$ = 2.2 min LCMS (ESI, pos. ion spectrum) m/z 509/511 (M + H) | prepared using the method described in Example 1 using INT9 |
| 135 | 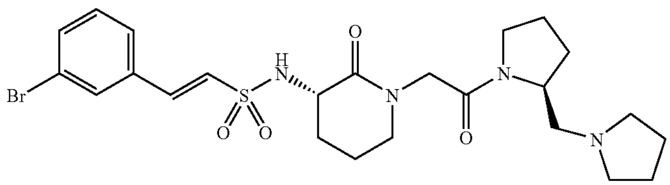 | HPLC (method 1) $t_R$ = 2.3 min LCMS (ESI, pos. ion spectrum) m/z 553/555 (M + H) | prepared using the method described in Example 1 using INT9 and INT29 |
| 136 | 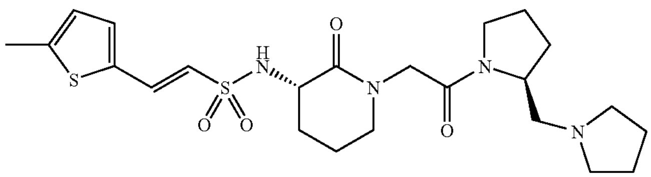 | HPLC (method 1) $t_R$ = 1.8 min LCMS (ESI, pos. ion spectrum) m/z 495 (M + H) | prepared using the method described in Example 1 using INT9 and INT27 |
| 137 | 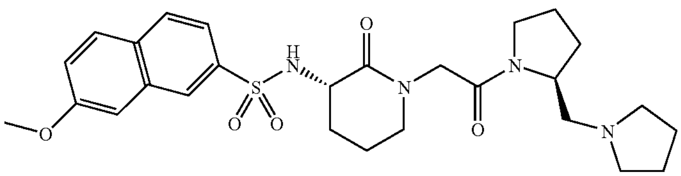 | HPLC (method 1) $t_R$ = 2.8 min LCMS (ESI, pos. ion spectrum) m/z 529 (M + H) | prepared using the method described in Example 1 using INT9 |
| 138 | 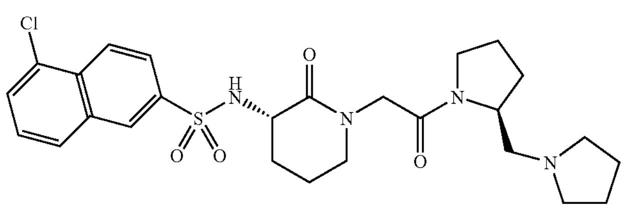 | HPLC (method 1) $t_R$ = 3.1 min LCMS (ESI, pos. ion spectrum) m/z 533/535 (M + H) | prepared using the method described in Example 1 using INT9 |
| 139 | 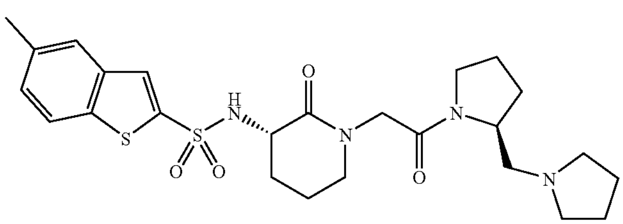 | HPLC (method 1) $t_R$ = 3.0 min LCMS (ESI, pos. ion spectrum) m/z 519 (M + H) | prepared using the method described in Example 1 using INT9 |
| 140 | 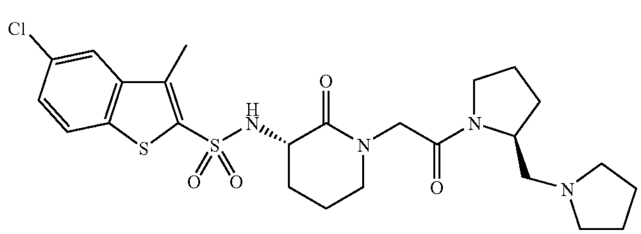 | HPLC (method 1) $t_R$ = 3.2 min LCMS (ESI, pos. ion spectrum) m/z 553/555 (M + H) | prepared using the method described in Example 1 using INT9 |

TABLE 2-continued

| Ex # | Structure | characterization | method |
|---|---|---|---|
| 141 | 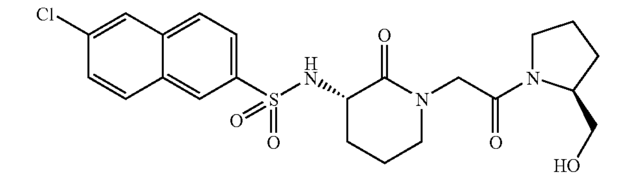 | HPLC (method 1) $t_R$ = 3.2 min LCMS (ESI, pos. ion spectrum) m/z 480/482 (M + 1) | Prepared using the method described in Example 48 |
| 142 | 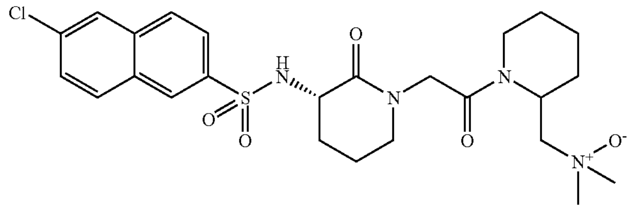 | HPLC (method 1) $t_R$ = 3.0 min LCMS (ESI, pos. ion spectrum) m/z 537/539 (M + 1) | Prepared using the method described in Example 50 |
| 143 | 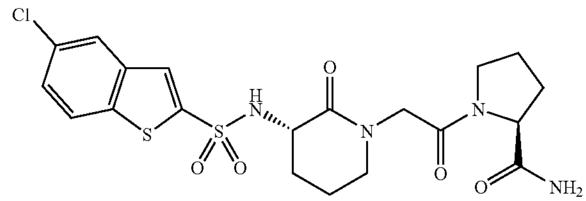 | HPLC (method 1) $t_R$ = 2.8 min LCMS (ESI, pos. ion spectrum) m/z 499/501 (M + H) | prepared using the method described in Example 130 using INT17 |
| 144 | 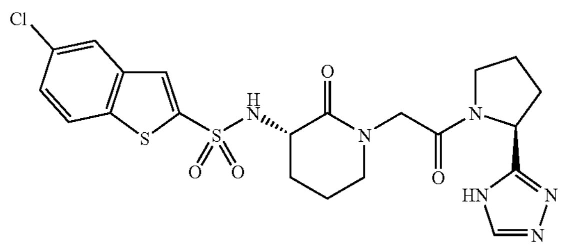 | HPLC (method 1) $t_R$ = 2.9 min LCMS (ESI, pos. ion spectrum) m/z 523/525 (M + H) | prepared using the method described in Example 130 using INT17 and INT66 |
| 145 | 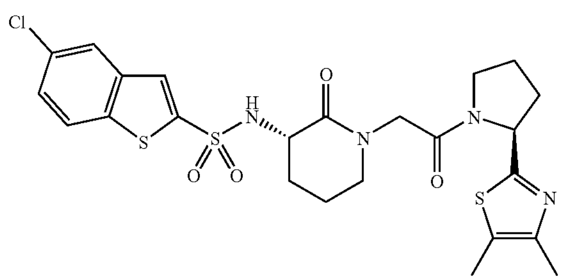 | HPLC (method 1) $t_R$ = 3.4 min LCMS (ESI, pos. ion spectrum) m/z 567/569 (M + H) | prepared using the method described in Example 130 using INT17 and INT63 |
| 146 | 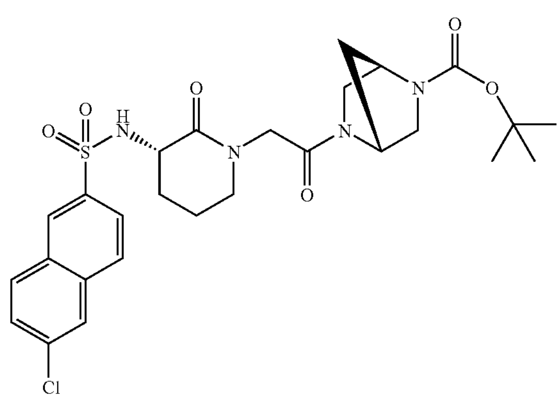 | HPLC (method 1) $t_R$ = 3.7 min LCMS (ESI, pos. ion spectrum) m/z 577/579 (M + 1) | Prepared using the method described in Example 48 |

TABLE 2-continued

| Ex # | Structure | characterization | method |
|---|---|---|---|
| 147 | 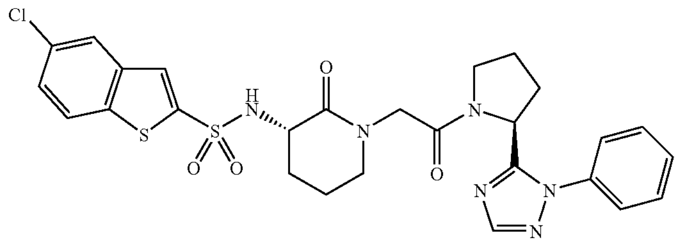 | HPLC (method 1) t_R = 3.3 min LCMS (ESI, pos. ion spectrum) m/z 599 (M + H) | prepared using the method described in Example 130 using INT17 and INT67 |
| 148 | 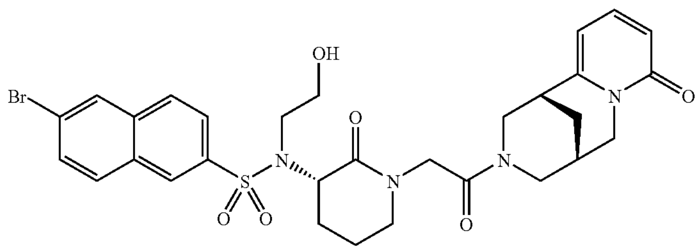 | HPLC (method 9) t_R = 1.5 min LCMS (method 6) (ESI, pos. ion spectrum) m/z 657/659 (M + 1) | Title compound of Example 148 |
| 149 | 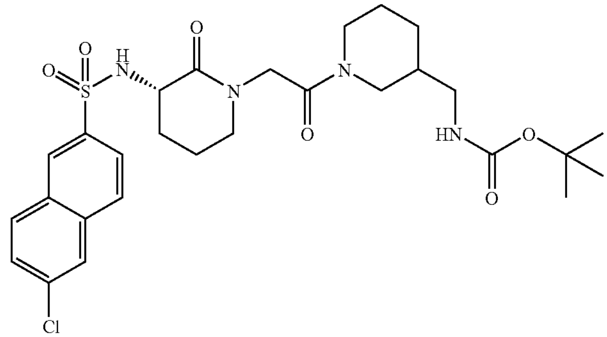 | HPLC (method 1) t_R = 4.1 min LCMS (ESI, pos. ion spectrum) m/z 593/595 (M + 1) | Prepared using the method described in Example 48 |
| 150 | 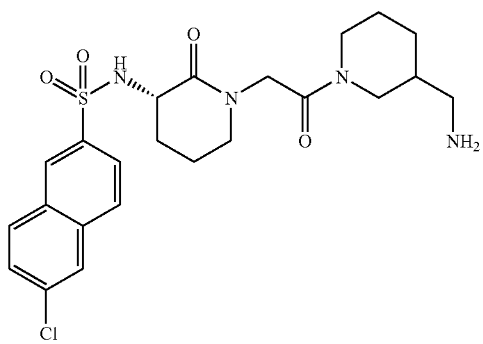 | HPLC (method 1) t_R = 2.9 min LCMS (ESI, pos. ion spectrum) m/z 493/495 (M + 1) | Prepared using the method described in Example 178 Step B using Example 149 title compound |
| 151 | 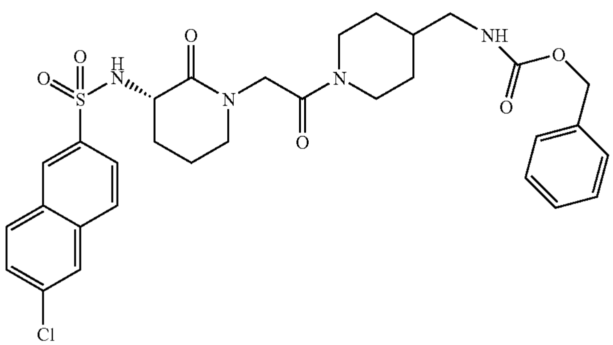 | HPLC (method 1) t_R = 3.6 min LCMS (ESI, pos. ion spectrum) m/z 627/629 (M + 1) | Prepared using the method described in Example 48 |

TABLE 2-continued

| Ex # | Structure | characterization | method |
|---|---|---|---|
| 152 | 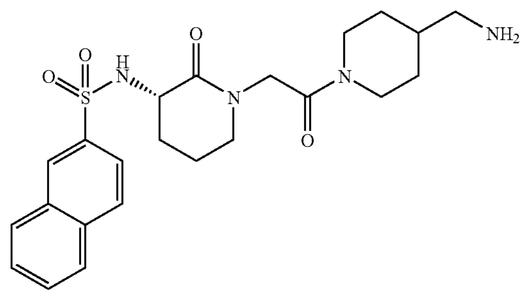 | HPLC (method 1) t_R = 2.6 min LCMS (ESI, pos. ion spectrum) m/z 459 (M + 1) | Title compound of Example 152 |
| 153 | 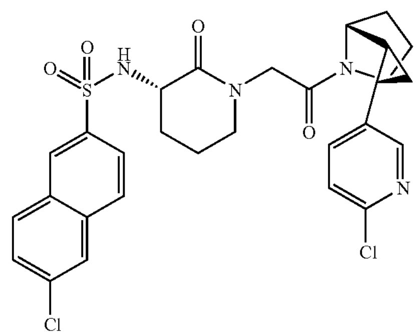 | HPLC (method 1) t_R = 3.3 min LCMS (ESI, pos. ion spectrum) m/z 587/589/591 (M + 1) | Prepared using the method described in Example 48 |
| 154 | 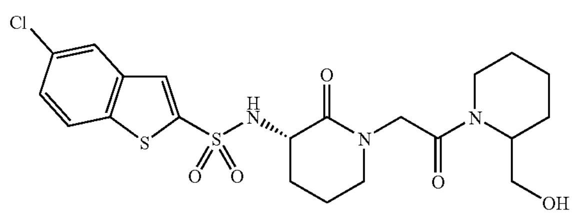 | HPLC (method 1) t_R = 2.6 min LCMS (ESI, pos. ion spectrum) m/z 500/502 (M + H) | prepared using the method described in Example 130 using INT17 |
| 155 | 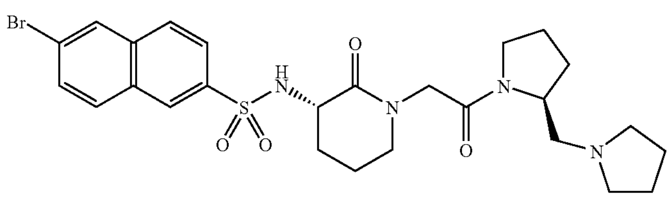 | HPLC (method 1) t_R = 2.6 min LCMS (ESI, pos. ion spectrum) m/z 577/579 (M + H) | prepared using the method described in Example 1 using INT9 |
| 156 | 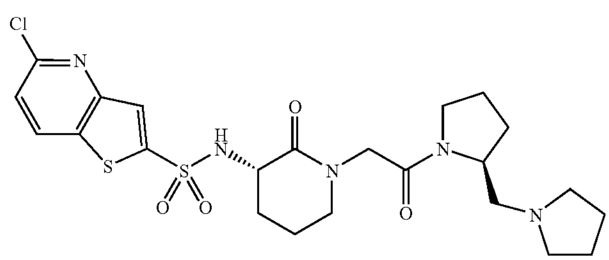 | HPLC (method 1) t_R = 2.0 min LCMS (ESI, pos. ion spectrum) m/z 540/542 (M + H) | prepared using the method described in Example 1 using INT9 |
| 157 | 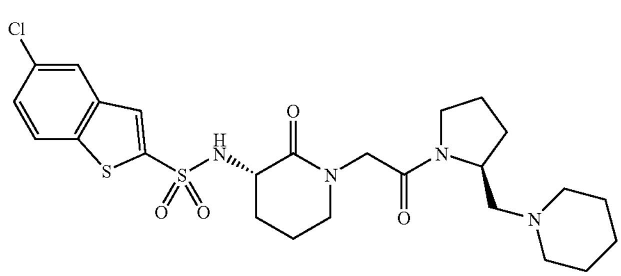 | HPLC (method 1) t_R = 2.6 min LCMS (ESI, pos. ion spectrum) m/z 553/555 (M + H) | prepared using the method described in Example 130 using INT17 |

TABLE 2-continued

| Ex # | Structure | characterization | method |
|---|---|---|---|
| 158 | 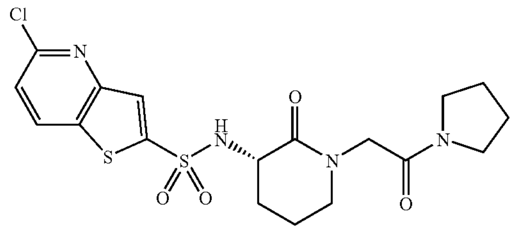 | HPLC (method 1) t_R = 2.5 min LCMS (ESI, pos. ion spectrum) m/z 457/459 (M + H) | prepared using the method described in Example 1 |
| 159 | 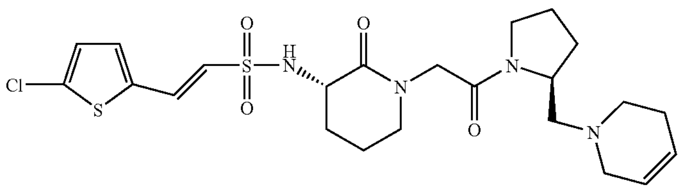 | HPLC (method 1) t_R = 2.7 min LRMS (ESI, pos. ion spectrum) m/z 527/529 (M + H) | prepared using the method described in Example 613 part A and INT49 |
| 160 | 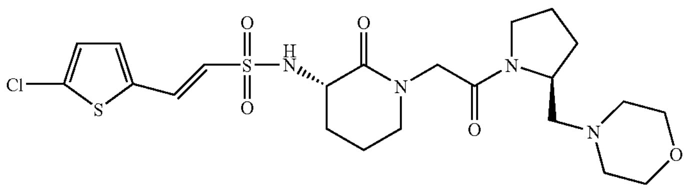 | HPLC (method 1) t_R = 2.6 min LRMS (ESI, pos. ion spectrum) m/z 531/533 (M + H) | prepared using the method described in Example 613 part A and INT5 |
| 161 | 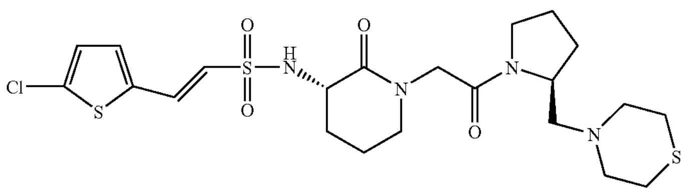 | HPLC (method 1) t_R = 2.7 min LRMS (ESI, pos. ion spectrum) m/z 547/549 (M + H) | prepared using the method described in Example 613 part A and INT32 |
| 162 | 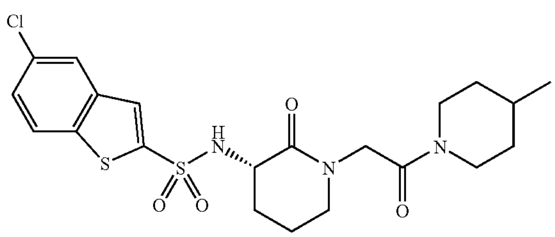 | HPLC (method 1) t_R = 3.4 min LCMS (ESI, pos. ion spectrum) m/z 484/486 (M + H) | prepared using the method described in Example 130 using INT17 |
| 163 | 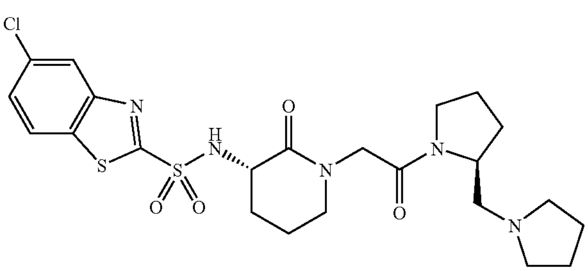 | HPLC (method 1) t_R = 2.3 min LCMS (ESI, pos. ion spectrum) m/z 540/542 (M + H) | prepared using the method described in Example 1using INT9 |
| 164 | 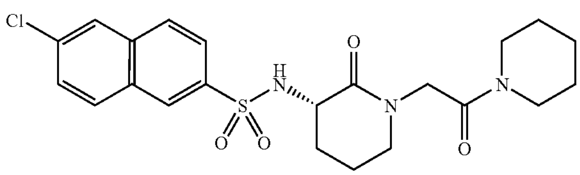 | HPLC (method 1) t_R = 3.2 min LCMS (ESI, pos. ion spectrum) m/z 464/466 (M + H) | prepared using the method described in Example 130 using INT15 |

TABLE 2-continued

| Ex # | Structure | characterization | method |
| --- | --- | --- | --- |
| 165 | 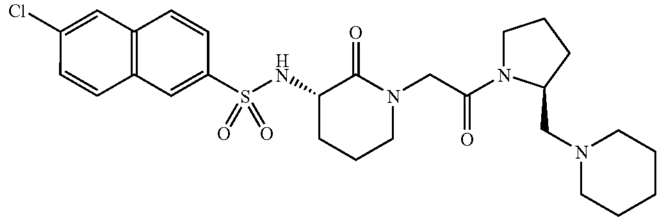 | HPLC (method 1) t_R = 2.6 min LCMS (ESI, pos. ion spectrum) m/z 547/549 (M + H) | prepared using the method described in Example 130 using INT15 |
| 166 | 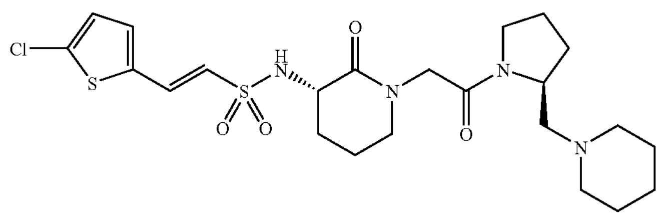 | HPLC (method 1) t_R = 2.3 min LCMS (ESI, pos. ion spectrum) m/z 529/531 (M + H) | prepared using the method described in Example 130 using INT11 |
| 167 | 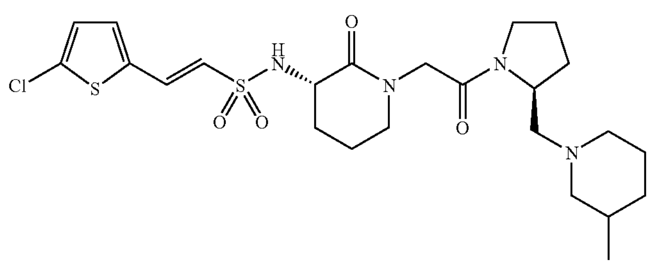 | HPLC (method 1) t_R = 3.8 min LRMS (ESI, pos. ion spectrum) m/z 543/545 (M + H) | prepared using the method described in Example 613 part A using INT42 |
| 168 | 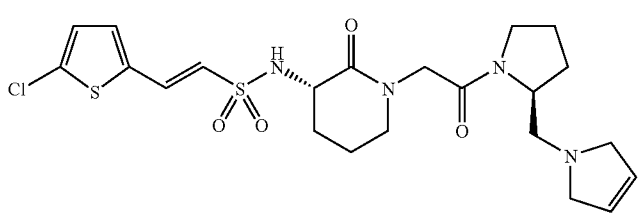 | HPLC (method 1) t_R = 3.5 min LRMS (ESI, neg. ion spectrum) m/z 511/513 (M − H) | prepared using the method described in Example 613 part A using INT36 |
| 169 | 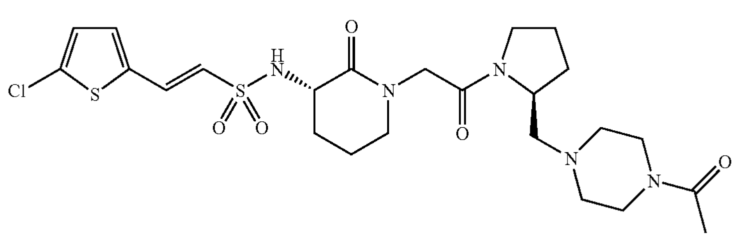 | HPLC (method 1) t_R = 2.6 min LRMS (ESI, pos. ion spectrum) m/z 572/574 (M + H) | prepared using the method described in Example 613 part A using INT37 |
| 170 | 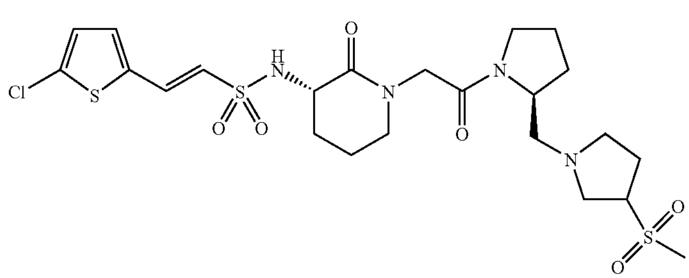 | HPLC (method 1) t_R = 2.6 min LRMS (ESI, pos. ion spectrum) m/z 593/595 (M + H) | prepared using the method described in Example 613 part A using INT35 |

TABLE 2-continued

| Ex # | Structure | characterization | method |
|---|---|---|---|
| 171 | 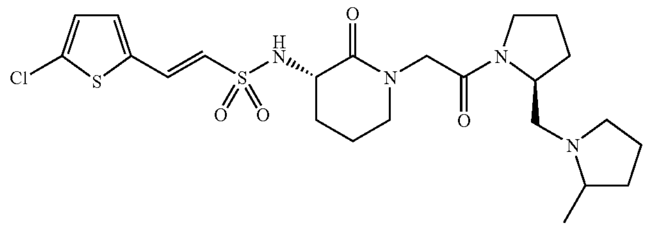 | HPLC (method 1) t_R = 2.8 min LRMS (ESI, pos. ion spectrum) m/z 529/531 (M + H) | prepared using the method described in Example 613 part A using INT38 |
| 172 | 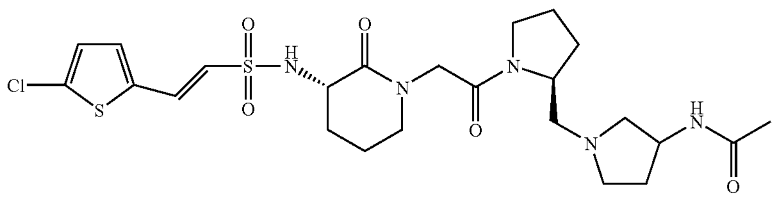 | HPLC (method 1) t_R = 2.7 min LRMS (ESI, pos. ion spectrum) m/z 572/574 (M + H) | prepared using the method described in Example 613 part A and INT33 |
| 173 | 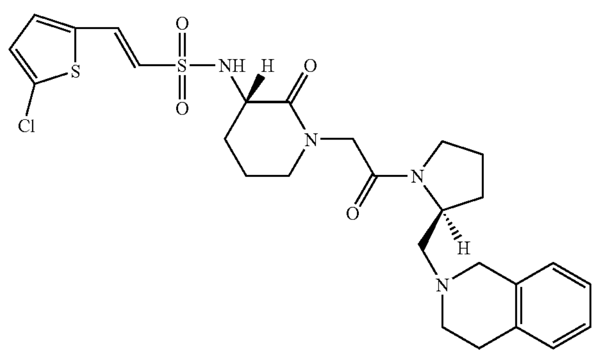 | HPLC (method 3) t_R = 2.7 min LCMS (ESI, pos. ion spectrum) m/z 577/579 (M + 1) | prepared using the method described in Example 130 using INT11 |
| 174 | 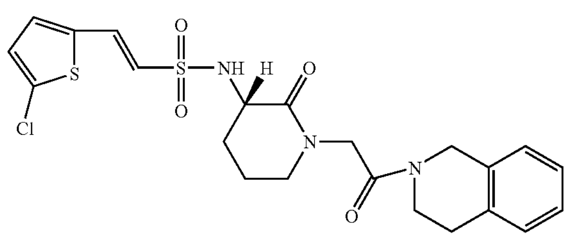 | HPLC (method 4) t_R = 1.5 min LCMS (ESI, pos. ion spectrum) m/z 494/496 (M + 1) | prepared using the method described in Example 130 using INT11 |
| 175 | 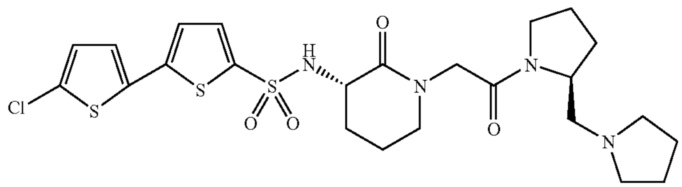 | HPLC (method 1) t_R = 2.8 min LCMS (ESI, pos. ion spectrum) m/z 571/573 (M + H) | prepared using the method described in Example 1 using INT9 |
| 176 | 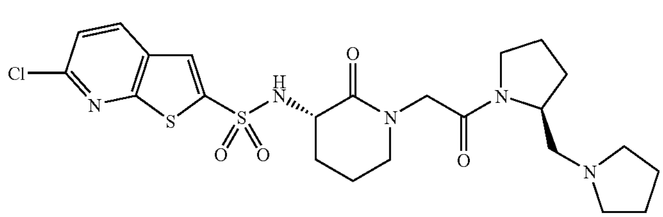 | HPLC (method 1) t_R = 2.2 min LCMS (ESI, pos. ion spectrum) m/z 540/542 (M + H) | prepared using the method described in Example 1 using INT9 |

TABLE 2-continued

| Ex # | Structure | characterization | method |
|---|---|---|---|
| 177 | (6-chloronaphthalene-2-sulfonamide linked to piperidinone-acetyl-azabicyclic-CH2OH, exo-isomers) | HPLC (method 1) t_R = 2.9 min LCMS (ESI, pos. ion spectrum) m/z 506/507 (M + 1) | Title compound of Example 177 |
| 178 | (6-chloronaphthalene-2-sulfonamide linked to piperidinone-acetyl-piperidinyl-CH2NH2) | HPLC (method 1) t_R = 2.6 min LCMS (ESI, pos. ion spectrum) m/z 493/495 (M + 1) | Title compound of Example 178 |
| 179 | (5-chlorothiophene-vinylsulfonamide linked to piperidinone-acetyl-pyrrolidinyl-methylthiazole) | HPLC (method 1) t_R = 3.0 min LCMS (ESI, pos. ion spectrum) m/z 529/531 (M + H) | prepared using the method described in Example 130 using INT11 and INT64 |
| 180 | (5-chlorothiophene-vinylsulfonamide linked to piperidinone-acetyl-pyrrolidinyl-pyrimidine) | HPLC (method 1) t_R = 2.8 min LCMS (ESI, pos. ion spectrum) m/z 510/512 (M + H) | prepared using the method described in Example 130 using INT11 and INT65 |
| 181 | (5-chlorothiophene-vinylsulfonamide linked to piperidinone-acetyl-pyrrolidinyl-pyrimidine N-oxide) | HPLC (method 1) t_R = 2.6 min LCMS (ESI, pos. ion spectrum) m/z 526/528 (M + H) | prepared using the method described in Example 130 using INT11 |
| 182 | (5-chlorobenzothiophene-2-sulfonamide linked to piperidinone-acetyl-pyrrolidinyl-CH2OH) | HPLC (method 3) t_R = 2.9 min LCMS (ESI, pos. ion spectrum) m/z 486/488 (M + 1) | prepared using the method described in Example 130 using INT16 |

TABLE 2-continued

| Ex # | Structure | characterization | method |
| --- | --- | --- | --- |
| 183 | 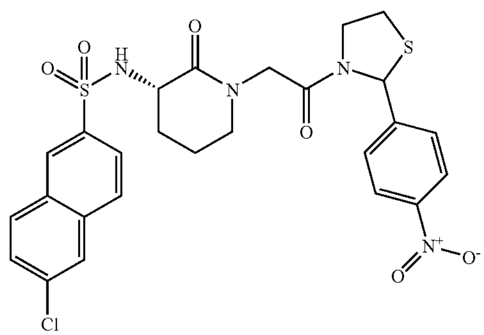 | LCMS (method 4) t_R = 1.5 min LCMS (ESI, pos. ion spectrum) m/z 589/591 (M + 1) | Title compound of Example 183 |
| 184 | 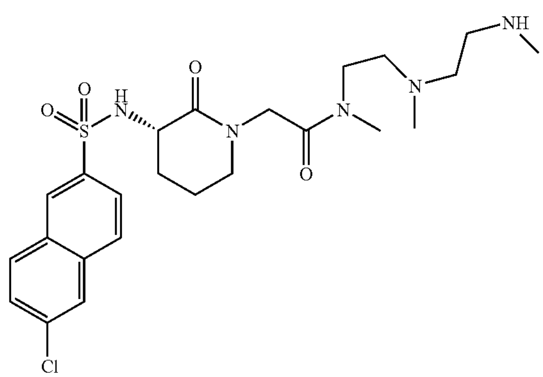 | LCMS (method 4) t_R = 1.2 min LCMS (ESI, pos. ion spectrum) m/z 524/526 (M + 1) | Prepared using the method described in Example 183 |
| 185 | 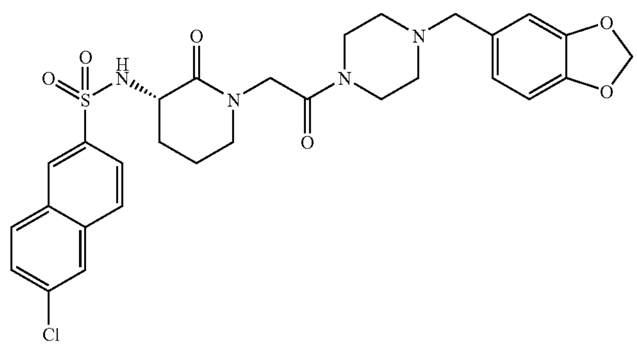 | LCMS (method 4) t_R = 1.2 min LCMS (ESI, pos. ion spectrum) m/z 599/601 (M + 1) | Prepared using the method described in Example 183 |
| 186 | 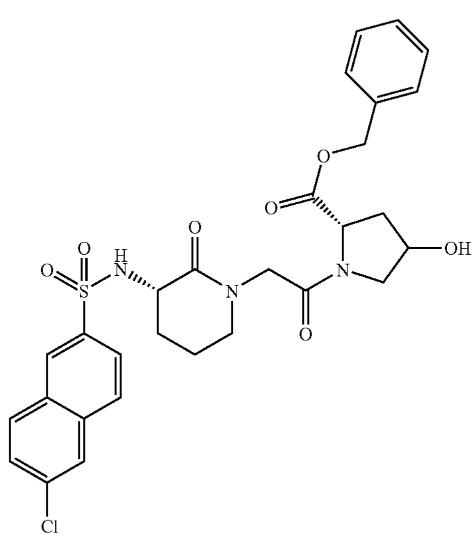 | LCMS (method 4) t_R = 1.5 min (ESI, pos. ion spectrum) m/z 600/602 (M + 1) | Prepared using the method described in Example 183 |

TABLE 2-continued

| Ex # | Structure | characterization | method |
| --- | --- | --- | --- |
| 187 | 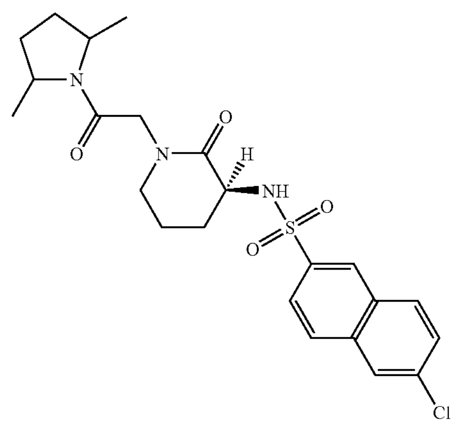 | LCMS (method 4) $t_R$ = 1.4 min (ESI, pos. ion spectrum) m/z 478/480 (M + 1) | Prepared using the method described in Example 183 |
| 188 | 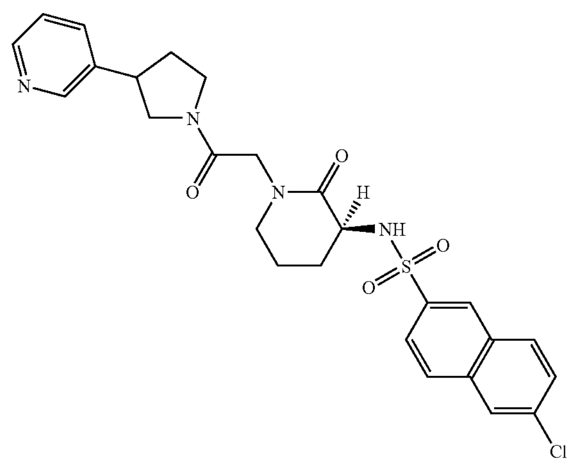 | LCMS (method 4) $t_R$ = 1.2 min (ESI, pos. ion spectrum) m/z 527/529 (M + 1) | Prepared using the method described in Example 183 |
| 189 | 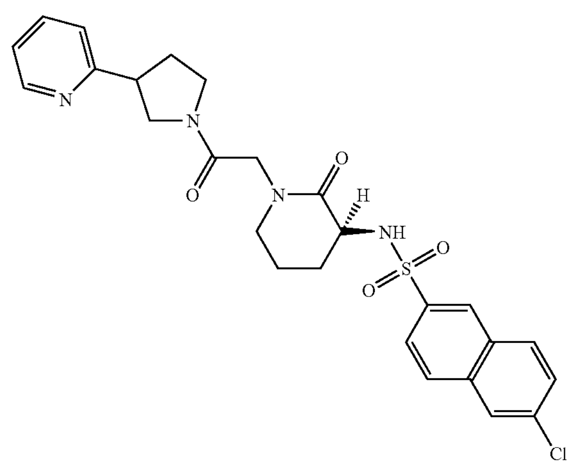 | LCMS (method 4) $t_R$ = 1.2 min (ESI, pos. ion spectrum) m/z 527/529 (M + 1) | Prepared using the method described in Example 183 |
| 190 | 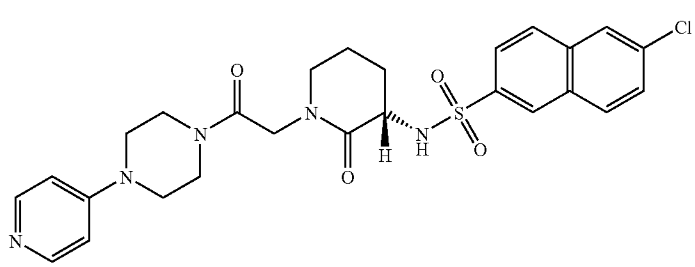 | LCMS (method 4) $t_R$ = 1.2 min (ESI, pos. ion spectrum) m/z 542/544 (M + 1) | Prepared using the method described in Example 183 |

TABLE 2-continued

| Ex # | Structure | characterization | method |
| --- | --- | --- | --- |
| 191 | 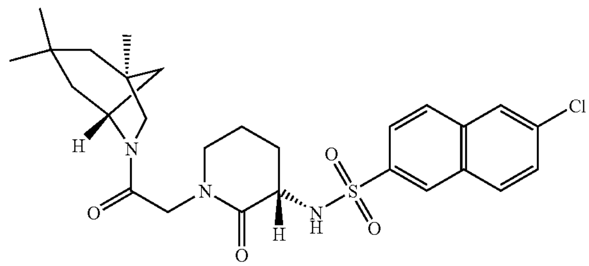 | LCMS (method 4) $t_R$ = 1.6 min (ESI, pos. ion spectrum) m/z 532/534 (M + 1) | Prepared using the method described in Example 183 |
| 192 | 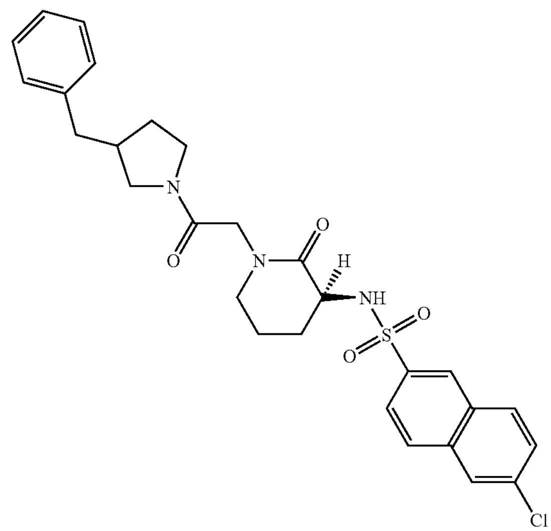 | LCMS (method 4) $t_R$ = 1.6 min (ESI, pos. ion spectrum) m/z 540/542 (M + 1) | Prepared using the method described in Example 183 |
| 193 | 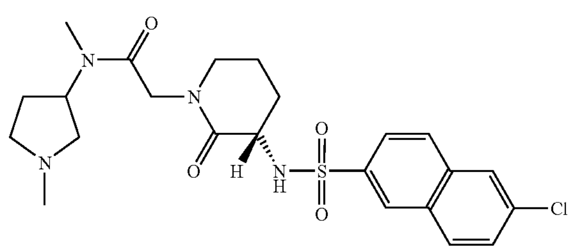 | LCMS (method 4) $t_R$ = 1.2 min (ESI, pos. ion spectrum) m/z 493/495 (M + 1) | Prepared using the method described in Example 183 |
| 194 | 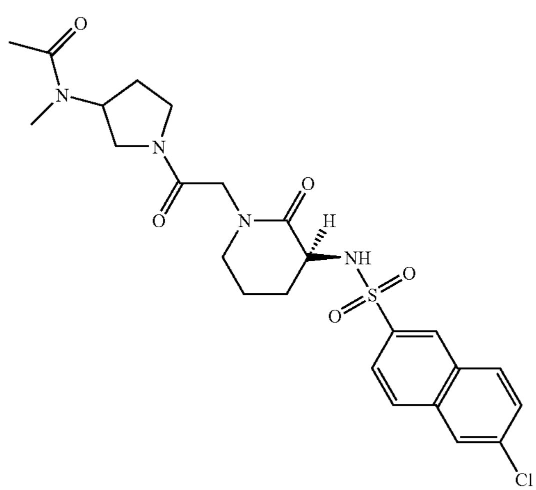 | LCMS (method 4) $t_R$ = 1.2 min (ESI, pos. ion spectrum) m/z 521/523 (M + 1) | Prepared using the method described in Example 183 |

TABLE 2-continued

| Ex # | Structure | characterization | method |
| --- | --- | --- | --- |
| 195 | 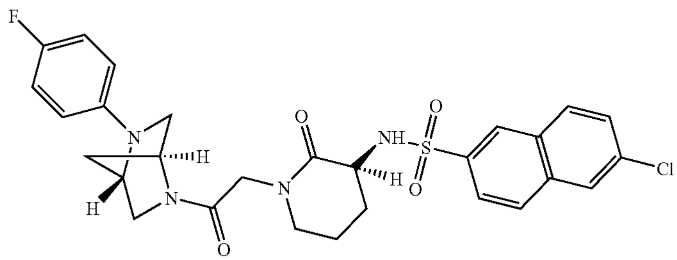 | LCMS (method 4) t_R = 1.5 min (ESI, pos. ion spectrum) m/z 571/573 (M + 1) | Prepared using the method described in Example 183 |
| 196 | 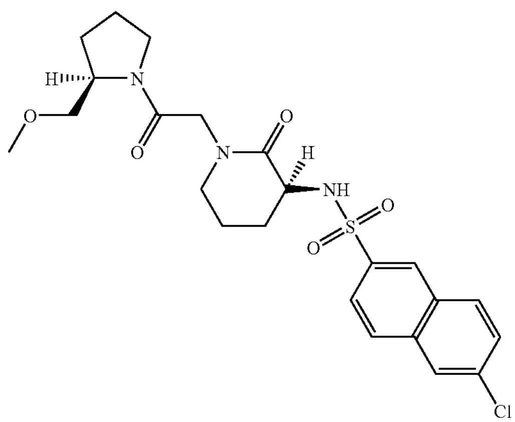 | LCMS (method 4) t_R = 1.4 min (ESI, pos. ion spectrum) m/z 494/496 (M + 1) | Prepared using the method described in Example 183 |
| 197 | 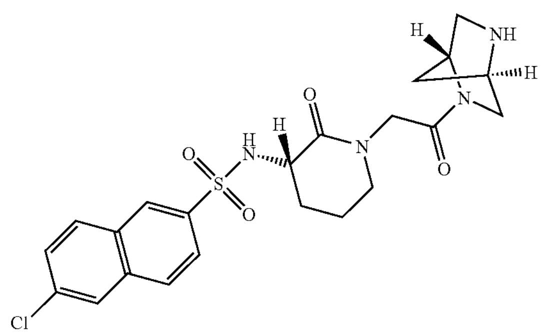 | LCMS (method 4) t_R = 1.1 min (ESI, pos. ion spectrum) m/z 477/479 (M + 1) | Prepared using the method described in Example 183 |
| 198 | 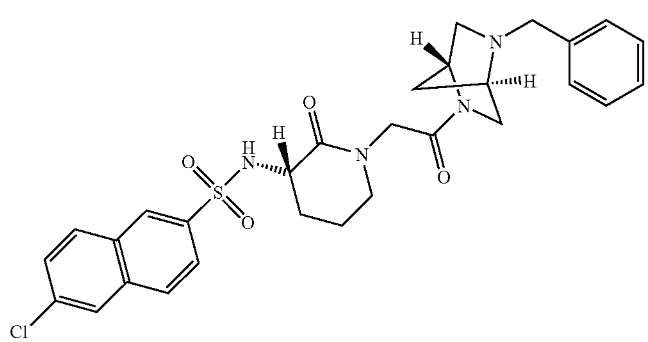 | LCMS (method 4) t_R = 1.3 min (ESI, pos. ion spectrum) m/z 567/569 (M + 1) | Prepared using the method described in Example 183 |

TABLE 2-continued

| Ex # | Structure | characterization | method |
|---|---|---|---|
| 199 | 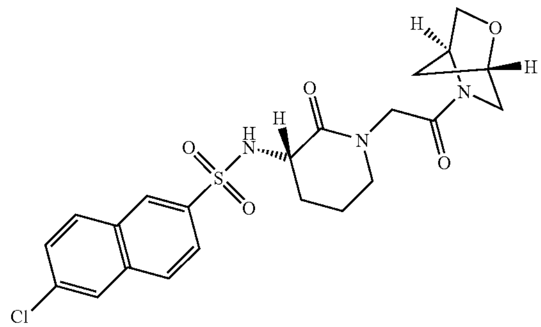 | LCMS (method 4) $t_R$ = 1.3 min (ESI, pos. ion spectrum) m/z 478/480 (M + 1) | Prepared using the method described in Example 183 |
| 200 | 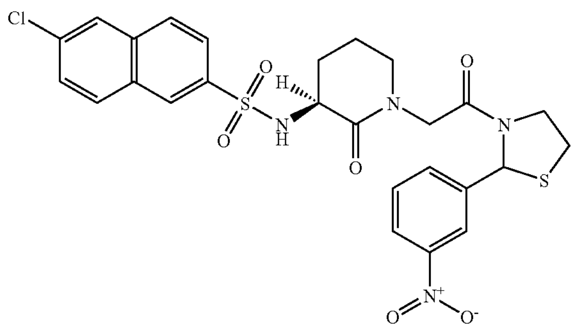 | LCMS (method 4) $t_R$ = 1.5 min (ESI, pos. ion spectrum) m/z 589/591 (M + 1) | Prepared using the method described in Example 183 |
| 201 | 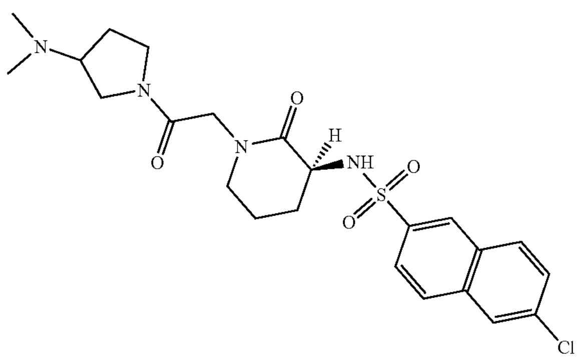 | LCMS (method 4) $t_R$ = 1.2 min (ESI, pos. ion specturm) m/z 493/495 (M + 1) | Prepared using the method described in Example 183 |
| 202 | 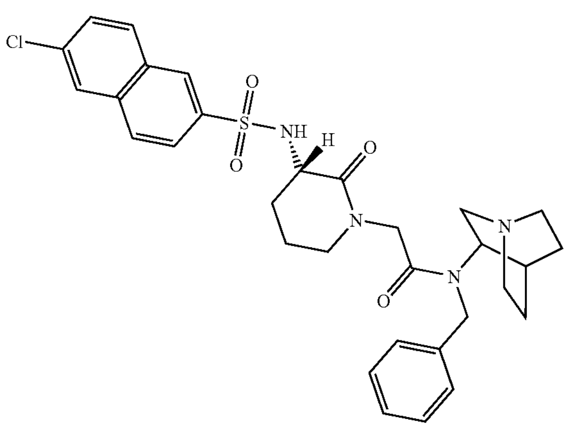 | LCMS (method 4) $t_R$ = 1.4 min (ESI, pos. ion spectrum) m/z 595/597 (M + 1) | Prepared using the method described in Example 183 |

TABLE 2-continued

| Ex # | Structure | characterization | method |
|---|---|---|---|
| 203 | 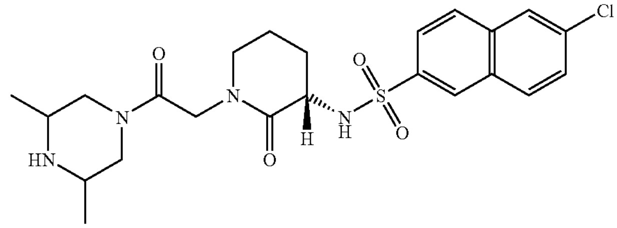 | LCMS (method 4) t_R = 1.1 min (ESI, pos. ion spectrum) m/z 493/495 (M + 1) | Prepared using the method described in Example 183 |
| 204 | 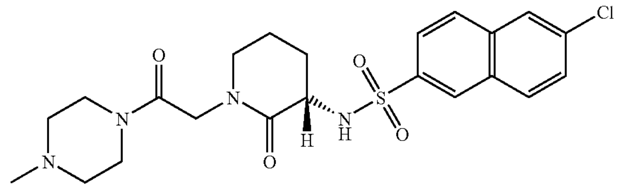 | LCMS (method 4) t_R = 1.2 min (ESI, pos. ion spectrum) m/z 479/481 (M + 1) | Prepared using the method described in Example 183 |
| 205 | 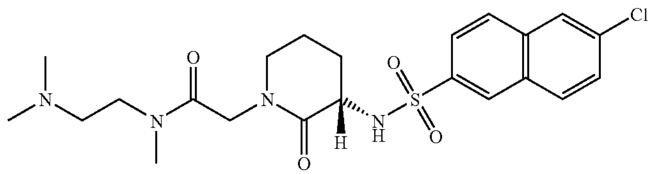 | LCMS (method 4) t_R = 1.2 min (ESI, pos. ion spectrum) m/z 481/483 (M + 1) | Prepared using the method described in Example 183 |
| 206 | 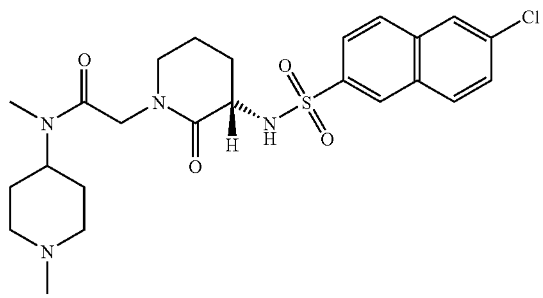 | LCMS (method 4) t_R = 1.2 min (ESI, pos. ion spectrum) m/z 507/509 (M + 1) | Prepared using the method described in Example 183 |
| 207 | 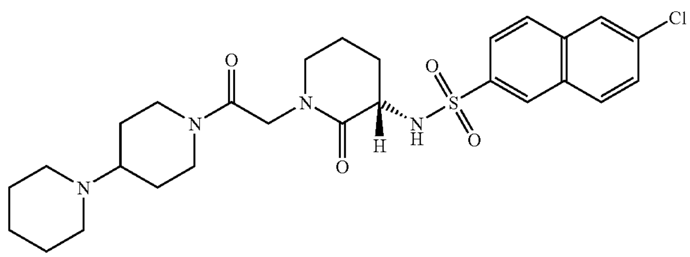 | LCMS (method 4) t_R = 1.2 min (ESI, pos. ion spectrum) m/z 547/549 (M + 1) | Prepared using the method described in Example 183 |
| 208 | 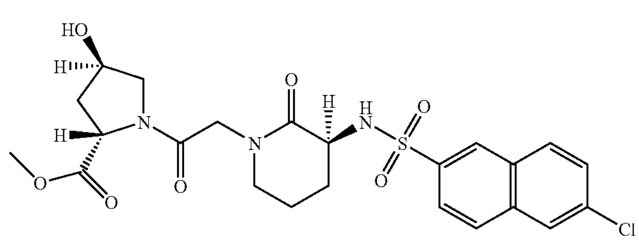 | LCMS (method 4) t_R = 1.3 min (ESI, pos. ion spectrum) m/z 524/526 (M + 1) | Prepared using the method described in Example 183 |

TABLE 2-continued

| Ex # | Structure | characterization | method |
|---|---|---|---|
| 209 | 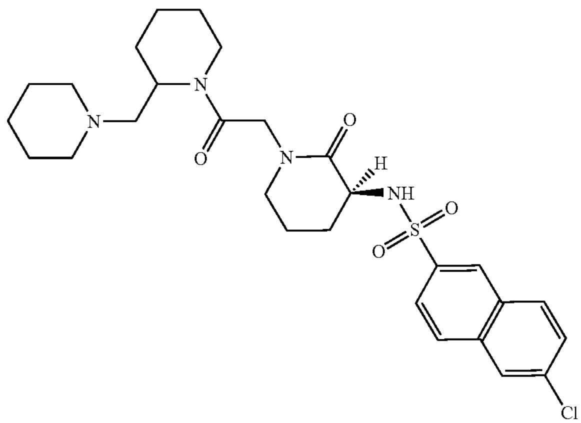 | LCMS (method 4) t_R = 1.3 min (ESI, pos. ion spectrum) m/z 561/563 (M + 1) | Prepared using the method described in Example 183 |
| 210 | 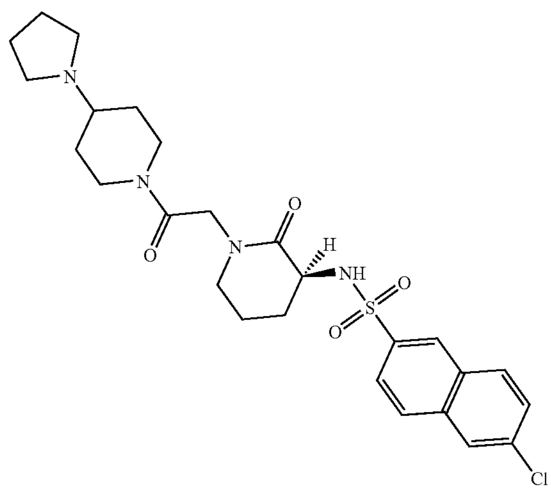 | LCMS (method 4) t_R = 1.2 min (ESI, pos. ion spectrum) m/z 533/535 (M + 1) | Prepared using the method described in Example 183 |
| 211 | 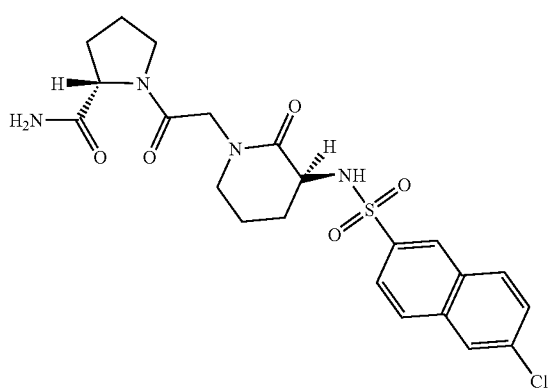 | LCMS (method 4) t_R = 1.2 min (ESI, pos. ion spectrum) m/z 493/495 (M + 1) | Prepared using the method described in Example 183 |
| 212 | 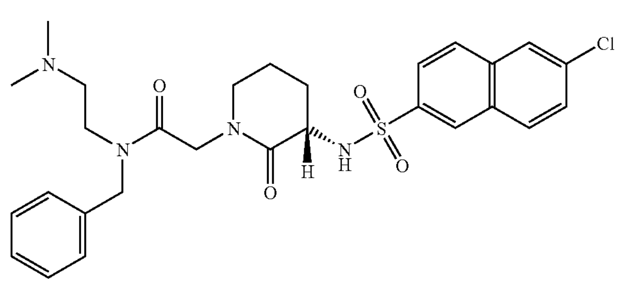 | LCMS (method 4) t_R = 1.3 min (ESI, pos. ion spectrum) m/z 557/559 (M + 1) | Prepared using the method described in Example 183 |

TABLE 2-continued

| Ex # | Structure | characterization | method |
|---|---|---|---|
| 213 | 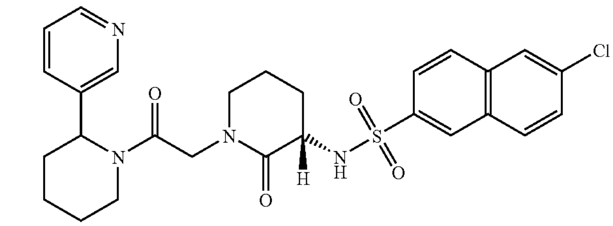 | LCMS (method 4) t_R = 1.2 min (ESI, pos. ion spectrum) m/z 541/543 (M + 1) | Prepared using the method described in Example 183 |
| 214 | 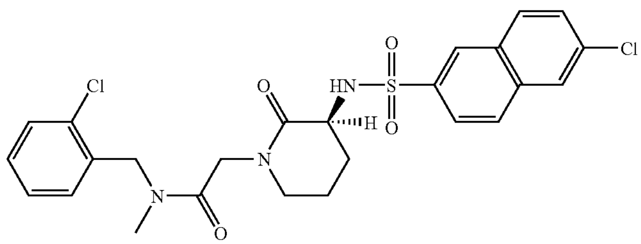 | LCMS (method 4) t_R = 1.6 min (ESI, pos. ion spectrum) m/z 534/536/538 (M + 1) | Prepared using the method described in Example 183 |
| 215 | 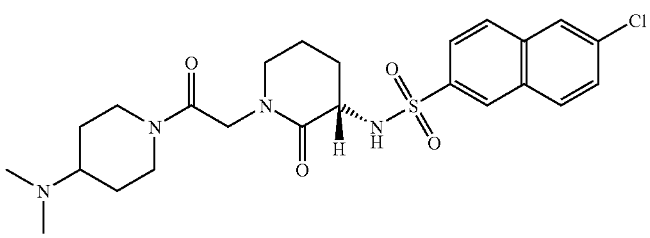 | LCMS (method 4) t_R = 1.2 min (ESI, pos. ion spectrum) m/z 507/509 (M + 1) | Prepared using the method described in Example 183 |
| 216 | 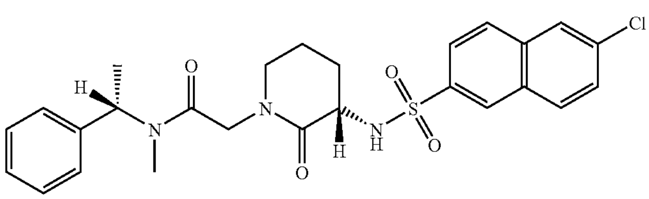 | LCMS (method 4) t_R = 1.5 min (ESI, pos. ion spectrum) m/z 514/516 (M + 1) | Prepared using the method described in Example 183 |
| 217 | 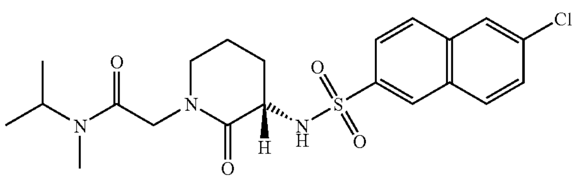 | LCMS (method 4) t_R = 1.3 min (ESI, pos. ion spectrum) m/z 452/454 (M + 1) | Prepared using the method described in Example 183 |
| 218 | 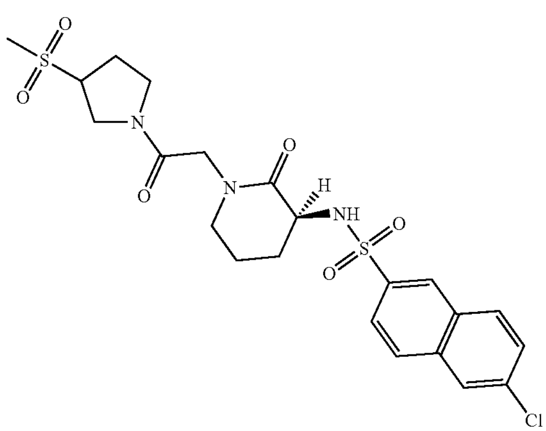 | LCMS (method 4) t_R = 1.2 min (ESI, pos. ion spectrum) m/z 528/530 (M + 1) | Prepared using the method described in Example 183 |

TABLE 2-continued

| Ex # | Structure | characterization | method |
| --- | --- | --- | --- |
| 219 | 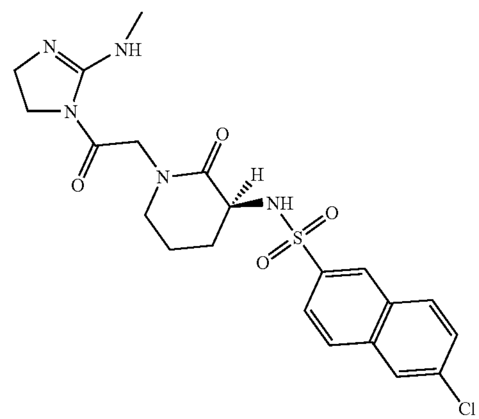 | LCMS (method 4) $t_R$ = 1.7 min (ESI, pos. ion spectrum) m/z 478/480 (M + 1) | Prepared using the method described in Example 183 |
| 220 | 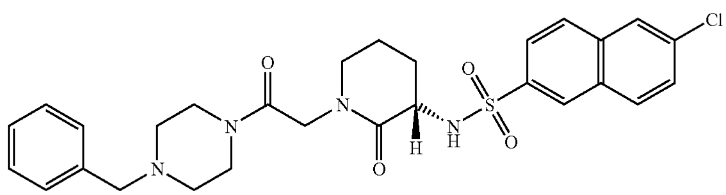 | LCMS (method 4) $t_R$ = 1.2 min (ESI, pos. ion spectrum) m/z 555/557 (M + 1) | Prepared using the method described in Example 183 |
| 221 | 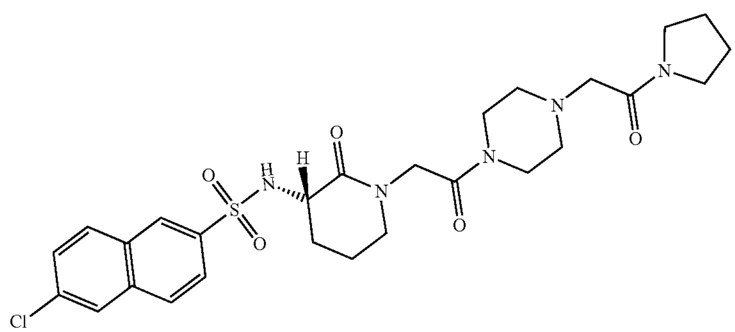 | LCMS (method 4) $t_R$ = 1.2 min (ESI, pos. ion spectrum) m/z 576/578 (M + 1) | Prepared using the method described in Example 183 |
| 222 | 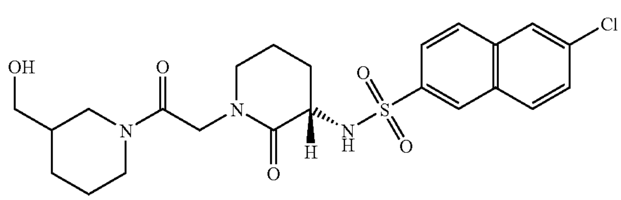 | LCMS (method 4) $t_R$ = 1.3 min (ESI, pos. ion spectrum) m/z 494/496 (M + 1) | Prepared using the method described in Example 183 |
| 223 | 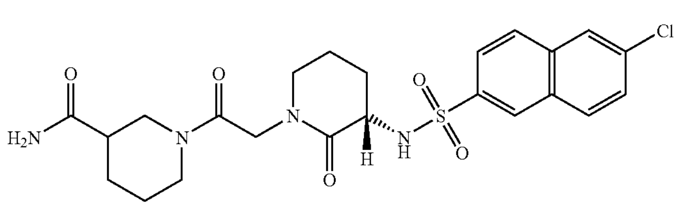 | LCMS (method 4) $t_R$ = 1.2 min (ESI, pos. ion spectrum) m/z 507/509 (M + 1) | Prepared using the method described in Example 183 |

TABLE 2-continued

| Ex # | Structure | characterization | method |
|---|---|---|---|
| 224 | 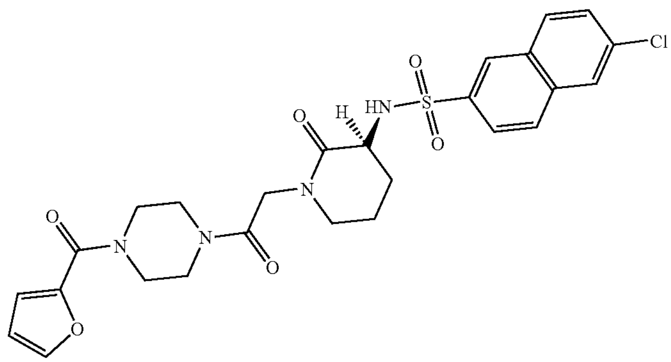 | LCMS (method 4) t_R = 1.3 min (ESI, pos. ion spectrum) m/z 559/561 (M + 1) | Prepared using the method described in Example 183 |
| 225 | 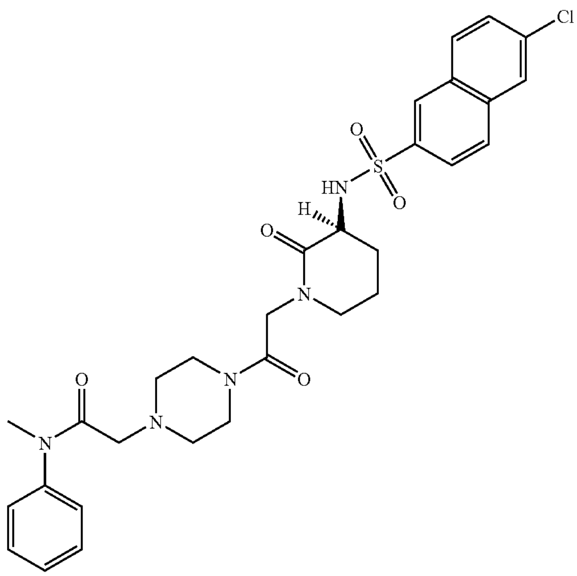 | LCMS (method 4) t_R = 1.3 min (ESI, pos. ion spectrum) m/z 612/614 (M + 1) | Prepared using the method described in Example 183 |
| 226 | 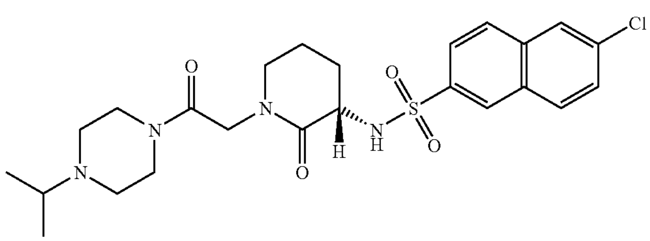 | LCMS (method 4) t_R = 1.2 min (ESI, pos. ion spectrum) m/z 507/509 (M + 1) | Prepared using the method described in Example 183 |
| 227 | 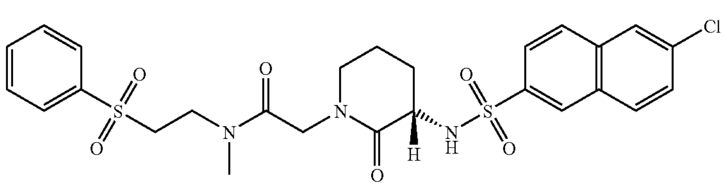 | LCMS (method 4) t_R = 1.4 min (ESI, pos. ion spectrum) m/z 578/580 (M + 1) | Prepared using the method described in Example 183 |
| 228 | 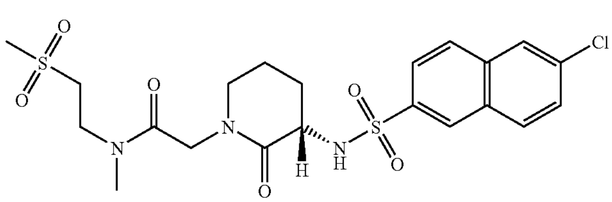 | LCMS (method 4) t_R = 1.2 min (ESI, pos. ion spectrum) m/z 516/518 (M + 1) | Prepared using the method described in Example 183 |

TABLE 2-continued

| Ex # | Structure | characterization | method |
| --- | --- | --- | --- |
| 229 | 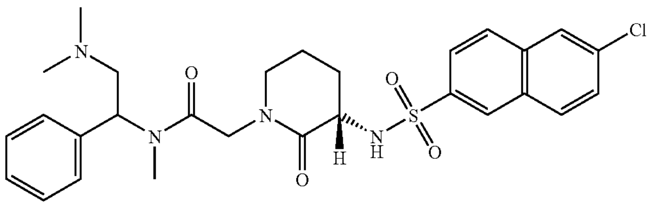 | LCMS (method 4) t_R = 1.3 min (ESI, pos. ion spectrum) m/z 557/559 (M + 1) | Prepared using the method described in Example 183 |
| 230 | 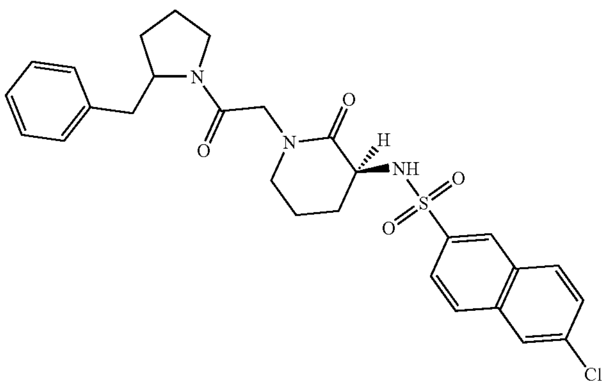 | LCMS (method 4) t_R = 1.6 min (ESI, pos. ion spectrum) m/z 540/542 (M + 1) | Prepared using the method described in Example 183 |
| 231 | 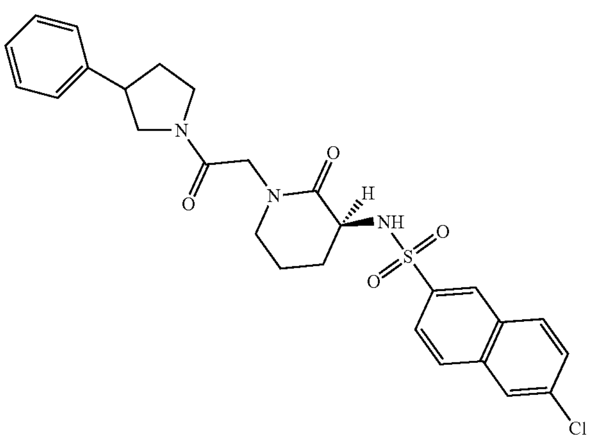 | LCMS (method 4) t_R = 1.5 min (ESI, pos. ion spectrum) m/z 526/528 (M + 1) | Prepared using the method described in Example 183 |
| 232 | 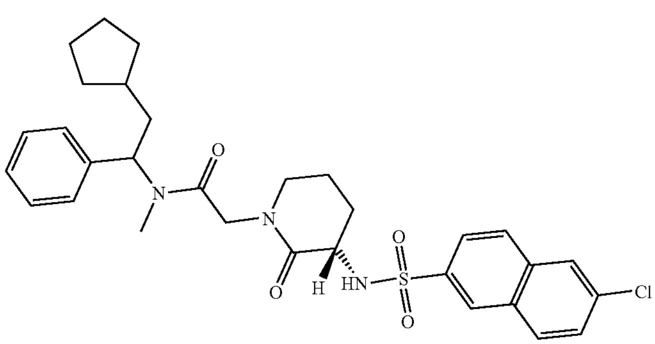 | LCMS (method 4) t_R = 1.3 min (ESI, pos. ion spectrum) m/z 583/585 (M + 1) | Prepared using the method described in Example 183 |

TABLE 2-continued

| Ex # | Structure | characterization | method |
|---|---|---|---|
| 233 | 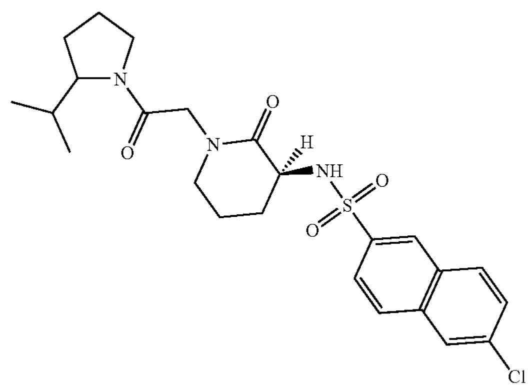 | LCMS (method 4) $t_R$ = 1.5 min (ESI, pos. ion spectrum) m/z 492/494 (M + 1) | Prepared using the method described in Example 183 |
| 234 | 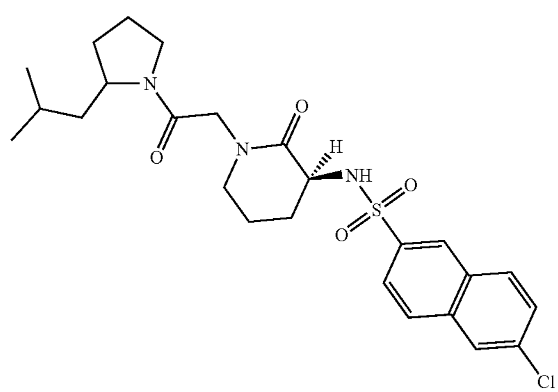 | LCMS (method 4) $t_R$ = 1.6 min (ESI, pos. ion spectrum) m/z 506/508 (M + 1) | Prepared using the method described in Example 183 |
| 235 | 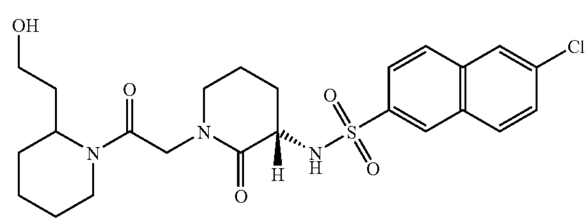 | LCMS (method 4) $t_R$ = 1.3 min (ESI, pos. ion spectrum) m/z 508/510 (M + 1) | Prepared using the method described in Example 183 |
| 236 | 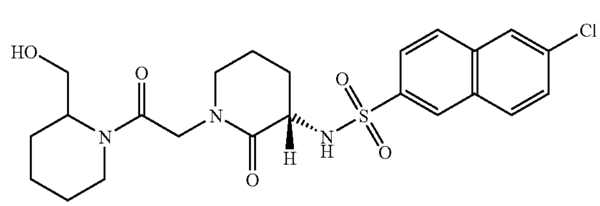 | LCMS (method 4) $t_R$ = 1.4 min (ESI, pos. ion spectrum) m/z 494/496 (M + 1) | Prepared using the method described in Example 183 |

TABLE 2-continued

| Ex # | Structure | characterization | method |
| --- | --- | --- | --- |
| 237 | 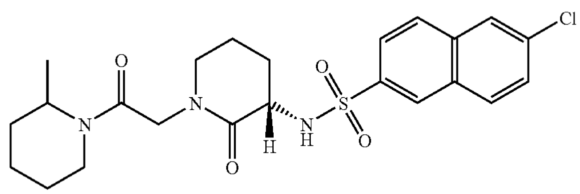 | LCMS (method 4) $t_R$ = 1.4 min (ESI, pos. ion spectrum) m/z 478/480 (M + 1) | Prepared using the method described in Example 183 |
| 238 | 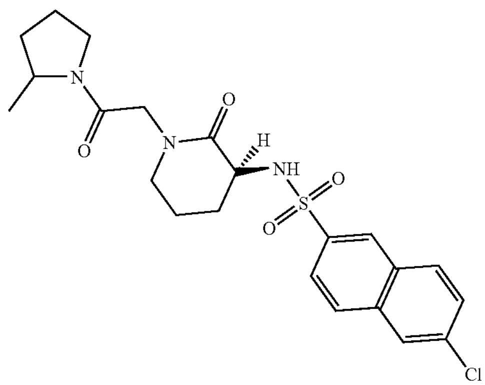 | LCMS (method 4) $t_R$ = 1.4 min (ESI, pos. ion spectrum) m/z 464/466 (M + 1) | Prepared using the method described in Example 183 |
| 239 | 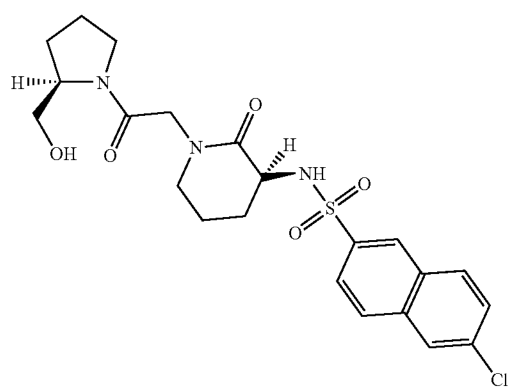 | LCMS (method 4) $t_R$ = 1.2 min (ESI, pos. ion spectrum) m/z 480/482 (M + 1) | Prepared using the method described in Example 183 |
| 240 | 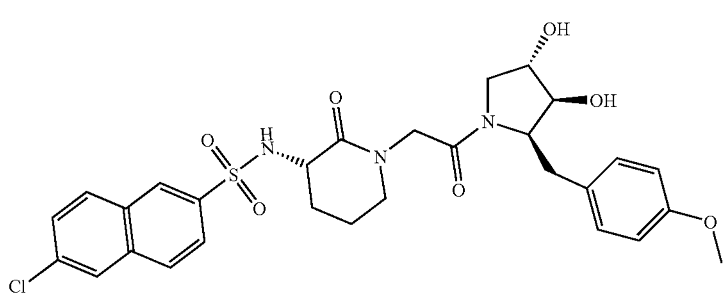 | LCMS (method 4) $t_R$ = 1.4 min (ESI, pos. ion spectrum) m/z 602/604 (M + 1) | Prepared using the method described in Example 183 |

TABLE 2-continued

| Ex # | Structure | characterization | method |
|---|---|---|---|
| 241 | 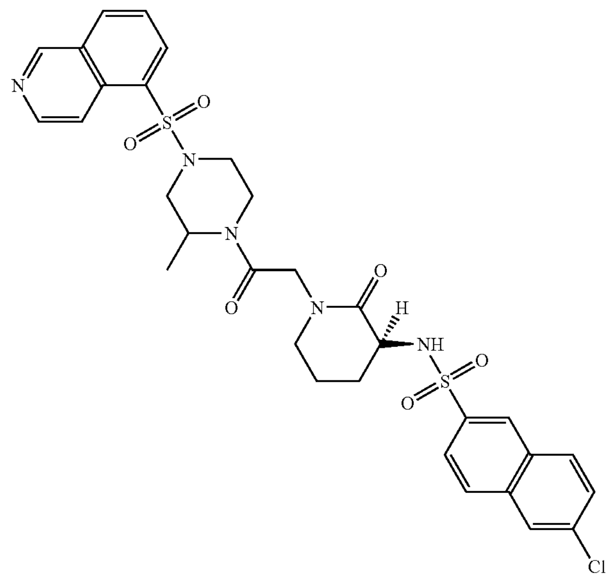 | LCMS (method 4) t_R = 1.3 min (ESI, pos. ion spectrum) m/z 670/672 (M + 1) | Prepared using the method described in Example 183 |
| 242 | 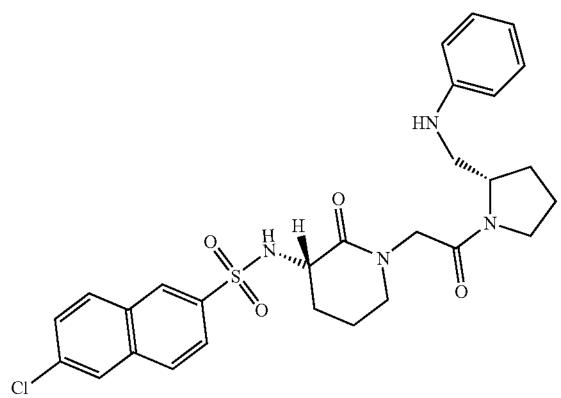 | LCMS (method 4) t_R = 1.3 min (ESI, pos. ion spectrum) m/z 555/557 (M + 1) | Prepared using the method described in Example 183 |
| 243 | 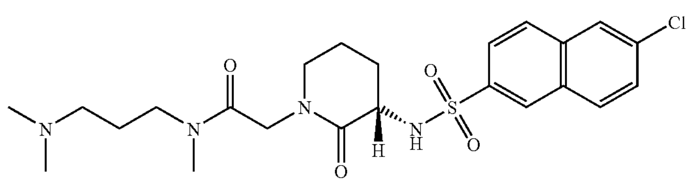 | LCMS (method 4) t_R = 1.2 min (ESI, pos. ion spectrum) m/z 495/497 (M + 1) | Prepared using the method described in Example 183 |
| 244 | 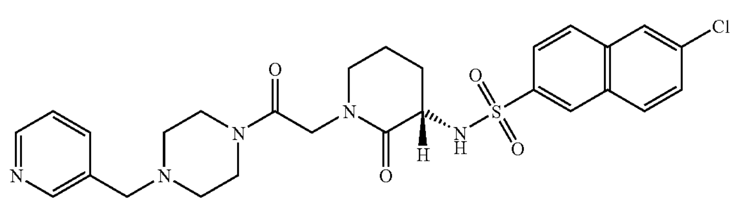 | LCMS (method 4) t_R = 1.1 min (ESI, pos. ion spectrum) m/z 556/558 (M + 1) | Prepared using the method described in Example 183 |
| 245 | 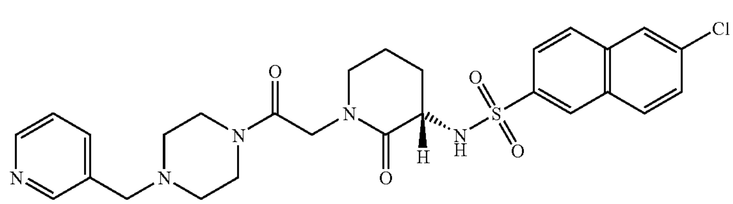 | LCMS (method 4) t_R = 1.2 min (ESI, pos. ion spectrum) m/z 556/558 (M + 1) | Prepared using the method described in Example 183 |

TABLE 2-continued

| Ex # | Structure | characterization | method |
|---|---|---|---|
| 246 | 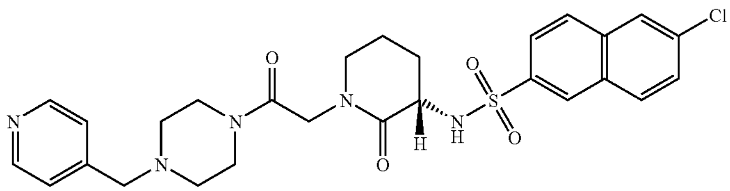 | LCMS (method 4) t_R = 1.1 min (ESI, pos. ion spectrum) m/z 556/558 (M + 1) | Prepared using the method described in Example 183 |
| 247 | 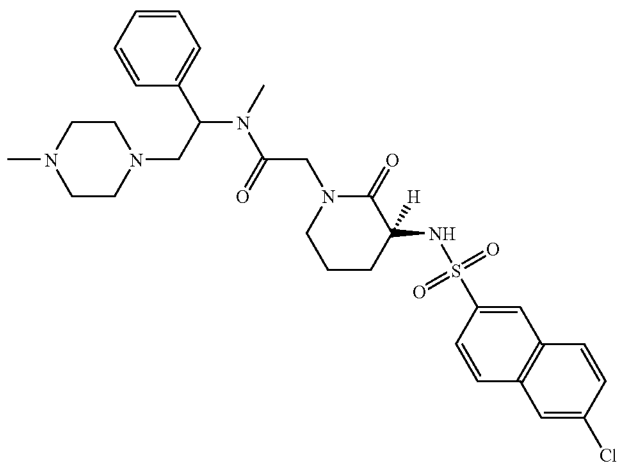 | LCMS (method 4) t_R = 1.3 min (ESI, pos. ion spectrum) m/z 612/614 (M + 1) | Prepared using the method described in Example 183 |
| 248 | 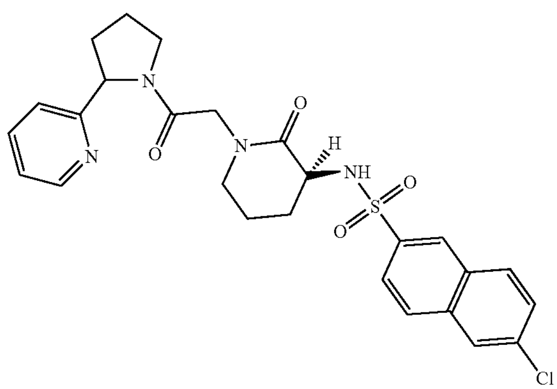 | LCMS (method 4) t_R = 1.2 min (ESI, pos. ion spectrum) m/z 527/529 (M + 1) | Prepared using the method described in Example 183 |
| 249 | 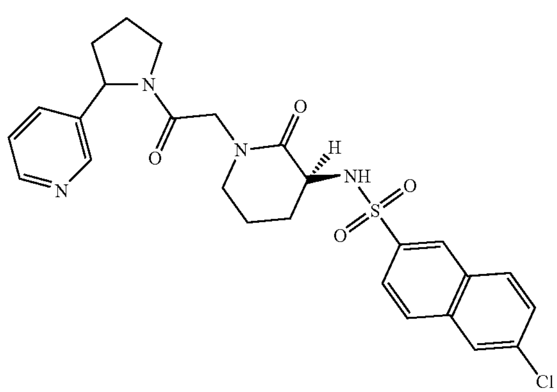 | LCMS (method 4) t_R = 1.2 min (ESI, pos. ion spectrum) m/z 527/529 (M + 1) | Prepared using the method described in Example 183 |

TABLE 2-continued

| Ex # | Structure | characterization | method |
| --- | --- | --- | --- |
| 250 | 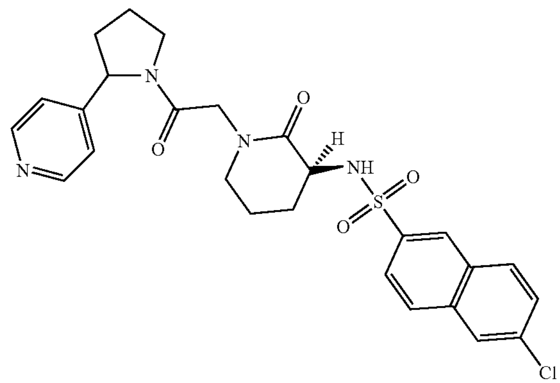 | LCMS (method 4) t_R = 1.2 min (ESI, pos. ion spectrum) m/z 527/529 (M + 1) | Prepared using the method described in Example 183 |
| 251 | 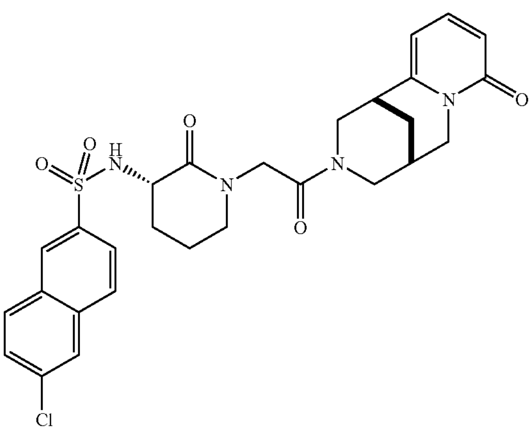 | LCMS (method 4) t_R = 1.3 min (ESI, pos. ion spectrum) m/z 569/571 (M + 1) | Prepared using the method described in Example 183 |
| 252 | 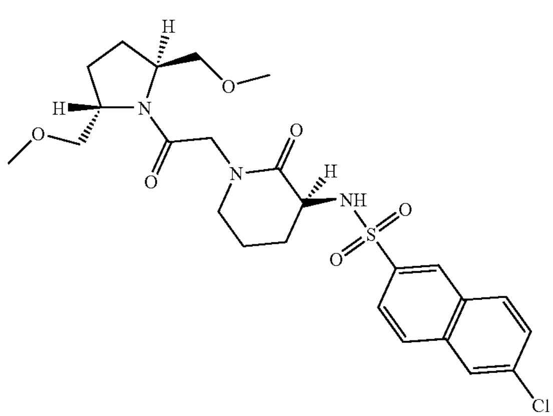 | LCMS (method 4) t_R = 1.4 min (ESI, pos. ion spectrum) m/z 538/540 (M + 1) | Prepared using the method described in Example 183 |

TABLE 2-continued

| Ex # | Structure | characterization | method |
|---|---|---|---|
| 253 | 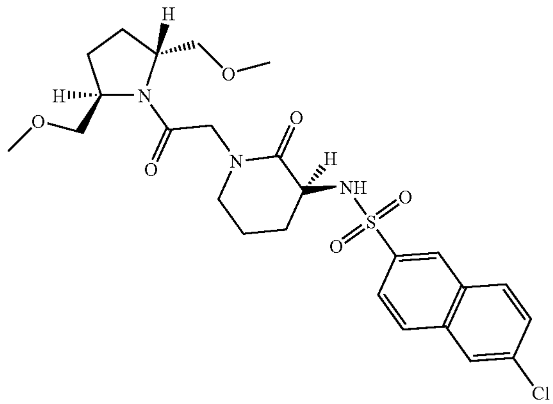 | LCMS (method 4) t$_R$ = 1.4 min (ESI, pos. ion spectrum) m/z 538/540 (M + 1) | Prepared using the method described in Example 183 |
| 254 | 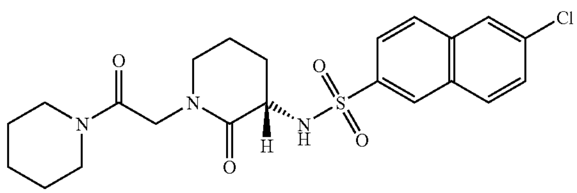 | LCMS (method 4) t$_R$ = 1.4 min (ESI, pos. ion spectrum) m/z 464/466 (M + 1) | Prepared using the method described in Example 183 |
| 255 | 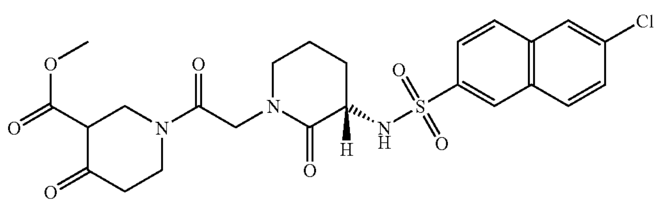 | LCMS (method 4) t$_R$ = 1.3 min (ESI, pos. ion spectrum) m/z 536/538 (M + 1) | Prepared using the method described in Example 183 |
| 256 | 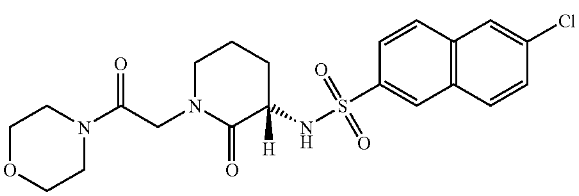 | LCMS (method 4) t$_R$ = 1.2 min (ESI, pos. ion spectrum) m/z 466/468 (M + 1) | Prepared using the method described in Example 183 |
| 257 | 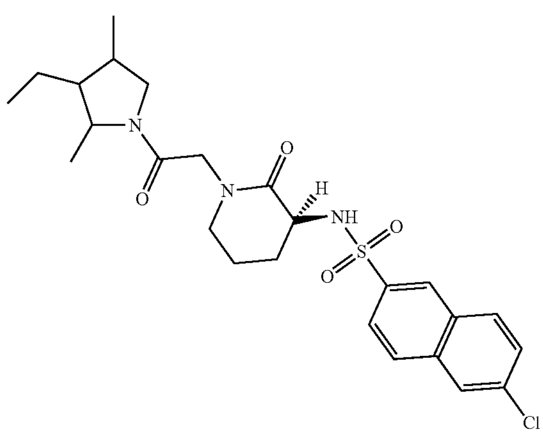 | LCMS (method 4) t$_R$ = 1.6 min (ESI, pos. ion spectrum) m/z 506/508 (M + 1) | Prepared using the method described in Example 183 |

TABLE 2-continued

| Ex # | Structure | characterization | method |
|---|---|---|---|
| 258 | 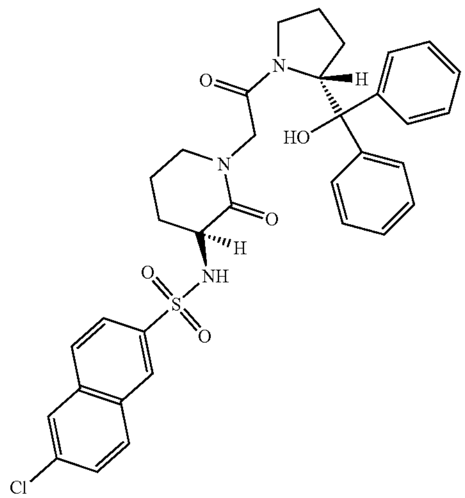 | LCMS (method 4) t$_R$ = 1.7 min (ESI, pos. ion spectrum) m/z 632/634 (M + 1) | Prepared using the method described in Example 183 |
| 259 | 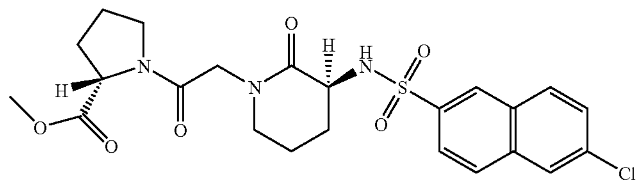 | LCMS (method 4) t$_R$ = 1.3 min (ESI, pos. ion spectrum) m/z 508/510 (M + 1) | Prepared using the method described in Example 183 |
| 260 | 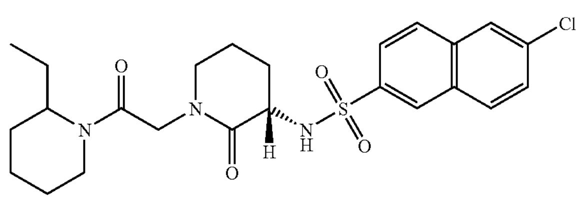 | LCMS (method 4) t$_R$ = 1.5 min (ESI, pos. ion spectrum) m/z 492/494 (M + 1) | Prepared using the method described in Example 183 |
| 261 | 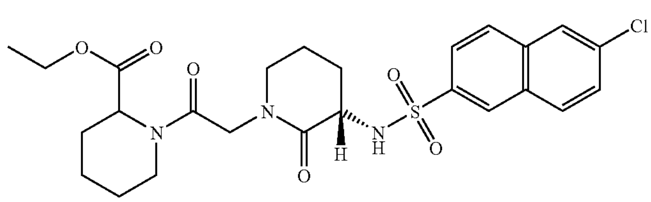 | LCMS (method 4) t$_R$ = 1.5 min (ESI, pos. ion spectrum) m/z 536/538 (M + 1) | Prepared using the method described in Example 183 |
| 262 | 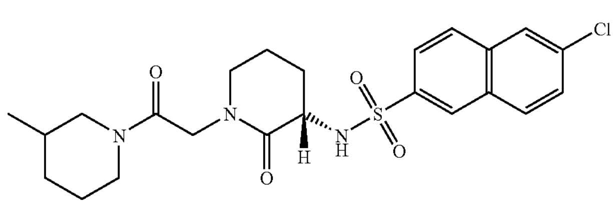 | LCMS (method 4) t$_R$ = 1.4 min (ESI, pos. ion spectrum) m/z 478/480 (M + 1) | Prepared using the method described in Example 183 |

TABLE 2-continued

| Ex # | Structure | characterization | method |
|---|---|---|---|
| 263 | 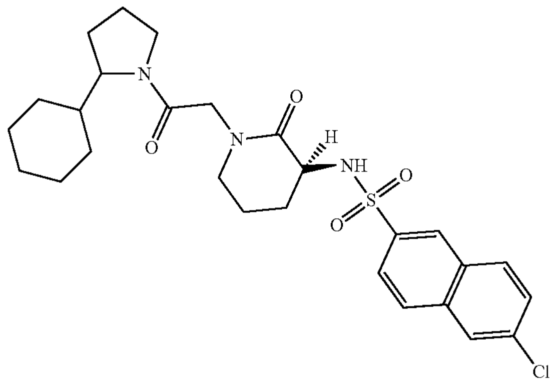 | LCMS (method 4) t$_R$ = 1.7 min (ESI, pos. ion spectrum) m/z 532/534 (M + 1) | Prepared using the method described in Example 183 |
| 264 | 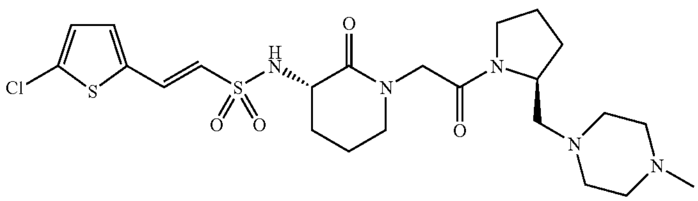 | HPLC (method 1) t$_R$ = 2.4 min LRMS (ESI, pos. ion spectrum) m/z 544/546 (M + H) | prepared using the method described in Example 613 part A using INT39 |
| 265 | 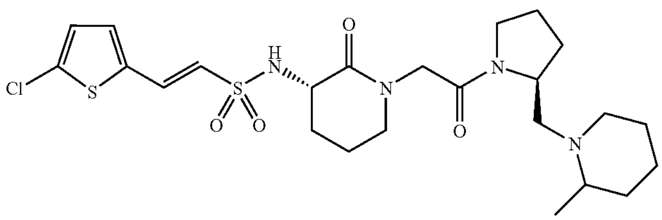 | HPLC (method 1) t$_R$ = 2.8 min LRMS (ESI, pos. ion spectrum) m/z 543/545 (M + H) | prepared using the method described in Example 613 part A using INT40 |
| 266 | 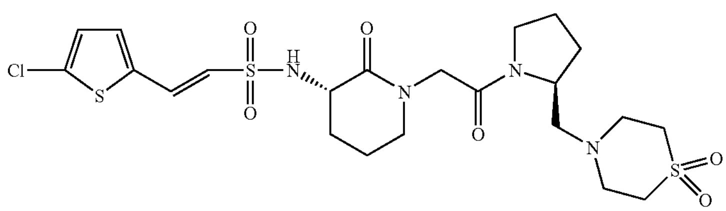 | HPLC (method 1) t$_R$ = 2.7 min LRMS (ESI, pos. ion spectrum) m/z 579/581 (M + H) | prepared using the method described in Example 613 part A using and INT41 |
| 267 | 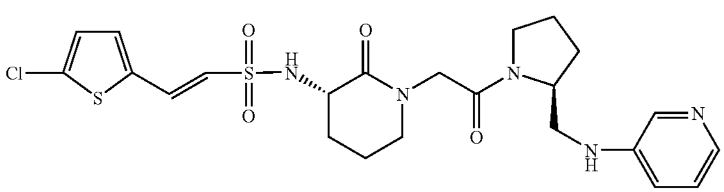 | HPLC (method 1) t$_R$ = 2.7 min LRMS (ESI, pos. ion spectrum) m/z 538/540 (M + H) | prepared using the method described in Example 613 part A using and INT34 |
| 268 | 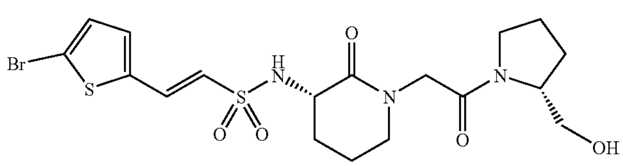 | HPLC (method 1) t$_R$ = 2.8 min LCMS (ESI, pos. ion spectrum) m/z 506/508 (M + H) | prepared using the method described in Example 130 using INT12 |

TABLE 2-continued

| Ex # | Structure | characterization | method |
|---|---|---|---|
| 269 | 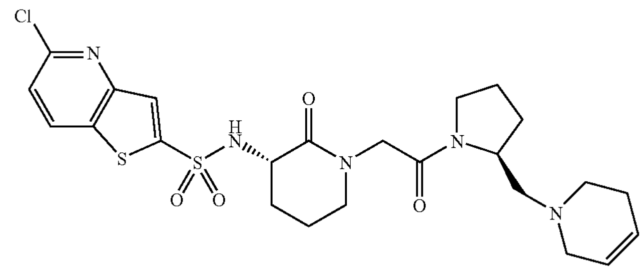 | HPLC (method 1) $t_R$ = 2.1 min LCMS (ESI, pos. ion spectrum) m/z 552/554 (M + H) | prepared using the method described in Example 130 using INT14 and INT49 |
| 270 | 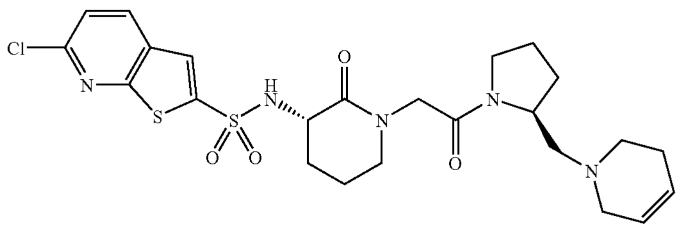 | HPLC (method 1) $t_R$ = 2.2 min LCMS (ESI, pos. ion spectrum) m/z 552/554 (M + H) | prepared using the method described in Example 130 using INT13 and INT49 |
| 271 | 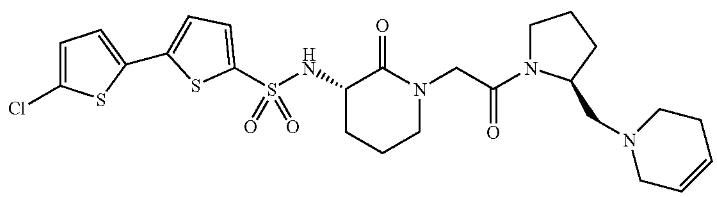 | HPLC (method 1) $t_R$ = 2.8 min LCMS (ESI, pos. ion spectrum) m/z 583/585 (M + H) | prepared using the method described in Example 130 using INT18 and INT49 |
| 272 | 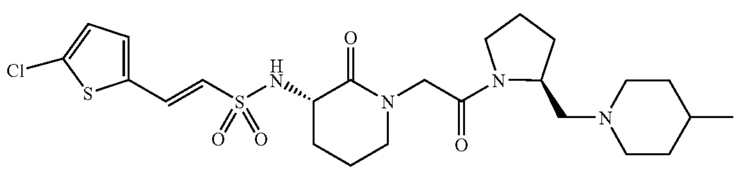 | HPLC (method 1) $t_R$ = 2.4 min LCMS (ESI, pos. ion spectrum) m/z 543/545 (M + H) | prepared using the method described in Example 130 using INT11 and INT51 |
| 273 | 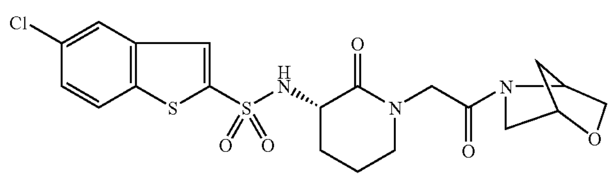 | HPLC (method 1) $t_R$ = 3.2 min LCMS (ESI, pos. ion spectrum) m/z 484/486 (M + 1) | Prepared using the method described in Example 48 using INT17 |
| 274 | 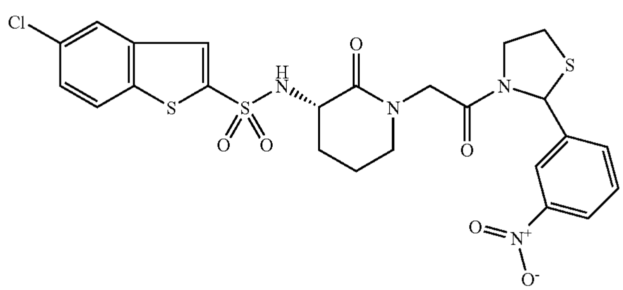 | HPLC (method 1) $t_R$ = 3.8 min LCMS (ESI, pos. ion spectrum) m/z 595/597 (M + 1) | Prepared using the method described in Example 48 using INT17 |
| 275 | 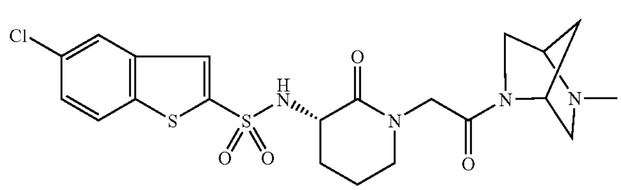 | HPLC (method 1) $t_R$ = 2.8 min LCMS (ESI, pos. ion spectrum) m/z 497/499 (M + 1) | Prepared using the method described in Example 48 using INT17 |

TABLE 2-continued

| Ex # | Structure | characterization | method |
|---|---|---|---|
| 276 | 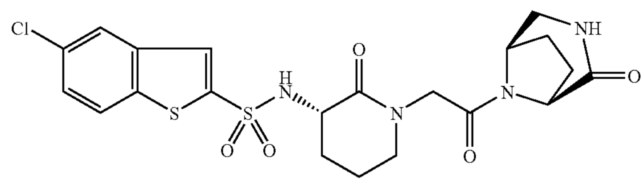 | HPLC (method 1) t_R = 3.2 min LCMS (ESI, pos. ion spectrum) m/z 511/513 (M + 1) | Prepared using the method described in Example 48 using INT17 |
| 277 | 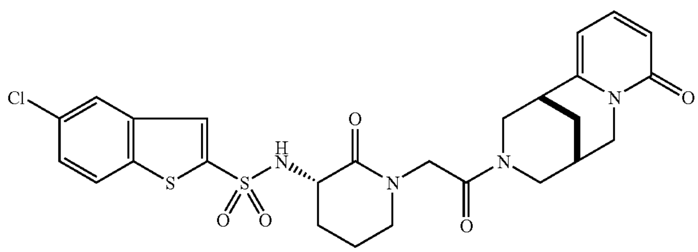 | HPLC (method 1) t_R = 2.9 min LCMS (ESI, pos. ion spectrum) m/z 575/577 (M + 1) | prepared using the method described in Example 130 using INT17 |
| 278 | 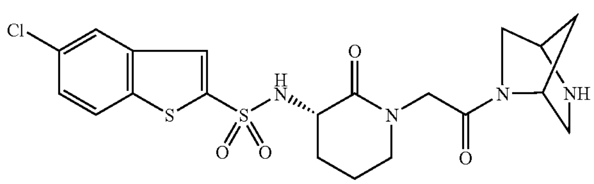 | HPLC (method 1) t_R = 2.9 min LCMS (ESI, pos. ion spectrum) m/z 484/485 (M + 1) | Prepared using the method described in Example 48 using INT17 |
| 279 | 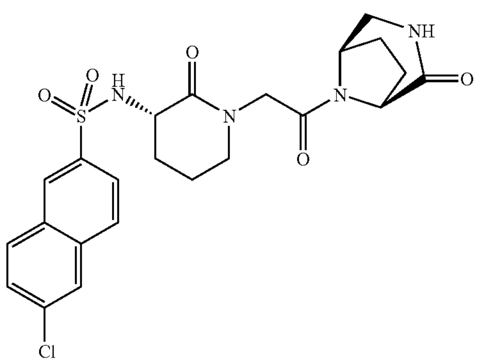 | HPLC (method 1) t_R = 3.2 min LCMS (ESI, pos. ion spectrum) m/z 505/507 (M + 1) | Prepared using the method described in Example 48 using INT15 |
| 280 | 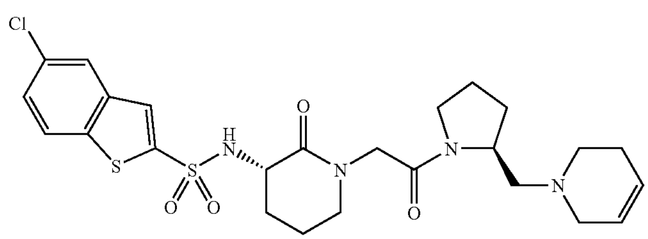 | HPLC (method 1) t_R = 2.4 min LCMS (ESI, pos. ion spectrum) m/z 551/553 (M + H) | prepared using the method described in Example 130 using INT17 and INT49 |
| 281 | 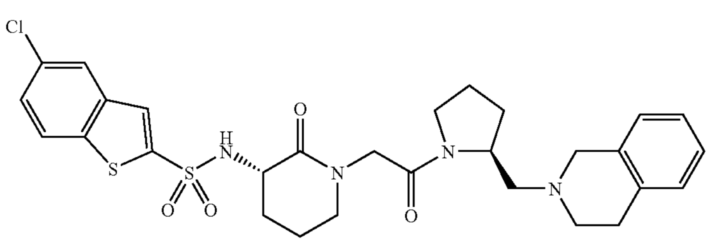 | HPLC (method 1) t_R = 2.8 min LCMS (ESI, pos. ion spectrum) m/z 601/603 (M + H) | prepared using the method described in Example 130 using INT17 and INT52 |

TABLE 2-continued

| Ex # | Structure | characterization | method |
|---|---|---|---|
| 282 | 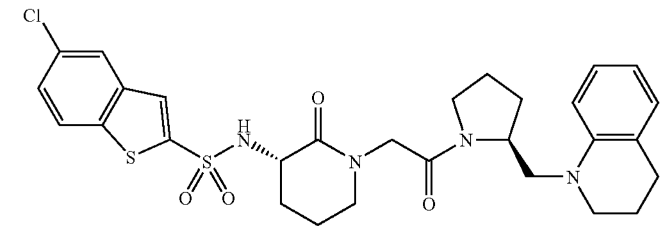 | HPLC (method 1) t_R = 4.0 min LCMS (ESI, pos. ion spectrum) m/z 601/603 (M + H) | prepared using the method described in Example 130 using INT17 and INT53 |
| 283 | 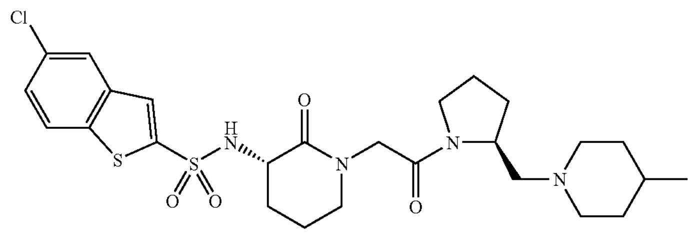 | HPLC (method 1) t_R = 2.7 min LCMS (ESI, pos. ion spectrum) m/z 567/569 (M + H) | prepared using the method described in Example 130 using INT17 and INT51 |
| 284 | 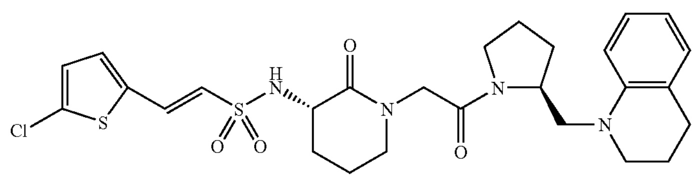 | HPLC (method 1) t_R = 3.8 min LCMS (ESI, pos. ion spectrum) m/z 577/579 (M + 1) | prepared using the method described in Example 130 using INT11 and INT53 |
| 285 | 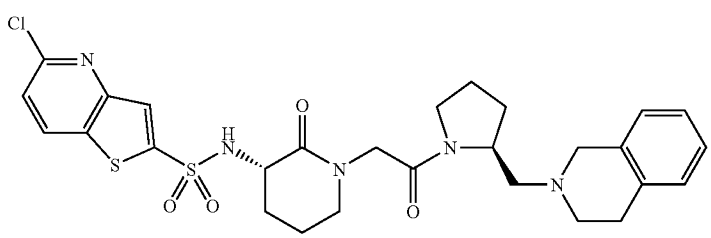 | HPLC (method 1) t_R = 2.4 min LCMS (ESI, pos. ion spectrum) m/z 602/604 (M + H) | prepared using the method described in Example 130 using INT14 and INT52 |
| 286 | 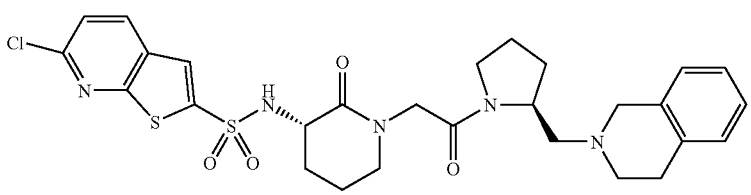 | HPLC (method 1) t_R = 2.6 min LCMS (ESI, pos. ion spectrum) m/z 602/604 (M + H) | prepared using the method described in Example 130 using INT13 and INT52 |
| 287 | 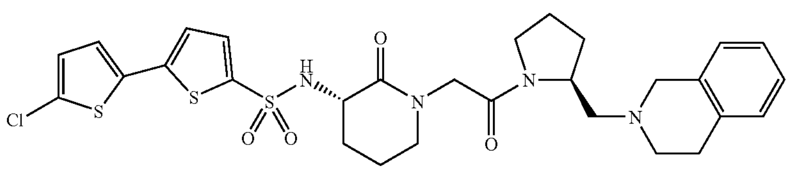 | HPLC (method 1) t_R = 3.1 min LCMS (ESI, pos. ion spectrum) m/z 633/635 (M + H) | prepared using the method described in Example 130 using INT18 and INT52 |
| 288 | 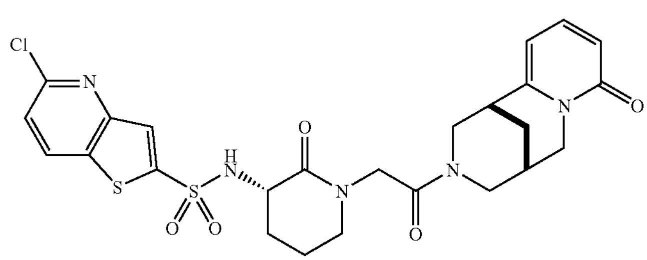 | HPLC (method 1) t_R = 2.4 min LCMS (ESI, pos. ion spectrum) m/z 576/578 (M + H) | prepared using the method described in Example 130 using INT14 |

TABLE 2-continued

| Ex # | Structure | characterization | method |
|---|---|---|---|
| 289 | 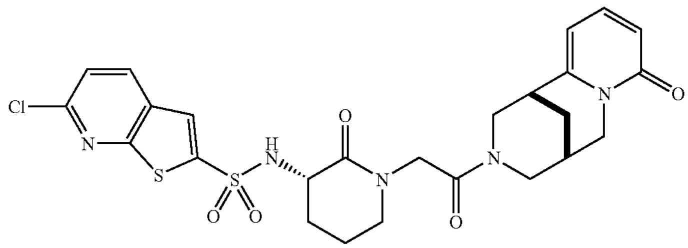 | HPLC (method 1) t_R = 2.6 min LCMS (ESI, pos. ion spectrum) m/z 576/578 (M + H) | prepared using the method described in Example 130 using INT13 |
| 290 | 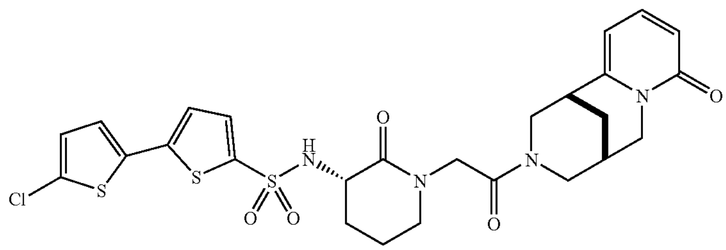 | HPLC (method 1) t_R = 3.2 min LCMS (ESI, pos. ion spectrum) m/z 607/609 (M + H) | prepared using the method described in Example 130 using INT18 |
| 291 | 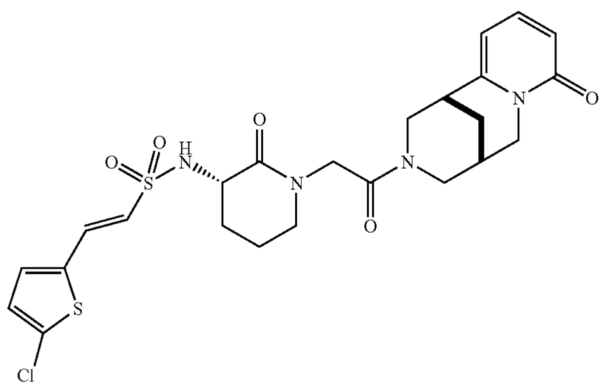 | HPLC (method 1) t_R = 3.0 min LRMS (ESI, pos. ion spectrum) m/z 551/553 (M + H) | prepared using the method described in Example 613 part A |
| 292 | 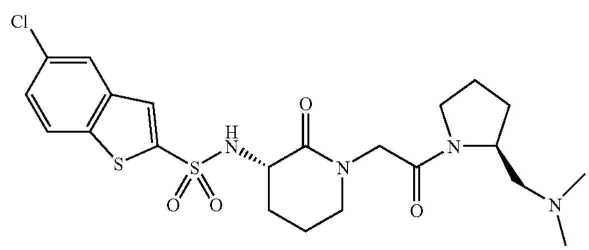 | HPLC (method 1) t_R = 2.4 min LCMS (ESI, pos. ion spectrum) m/z 513/515 (M + H) | Title compound of Example 292 |
| 293 | 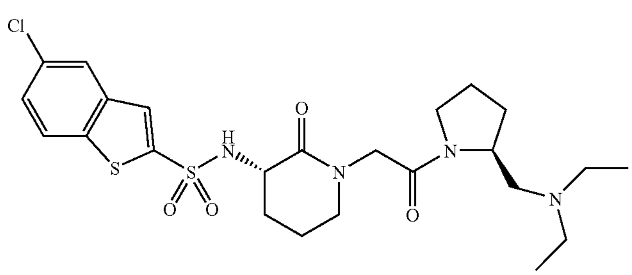 | HPLC (method 1) t_R = 2.5 min LCMS (ESI, pos. ion spectrum) m/z 541/543 (M + H) | prepared using the method described in Example 292 using INT23 |

TABLE 2-continued

| Ex # | Structure | characterization | method |
|---|---|---|---|
| 294 | 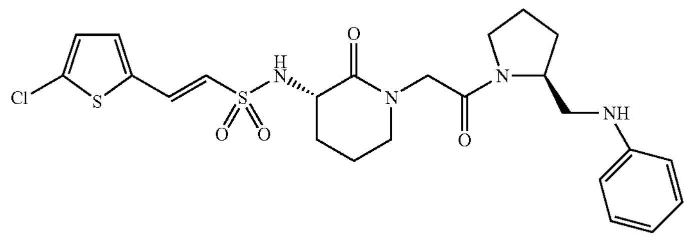 | HPLC (method 1) t_R = 3.0 min LCMS (ESI, pos. ion spectrum) m/z 537/539 (M + H) | prepared using the method described in Example 130 using INT11 |
| 295 | 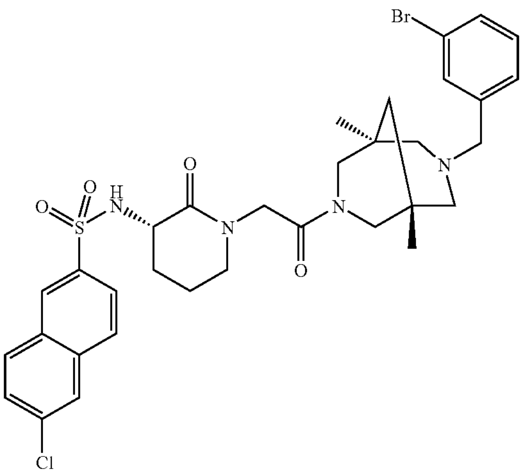 | HPLC (method 1) t_R = 3.5 min LCMS (ESI, pos. ion spectrum) m/z 745/747/749 (M + 1) | Prepared using the method described in Example 48 using INT10 |
| 296 | 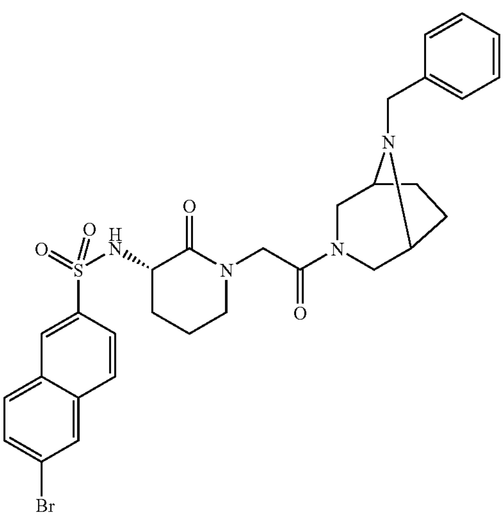 | HPLC (method 1) t_R = 3.2 min LCMS (ESI, pos. ion spectrum) m/z 625/627 (M + 1) | Prepared using the method described in Example 48 using INT10 |

TABLE 2-continued

| Ex # | Structure | characterization | method |
|---|---|---|---|
| 297 | 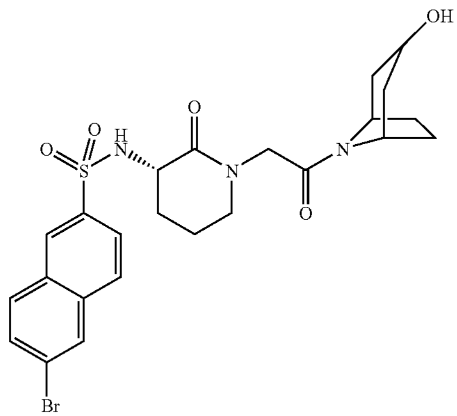 | HPLC (method 1) $t_R$ = 3.2 min LCMS (ESI, pos. ion spectrum) m/z 550/552 (M + 1) | Prepared using the method described in Example 48 using INT10 |
| 298 | 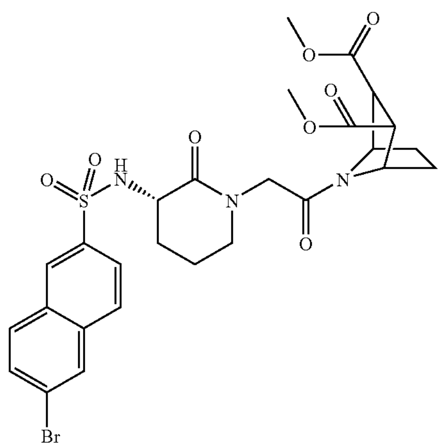 | HPLC (method 1) $t_R$ = 3.6 min LCMS (ESI, pos. ion spectrum) m/z 636/638 (M + 1) | Prepared using the method described in Example 48 using INT10 |
| 299 | 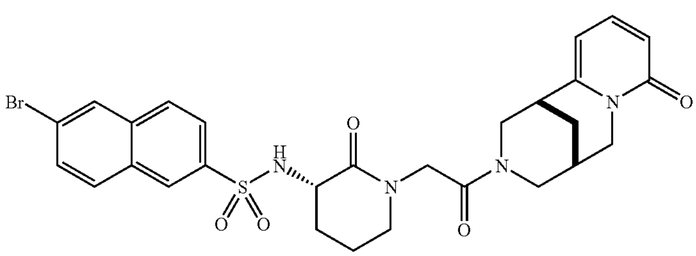 | HPLC (method 1) $t_R$ = 3.4 min LCMS (ESI, pos. ion spectrum) m/z 613/615 (M + 1) | Prepared using the method described in Example 48 using INT10 |
| 300 | 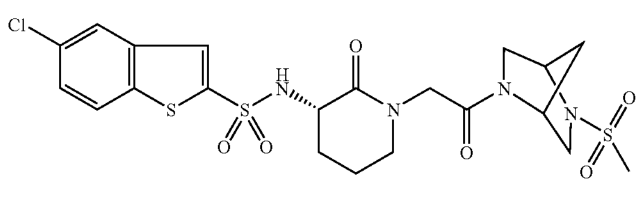 | HPLC (method 1) $t_R$ = 3.2 min LCMS (ESI, pos. ion spectrum) m/z 561/563 (M + 1) | From title compound of Example 278 using the using the method described in Example 21 |
| 301 | 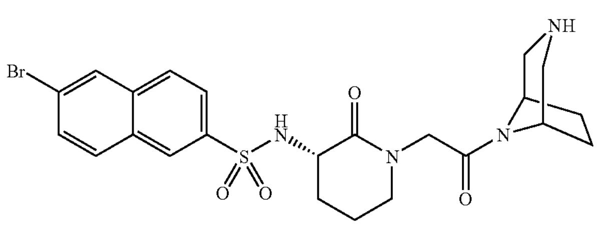 | HPLC (method 1) $t_R$ = 2.9 min LCMS (ESI, pos. ion spectrum) m/z 535/537 (M + 1) | Prepared using INT10 using the methods described in Example 48 and Example 178 part B |

TABLE 2-continued

| Ex # | Structure | characterization | method |
|---|---|---|---|
| 302 | 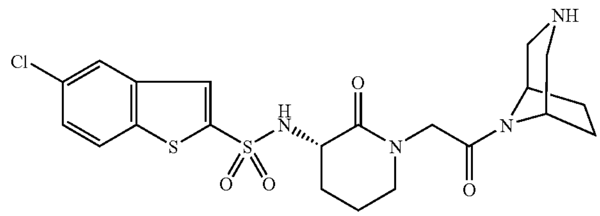 | HPLC (method 1) t_R = 2.8 min LCMS (ESI, pos. ion spectrum) m/z 497/499 (M + 1) | Prepared using INT17 using the methods described in Example 48 and Example 178 part B |
| 303 | 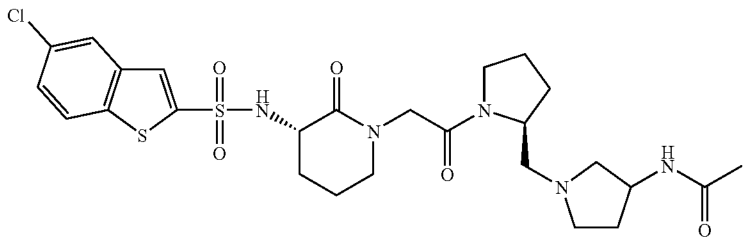 | HPLC (method 1) t_R = 3.0 min LRMS (ESI, pos. ion spectrum) m/z 596/598 (M + H) | prepared using the method described in Example 613 part A and INT33 and INT17 |
| 304 | 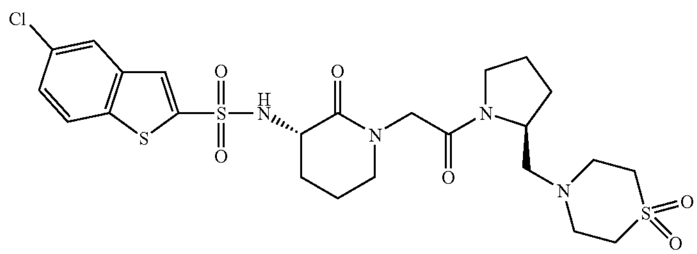 | HPLC (method 1) t_R = 3.0 min LRMS (ESI, pos. ion spectrum) m/z 603/605 (M + H) | prepared using the method described in Example 613 part A and INT41 and INT17 |
| 305 | 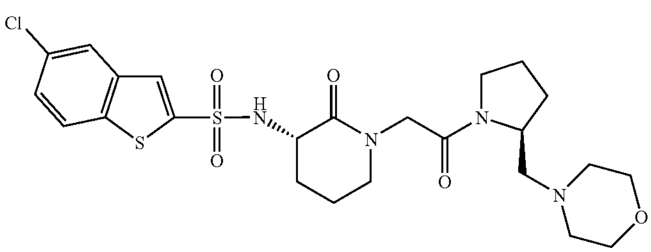 | HPLC (method 1) t_R = 2.9 min LRMS (ESI, pos. ion spectrum) m/z 555/557 (M + H) | prepared using the method described in Example 613 part A and INT17 and INT5 |
| 306 | 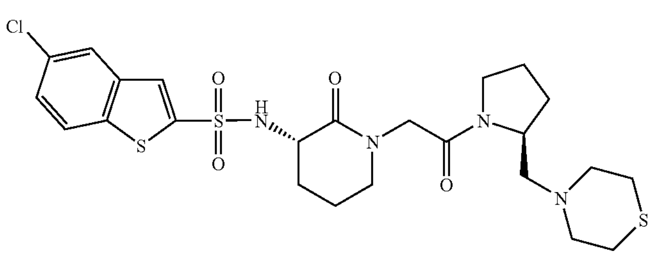 | HPLC (method 1) t_R = 3.0 min LRMS (ESI, pos. ion spectrum) m/z 571/573 (M + H) | prepared using the method described in Example 613 part A and INT17 and INT32 |
| 307 | 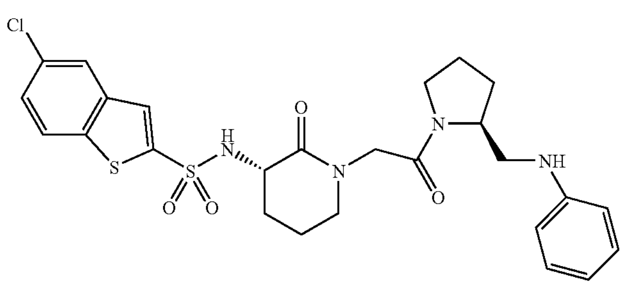 | HPLC (method 1) t_R = 3.3 min LCMS (ESI, pos. ion spectrum) m/z 561/563 (M + H) | prepared using the method described in Example 130 using INT17 |

TABLE 2-continued

| Ex # | Structure | characterization | method |
|---|---|---|---|
| 308 | 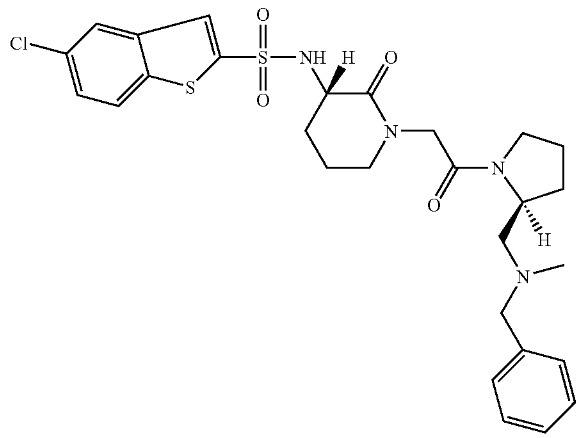 | HPLC (method 3) t_R = 3.0 min LCMS (ESI, pos. ion spectrum) m/z 589/591 (M + 1) | prepared using the method described in Example 400 using INT23 |
| 309 | 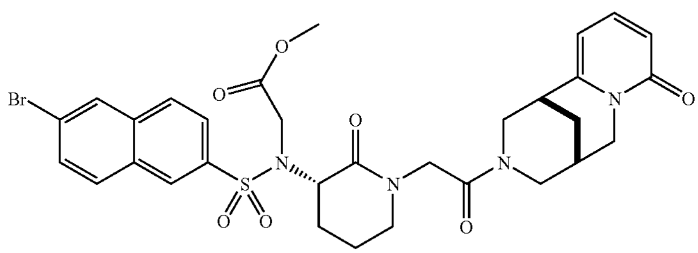 | HPLC (method 9) t_R = 1.6 min LCMS (method 6) (ESI, pos. ion spectrum) m/z 685 (M + 1) | prepared using the methods described in Example 148 Part A using the title compound of Example 299 |
| 310 | 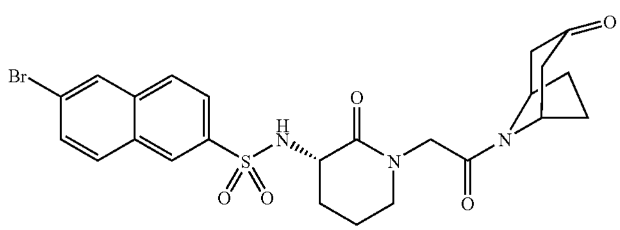 | HPLC (method 1) t_R = 3.4 min LCMS (ESI, pos. ion spectrum) m/z 548/550 (M + 1) | Prepared using the method described in Example 48 using INT10 |
| 311 | 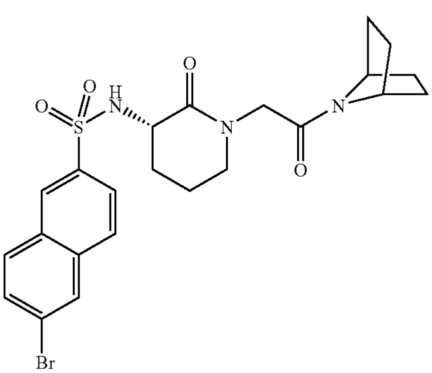 | HPLC (method 1) t_R = 3.5 min LCMS (ESI, pos. ion spectrum) m/z 520/522 (M + 1) | Title compound of Example 311 |
| 312 | 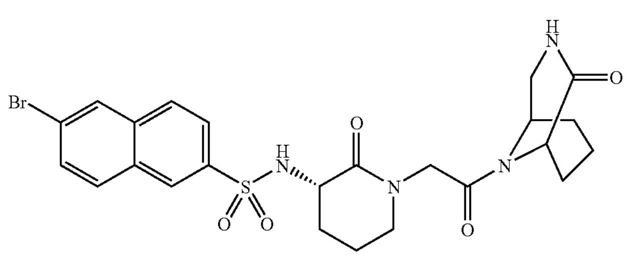 | HPLC (method 1) t_R = 3.3 min LCMS (ESI, pos. ion spectrum) m/z 563/565 (M + 1) | Prepared using the method described in Example 48 using INT10 |

TABLE 2-continued

| Ex # | Structure | characterization | method |
|---|---|---|---|
| 313 | 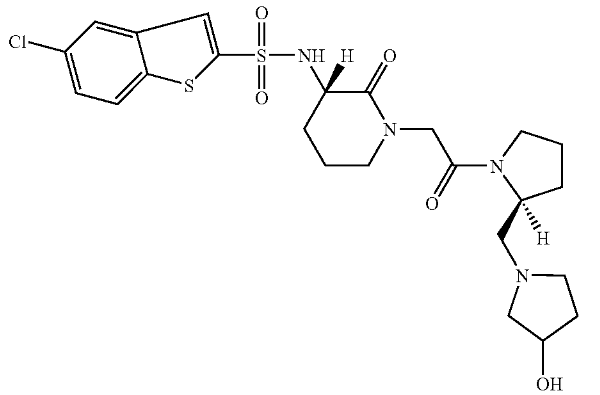 | HPLC (method 4) $t_R$ = 1.4 min LCMS (ESI, pos. ion spectrum) m/z 555/557 (M + 1) | prepared using the method described in Example 400 using INT23 |
| 314 | 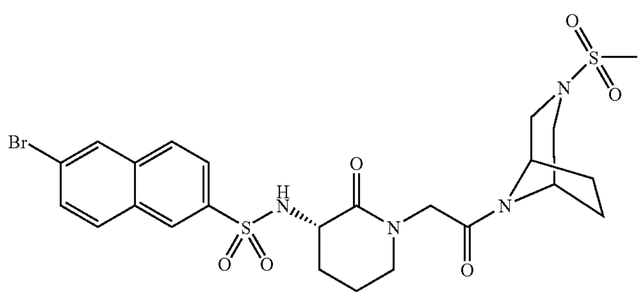 | HPLC (method 1) $t_R$ = 3.4 min LCMS (ESI, pos. ion spectrum) m/z 613/615 (M + 1) | Prepared From the title compound of Example 301 using the method described in Example 21 |
| 315 | 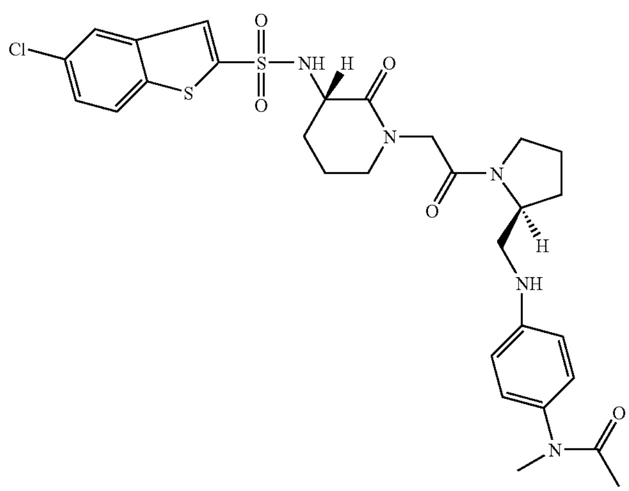 | HPLC (method 3) $t_R$ = 3.1 min LCMS (ESI, pos. ion spectrum) m/z 632/634 (M + 1) | prepared using the method described in Example 400 using INT23 |
| 316 | 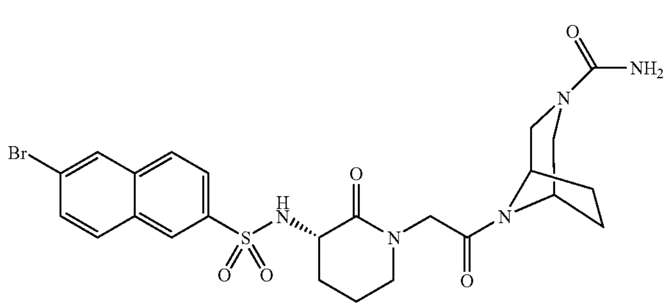 | HPLC (method 1) $t_R$ = 3.3 min LCMS (ESI, pos. ion spectrum) m/z 578/580 (M + 1) | Title compound of Example 316 |

TABLE 2-continued

| Ex # | Structure | characterization | method |
| --- | --- | --- | --- |
| 317 | 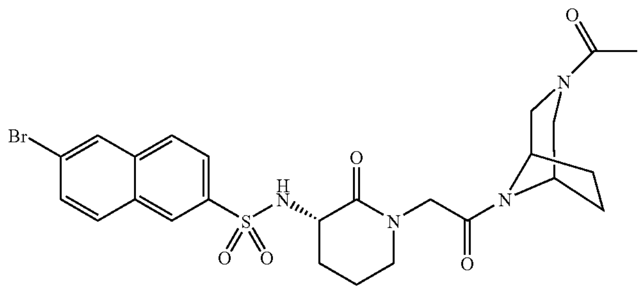 | HPLC (method 1) t_R = 3.4 min LCMS (ESI, pos. ion spectrum) m/z 577/579 (M + 1) | Title compound of Example 317 |
| 318 | 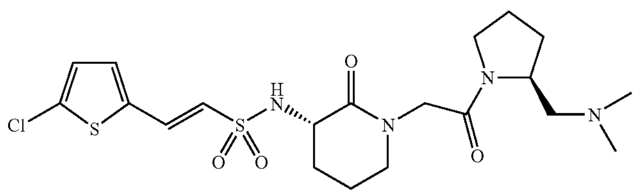 | HPLC (method 1) t_R = 2.1 min LCMS (ESI, pos. ion spectrum) m/z 489/491 (M + H) | prepared using the method described in Example 130 using INT11 |
| 319 | 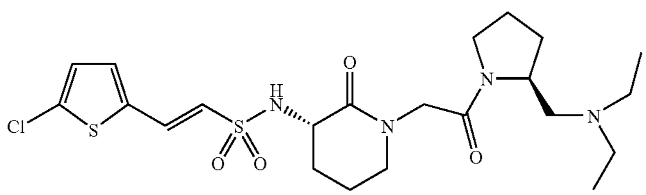 | HPLC (method 1) t_R = 2.2 min LCMS (ESI, pos. ion spectrum) m/z 517/519 (M + H) | prepared using the method described in Example 130 using INT11 |
| 320 | 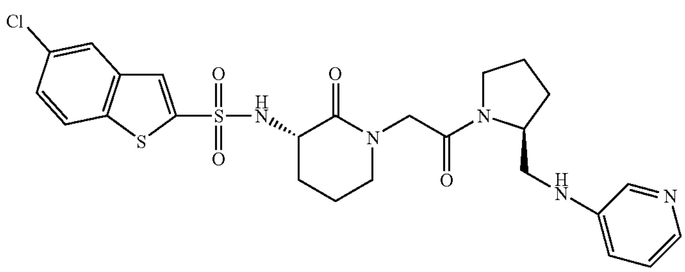 | HPLC (method 1) t_R = 2.9 min LRMS (ESI, pos. ion spectrum) m/z 561/563 (M+) | prepared using the method described in Example 613 part A and INT17 and INT34 |
| 321 | 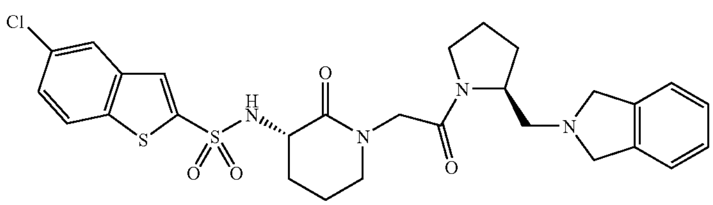 | HPLC (method 1) t_R = 2.8 min LCMS (ESI, pos. ion spectrum) m/z 587/589 (M + H) | prepared using the method described in Example 400 using INT23 |
| 322 | 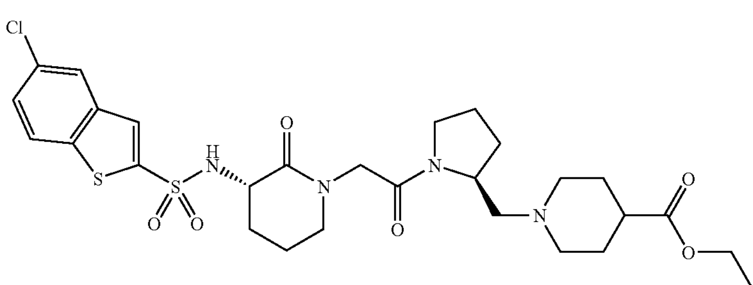 | HPLC (method 2) t_R = 1.4 min LCMS (ESI, pos. ion spectrum) m/z 625/627 (M + H) | prepared using the method described in Example 400 using INT23 |

TABLE 2-continued

| Ex # | Structure | characterization | method |
|---|---|---|---|
| 323 | 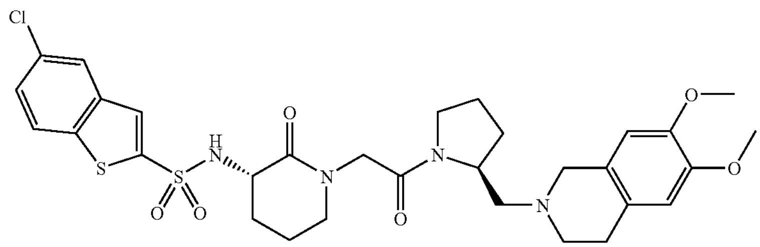 | HPLC (method 2) $t_R$ = 1.4 min LCMS (ESI, pos. ion spectrum) m/z 661/663 (M + H) | prepared using the method described in Example 400 using INT23 |
| 324 | 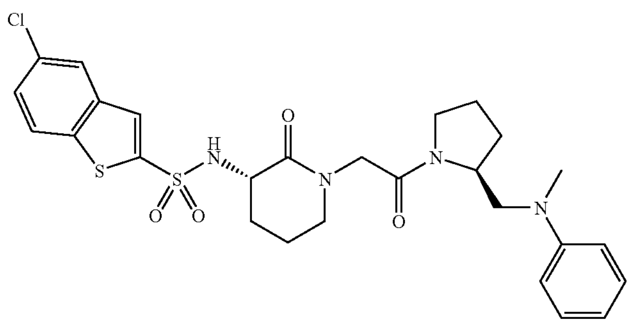 | HPLC (method 2) $t_R$ = 1.8 min LCMS (ESI, pos. ion spectrum) m/z 575/577 (M + H) | prepared using the method described in Example 400 using INT23 |
| 325 | 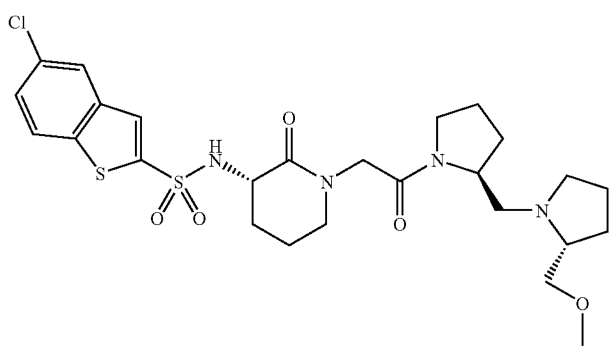 | HPLC (method 2) $t_R$ = 1.4 min LCMS (ESI, pos. ion spectrum) m/z 583/585 (M + H) | prepared using the method described in Example 400 using INT23 |
| 326 | 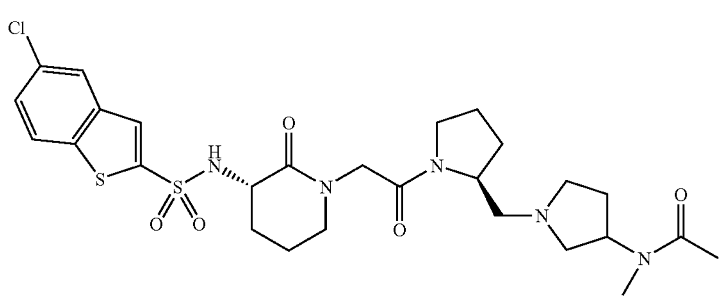 | HPLC (method 2) $t_R$ = 1.4 min LCMS (ESI, pos. ion spectrum) m/z 610/612 (M + H) | prepared using the method described in Example 400 using INT23 |

| Ex # | Structure | characterization | method |
|---|---|---|---|
| 327 | 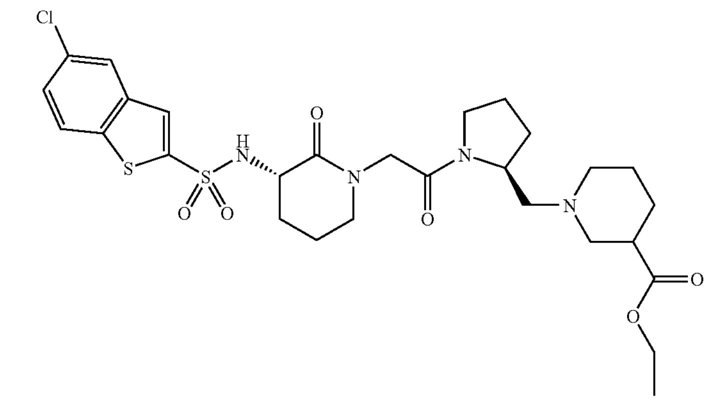 | HPLC (method 2) $t_R$ = 1.5 min LCMS (ESI, pos. ion spectrum) m/z 625/627 (M + H) | prepared using the method described in Example 400 using INT23 |
| 328 | 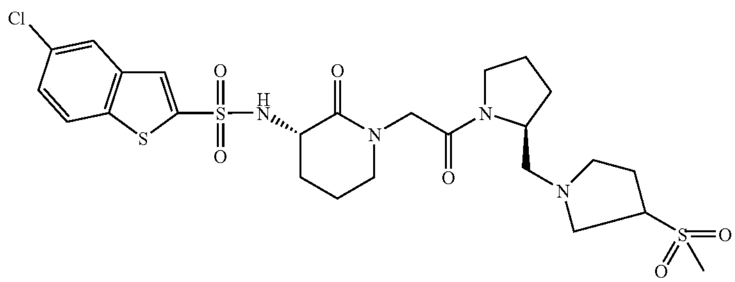 | HPLC (method 1) $t_R$ = 2.9 min LRMS (ESI; pos. ion spectrum) m/z 616/618 (M + H) | prepared using the method described in Example 613 part A and INT17 and INT35 |
| 329 | 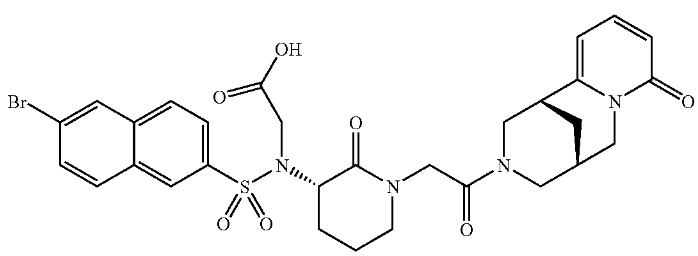 | HPLC (method 9) $t_R$ = 1.5 min LCMS (method 6) (ESI, pos. ion spectrum) m/z 671 (M + 1) | prepared using the methods described in Example INT3 part B using the title compound of Example 309 |
| 330 | 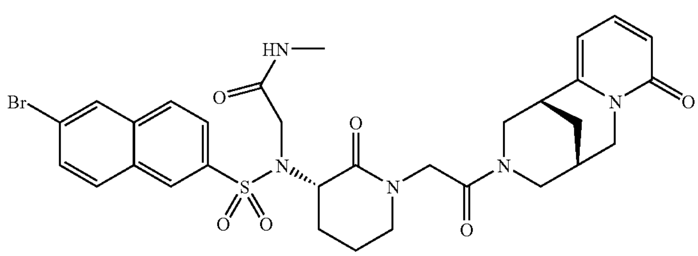 | HPLC (method 10) $t_R$ = 7.2 min LCMS (method 6) (ESI, pos. ion spectrum) m/z 684 (M + 1) | prepared using the methods described in Example 130 using the title compound of Example 329 |
| 331 | 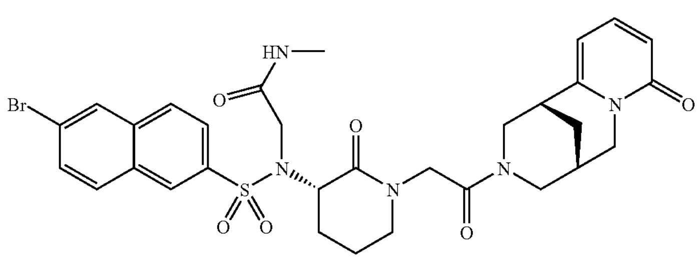 | HPLC (method 5) $t_R$ = 1.0 min LCMS (ESI, pos. ion spectrum) m/z 509/511 (M + 1) | Title compound of Example 331 |

| Ex # | Structure | characterization | method |
|---|---|---|---|
| 332 | 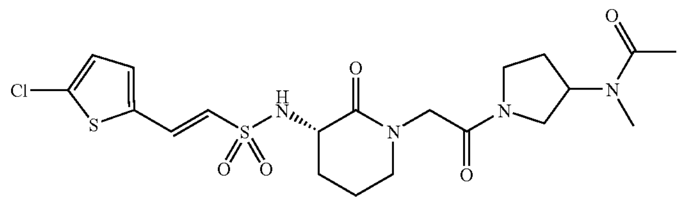 | HPLC (method 5) $t_R$ = 1.1 min LCMS (ESI, pos. ion spectrum) m/z 503/505 (M + 1) | prepared using the method described for Example 331 |
| 333 | 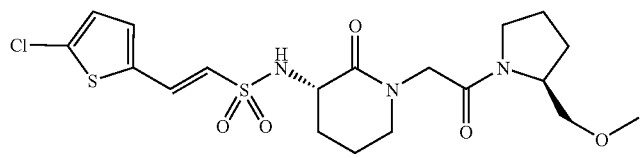 | HPLC (method 5) $t_R$ = 1.2 min LCMS (ESI, pos. ion spectrum) m/z 476/478 (M + 1) | prepared using the method described for Example 331 |
| 334 | 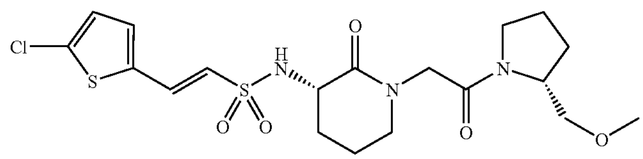 | HPLC (method 5) $t_R$ = 1.2 min LCMS (ESI, pos. ion spectrum) m/z 476/478 (M + 1) | prepared using the method described for Example 331 |
| 335 | 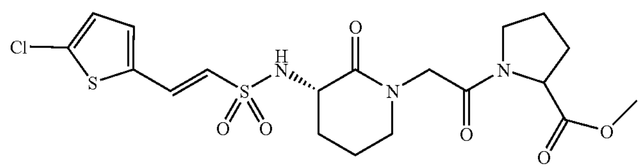 | HPLC (method 5) $t_R$ = 1.2 min LCMS (ESI, pos. ion spectrum) m/z 490/492 (M + 1) | prepared using the method described for Example 331 |
| 336 | 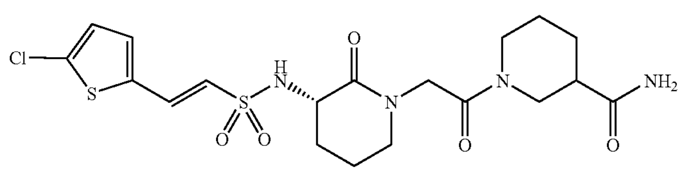 | HPLC (method 5) $t_R$ = 1.1 min LCMS (ESI, pos. ion spectrum) m/z 489/491 (M + 1) | prepared using the method described for Example 331 |
| 337 | 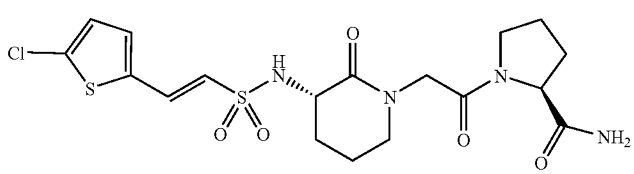 | HPLC (method 5) $t_R$ = 1.0 min LCMS (ESI, pos. ion spectrum) m/z 475/477 (M + 1) | prepared using the method described for Example 331 |
| 338 | 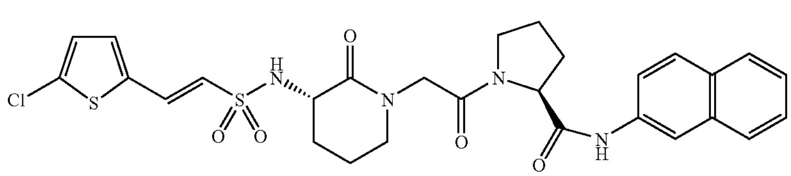 | HPLC (method 5) $t_R$ = 1.6 min LCMS (ESI, pos. ion spectrum) m/z 601/603 (M + 1) | prepared using the method described for Example 331 |
| 339 | 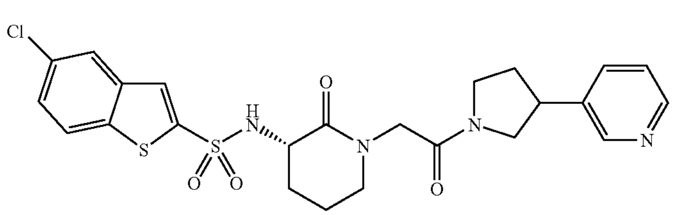 | HPLC (method 5) $t_R$ = 1.2 min LCMS (ESI, pos. ion spectrum) m/z 533/535 (M + 1) | prepared using the method described for Example 331 |

| Ex # | Structure | characterization | method |
|---|---|---|---|
| 340 | 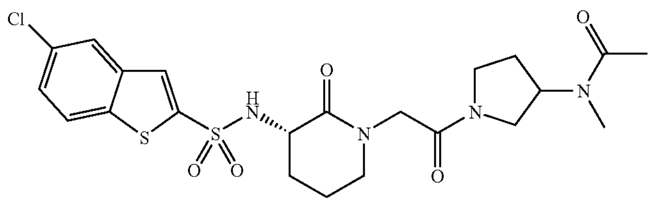 | HPLC (method 5) t_R = 1.3 min LCMS (ESI, pos. ion spectrum) m/z 527/529 (M + 1) | prepared using the method described for Example 331 |
| 341 | 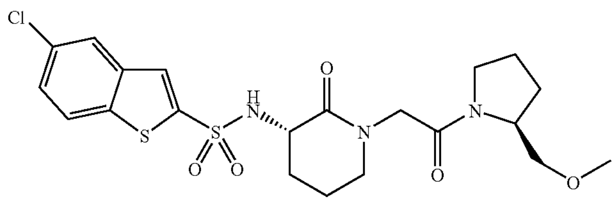 | HPLC (method 5) t_R = 1.3 min LCMS (ESI, pos. ion spectrum) m/z 500/502 (M + 1) | prepared using the method described for Example 331 |
| 342 | 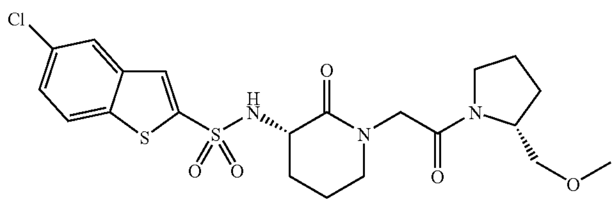 | HPLC (method 5) t_R = 1.3 min LCMS (ESI, pos. ion spectrum) m/z 500/502 (M + 1) | prepared using the method described for Example 331 |
| 343 | 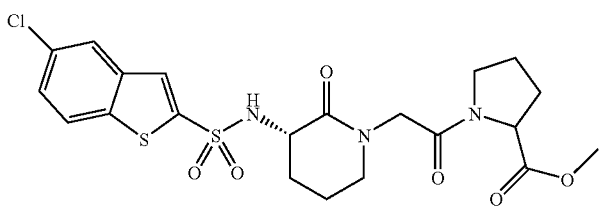 | HPLC (method 5) t_R = 1.3 min LCMS (ESI, pos. ion spectrum) m/z 514/516 (M + 1) | prepared using the method described for Example 331 |
| 344 | 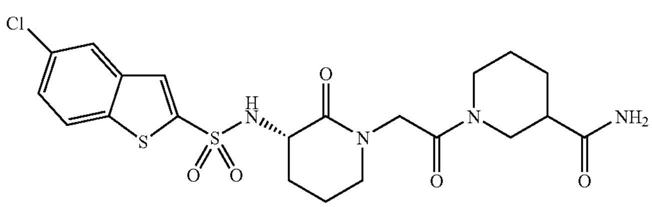 | HPLC (method 5) t_R = 1.2 min LCMS (ESI, pos. ion spectrum) m/z 513/515 (M + 1) | prepared using the method described for Example 331 |
| 345 | 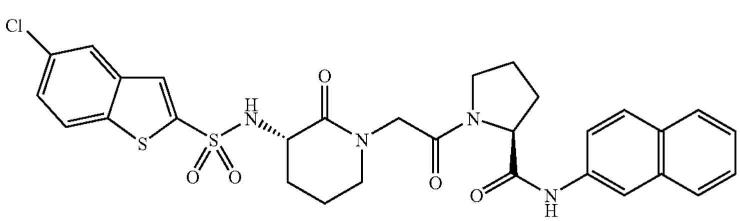 | HPLC (method 5) t_R = 1.6 min LCMS (ESI, pos. ion spectrum) m/z 625/627 (M + 1) | prepared using the method described for Example 331 |
| 346 | 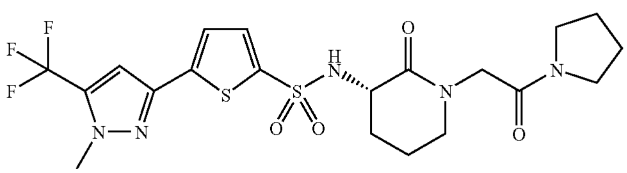 | HPLC (method 5) t_R = 1.3 min LCMS (ESI, pos. ion spectrum) m/z 520 (M + 1) | prepared using the method described for Example 331 |

-continued

| Ex # | Structure | characterization | method |
|---|---|---|---|
| 347 | 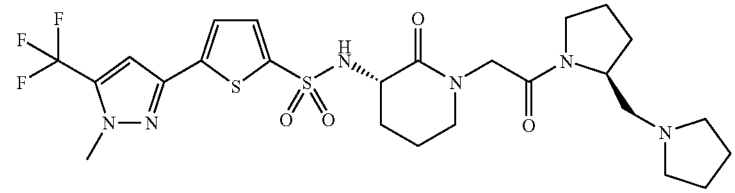 | HPLC (method 5) t_R = 1.2 min LCMS (ESI, pos. ion spectrum) m/z 603 (M + 1) | prepared using the method described for Example 331 |
| 348 | 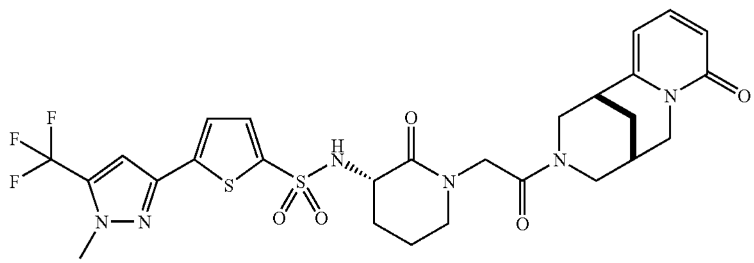 | HPLC (method 5) t_R = 1.3 min LCMS (ESI, pos. ion spectrum) m/z 639 (M + 1) | prepared using the method described for Example 331 |
| 349 | 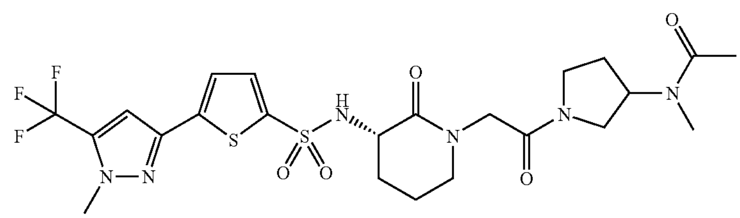 | HPLC (method 5) t_R = 1.2 min LCMS (ESI, pos. ion spectrum) m/z 591 (M + 1) | prepared using the method described for Example 331 |
| 350 | 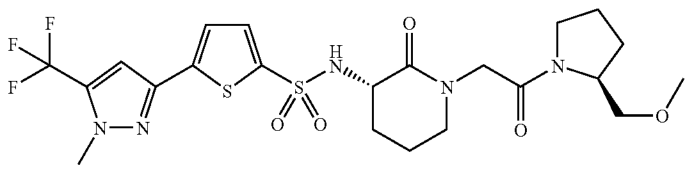 | HPLC (method 5) t_R = 1.3 min LCMS (ESI, pos. ion spectrum) m/z 564 (M + 1) | prepared using the method described for Example 331 |
| 351 | 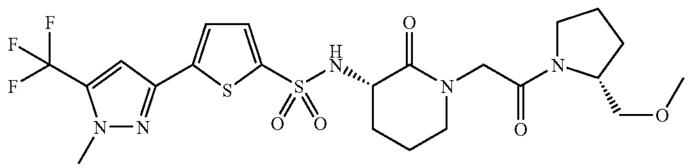 | HPLC (method 5) t_R = 1.3 min LCMS (ESI, pos. ion spectrum) m/z 564 (M + 1) | prepared using the method described for Example 331 |
| 352 | 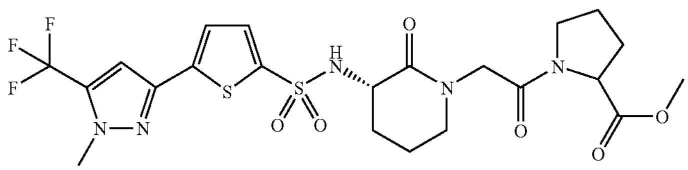 | HPLC (method 5) t_R = 1.3 min LCMS (ESI, pos. ion spectrum) m/z 578 (M + 1) | prepared using the method described for Example 331 |
| 353 | 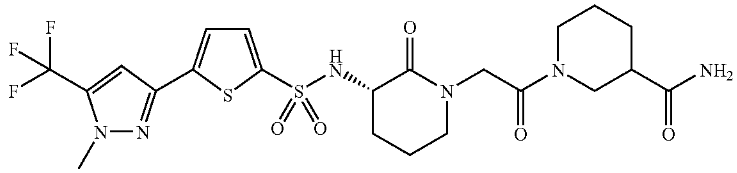 | HPLC (method 5) t_R = 1.8 min LCMS (ESI, pos. ion spectrum) m/z 577 (M + 1) | prepared using the method described for Example 331 |
| 354 | 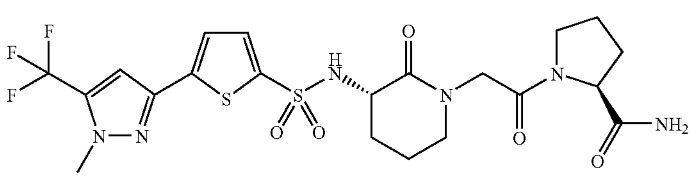 | HPLC (method 5) t_R = 1.2 min LCMS (ESI, pos. ion spectrum) m/z 563 (M + 1) | prepared using the method described for Example 331 |

-continued

| Ex # | Structure | characterization | method |
|---|---|---|---|
| 355 | 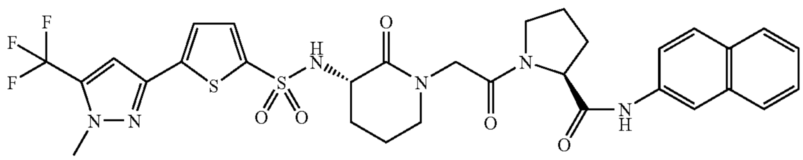 | HPLC (method 5) $t_R$ = 1.6 min LCMS (ESI, pos. ion spectrum) m/z 689 (M + 1) | prepared using the method described for Example 331 |
| 356 | 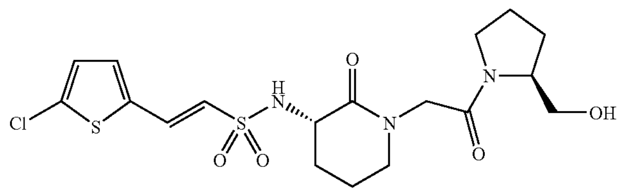 | HPLC (method 5) $t_R$ = 1.1 min LCMS (ESI, pos. ion spectrum) m/z 462/464 (M + 1) | prepared using the method described for Example 331 |
| 357 | 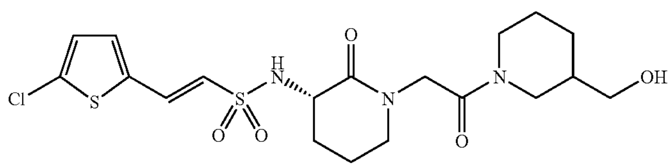 | HPLC (method 5) $t_R$ = 1.1 min LCMS (ESI, pos. ion spectrum) m/z 476/478 (M + 1) | prepared using the method described for Example 331 |
| 358 | 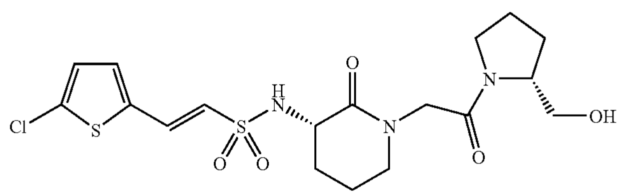 | HPLC (method 5) $t_R$ = 1.1 min LCMS (ESI, pos. ion spectrum) m/z 462/464 (M + 1) | prepared using the method described for Example 331 |
| 359 | 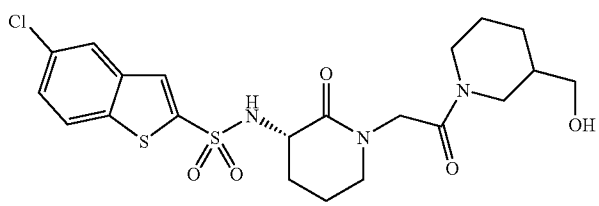 | HPLC (method 5) $t_R$ = 1.3 min LCMS (ESI, pos. ion spectrum) m/z 500/502 (M + 1) | prepared using the method described for Example 331 |
| 360 | 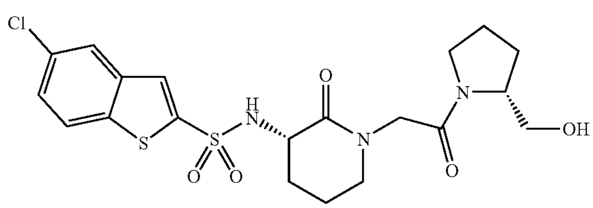 | HPLC (method 6) $t_R$ = 1.5 min LCMS (ESI, pos. ion spectrum) m/z 486/488 (M + 1) | prepared using the method described for Example 331 |
| 361 | 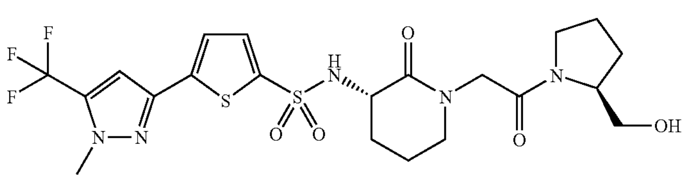 | HPLC (method 6) $t_R$ = 1.5 min LCMS (ESI, pos. ion spectrum) m/z 550 (M + 1) | prepared using the method described for Example 331 |
| 362 | 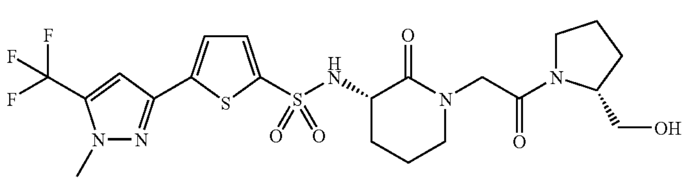 | HPLC (method 6) $t_R$ = 1.5 min LCMS (ESI, pos. ion spectrum) m/z 550 (M + 1) | prepared using the method described for Example 331 |

-continued

| Ex # | Structure | characterization | method |
|---|---|---|---|
| 363 | 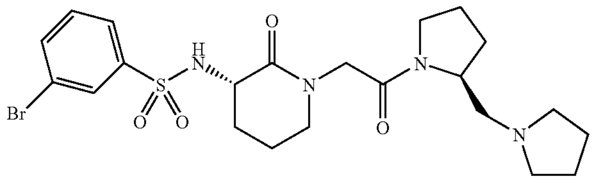 | HPLC (method 2) $t_R$ = 1.5 min LCMS (ESI, pos. ion spectrum) m/z 527/529 (M + 1) | prepared using the method described for Example 1 using INT9 |
| 364 | 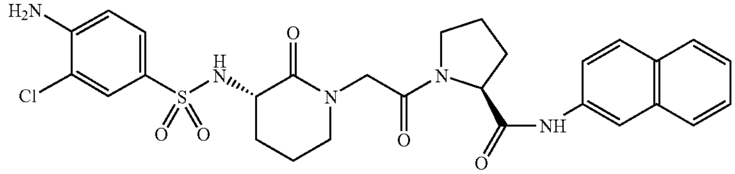 | HPLC (method 5) $t_R$ = 1.6 min LCMS (ESI, pos. ion spectrum) m/z 584/586 (M + 1) | prepared using the method described for Example 331 |
| 365 | 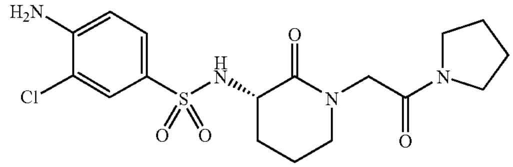 | HPLC (method 5) $t_R$ = 1.1 min LCMS (ESI, pos. ion spectrum) m/z 415/417 (M + 1) | prepared using the method described for Example 331 |
| 366 | 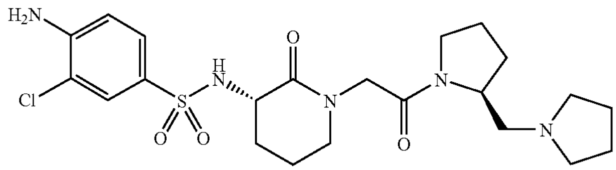 | HPLC (method 5) $t_R$ = 1.0 min LCMS (ESI, pos. ion spectrum) m/z 498/500 (M + 1) | prepared using the method described for Example 331 |
| 367 | 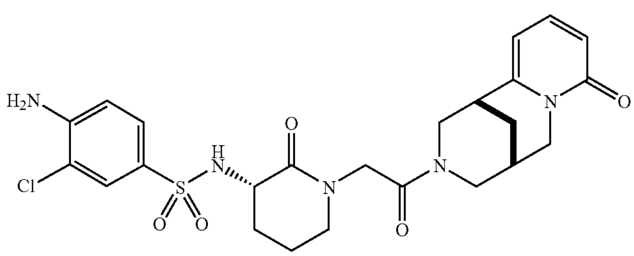 | HPLC (method 5) $t_R$ = 1.0 min LCMS (ESI, pos. ion spectrum) m/z 534/536 (M + 1) | prepared using the method described for Example 331 |
| 368 | 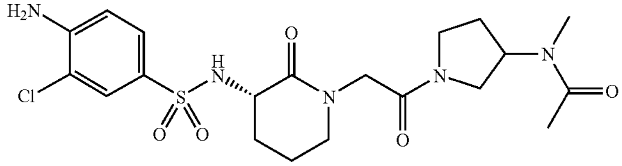 | HPLC (method 5) $t_R$ = 1.0 min LCMS (ESI, pos. ion spectrum) m/z 486/488 (M + 1) | prepared using the method described for Example 331 |
| 369 | 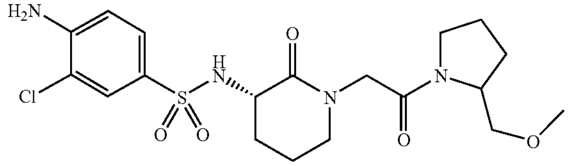 | HPLC (method 5) $t_R$ = 1.2 min LCMS (ESI, pos. ion spectrum) m/z 459/461 (M + 1) | prepared using the method described for Example 331 |
| 370 | 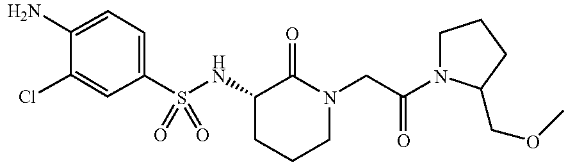 | HPLC (method 5) $t_R$ = 1.2 min LCMS (ESI, pos. ion spectrum) m/z 459/461 (M + 1) | prepared using the method described for Example 331 |

-continued

| Ex # | Structure | characterization | method |
|---|---|---|---|
| 371 | 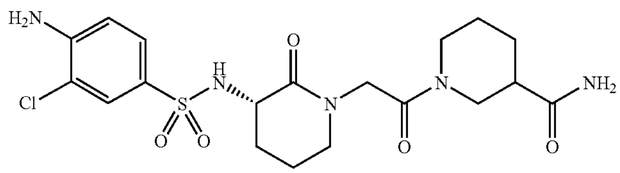 | HPLC (method 5) $t_R$ = 1.0 min LCMS (ESI, pos. ion spectrum) m/z 472/474 (M + 1) | prepared using the method described for Example 331 |
| 372 | 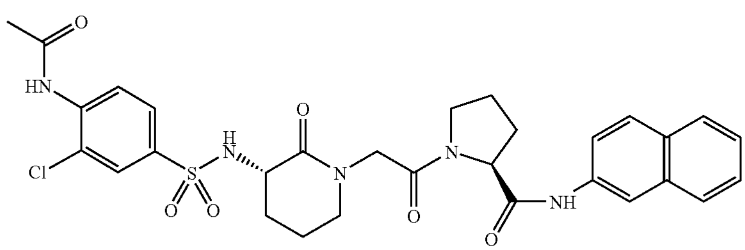 | HPLC (method 5) $t_R$ = 1.6 min LCMS (ESI, pos. ion spectrum) m/z 626/628 (M + 1) | Title compound of Example 372 |
| 373 | 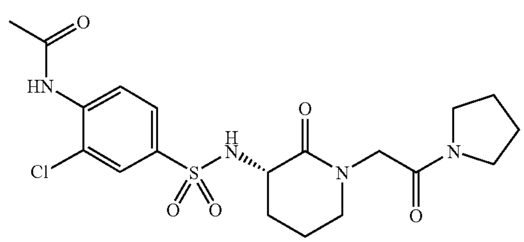 | HPLC (method 5) $t_R$ = 1.0 min LCMS (ESI, pos. ion spectrum) m/z 457/459 (M + 1) | prepared using the method described for Example 372 |
| 374 | 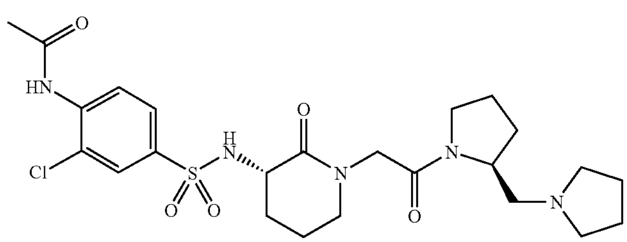 | HPLC (method 5) $t_R$ = 1.0 min LCMS (ESI, pos. ion spectrum) m/z 540/542 (M + 1) | prepared using the method described for Example 372 |
| 375 | 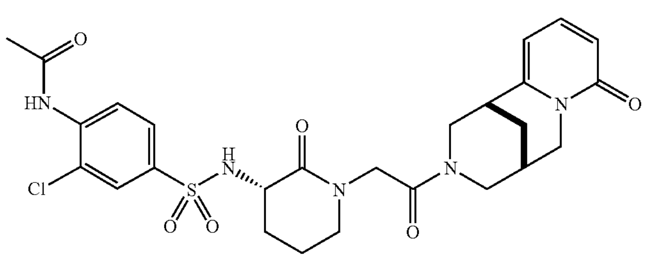 | HPLC (method 5) $t_R$ = 1.0 min LCMS (ESI, pos. ion spectrum) m/z 576/578 (M + 1) | prepared using the method described for Example 372 |
| 376 | 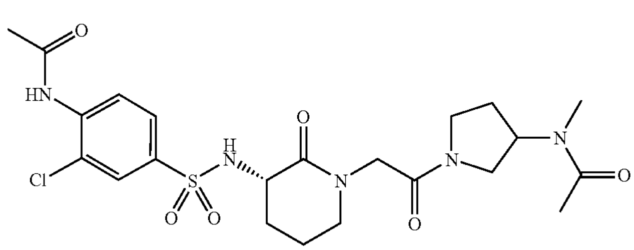 | HPLC (method 5) $t_R$ = 1.0 min LCMS (ESI, pos. ion spectrum) m/z 528/530 (M + 1) | prepared using the method described for Example 372 |

-continued

| Ex # | Structure | characterization | method |
|---|---|---|---|
| 377 | 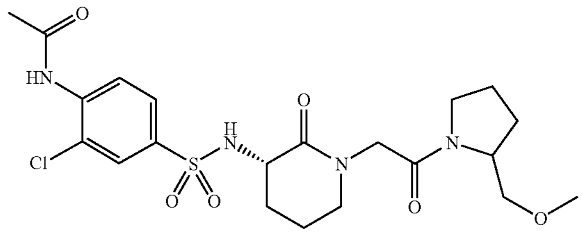 | HPLC (method 5) t$_R$ = 1.1 min LCMS (ESI, pos. ion spectrum) m/z 501/503 (M + 1) | prepared using the method described for Example 372 |
| 378 | 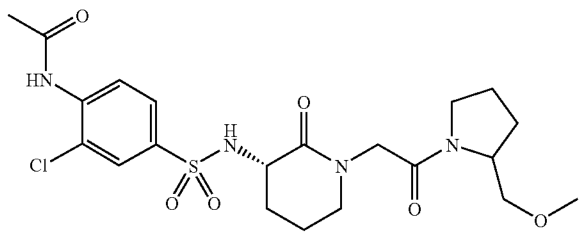 | HPLC (method 5) t$_R$ = 1.1 min LCMS (ESI, pos. ion spectrum) m/z 501/503 (M + 1) | prepared using the method described for Example 372 |
| 379 | 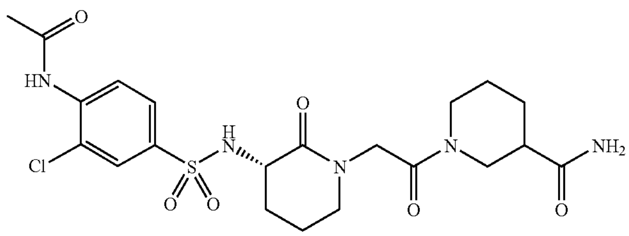 | HPLC (method 5) t$_R$ = 0.9 min LCMS (ESI, pos. ion spectrum) m/z 514/516 (M + 1) | prepared using the method described for Example 372 |
| 380 | 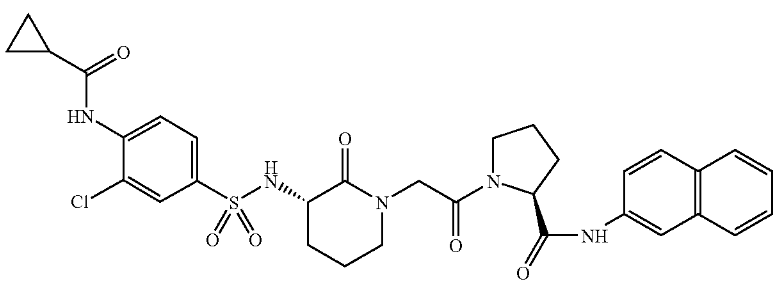 | HPLC (method 5) t$_R$ = 1.7 min LCMS (ESI, pos. ion spectrum) m/z 652/654 (M + 1) | prepared using the method described for Example 372 |
| 381 | 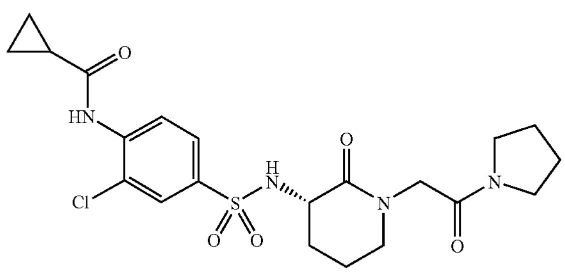 | HPLC (method 5) t$_R$ = 1.3 min LCMS (ESI, pos. ion spectrum) m/z 483/485 (M + 1) | prepared using the method described for Example 372 |
| 382 | 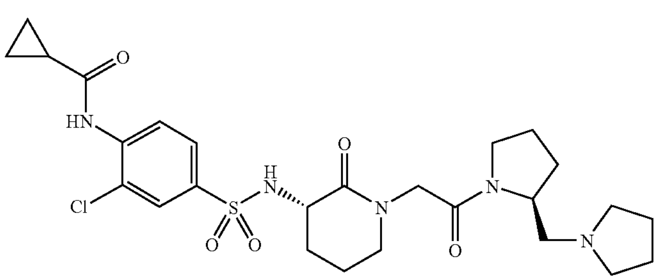 | HPLC (method 5) t$_R$ = 1.2 min LCMS (ESI, pos. ion spectrum) m/z 566/568 (M + 1) | prepared using the method described for Example 372 |

| Ex # | Structure | characterization | method |
| --- | --- | --- | --- |
| 383 | 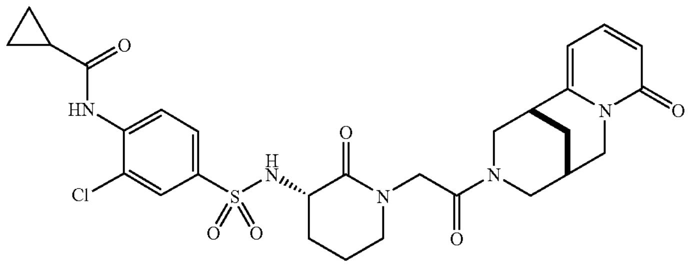 | HPLC (method 5) $t_R$ = 1.2 min LCMS (ESI, pos. ion spectrum) m/z 602/604 (M + 1) | prepared using the method described for Example 372 |
| 384 | 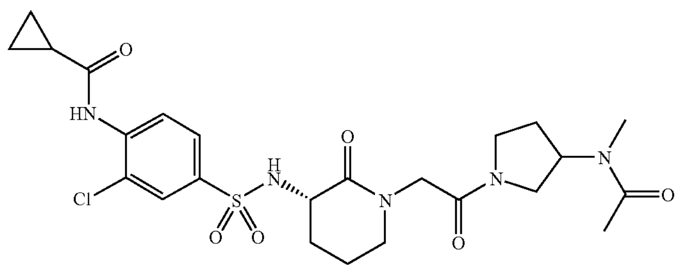 | HPLC (method 5) $t_R$ = 1.2 min LCMS (ESI, pos. ion spectrum) m/z 554/556 (M + 1) | prepared using the method described for Example 372 |
| 385 | 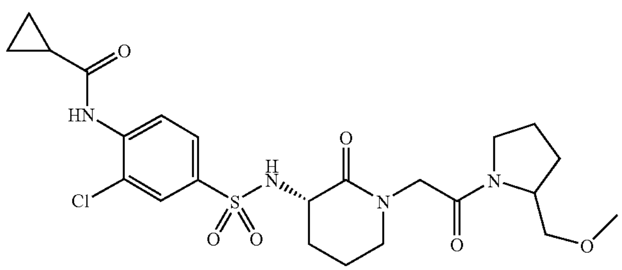 | HPLC (method 5) $t_R$ = 1.3 min LCMS (ESI, pos. ion spectrum) m/z 527/529 (M + 1) | prepared using the method described for Example 372 |
| 386 | 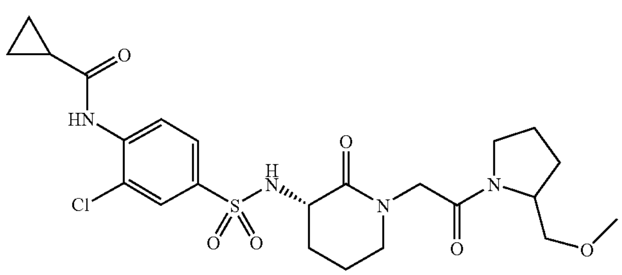 | HPLC (method 5) $t_R$ = 1.3 min LCMS (ESI, pos. ion spectrum) m/z 527/529 (M + 1) | prepared using the method described for Example 372 |
| 387 | 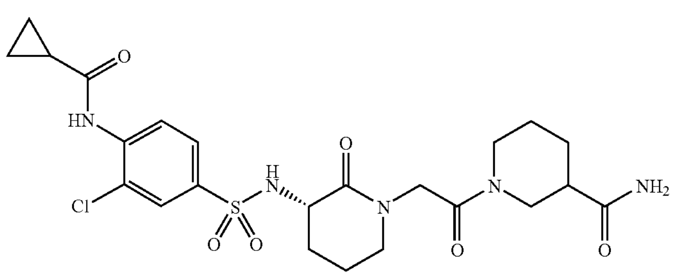 | HPLC (method 5) $t_R$ = 1.2 min LCMS (ESI, pos. ion spectrum) m/z 540/542 (M + 1) | prepared using the method described for Example 372 |

| Ex # | Structure | characterization | method |
|---|---|---|---|
| 388 | 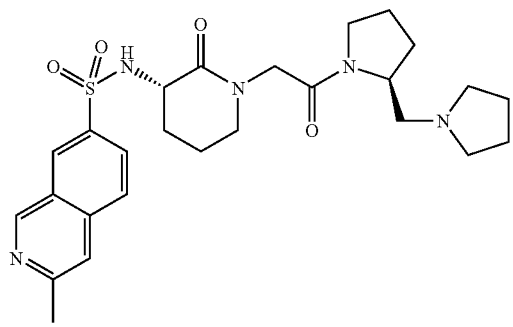 | HPLC (method 1) $t_R$ = 1.5 min LCMS (ESI, pos. ion spectrum) m/z 514 (M + 1) | Prepared using the method described in Example 48 using INT68 |
| 389 | 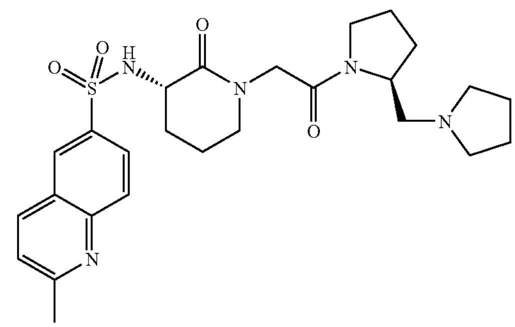 | HPLC (method 1) $t_R$ = 1.5 min LCMS (ESI, pos. ion spectrum) m/z 514 (M + 1) | Prepared using the method described in Example 48 using INT69 |
| 390 | 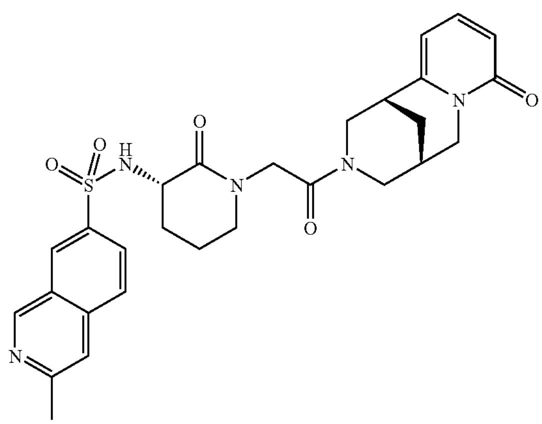 | HPLC (method 1) $t_R$ = 1.8 min LCMS (ESI, pos. ion spectrum) m/z 550 (M + 1) | Prepared using the method described in Example 48 using INT68 |
| 391 | 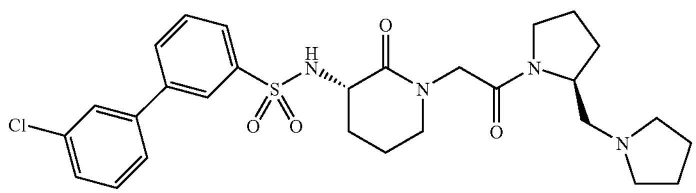 | HPLC (method 2) $t_R$ = 1.9 min LCMS (ESI, pos. ion spectrum) m/z 559/561 (M + 1) | Title compound of Example 391 |
| 392 | 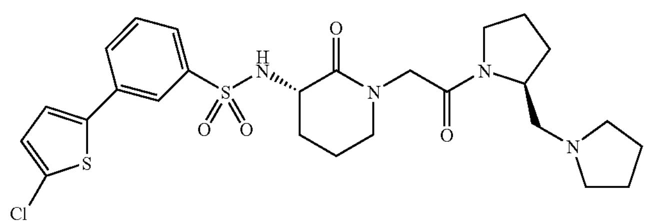 | HPLC (method 2) $t_R$ = 1.9 min LCMS (ESI, pos. ion spectrum) m/z 565/567 (M + 1) | prepared using the method described in Example 391 |

-continued

| Ex # | Structure | characterization | method |
|---|---|---|---|
| 393 | 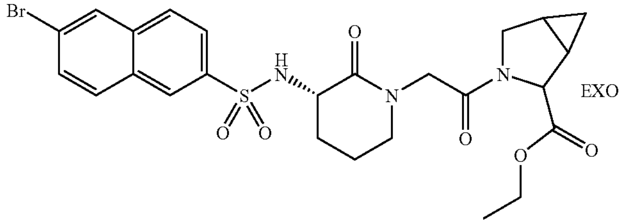 | HPLC (method 1) t_R = 3.6 min LCMS (ESI, pos. ion spectrum) m/z 578/580 (M + 1) | Prepared using the method described in Example 48 using INT10 |
| 394 | 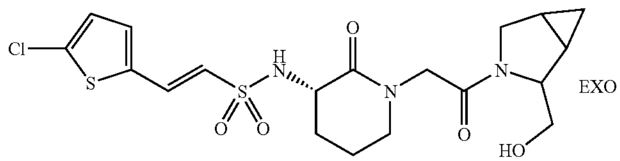 | HPLC (method 1) t_R = 3.1 min LCMS (ESI, pos. ion spectrum) m/z 474/476 (M + 1) | Prepared using the method described in Example 48 using INT11 |
| 395 | 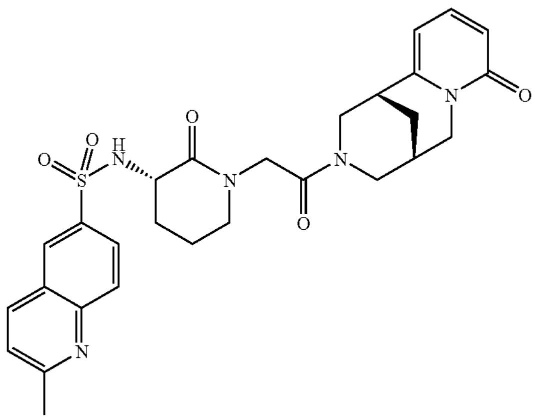 | HPLC (method 1) t_R = 1.8 min LCMS (ESI, pos. ion spectrum) m/z 550 (M + 1) | Prepared using the method described in Example 48 using INT69 |
| 396 | 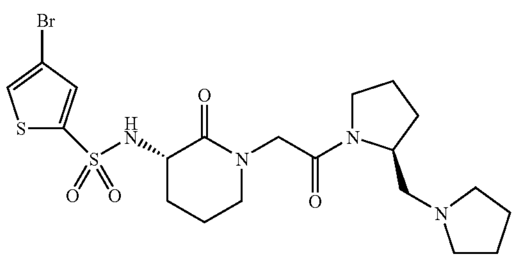 | HPLC (method 2) t_R = 1.5 min LCMS (ESI, pos. ion spectrum) m/z 533/535 (M + 1) | prepared using the method described in Example 1 using INT9 |
| 397 | 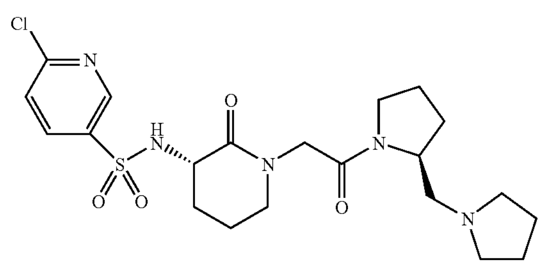 | HPLC (method 2) t_R = 1.3 min LCMS (ESI, pos. ion spectrum) m/z 484/486 (M + 1) | prepared using the method described in Example 1 using INT9 |
| 398 | 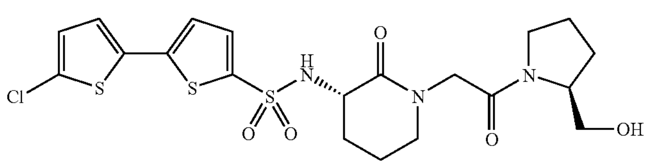 | HPLC (method 1) t_R = 3.3 min LCMS (ESI, pos. ion spectrum) m/z 518/520 (M + H) | prepared using the method described in Example 130 using INT18 |

| Ex # | Structure | characterization | method |
|---|---|---|---|
| 399 | 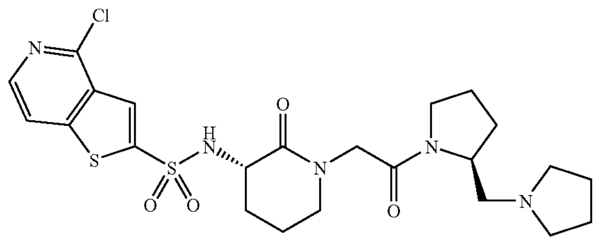 | HPLC (method 1) $t_R$ = 2.0 min LCMS (ESI, pos. ion spectrum) m/z 540/542 (M + H) | prepared using the method described in Example 1 using INT9 |
| 400 | 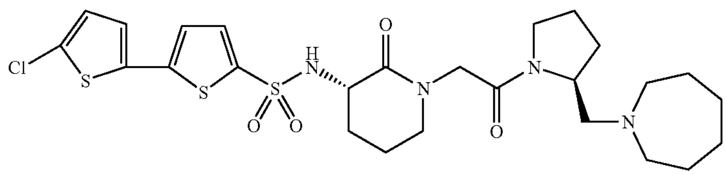 | HPLC (method 1) $t_R$ = 3.0 min LCMS (ESI, pos. ion spectrum) m/z 599/601 (M + H) | Title compound of Example 400 |
| 401 | 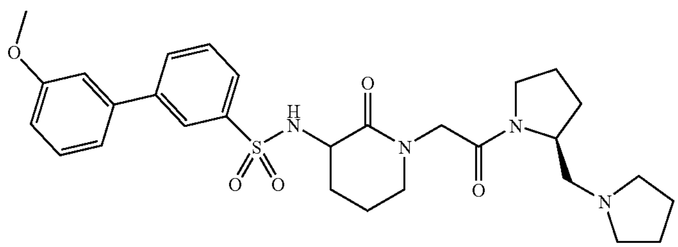 | HPLC (method 2) $t_R$ = 1.8 min LCMS (ESI, pos. ion spectrum) m/z 555 (M + 1) | Title compound of Example 401 |
| 402 | 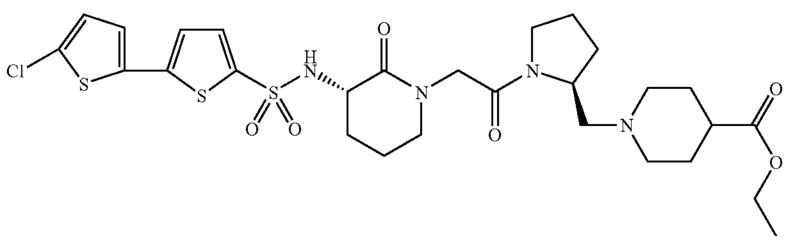 | HPLC (method 1) $t_R$ = 3.0 min LCMS (ESI, pos. ion spectrum) m/z 657/659 (M + H) | prepared using the method described in Example 400 using INT20 |
| 403 | 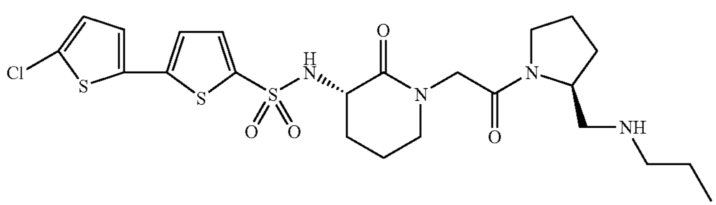 | HPLC (method 1) $t_R$ = 2.9 min LCMS (ESI, pos. ion spectrum) m/z 559/561 (M + H) | prepared using the method described in Example 400 using INT20 |
| 404 | 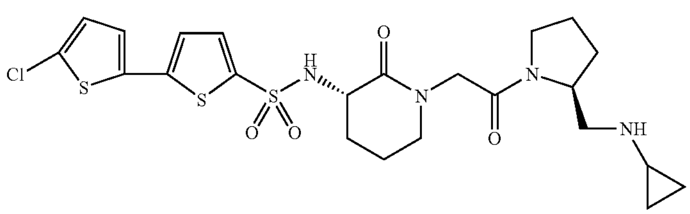 | HPLC (method 1) $t_R$ = 2.9 min LCMS (ESI, pos. ion spectrum) m/z 557/559 (M + H) | prepared using the method described in Example 400 using INT20 |
| 405 | 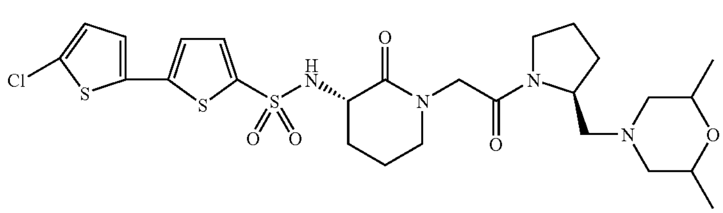 | HPLC (method 1) $t_R$ = 3.0 min LCMS (ESI, pos. ion spectrum) m/z 615/617 (M + 1) | prepared using the method described in Example 400 using INT20 |

| Ex # | Structure | characterization | method |
|---|---|---|---|
| 406 | 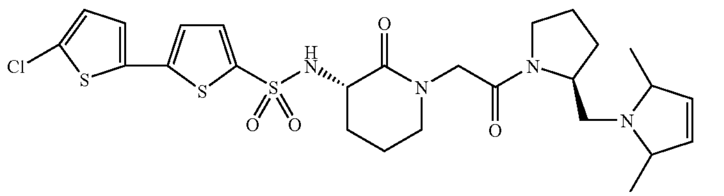 | HPLC (method 1) t_R = 2.9 min LCMS (ESI, pos. ion spectrum) m/z 597/599 (M + H) | prepared using the method described in Example 400 using INT20 |
| 407 | 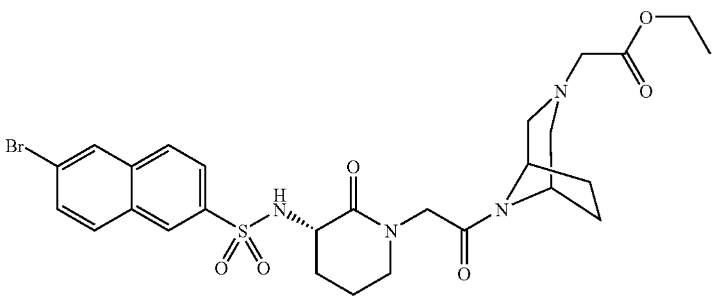 | HPLC (method 1) t_R = 3.2 min LCMS (ESI, pos. ion spectrum) m/z 621/623 (M + 1) | Title compound of Example 407 |
| 408 | 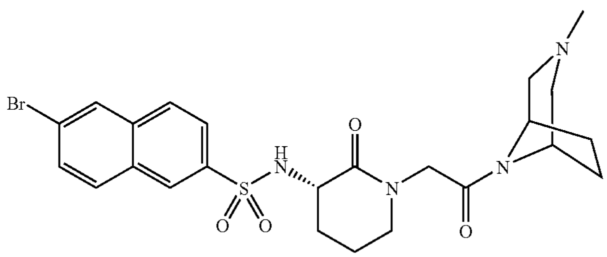 | HPLC (method 1) t_R = 2.9 min LCMS (ESI, pos. ion spectrum) m/z 549/551 (M + 1) | Prepared using the method described in Example 407 |
| 409 | 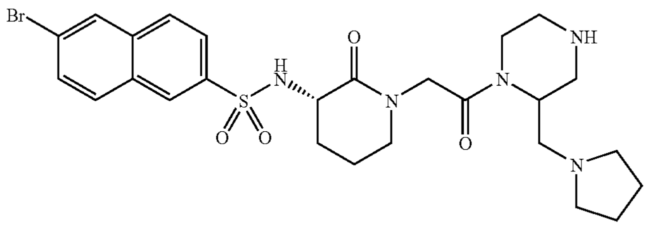 | HPLC (method 1) t_R = 2.7 min LCMS (ESI, pos. ion spectrum) m/z 592/594 (M + 1) | Title compound of Example 409 |
| 410 | 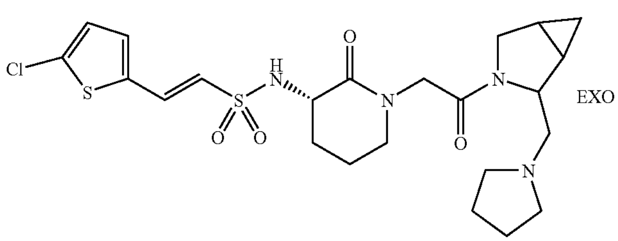 | HPLC (method 1) t_R = 2.7 min LCMS (ESI, pos. ion spectrum) m/z 527/529 (M + 1) | Title compound of Example 410 |
| 411 | 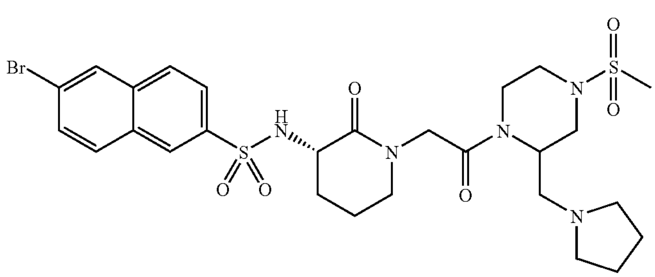 | LCMS (Conditon YS1) t_R = 2.9 min (ESI, pos. ion spectrum) m/z 670/672 (M + 1) | Prepared using example 409 using the method described in Example 21 |

| Ex # | Structure | characterization | method |
|---|---|---|---|
| 412 | 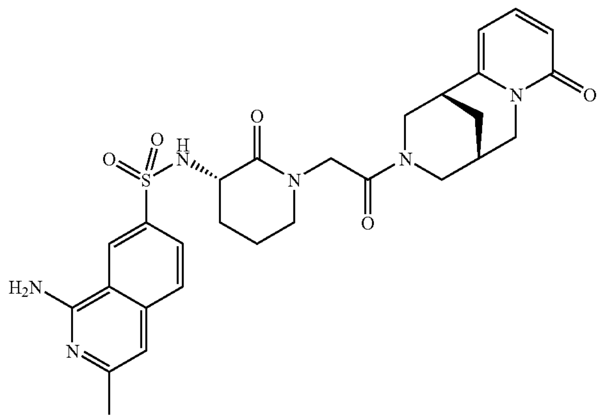 | HPLC (method 1) $t_R$ = 2.0 min LCMS (ESI, pos. ion spectrum) m/z 565 (M + 1) | Title compound of Example 412 |
| 413 | 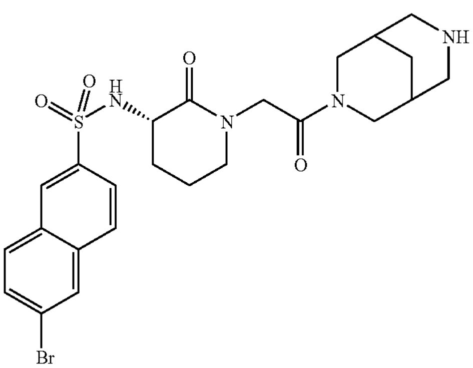 | HPLC (method 1) $t_R$ = 3.0 min LCMS (ESI, pos. ion spectrum) m/z 549/551 (M + 1) | Prepared using the method described in Example 48 using INT10 |
| 414 | 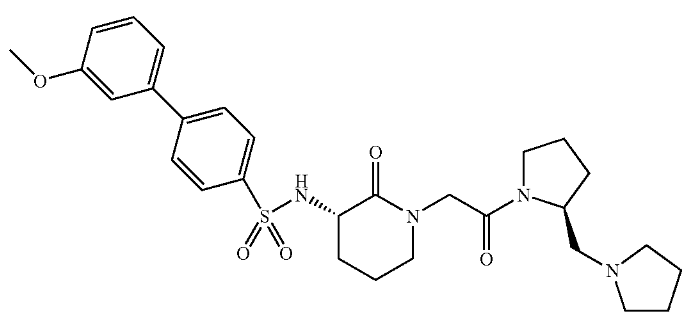 | HPLC (method 2) $t_R$ = 1.8 min LCMS (ESI, pos. ion spectrum) m/z 555 (M + 1) | Title compound of Example 414 |
| 415 | 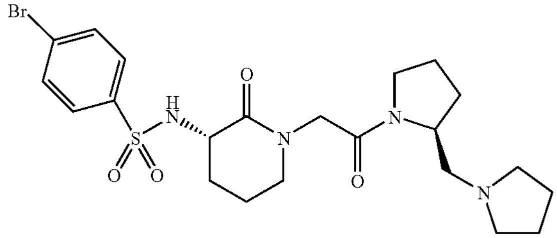 | HPLC (method 2) $t_R$ = 1.5 min LCMS (ESI, pos. ion spectrum) m/z 527/529 (M + 1) | Title compound of Example 414 |

-continued

| Ex # | Structure | characterization | method |
| --- | --- | --- | --- |
| 416 | 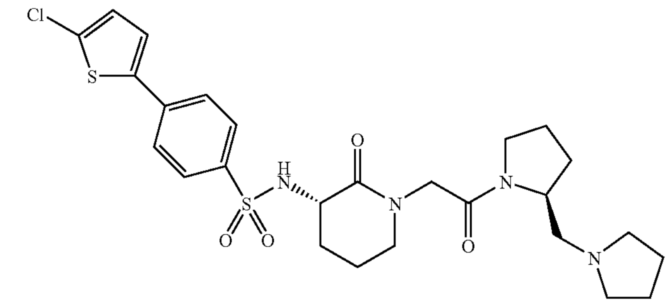 | HPLC (method 2) $t_R$ = 2.0 min LCMS (ESI, pos. ion spectrum) m/z 565/567 (M + 1) | prepared using the method described in Example 414 |
| 417 | 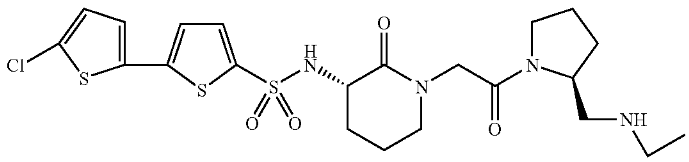 | HPLC (method 1) $t_R$ = 2.8 min LCMS (ESI, pos. ion spectrum) m/z 545/547 (M + H) | prepared using the method described in Example 400 using INT20 |
| 418 | 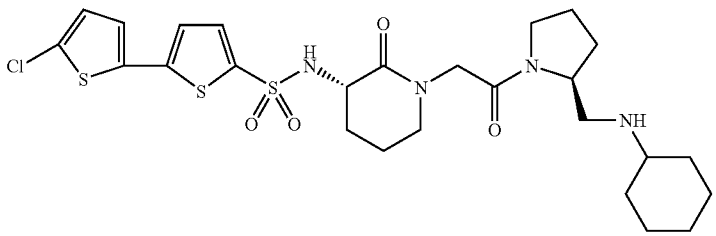 | HPLC (method 1) $t_R$ = 3.1 min LCMS (ESI, pos. ion spectrum) m/z 599/601 (M + H) | prepared using the method described in Example 400 using INT20 |
| 419 | 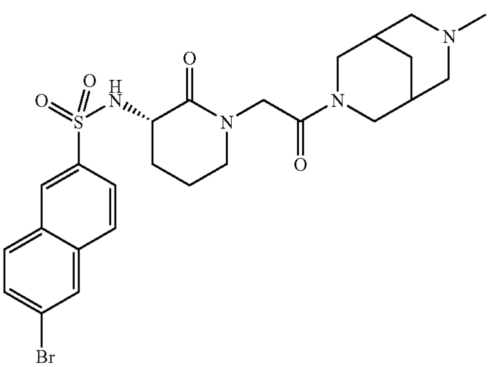 | HPLC (method 1) $t_R$ = 3.0 min LCMS (ESI, pos. ion spectrum) m/z 563/565 (M + 1) | Prepared using the method described in Example 407 |
| 420 | 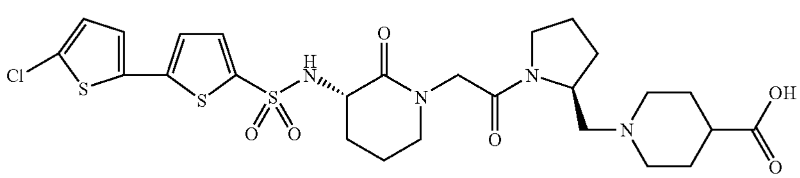 | HPLC (method 1) $t_R$ = 2.8 min LCMS (ESI, pos. ion spectrum) m/z 629/631 (M + H) | prepared using the method described in Example 400 using INT20 |
| 421 | 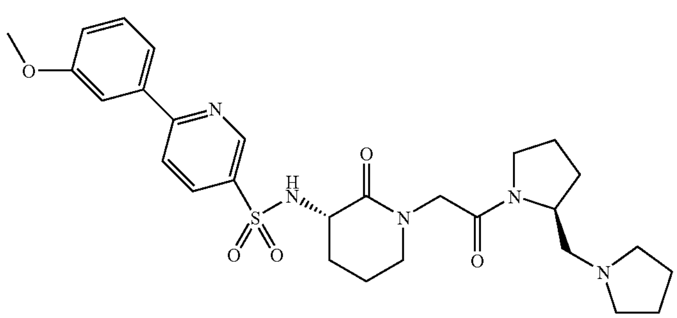 | HPLC (method 1) $t_R$ = 1.5 min LCMS (ESI, pos. ion spectrum) m/z 514 (M + 1) | prepared using the method described in Example 48 using INT69 |

-continued

| Ex # | Structure | characterization | method |
|---|---|---|---|
| 422 | 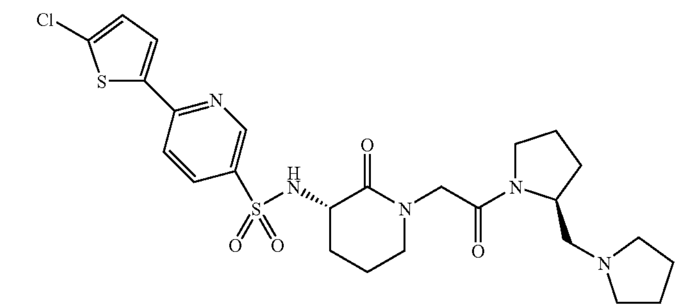 | HPLC (method 2) $t_R$ = 1.9 min LCMS (ESI, pos. ion spectrum) m/z 566/568 (M + 1) | prepared using the method described in Example 421 using the title compound of Example 397 |
| 423 | 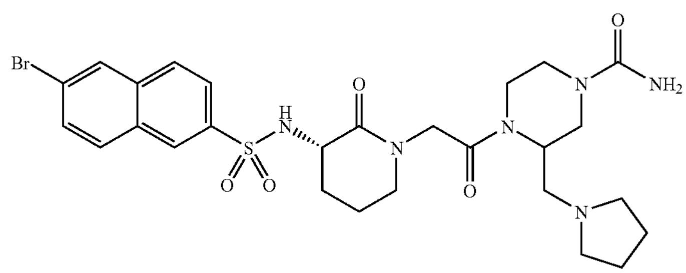 | HPLC (method 1) $t_R$ = 2.9 min LCMS (ESI, pos. ion spectrum) m/z 635/637 (M + 1) | Prepared using title compound of Example 409 using the method described in Example 316 |
| 424 | 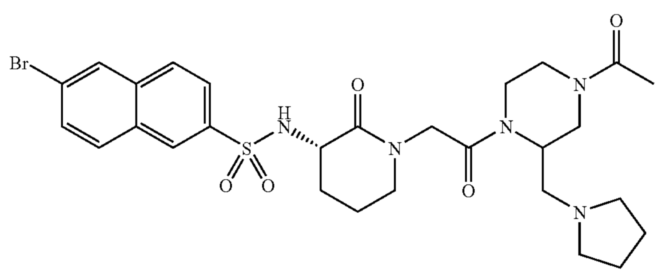 | HPLC (method 1) $t_R$ = 2.9 min LCMS (ESI, pos. ion spectrum) m/z 634/636 (M + 1) | Prepared using title compound of Example 409 using the method described Example 317 |
| 425 | 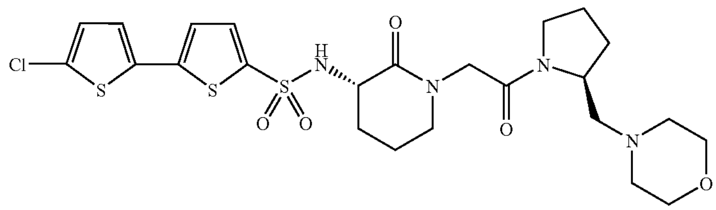 | HPLC (method 3) $t_R$ = 2.9 min LCMS (ESI, pos. ion spectrum) m/z 587/589 (M + 1) | prepared using the method described in Example 400 using INT18 |
| 426 | 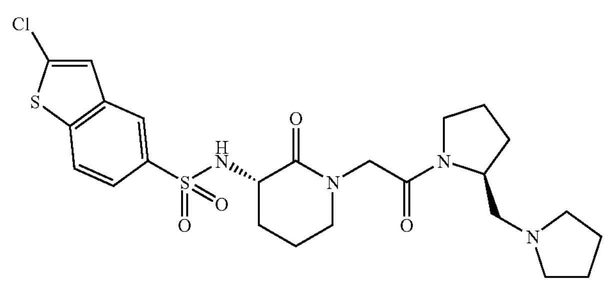 | HPLC (method 2) $t_R$ = 1.8 min LCMS (ESI, pos. ion spectrum) m/z 539/541 (M + 1) | prepared using the method described in Example 1 with INT1 and INT9 |
| 427 | 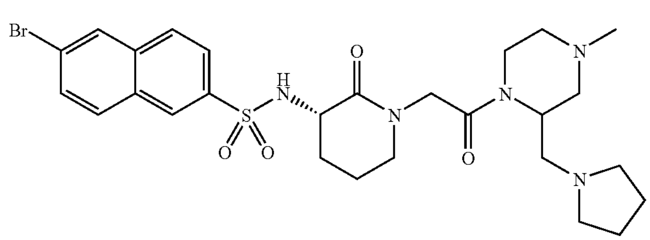 | HPLC (method 1) $t_R$ = 2.8 min LCMS (ESI, pos. ion spectrum) m/z 606/608 (M + 1) | Prepared using title compound of Example 409 using the method described in Example 407 |

-continued

| Ex # | Structure | characterization | method |
|---|---|---|---|
| 428 | 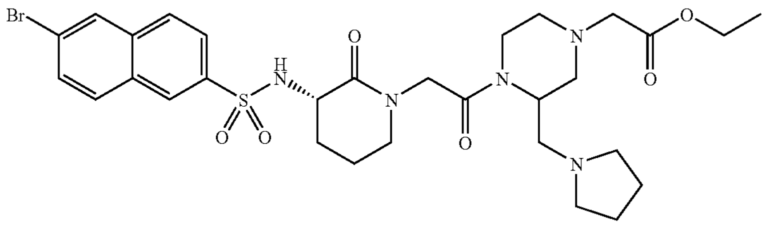 | HPLC (method 1) $t_R$ = 3.1 min LCMS (ESI, pos. ion spectrum) m/z 678/680 (M + 1) | Prepared using title compound of Example 409 using the method described in Example 407 |
| 429 | 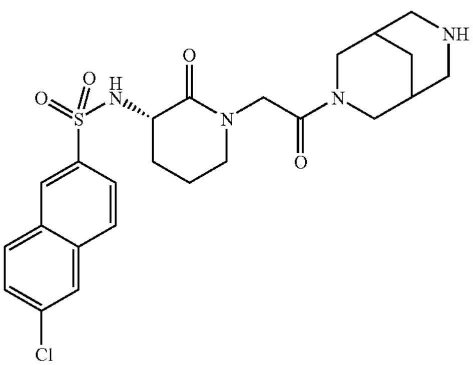 | HPLC (method 1) $t_R$ = 2.6 min LCMS (ESI, pos. ion spectrum) m/z 505/507 (M + 1) | Title compound of Example 429 |
| 430 | 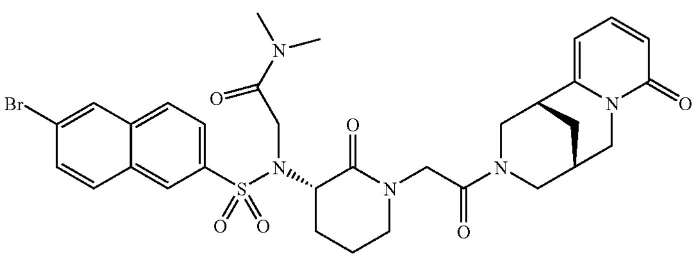 | HPLC (method 10) $t_R$ = 6.6 min LCMS (method 6) (ESI, pos. ion spectrum) m/z 697 (M + 1) | prepared using the methods described in Example 130 using the title compound of Example 329 |
| 431 | 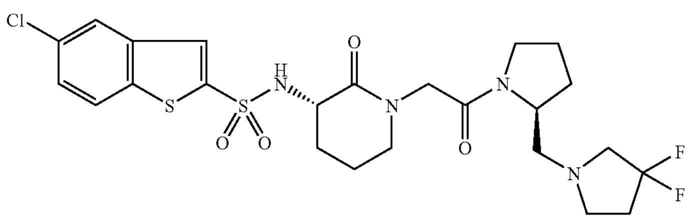 | HPLC (method 1) $t_R$ = 3.0 min LCMS (ESI, pos. ion spectrum) m/z 575/577 (M + H) | Title compound of Example 431 |
| 432 | 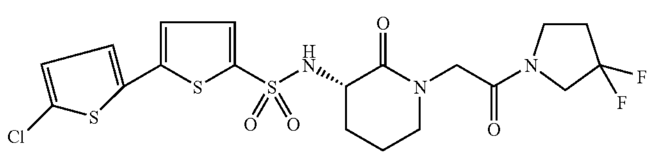 | HPLC (method 1) $t_R$ = 2.7 min LRMS (ESI, pos. ion spectrum) m/z 524/526 (M + H) | prepared using the method described in Example 613 part A using INT18 and Example 431 part C compound and 2 equiv. of triethylamine |
| 433 | 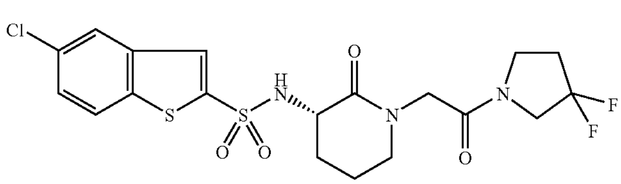 | HPLC (method 1) $t_R$ = 2.7 min LRMS (ESI, pos. ion spectrum) m/z 492/494 (M + H) | prepared using the method described in Example 613 part A using INT17 and Example 431 part C compound and 2 equiv. of triethylamine |

-continued

| Ex # | Structure | characterization | method |
|---|---|---|---|
| 434 | 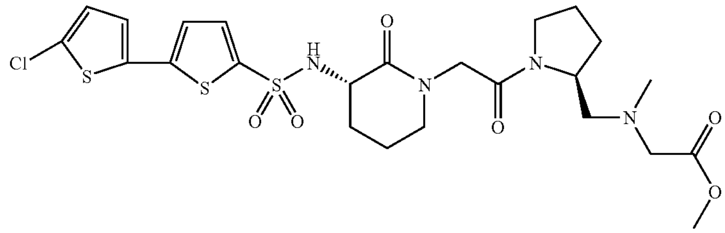 | HPLC (method 1) $t_R$ = 2.8 min LCMS (ESI, pos. ion spectrum) m/z 603/605 (M + H) | prepared using the method described in Example 400 using INT20 |
| 435 | 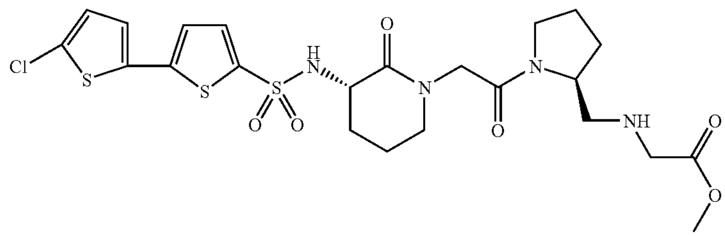 | HPLC (method 1) $t_R$ = 2.8 min LCMS (ESI, pos. ion spectrum) m/z 589/591 (M + H) | prepared using the method described in Example 400 using INT20 |
| 436 | 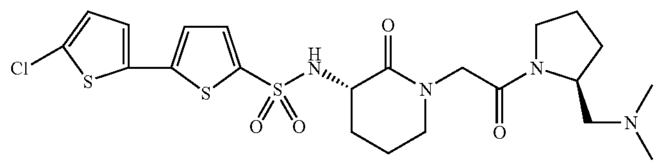 | HPLC (method 1) $t_R$ = 2.7 min LCMS (ESI, pos. ion spectrum) m/z 545/547 (M + H) | prepared using the method described in Example 400 using INT20 |
| 437 | 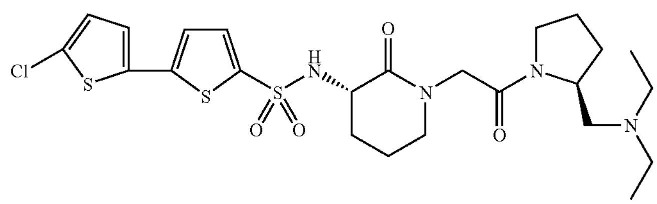 | HPLC (method 1) $t_R$ = 2.8 min LCMS (ESI, pos. ion spectrum) m/z 573/575 (M + H) | prepared using the method described in Example 400 using INT20 |
| 438 | 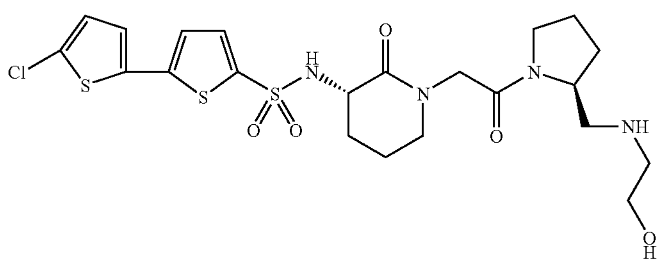 | HPLC (method 1) $t_R$ = 2.7 min LCMS (ESI, pos. ion spectrum) m/z 561/563 (M + H) | prepared using the method described in Example 400 using INT20 |
| 439 | 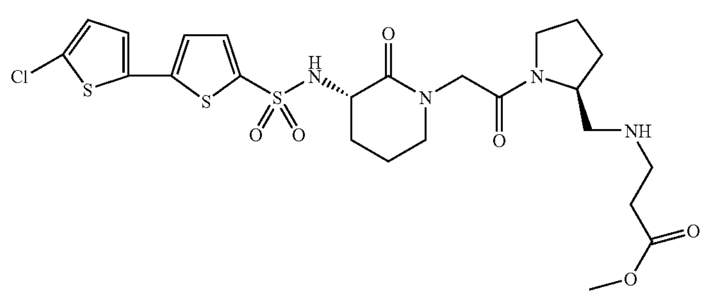 | HPLC (method 1) $t_R$ = 2.8 min LCMS (ESI, pos. ion spectrum) m/z 603/605 (M + H) | prepared using the method described in Example 400 using INT20 |

-continued

| Ex # | Structure | characterization | method |
|---|---|---|---|
| 440 | 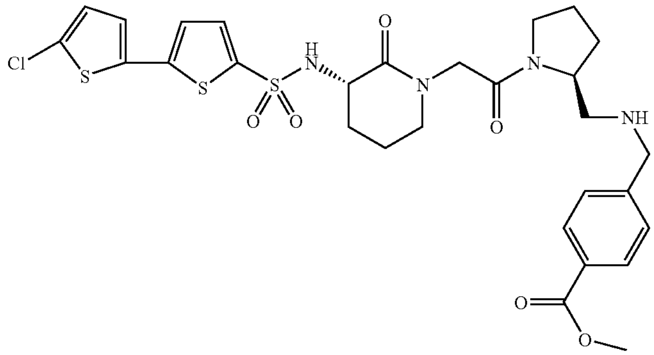 | HPLC (method 1) $t_R$ = 3.0 min LCMS (ESI, pos. ion spectrum) m/z 665/667 (M + H) | prepared using the method described in Example 400 using INT20 |
| 441 | 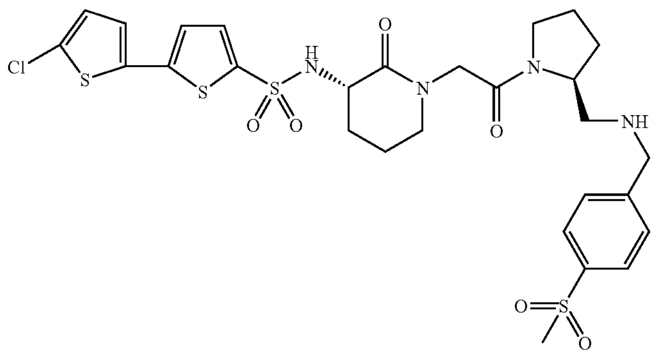 | HPLC (method 1) $t_R$ = 2.7 min LCMS (ESI, pos. ion spectrum) m/z 685/687 (M + H) | prepared using the method described in Example 400 using INT20 |
| 442 | 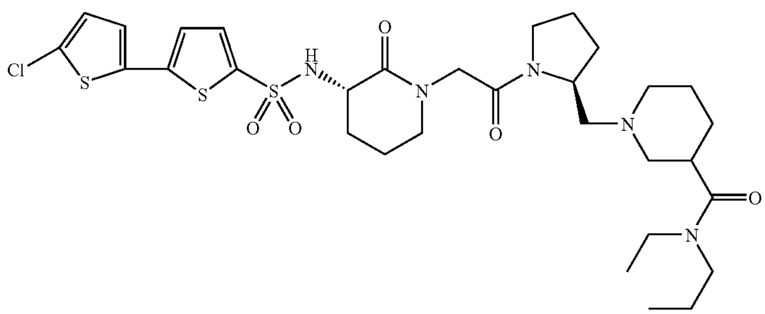 | HPLC (method 1) $t_R$ = 3.0 min LCMS (ESI, pos. ion spectrum) m/z 684/686 (M + H) | prepared using the method described in Example 400 using INT20 |
| 443 | 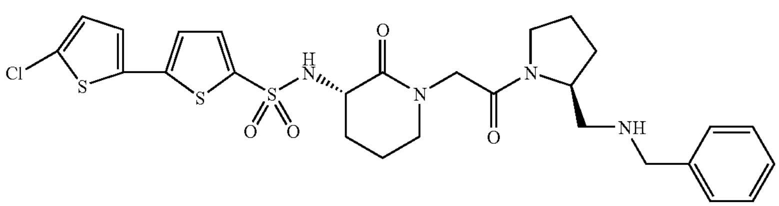 | HPLC (method 1) $t_R$ = 3.0 min LCMS (ESI, pos. ion spectrum) m/z 607/609 (M + H) | prepared using the method described in Example 400 using INT20 |
| 444 | 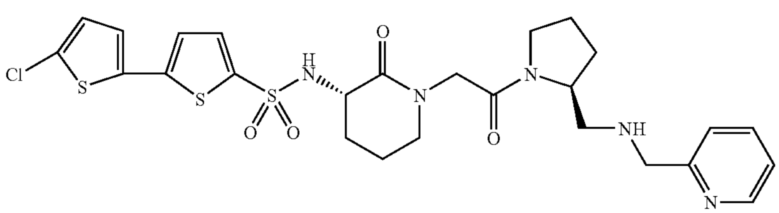 | HPLC (method 1) $t_R$ = 2.8 min LCMS (ESI, pos. ion spectrum) m/z 608/610 (M + H) | prepared using the method described in Example 400 using INT20 |

-continued

| Ex # | Structure | characterization | method |
|---|---|---|---|
| 445 | 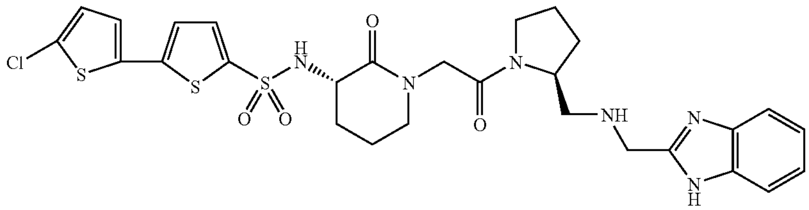 | HPLC (method 1) $t_R$ = 3.1 min LCMS (ESI, pos. ion spectrum) m/z 647/649 (M + H) | prepared using the method described in Example 400 using INT20 |
| 446 | 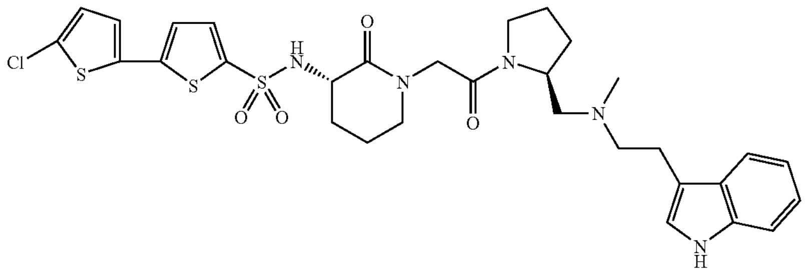 | HPLC (method 1) $t_R$ = 3.1 min LCMS (ESI, pos. ion spectrum) m/z 674/676 (M + H) | prepared using the method described in Example 400 using INT20 |
| 447 | 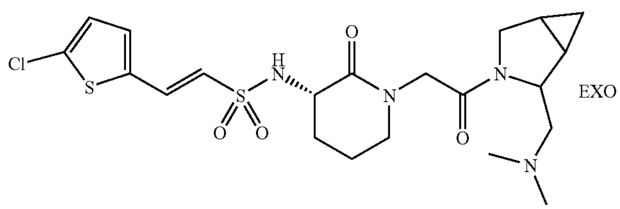 | HPLC (method 1) $t_R$ = 2.7 min LCMS (ESI, pos. ion spectrum) m/z 501/503 (M + 1) | Prepared using the method described in Example 410 |
| 448 | 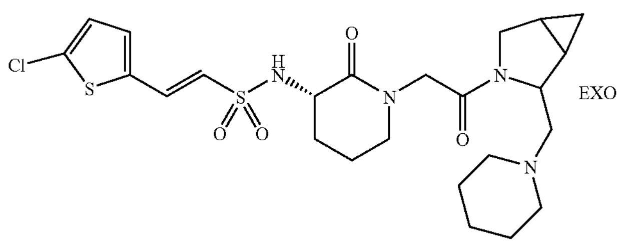 | HPLC (method 1) $t_R$ = 2.7 min LCMS (ESI, pos. ion spectrum) m/z 541/543 (M + 1) | Prepared using the method described in Example 410 |
| 449 | 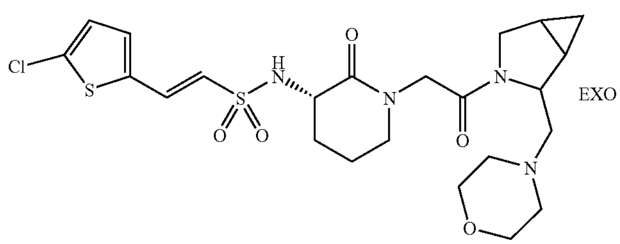 | HPLC (method 1) $t_R$ = 2.6 min LCMS (ESI, pos. ion spectrum) m/z 543/545 (M + 1) | Prepared using the method described in Example 410 |
| 450 | 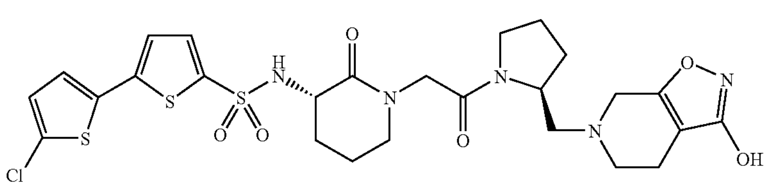 | HPLC (method 1) $t_R$ = 2.8 min LCMS (ESI, pos. ion spectrum) m/z 640/642 (M + H) | prepared using the method described in Example 400 using INT20 |
| 451 | 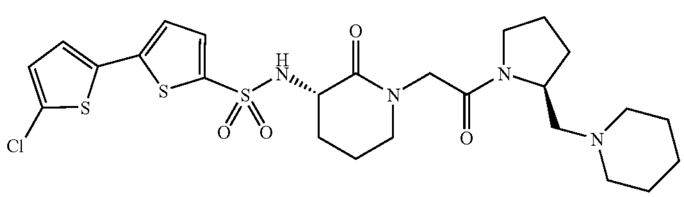 | HPLC (method 1) $t_R$ = 2.8 min LCMS (ESI, pos. ion spectrum) m/z 585/587 (M + H) | prepared using the method described in Example 400 using INT20 |

-continued

| Ex # | Structure | characterization | method |
|---|---|---|---|
| 452 | 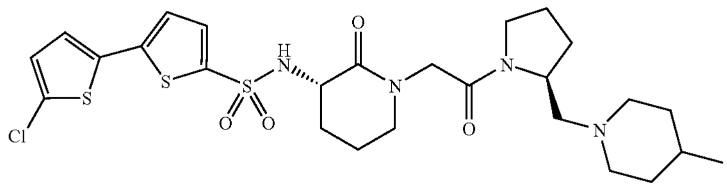 | HPLC (method 1) $t_R$ = 2.9 min LCMS (ESI, pos. ion spectrum) m/z 599/601 (M + H) | prepared using the method described in Example 400 using INT20 |
| 453 | 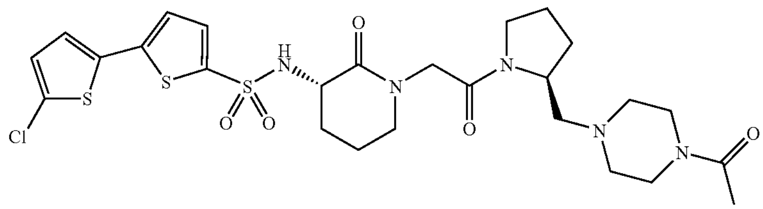 | HPLC (method 1) $t_R$ = 2.6 min LCMS (ESI, pos. ion spectrum) m/z 628/630 (M + H) | prepared using the method described in Example 400 using INT20 |
| 454 | 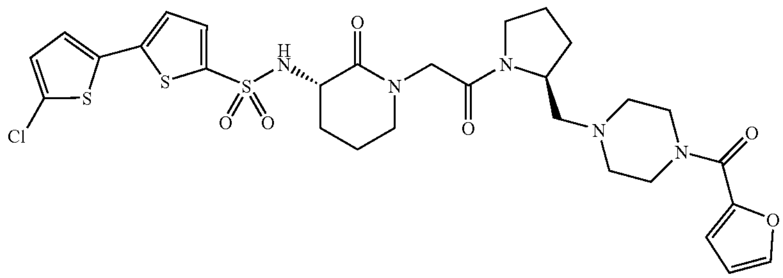 | HPLC (method 1) $t_R$ = 2.8 min LCMS (ESI, pos. ion spectrum) m/z 680/682 (M + H) | prepared using the method described in Example 400 using INT20 |
| 455 | 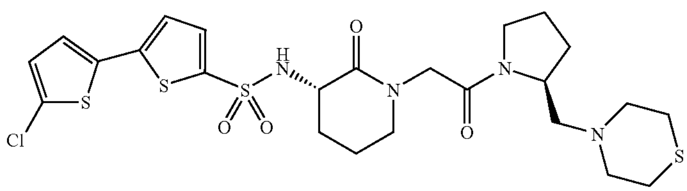 | HPLC (method 1) $t_R$ = 2.8 min LCMS (ESI, pos. ion spectrum) m/z 603/605 (M + H) | prepared using the method described in Example 400 using INT20 |
| 456 | 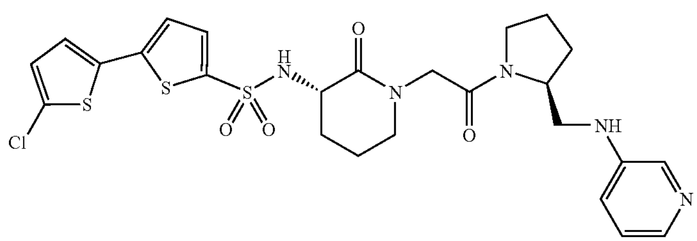 | HPLC (method 1) $t_R$ = 3.3 min LCMS (ESI, pos. ion spectrum) m/z 594/596 (M + H) | prepared using the method described in Example 400 using INT20 |
| 457 | 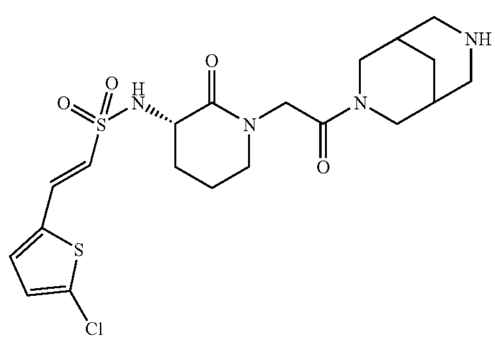 | HPLC (method 1) $t_R$ = 2.6 min LCMS (ESI, pos. ion spectrum) m/z 487/489 (M + 1) | Prepared using the method described in Example 429 using INT11 |

| Ex # | Structure | characterization | method |
|---|---|---|---|
| 458 | 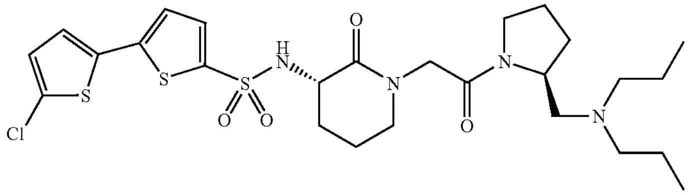 | HPLC (method 1) $t_R$ = 2.9 min LCMS (ESI, pos. ion spectrum) m/z 601/603 (M + H) | prepared using the method described in Example 400 using INT20 |
| 459 | 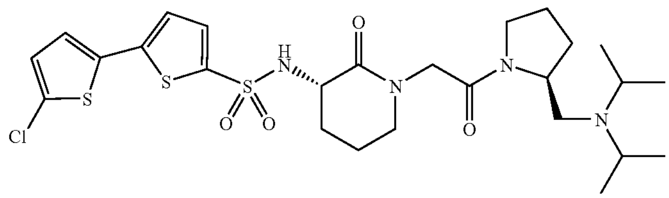 | HPLC (method 1) $t_R$ = 2.8 min LCMS (ESI, pos. ion spectrum) m/z 601/603 (M + H) | prepared using the method described in Example 400 using INT20 |
| 460 | 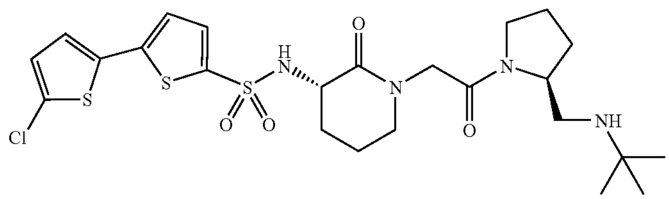 | HPLC (method 1) $t_R$ = 2.8 min LCMS (ESI, pos. ion spectrum) m/z 573/575 (M + H) | prepared using the method described in Example 400 using INT20 |
| 461 | 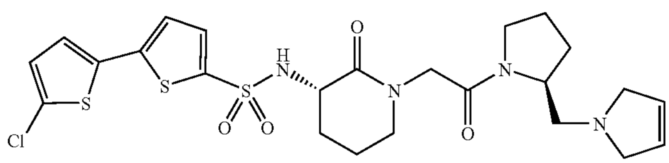 | HPLC (method 1) $t_R$ = 2.7 min LCMS (ESI, pos. ion spectrum) m/z 569/571 (M + H) | prepared using the method described in Example 400 using INT20 |
| 462 | 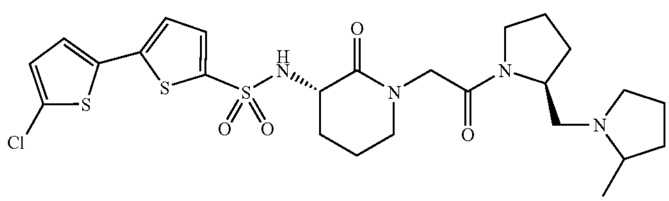 | HPLC (method 1) $t_R$ = 2.8 min LCMS (ESI, pos. ion spectrum) m/z 585/587 (M + H) | prepared using the method described in Example 400 using INT20 |
| 463 | 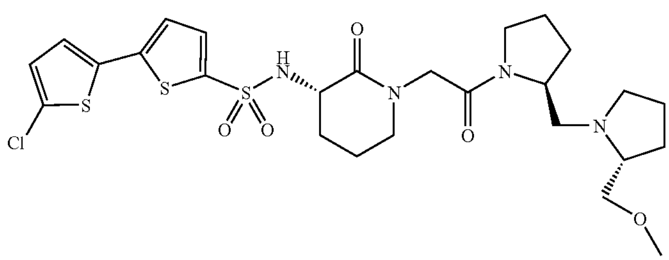 | HPLC (method 1) $t_R$ = 2.8 min LCMS (ESI, pos. ion spectrum) m/z 615/617 (M + H) | prepared using the method described in Example 400 using INT20 |
| 464 | 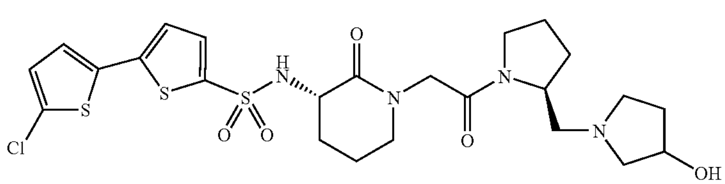 | HPLC (method 1) $t_R$ = 2.7 min LCMS (ESI, pos. ion spectrum) m/z 587/589 (M + H) | prepared using the method described in Example 400 using INT20 |

-continued

| Ex # | Structure | characterization | method |
|---|---|---|---|
| 465 | 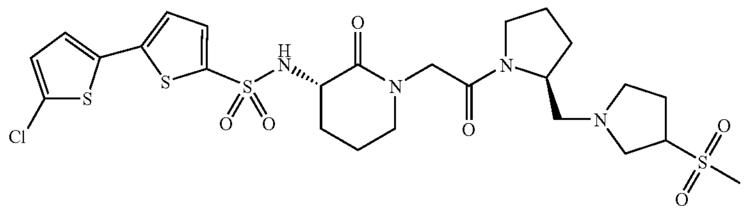 | HPLC (method 1) $t_R$ = 2.7 min LCMS (ESI, pos. ion spectrum) m/z 649/651 (M + H) | prepared using the method described in Example 400 using INT20 |
| 466 | 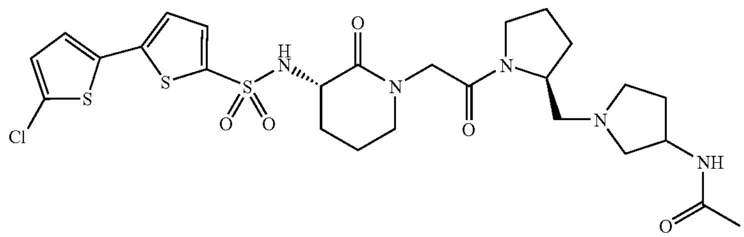 | HPLC (method 1) $t_R$ = 2.7 min LCMS (ESI, pos. ion spectrum) m/z 628/630 (M + H) | prepared using the method described in Example 400 using INT20 |
| 467 | 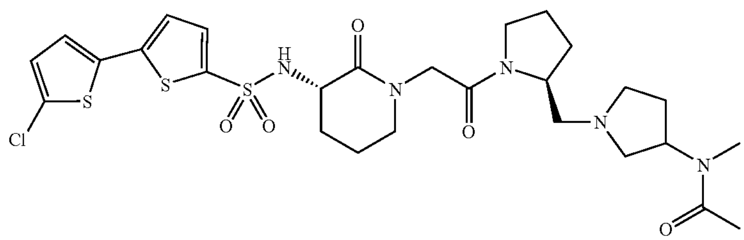 | HPLC (method 1) $t_R$ = 2.8 min LCMS (ESI, pos. ion spectrum) m/z 642/644 (M + H) | prepared using the method described in Example 400 using INT20 |
| 468 | 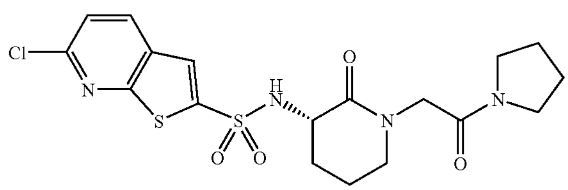 | HPLC (method 1) $t_R$ = 2.7 min LCMS (ESI, pos. ion spectrum) m/z 457/459 (M + H) | prepared using the method described in Example 130 using INT13 |
| 469 | 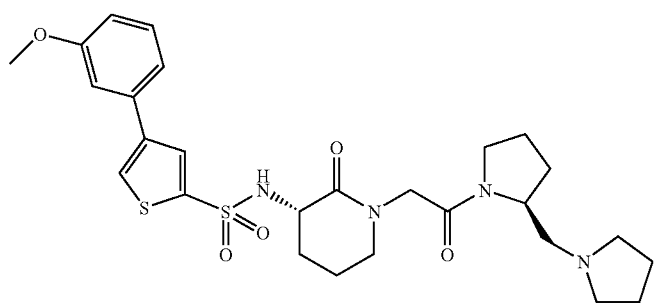 | HPLC (method 2) $t_R$ = 1.8 min LCMS (ESI, pos. ion spectrum) m/z 561 (M + 1) | prepared using the method described in Example 421 using the title compound of Example 396 |
| 470 | 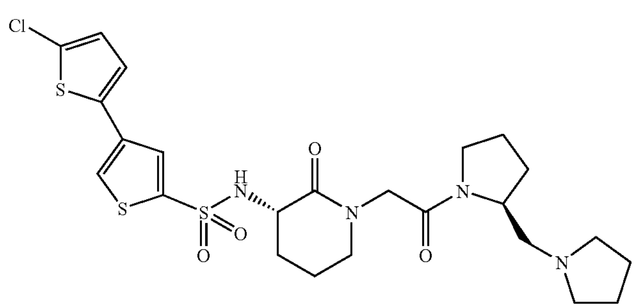 | HPLC (method 2) $t_R$ = 1.9 min LCMS (ESI, pos. ion spectrum) m/z 571/573 (M + 1) | prepared using the method described in Example 421 using the title compound of Example 396 |

-continued

| Ex # | Structure | characterization | method |
|---|---|---|---|
| 471 | 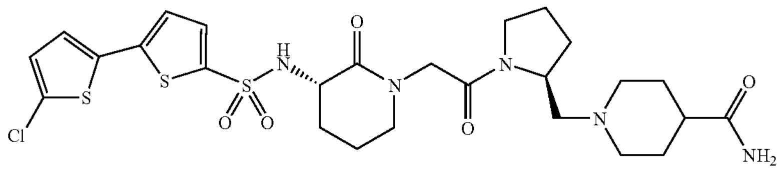 | HPLC (method 1) $t_R$ = 2.7 min LCMS (ESI, pos. ion spectrum) m/z 628/630 (M + H) | prepared using the method described in Example 400 using INT20 |
| 472 | 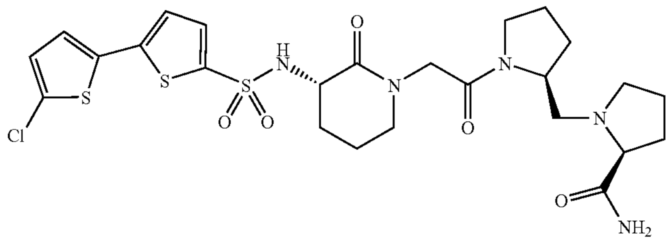 | HPLC (method 1) $t_R$ = 2.7 min LCMS (ESI, pos. ion spectrum) m/z 614/616 (M + H) | prepared using the method described in Example 400 using INT20 |
| 473 | 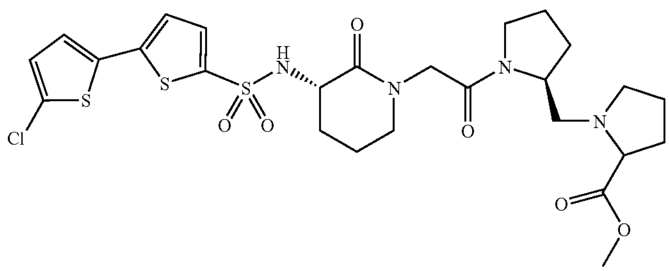 | HPLC (method 1) $t_R$ = 2.8 min LCMS (ESI, pos. ion spectrum) m/z 629/631 (M + H) | prepared using the method described in Example 400 using INT20 |
| 474 | 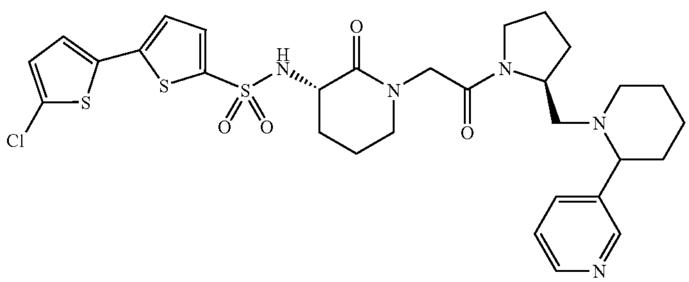 | HPLC (method 1) $t_R$ = 2.7 min LCMS (ESI, pos. ion spectrum) m/z 662/664 (M + H) | prepared using the method described in Example 400 using INT20 |
| 475 | 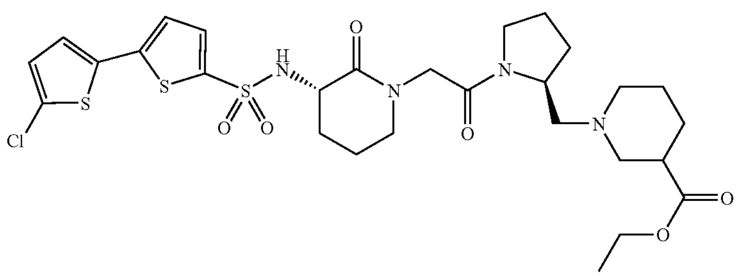 | HPLC (method 1) $t_R$ = 2.9 min LCMS (ESI, pos. ion spectrum) m/z 657/659 (M + H) | prepared using the method described in Example 400 using INT20 |
| 476 | 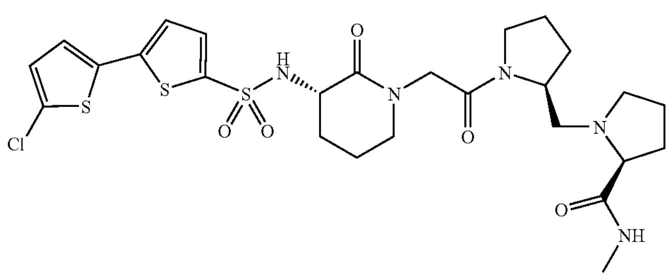 | HPLC (method 1) $t_R$ = 2.8 min LCMS (ESI, pos. ion spectrum) m/z 628/630 (M + H) | prepared using the method described in Example 400 using INT20 |

-continued

| Ex # | Structure | characterization | method |
|---|---|---|---|
| 477 | 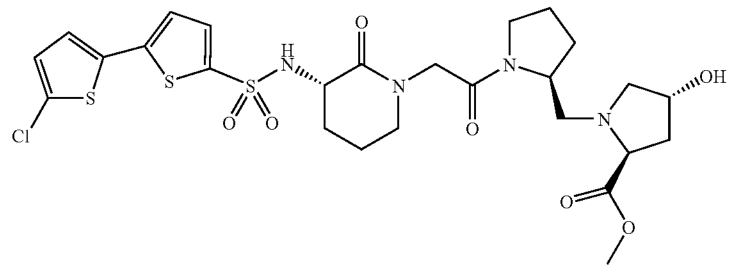 | HPLC (method 1) $t_R$ = 2.8 min LCMS (ESI, pos. ion spectrum) m/z 645/647 (M + H) | prepared using the method described in Example 400 using INT20 |
| 478 | 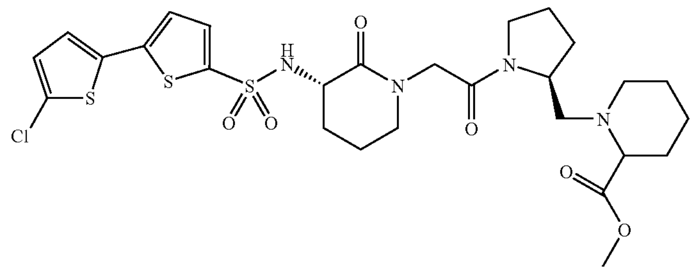 | HPLC (method 1) $t_R$ = 2.9 min LCMS (ESI, pos. ion spectrum) m/z 643/645 (M + H) | prepared using the method described in Example 400 using INT20 |
| 479 | 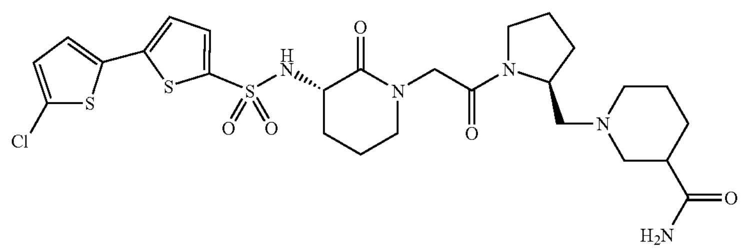 | HPLC (method 1) $t_R$ = 2.7 min LCMS (ESI, pos. ion spectrum) m/z 628/630 (M + H) | prepared using the method described in Example 400 using INT20 |
| 480 | 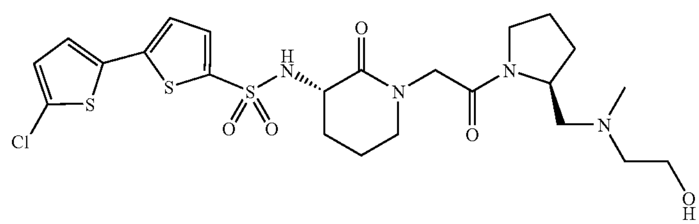 | HPLC (method 1) $t_R$ = 2.7 min LCMS (ESI, pos. ion spectrum) m/z 575/577 (M + H) | prepared using the method described in Example 400 using INT20 |
| 481 | 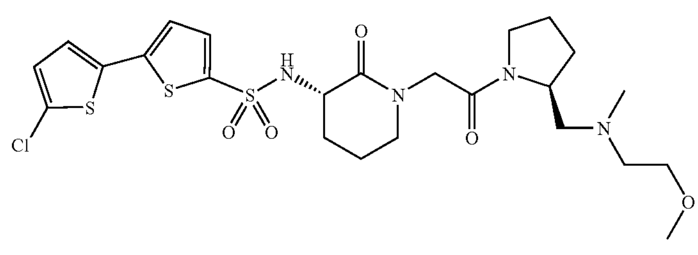 | HPLC (method 1) $t_R$ = 2.7 min LCMS (ESI, pos. ion spectrum) m/z 589/591 (M + H) | prepared using the method described in Example 400 using INT20 |
| 482 | 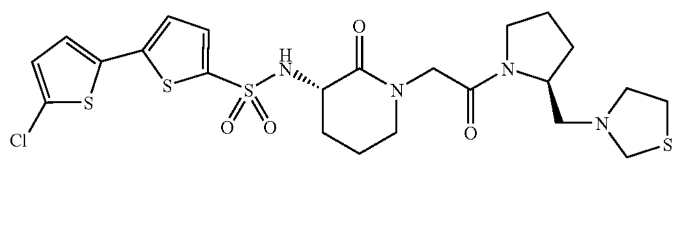 | HPLC (method 1) $t_R$ = 2.8 min LCMS (ESI, pos. ion spectrum) m/z 589/591 (M + H) | prepared using the method described in Example 400 using INT20 |

| Ex # | Structure | characterization | method |
|---|---|---|---|
| 483 | 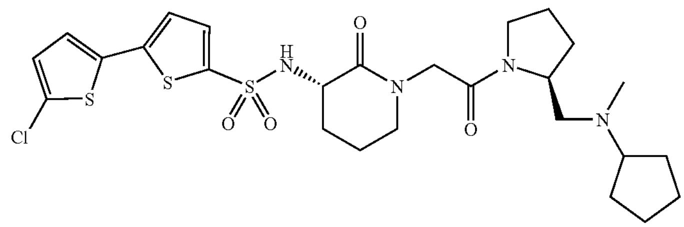 | HPLC (method 1) $t_R$ = 2.9 min LCMS (ESI, pos. ion spectrum) m/z 599/601 (M + H) | prepared using the method described in Example 400 using INT20 |
| 484 | 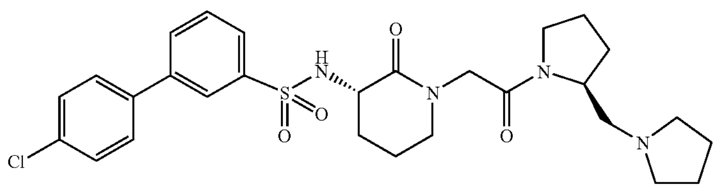 | HPLC (method 2) $t_R$ = 1.9 min LCMS (ESI, pos. ion spectrum) m/z 559/561 (M + 1) | prepared using the method described in Example 421 using the title compound of Example 363 |
| 485 | 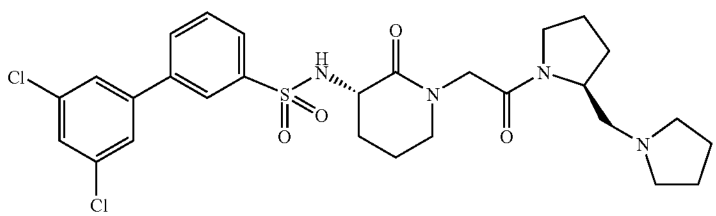 | HPLC (method 2) $t_R$ = 1.9 min LCMS (ESI, pos. ion spectrum) m/z 593/595 (M + 1) | prepared using the method described in Example 421 using the title compound of Example 363 |
| 486 | 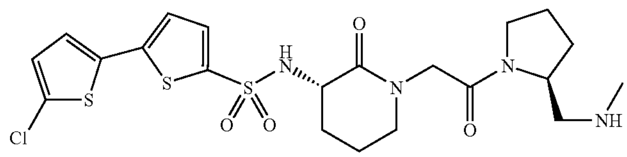 | HPLC (method 1) $t_R$ = 2.7 min LCMS (ESI, pos. ion spectrum) m/z 531/533 (M + H) | prepared using the method described in Example 400 using INT20 |
| 487 | 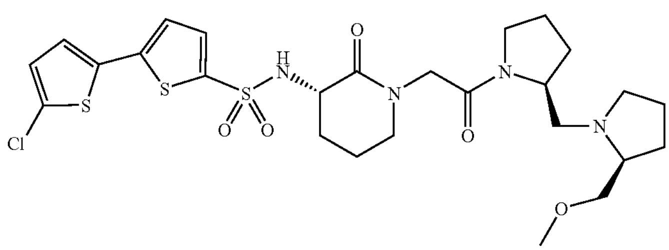 | HPLC (method 1) $t_R$ = 2.8 min LCMS (ESI, pos. ion spectrum) m/z 615/617 (M + H) | prepared using the method described in Example 400 using INT20 |
| 488 | 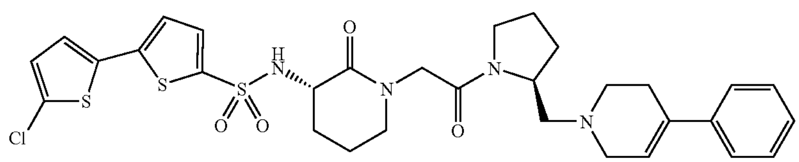 | HPLC (method 1) $t_R$ = 3.2 min LCMS (ESI, pos. ion spectrum) m/z 659/661 (M + H) | prepared using the method described in Example 400 using INT20 |
| 489 | 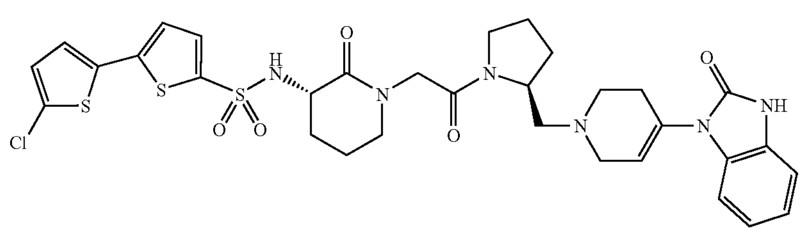 | HPLC (method 1) $t_R$ = 2.9 min LCMS (ESI, pos. ion spectrum) m/z 715/717 (M + H) | prepared using the method described in Example 400 using INT20 |

| Ex # | Structure | characterization | method |
|------|-----------|------------------|--------|
| 490 | 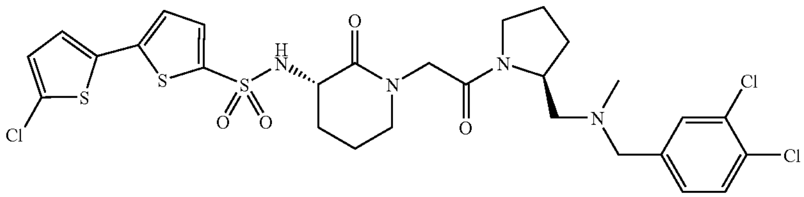 | HPLC (method 1) $t_R$ = 3.3 min LCMS (ESI, pos. ion spectrum) m/z 689/691/693 (M + H) | prepared using the method described in Example 400 using INT20 |
| 491 | 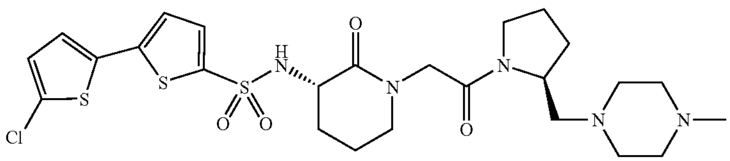 | HPLC (method 1) $t_R$ = 2.5 min LCMS (ESI, pos. ion spectrum) m/z 600/602 (M + H) | prepared using the method described in Example 400 using INT20 |
| 492 | 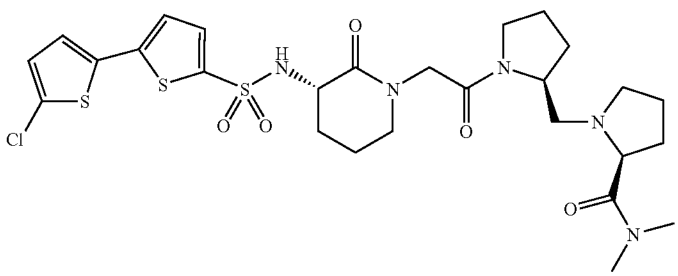 | HPLC (method 1) $t_R$ = 2.8 min LCMS (ESI, pos. ion spectrum) m/z 642/644 (M + H) | prepared using the method described in Example 400 using INT20 |
| 493 | 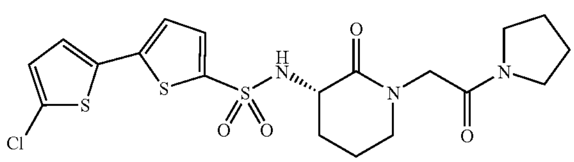 | HPLC (method 1) $t_R$ = 3.4 min LCMS (ESI, pos. ion spectrum) m/z 488/490 (M + H) | prepared using the method described in Example 400 using INT20 |
| 494 | 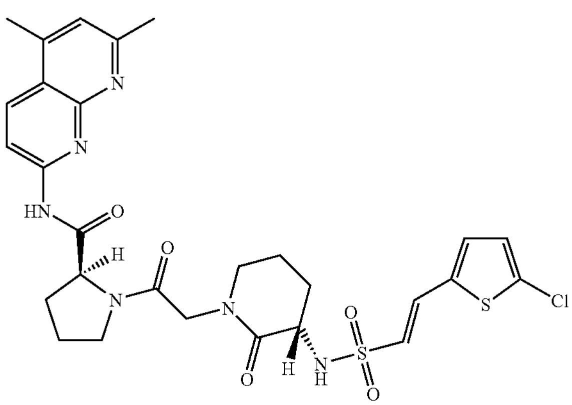 | HPLC (method 6) $t_R$ = 1.4 min LCMS (ESI, pos. ion spectrum) m/z 631/633 (M + 1) | Title compound of Example 494 |

| Ex # | Structure | characterization | method |
|---|---|---|---|
| 495 | 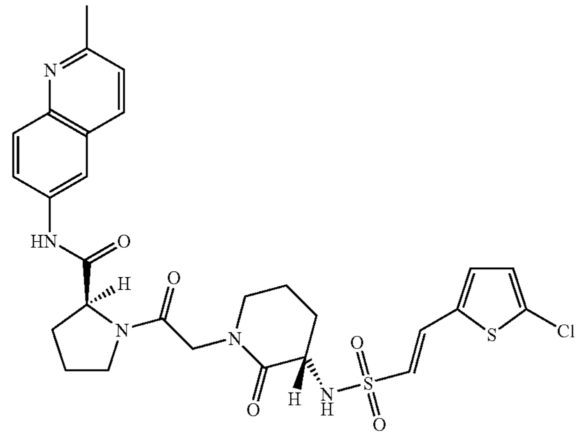 | HPLC (method 6) $t_R$ = 1.4 min LCMS (ESI, pos. ion spectrum) m/z 616/618 (M + 1) | Prepared using the methods described in Example 494 |
| 496 | 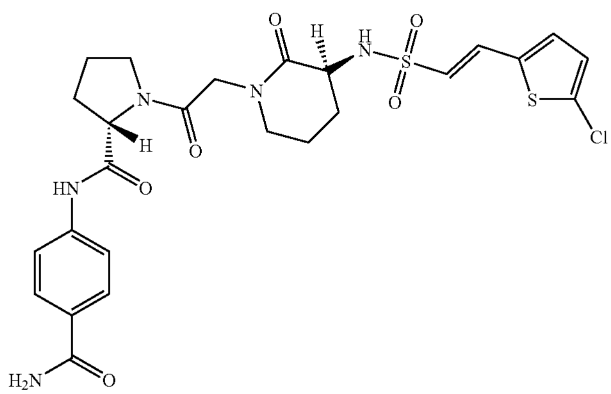 | HPLC (method 6) $t_R$ = 1.4 min LCMS (ESI, pos. ion spectrum) m/z 594/596 (M + 1) | Prepared using the methods described in Example 494 |
| 497 | 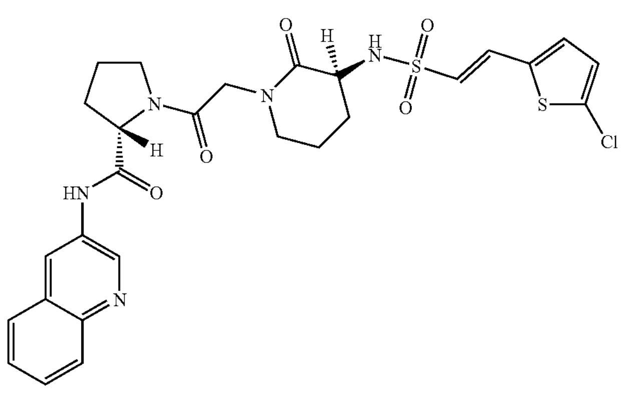 | HPLC (method 6) $t_R$ = 1.5 min LCMS (ESI, pos. ion spectrum) m/z 602/604 (M + 1) | Prepared using the methods described in Example 494 |

-continued

| Ex # | Structure | characterization | method |
|---|---|---|---|
| 498 | 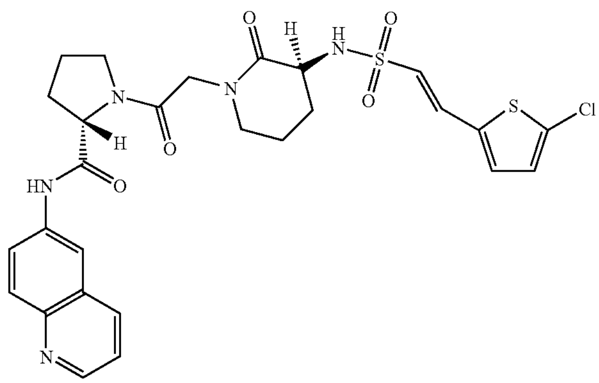 | HPLC (method 6) t_R = 1.4 min LCMS (ESI, pos. ion spectrum) m/z 602/604 (M + 1) | Prepared using the methods described in Example 494 |
| 499 | 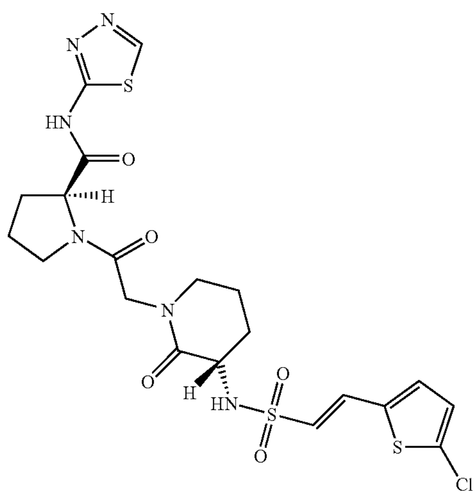 | HPLC (method 6) t_R = 1.5 min LCMS (ESI, pos. ion spectrum) m/z 559/561 (M + 1) | Prepared using the methods described in Example 494 |
| 500 | 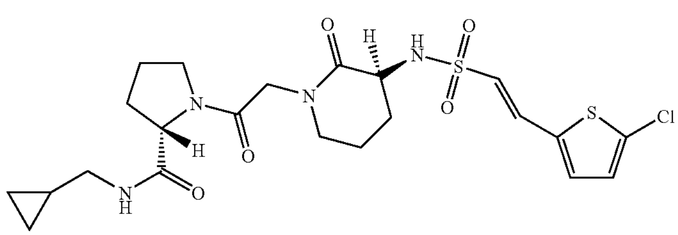 | HPLC (method 6) t_R = 1.6 min LCMS (ESI, pos. ion spectrum) m/z 529/531 (M + 1) | Prepared using the methods described in Example 494 |
| 501 | 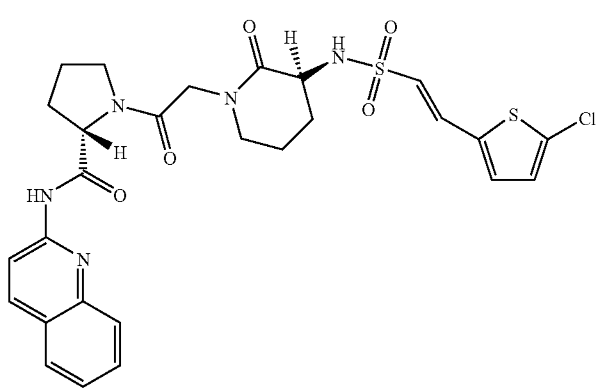 | HPLC (method 6) t_R = 1.6 min LCMS (ESI, pos. ion spectrum) m/z 602/604 (M + 1) | Prepared using the methods described in Example 494 |

-continued

| Ex # | Structure | characterization | method |
|---|---|---|---|
| 502 | 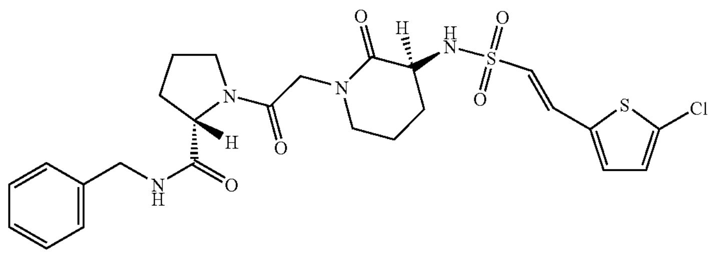 | HPLC (method 6) $t_R$ = 1.7 min LCMS (ESI, pos. ion spectrum) m/z 565/567 (M + 1) | Prepared using the methods described in Example 494 |
| 503 | 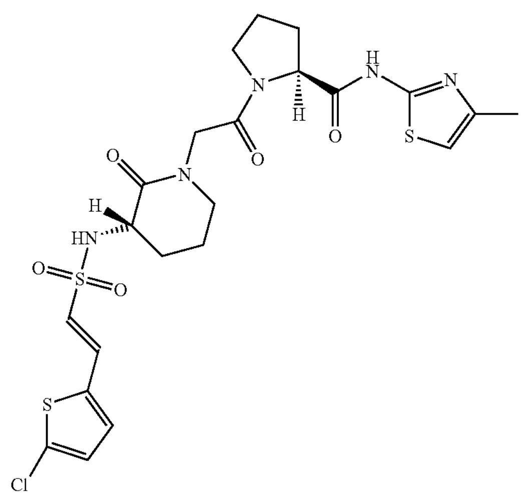 | HPLC (method 6) $t_R$ = 1.7 min LCMS (ESI, pos. ion spectrum) m/z 572/574 (M + 1) | Prepared using the methods described in Example 494 |
| 504 | 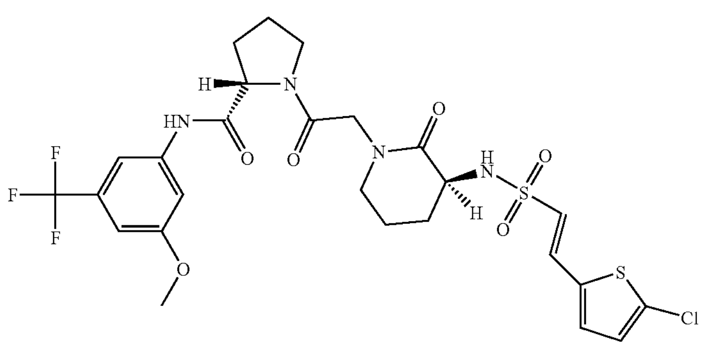 | HPLC (method 6) $t_R$ = 2.0 min LCMS (ESI, pos. ion spectrum) m/z 649/651 (M + 1) | Prepared using the methods described in Example 494 |
| 505 | 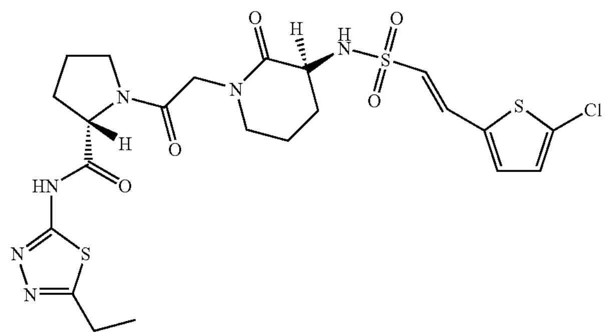 | HPLC (method 6) $t_R$ = 1.6 min LCMS (ESI, pos. ion spectrum) m/z 587/589 (M + 1) | Prepared using the methods described in Example 494 |

-continued

| Ex # | Structure | characterization | method |
|---|---|---|---|
| 506 | 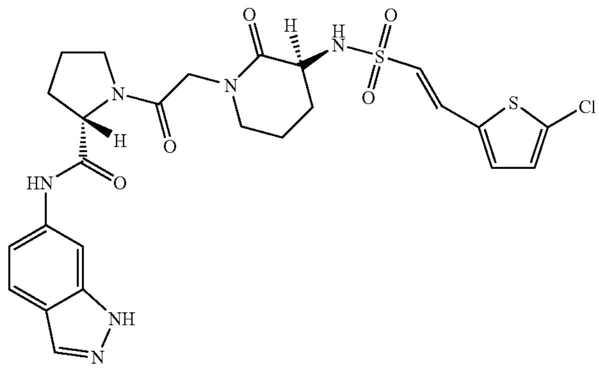 | HPLC (method 6) $t_R$ = 1.6 min LCMS (ESI, pos. ion spectrum) m/z 591/593 (M + 1) | Prepared using the methods described in Example 494 |
| 507 | 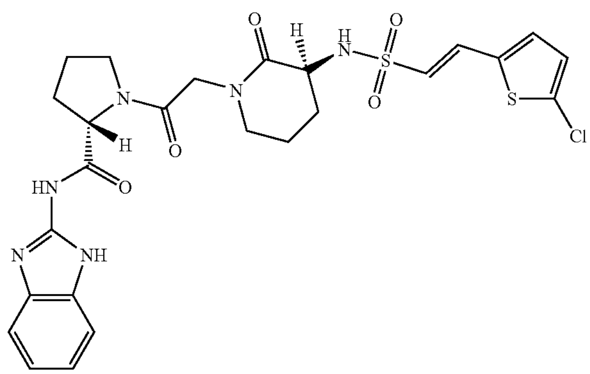 | HPLC (method 6) $t_R$ = 1.6 min LCMS (ESI, pos. ion spectrum) m/z 591/593 (M + 1) | Prepared using the methods described in Example 494 |
| 508 | 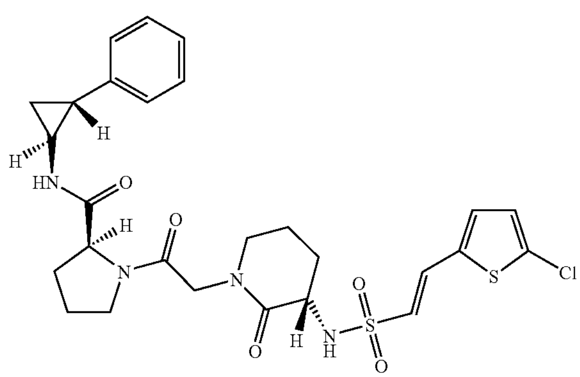 | HPLC (method 6) $t_R$ = 1.7 min LCMS (ESI, pos. ion spectrum) m/z 591/593 (M + 1) | Prepared using the methods described in Example 494 |

-continued

| Ex # | Structure | characterization | method |
|---|---|---|---|
| 509 | 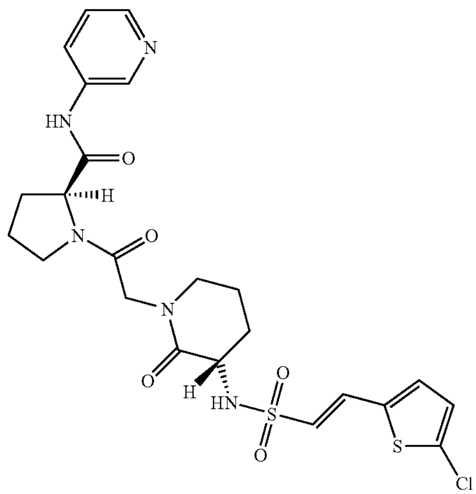 | HPLC (method 6) $t_R$ = 1.4 min LCMS (ESI, pos. ion spectrum) m/z 552/554 (M + 1) | Prepared using the methods described in Example 494 |
| 510 | 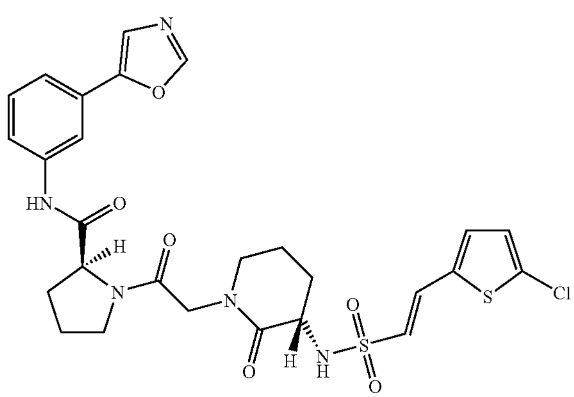 | HPLC (method 6) $t_R$ = 1.7 min LCMS (ESI, pos. ion spectrum) m/z 618/620 (M + 1) | Prepared using the methods described in Example 494 |
| 511 | 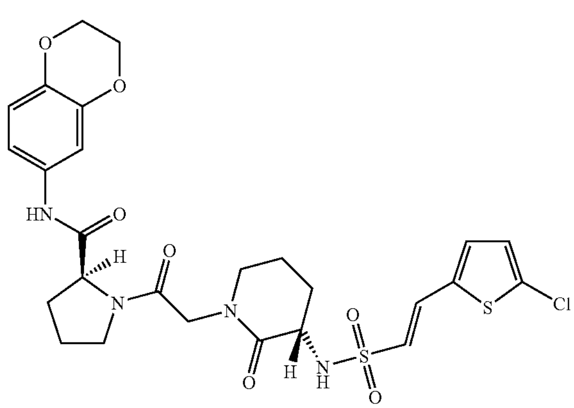 | HPLC (method 6) $t_R$ = 1.4 min LCMS (ESI, pos. ion spectrum) m/z 609/611 (M + 1) | Prepared using the methods described in Example 494 |

-continued

| Ex # | Structure | characterization | method |
|---|---|---|---|
| 512 | 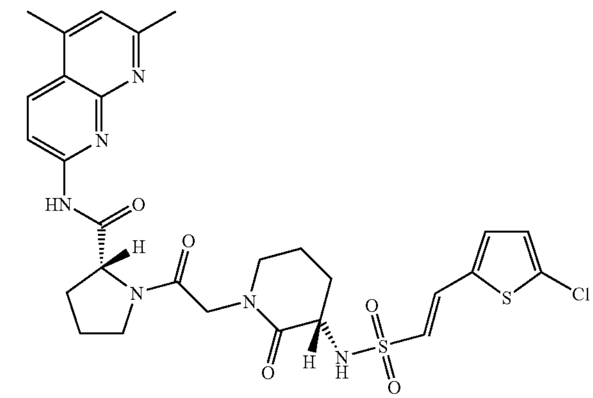 | HPLC (method 6) $t_R$ = 1.5 min LCMS (ESI, pos. ion spectrum) m/z 631/633 (M + 1) | Prepared using the methods described in Example 494 |
| 513 | 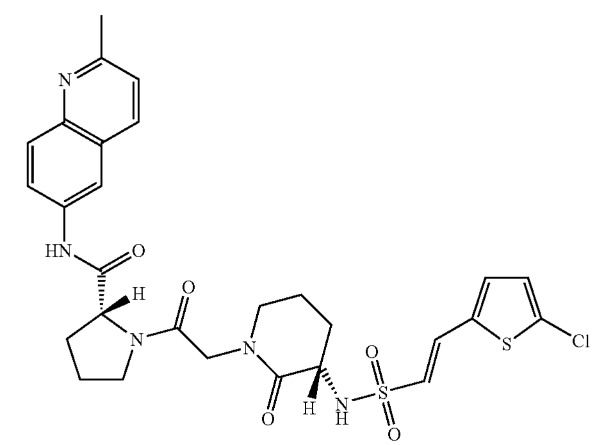 | HPLC (method 6) $t_R$ = 1.4 min LCMS (ESI, pos. ion spectrum) m/z 616/618 (M + 1) | Prepared using the methods described in Example 494 |
| 514 | 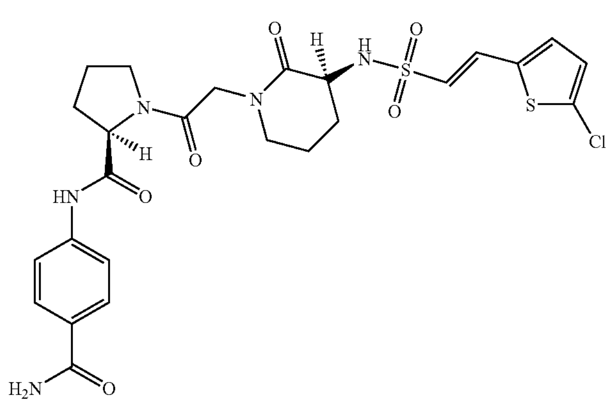 | HPLC (method 6) $t_R$ = 1.5 min LCMS (ESI, pos. ion spectrum) m/z 594/596 (M + 1) | Prepared using the methods described in Example 494 |

| Ex # | Structure | characterization | method |
|---|---|---|---|
| 515 | 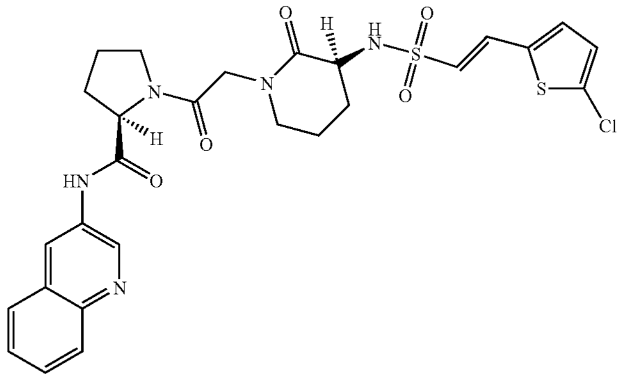 | HPLC (method 6) $t_R$ = 1.6 min LCMS (ESI, pos. ion spectrum) m/z 602/604 (M + 1) | Prepared using the methods described in Example 494 |
| 516 | 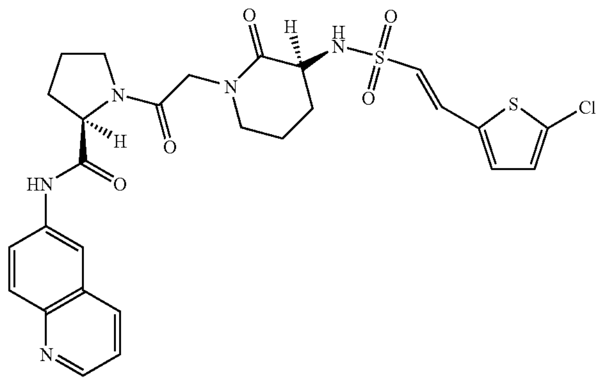 | HPLC (method 6) $t_R$ = 1.4 min LCMS (ESI, pos. ion spectrum) m/z 602/604 (M + 1) | Prepared using the methods described in Example 494 |
| 517 | 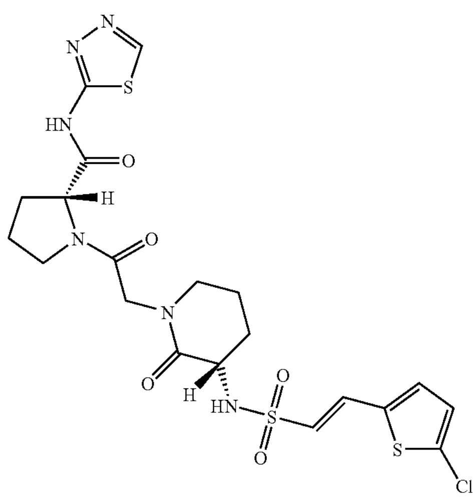 | HPLC (method 6) $t_R$ = 1.5 min LCMS (ESI, pos. ion spectrum) m/z 559/561 (M + 1) | Prepared using the methods described in Example 494 |
| 518 | 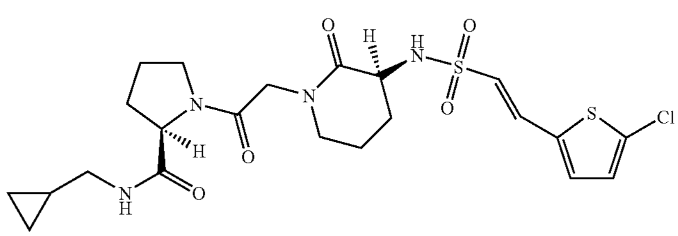 | HPLC (method 6) $t_R$ = 1.6 min LCMS (ESI, pos. ion spectrum) m/z 529/531 (M + 1) | Prepared using the methods described in Example 494 |

-continued

| Ex # | Structure | characterization | method |
|---|---|---|---|
| 519 | 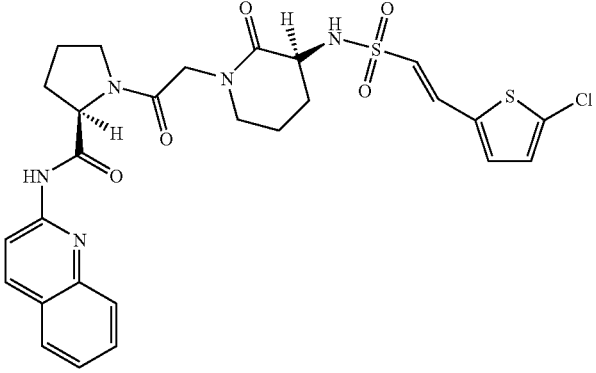 | HPLC (method 6) $t_R$ = 1.6 min LCMS (ESI, pos. ion spectrum) m/z 602/604 (M + 1) | Prepared using the methods described in Example 494 |
| 520 | 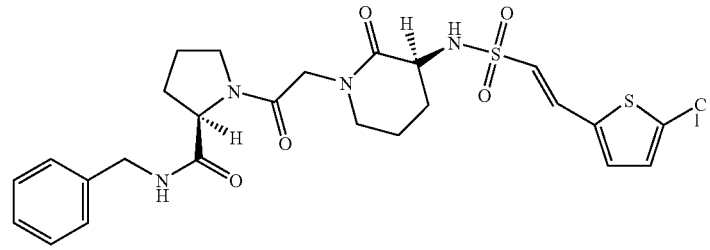 | HPLC (method 6) $t_R$ = 1.7 min LCMS (ESI, pos. ion spectrum) m/z 565/567 (M + 1) | Prepared using the methods described in Example 494 |
| 521 | 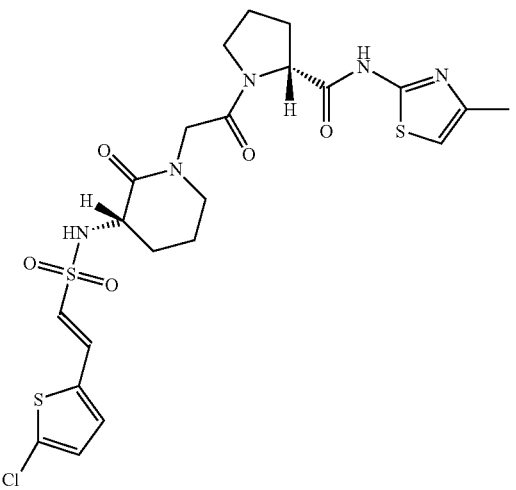 | HPLC (method 6) $t_R$ = 1.7 min LCMS (ESI, pos. ion spectrum) m/z 572/574 (M + 1) | Prepared using the methods described in Example 494 |
| 522 | 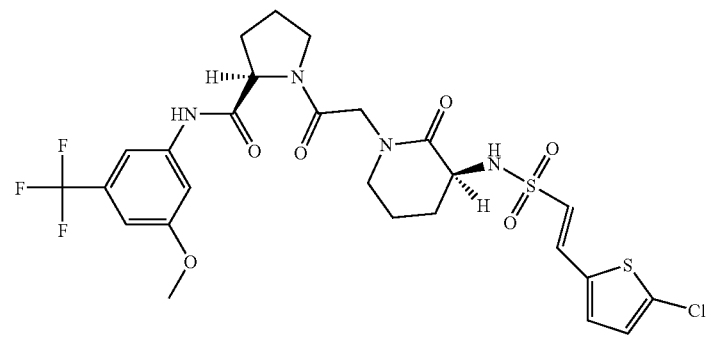 | HPLC (method 6) $t_R$ = 2.0 min LCMS (ESI, pos. ion spectrum) m/z 649/651 (M + 1) | Prepared using the methods described in Example 494 |

-continued

| Ex # | Structure | characterization | method |
|---|---|---|---|
| 523 | 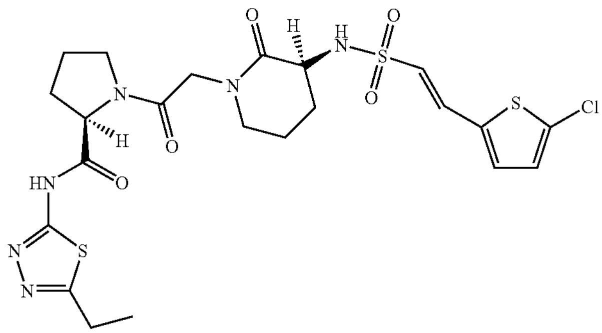 | HPLC (method 6) $t_R$ = 1.7 min LCMS (ESI, pos. ion spectrum) m/z 587/589 (M + 1) | Prepared using the methods described in Example 494 |
| 524 | 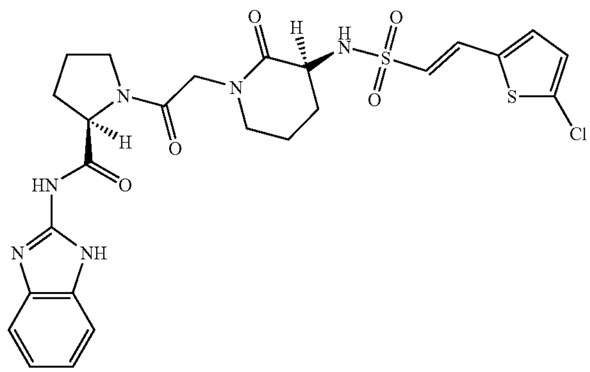 | HPLC (method 6) $t_R$ = 1.6 min LCMS (ESI, pos. ion spectrum) m/z 591/593 (M + 1) | Prepared using the methods described in Example 494 |
| 525 | 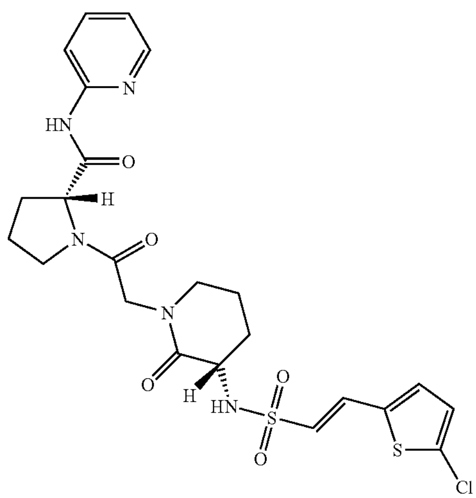 | HPLC (method 6) $t_R$ = 1.4 min LCMS (ESI, pos. ion spectrum) m/z 552/554 + C94 (M + 1) | Prepared using the methods described in Example 494 |
| 526 | 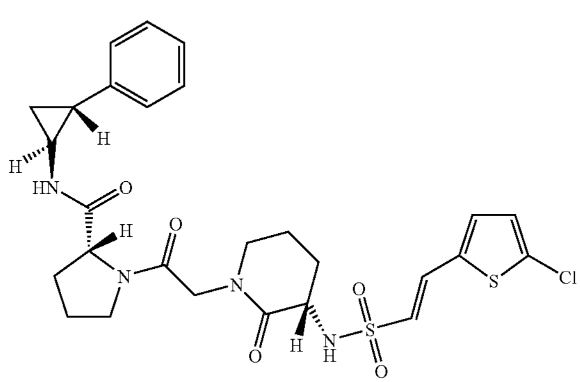 | HPLC (method 6) $t_R$ = 1.8 min LCMS (ESI, pos. ion spectrum) m/z 591/593 (M + 1) | Prepared using the methods described in Example 494 |

| Ex # | Structure | characterization | method |
|---|---|---|---|
| 527 | 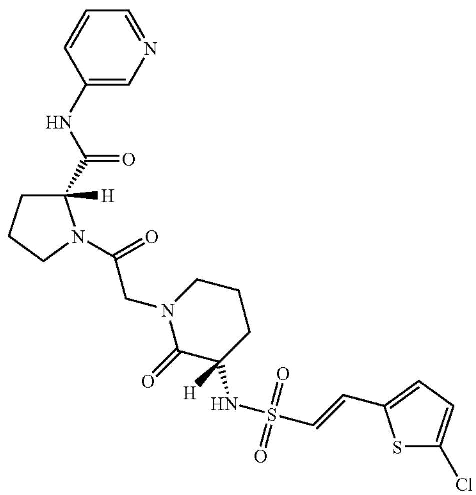 | HPLC (method 6) $t_R$ = 1.4 min LCMS (ESI, pos. ion spectrum) m/z 552/554 (M + 1) | Prepared using the methods described in Example 494 |
| 528 | 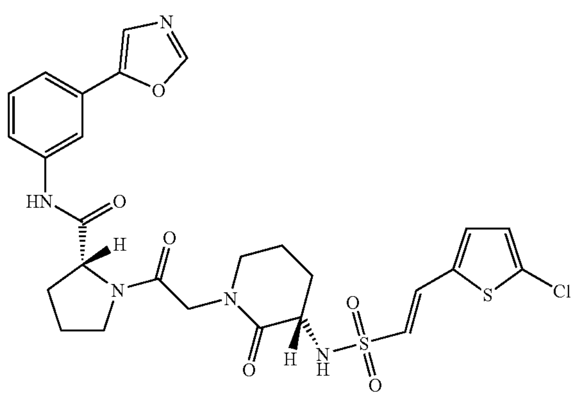 | HPLC (method 6) $t_R$ = 1.7 min LCMS (ESI, pos. ion spectrum) m/z 618/620 (M + 1) | Prepared using the methods described in Example 494 |
| 529 | 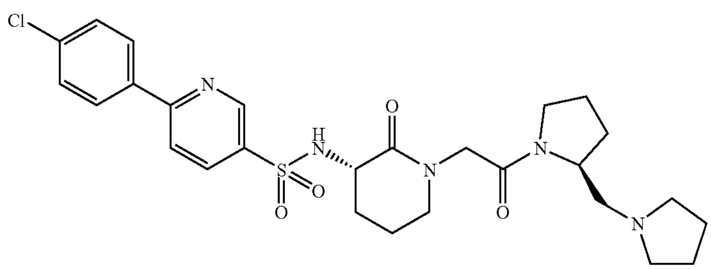 | HPLC (method 2) $t_R$ = 1.8 min LCMS (ESI, pos. ion spectrum) m/z 560/562 (M + 1) | prepared using the method described in Example 421 |
| 530 | 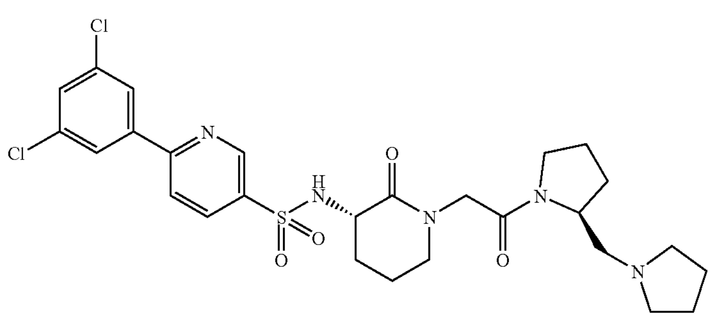 | HPLC (method 2) $t_R$ = 2.1 min LCMS (ESI, pos. ion spectrum) m/z 594/596 (M + 1) | prepared using the method described in Example 421 |

| Ex # | Structure | characterization | method |
|---|---|---|---|
| 531 | 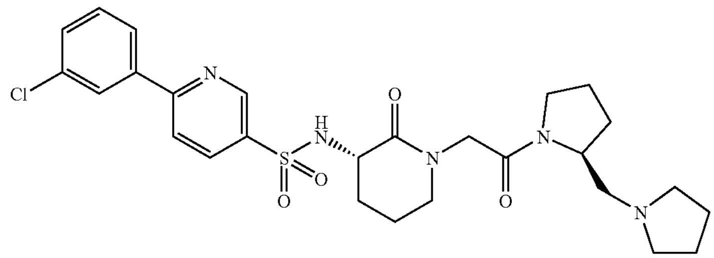 | HPLC (method 2) t_R = 1.8 min LCMS (ESI, pos. ion spectrum) m/z 560/562 (M + 1) | prepared using the method described in Example 421 |
| 532 | 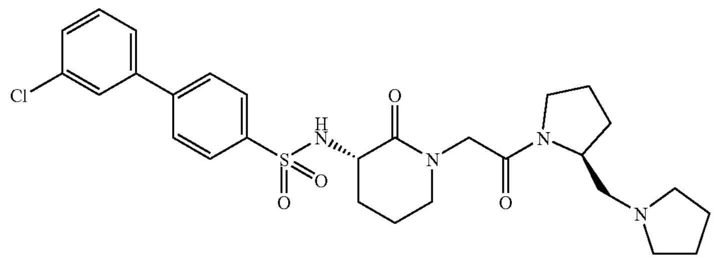 | LCMS (method 4) t_R = 1.5 min (ESI, pos. ion spectrum) m/z 559/561 (M + 1) | Title compound of Example 532 |
| 533 | 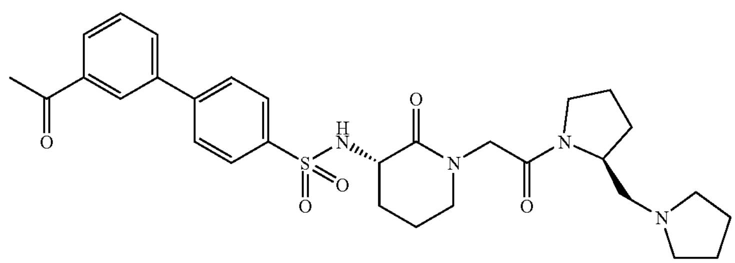 | LCMS (method 4) t_R = 1.6 min (ESI, pos. ion spectrum) m/z 567 (M + 1) | prepared using the method described in Example 532 |
| 534 | 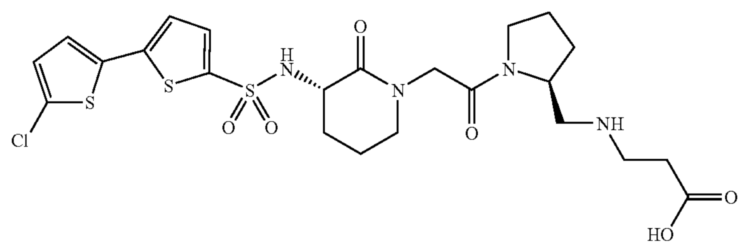 | HPLC (method 1) t_R = 2.8 min LCMS (ESI, pos. ion spectrum) m/z 589/591 (M + H) | Title compound of Example 534 |
| 535 | 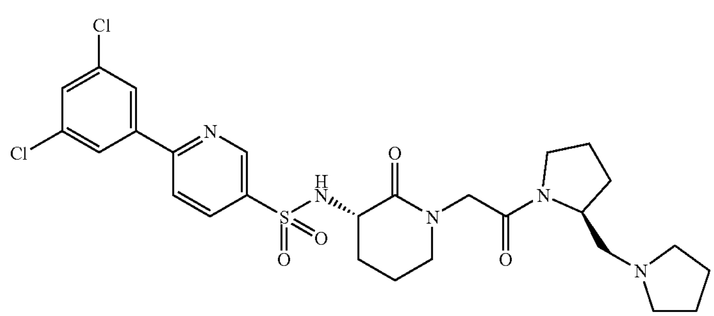 | HPLC (method 1) t_R = 2.8 min LCMS (ESI, pos. ion spectrum) m/z 651/653 (M + H) | prepared using the title compound of Example 440 and INT20 using the method described in Example 534 |
| 536 | 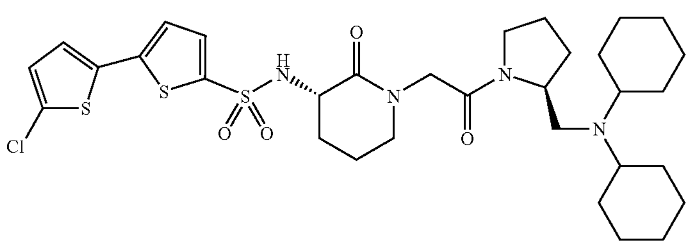 | HPLC (method 1) t_R = 3.3 min LCMS (ESI, pos. ion spectrum) m/z 681/683 (M + H) | prepared using the method described in Example 400 using INT20 |

-continued

| Ex # | Structure | characterization | method |
|---|---|---|---|
| 537 | 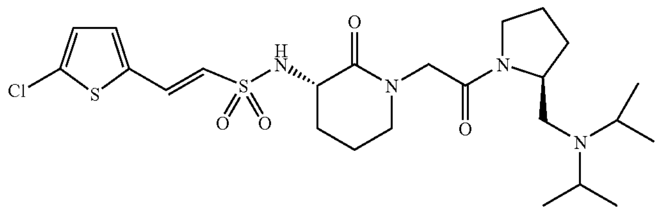 | HPLC (method 1) $t_R$ = 2.3 min LCMS (ESI, pos. ion spectrum) m/z 545/547 (M + H) | prepared using the method described in Example 400 using INT22 |
| 538 | 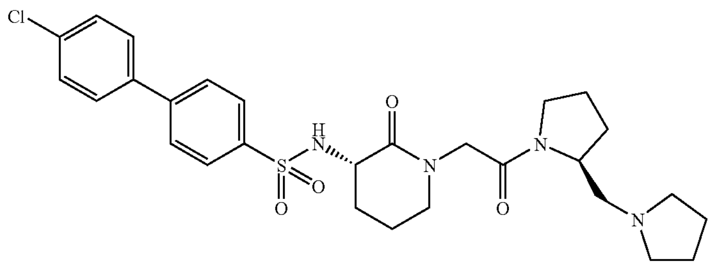 | LCMS (method 4) $t_R$ = 1.5 min (ESI, pos. ion spectrum) m/z 559/561 (M + 1) | prepared using the method described in Example 421 using the title compound of Example 415 |
| 539 | 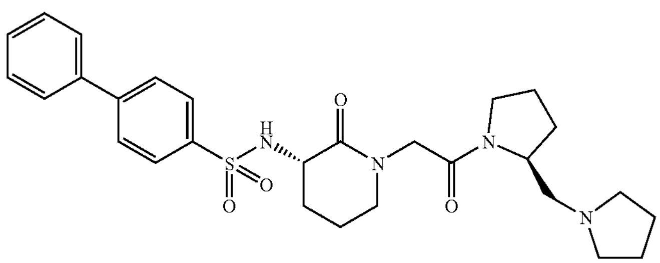 | LCMS (method 4) $t_R$ = 1.4 min (ESI, pos. ion spectrum) m/z 521 (M + 1) | prepared using the method described in Example 421 using the title compound of Example 415 |
| 540 | 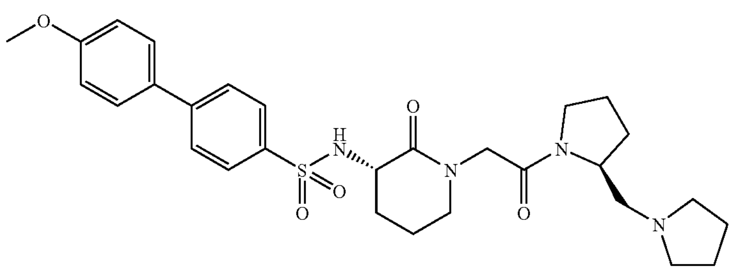 | LCMS (method 4) $t_R$ = 1.4 min (ESI, pos. ion spectrum) m/z 555 (M + 1) | prepared using the method described in Example 421 using the title compound of Example 415 |
| 541 | 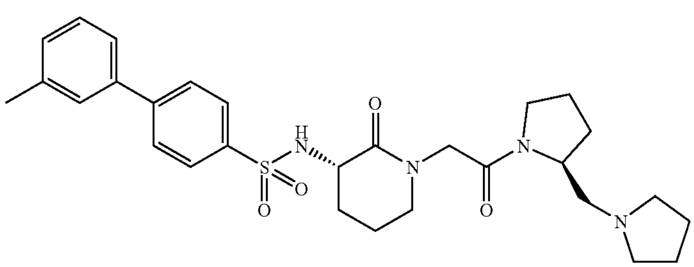 | LCMS (method 4) $t_R$ = 1.5 min (ESI, pos. ion spectrum) m/z 539 (M + 1) | prepared using the method described in Example 421 using the title compound of Example 415 |
| 542 | 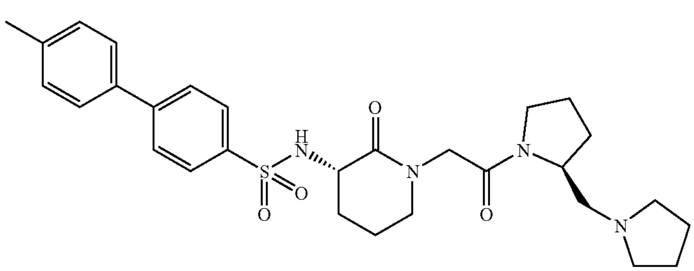 | LCMS (method 4) $t_R$ = 1.5 min (ESI, pos. ion spectrum) m/z 539 (M + 1) | prepared using the method described in Example 532 |

-continued

| Ex # | Structure | characterization | method |
|---|---|---|---|
| 543 | 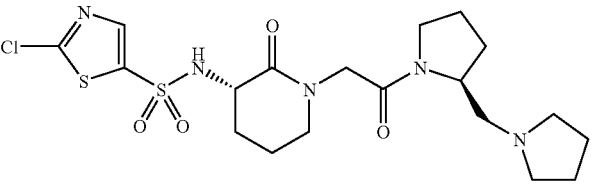 | HPLC (method 2) $t_R$ = 1.3 min LCMS (ESI, pos. ion spectrum) m/z 490/492 (M + 1) | prepared using the method described in Example 1 using INT9 |
| 544 | 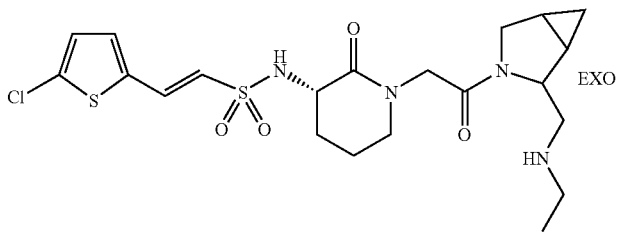 | HPLC (method 1) $t_R$ = 2.3 min LCMS (ESI, pos. ion spectrum) m/z 501/503 (M + 1) | Prepared using the method described in Example 410 |
| 545 | 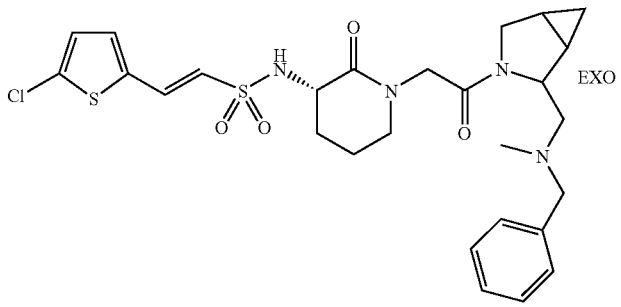 | HPLC (method 1) $t_R$ = 2.7 min LCMS (ESI, pos. ion spectrum) m/z 577/579 (M + 1) | Prepared using the method described in Example 410 |
| 546 | 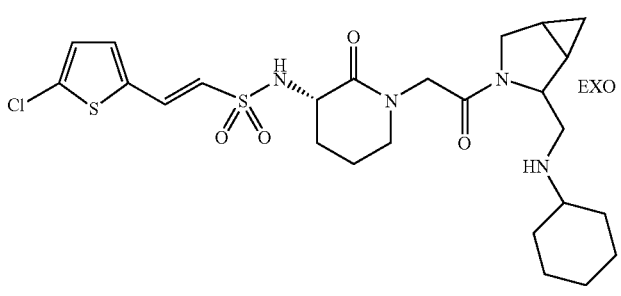 | HPLC (method 1) $t_R$ = 2.7 min LCMS (ESI, pos. ion spectrum) m/z 555/557 (M + 1) | Prepared using the method described in Example 410 |
| 547 | 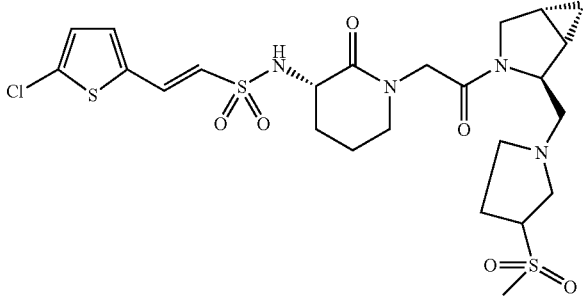 | HPLC (method 1) $t_R$ = 2.2 min LCMS (ESI, pos. ion spectrum) m/z 605/607 (M + 1) | Prepared using the method described in Example 410 |
| 548 | 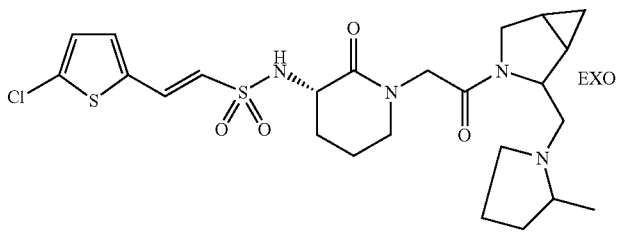 | HPLC (method 1) $t_R$ = 2.3 min LCMS (ESI, pos. ion spectrum) m/z 541/543 (M + 1) | Prepared using the method described in Example 410 |

| Ex # | Structure | characterization | method |
|---|---|---|---|
| 549 | 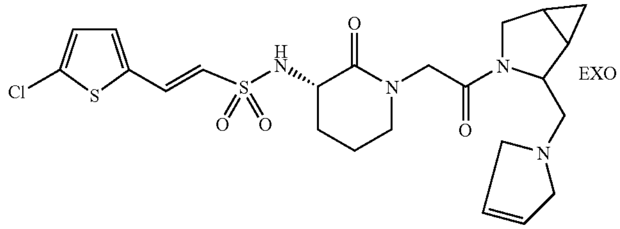 | HPLC (method 1) $t_R$ = 2.2 min LCMS (ESI, pos. ion spectrum) m/z 525/527 (M + 1) | Prepared using the method described in Example 410 |
| 550 | 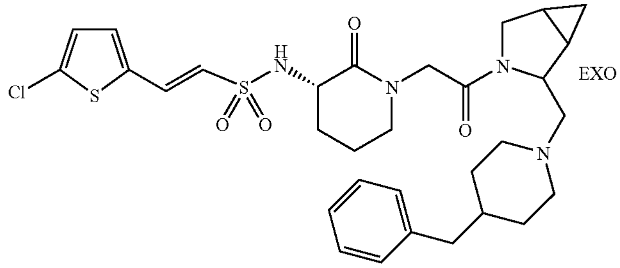 | HPLC (method 1) $t_R$ = 2.9 min LCMS (ESI, pos. ion spectrum) m/z 631/633 (M + 1) | Prepared using the method described in Example 410 |
| 551 | 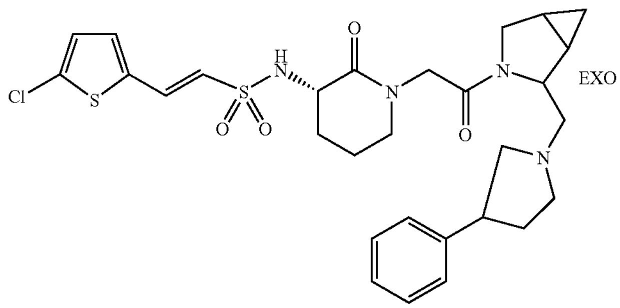 | HPLC (method 1) $t_R$ = 2.8 min LCMS (ESI, pos. ion spectrum) m/z 603/605 (M + 1) | Prepared using the method described in Example 410 |
| 552 | 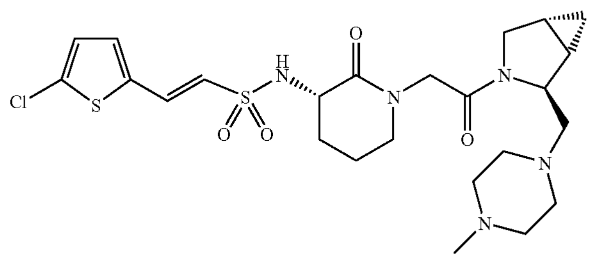 | HPLC (method 1) $t_R$ = 2.2 min LCMS (ESI, pos. ion spectrum) m/z 556/558 (M + 1) | Prepared using the method described in Example 410 |
| 553 | 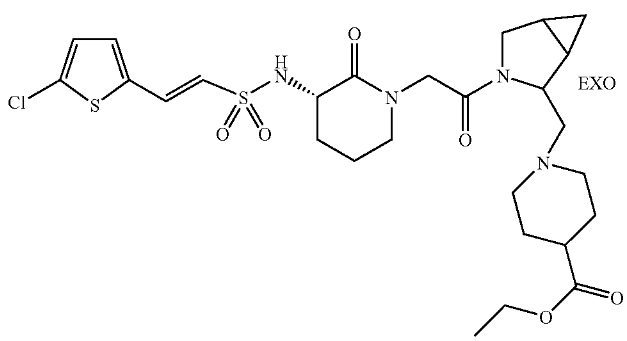 | HPLC (method 1) $t_R$ = 2.5 min LCMS (ESI, pos. ion spectrum) m/z 613/615 (M + 1) | Prepared using the method described in Example 410 |

| Ex # | Structure | characterization | method |
|---|---|---|---|
| 554 | 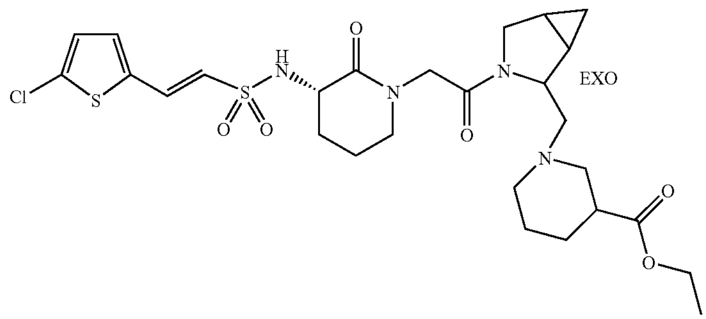 | HPLC (method 1). $t_R$ = 2.5 min LCMS (ESI, pos. ion spectrum) m/z 613/615 (M + 1) | Prepared using the method described in Example 410 |
| 555 | 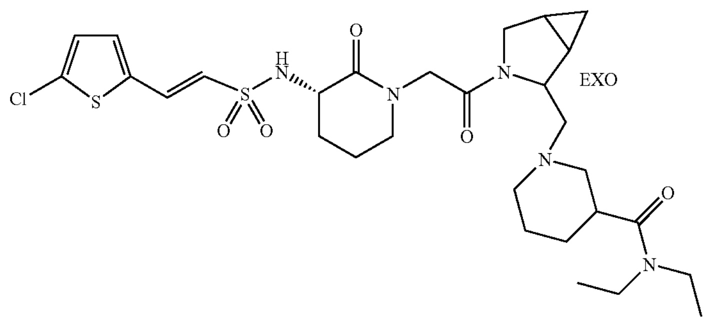 | HPLC (method 1) $t_R$ = 2.6 min LCMS (ESI, pos. ion spectrum) m/z 640/642 (M + 1) | Prepared using the method described in Example 410 |
| 556 | 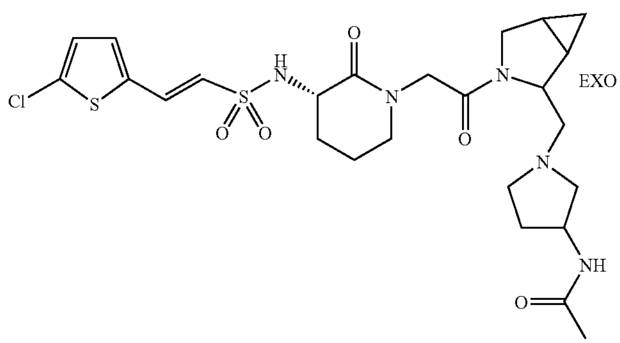 | HPLC (method 1) $t_R$ = 1.3 min LCMS (ESI, pos. ion spectrum) m/z 584/586 (M + 1) | Prepared using the method described in Example 410 |
| 557 | 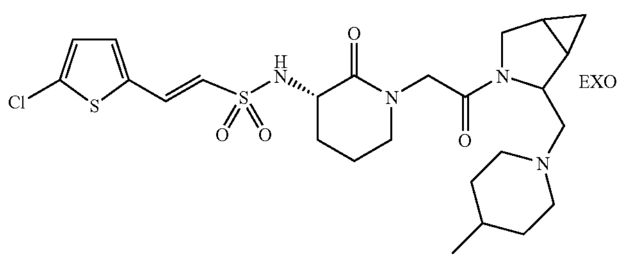 | HPLC (method 1) $t_R$ = 2.6 min LCMS (ESI, pos. ion spectrum) m/z 555/557 (M + 1) | Prepared using the method described in Example 410 |
| 558 | 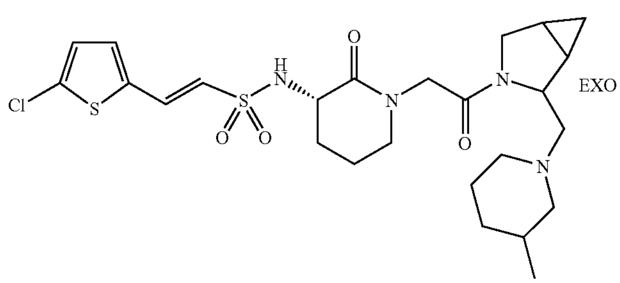 | HPLC (method 1) $t_R$ = 2.6 min LCMS (ESI, pos. ion spectrum) m/z 555/557 (M + 1) | Prepared using the method described in Example 410 |

-continued

| Ex # | Structure | characterization | method |
|---|---|---|---|
| 559 | 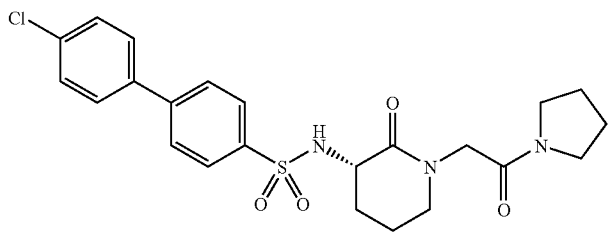 | HPLC (method 1) $t_R$ = 3.6 min LCMS (ESI, pos. ion spectrum) m/z 476/478 (M + 1) | Prepared using the methods described in Example INT3 and Example 48 |
| 560 | 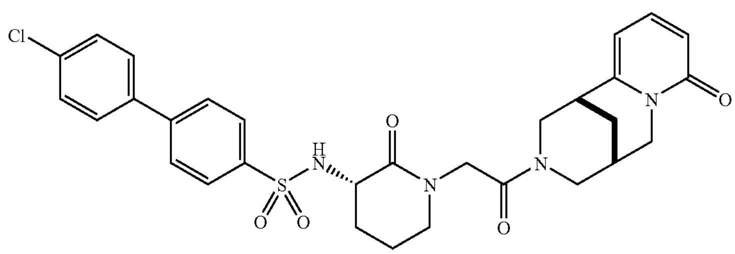 | HPLC (method 1) $t_R$ = 3.5 min LCMS (ESI, pos. ion spectrum) m/z 595/597 (M + 1) | Prepared using the methods described in Example INT3 and Example 48 |
| 561 | 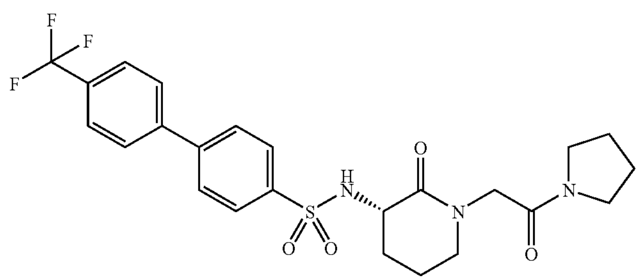 | HPLC (method 1) $t_R$ = 3.6 min LCMS (ESI, pos. ion spectrum) m/z 510 (M + 1) | Prepared using the methods described in Example INT3 and Example 48 |
| 562 | 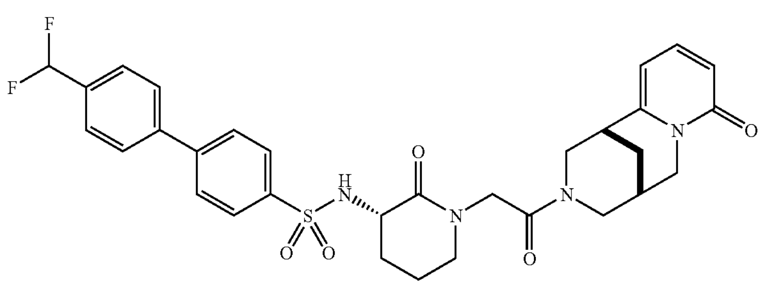 | HPLC (method 1) $t_R$ = 3.5 min LCMS (ESI, pos. ion spectrum) m/z 629 (M + 1) | Prepared using the method described in Example 48 |
| 563 | 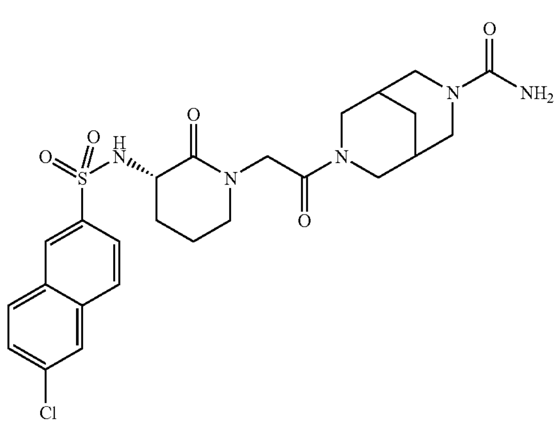 | HPLC (method 1) $t_R$ = 3.2 min LCMS (ESI, pos. ion spectrum) m/z 548/550 (M + 1) | Prepared using the method described in Example 316 using the title compound of Example 429 |

-continued

| Ex # | Structure | characterization | method |
|---|---|---|---|
| 564 | 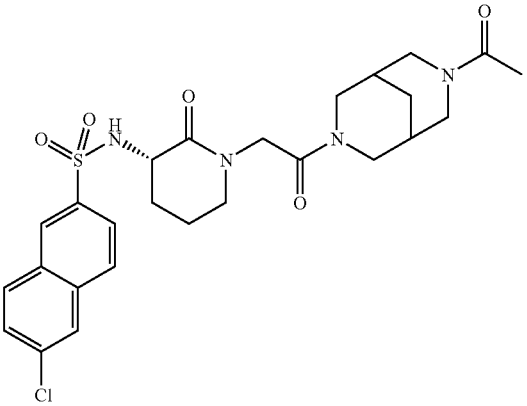 | HPLC (method 1) t_R = 3.3 min LCMS (ESI, pos. ion spectrum) m/z 547/549 (M + 1) | Prepared using the method described in Example 317 using the title compound of Example 429 |
| 565 | 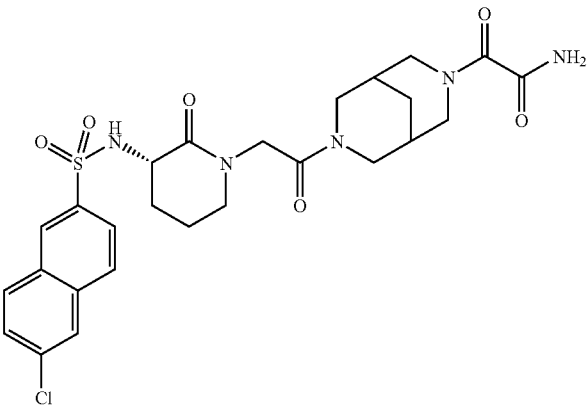 | HPLC (method 1) t_R = 3.2 min LCMS (ESI, pos. ion spectrum) m/z 576/578 (M + 1) | Prepared using the method described in Example 48 using the title compound of Example 429 |
| 566 | 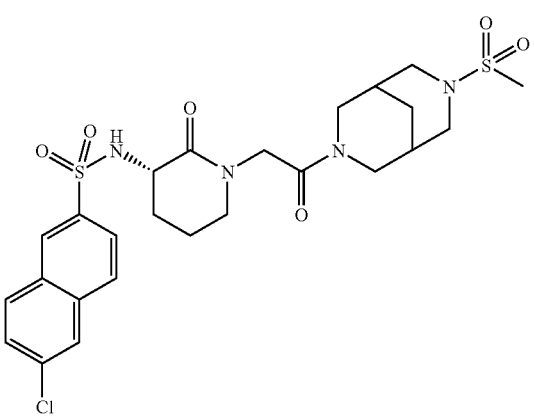 | HPLC (method 1) t_R = 3.4 min LCMS (ESI, pos. ion spectrum) m/z 583/585 (M + 1) | Prepared using the method described in Example 21 using the title compound of Example 429 |

-continued

| Ex # | Structure | characterization | method |
|---|---|---|---|
| 567 | 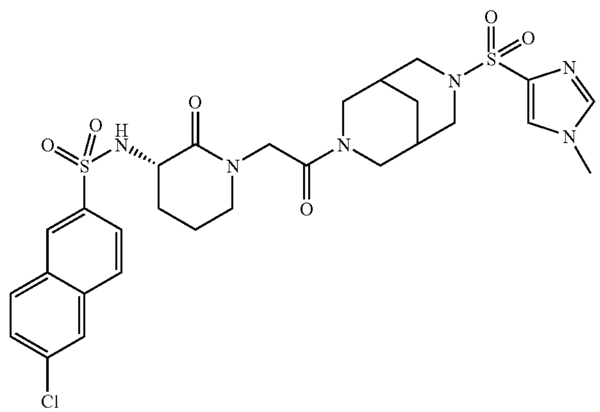 | HPLC (method 1) $t_R$ = 3.4 min LCMS (ESI, pos. ion spectrum) m/z 649/561 (M + 1) | Prepared using the method described in Example 21 using the title compound of Example 429 |
| 568 | 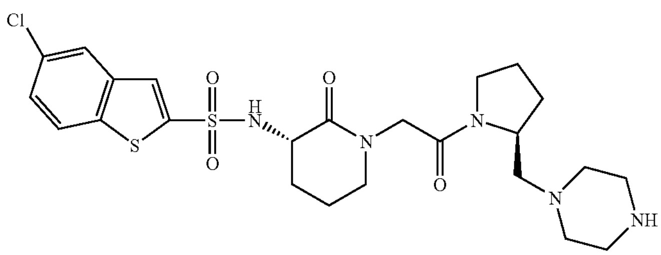 | HPLC (method 1) $t_R$ = 2.6 min LRMS (ESI, pos. ion spectrum) m/z 554/556 (M + H) | Prepared using the method described in Example 613 |
| 569 | 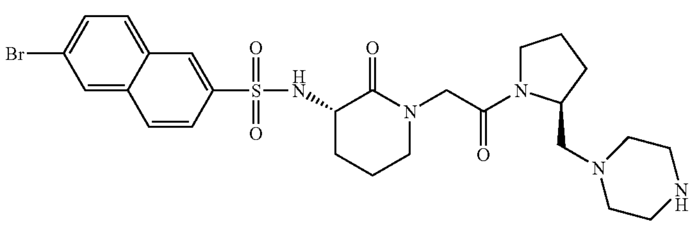 | HPLC (method 1) $t_R$ = 2.7 min LRMS (ESI, pos. ion spectrum) m/z 592/594 (M + H) | Prepared using the method described in Example 613 |
| 570 | 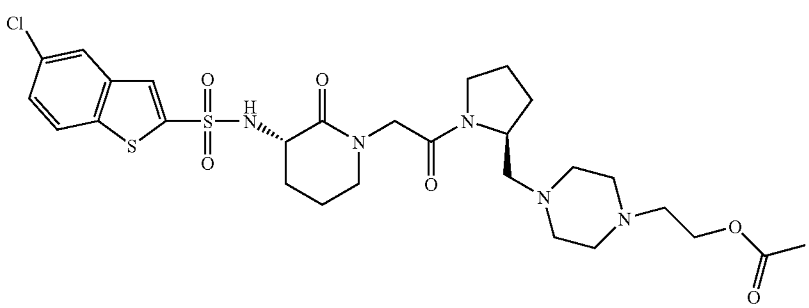 | HPLC (method 1) $t_R$ = 2.9 min LRMS (ESI, pos. ion spectrum) m/z 640/642 (M + H) | Title compound of Example 570 |
| 571 | 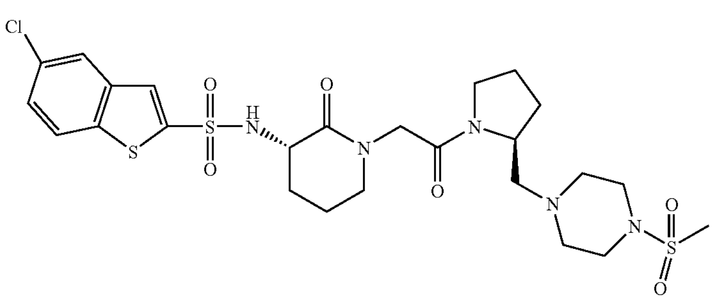 | HPLC (method 1) $t_R$ = 2.7 min LRMS (ESI, pos. ion spectrum) m/z 632/634 (M + H) | Title compound of Example 571 |

-continued

| Ex # | Structure | characterization | method |
|---|---|---|---|
| 572 | 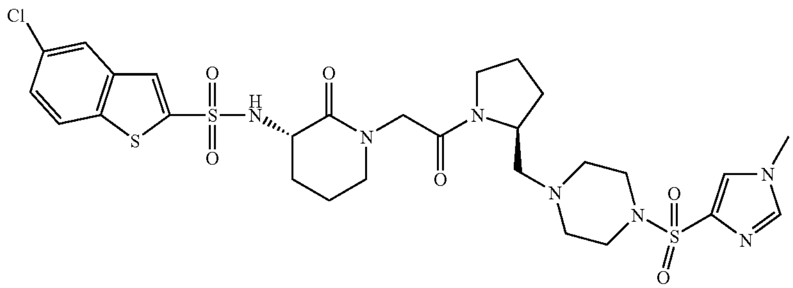 | HPLC (method 1) $t_R$ = 2.9 min LRMS (ESI, pos. ion spectrum) m/z 698/700 (M + H) | Prepared using the method described in Example 571 |
| 573 | 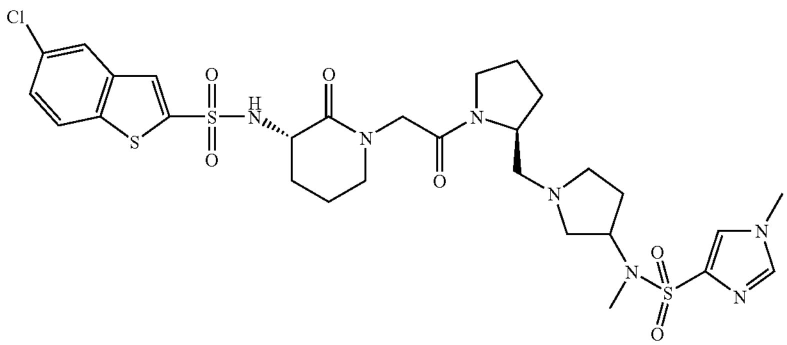 | HPLC (method 1) $t_R$ = 3.0 min LRMS (ESI, pos. ion spectrum) m/z 712/714 (M + H) | Prepared using the method described in Example 571 using the title compound of Example 615 |
| 574 | 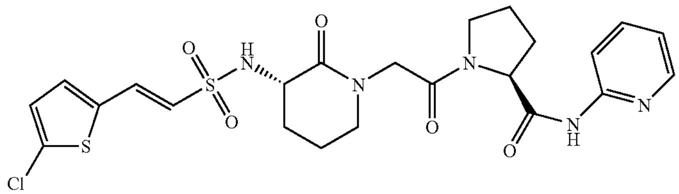 | HPLC (method 6) $t_R$ = 1.4 min LCMS (ESI, pos. ion spectrum) m/z 552/554 (M + 1) | Title compound of Example 574 |
| 575 | 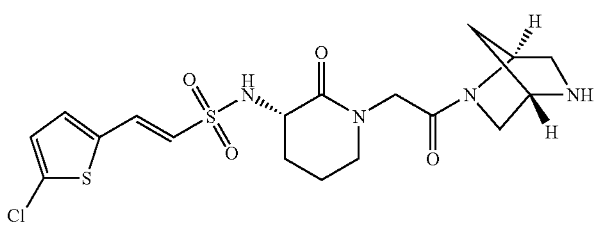 | HPLC (method 6) $t_R$ = 1.3 min LCMS (ESI, pos. ion spectrum) m/z 459/461 (M + 1) | Title compound of Example 575 |
| 576 | 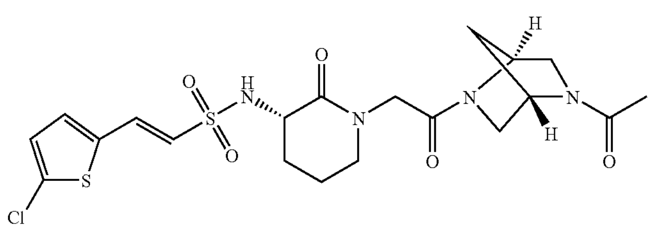 | HPLC (method 6) $t_R$ = 1.3 min LCMS (ESI, pos. ion spectrum) m/z 501/503 (M + 1) | Prepared using the method described in Example 575 |
| 577 | 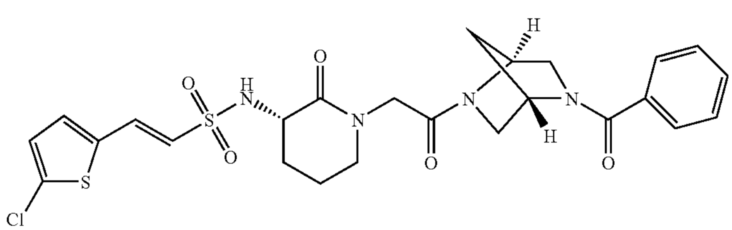 | HPLC (method 6) $t_R$ = 1.6 min LCMS (ESI, pos. ion spectrum) m/z 563/565 (M + 1) | Prepared using the method described in Example 575 |

| Ex # | Structure | characterization | method |
|---|---|---|---|
| 578 | 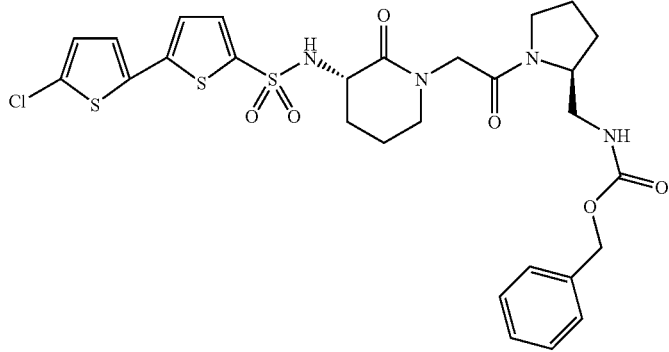 | HPLC (method 1)<br>$t_R$ = 4.0 min<br>LCMS (ESI, pos.<br>ion spectrum) m/z<br>649/651 (M − H) | Title compound<br>of Example 578 |
| 579 | 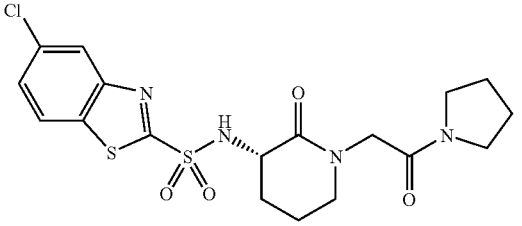 | HPLC (method 3)<br>$t_R$ = 2.6 min<br>LCMS (ESI, pos.<br>ion spectrum) m/z<br>457/459 (M + 1) | prepared using<br>the method<br>described<br>in Example 1<br>using INT25 |
| 580 | 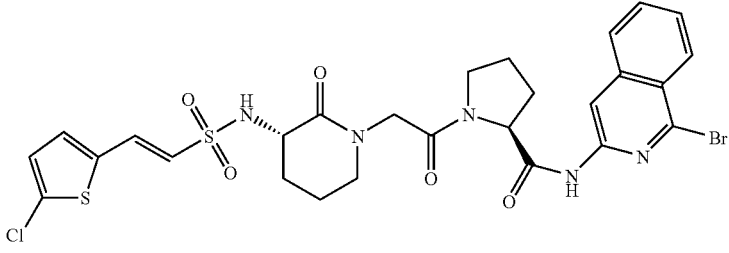 | HPLC (method 6)<br>$t_R$ = 2.0 min<br>LCMS (ESI, pos.<br>ion spectrum) m/z<br>680/682 (M + 1) | Prepared using<br>the methods<br>described<br>in Example 494 |
| 581 | 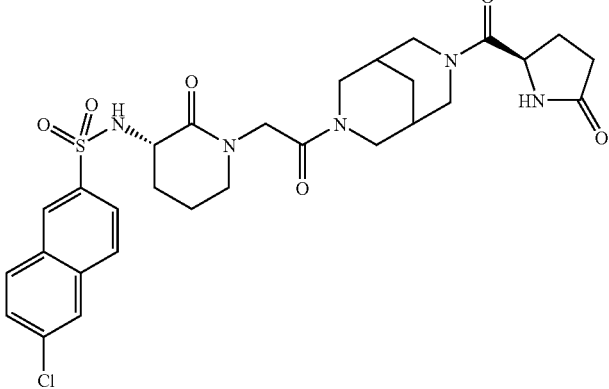 | HPLC (method 1)<br>$t_R$ = 3.3 min<br>LCMS (ESI, pos.<br>ion spectrum) m/z<br>616/618 (M + 1) | Prepared using<br>the method<br>described<br>in Example 48<br>using the title<br>compound of<br>Example 429 |

-continued

| Ex # | Structure | characterization | method |
|---|---|---|---|
| 582 | 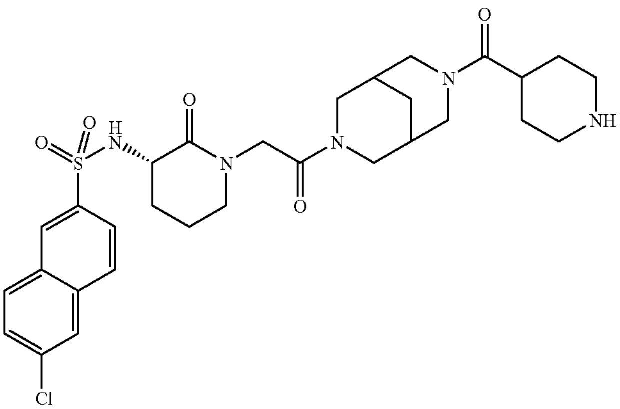 | HPLC (method 1) $t_R$ = 3.0 min LCMS (ESI, pos. ion spectrum) m/z 616/618 (M + 1) | Prepared using the methods described in Example 48 and 178 part B using the title compound of Example 429 and 1-(1,1-dimethyl-ethyl) 1,4-Piperidinedi-carboxylate |
| 583 | 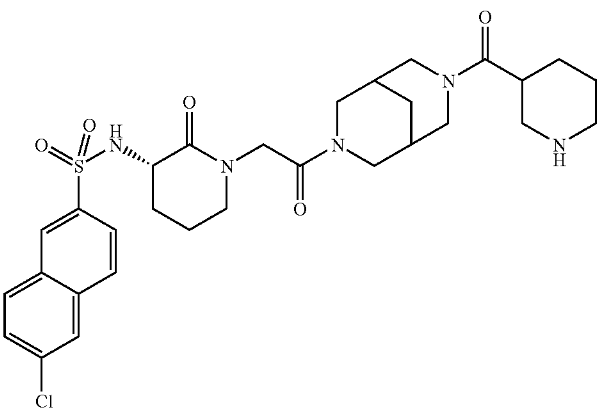 | HPLC (method 1) $t_R$ = 3.0 min LCMS (ESI, pos. ion spectrum) m/z 616/618 (M + 1) | From EXAMPLE 429 Prepared using the method described in Examples 48 and 178 part B1-(1,1-dimethylethyl) 1,3-Piperidinedi-carboxylate |
| 584 | 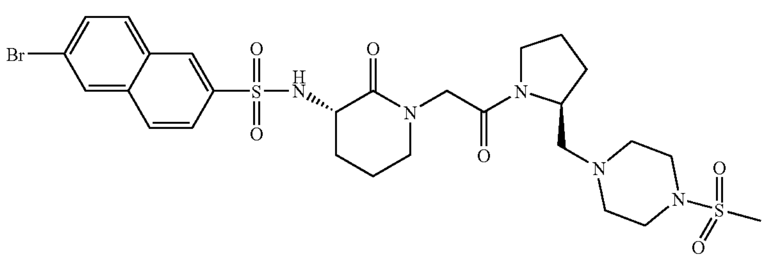 | HPLC (method 1) $t_R$ = 3.0 min LRMS (ESI, pos. ion spectrum) m/z 670/672 (M + H) | Prepared using the method described in Example 571 using the title compound of Example 569 |
| 585 | 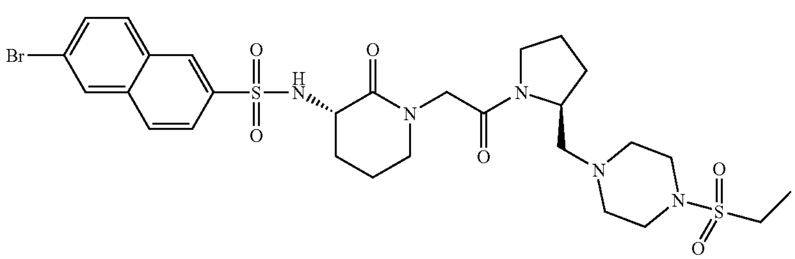 | HPLC (method 1) $t_R$ = 3.1 min LRMS (ESI, pos. ion spectrum) m/z 684/686 (M + H) | Prepared using the method described in Example 571 using the title compound of Example 569 |
| 586 | 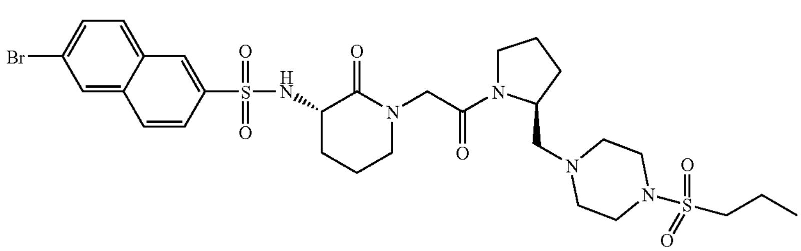 | HPLC (method 1) $t_R$ = 3.2 min LRMS (ESI, pos. ion spectrum) m/z 698/700 (M + H) | Prepared using the method described in Example 571 using the title compound of Example 569 |

-continued

| Ex # | Structure | characterization | method |
|---|---|---|---|
| 587 | 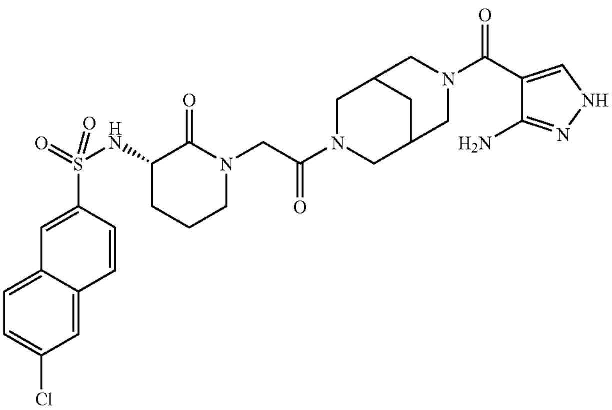 | HPLC (method 1) $t_R$ = 3.1 min LCMS (ESI, pos. ion spectrum) m/z 614/616 (M + 1) | Prepared using the method described in Example 48 using the title compound of Example 429 |
| 588 | 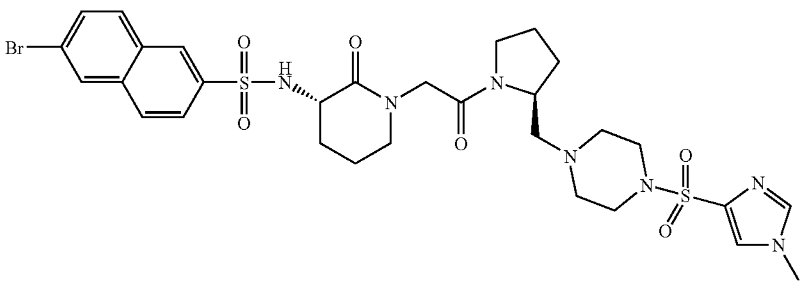 | HPLC (method 1) $t_R$ = 3.21 min LRMS (ESI, pos. ion spectrum) m/z 736/738 (M + H) | Prepared using the method described in Example 571 using the title compound of Example 569 |
| 589 | 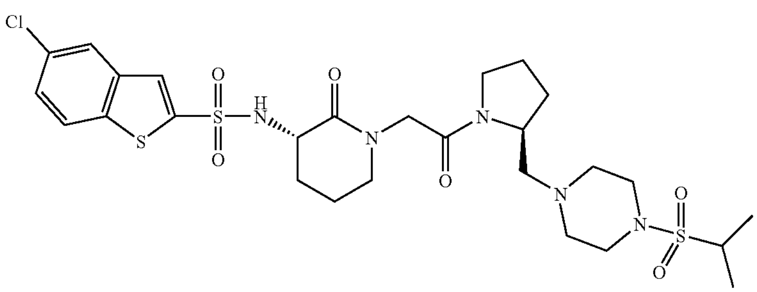 | HPLC (method 1) $t_R$ = 3.1 min LRMS (ESI, pos. ion spectrum) m/z 660/662 (M + H) | Prepared using the method described in Example 571 using the title compound of Example 568 at elevated temperature |
| 590 | 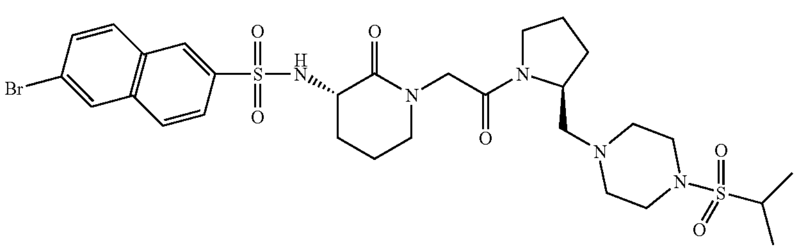 | HPLC (method 1) $t_R$ = 3.2 min LRMS (ESI, pos. ion spectrum) m/z 699/701 (M + H) | Prepared using the method described in Example 571 using the title compound of Example 569 at elevated temperature |
| 591 | 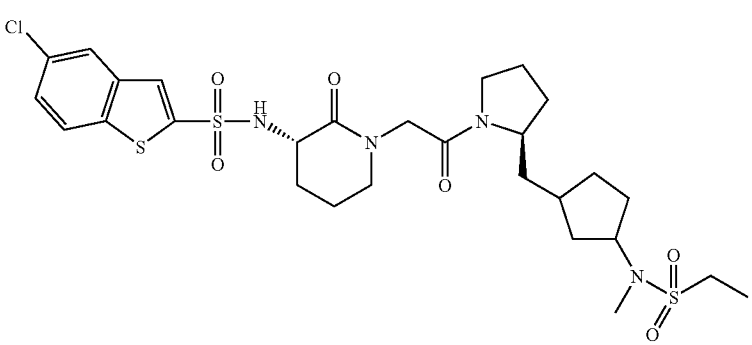 | HPLC (method 1) $t_R$ = 3.0 min LRMS (ESI, pos. ion spectrum) m/z 660/662 (M + H) | Prepared using the method described in Example 571 using the title compound of Example 615 |

-continued

| Ex # | Structure | characterization | method |
|---|---|---|---|
| 592 | 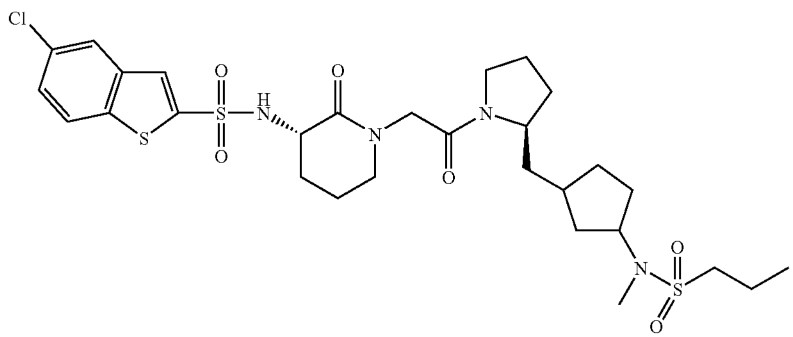 | HPLC (method 1) t_R = 3.1 min LRMS (ESI, pos. ion spectrum) m/z 674/676 (M + H) | Prepared using the method described in Example 571 using the title compound of Example 615 |
| 593 | 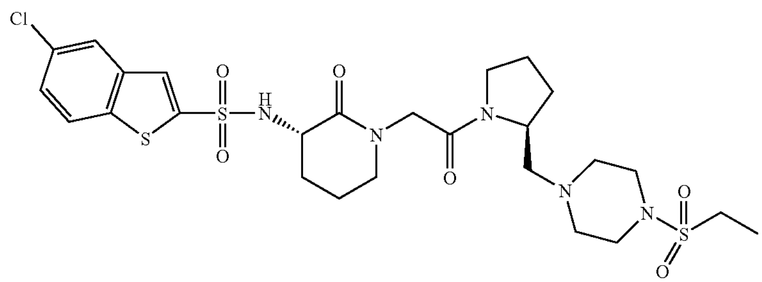 | HPLC (method 1) t_R = 3.0 min LRMS (ESI, pos. ion spectrum) m/z 646/648 (M + H) | Prepared using the method described in Example 571 using the title compound of Example 568 |
| 594 | 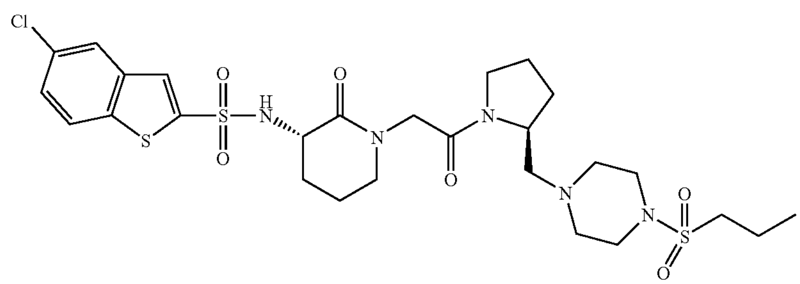 | HPLC (method 1) t_R = 3.1 min LRMS (ESI, pos. ion spectrum) m/z 660/662 (M + H) | Prepared using the method described in Example 571 using the title compound of Example 568 |
| 595 | 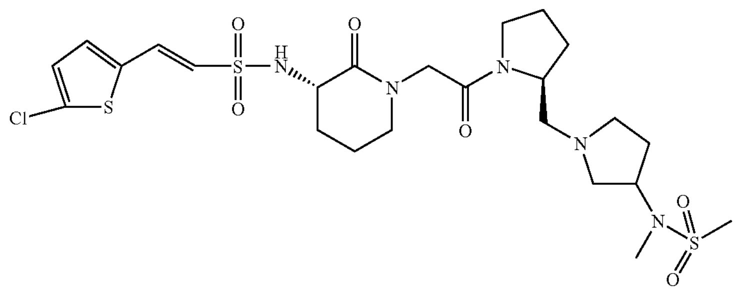 | HPLC (method 1) t_R = 2.7 min LRMS (ESI, pos. ion spectrum) m/z 622/624 (M + H) | Prepared using the method described in Example 571 using the title compound of Example 613 |
| 596 | 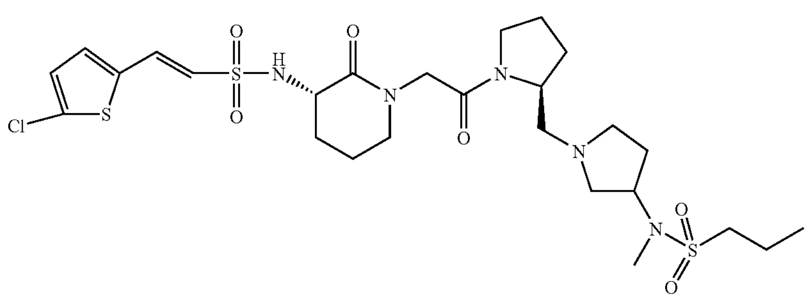 | HPLC (method 1) t_R = 2.9 min LRMS (ESI, pos. ion spectrum) m/z 650/652 (M + H) | Prepared using the method described in Example 571 using the title compound of Example 613 |

| Ex # | Structure | characterization | method |
|---|---|---|---|
| 597 | 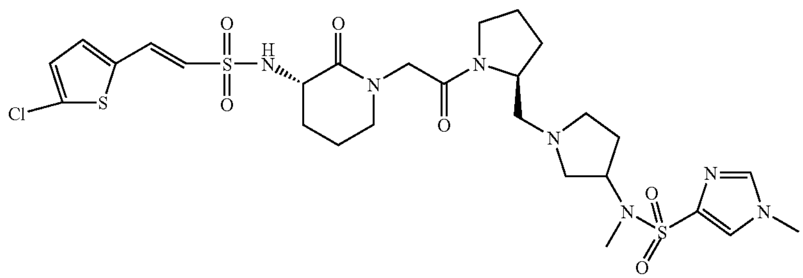 | HPLC (method 1) $t_R$ = 2.8 min LRMS (ESI, pos. ion spectrum) m/z 688/690 (M + H) | Prepared using the method described in Example 571 using the title compound of Example 613 |
| 598 | 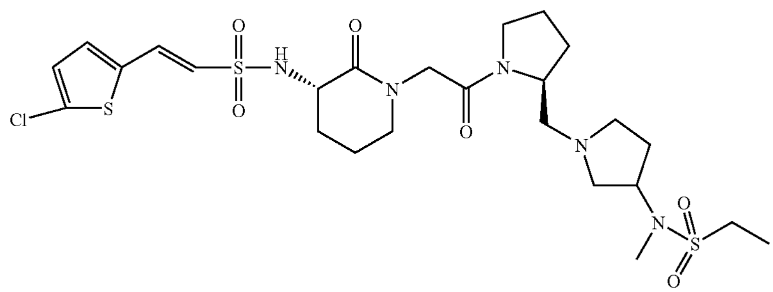 | HPLC (method 1) $t_R$ = 2.8 min LRMS (ESI, pos. ion spectrum) m/z 636/638 (M + H) | Prepared using the method described in Example 571 using the title compound of Example 613 |
| 599 | 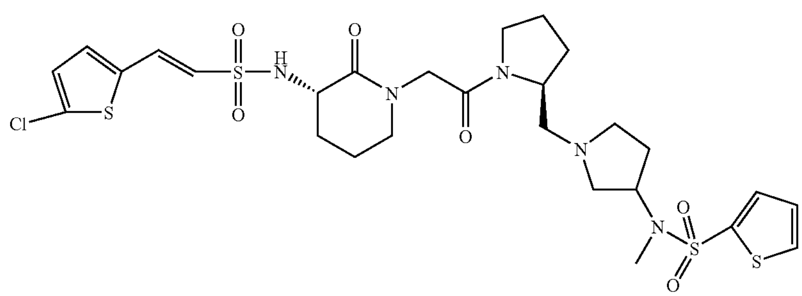 | HPLC (method 1) $t_R$ = 3.0 min LRMS (ESI, pos. ion spectrum) m/z 690/692 (M + H) | Prepared using the method described in Example 571 using the title compound of Example 613 |
| 600 | 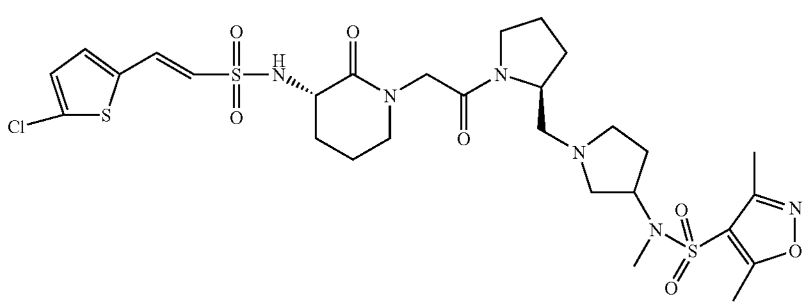 | HPLC (method 1) $t_R$ = 3.1 min LRMS (ESI, pos. ion spectrum) m/z 703/705 (M + H) | Prepared using the method described in Example 571 using the title compound of Example 613 |
| 601 | 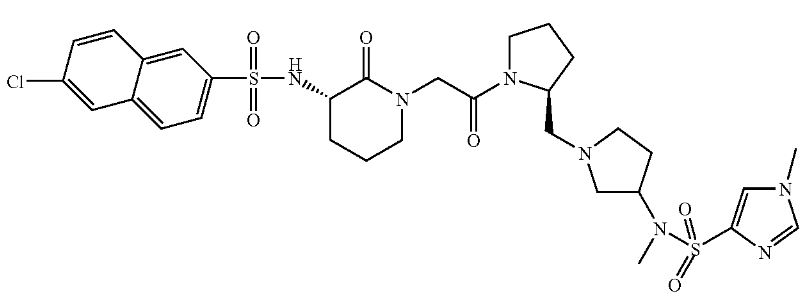 | HPLC (method 1) $t_R$ = 3.1 min LRMS (ESI, pos. ion spectrum) m/z 706/708 (M + H) | Prepared using the method described in Example 571 using the title compound of Example 614 |

-continued

| Ex # | Structure | characterization | method |
|---|---|---|---|
| 602 | 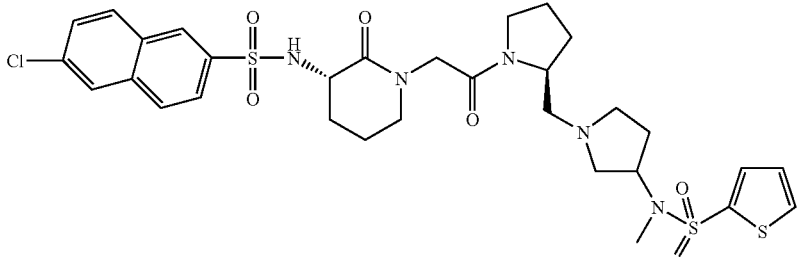 | HPLC (method 1) t$_R$ = 3.2 min LRMS (ESI, pos. ion spectrum) m/z 708/710 (M + H) | Prepared using the method described in Example 571 using the title compound of Example 614 |
| 603 | 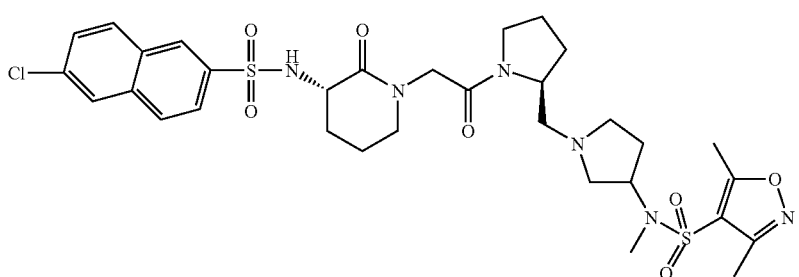 | HPLC (method 1) t$_R$ = 3.3 min LRMS (ESI, pos. ion spectrum) m/z 721/723 (M + H) | Prepared using the method described in Example 571 using the title compound of Example 614 |
| 604 | 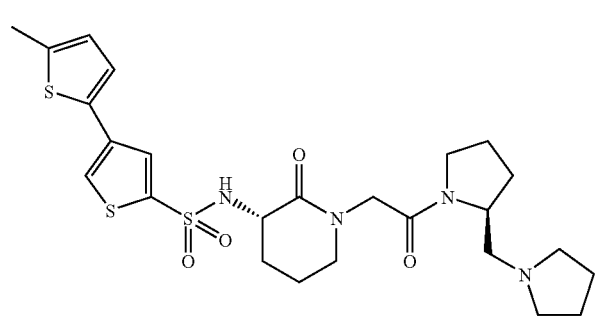 | HPLC (method 2) t$_R$ = 1.8 min LCMS (ESI, pos. ion spectrum) m/z 551 (M − 1) | Title compound of Example 604 |
| 605 | 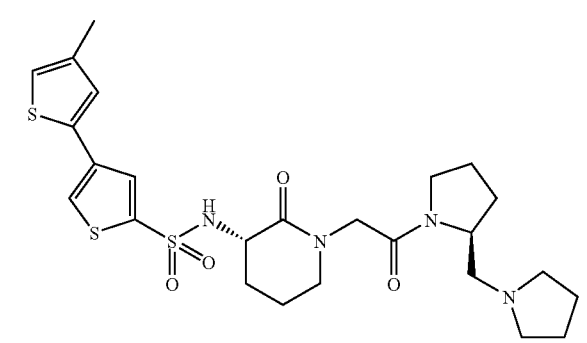 | HPLC (method 2) t$_R$ = 1.9 min LCMS (ESI, pos. ion spectrum) m/z 551 (M + 1) | prepared using the method described in Example 604 |
| 606 | 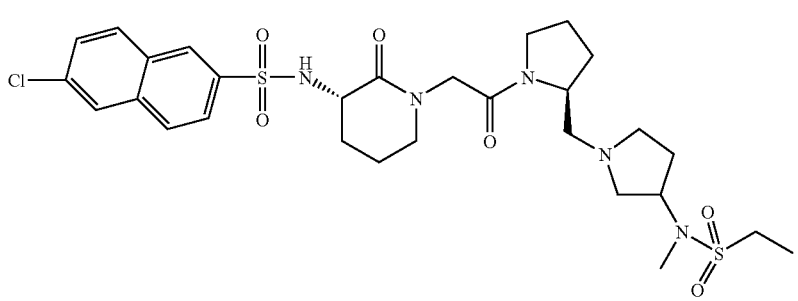 | HPLC (method 1) t$_R$ = 3.1 min LRMS (ESI, pos. ion spectrum) m/z 654/656 (M + H) | Prepared using the method described in Example 571 using the title compound of Example 614 |

-continued

| Ex # | Structure | characterization | method |
|---|---|---|---|
| 607 | 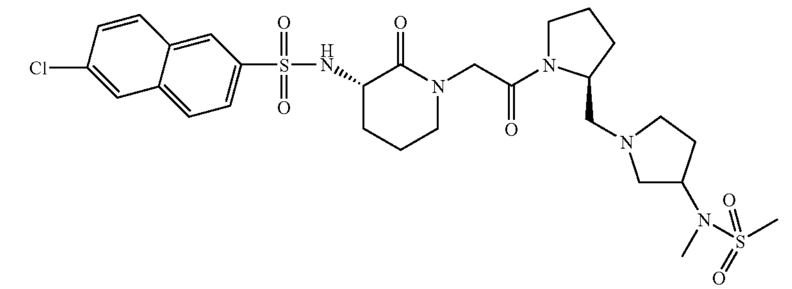 | HPLC (method 1) t_R = 3.3 min LRMS (ESI, pos. ion spectrum) m/z 721/723 (M + H) | Prepared using the method described in Example 571 using the title compound of Example 614 |
| 608 | 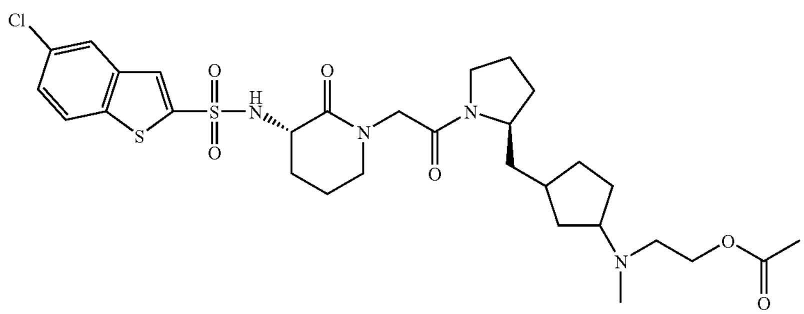 | HPLC (method 1) t_R = 3.1 min LRMS (ESI, pos. ion spectrum) m/z 654/656 (M − H) | Title compound of Example 608 |
| 609 | 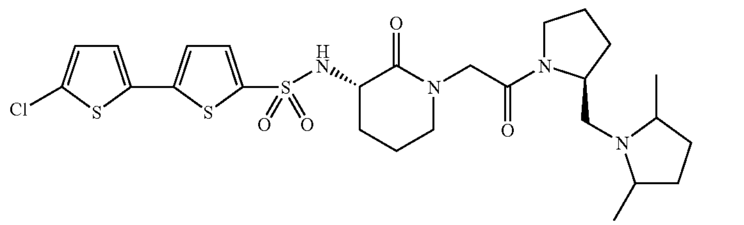 | HPLC (method 1) t_R = 2.8 min LCMS (ESI, pos. ion spectrum) m/z 599/601 (M + H) | prepared using the method described in Example 400 using INT20 |
| 610 | 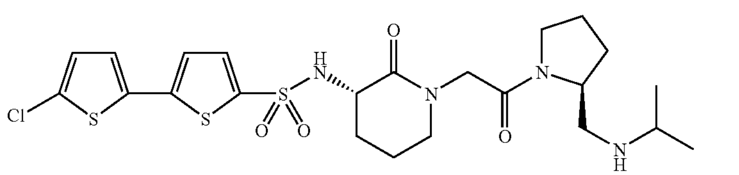 | HPLC (method 1) t_R = 2.7 min LCMS (ESI, pos. ion spectrum) m/z 559/561 (M + H) | prepared using the method described in Example 400 using INT20 |
| 611 | 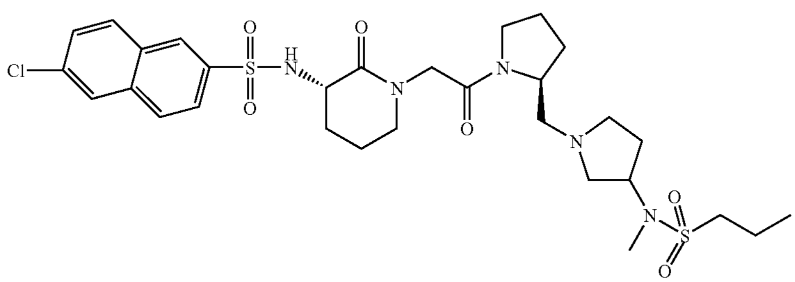 | HPLC (method 1) t_R = 3.2 min LRMS (ESI, pos. ion spectrum) m/z 668/670 (M + H) | Prepared using the method described in Example 571 using the title compound of Example 614 |
| 612 | 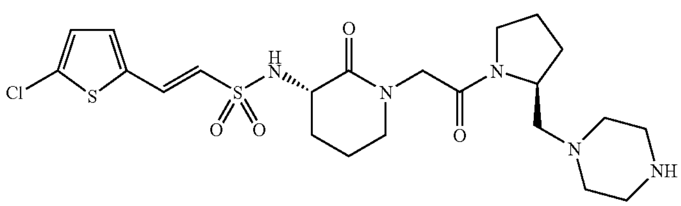 | HPLC (method 1) t_R = 2.2 min LRMS (ESI, pos. ion spectrum) m/z 530/532 (M + H) | Prepared using the method described in Example 613 |

| Ex # | Structure | characterization | method |
|---|---|---|---|
| 613 | 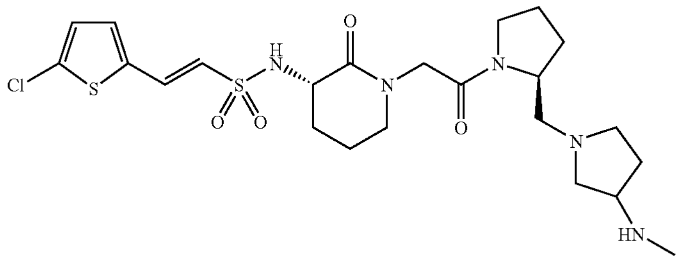 | HPLC (method 1) $t_R$ = 2.1 min LRMS (ESI, pos. ion spectrum) m/z 544/546 (M − H) | Title compound of Example 613 |
| 614 | 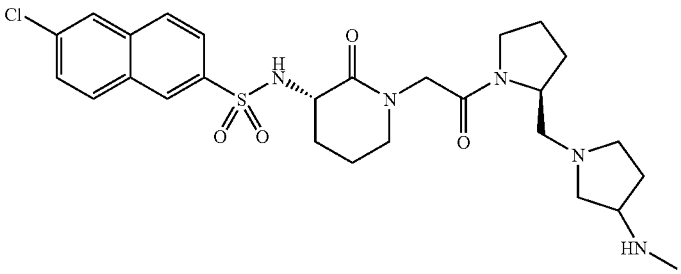 | HPLC (method 1) $t_R$ = 2.7 min LRMS (ESI, pos. ion spectrum) m/z 562/564 (M − H) | Prepared using the method described in Example 613 part A using INT15 |
| 615 | 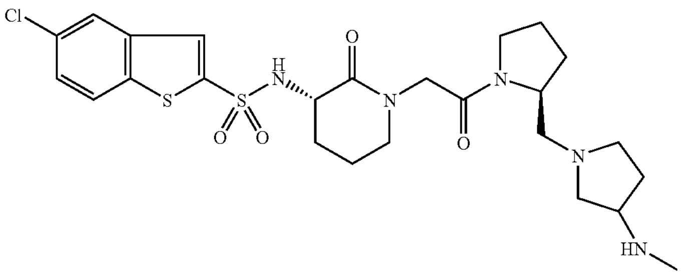 | HPLC (method 1) $t_R$ = 2.5 min LRMS (ESI, pos. ion spectrum) m/z 568 (M − H) | Prepared using the method described in Example 613 part A using INT17 |
| 616 | 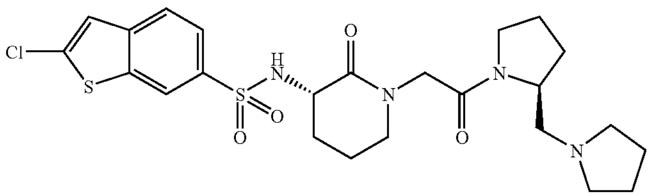 | HPLC (method 2) $t_R$ = 1.8 min LCMS (ESI, pos. ion spectrum) m/z 539/541 (M + 1) | prepared using the method described in Example 1 with INT 2 and INT9 |
| 617 | 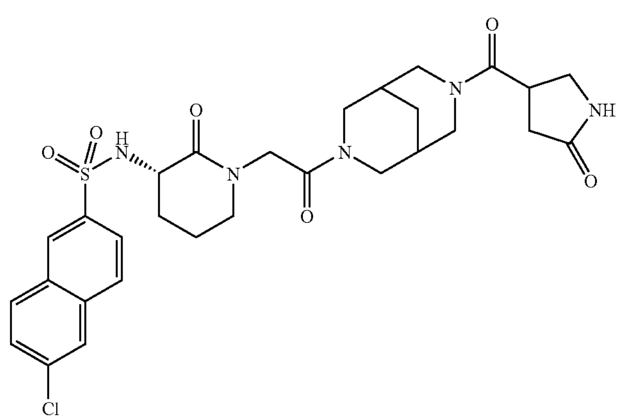 | HPLC (method 1) $t_R$ = 3.2 min LCMS (ESI, pos. ion spectrum) m/z 616/618 (M + 1) | Prepared using the method described in Example 48 using the title compound of Example 429 |

-continued

| Ex # | Structure | characterization | method |
|---|---|---|---|
| 618 | 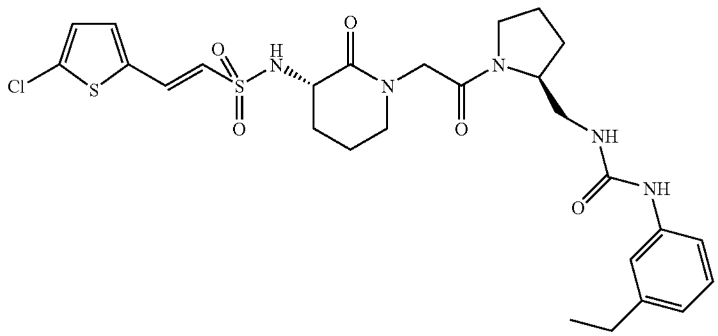 | HPLC (method 7) $t_R$ = 3.7 min LCMS (method 6) (ESI, pos. ion spectrum) m/z 608/610 (M − 1) | Title compound of Example 618 |
| 619 | 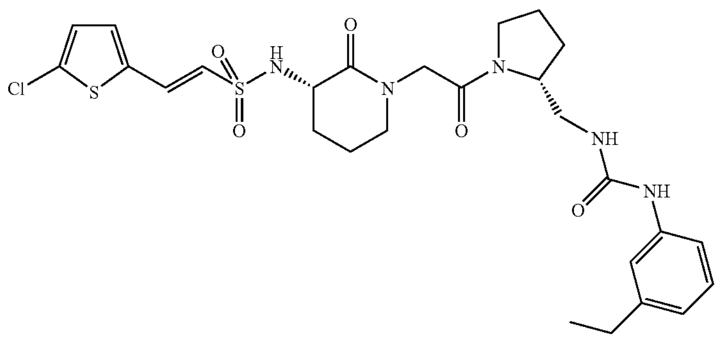 | HPLC (method 7) $t_R$ = 3.7 min LCMS (method 6) (ESI, pos. ion spectrum) m/z 608/610 (M − 1) | Title compound of Example 619 |
| 620 | 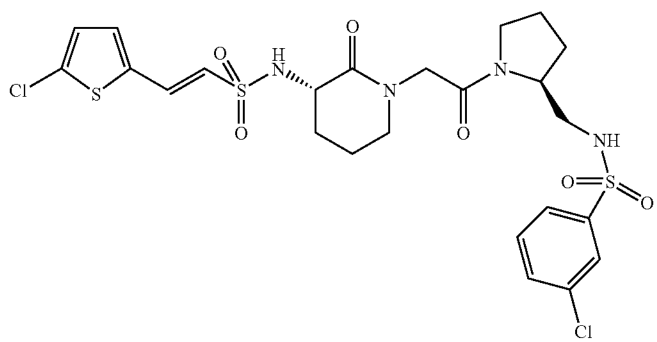 | HPLC (method 7) $t_R$ = 3.5 min LCMS (method 6) (ESI, pos. ion spectrum) m/z 635/637/639 (M − 1) | Title compound of Example 620 |
| 621 | 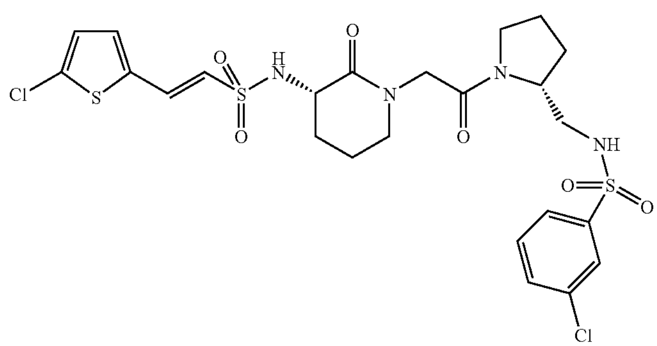 | HPLC (method 7) $t_R$ = 3.5 min LCMS (method 6) (ESI, pos. ion spectrum) m/z 635/637/639 (M − 1) | Title compound of Example 621 |
| 622 | 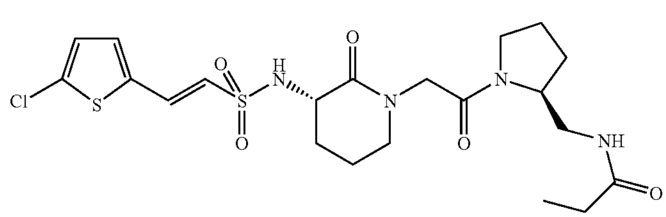 | HPLC (method 7) $t_R$ = 2.9 min LCMS (method 6) (ESI, pos. ion spectrum) m/z 517/519 (M − 1) | Title compound of Example 622 |

| Ex # | Structure | characterization | method |
|---|---|---|---|
| 623 | 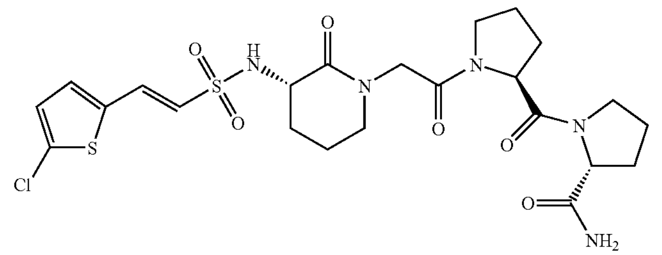 | HPLC (method 6) $t_R$ = 1.4 min LCMS (ESI, pos. ion spectrum) m/z 572/574 (M + 1) | Prepared using the methods described in Example 494 |
| 624 | 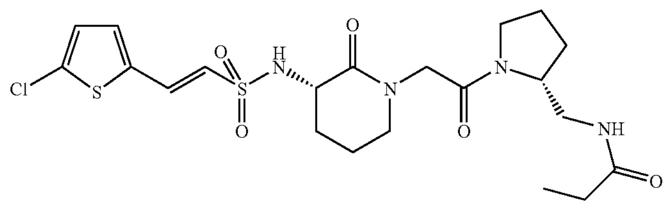 | HPLC (method 7) $t_R$ = 2.9 min LCMS (method 6) (ESI, pos. ion spectrum) m/z 517/519 (M − 1) | Title compound of Example 624 |
| 625 | 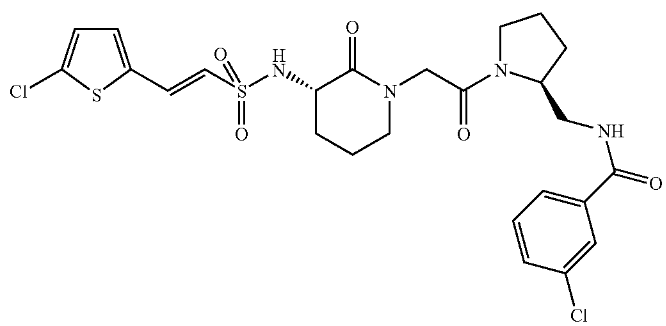 | HPLC (method 7) $t_R$ = 3.5 min LCMS (method 6) (ESI, pos. ion spectrum) m/z 599/601/603 (M + 1) | Prepared using the procedures described in Example 622 |
| 626 | 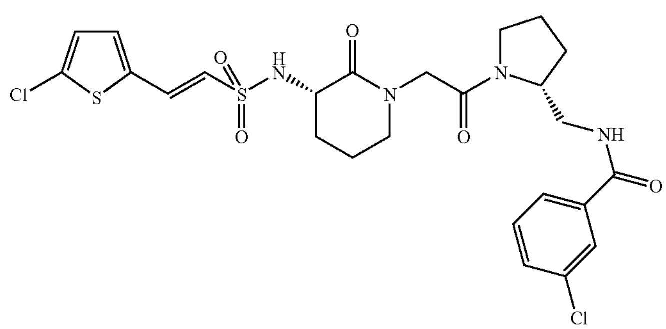 | HPLC (method 7) $t_R$ = 3.5 min LCMS (method 6) (ESI, pos. ion spectrum) m/z 599/601/603 (M + 1) | Prepared using the procedures described in Example 622 |
| 627 | 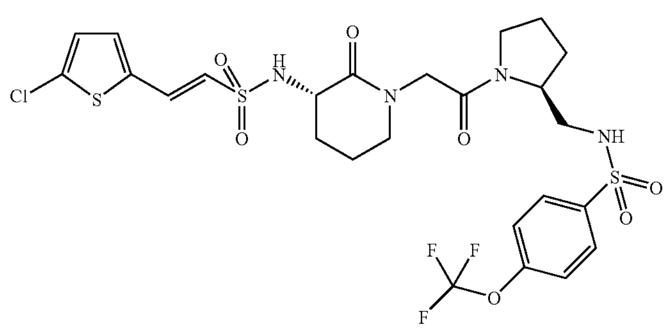 | HPLC (method 6) $t_R$ = 1.8 min LCMS (method 6) (ESI, pos. ion spectrum) m/z 685/687 (M + 1) | Prepared using the procedures described in Example 620 |

| Ex # | Structure | characterization | method |
|---|---|---|---|
| 628 | 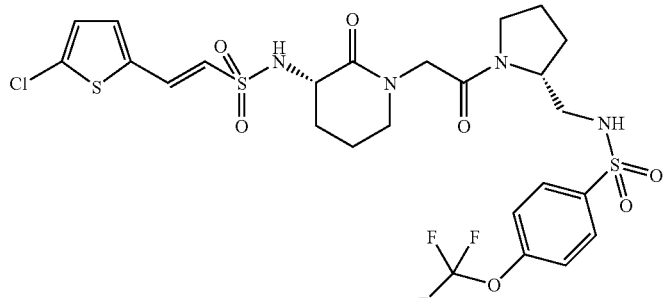 | HPLC (method 6) $t_R$ = 1.8 min LCMS (method 6) (ESI, pos. ion spectrum) m/z 685/687 (M + 1) | Prepared using the procedures described in Example 620 |
| 629 | 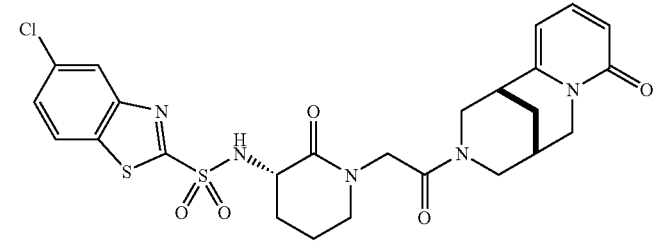 | HPLC (method 1) $t_R$ = 2.7 min LCMS (ESI, pos. ion spectrum) m/z 576/578 (M + H) | prepared using the method described in Example 130 using INT19 |
| 630 | 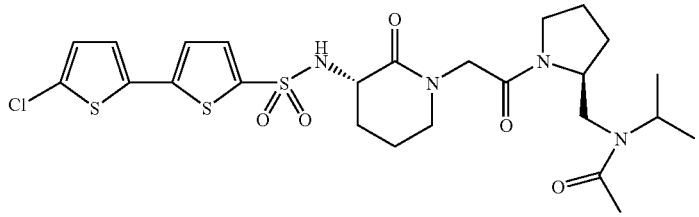 | HPLC (method 1) $t_R$ = 3.5 min LCMS (ESI, pos. ion spectrum) m/z 601/603 (M − H) | Title compound of Example 630 |
| 631 | 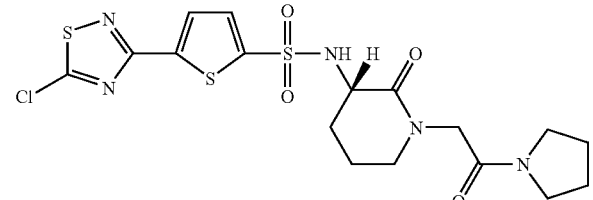 | HPLC (method 3) $t_R$ = 2.7 min LCMS (ESI, pos. ion spectrum) m/z 490/492 (M + 1) | prepared using the method described in Example 1 |
| 632 | 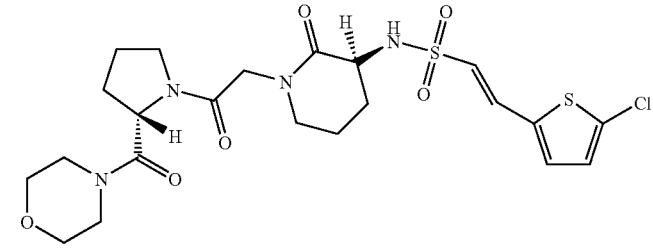 | HPLC (method 6) $t_R$ = 1.5 min LCMS (ESI, pos. ion spectrum) m/z 545/547 (M + 1) | Prepared using the methods described in Example 494 |
| 633 | 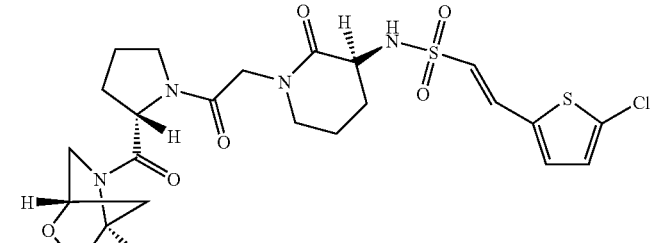 | HPLC (method 6) $t_R$ = 1.4 min LCMS (ESI, pos. ion spectrum) m/z 557/559 (M + 1) | Prepared using the methods described in Example 494 |

-continued

| Ex # | Structure | characterization | method |
|---|---|---|---|
| 634 | 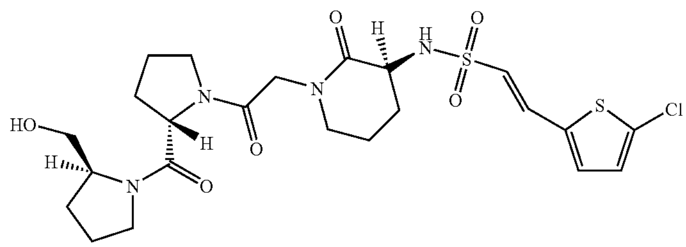 | HPLC (method 6) t$_R$ = 1.5 min LCMS (ESI, pos. ion spectrum) m/z 559/561 (M + 1) | Prepared using the methods described in Example 494 |
| 635 | 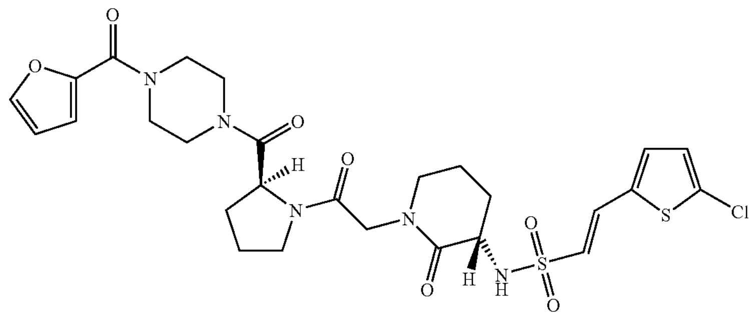 | HPLC (method 6) t$_R$ = 1.5 min LCMS (ESI, pos. ion spectrum) m/z 638/640 (M + 1) | Prepared using the methods described in Example 494 |
| 636 | 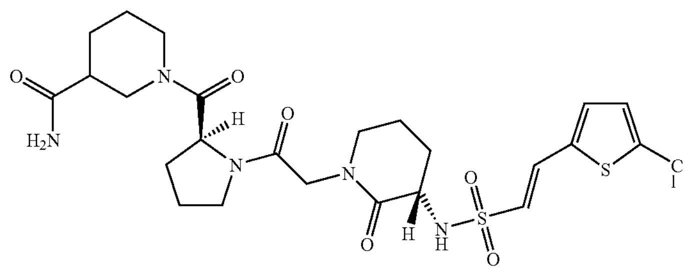 | HPLC (method 6) t$_R$ = 1.4 min LCMS (ESI, pos. ion spectrum) m/z 586/588 (M + 1) | Prepared using the methods described in Example 494 |
| 637 | 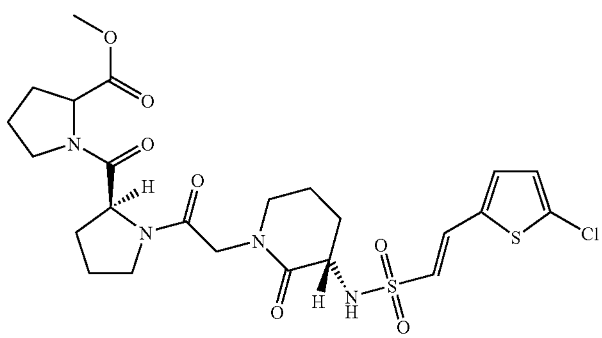 | HPLC (method 6) t$_R$ = 1.6 min LCMS (ESI, pos. ion spectrum) m/z 587/589 (M + 1) | Prepared using the methods described in Example 494 |
| 638 | 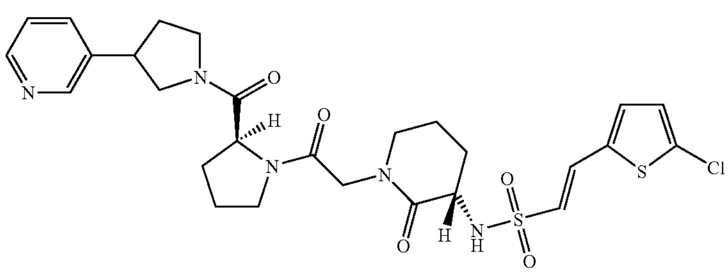 | HPLC (method 6) t$_R$ = 1.3 min LCMS (ESI, pos. ion spectrum) m/z 606/608 (M + 1) | Prepared using the methods described in Example 494 |

-continued

| Ex # | Structure | characterization | method |
|---|---|---|---|
| 639 | 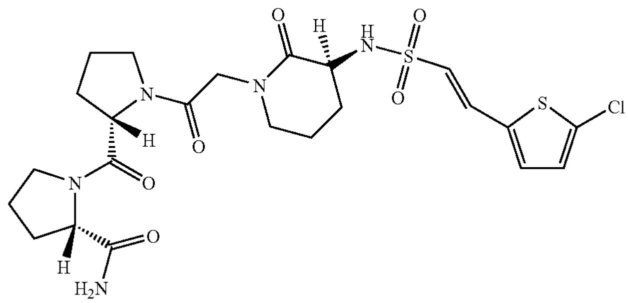 | HPLC (method 6) $t_R$ = 1.4 min LCMS (ESI, pos. ion spectrum) m/z 572/574 (M + 1) | Prepared using the methods described in Example 494 |
| 640 | 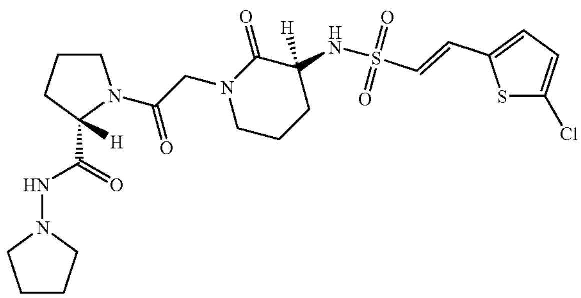 | HPLC (method 6) $t_R$ = 1.4 min LCMS (ESI, pos. ion spectrum) m/z 544/546 (M + 1) | Prepared using the methods described in Example 494 |
| 641 | 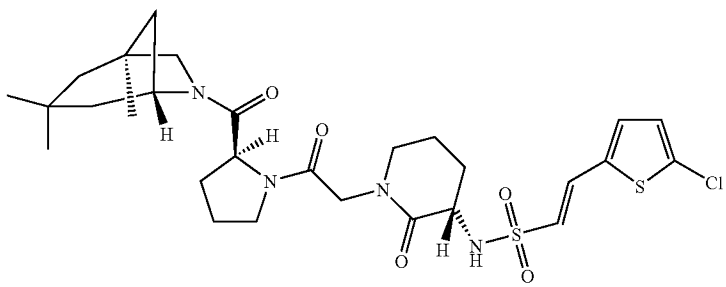 | HPLC (method 6) $t_R$ = 2.0 min LCMS (ESI, pos. ion spectrum) m/z 611/613 (M + 1) | Prepared using the methods described in Example 494 |
| 642 | 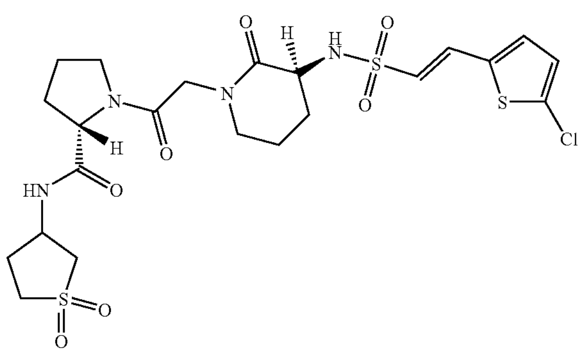 | HPLC (method 6) $t_R$ = 1.4 min LCMS (ESI, pos. ion spectrum) m/z 593/595 (M + 1) | Prepared using the methods described in Example 494 |
| 643 | 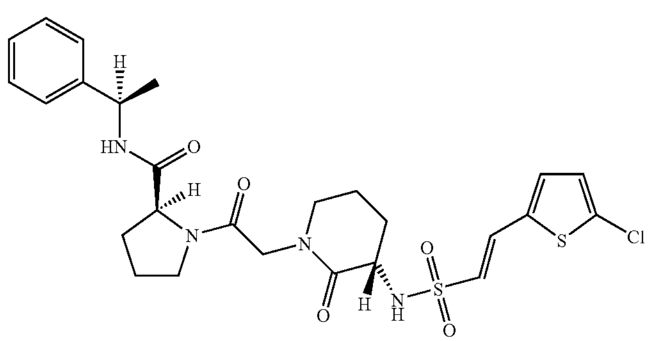 | HPLC (method 6) $t_R$ = 1.8 min LCMS (ESI, pos. ion spectrum) m/z 579/581 (M + 1) | Prepared using the methods described in Example 494 |

-continued

| Ex # | Structure | characterization | method |
|---|---|---|---|
| 644 | 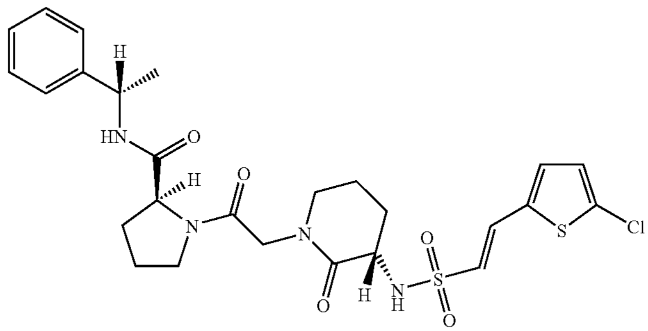 | HPLC (method 6) $t_R$ = 1.8 min LCMS (ESI, pos. ion spectrum) m/z 579/581 (M + 1) | Prepared using the methods described in Example 494 |
| 645 | 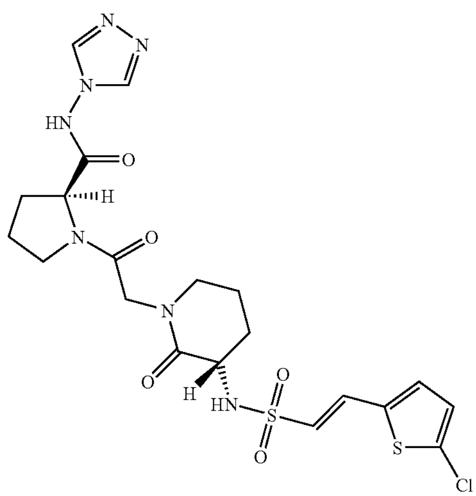 | HPLC (method 6) $t_R$ = 1.3 min LCMS (ESI, pos. ion spectrum) m/z 542/544 (M + 1) | Prepared using the methods described in Example 494 |
| 646 | 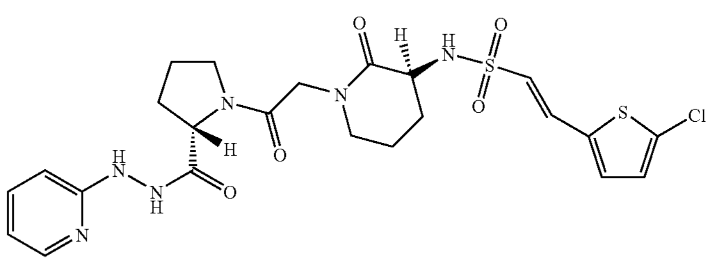 | HPLC (method 6) $t_R$ = 1.3 min LCMS (ESI, pos. ion spectrum) m/z 567/569 (M + 1) | Prepared using the methods described in Example 494 |
| 647 | 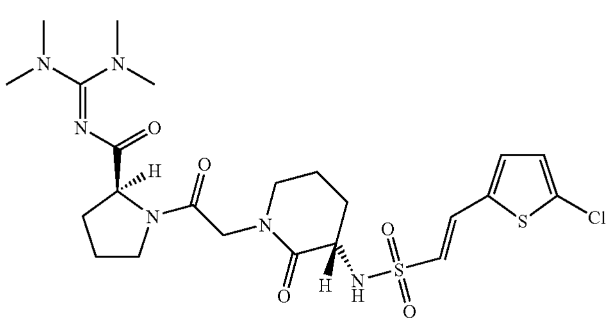 | HPLC (method 6) $t_R$ = 1.3 min LCMS (ESI, pos. ion spectrum) m/z 573/575 (M + 1) | Prepared using the methods described in Example 494 |

-continued

| Ex # | Structure | characterization | method |
|---|---|---|---|
| 648 | 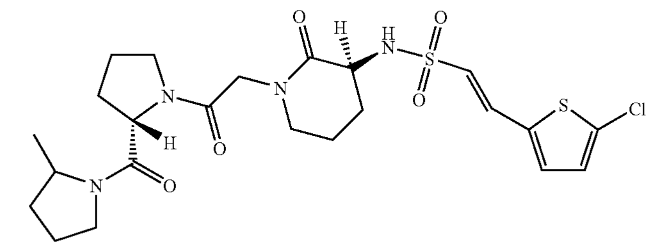 | HPLC (method 6) $t_R$ = 1.6 min LCMS (ESI, pos. ion spectrum) m/z 543/545 (M + 1) | Prepared using the methods described in Example 494 |
| 649 | 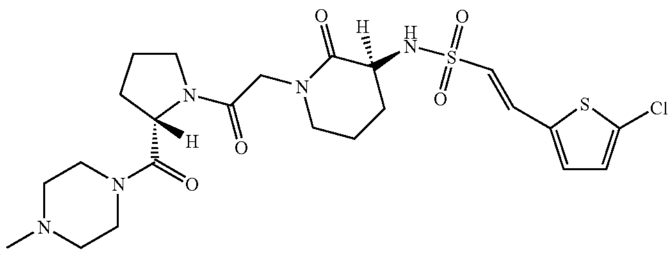 | HPLC (method 6) $t_R$ = 1.3 min LCMS (ESI, pos. ion spectrum) m/z 558/560 (M + 1) | Prepared using the methods described in Example 494 |

| Ex # | Structure | characterization | method |
|---|---|---|---|
| 650 | 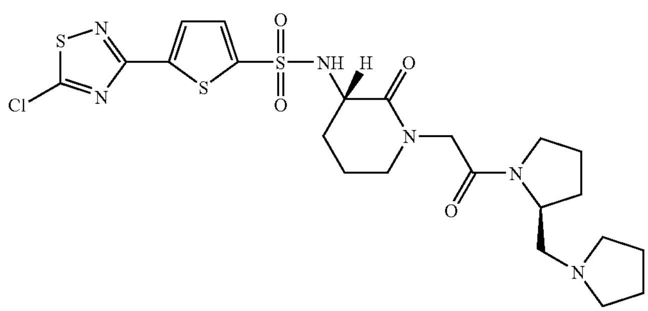 | HPLC (method 4) $t_R$ = 1.4 min LCMS (ESI, pos. ion spectrum) m/z 573/575 (M + 1) | prepared using the method described in Example 1 using INT9 |
| 651 | 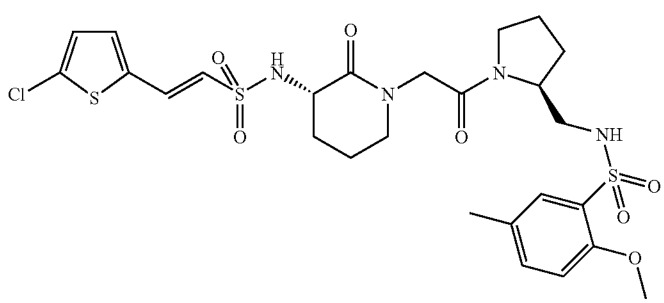 | HPLC (method 6) $t_R$ = 1.7 min LCMS (method 6) (ESI, pos. ion spectrum) m/z 645/647 (M + 1) | Prepared using the procedures described in Example 620 |
| 652 | 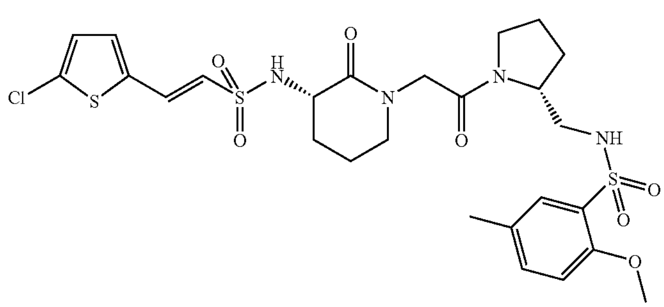 | HPLC (method 7) $t_R$ = 3.4 min LCMS (method 6) (ESI, pos. ion spectrum) m/z 645/647 (M + 1) | Prepared using the procedures described in Example 620 |

| Ex # | Structure | characterization | method |
|---|---|---|---|
| 653 | 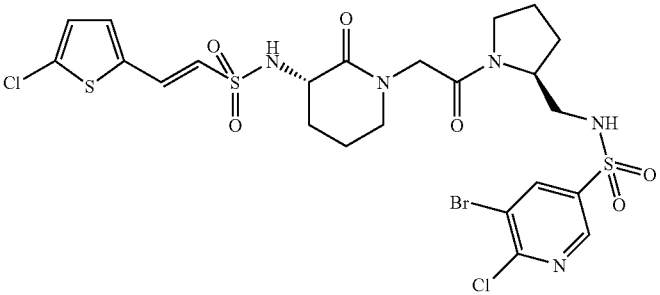 | HPLC (method 6) $t_R$ = 1.8 min LCMS (method 6) (ESI, pos. ion spectrum) m/z 714/716/718 (M + 1) | Prepared using the procedures described in Example 620 |
| 654 | 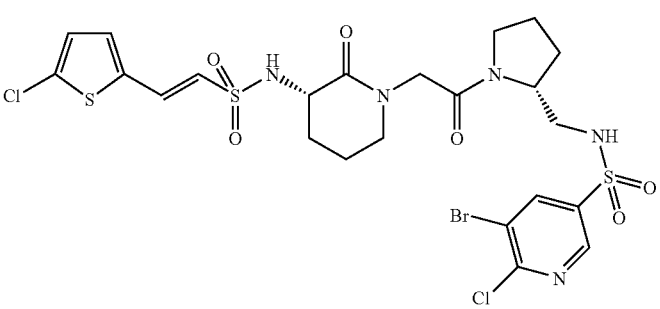 | HPLC (method 6) $t_R$ = 1.8 min LCMS (method 6) (ESI, pos. ion spectrum) m/z 714/716/718 (M + 1) | Prepared using the procedures described in Example 620 |
| 655 | 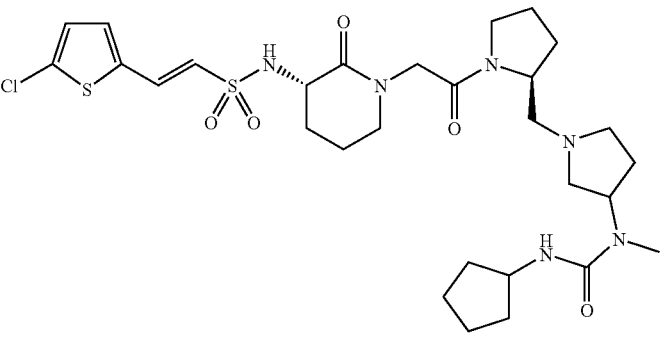 | HPLC (method 1) $t_R$ = 3.2 min LRMS (ESI, pos. ion spectrum) m/z 655 (M + H) | Title compound of Example 655 |
| 656 | 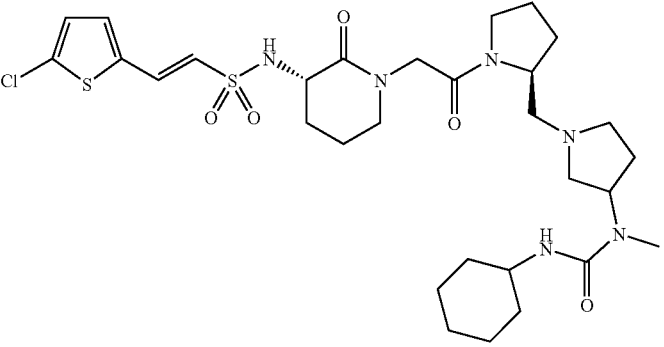 | HPLC (method 1) $t_R$ = 3.3 min LRMS (ESI, pos. ion spectrum) m/z 669 (M + H) | Prepared using the procedure described in Example 655 |

| Ex # | Structure | characterization | method |
|---|---|---|---|
| 657 | 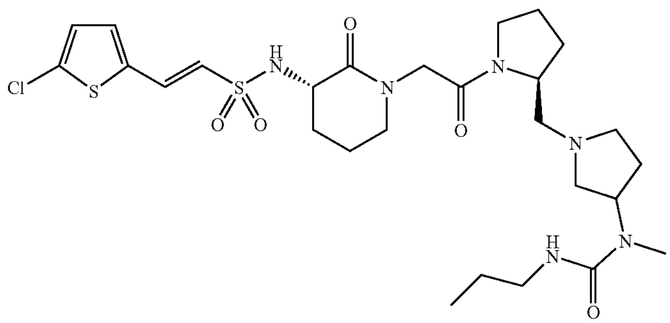 | HPLC (method 1) $t_R$ = 3.2 min LRMS (ESI, pos. ion spectrum) m/z 629/631 (M + H) | Prepared using the procedure described in Example 655 |
| 658 | 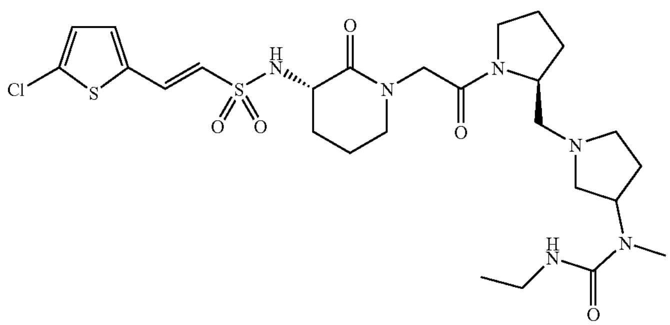 | HPLC (method 1) $t_R$ = 2.8 min LRMS (ESI, pos. ion spectrum) m/z 615/617 (M + H) | Prepared using the procedure described in Example 655 |
| 659 | 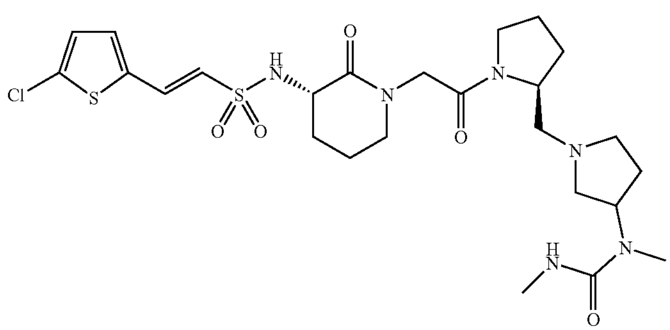 | HPLC (method 1) $t_R$ = 2.7 min LRMS (ESI, pos. ion spectrum) m/z 601/603 (M + H) | Prepared using the procedure described in Example 655 |
| 660 | 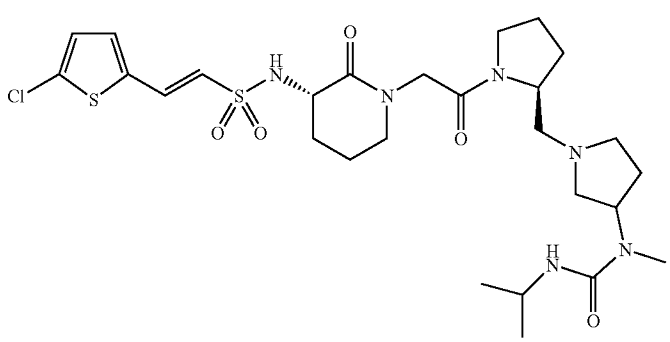 | HPLC (method 1) $t_R$ = 3.0 min LRMS (ESI, pos. ion spectrum) m/z 629/631 (M + H) | Prepared using the procedure described in Example 655 |

| Ex # | Structure | characterization | method |
|---|---|---|---|
| 661 | 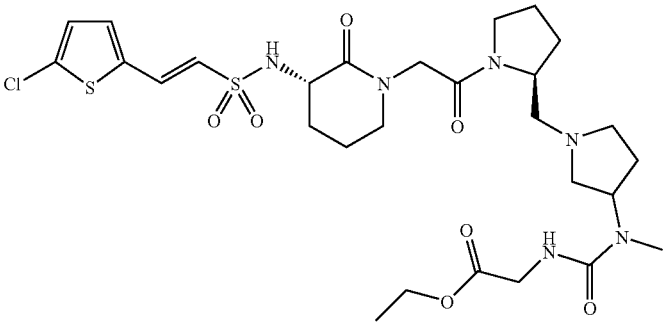 | HPLC (method 1) $t_R$ = 2.9 min LRMS (ESI, pos. ion spectrum) m/z 673/675 (M + H) | Prepared using the procedure described in Example 655 |
| 662 | 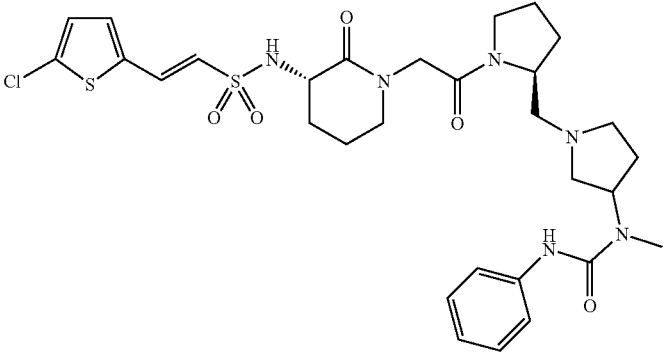 | HPLC (method 1) $t_R$ = 3.1 min LRMS (ESI, pos. ion spectrum) m/z 663/665 (M + H) | Prepared using the procedure described in Example 655 |
| 663 | 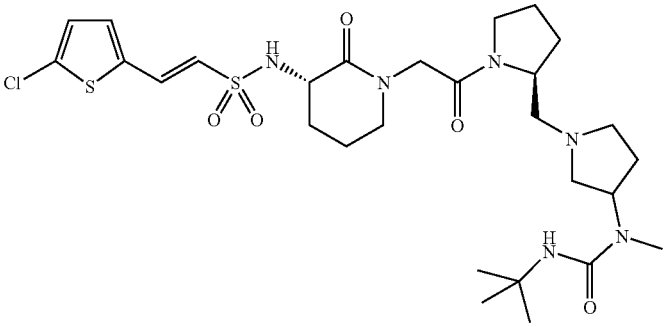 | HPLC (method 1) $t_R$ = 3.1 min LRMS (ESI, pos. ion spectrum) m/z 643/645 (M + H) | Prepared using the procedure described in Example 655 |
| 664 | 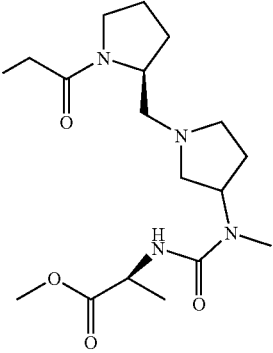 | HPLC (method 1) $t_R$ = 2.9 min LRMS (ESI, pos. ion spectrum) m/z 673/675 (M + H) | Prepared using the procedure described in Example 655 |

| Ex # | Structure | characterization | method |
|---|---|---|---|
| 665 | 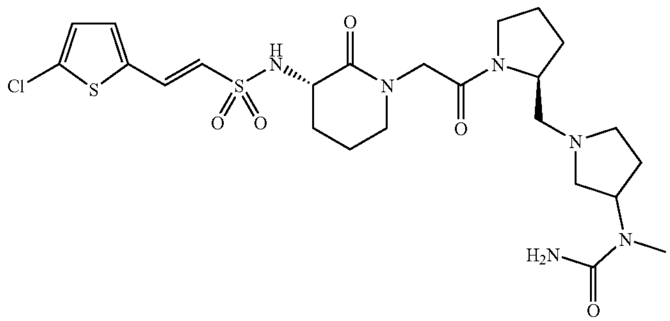 | HPLC (method YW1) $t_R$ = 2.6 min LRMS (ESI, pos. ion spectrum) m/z 587/589 (M + H) | Prepared using the procedure described in Example 655 |
| 666 | 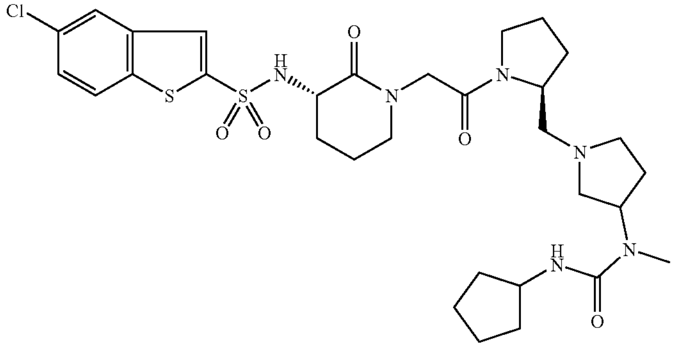 | HPLC (method 1) $t_R$ = 3.4 min LRMS (ESI, pos. ion spectrum) m/z 679/681 (M + H) | Prepared using the procedure described in Example 655 using the title compound of Example 615 |
| 667 | 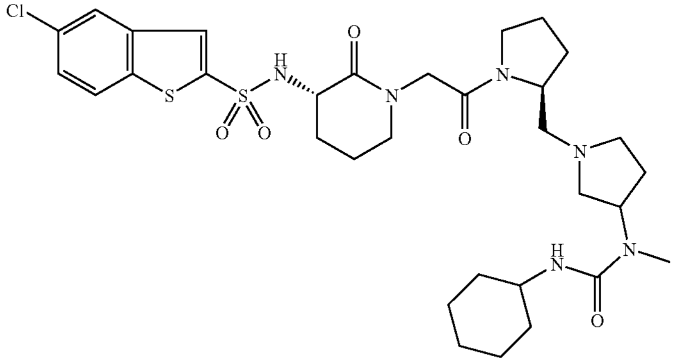 | HPLC (method 1) $t_R$ = 3.5 min LRMS (ESI, pos. ion spectrum) m/z 693/695 (M + H) | Prepared using the procedure described in Example 655 using the title compound of Example 615 |
| 668 | 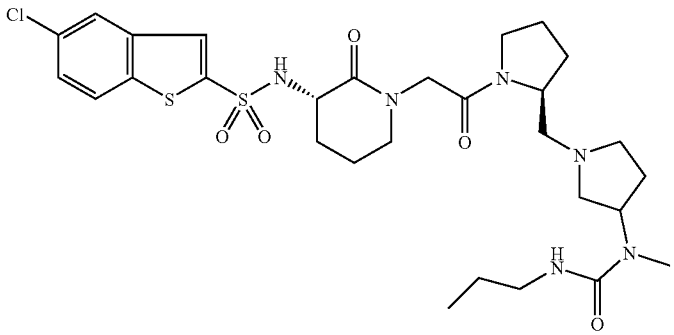 | HPLC (method 1) $t_R$ = 3.2 min LRMS (ESI, pos. ion spectrum) m/z 653/655 (M + H) | Prepared using the procedure described in Example 655 using the title compound of Example 615 |

-continued

| Ex # | Structure | characterization | method |
|---|---|---|---|
| 669 | 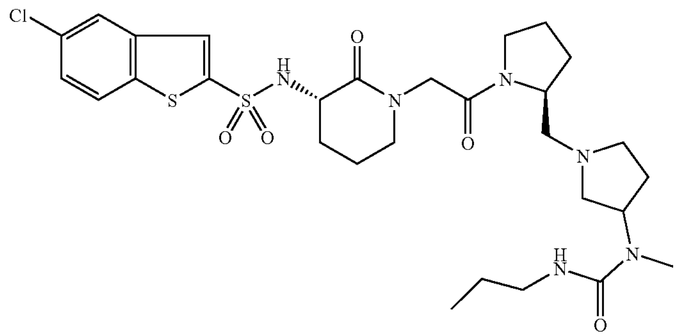 | HPLC (method 1) $t_R$ = 3.1 min LRMS (ESI, pos. ion spectrum) m/z 639/641 (M + H) | Prepared using the procedure described in Example 655 using the title compound of Example 615 |
| 670 | 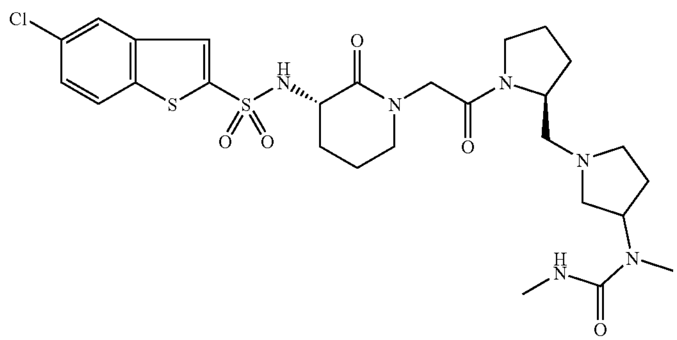 | HPLC (method 1) $t_R$ = 3.0 min LRMS (ESI, pos. ion spectrum) m/z 625/627 (M + H) | Prepared using the procedure described in Example 655 using the title compound of Example 615 |
| 671 | 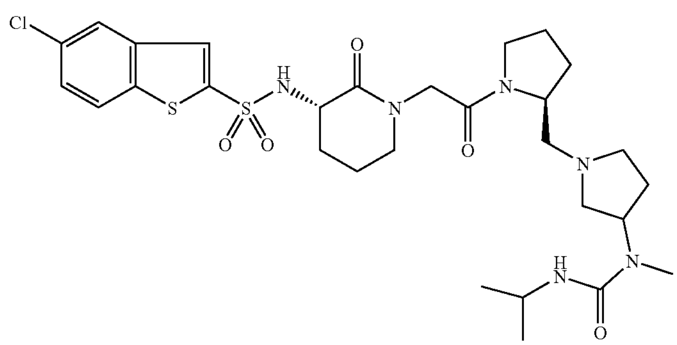 | HPLC (method 1) $t_R$ = 3.2 min LRMS (ESI, pos. ion spectrum) m/z 653/655 (M + H) | Prepared using the procedure described in Example 655 using the title compound of Example 615 |
| 672 | 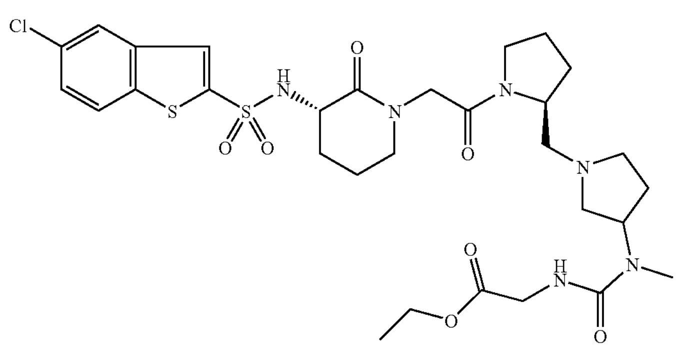 | HPLC (method 1) $t_R$ = 3.1 min LRMS (ESI, pos. ion spectrum) m/z 697/699 (M + H) | Prepared using the procedure described in Example 655 using the title compound of Example 615 |

| Ex # | Structure | characterization | method |
| --- | --- | --- | --- |
| 673 | 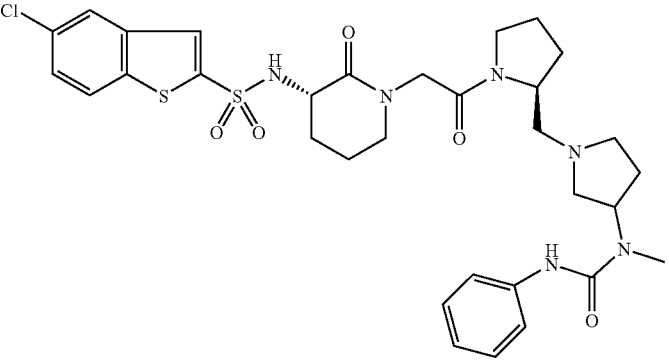 | HPLC (method 1) t_R = 3.3 min LRMS (ESI, pos. ion spectrum) m/z 687/689 (M + H) | Prepared using the procedure described in Example 655 using the title compound of Example 615 |
| 674 | 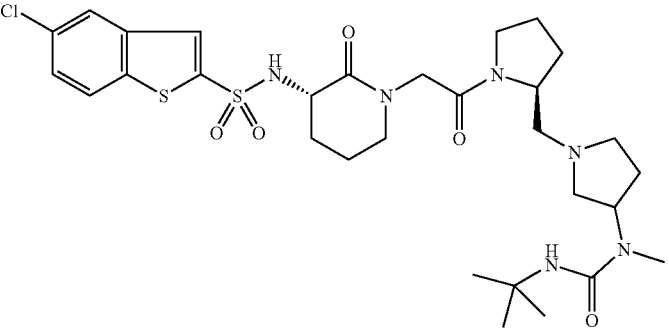 | HPLC (method 1) t_R = 3.3 min LRMS (ESI, pos. ion spectrum) m/z 667/669 (M + H) | Prepared using the procedure described in Example 655 using the title compound of Example 615 |
| 675 | 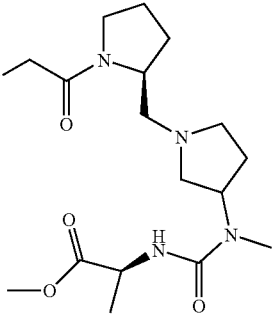 | HPLC (method 1) t_R = 3.1 min LRMS (ESI, pos. ion spectrum) m/z 697/699 (M + H) | Prepared using the procedure described in Example 655 using the title compound of Example 615 |
| 676 | 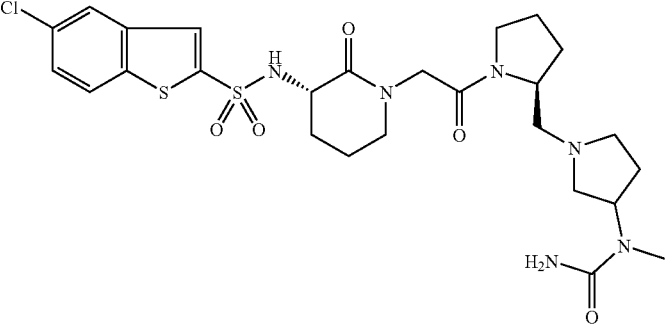 | HPLC (method 1) t_R = 2.9 min LRMS (ESI, pos. ion spectrum) m/z 611/613 (M + H) | Prepared using the procedure described in Example 655 using the title compound of Example 615 |

| Ex # | Structure | characterization | method |
|---|---|---|---|
| 677 | 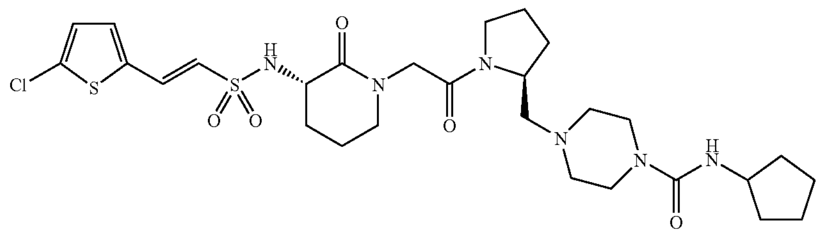 | HPLC (method 1) $t_R$ = 3.0 min LRMS (ESI, pos. ion spectrum) m/z 641/643 (M + H) | Prepared using the procedure described in Example 655 using the title compound of Example 612 |
| 678 | 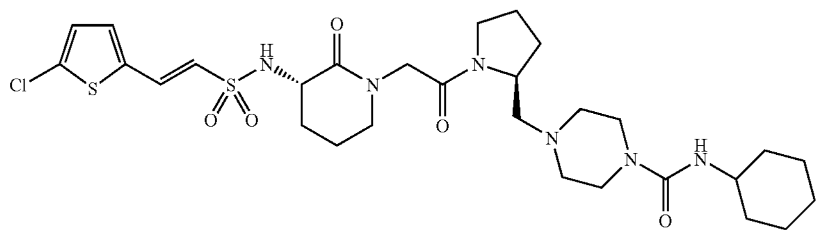 | HPLC (method 1) $t_R$ = 3.2 min LRMS (ESI, pos. ion spectrum) m/z 655/657 (M + H) | Prepared using the procedure described in Example 655 using the title compound of Example 612 |
| 679 | 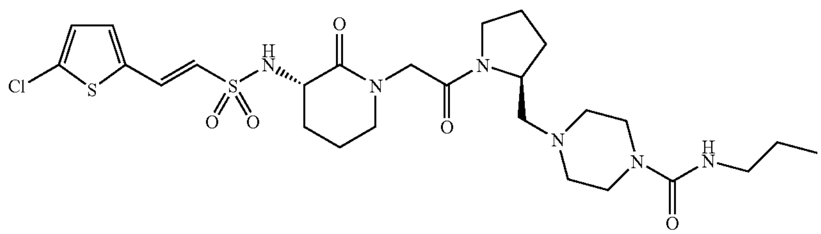 | HPLC (method 1) $t_R$ = 2.8 min LRMS (ESI, pos. ion spectrum) m/z 615/617 (M + H) | Prepared using the procedure described in Example 655 using the title compound of Example 612 |
| 680 | 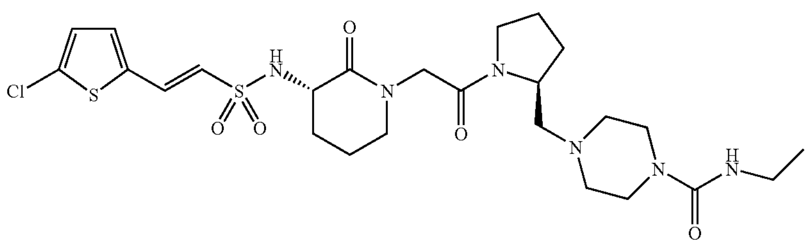 | HPLC (method 1) $t_R$ = 2.7 min LRMS (ESI, pos. ion spectrum) m/z 601/603 (M + H) | Prepared using the procedure described in Example 655 using the title compound of Example 612 |
| 681 | 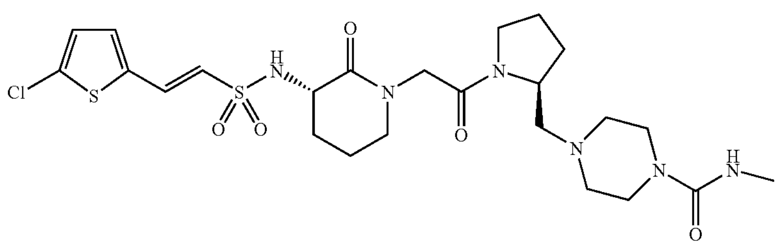 | HPLC (method 1) $t_R$ = 2.6 min LRMS (ESI, pos. ion spectrum) m/z 587/589 (M + H) | Prepared using the procedure described in Example 655 using the title compound of Example 612 |
| 682 | 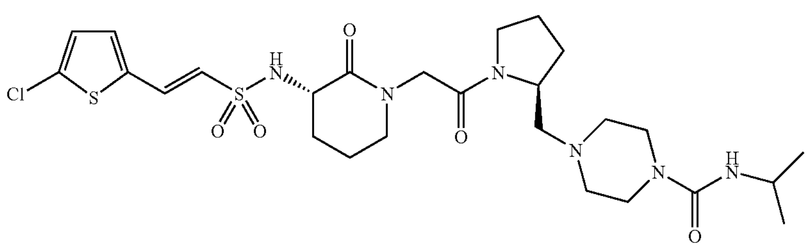 | HPLC (method 1) $t_R$ = 2.8 min LRMS (ESI, pos. ion spectrum) m/z 615/617 (M + H) | Prepared using the procedure described in Example 655 using the title compound of Example 612 |

-continued

| Ex # | Structure | characterization | method |
|---|---|---|---|
| 683 | 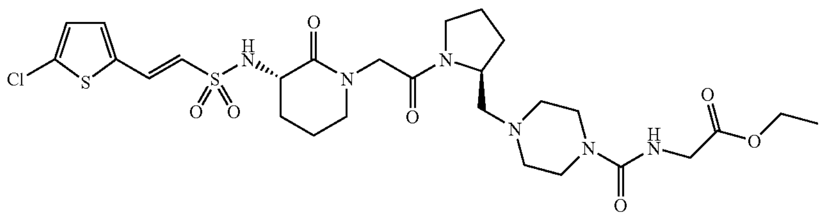 | HPLC (method 1) $t_R$ = 2.8 min LRMS (ESI, pos. ion spectrum) m/z 659/661 (M + H) | Prepared using the procedure described in Example 655 using the title compound of Example 612 |
| 684 | 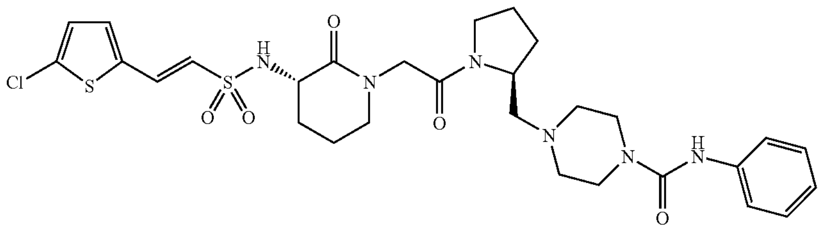 | HPLC (method 1) $t_R$ = 3.0 min LRMS (ESI, pos. ion spectrum) m/z 649/651 (M + H) | Prepared using the procedure described in Example 655 using the title compound of Example 612 |
| 685 | 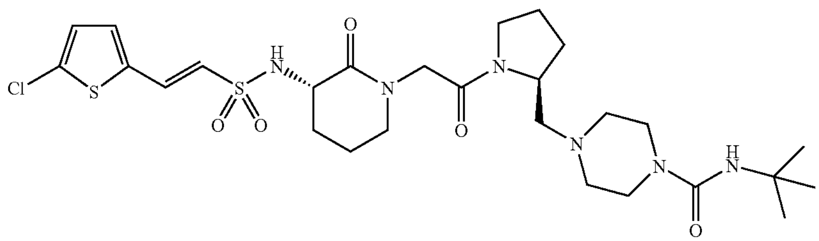 | HPLC (method 1) $t_R$ = 3.0 min LRMS (ESI, pos. ion spectrum) m/z 629/631 (M + H) | Prepared using the procedure described in Example 655 using the title compound of Example 612 |
| 686 | 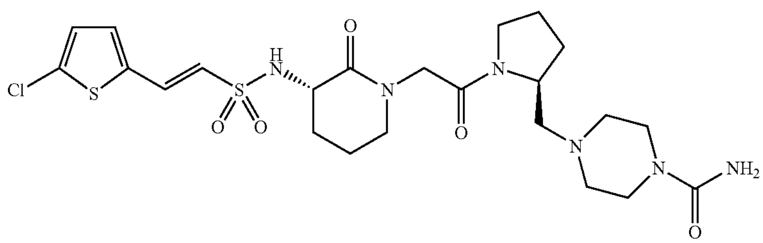 | HPLC (method 1) $t_R$ = 2.5 min LRMS (ESI, pos. ion spectrum) m/z 573/575 (M + H) | Prepared using the procedure described in Example 655 using the title compound of Example 612 |
| 687 | 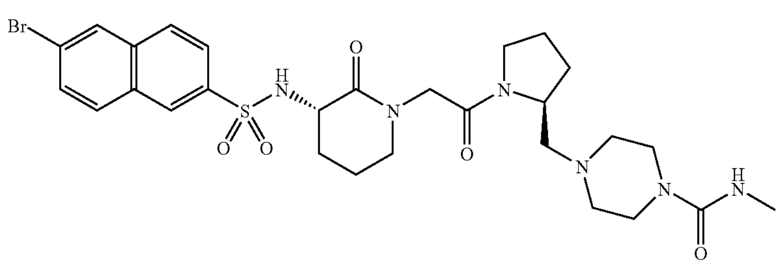 | HPLC (method 1) $t_R$ = 3.0 min LRMS (ESI, pos. ion spectrum) m/z 649/651 (M + H) | Prepared using the procedure described in Example 655 using the title compound of Example 569 |
| 688 | 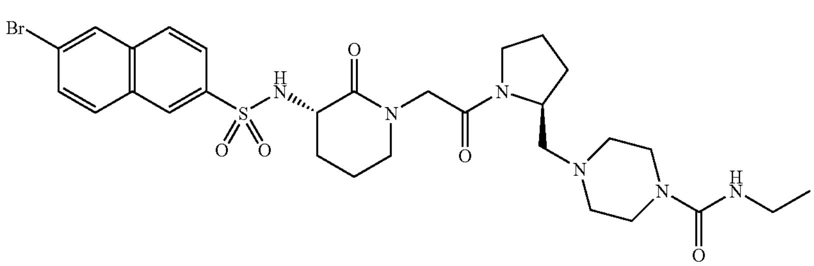 | HPLC (method 1) $t_R$ = 3.0 min LRMS (ESI, pos. ion spectrum) m/z 663/665 (M + H) | Prepared using the procedure described in Example 655 using the title compound of Example 569 |

| Ex # | Structure | characterization | method |
|---|---|---|---|
| 689 | 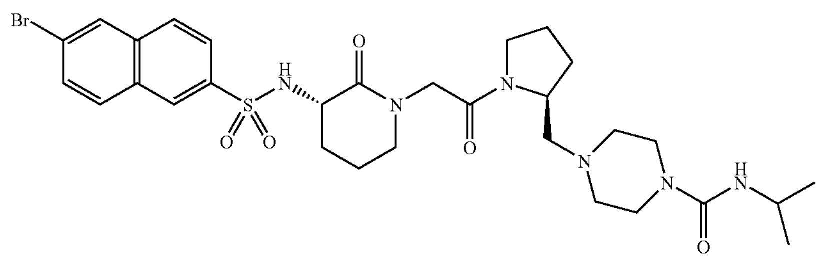 | HPLC (method 1) $t_R$ = 3.2 min LRMS (ESI, pos. ion spectrum) m/z 677/679 (M + H) | Prepared using the procedure described in Example 655 using the title compound of Example 569 |
| 690 | 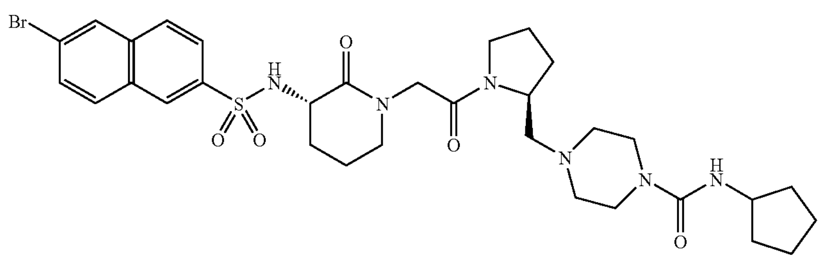 | HPLC (method 1) $t_R$ = 3.4 min LRMS (ESI, pos. ion spectrum) m/z 703/705 (M + H) | Prepared using the procedure described in Example 655 using the title compound of Example 569 |
| 691 | 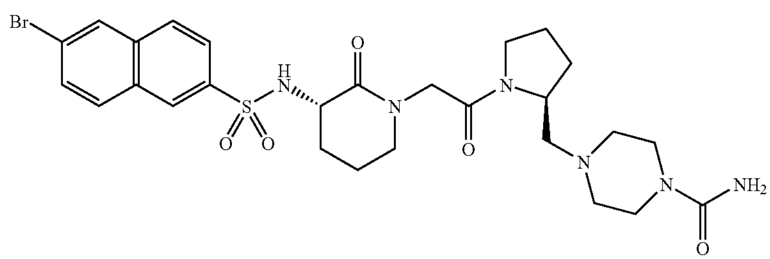 | HPLC (method 1) $t_R$ = 2.9 min LRMS (ESI, pos. ion spectrum) m/z 635/637 (M + H) | Prepared using the procedure described in Example 655 using the title compound of Example 569 |
| 692 | 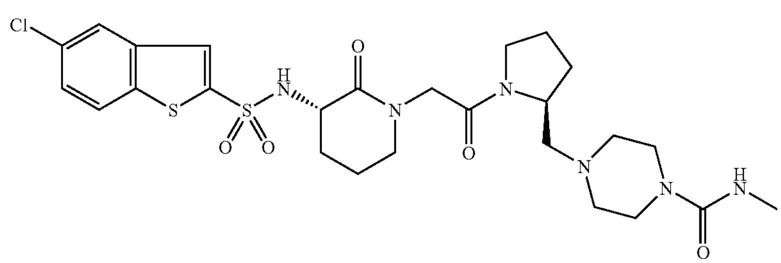 | HPLC (method 1) $t_R$ = 2.9 min LRMS (ESI, pos. ion spectrum) m/z 611/613 (M + H) | Prepared using the procedure described in Example 655 using the title compound of Example 568 |
| 693 | 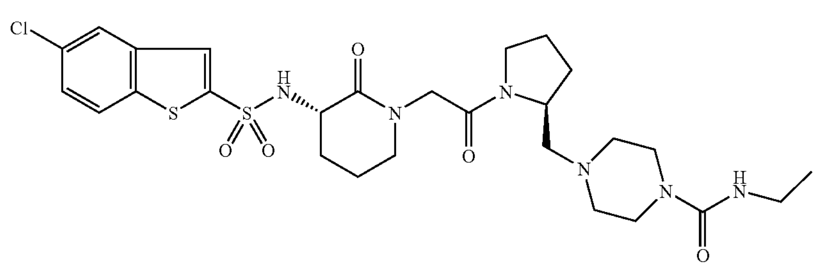 | HPLC (method 1) $t_R$ = 3.0 min LRMS (ESI, pos. ion spectrum) m/z 625/627 (M + H) | Prepared using the procedure described in Example 655 using the title compound of Example 568 |
| 694 | 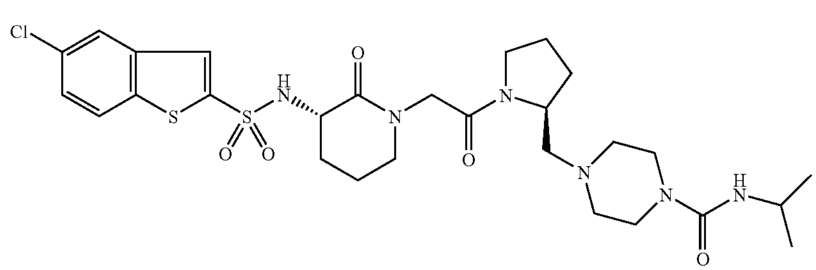 | HPLC (method 1) $t_R$ = 3.1 min LRMS (ESI, pos. ion spectrum) m/z 639/641 (M + H) | Prepared using the procedure described in Example 655 using the title compound of Example 568 |

| Ex # | Structure | characterization | method |
|---|---|---|---|
| 695 | 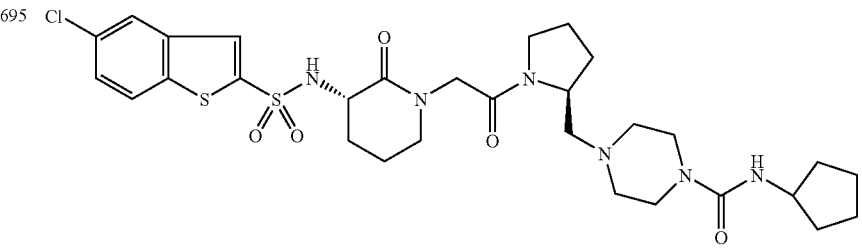 | HPLC (method 1) $t_R$ = 3.3 min LRMS (ESI, pos. ion spectrum) m/z 665/667 (M + H) | Prepared using the procedure described in Example 655 using the title compound of Example 568 |
| 696 | 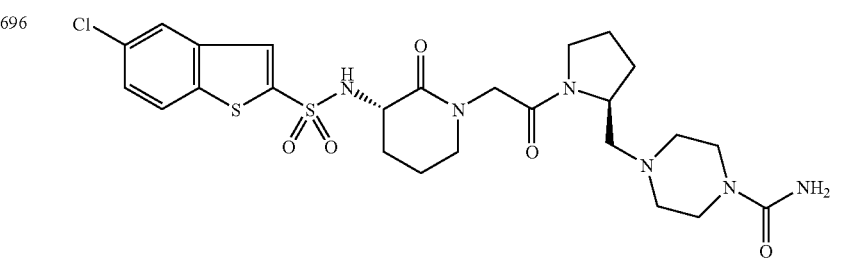 | HPLC (method 1) $t_R$ = 2.8 min LRMS (ESI, pos. ion spectrum) m/z 597/599 (M + H) | Prepared using the procedure described in Example 655 using the title compound of Example 568 |
| 697 | 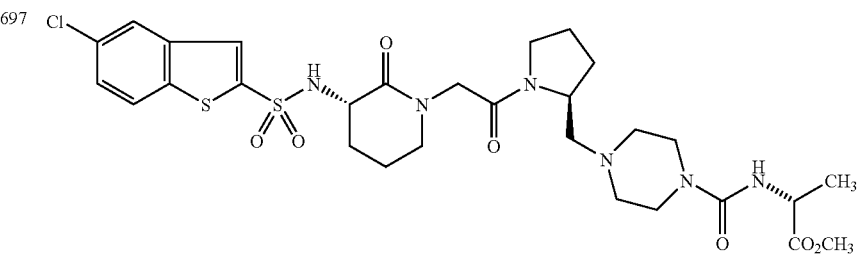 | HPLC (method 1) $t_R$ = 3.1 min LRMS (ESI, pos. ion spectrum) m/z 683/685 (M + H) | Prepared using the procedure described in Example 655 using the title compound of Example 568 |
| 698 | 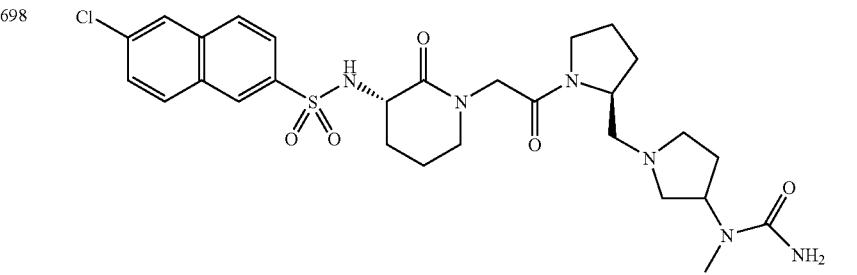 | HPLC (method 1) $t_R$ = 3.0 min LRMS (ESI, pos. ion spectrum) m/z 605/607 (M + H) | Prepared using the procedure described in Example 655 using the title compound of Example 614 |
| 699 | 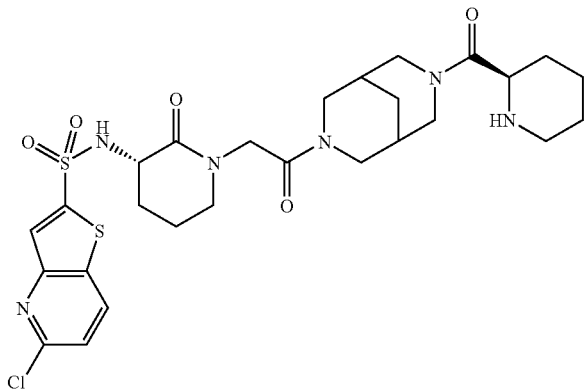 | HPLC (method 1) $t_R$ = 2.7 min LCMS (ESI, pos. ion spectrum) m/z 623/625 (M + 1) | Prepared using the method described in Examples 48 and 178 part B using title compound of Example 702 and 1-(1,1-dimethyl-ethyl) (2R)-1,2-piperidinedi-carboxylate |

-continued

| Ex # | Structure | characterization | method |
|---|---|---|---|
| 700 | 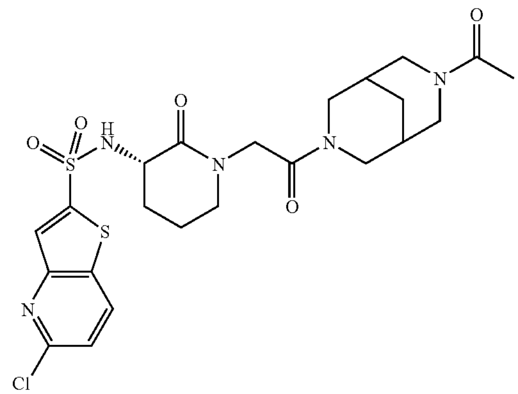 | HPLC (method 1) $t_R$ = 2.9 min LCMS (ESI, pos. ion spectrum) m/z 554/556 (M + 1) | Prepared using the method described in Example 317 using the title compound of Example 702 |
| 701 | 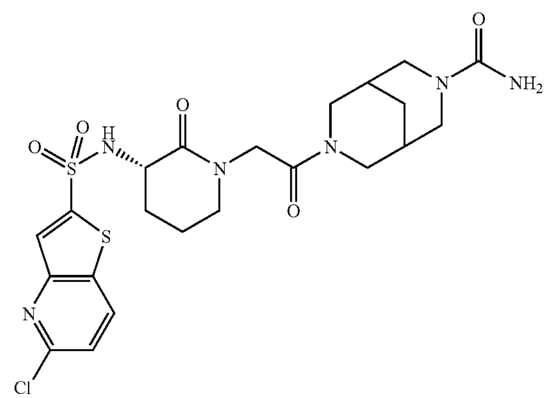 | HPLC (method 1) $t_R$ = 2.7 min LCMS (ESI, pos. ion spectrum) m/z 555/557 (M + 1) | Prepared using the method described in Example 316 using the title compound of Example 702 |
| 702 | 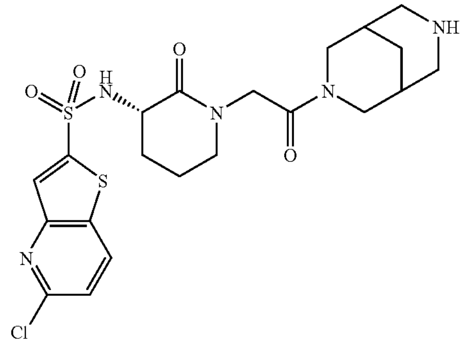 | HPLC (method 1) $t_R$ = 2.4 min LCMS (ESI, pos. ion spectrum) m/z 512/514 (M + 1) | Prepared using the method described in Example 429 using INT14 |
| 703 | 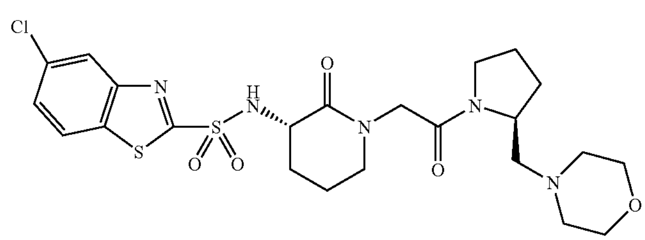 | HPLC (method 1) $t_R$ = 2.2 min LCMS (ESI, pos. ion spectrum) m/z 556/558 (M + H) | prepared using the method described in Example 130 using INT19 |

-continued

| Ex # | Structure | characterization | method |
|---|---|---|---|
| 704 | 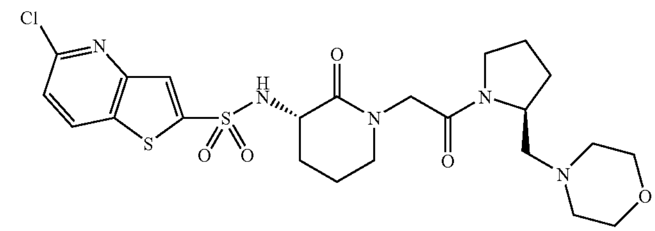 | HPLC (method 1) t_R = 2.0 min LCMS (ESI, pos. ion spectrum) m/z 556/558 (M + H) | prepared using the method described in Example 130 using INT14 |
| 705 | 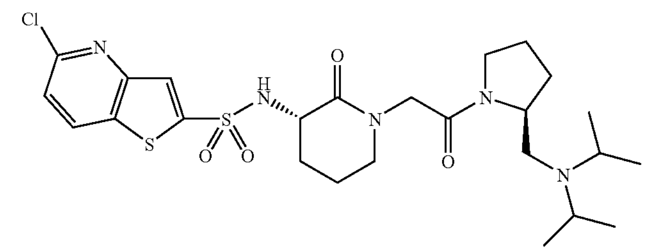 | HPLC (method 1) t_R = 2.1 min LCMS (ESI, pos. ion spectrum) m/z 570/572 (M + H) | prepared using the method described in Example 400 using INT21 |
| 706 | 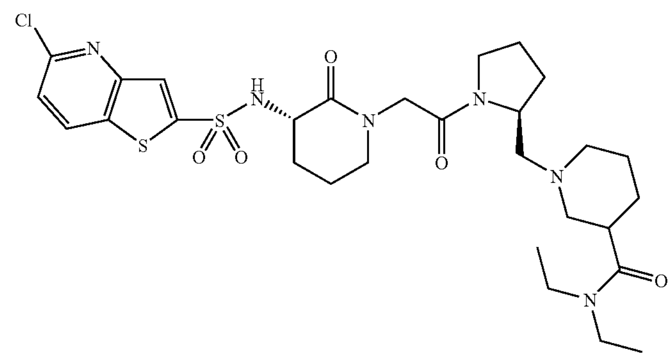 | HPLC (method 1) t_R = 2.5 min LCMS (ESI, pos. ion spectrum) m/z 653/655 (M + H) | prepared using the method described in Example 400 using INT21 |
| 707 | 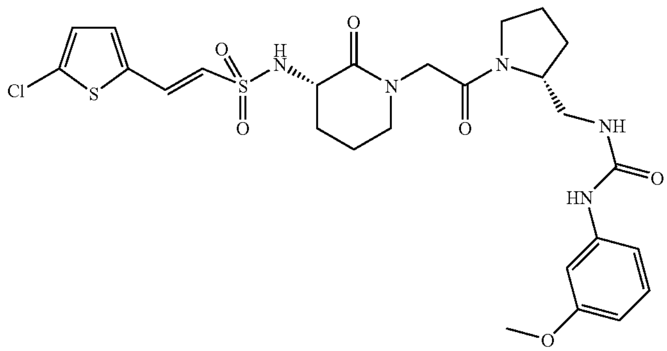 | HPLC (method 6) t_R = 1.6 min LCMS (method 6) (ESI, pos. ion spectrum) m/z 610/612 (M + 1) | Prepared using the procedures described in Example 618 |
| 708 | 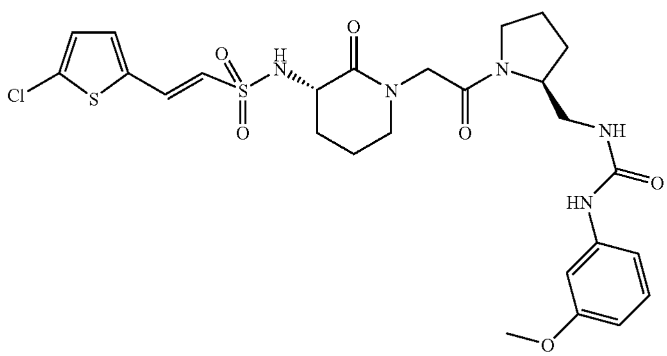 | HPLC (method 7) t_R = 3.2 min LCMS (method 6) (ESI, pos. ion spectrum) m/z 610/612 (M + 1) | Prepared using the procedures described in Example 618 |

-continued

| Ex # | Structure | characterization | method |
|---|---|---|---|
| 709 | 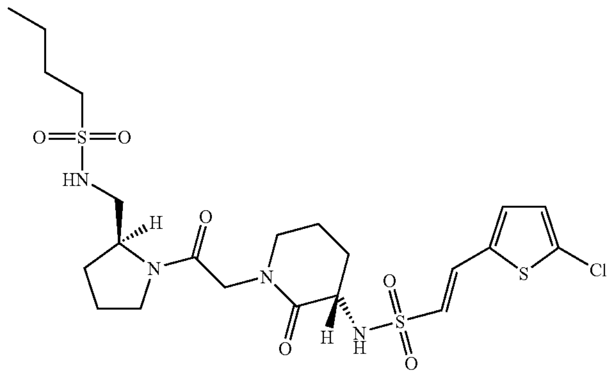 | HPLC (method 6) $t_R$ = 1.7 min LCMS (method 6) (ESI, pos. ion spectrum) m/z 581/583 (M + 1) | Prepared using the procedures described in Example 620 |
| 710 | 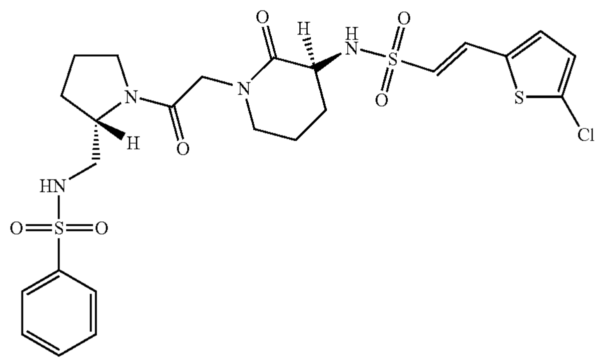 | HPLC (method 6) $t_R$ = 1.7 min LCMS (method 6) (ESI, pos. ion spectrum) m/z 601/603 (M + 1) | Prepared using the procedures described in Example 620 |
| 711 | 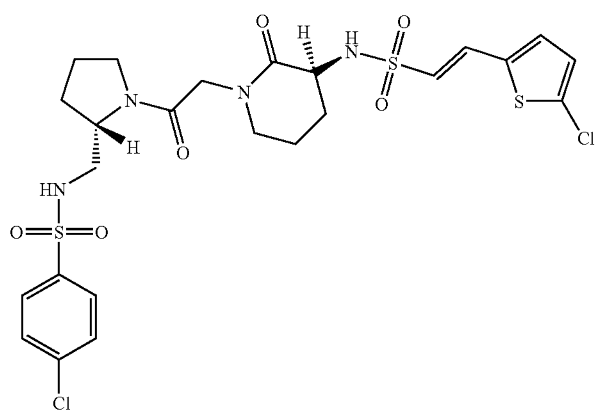 | HPLC (method 6) $t_R$ = 1.8 min LCMS (method 6) (ESI, pos. ion spectrum) m/z 635/637/639 (M + 1) | Prepared using the procedures described in Example 620 |
| 712 | 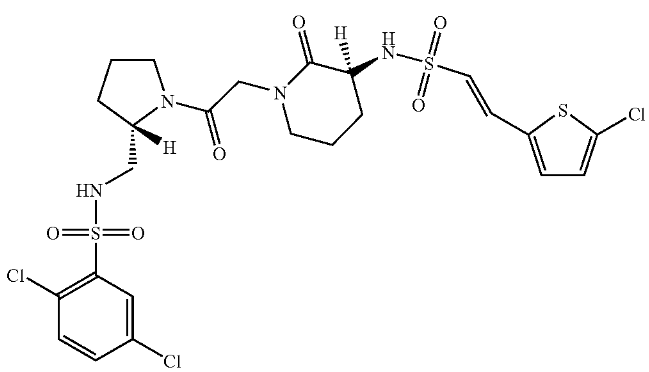 | HPLC (method 6) $t_R$ = 1.8 min LCMS (method 6) (ESI, pos. ion spectrum) m/z 669/671/673 (M + 1) | Prepared using the procedures described in Example 620 |

-continued

| Ex # | Structure | characterization | method |
|---|---|---|---|
| 713 | 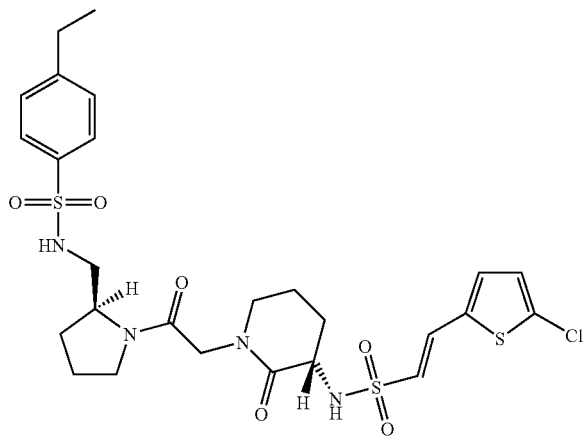 | HPLC (method 6) t_R = 1.8 min LCMS (method 6) (ESI, pos. ion spectrum) m/z 629/631 (M + 1) | Prepared using the procedures described in Example 620 |
| 714 | 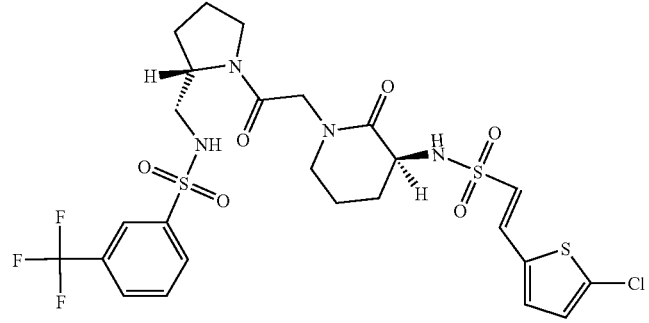 | HPLC (method 6) t_R = 1.8 min LCMS (method 6) (ESI, pos. ion spectrum) m/z 669/671 (M + 1) | Prepared using the procedures described in Example 620 |
| 715 | 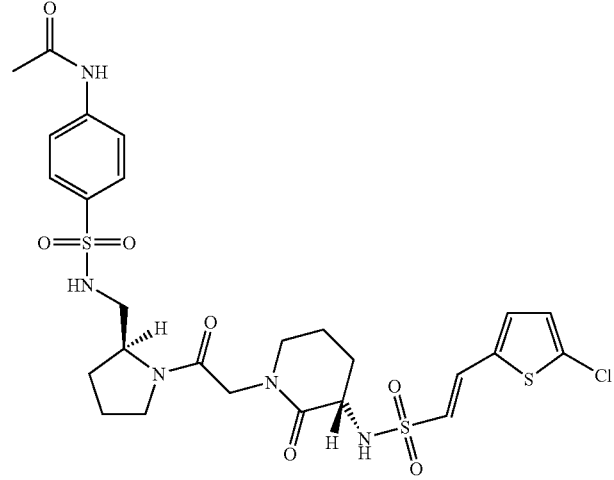 | HPLC (method 6) t_R = 1.5 min LCMS (method 6) (ESI, pos. ion spectrum) m/z 658/660 (M + 1) | Prepared using the procedures described in Example 620 |
| 716 | 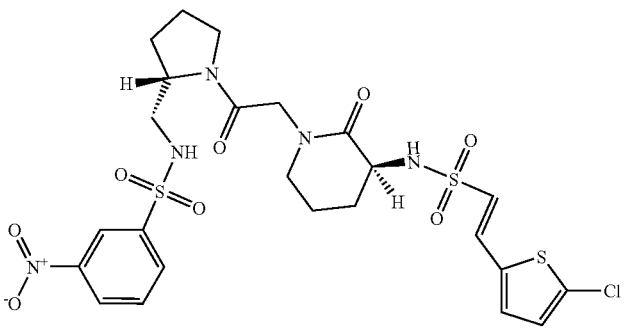 | HPLC (method 6) t_R = 1.7 min LCMS (method 6) (ESI, pos. ion spectrum) m/z 646/648 (M + 1) | Prepared using the procedures described in Example 620 |

-continued

| Ex # | Structure | characterization | method |
|------|-----------|------------------|--------|
| 717 | 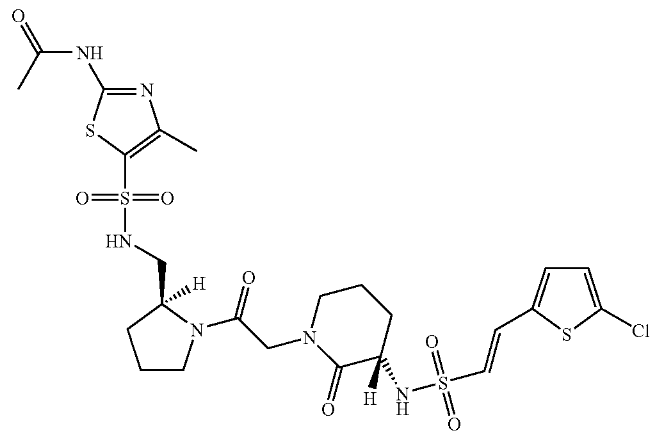 | HPLC (method 6) t$_R$ = 1.6 min LCMS (method 6) (ESI, pos. ion spectrum) m/z 679/681 (M + 1) | Prepared using the procedures described in Example 620 |
| 718 | 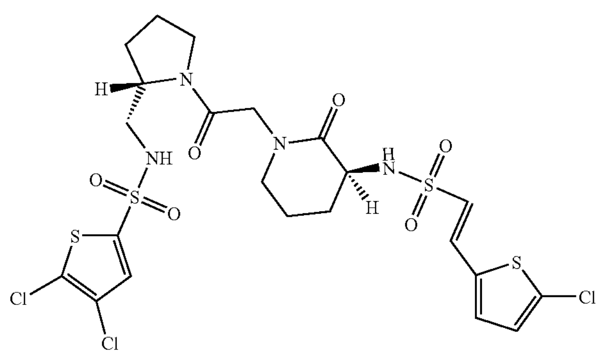 | HPLC (method 6) t$_R$ = 2.0 min LCMS (method 6) (ESI, pos. ion spectrum) m/z 675/677/679 (M + 1) | Prepared using the procedures described in Example 620 |
| 719 | 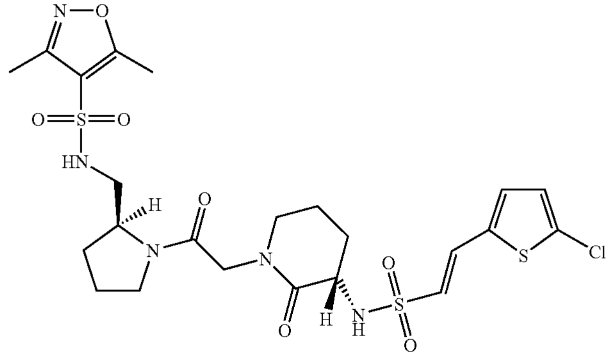 | HPLC (method 6) t$_R$ = 1.7 min LCMS (method 6) (ESI, pos. ion spectrum) m/z 620/622 (M + 1) | Prepared using the procedures described in Example 620 |

-continued

| Ex # | Structure | characterization | method |
| --- | --- | --- | --- |
| 720 | 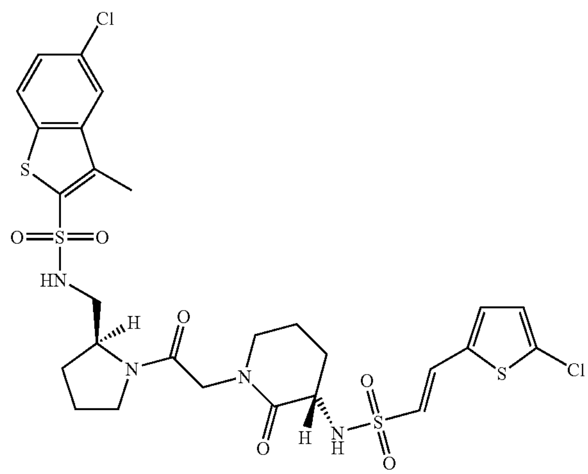 | HPLC (method 6) $t_R$ = 2.0 min LCMS (method 6) (ESI, pos. ion spectrum) m/z 705/707/709 (M + 1) | Prepared using the procedures described in Example 620 |
| 721 | 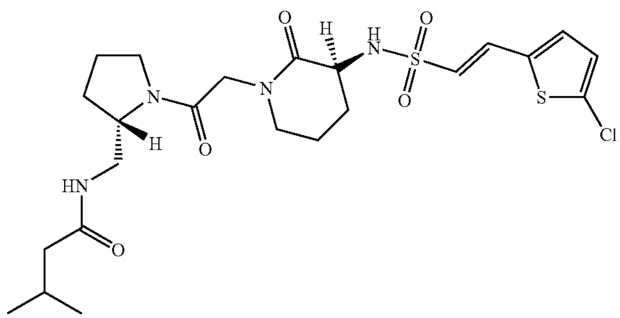 | HPLC (method 6) $t_R$ = 1.6 min LCMS (method 6) (ESI, pos. ion spectrum) m/z 545/547 (M + 1) | Prepared using the procedures described in Example 622 |
| 722 | 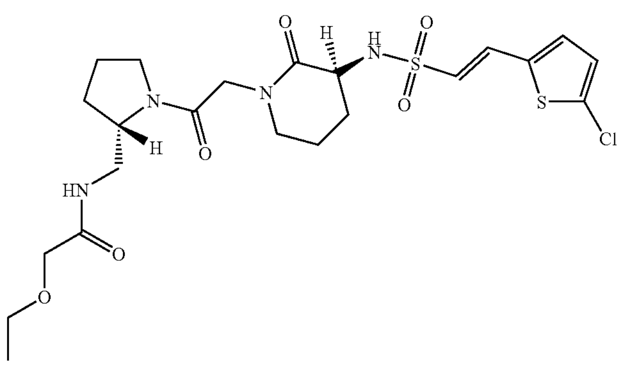 | HPLC (method 6) $t_R$ = 1.5 min LCMS (method 6) (ESI, pos. ion spectrum) m/z 547/549 (M + 1) | Prepared using the procedures described in Example 622 |
| 723 | 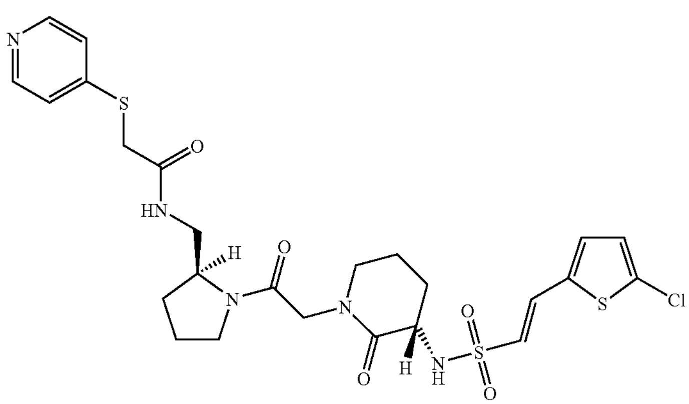 | HPLC (method 6) $t_R$ = 1.4 min LCMS (method 6) (ESI, pos. ion spectrum) m/z 612/614 (M + 1) | Prepared using the procedures described in Example 622 |

-continued

| Ex # | Structure | characterization | method |
|---|---|---|---|
| 724 | 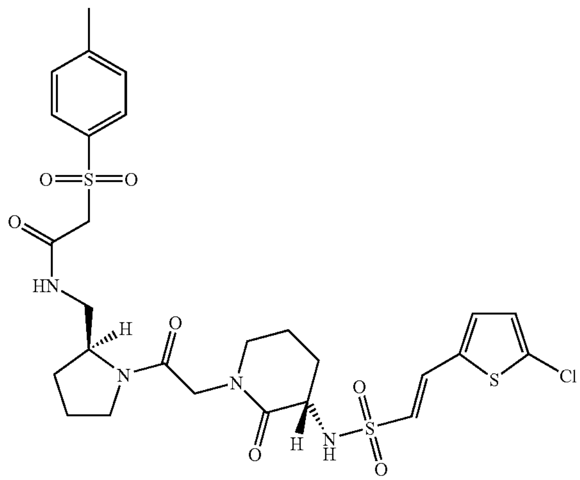 | HPLC (method 6) $t_R$ = 1.6 min LCMS (method 6) (ESI, pos. ion spectrum) m/z 657/659 (M + 1) | Prepared using the procedures described in Example 622 |
| 725 | 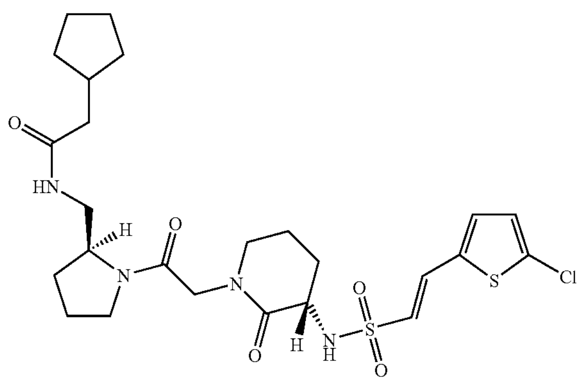 | HPLC (method 6) $t_R$ = 1.8 min LCMS (method 6) (ESI, pos. ion spectrum) m/z 571/573 (M + 1) | Prepared using the procedures described in Example 622 |
| 726 | 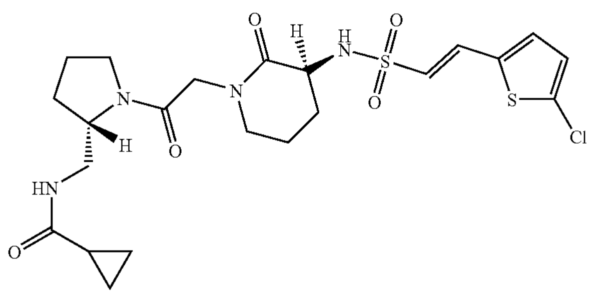 | HPLC (method 6) $t_R$ = 1.6 min LCMS (method 6) (ESI, pos. ion spectrum) m/z 529/531 (M + 1) | Prepared using the procedures described in Example 622 |
| 727 | 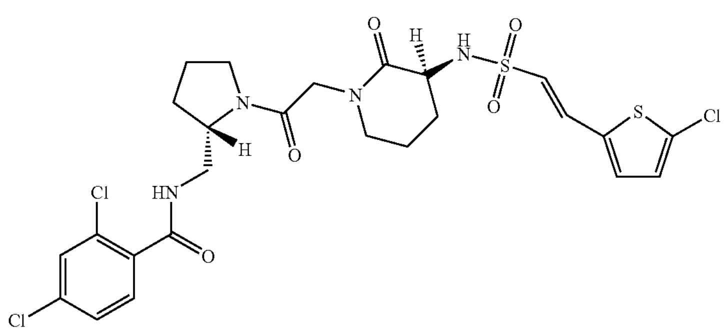 | HPLC (method 6) $t_R$ = 1.8 min LCMS (method 6) (ESI, pos. ion spectrum) m/z 633/635/637 (M + 1) | Prepared using the procedures described in Example 622 |

| Ex # | Structure | characterization | method |
|---|---|---|---|
| 728 | 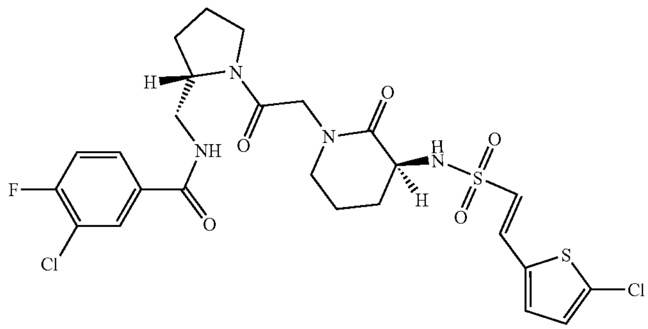 | HPLC (method 6) t_R = 1.8 min LCMS (method 6) (ESI, pos. ion spectrum) m/z 617/619/621 (M + 1) | Prepared using the procedures described in Example 622 |
| 729 | 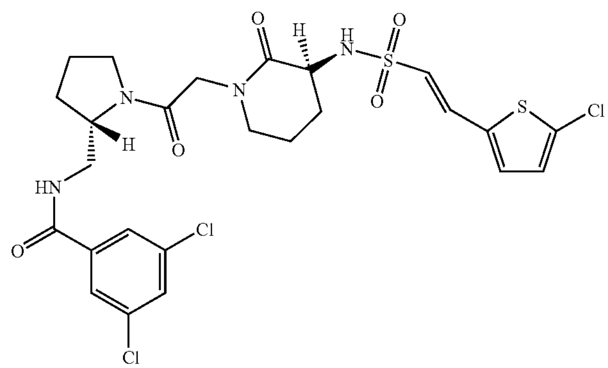 | HPLC (method 6) t_R = 2.0 min LCMS (method 6) (ESI, pos. ion spectrum) m/z 633/635/637 (M + 1) | Prepared using the procedures described in Example 622 |
| 730 | 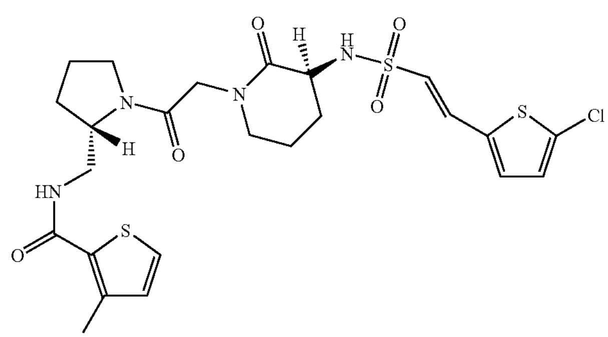 | HPLC (method 6) t_R = 1.7 min LCMS (method 6) (ESI, pos. ion spectrum) m/z 585/587 (M + 1) | Prepared using the procedures described in Example 622 |
| 731 | 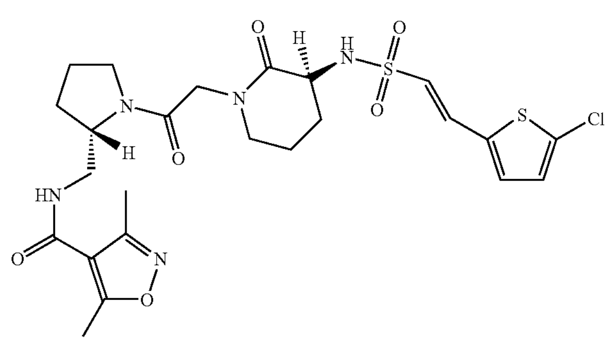 | HPLC (method 6) t_R = 1.5 min LCMS (method 6) (ESI, pos. ion spectrum) m/z 584/586 (M + 1) | Prepared using the procedures described in Example 622 |

| Ex # | Structure | characterization | method |
|---|---|---|---|
| 732 | 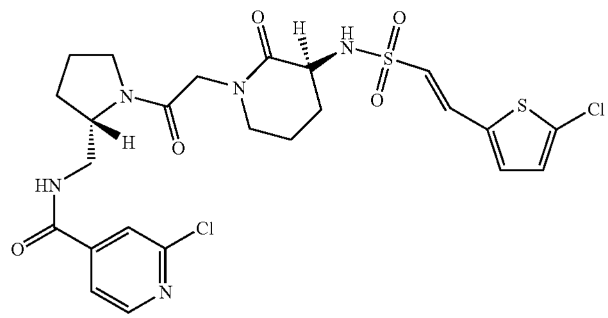 | HPLC (method 6) $t_R$ = 1.6 min LCMS (method 6) (ESI, pos. ion spectrum) m/z 600/602/604 (M + 1) | Prepared using the procedures described in Example 622 |
| 733 | 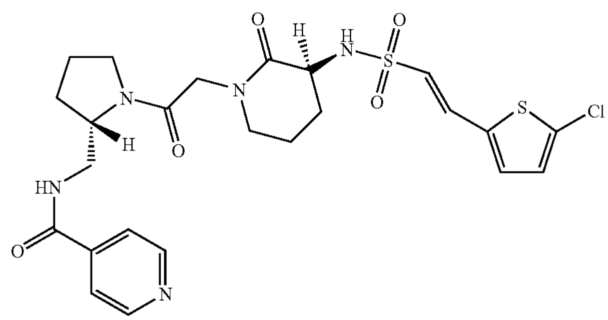 | HPLC (method 6) $t_R$ = 1.3 min LCMS (method 6) (ESI, pos. ion spectrum) m/z 566/568 (M + 1) | Prepared using the procedures described in Example 622 |
| 734 | 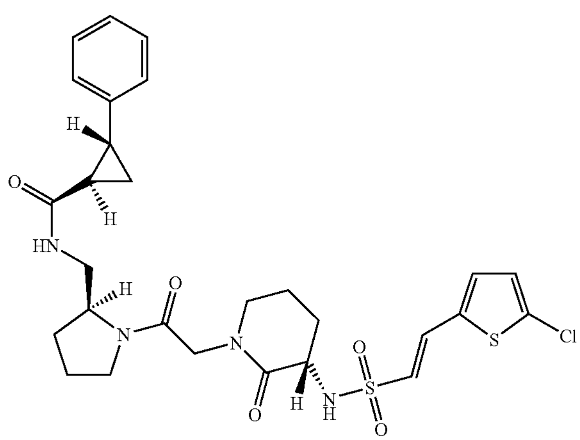 | HPLC (method 6) $t_R$ = 1.8 min LCMS (method 6) (ESI, pos. ion spectrum) m/z 605/607 (M + 1) | Prepared using the procedures described in Example 622 |
| 735 | 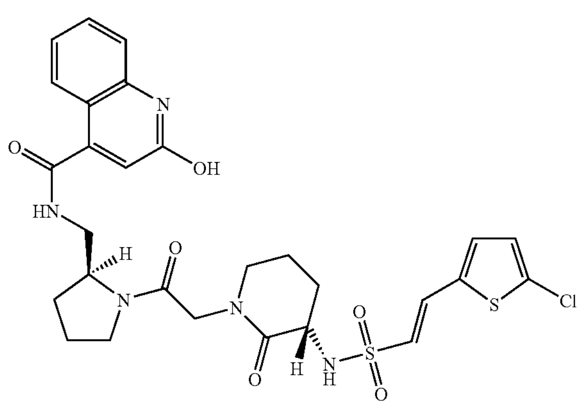 | HPLC (method 6) $t_R$ = 1.6 min LCMS (method 6) (ESI, pos. ion spectrum) m/z 632/634 (M + 1) | Prepared using the procedures described in Example 622 |

| Ex # | Structure | characterization | method |
|---|---|---|---|
| 736 | 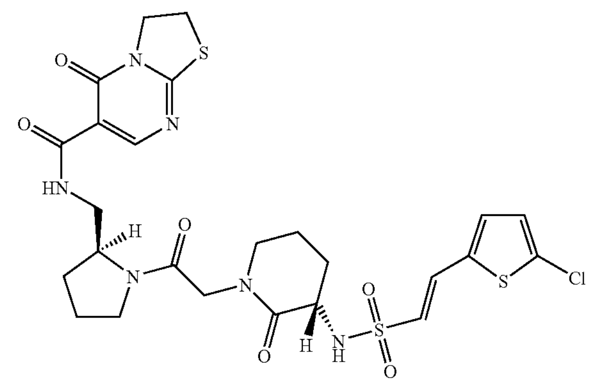 | HPLC (method 6) $t_R$ = 1.5 min LCMS (method 6) (ESI, pos. ion spectrum) m/z 641/643 (M + 1) | Prepared using the procedures described in Example 622 |
| 737 | 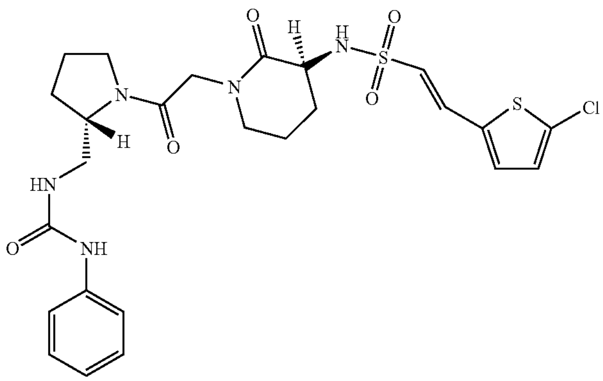 | HPLC (method 6) $t_R$ = 1.8 min LCMS (method 6) (ESI, pos. ion spectrum) m/z 580/582 (M + 1) | Prepared using the procedures described in Example 618 |
| 738 | 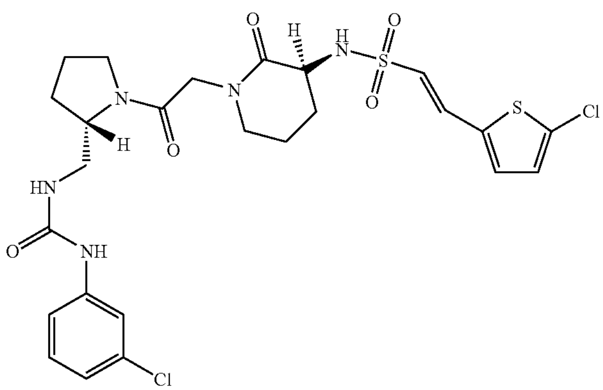 | HPLC (method 6) $t_R$ = 1.9 min LCMS (method 6) (ESI, pos. ion spectrum) m/z 614/616/618 (M + 1) | Prepared using the procedures described in Example 618 |
| 739 | 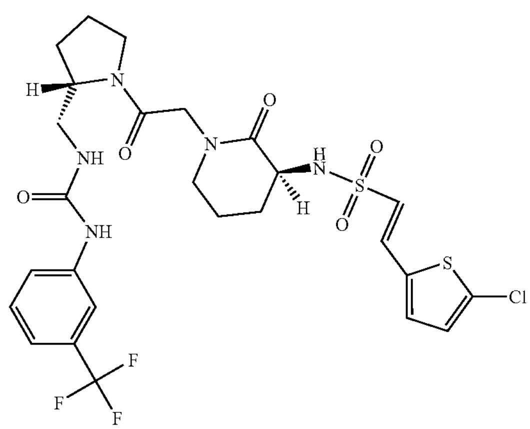 | HPLC (method 6) $t_R$ = 1.9 min LCMS (method 6) (ESI, pos. ion spectrum) m/z 648/650 (M + 1) | Prepared using the procedures described in Example 618 |

-continued

| Ex # | Structure | characterization | method |
|---|---|---|---|
| 740 | 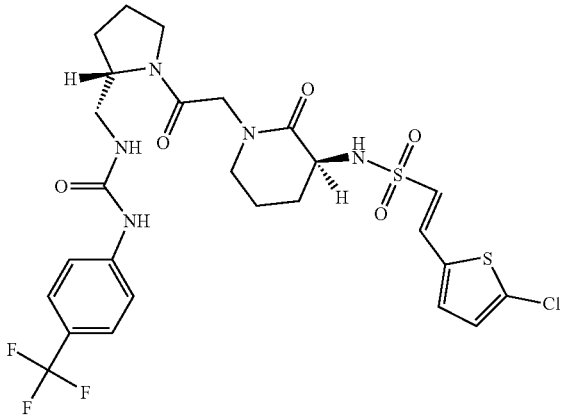 | HPLC (method 6) $t_R$ = 1.9 min LCMS (method 6) (ESI, pos. ion spectrum) m/z 648/650 (M + 1) | Prepared using the procedures described in Example 618 |
| 741 | 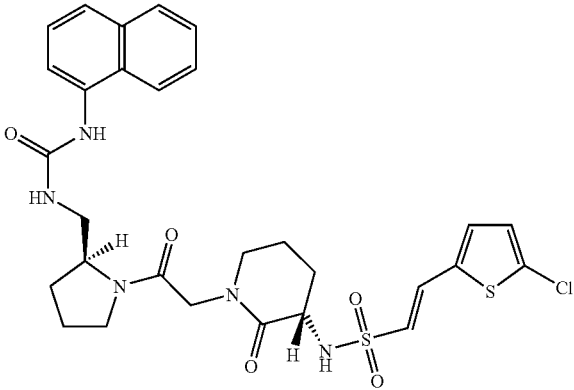 | HPLC (method 6) $t_R$ = 1.9 min LCMS (method 6) (ESI, pos. ion spectrum) m/z 630/632 (M + 1) | Prepared using the procedures described in Example 618 |
| 742 | 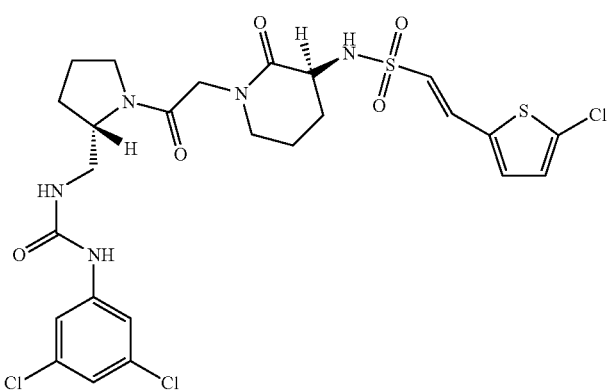 | HPLC (method 6) $t_R$ = 2.1 min LCMS (method 6) (ESI, pos. ion spectrum) m/z 648/650/652 (M + 1) | Prepared using the procedures described in Example 618 |

-continued

| Ex # | Structure | characterization | method |
|---|---|---|---|
| 743 | 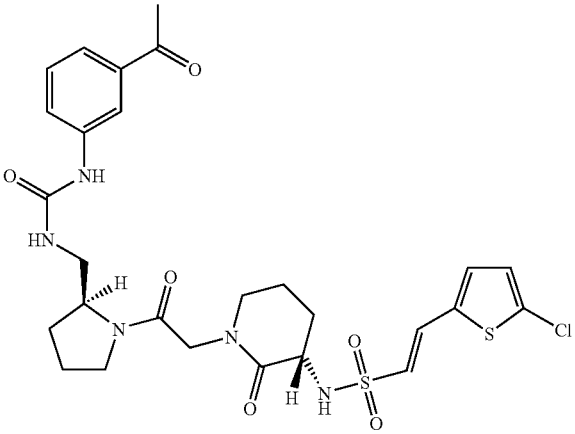 | HPLC (method 6) $t_R$ = 1.7 min LCMS (method 6) (ESI, pos. ion spectrum) m/z 622/624 (M + 1) | Prepared using the procedures described in Example 618 |
| 744 | 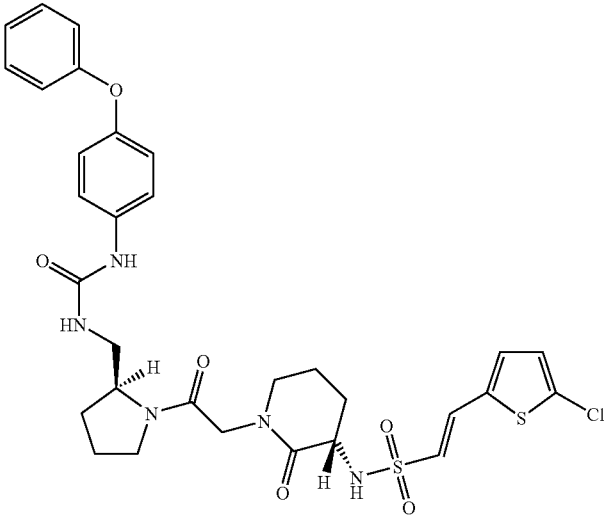 | HPLC (method 8) $t_R$ = 1.8 min LCMS (method 8) (ESI, neg. ion spectrum) m/z 670/672 (M − 1) | Prepared using the procedures described in Example 618 |
| 745 | 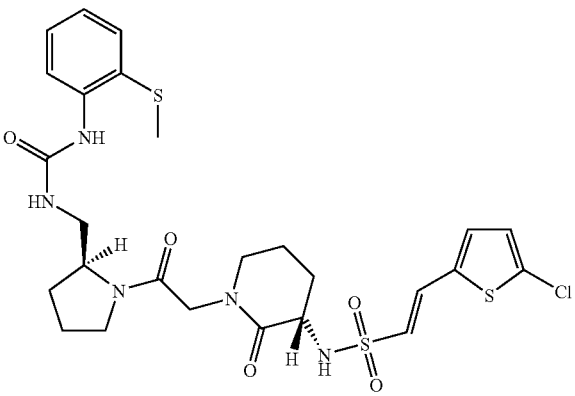 | HPLC (method 8) $t_R$ = 1.6 min LCMS (method 8) (ESI, neg. ion spectrum) m/z 624/626 (M − 1) | Prepared using the procedures described in Example 618 |

| Ex # | Structure | characterization | method |
|---|---|---|---|
| 746 | 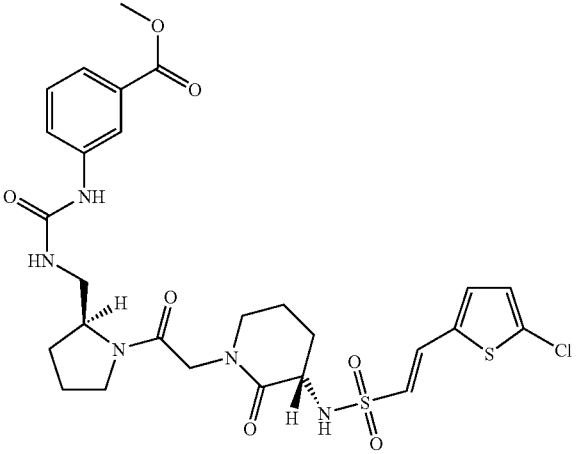 | HPLC (method 8) $t_R$ = 1.5 min LCMS (method 8) (ESI, neg. ion spectrum) m/z 636/638 (M − 1) | Prepared using the procedures described in Example 618 |
| 747 | 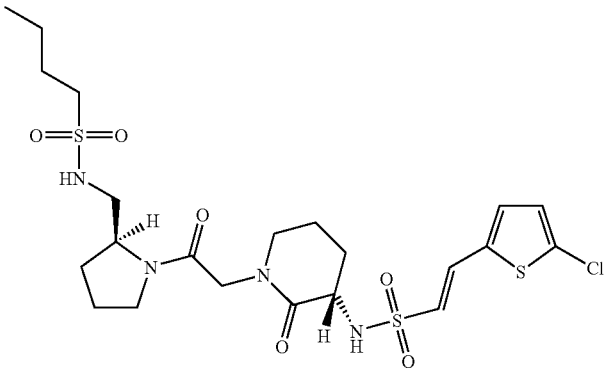 | HPLC (method 6) $t_R$ = 1.7 min LCMS (method 6) (ESI, pos. ion spectrum) m/z 581/583 (M + 1) | Prepared using the procedures described in Example 620 |
| 748 | 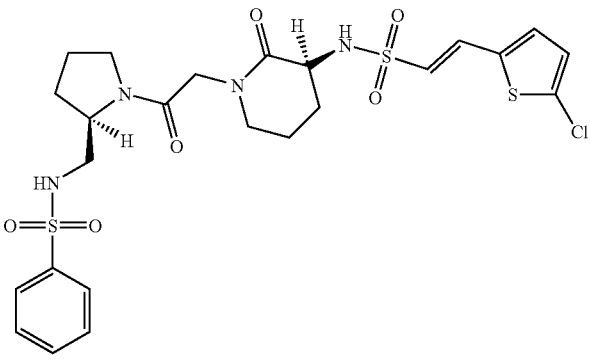 | HPLC (method 6) $t_R$ = 1.7 min LCMS (method 6) (ESI, pos. ion spectrum) m/z 601/603 (M + 1) | Prepared using the procedures described in Example 620 |

| Ex # | Structure | characterization | method |
|---|---|---|---|
| 749 | 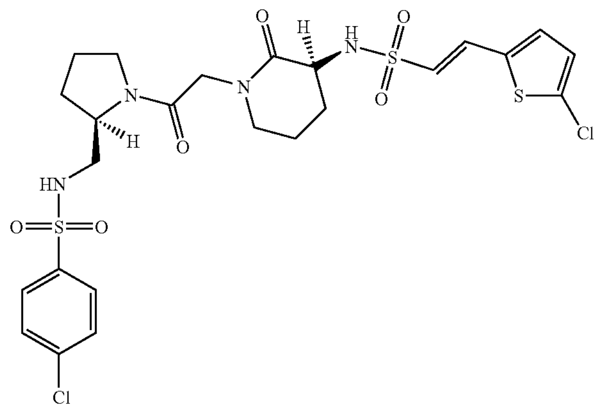 | HPLC (method 6) $t_R$ = 1.8 min LCMS (method 6) (ESI, pos. ion spectrum) m/z 635/637/639 (M + 1) | Prepared using the procedures described in Example 620 |
| 750 | 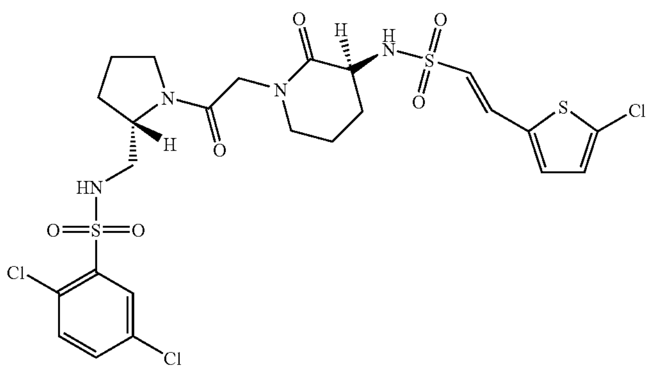 | HPLC (method 6) $t_R$ = 1.9 min LCMS (method 6) (ESI, pos. ion spectrum) m/z 669/671/673 (M + 1) | Prepared using the procedures described in Example 620 |
| 751 | 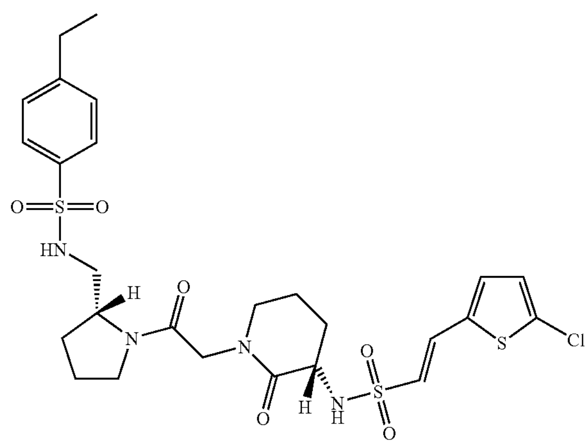 | HPLC (method 6) $t_R$ = 1.8 min LCMS (method 6) (ESI, pos. ion spectrum) m/z 629/631 (M + 1) | Prepared using the procedures described in Example 620 |
| 752 | 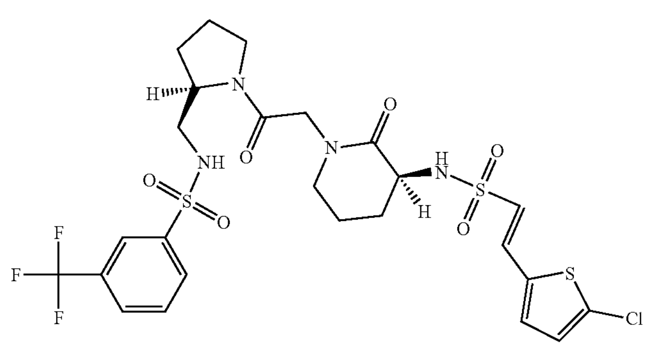 | HPLC (method 6) $t_R$ = 1.9 min LCMS (method 6) (ESI, pos. ion spectrum) m/z 669/671 (M + 1) | Prepared using the procedures described in Example 620 |

-continued

| Ex # | Structure | characterization | method |
|---|---|---|---|
| 753 | 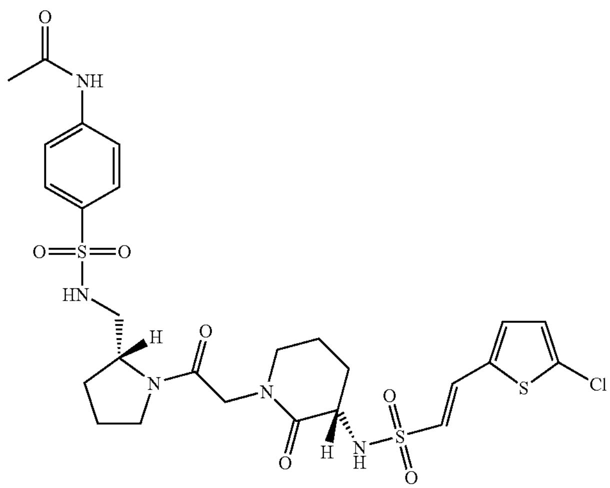 | HPLC (method 6) t_R = 1.5 min LCMS (method 6) (ESI, pos. ion spectrum) m/z 658/660 (M + 1) | Prepared using the procedures described in Example 620 |
| 754 | 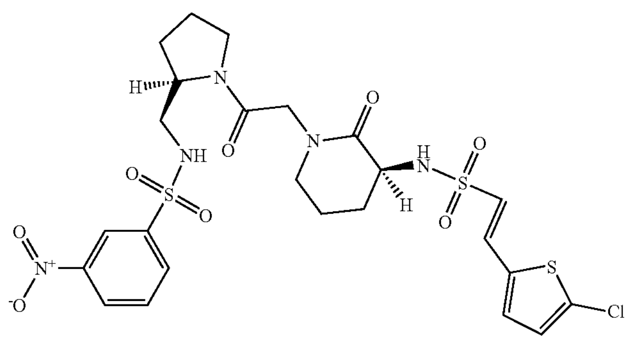 | HPLC (method 8) t_R = 1.6 min LCMS (method 8) (ESI, neg. ion spectrum) m/z 644/646 (M − 1) | Prepared using the procedures described in Example 620 |
| 755 | 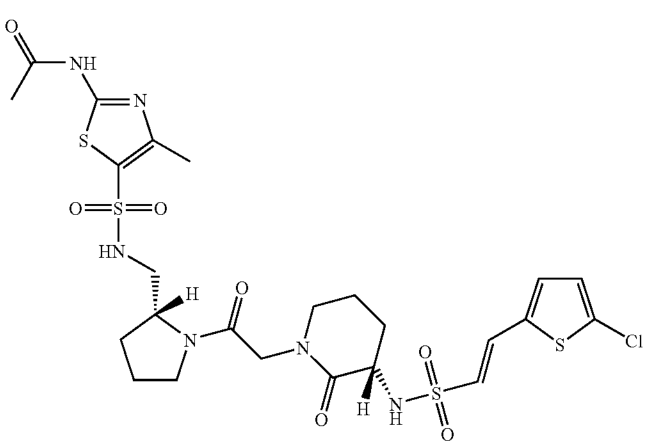 | HPLC (method 6) t_R = 1.6 min LCMS (method 6) (ESI, pos. ion spectrum) m/z 679/681 (M + 1) | Prepared using the procedures described in Example 620 |

| Ex # | Structure | characterization | method |
|---|---|---|---|
| 756 | 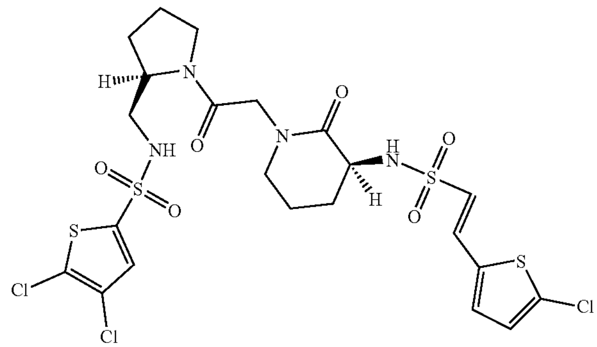 | HPLC (method 6) $t_R$ = 2.0 min LCMS (method 6) (ESI, pos. ion spectrum) m/z 675/677/679 (M + 1) | Prepared using the procedures described in Example 620 |
| 757 | 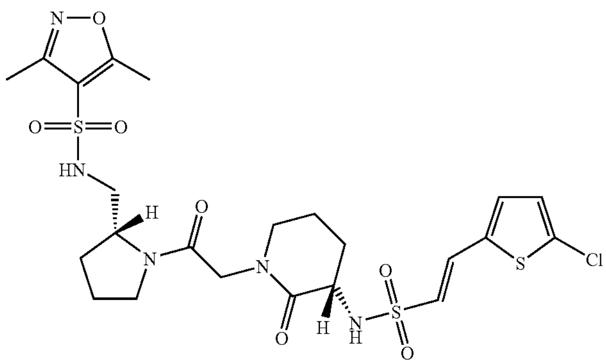 | HPLC (method 6) $t_R$ = 1.6 min LCMS (method 6) (ESI, pos. ion spectrum) m/z 620/622 (M + 1) | Prepared using the procedures described in Example 620 |
| 758 | 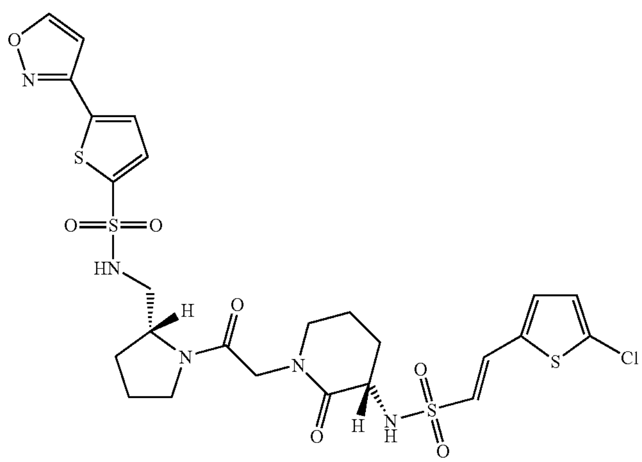 | HPLC (method 6) $t_R$ = 1.7 min LCMS (method 6) (ESI, pos. ion spectrum) m/z 674/676 (M + 1) | Prepared using the procedures described in Example 620 |
| 759 | 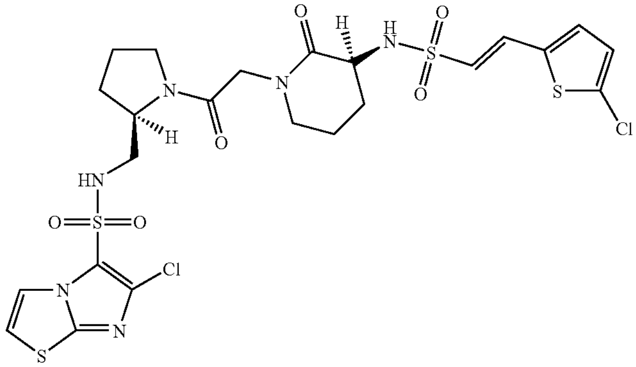 | HPLC (method 6) $t_R$ = 1.7 min LCMS (method 6) (ESI, pos. ion spectrum) m/z 681/683/685 (M + 1) | Prepared using the procedures described in Example 620 |

| Ex # | Structure | characterization | method |
|---|---|---|---|
| 760 | 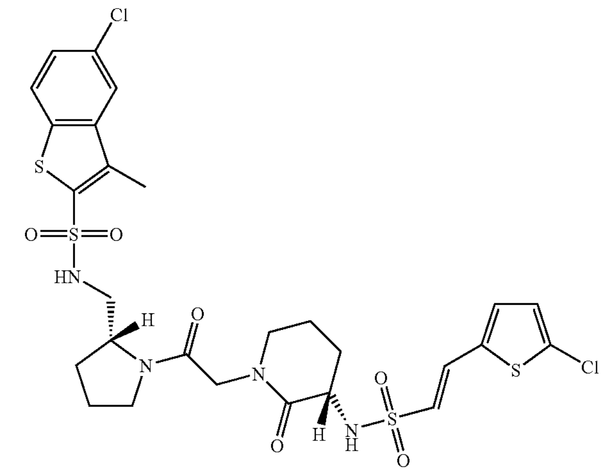 | HPLC (method 5) $t_R$ = 2.1 min LCMS (method 6) (ESI, pos. ion spectrum) m/z 705/707/709 (M + 1) | Prepared using the procedures described in Example 620 |
| 761 | 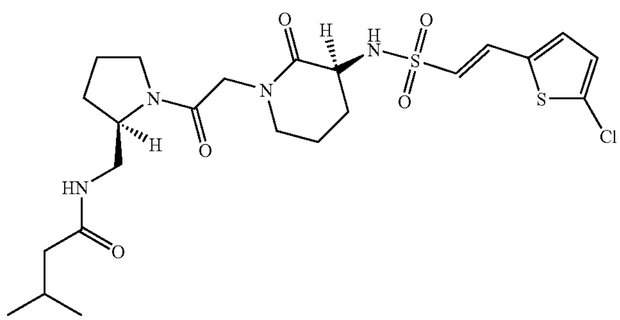 | HPLC (method 8) $t_R$ = 1.4 min LCMS (method 8) (ESI, neg. ion spectrum) m/z 543/545 (M − 1) | Prepared using the procedures described in Example 622 |
| 762 | 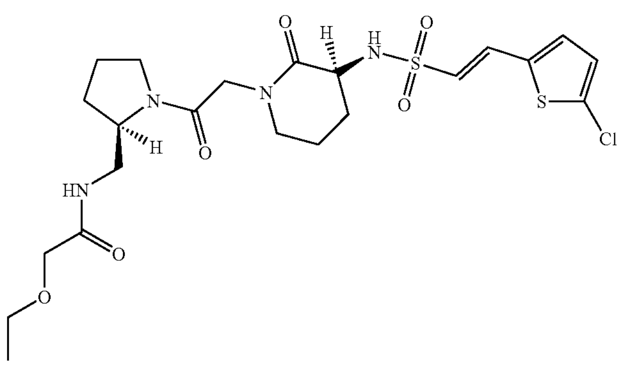 | HPLC (method 8) $t_R$ = 1.3 min LCMS (method 8) (ESI, neg. ion spectrum) m/z 545/547 (M − 1) | Prepared using the procedures described in Example 622 |
| 763 | 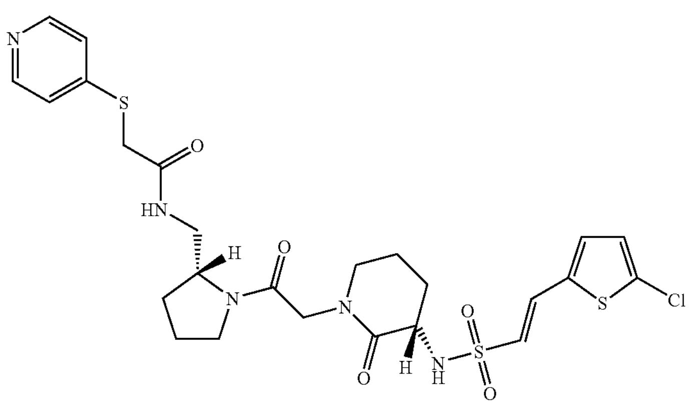 | HPLC (method 8) $t_R$ = 1.4 min LCMS (method 8) (ESI, neg. ion spectrum) m/z 612/614 (M − 1) | Prepared using the procedures described in Example 622 |

US 7,166,586 B2
351 352

-continued

| Ex # | Structure | characterization | method |
|---|---|---|---|
| 764 | 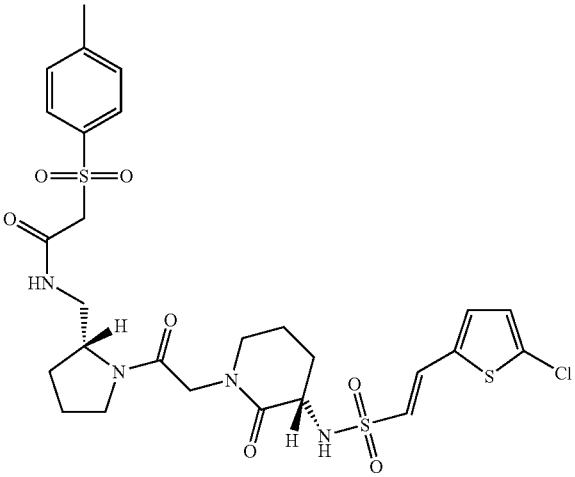 | HPLC (method 8) $t_R$ = 1.5 min LCMS (method 8) (ESI, neg. ion spectrum) m/z 655/657 (M − 1) | Prepared using the procedures described in Example 622 |
| 765 | 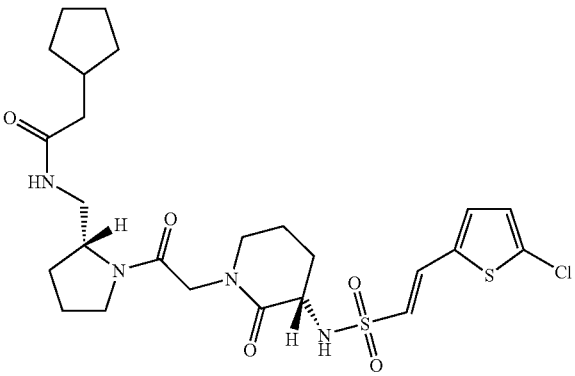 | HPLC (method 8) $t_R$ = 1.5 min LCMS (method 8) (ESI, neg. ion spectrum) m/z 569/571 (M − 1) | Prepared using the procedures described in Example 622 |
| 766 | 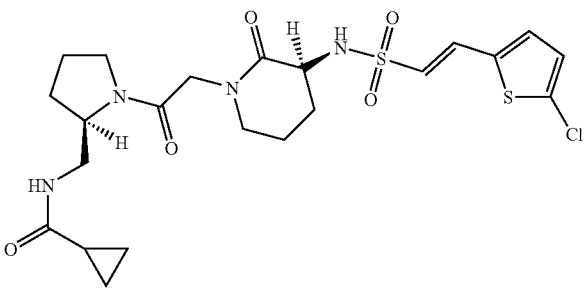 | HPLC (method 8) $t_R$ = 1.3 min LCMS (method 8) (ESI, neg. ion spectrum) m/z 527/529 (M − 1) | Prepared using the procedures described in Example 622 |
| 767 | 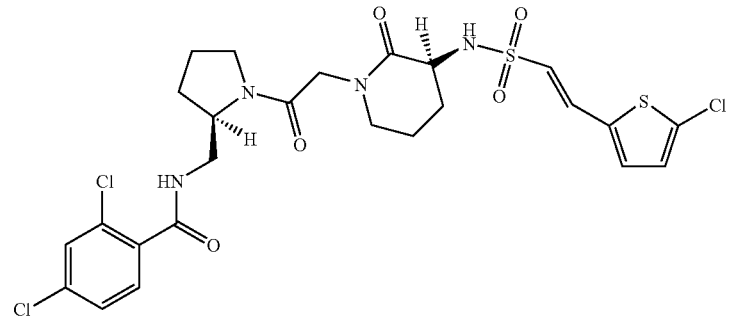 | HPLC (method 8) $t_R$ = 1.6 min LCMS (method 8) (ESI, neg. ion spectrum) m/z 631/633/635 (M − 1) | Prepared using the procedures described in Example 622 |

-continued

| Ex # | Structure | characterization | method |
|---|---|---|---|
| 768 | 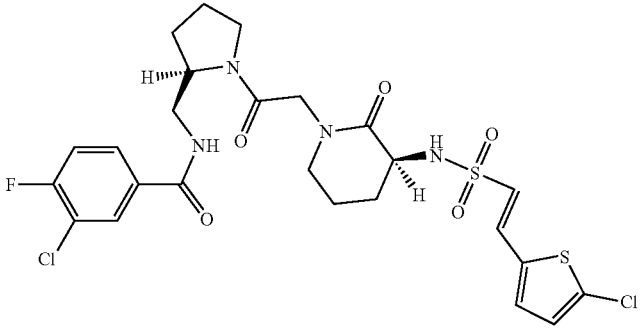 | HPLC (method 8) t_R = 1.6 min LCMS (method 8) (ESI, neg. ion spectrum) m/z 615/617/619 (M − 1) | Prepared using the procedures described in Example 622 |
| 769 | 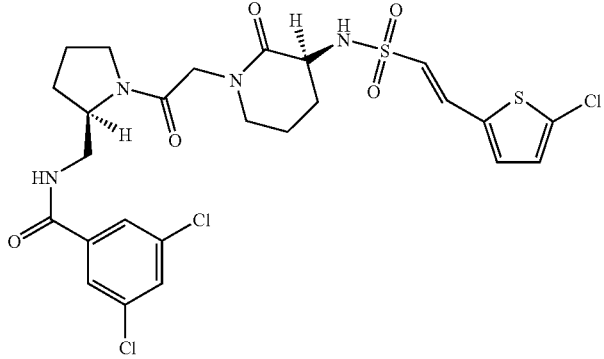 | HPLC (method 8) t_R = 1.8 min LCMS (method 8) (ESI, neg. ion spectrum) m/z 631/633/635 (M − 1) | Prepared using the procedures described in Example 622 |
| 770 | 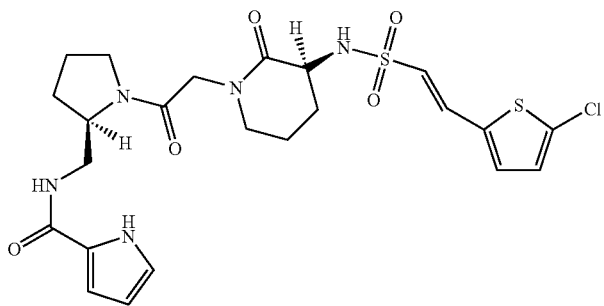 | HPLC (method 6) t_R = 1.7 min LCMS (method 6) (ESI, pos. ion spectrum) m/z 554/556 (M + 1) | Prepared using the procedures described in Example 622 |
| 771 | 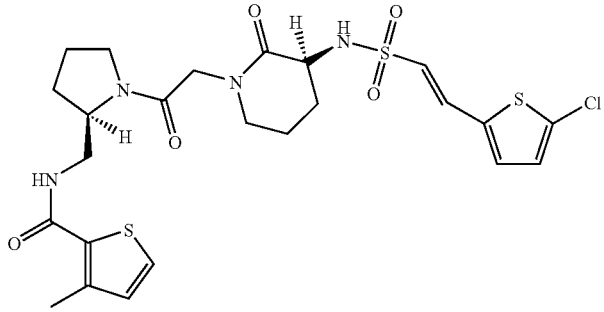 | HPLC (method 8) t_R = 1.5 min LCMS (method 8) (ESI, neg. ion spectrum) m/z 583/585 (M − 1) | Prepared using the procedures described in Example 622 |

-continued

| Ex # | Structure | characterization | method |
|---|---|---|---|
| 772 | 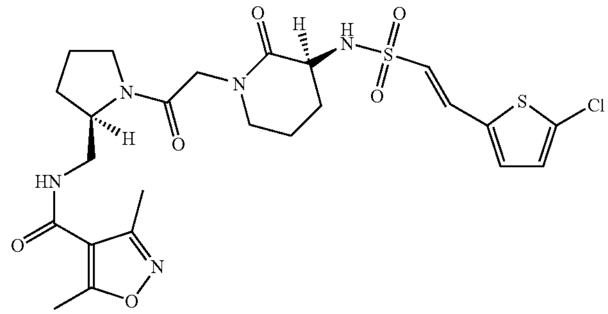 | HPLC (method 8) $t_R$ = 1.4 min LCMS (method 8) (ESI, neg. ion spectrum) m/z 582/584 (M − 1) | Prepared using the procedures described in Example 622 |
| 773 | 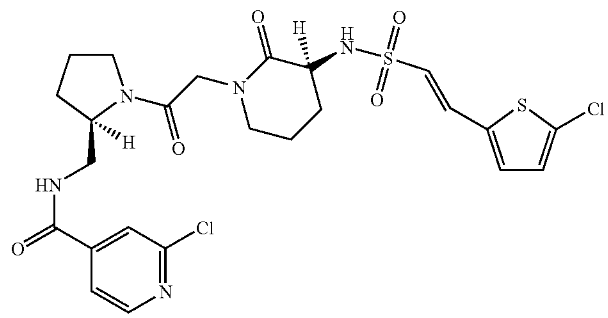 | HPLC (method 8) $t_R$ = 1.4 min LCMS (method 8) (ESI, neg. ion spectrum) m/z 597/599/601 (M − 1) | Prepared using the procedures described in Example 622 |
| 774 | 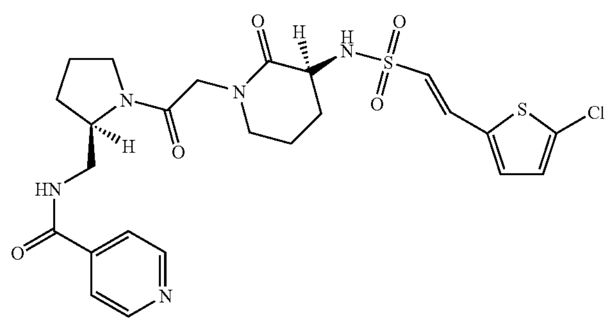 | HPLC (method 8) $t_R$ = 1.3 min LCMS (method 8) (ESI, neg. ion spectrum) m/z 564/566 (M − 1) | Prepared using the procedures described in Example 622 |
| 775 | 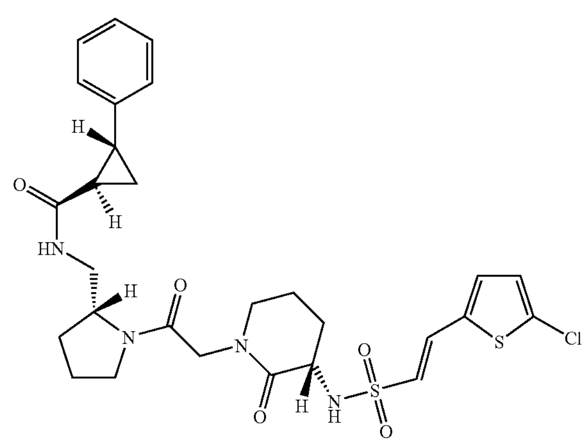 | HPLC (method 8) $t_R$ = 1.6 min LCMS (method 8) (ESI, neg. ion spectrum) m/z 603/605 (M − 1) | Prepared using the procedures described in Example 622 |

-continued

| Ex # | Structure | characterization | method |
|---|---|---|---|
| 776 | 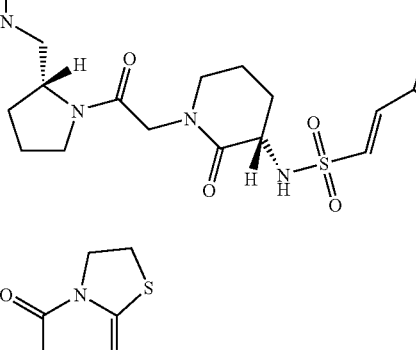 | HPLC (method 8) $t_R$ = 1.3 min LCMS (method 8) (ESI, neg. ion spectrum) m/z 630/632 (M − 1) | Prepared using the procedures described in Example 622 |
| 777 | 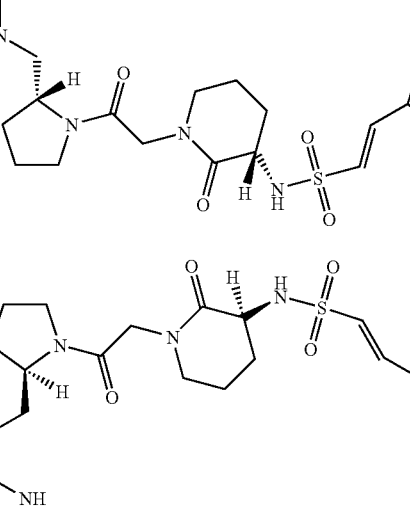 | HPLC (method 8) $t_R$ = 1.3 min LCMS (method 8) (ESI, neg. ion spectrum) m/z 638/640 (M − 1) | Prepared using the procedures described in Example 622 |
| 778 | 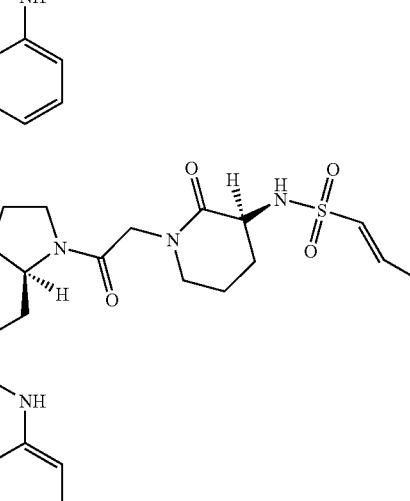 | HPLC (method 6) $t_R$ = 1.8 min LCMS (method 6) (ESI, pos. ion spectrum) m/z 580/582 (M + 1) | Prepared using the procedures described in Example 618 |
| 779 | 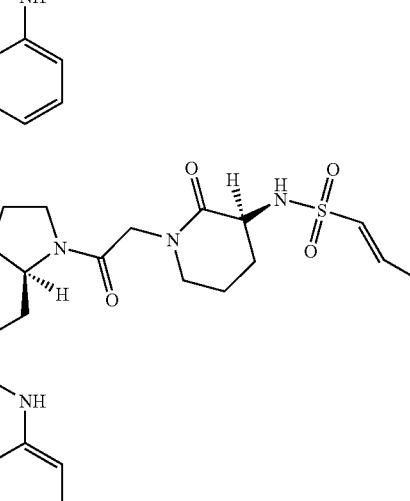 | HPLC (method 6) $t_R$ = 1.9 min LCMS (method 6) (ESI, pos. ion spectrum) m/z 614/616/618 (M + 1) | Prepared using the procedures described in Example 618 |

-continued

| Ex # | Structure | characterization | method |
|---|---|---|---|
| 780 | 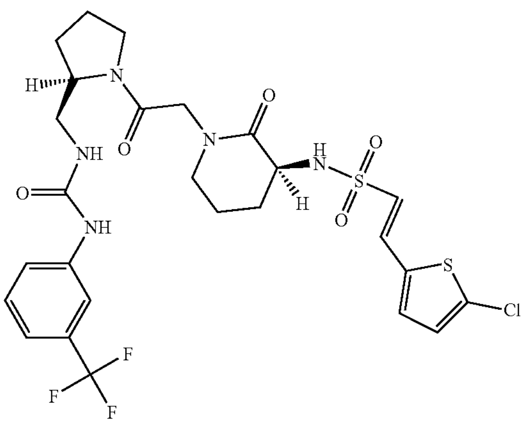 | HPLC (method 6) $t_R$ = 1.9 min LCMS (method 6) (ESI, pos. ion spectrum) m/z 648/650 (M + 1) | Prepared using the procedures described in Example 618 |
| 781 | 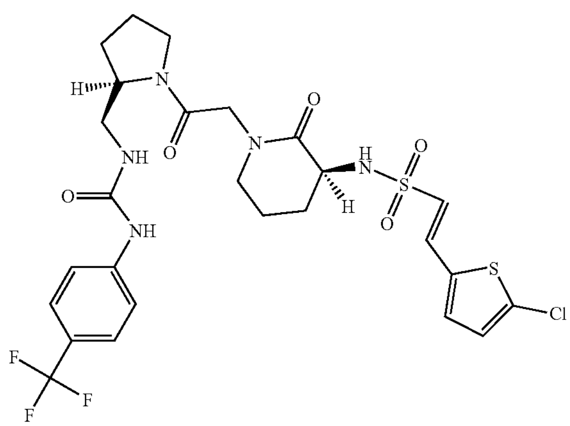 | HPLC (method 6) $t_R$ = 1.9 min LCMS (method 6) (ESI, pos. ion spectrum) m/z 648/650 (M + 1) | Prepared using the procedures described in Example 618 |
| 782 | 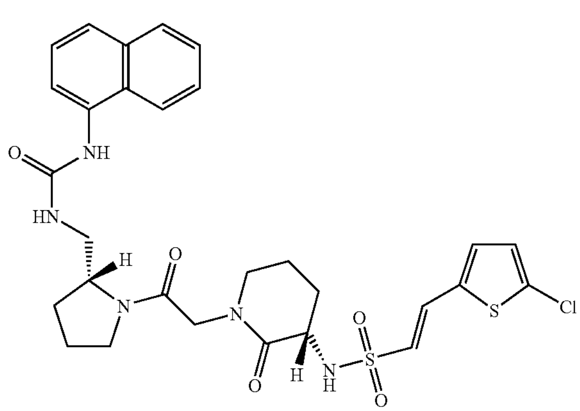 | HPLC (method 8) $t_R$ = 1.6 min LCMS (method 8) (ESI, neg. ion spectrum) m/z 628/630 (M − 1) | Prepared using the procedures described in Example 618 |

| Ex # | Structure | characterization | method |
|---|---|---|---|
| 783 | 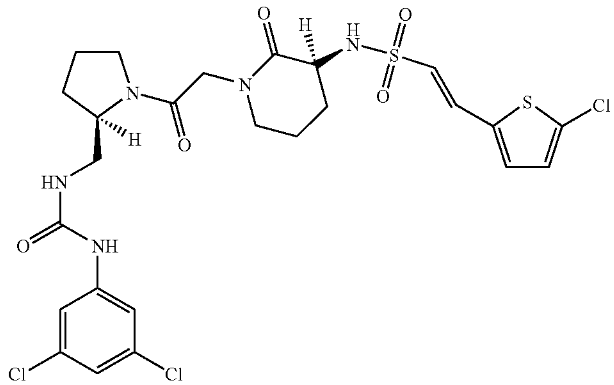 | HPLC (method 6) t_R = 2.1 min LCMS (method 6) (ESI, pos. ion spectrum) m/z 648/650/652 (M + 1) | Prepared using the procedures described in Example 618 |
| 784 | 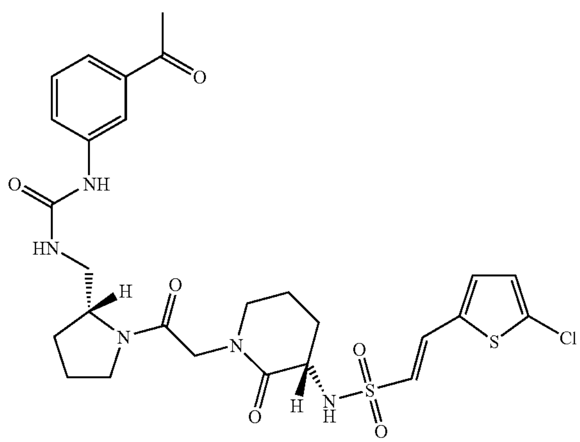 | HPLC (method 8) t_R = 1.4 min LCMS (method 8) (ESI, neg. ion spectrum) m/z 620/622 (M − 1) | Prepared using the procedures described in Example 618 |
| 785 | 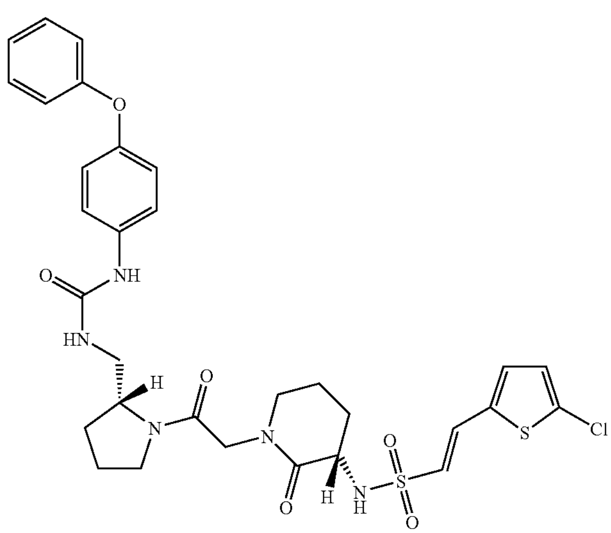 | HPLC (method 8) t_R = 1.8 min LCMS (method 8) (ESI, neg. ion spectrum) m/z 670/672 (M − 1) | Prepared using the procedures described in Example 618 |

| Ex # | Structure | characterization | method |
|---|---|---|---|
| 786 | 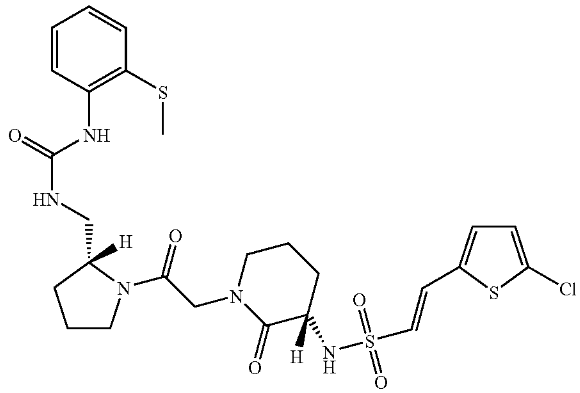 | HPLC (method 8) $t_R$ = 1.6 min LCMS (method 8) (ESI, neg. ion spectrum) m/z 624/626 (M − 1) | Prepared using the procedures described in Example 618 |
| 787 | 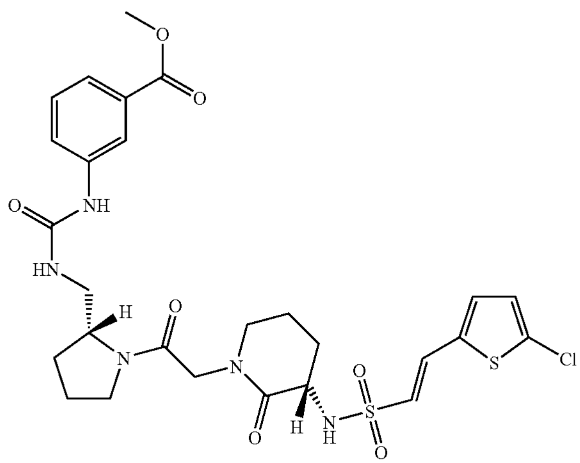 | HPLC (method 8) $t_R$ = 1.5 min LCMS (method 8) (ESI, neg. ion spectrum) m/z 636/638 (M − 1) | Prepared using the procedures described in Example 618 |
| 788 | 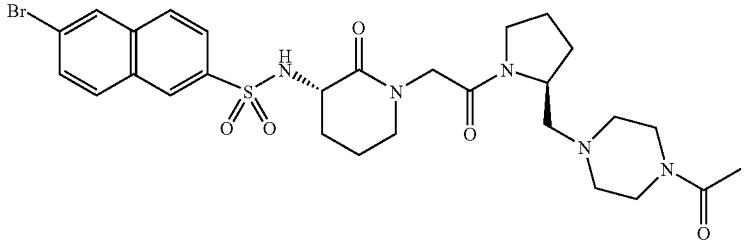 | HPLC (method 1) $t_R$ = 3.0 min LRMS (ESI, pos. ion spectrum) m/z 634/636 (M + H) | Title compound of Example 788 |
| 789 | 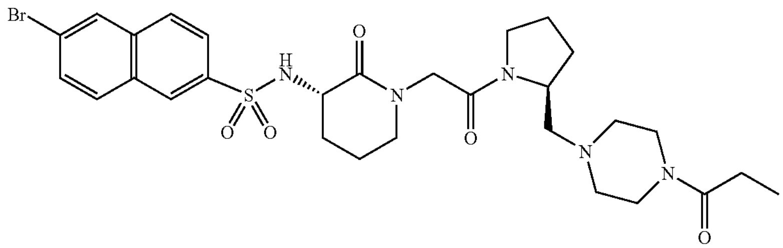 | HPLC (method 1) $t_R$ = 3.1 min LRMS (ESI, pos. ion spectrum) m/z 648/650 (M + H) | Prepared using the procedure described in Example 788 |

-continued

| Ex # | Structure | characterization | method |
|---|---|---|---|
| 790 | 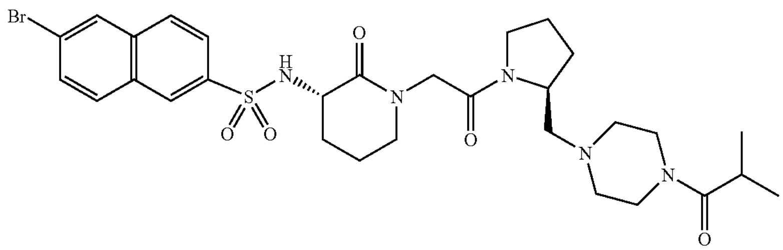 | HPLC (method 1) $t_R$ = 3.1 min LRMS (ESI, pos. ion spectrum) m/z 662/664 (M + H) | Prepared using the procedure described in Example 788 |
| 791 | 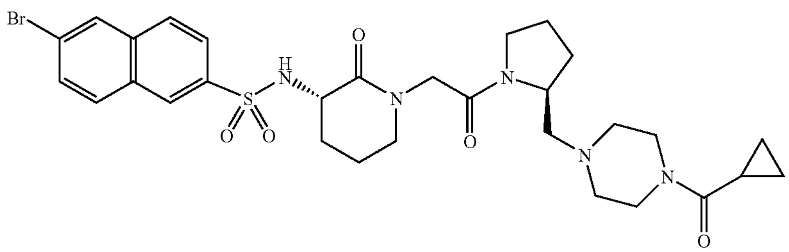 | HPLC (method 1) $t_R$ = 3.1 min LRMS (ESI, pos. ion spectrum) m/z 660/662 (M + H) | Prepared using the procedure described in Example 788 |
| 792 | 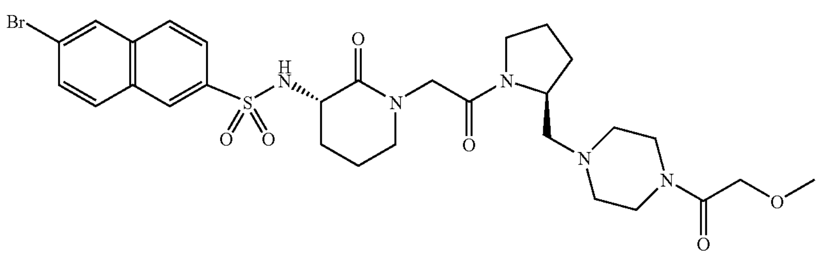 | HPLC (method 1) $t_R$ = 3.0 min LRMS (ESI, pos. ion spectrum) m/z 664/666 (M + H) | Prepared using the procedure described in Example 788 |
| 793 | 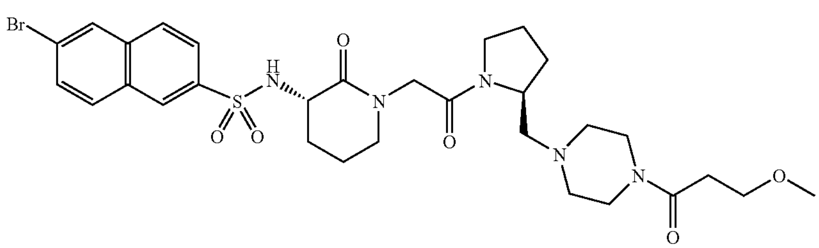 | HPLC (method 1) $t_R$ = 3.0 min LRMS (ESI, pos. ion spectrum) m/z 678/680 (M + H) | Prepared using the procedure described in Example 788 |
| 794 | 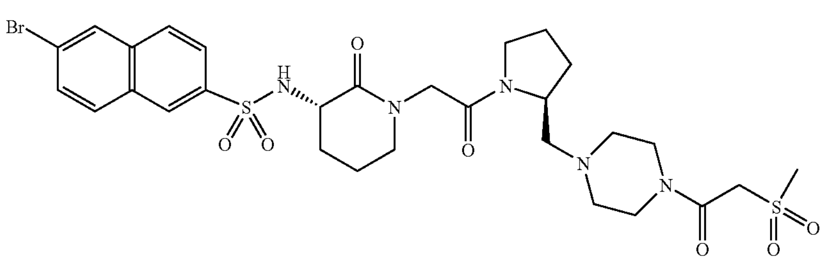 | HPLC (method 1) $t_R$ = 2.9 min LRMS (ESI, pos. ion spectrum) m/z 712/714 (M + H) | Prepared using the procedure described in Example 788 |
| 795 | 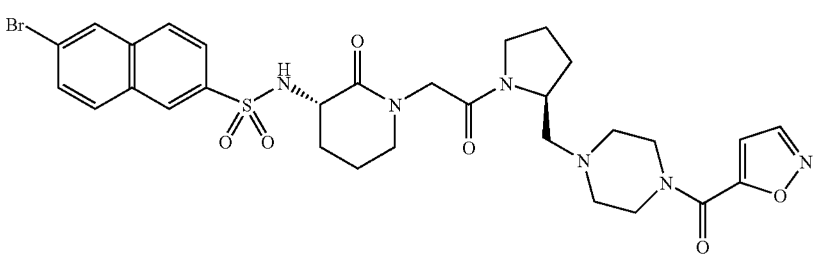 | HPLC (method 1) $t_R$ = 3.0 min LRMS (ESI, pos. ion spectrum) m/z 687/689 (M + H) | Prepared using the procedure described in Example 788 |

| Ex # | Structure | characterization | method |
|---|---|---|---|
| 796 | (structure) | HPLC (method 1) t_R = 3.1 min LRMS (ESI, pos. ion spectrum) m/z 702/704 (M + H) | Prepared using the procedure described in Example 788 |
| 797 | (structure) | HPLC (method 1) t_R = 2.9 min LRMS (ESI, pos. ion spectrum) m/z 596/598 (M + H) | Prepared using the procedure described in Example 788 using the title compound of Example 568 |
| 798 | (structure) | HPLC (method 1) t_R = 3.0 min LRMS (ESI, pos. ion spectrum) m/z 610/612 (M + H) | Prepared using the procedure described in Example 788 using the title compound of Example 568 |
| 799 | (structure) | HPLC (method 1) t_R = 3.1 min LRMS (ESI, pos. ion spectrum) m/z 624/626 (M + H) | Prepared using the procedure described in Example 788 using the title compound of Example 568 |
| 800 | (structure) | HPLC (method 1) t_R = 3.0 min LRMS (ESI, pos. ion spectrum) m/z 622/624 (M + H) | Prepared using the procedure described in Example 788 using the title compound of Example 568 |
| 801 | (structure) | HPLC (method 1) t_R = 2.9 min LRMS (ESI, pos. ion spectrum) m/z 626/628 (M + H) | Prepared using the procedure described in Example 788 using the title compound of Example 568 |

-continued

| Ex # | Structure | characterization | method |
|---|---|---|---|
| 802 | 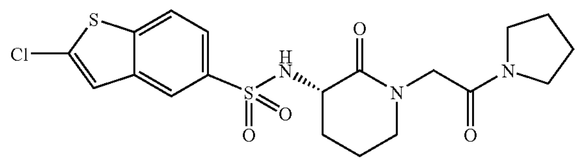 | HPLC (method 2) t_R = 2.1 min LCMS (ESI, pos. ion spectrum) m/z 456/458 (M + 1) | prepared using the method described in Example 130 with INT3 |
| 803 | 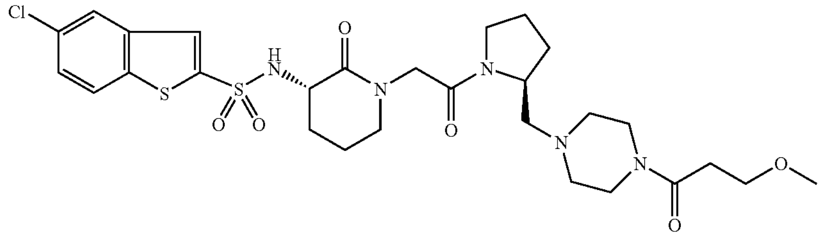 | HPLC (method 1) t_R = 3.0 min LRMS (ESI, pos. ion spectrum) m/z 640/642 (M + H) | Prepared using the procedure described in Example 788 using the title compound of Example 568 |
| 804 | 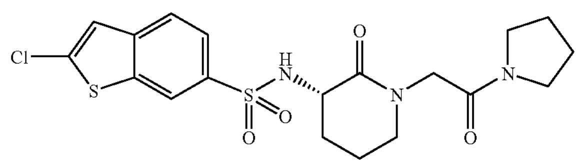 | HPLC (method 2) t_R = 2.0 min LCMS (ESI, pos. ion spectrum) m/z 456/458 (M + 1) | prepared using the method described in Example 130 with INT4 |
| 805 | 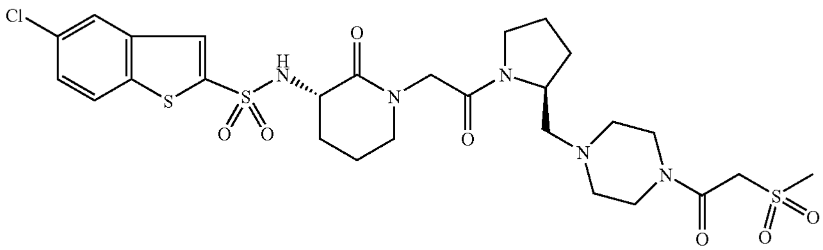 | HPLC (method 1) t_R = 2.8 min LRMS (ESI, pos. ion spectrum) m/z 674/676 (M + H) | Prepared using the procedure described in Example 788 using the title compound of Example 568 |
| 806 | 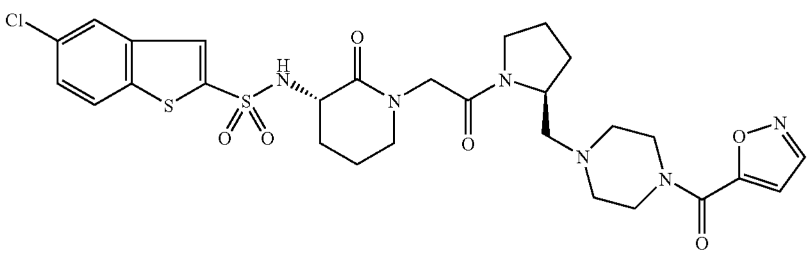 | HPLC (method 1) t_R = 3.0 min LRMS (ESI, pos. ion spectrum) m/z 649/651 (M + H) | Prepared using the procedure described in Example 788 using the title compound of Example 568 |
| 807 | 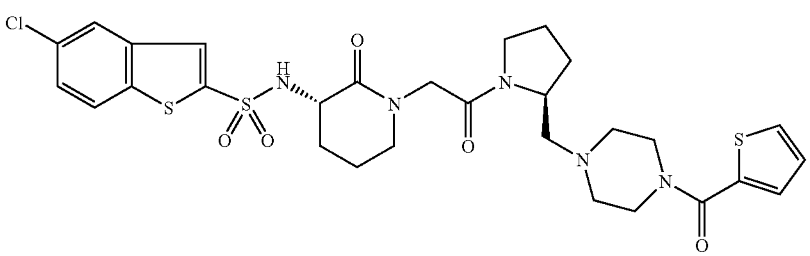 | HPLC (method 1) t_R = 3.1 min LRMS (ESI, pos. ion spectrum) m/z 664/666 (M + H) | Prepared using the procedure described in Example 788 using the title compound of Example 568 |
| 808 | 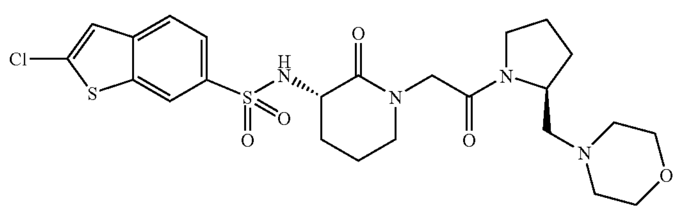 | HPLC (method 2) t_R = 1.8 min LCMS (ESI, pos. ion spectrum) m/z 555/557 (M + 1) | prepared using the method described in Example 130 with INT4 and INT5 |

| Ex # | Structure | characterization | method |
|---|---|---|---|
| 809 | 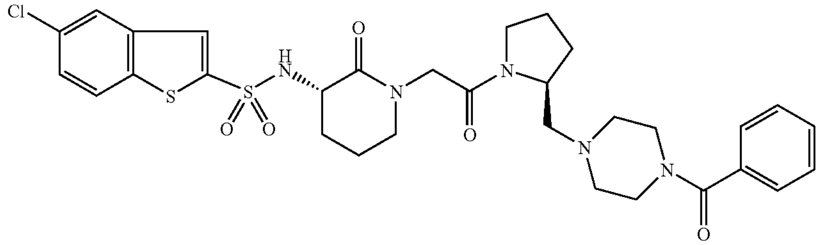 | HPLC (method 1) t_R = 3.2 min LRMS (ESI, pos. ion spectrum) m/z 658/660 (M + H) | Prepared using the procedure described in Example 788 using the title compound of Example 568 |
| 810 | 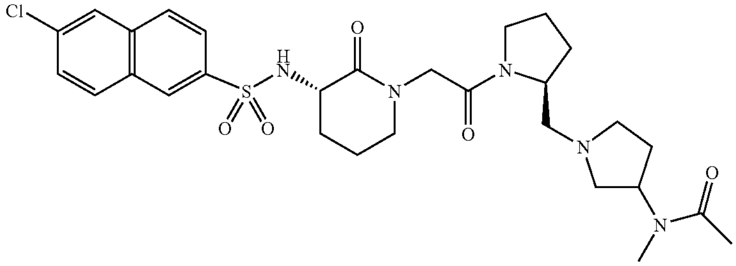 | HPLC (method 1) t_R = 3.1 min LRMS (ESI, pos. ion spectrum) m/z 604/606 (M + H) | Prepared using the procedure described in Example 788 using the title compound of Example 614 |
| 811 | 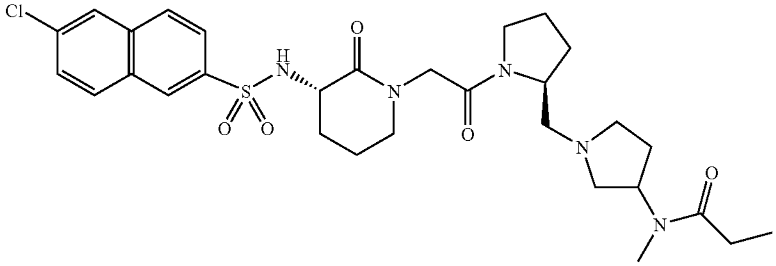 | HPLC (method 1) t_R = 3.2 min LRMS (ESI, pos. ion spectrum) m/z 618/620 (M + H) | Prepared using the procedure described in Example 788 using the title compound of Example 614 |
| 812 | 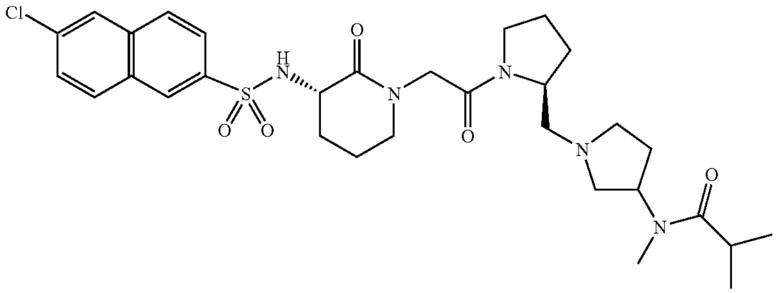 | HPLC (method 1) t_R = 3.3 min LRMS (ESI, pos. ion spectrum) m/z 632/634 (M + H) | Prepared using the procedure described in Example 788 using the title compound of Example 614 |
| 813 | 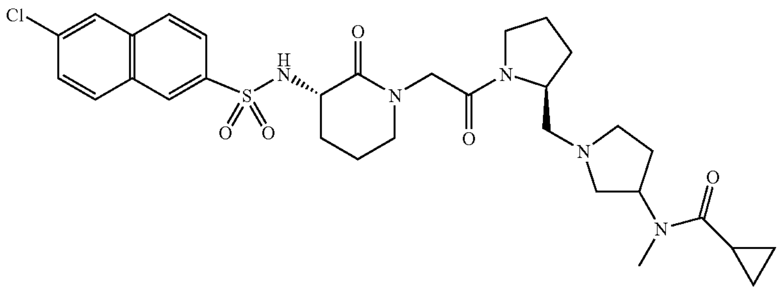 | HPLC (method 1) t_R = 3.2 min LRMS (ESI, pos. ion spectrum) m/z 630/632 (M + H) | Prepared using the procedure described in Example 788 using the title compound of Example 614 |

-continued

| Ex # | Structure | characterization | method |
|---|---|---|---|
| 814 | 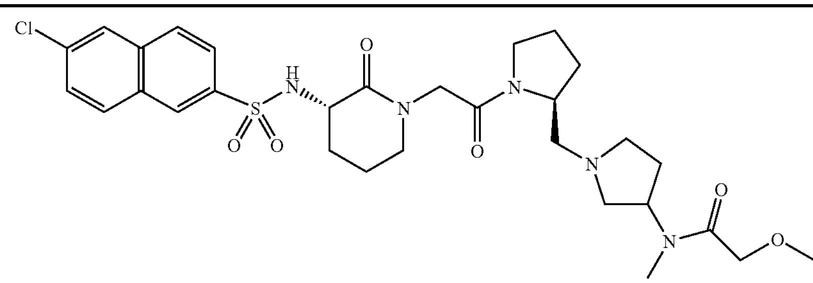 | HPLC (method 1) t_R = 3.1 min LRMS (ESI, pos. ion spectrum) m/z 634/636 (M + H) | Prepared using the procedure described in Example 788 using the title compound of Example 614 |
| 815 | 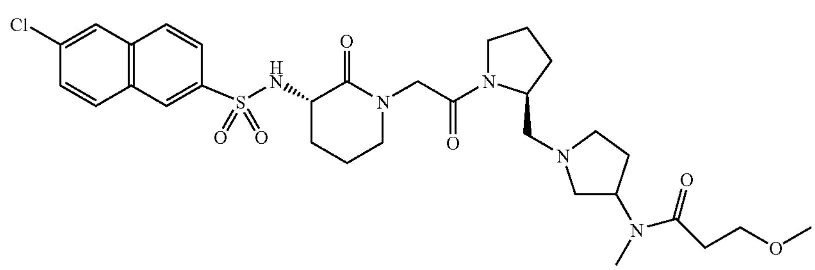 | HPLC (method 1) t_R = 3.1 min LRMS (ESI, pos. ion spectrum) m/z 648/650 (M + H) | Prepared using the procedure described in Example 788 using the title compound of Example 614 |
| 816 | 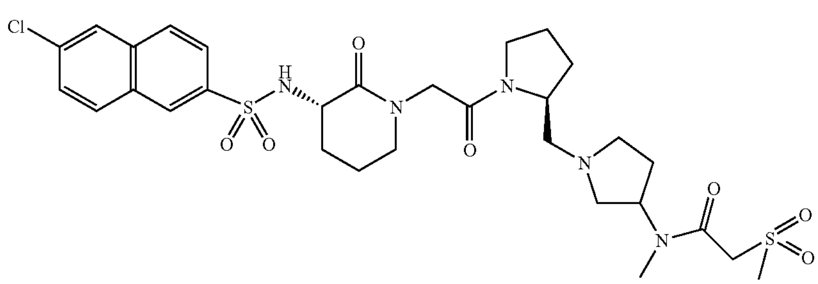 | HPLC (method 1) t_R = 3.0 min LRMS (ESI, pos. ion spectrum) m/z 682/684 (M + H) | Prepared using the procedure described in Example 788 using the title compound of Example 614 |
| 817 | 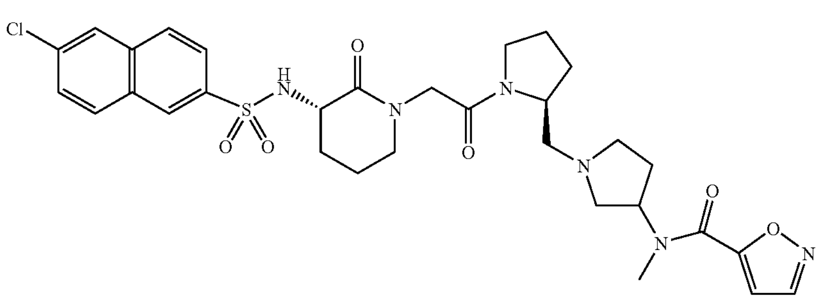 | HPLC (method 1) t_R = 3.1 min LRMS (ESI, pos. ion spectrum) m/z 657/659 (M + H) | Prepared using the procedure described in Example 788 using the title compound of Example 614 |
| 818 | 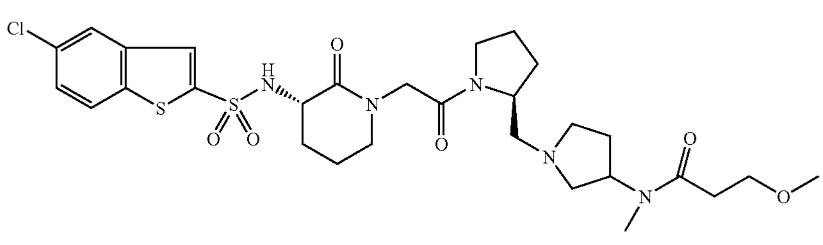 | HPLC (method 1) t_R = 3.1 min LRMS (ESI, pos. ion spectrum) m/z 654/656 (M + H) | Prepared using the procedure described in Example 788 using the title compound of Example 615 |
| 819 | 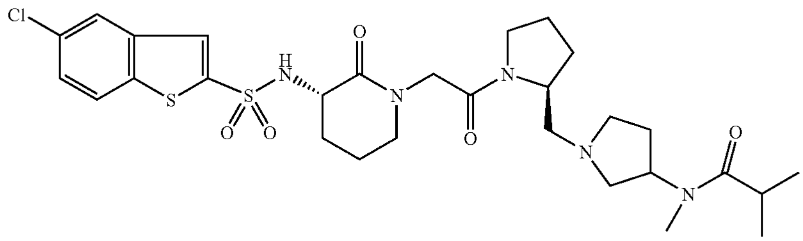 | HPLC (method 1) t_R = 3.3 min LRMS (ESI, pos. ion spectrum) m/z 638/640 (M + H) | Prepared using the procedure described in Example 788 using the title compound of Example 615 |

-continued

| Ex # | Structure | characterization | method |
|---|---|---|---|
| 820 | 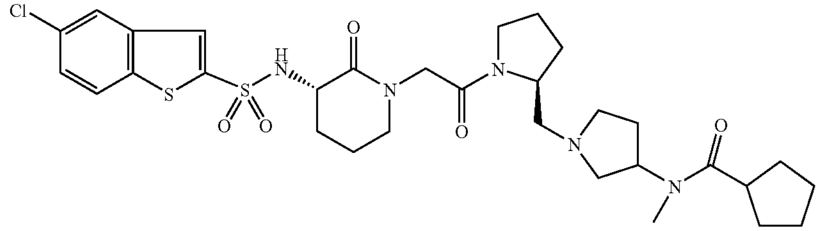 | HPLC (method 1) $t_R$ = 3.4 min LRMS (ESI, pos. ion spectrum) m/z 664/666 (M + H) | Prepared using the procedure described in Example 788 using the title compound of Example 615 |
| 821 | 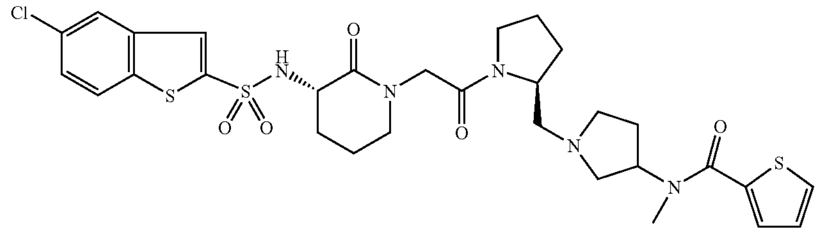 | HPLC (method 1) $t_R$ = 3.3 min LRMS (ESI, pos. ion spectrum) m/z 678/680 (M + H) | Prepared using the procedure described in Example 788 using the title compound of Example 615 |
| 822 | 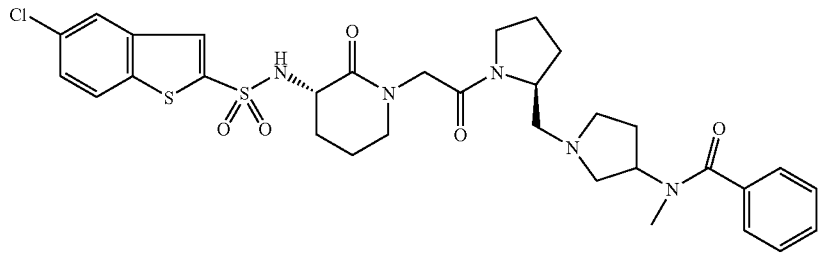 | HPLC (method 1) $t_R$ = 3.3 min LRMS (ESI, pos. ion spectrum) m/z 672/674 (M + H) | Prepared using the procedure described in Example 788 using the title compound of Example 615 |
| 823 | 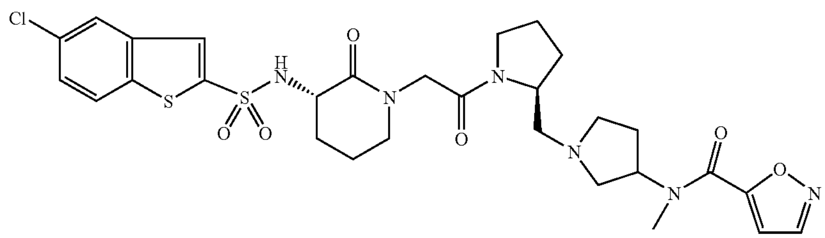 | HPLC (method 1) $t_R$ = 3.1 min LRMS (ESI, pos. ion spectrum) m/z 663/665 (M + H) | Prepared using the procedure described in Example 788 using the title compound of Example 615 |
| 824 | 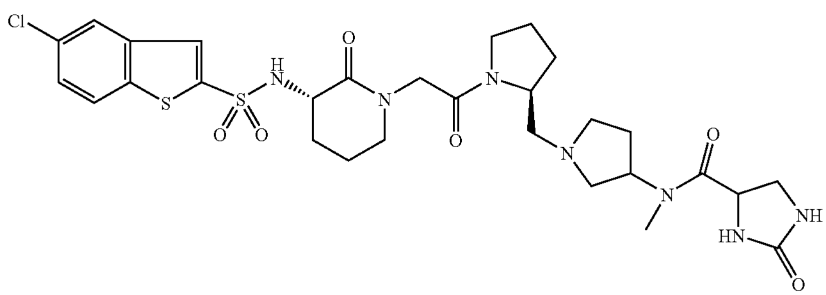 | HPLC (method 1) $t_R$ = 2.9 min LRMS (ESI, pos. ion spectrum) m/z 680/682 (M + H) | Prepared using the procedure described in Example 613 Part A using the title compound of Example 615 and using 1/1 DMF/acetonitrile for solvent |
| 825 | 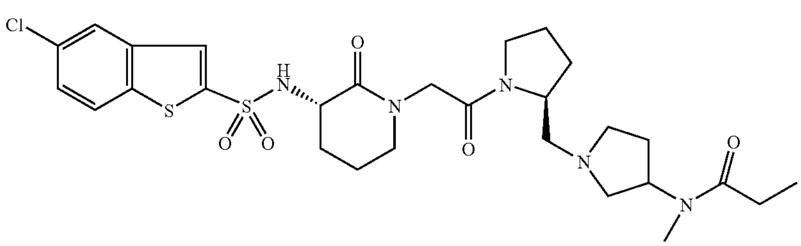 | HPLC (method 1) $t_R$ = 3.1 min LRMS (ESI, pos. ion spectrum) m/z 624/626 (M + H) | Prepared using the procedure described in Example 613 Part A using the title compound of Example 615 and using 1/1 DMF/acetonitrile for solvent |

-continued

| Ex # | Structure | characterization | method |
|---|---|---|---|
| 826 | 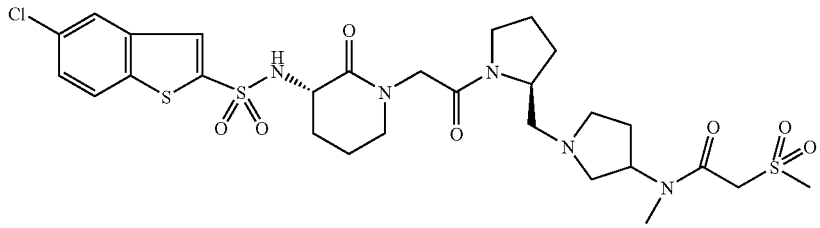 | HPLC (method 1) $t_R$ = 3.0 min LRMS (ESI, pos. ion spectrum) m/z 688/690 (M + H) | Prepared using the procedure described in Example 613 Part A using the title compound of Example 615 and using 1/1 DMF/acetonitrile for solvent |
| 827 | 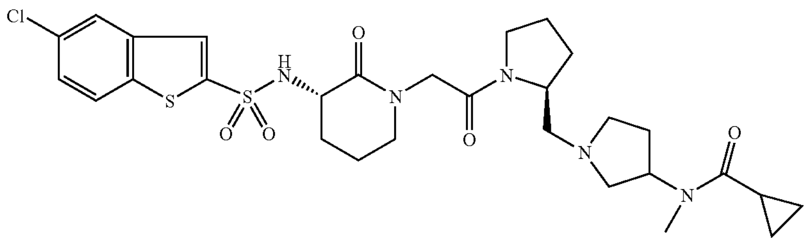 | HPLC (method 1) $t_R$ = 3.2 min LRMS (ESI, pos. ion spectrum) m/z 636/638 (M + H) | Prepared using the procedure described in Example 613 Part A using the title compound of Example 615 and using 1/1 DMF/acetonitrile for solvent |
| 828 | 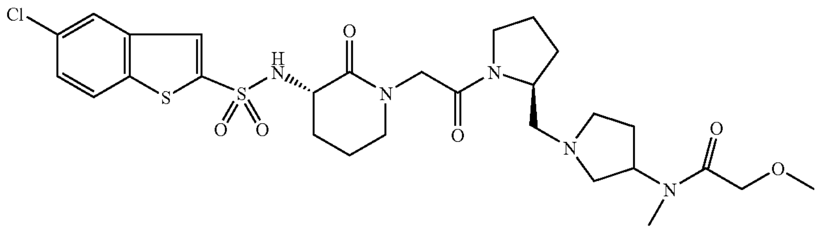 | HPLC (method 1) $t_R$ = 3.0 min LRMS (ESI, pos. ion spectrum) m/z 640/642 (M + H) | Prepared using the procedure described in Example 788 using the title compound of Example 615 |
| 829 | 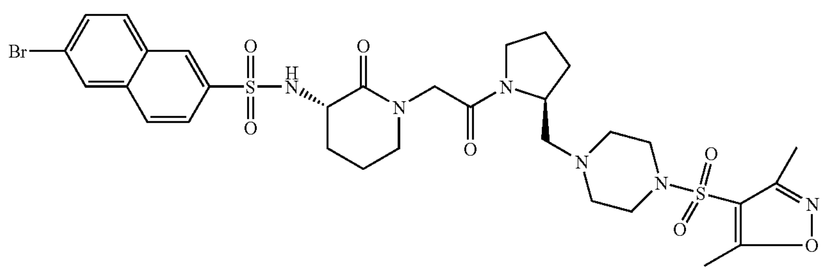 | HPLC (method 1) $t_R$ = 3.5 min LRMS (ESI, pos. ion spectrum) m/z 751/753 (M + H) | Prepared using the method described in Example 571 using the title compound of Example 569 |
| 830 | 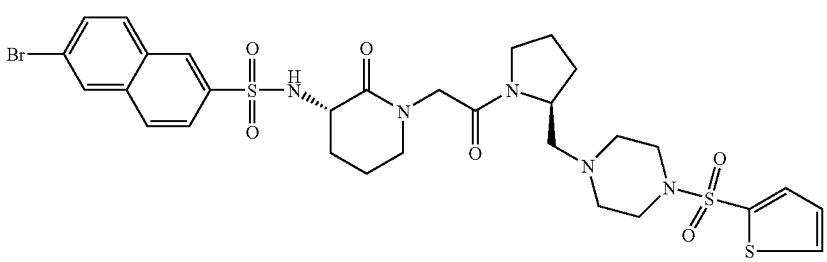 | HPLC (method 1) $t_R$ = 3.3 min LRMS (ESI, pos. ion spectrum) m/z 738/740 (M + H) | Prepared using the method described in Example 571 using the title compound of Example 569 |
| 831 | 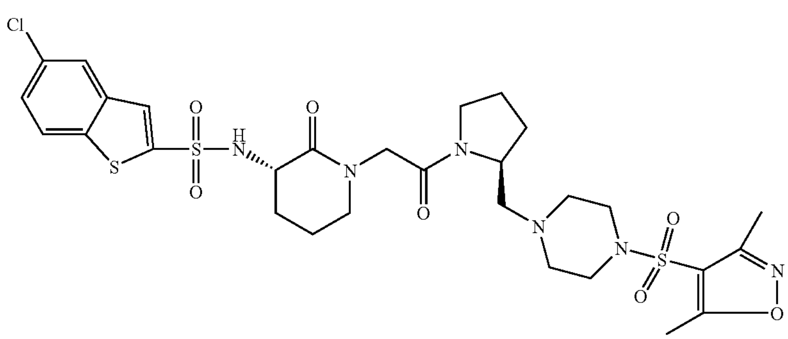 | HPLC (method 1) $t_R$ = 3.4 min LRMS (ESI, pos. ion spectrum) m/z 713/715 (M + H) | Prepared using the method described in Example 571 using the title compound of Example 568 |

| Ex # | Structure | characterization | method |
| --- | --- | --- | --- |
| 832 | 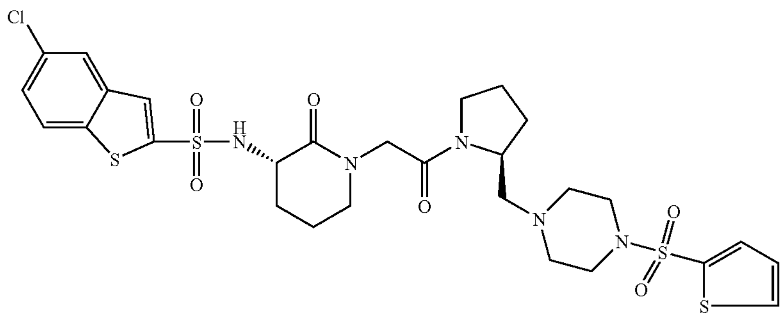 | HPLC (method 1) $t_R$ = 3.1 min LRMS (ESI, pos. ion spectrum) m/z 700/702 (M + H) | Prepared using the method described in Example 571 using the title compound of Example 568 |
| 833 | 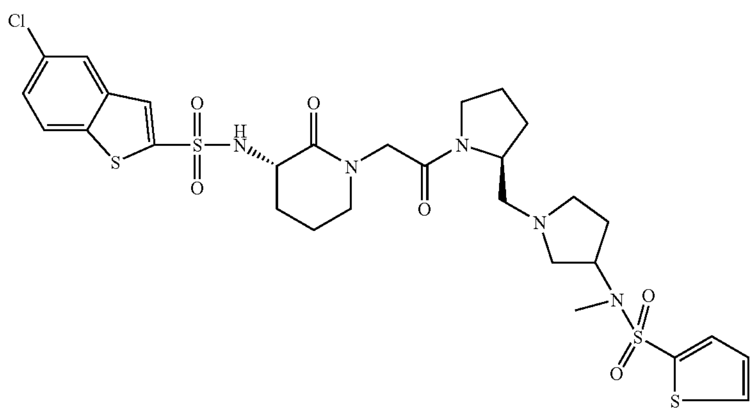 | HPLC (method 1) $t_R$ = 3.2 min LRMS (ESI, pos. ion spectrum) m/z 714/716 (M + H) | Prepared using the method described in Example 571 using the title compound of Example 615 |
| 834 | 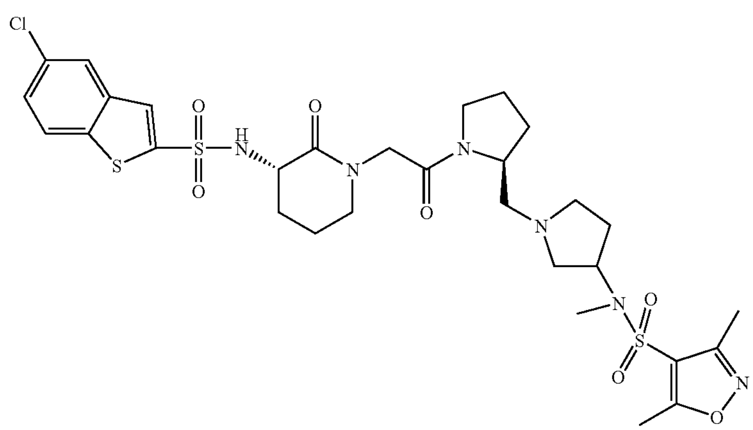 | HPLC (method 1) $t_R$ = 3.3 min LRMS (ESI, pos. ion spectrum) m/z 727/729 (M + H) | Prepared using the method described in Example 571 using the title compound of Example 615 |
| 835 | 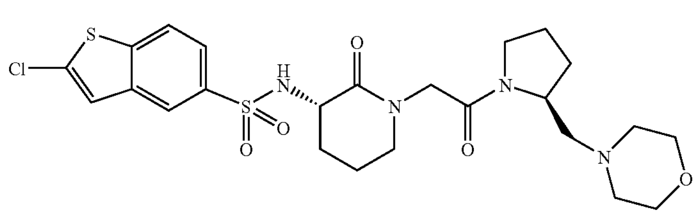 | HPLC (method 2) $t_R$ = 1.8 min LCMS (ESI, pos. ion spectrum) m/z 555/557 (M + 1) | prepared using the method described in Example 130 with INT3 and INT5 |
| 836 | 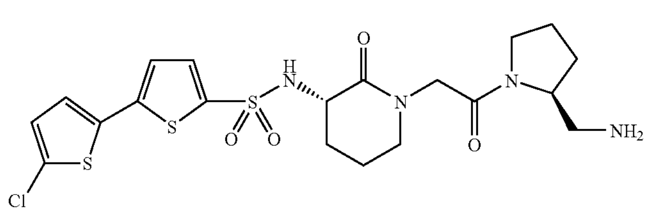 | HPLC (method 1) $t_R$ = 3.3 min LCMS (ESI, pos. ion spectrum) m/z 517/519 (M + H) | Title compound of Example 836 |

| Ex # | Structure | characterization | method |
|---|---|---|---|
| 837 | 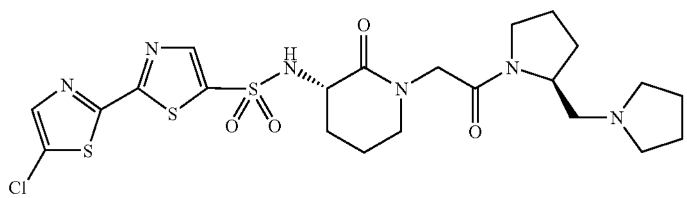 | HPLC (method 1) $t_R$ = 2.5 min LCMS (ESI, pos. ion spectrum) m/z 573/575 (M + H) | prepared using the method described in Example 1 using INT9 and INT24 |
| 838 | 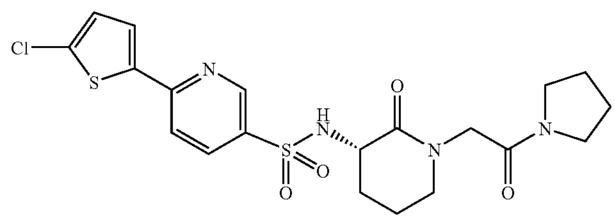 | HPLC (method 2) $t_R$ = 2.1 min LCMS (ESI, pos. ion spectrum) m/z 483/485 (M + 1) | prepared using the method described in Example 130 using INT6 |
| 839 | 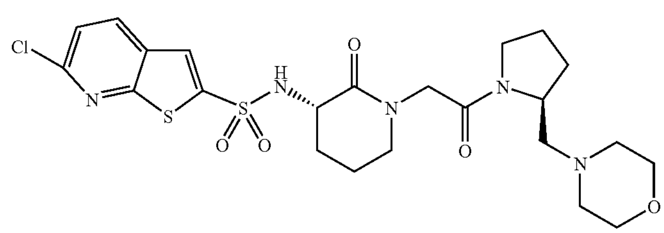 | HPLC (method 3) $t_R$ = 2.2 min LCMS (ESI, pos. ion spectrum) m/z 556/558 (M + 1) | prepared using the method described in Example 130 using INT5 and INT13 |
| 840 | 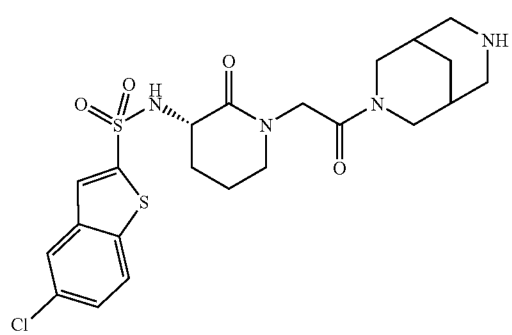 | HPLC (method 1) $t_R$ = 2.9 min LCMS (ESI, pos. ion spectrum) m/z 511/513 (M + 1) | Prepared using the method described in Example 429 using INT17 |
| 841 | 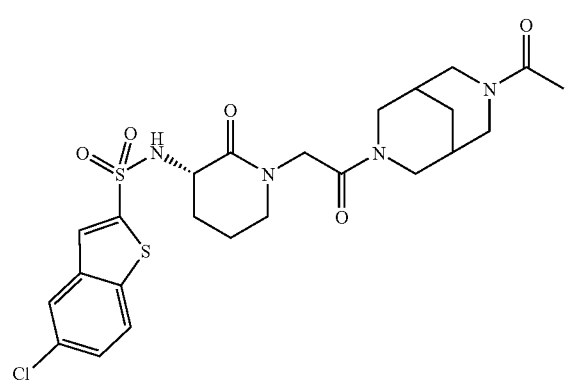 | HPLC (method 1) $t_R$ = 3.3 min LCMS (ESI, pos. ion spectrum) m/z 553/555 (M + 1) | Prepared using the method described in Example 317 using the title compound of Example 840 |

| Ex # | Structure | characterization | method |
|---|---|---|---|
| 842 | 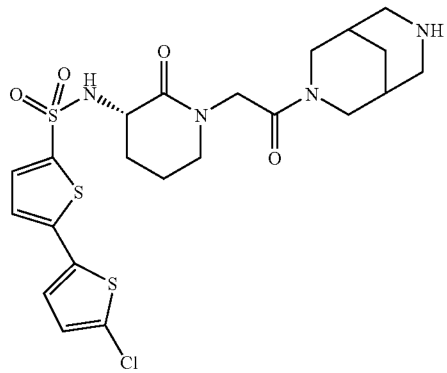 | HPLC (method 1) t_R = 3.2 min LCMS (ESI, pos. ion spectrum) m/z 543/545 (M + 1) | Prepared using the method described in Example 429 using INT18 |
| 843 | 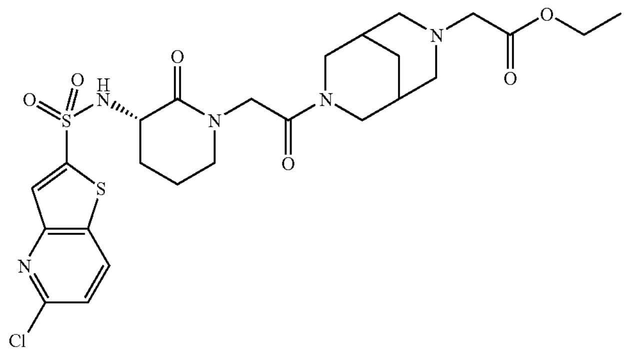 | HPLC (method 1) t_R = 2.7 min LCMS (ESI, pos. ion spectrum) m/z 598/600 (M + 1) | From title compound of Example 702 using using the method described in Example 407 |
| 844 | 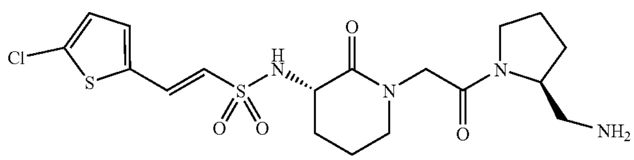 | HPLC (method 6) t_R = 1.2 min LCMS (method 6) (ESI, pos. ion spectrum) m/z | Title compound of Example 844 |
| 845 | 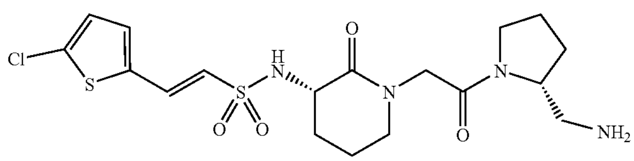 | HPLC (method 6) t_R = 1.3 min LCMS (method 6) (ESI, pos. ion spectrum) m/z 461/463 (M + 1) | Title compound of Example 845 |
| 846 | 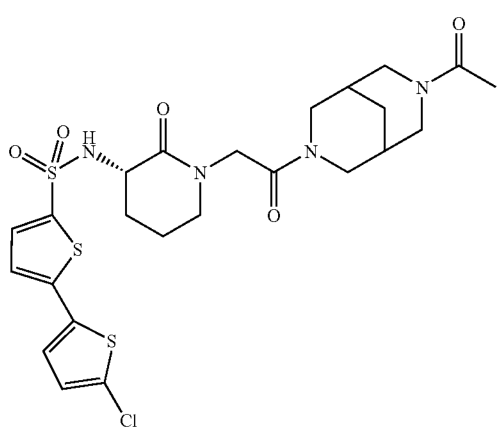 | HPLC (method 1) t_R = 3.6 min LCMS (ESI, pos. ion spectrum) m/z 585/587 (M + 1) | Prepared using the method described in Example 317 using the title compound of Example 842 |

| Ex # | Structure | characterization | method |
| --- | --- | --- | --- |
| 847 | 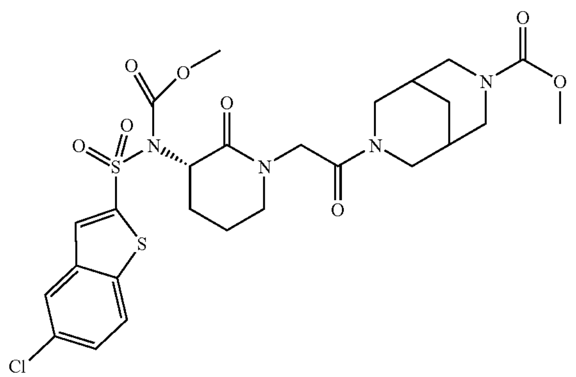 | HPLC (method 1) $t_R$ = 3.6 min LCMS (ESI, pos. ion spectrum) m/z 627/629 (M + 1) | Title compound of Example 847 |
| 848 | 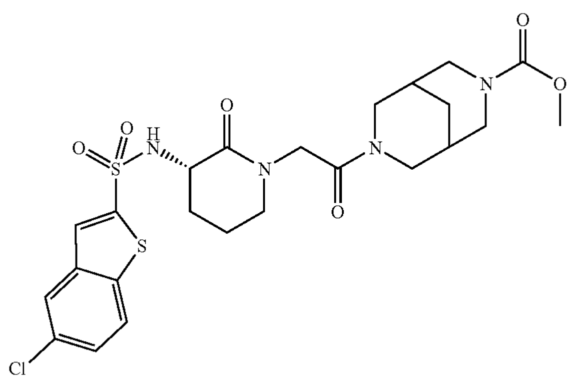 | HPLC (method 1) $t_R$ = 3.5 min LCMS (ESI, pos. ion spectrum) m/z 569/571 (M + 1) | Title compound of Example 848 |
| 849 | 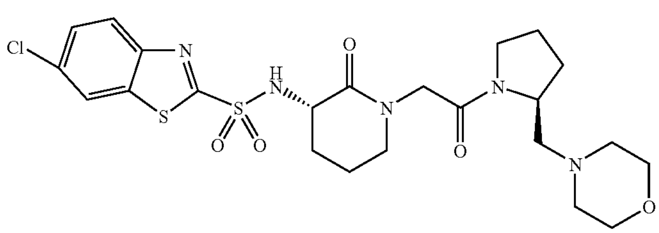 | HPLC (method 3) $t_R$ = 2.4 min LCMS (ESI, pos. ion spectrum) m/z 556/558 (M + 1) | prepared using the method described in Example 130 using INT5 and INT19 |
| 850 | 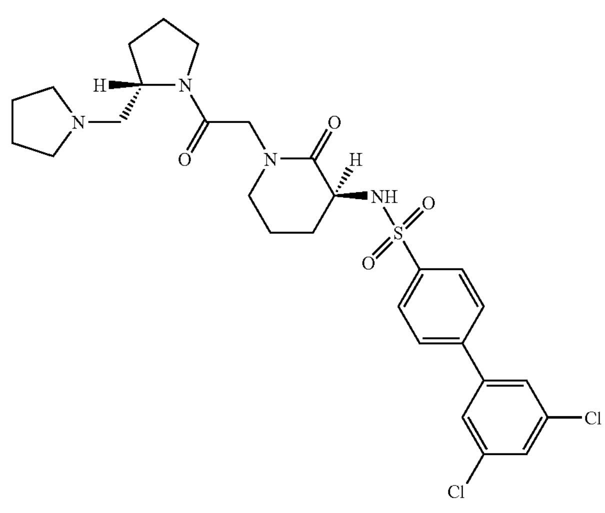 | LCMS (method 4) $t_R$ = 1.7 min (ESI, pos. ion spectrum) m/z 593/595 (M + 1) | Title compound of Example 850 |

-continued

| Ex # | Structure | characterization | method |
|---|---|---|---|
| 851 | 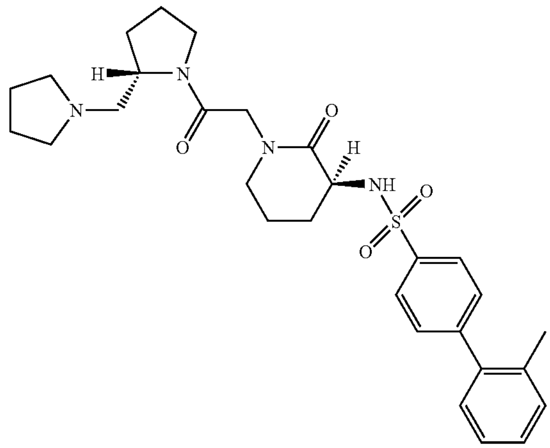 | LCMS (method 4) $t_R$ = 1.5 min (ESI, pos. ion spectrum) m/z 539 (M + 1) | prepared using the method described in Example 850 |
| 852 | 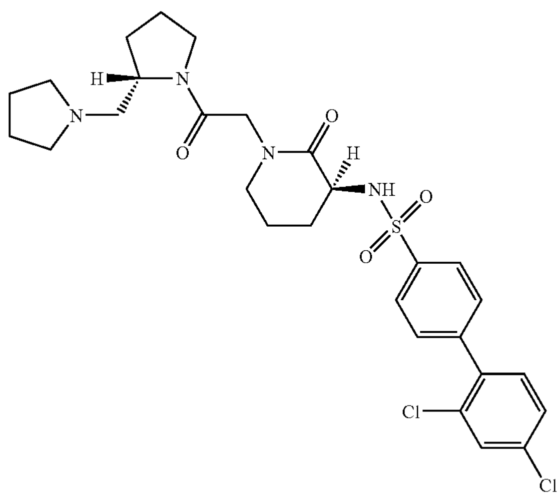 | LCMS (method 4) $t_R$ = 1.7 min (ESI, pos. ion spectrum) m/z 593/595 (M + 1) | prepared using the method described in Example 850 |
| 853 | 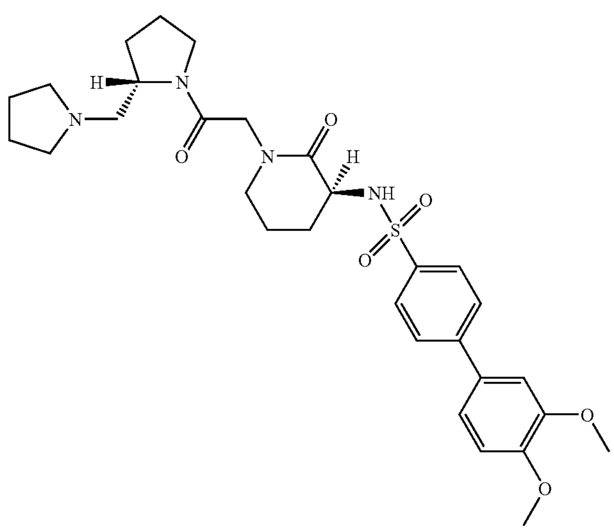 | LCMS (method 4) $t_R$ = 1.3 min (ESI, pos. ion spectrum) m/z 585 (M + 1) | prepared using the method described in Example 850 |

-continued

| Ex # | Structure | characterization | method |
|---|---|---|---|
| 854 | 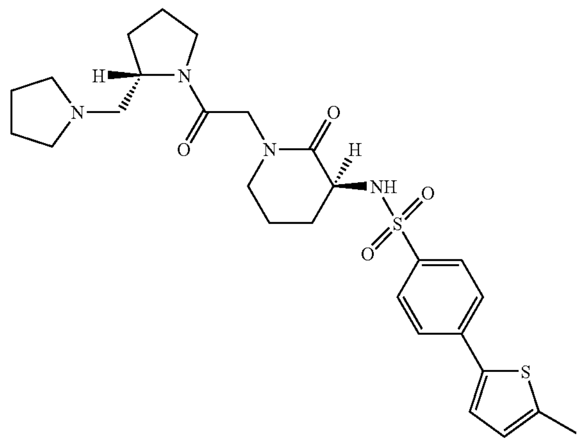 | LCMS (method 4) $t_R$ = 1.5 min (ESI, pos. ion spectrum) m/z 545 (M + 1) | prepared using the method described in Example 850 |
| 855 | 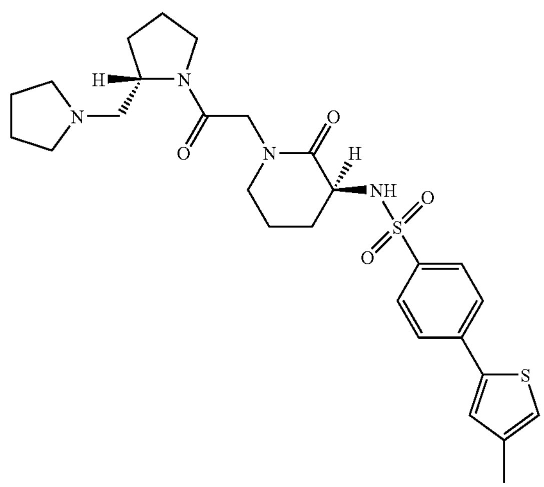 | LCMS (method 4) $t_R$ = 1.5 min (ESI, pos. ion spectrum) m/z 545 (M + 1) | prepared using the method described in Example 850 |
| 856 | 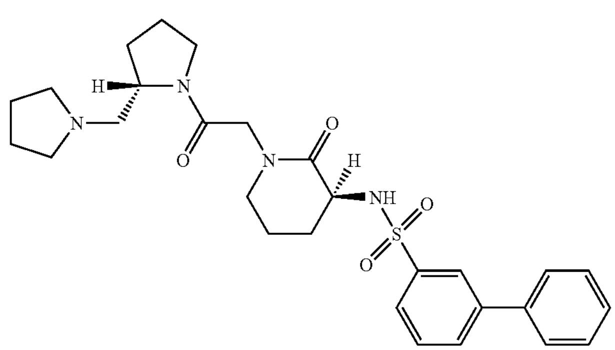 | LCMS (method 4) $t_R$ = 1.4 min (ESI, pos. ion spectrum) m/z 525 (M + 1) | prepared using the method described in Example 850 |

-continued

| Ex # | Structure | characterization | method |
|---|---|---|---|
| 857 | 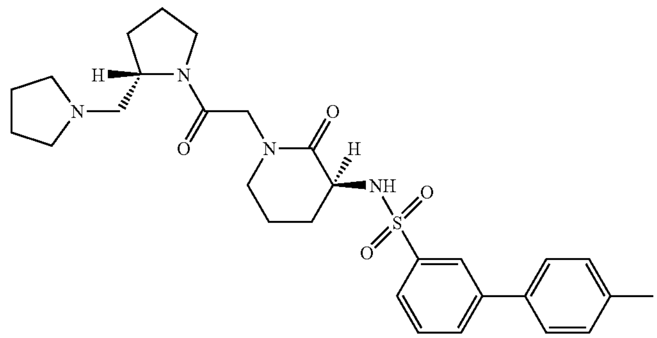 | LCMS (method 4) t_R = 1.5 min (ESI, pos. ion spectrum) m/z 539 (M + 1) | prepared using the method described in Example 850 |
| 858 | 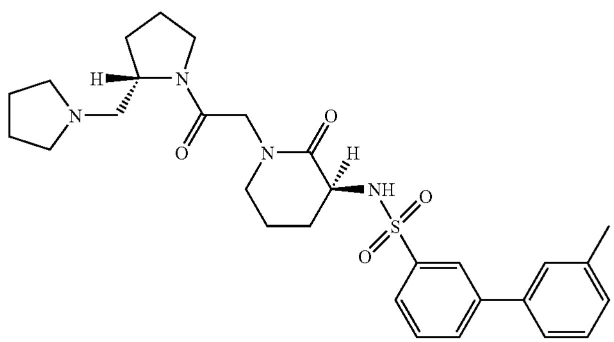 | LCMS (method 4) t_R = 1.5 min (ESI, pos. ion spectrum) m/z 539 (M + 1) | prepared using the method described in Example 850 |
| 859 | 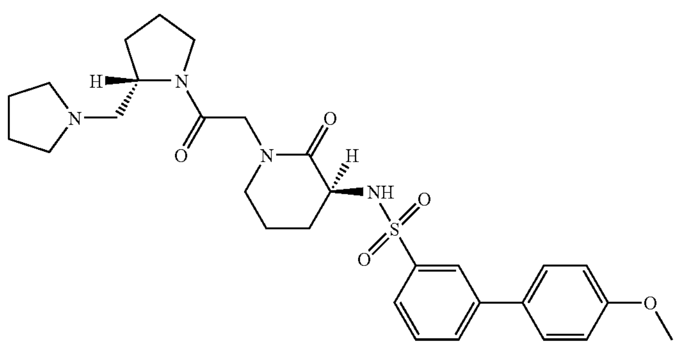 | LCMS (method 4) t_R = 1.4 min (ESI, pos. ion spectrum) m/z 555 (M + 1) | prepared using the method described in Example 850 |
| 860 | 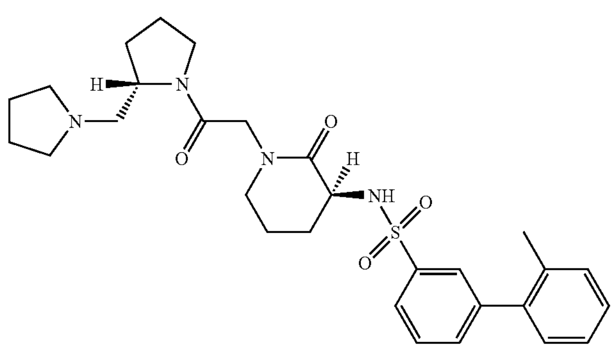 | LCMS (method 4) t_R = 1.5 min (ESI, pos. ion spectrum) m/z 539 (M + 1) | prepared using the method described in Example 850 |

| Ex # | Structure | characterization | method |
| --- | --- | --- | --- |
| 861 | 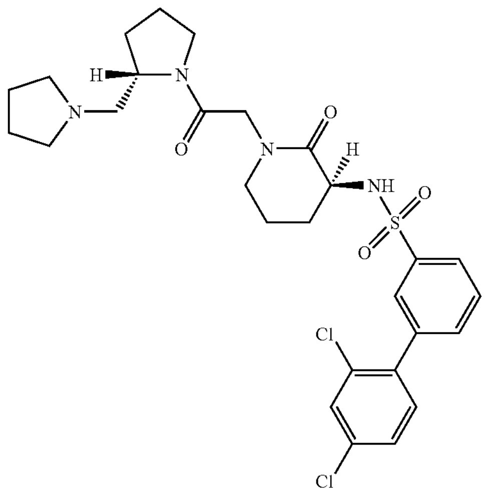 | LCMS (method 4) t_R = 1.6 min (ESI, pos. ion spectrum) m/z 593/595 (M + 1) | prepared using the method described in Example 850 |
| 862 | 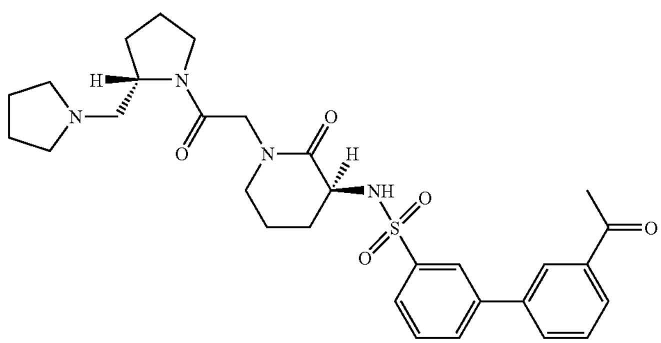 | LCMS (method 4) t_R = 1.3 min (ESI, pos. ion spectrum) m/z 567 (M + 1) | prepared using the method described in Example 850 |
| 863 | 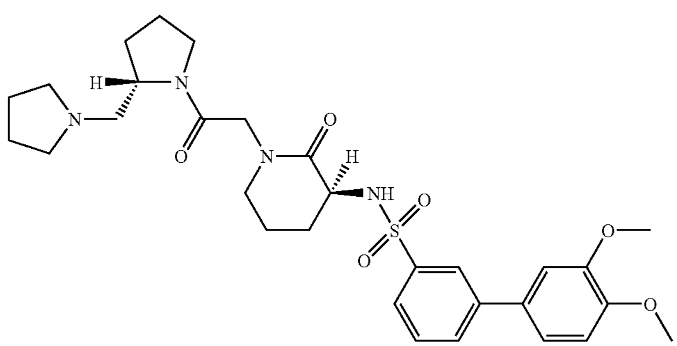 | LCMS (method 4) t_R = 1.3 min (ESI, pos. ion spectrum) m/z 585 (M + 1) | prepared using the method described in Example 850 |
| 864 | 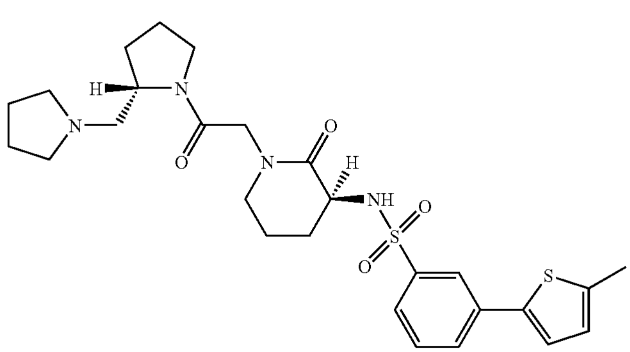 | LCMS (method 4) t_R = 1.5 min (ESI, pos. ion spectrum) m/z 545 (M + 1) | prepared using the method described in Example 850 |

| Ex # | Structure | characterization | method |
| --- | --- | --- | --- |
| 865 | 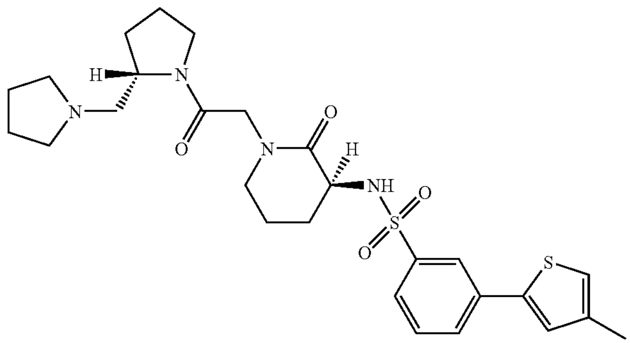 | LCMS (method 4) t_R = 1.5 min (ESI, pos. ion spectrum) m/z 545 (M + 1) | prepared using the method described in Example 850 |
| 866 | 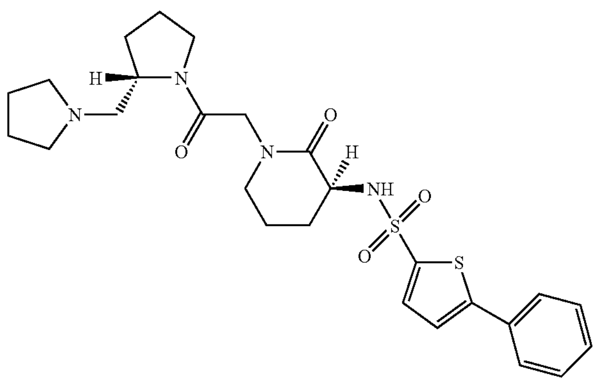 | LCMS (method 4) t_R = 1.4 min (ESI, pos. ion spectrum) m/z 531 (M + 1) | prepared using the method described in Example 850 |
| 867 | 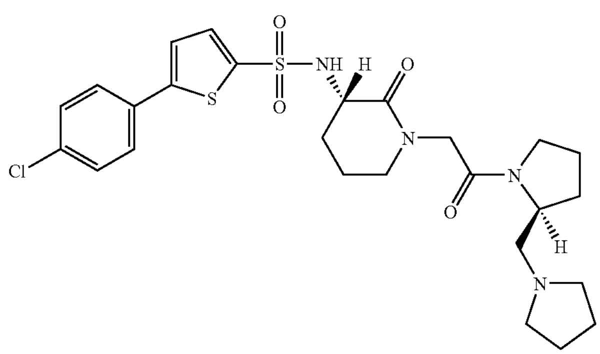 | LCMS (method 4) t_R = 1.5 min (ESI, pos. ion spectrum) m/z 565/567 (M + 1) | prepared using the method described in Example 850 |
| 868 | 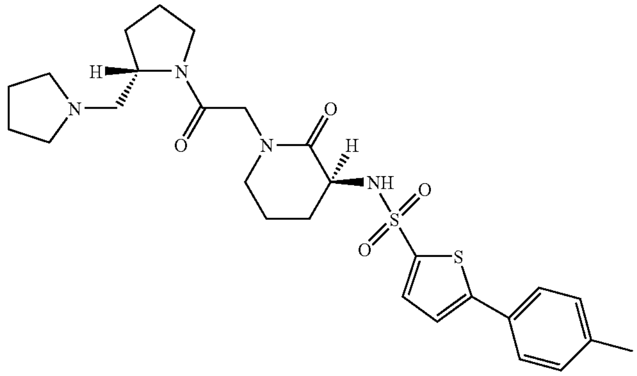 | LCMS (method 4) t_R = 1.5 min (ESI, pos. ion spectrum) m/z 545 (M + 1) | prepared using the method described in Example 850 |

-continued

| Ex # | Structure | characterization | method |
|---|---|---|---|
| 869 | 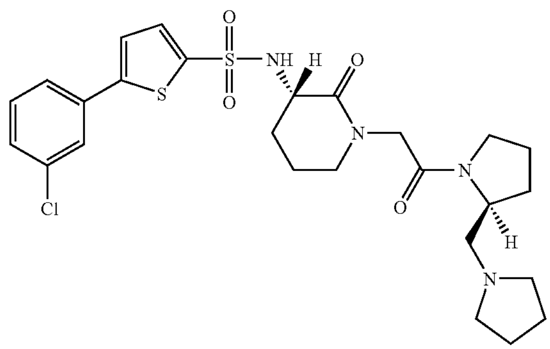 | LCMS (method 4) t_R = 1.5 min (ESI, pos. ion spectrum) m/z 565/567 (M + 1) | prepared using the method described in Example 850 |
| 870 | 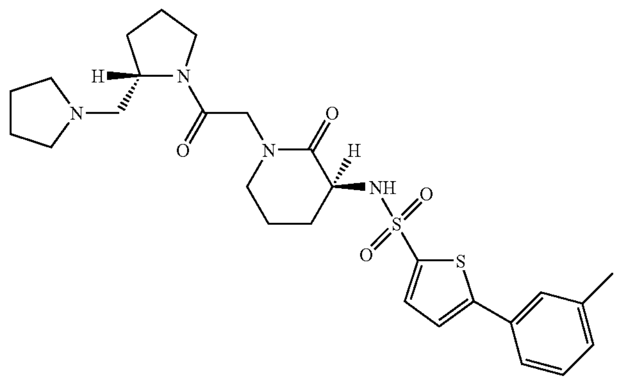 | LCMS (method 4) t_R = 1.5 min (ESI, pos. ion spectrum) m/z 545 (M + 1) | prepared using the method described in Example 850 |
| 871 | 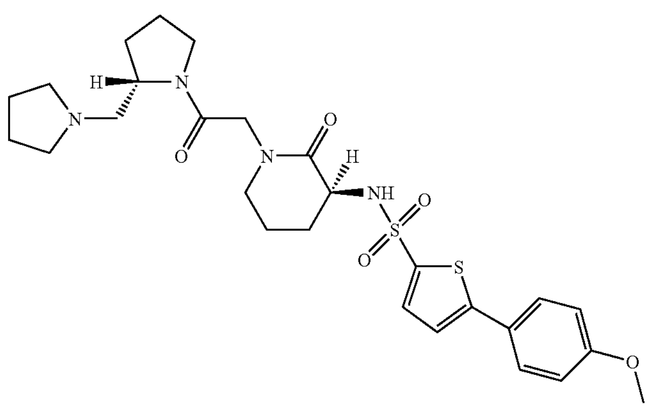 | LCMS (method 4) t_R = 1.4 min (ESI, pos. ion spectrum) m/z 561 (M + 1) | prepared using the method described in Example 850 |
| 872 | 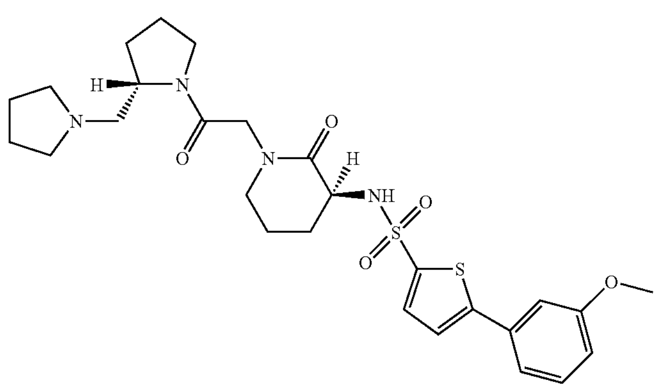 | LCMS (method 4) t_R = 1.4 min (ESI, pos. ion spectrum) m/z 561 (M + 1) | prepared using the method described in Example 850 |

-continued

| Ex # | Structure | characterization | method |
|---|---|---|---|
| 873 | 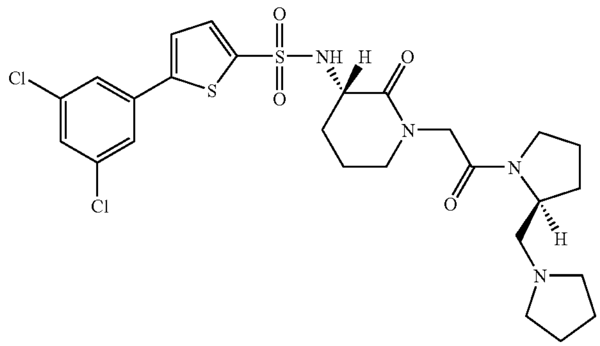 | LCMS (method 4) $t_R$ = 1.7 min (ESI, pos. ion spectrum) m/z 599/601 (M + 1) | prepared using the method described in Example 850 |
| 874 | 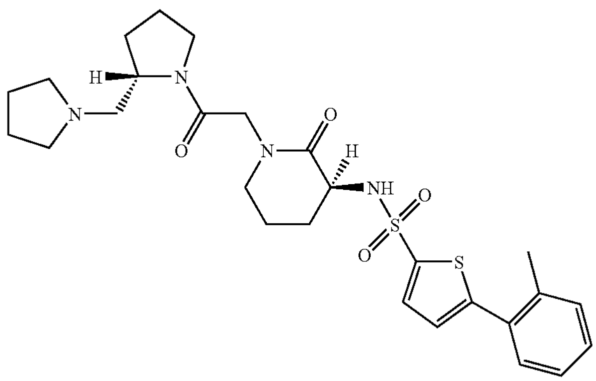 | LCMS (method 4) $t_R$ = 1.5 min (ESI, pos. ion spectrum) m/z 545 (M + 1) | prepared using the method described in Example 850 |
| 875 | 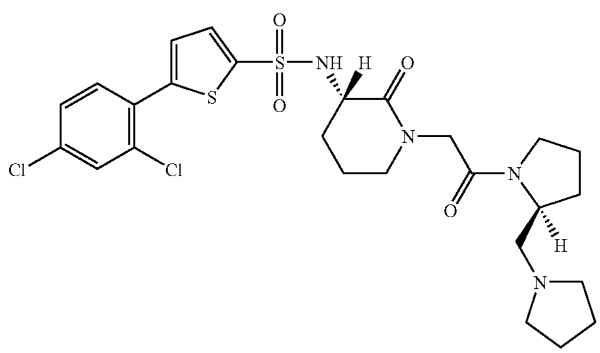 | LCMS (method 4) $t_R$ = 1.7 min (ESI, pos. ion spectrum) m/z 599/601 (M + 1) | prepared using the method described in Example 850 |
| 876 | 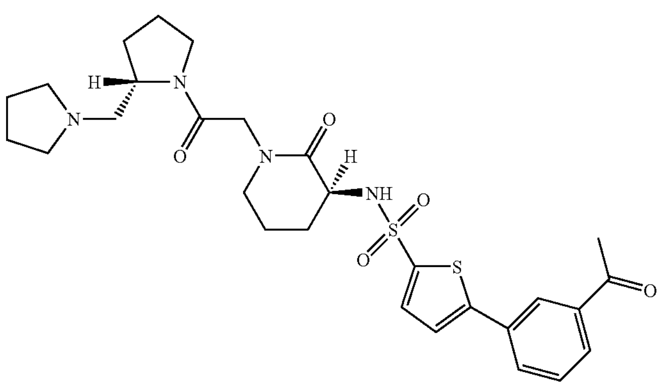 | LCMS (method 4) $t_R$ = 1.3 min (ESI, pos. ion spectrum) m/z 573 (M + 1) | prepared using the method described in Example 850 |

-continued

| Ex # | Structure | characterization | method |
|---|---|---|---|
| 877 | 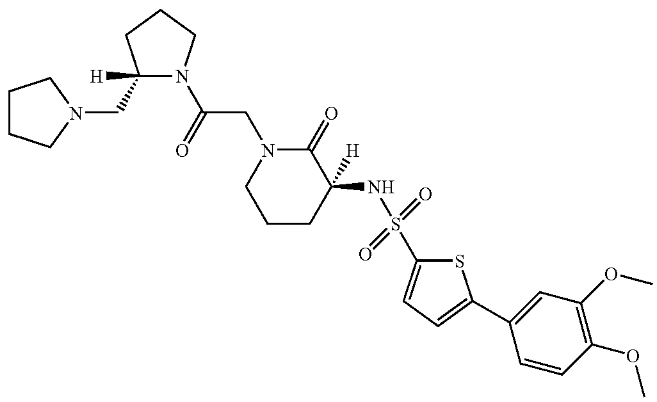 | LCMS (method 4) t$_R$ = 1.3 min (ESI, pos. ion spectrum) m/z 591 (M + 1) | prepared using the method described in Example 850 |
| 878 | 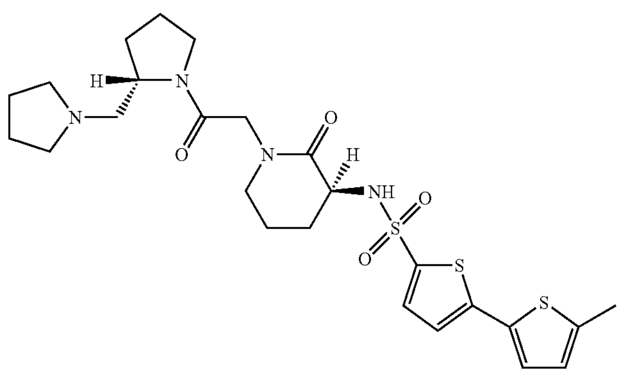 | LCMS (method 4) t$_R$ = 1.5 min (ESI, pos. ion spectrum) m/z 551 (M + 1) | prepared using the method described in Example 850 |
| 879 | 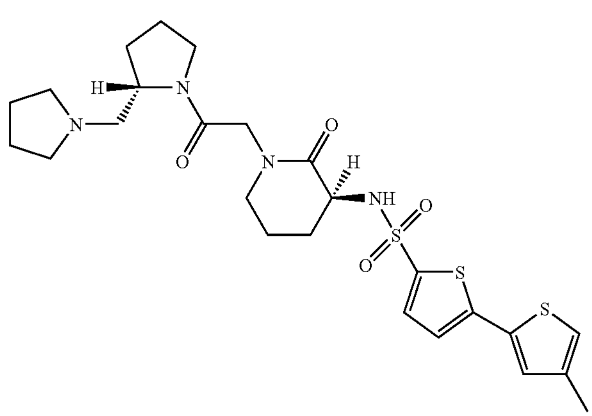 | LCMS (method 4) t$_R$ = 1.5 min (ESI, pos. ion spectrum) m/z 551 (M + 1) | prepared using the method described in Example 850 |

-continued

| Ex # | Structure | characterization | method |
|---|---|---|---|
| 880 | 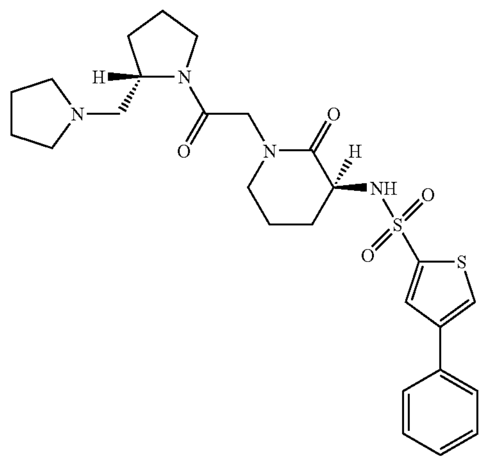 | LCMS (method 4) t<sub>R</sub> = 1.3 min (ESI, pos. ion spectrum) m/z 531 (M + 1) | prepared using the method described in Example 850 |
| 881 | 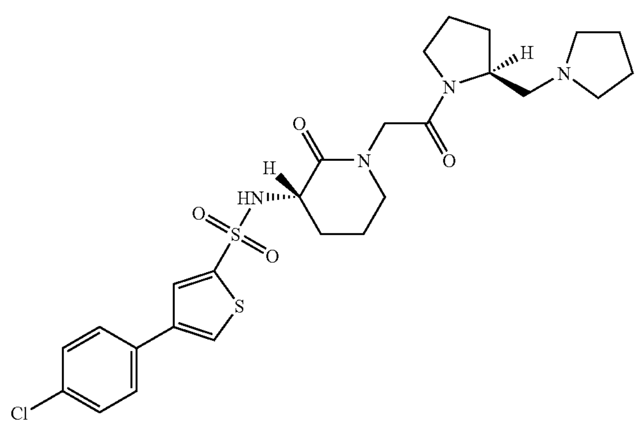 | LCMS (method 4) t<sub>R</sub> = 1.5 min (ESI, pos. ion spectrum) m/z 565/567 (M + 1) | prepared using the method described in Example 850 |
| 882 | 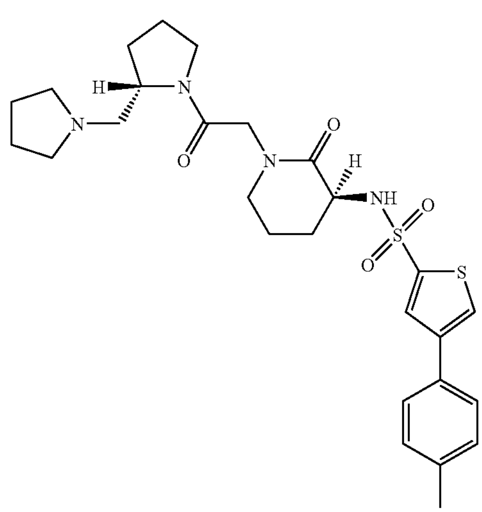 | LCMS (method 4) t<sub>R</sub> = 1.5 min (ESI, pos. ion spectrum) m/z 545 (M + 1) | prepared using the method described in Example 850 |

| Ex # | Structure | characterization | method |
|---|---|---|---|
| 883 | 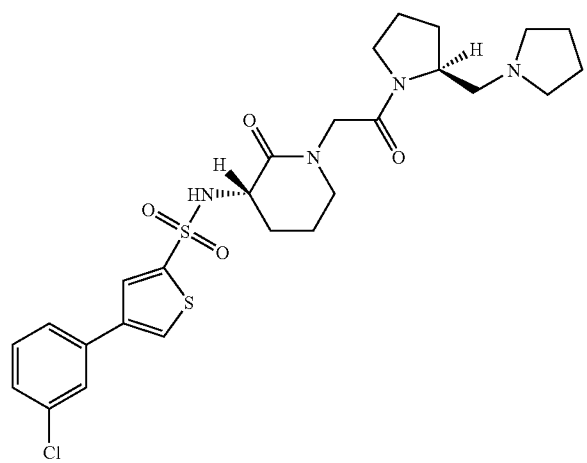 | LCMS (method 4) $t_R$ = 1.5 min (ESI, pos. ion spectrum) m/z 565/567 (M + 1) | prepared using the method described in Example 850 |
| 884 | 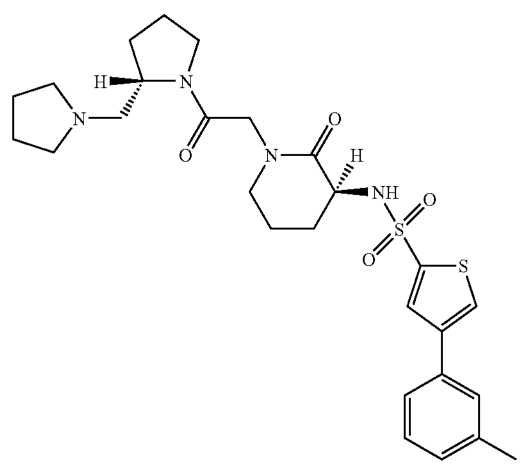 | LCMS (method 4) $t_R$ = 1.5 min (ESI, pos. ion spectrum) m/z 545 (M + 1) | prepared using the method described in Example 850 |
| 885 | 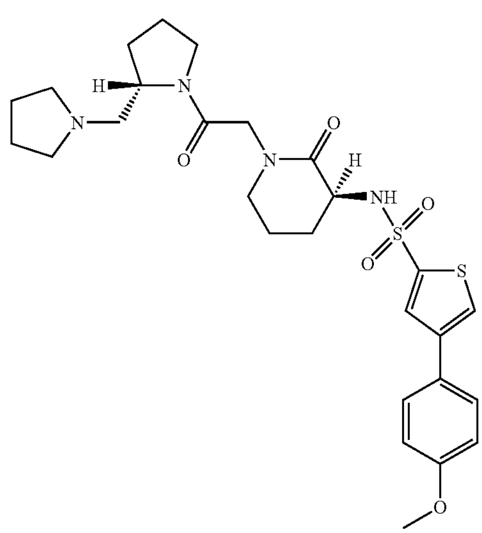 | LCMS (method 4) $t_R$ = 1.4 min (ESI, pos. ion spectrum) m/z 561 (M + 1) | prepared using the method described in Example 850 |

-continued
| Ex # | Structure | characterization | method |
|---|---|---|---|
| 886 | 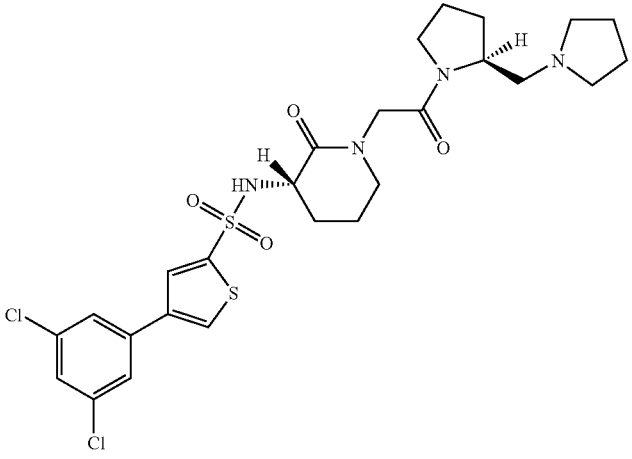 | LCMS (method 4) $t_R$ = 1.7 min (ESI, pos. ion spectrum) m/z 599/601 (M + 1) | prepared using the method described in Example 850 |
| 887 | 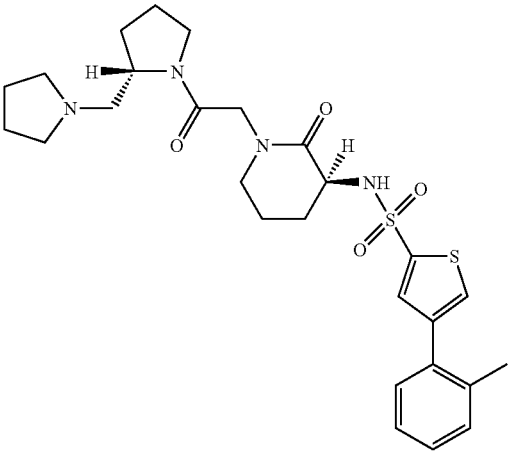 | LCMS (method 4) $t_R$ = 1.4 min (ESI, pos. ion spectrum) m/z 545 (M + 1) | prepared using the method described in Example 850 |
| 888 | 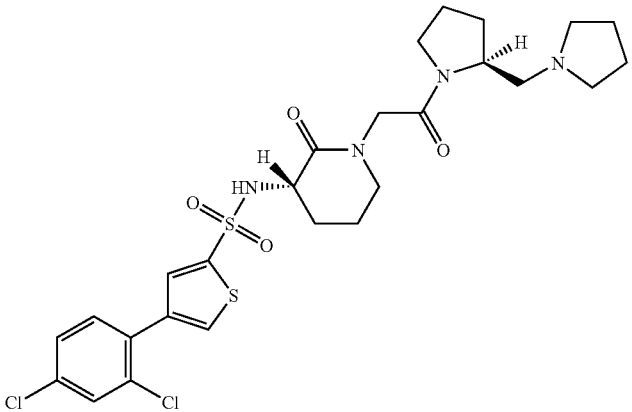 | LCMS (method 4) $t_R$ = 1.6 min (ESI, pos. ion spectrum) m/z 599/601 (M + 1) | prepared using the method described in Example 850 |

-continued

| Ex # | Structure | characterization | method |
|---|---|---|---|
| 889 | 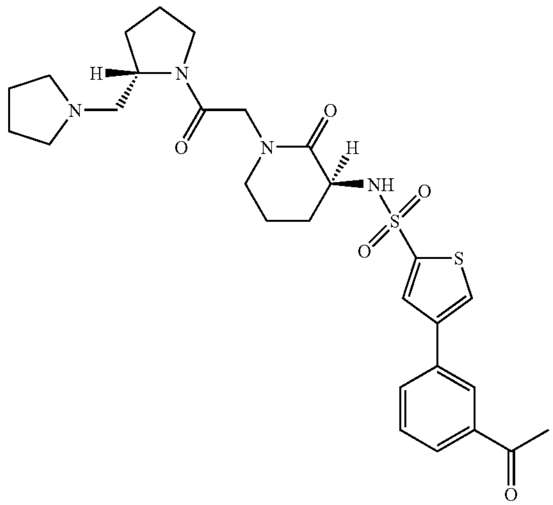 | LCMS (method 4) $t_R$ = 1.2 min (ESI, pos. ion spectrum) m/z 573 (M + 1) | prepared using the method described in Example 850 |
| 890 | 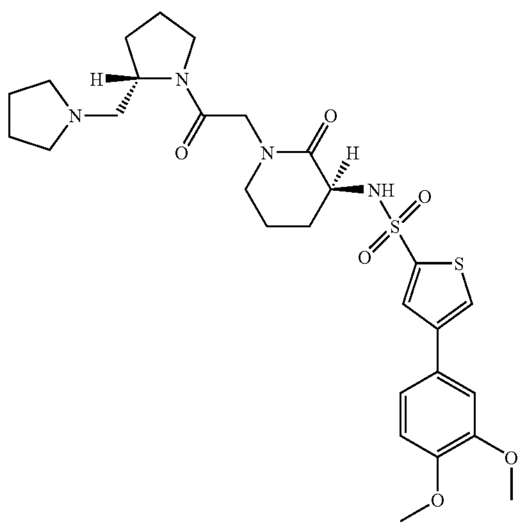 | LCMS (method 4) $t_R$ = 1.2 min (ESI, pos. ion spectrum) m/z 591 (M + 1) | prepared using the method described in Example 850 |
| 891 | 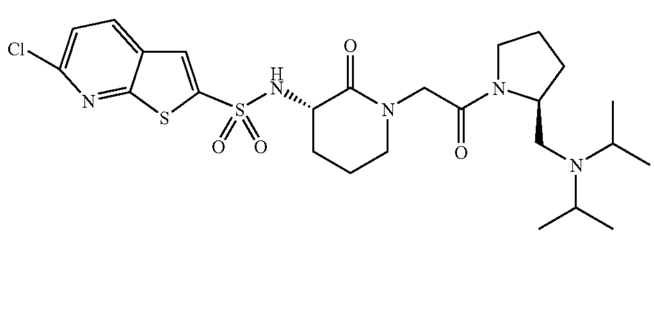 | HPLC (method 3) $t_R$ = 2.4 min LCMS (ESI, pos. ion spectrum) m/z 570/572 (M + 1) | prepared using the method described in Example 130 using INT13 |

-continued

| Ex # | Structure | characterization | method |
|---|---|---|---|
| 892 | 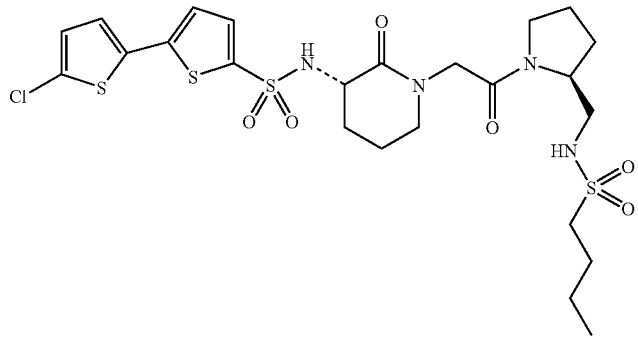 | HPLC (method 7) t_R = 3.7 min LCMS (method 6) (ESI, pos. ion spectrum) m/z 637/639 (M + 1) | Title compound of Example 892 |
| 893 | 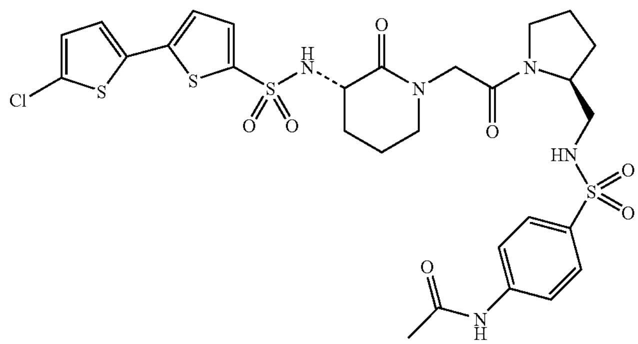 | HPLC (method 7) t_R = 3.5 min LCMS (method 6) (ESI, pos. ion spectrum) m/z 714/716 (M + 1) | Prepared using the method described in Example 892 |
| 894 | 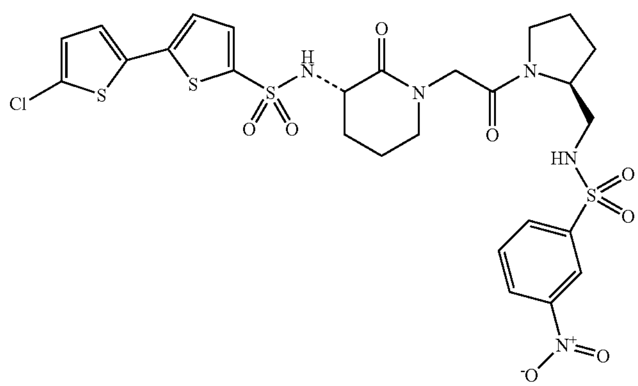 | HPLC (method 7) t_R = 3.8 min LCMS (method 6) (ESI, pos. ion spectrum) m/z 702/704 (M + 1) | Prepared using the method described in Example 892 |
| 895 | 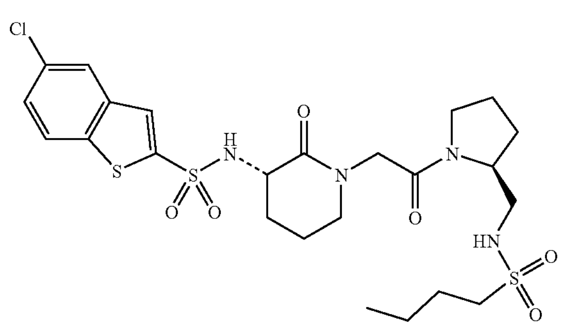 | HPLC (method 7) t_R = 3.5 min LCMS (method 6) (ESI, pos. ion spectrum) m/z 605/607 (M + 1) | Prepared using the method described in Example 892 |

-continued

| Ex # | Structure | characterization | method |
|---|---|---|---|
| 896 | 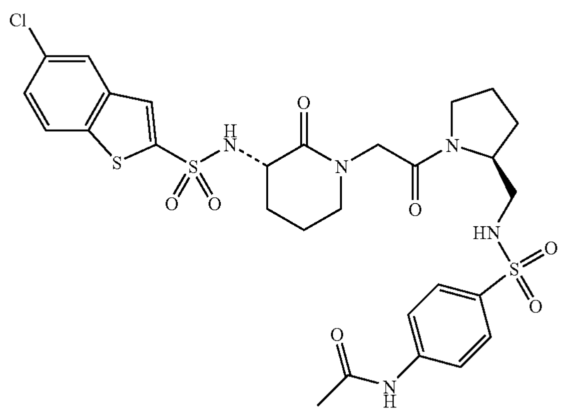 | HPLC (method 7) $t_R$ = 3.3 min LCMS (method 6) (ESI, pos. ion spectrum) m/z 682/684 (M + 1) | Prepared using the method described in Example 892 |
| 897 | 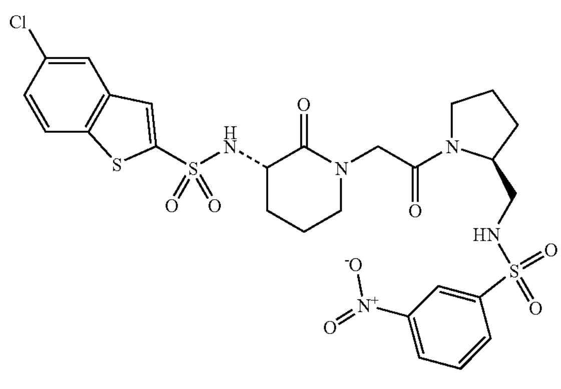 | HPLC (method 7) $t_R$ = 3.6 min LCMS (method 6) (ESI, pos. ion spectrum) m/z 670/672 (M + 1) | Prepared using the method described in Example 892 |
| 898 | 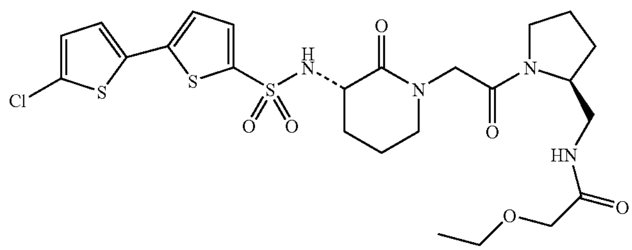 | HPLC (method 7) $t_R$ = 3.5 min LCMS (method 6) (ESI, pos. ion spectrum) m/z 603/605 (M + 1) | Title compound of Example 898 |
| 899 | 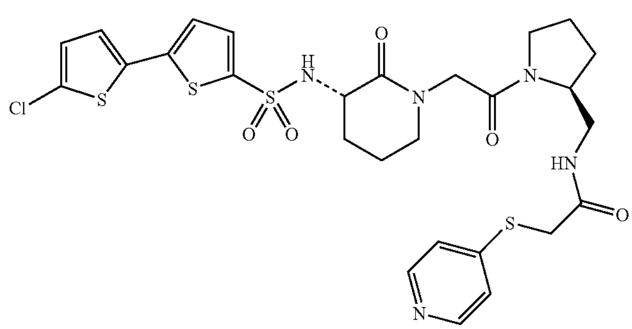 | HPLC (method 7) $t_R$ = 2.7 min LCMS (method 6) (ESI, pos. ion spectrum) m/z 668/670 (M + 1) | Prepared using the method described in Example 898 |

-continued

| Ex # | Structure | characterization | method |
|---|---|---|---|
| 900 | 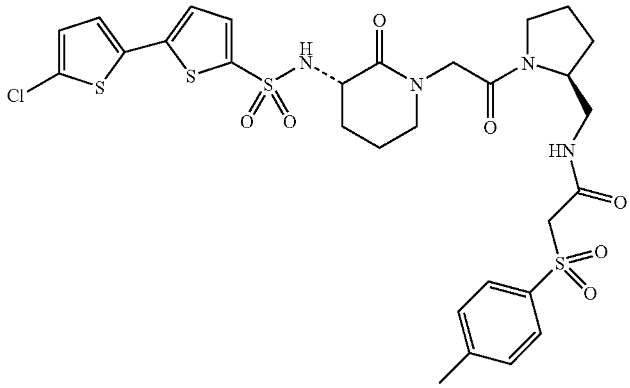 | HPLC (method 7) t_R = 3.7 min LCMS (method 6) (ESI, pos. ion spectrum) m/z 713/715 (M + 1) | Prepared using the method described in Example 898 |
| 901 | 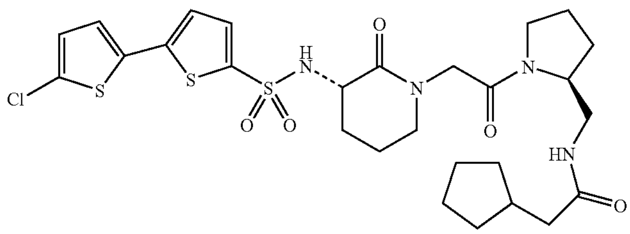 | HPLC (method 7) t_R = 3.9 min LCMS (method 6) (ESI, pos. ion spectrum) m/z 627/629 (M + 1) | Prepared using the method described in Example 898 |
| 902 | 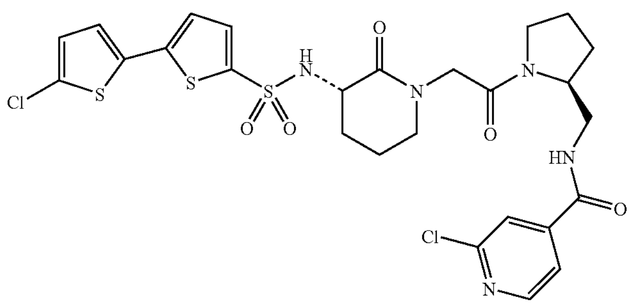 | HPLC (method 7) t_R = 3.7 min LCMS (method 6) (ESI, pos. ion spectrum) m/z 656/658/660 (M + 1) | Prepared using the method described in Example 898 |
| 903 | 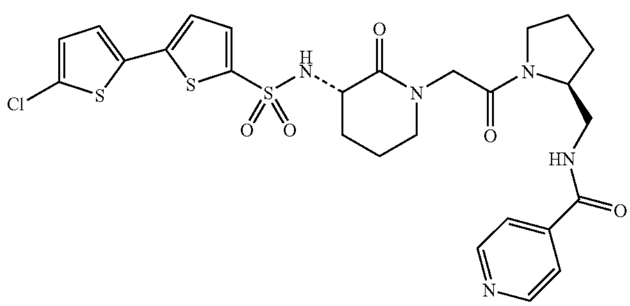 | HPLC (method 7) t_R = 3.2 min LCMS (method 6) (ESI, pos. ion spectrum) m/z 622/624 (M + 1) | Prepared using the method described in Example 898 |
| 904 | 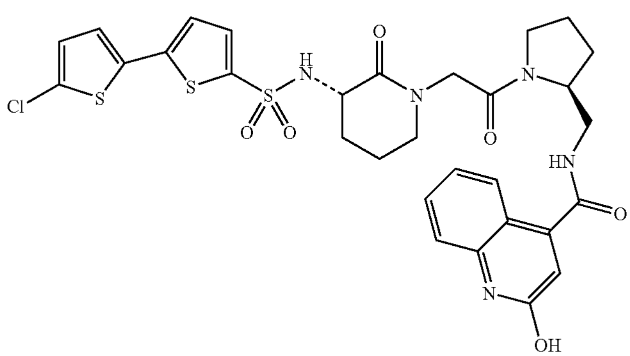 | HPLC (method 7) t_R = 3.5 min LCMS (method 6) (ESI, pos. ion spectrum) m/z 688/690 (M + 1) | Prepared using the method described in Example 898 |

-continued

| Ex # | Structure | characterization | method |
|---|---|---|---|
| 905 | 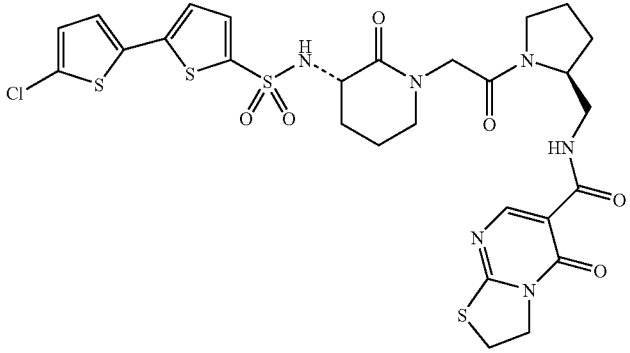 | HPLC (method 7) $t_R$ = 3.5 min LCMS (method 6) (ESI, pos. ion spectrum) m/z 697/699 (M + 1) | Prepared using the method described in Example 898 |
| 906 | 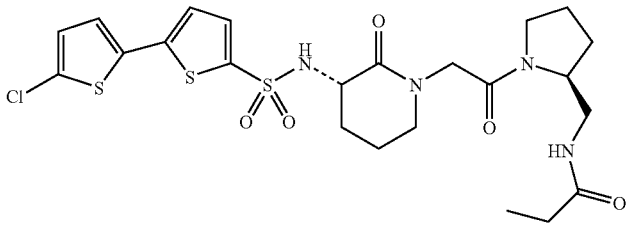 | HPLC (method 7) $t_R$ = 3.5 min LCMS (method 6) (ESI, pos. ion spectrum) m/z 573/575 (M + 1) | Prepared using the method described in Example 898 |
| 907 | 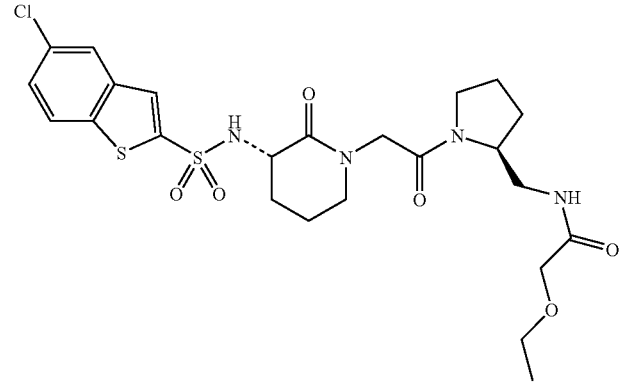 | HPLC (method 7) $t_R$ = 3.3 min LCMS (method 6) (ESI, pos. ion spectrum) m/z 571/573 (M + 1) | Title compound of Example 907 |
| 908 | 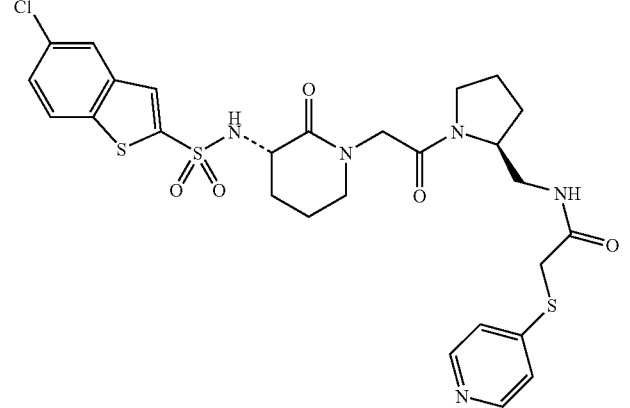 | HPLC (method 7) $t_R$ = 2.5 min LCMS (method 6) (ESI, pos. ion spectrum) m/z 636/638 (M + 1) | Prepared using the method described in Example 907 |

-continued

| Ex # | Structure | characterization | method |
|---|---|---|---|
| 909 | 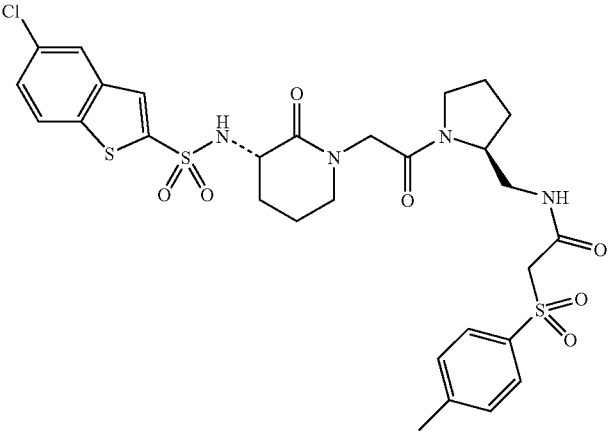 | HPLC (method 7) $t_R$ = 3.5 min LCMS (method 6) (ESI, pos. ion spectrum) m/z 681/683 (M + 1) | Prepared using the method described in Example 907 |
| 910 | 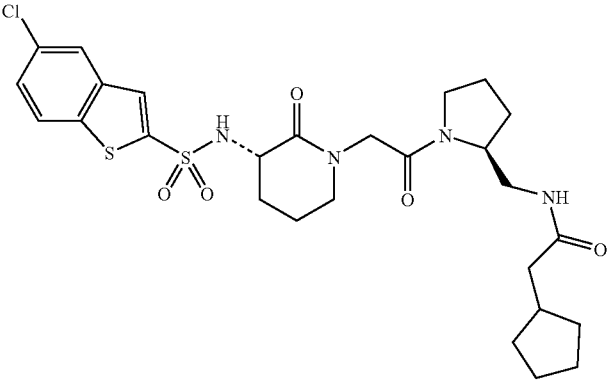 | HPLC (method 7) $t_R$ = 3.9 min LCMS (method 6) (ESI, pos. ion spectrum) m/z 595/597 (M + 1) | Prepared using the method described in Example 907 |
| 911 | 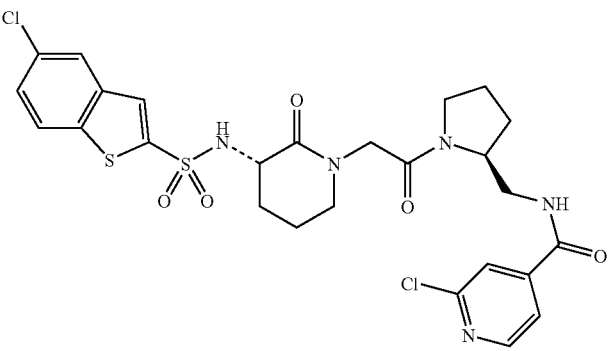 | HPLC (method 7) $t_R$ = 3.5 min LCMS (method 6) (ESI, pos. ion spectrum) m/z 624/626/628 (M + 1) | Prepared using the method described in Example 907 |
| 912 | 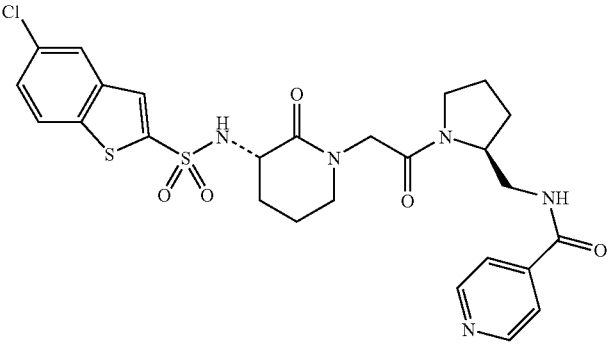 | HPLC (method 7) $t_R$ = 3.2 min LCMS (method 6) (ESI, pos. ion spectrum) m/z 590/592 (M + 1) | Prepared using the method described in Example 907 |

-continued

| Ex # | Structure | characterization | method |
|---|---|---|---|
| 913 | 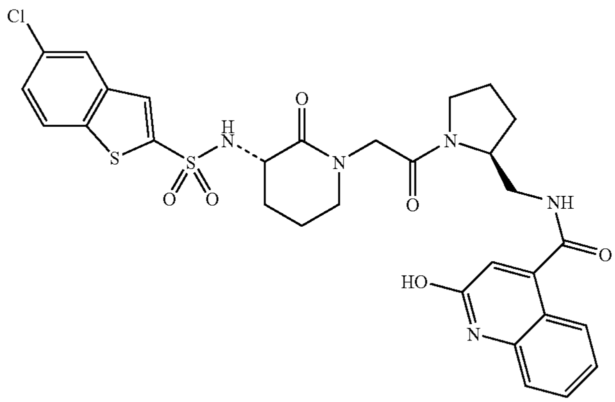 | HPLC (method 7) $t_R$ = 3.3 min LCMS (method 6) (ESI, pos. ion spectrum) m/z 656/658 (M + 1) | Prepared using the method described in Example 907 |
| 914 | 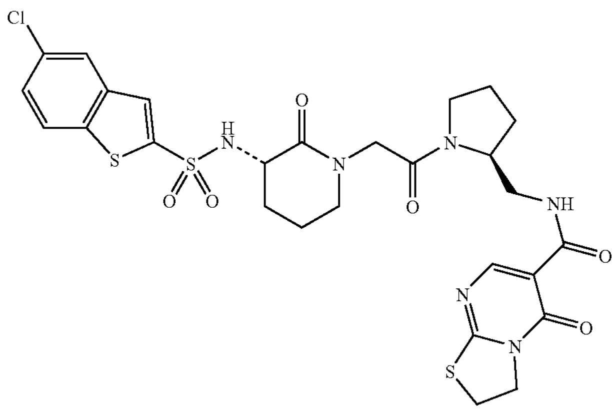 | HPLC (method 7) $t_R$ = 3.2 min LCMS (method 6) (ESI, pos. ion spectrum) m/z 665/667 (M + 1) | Prepared using the method described in Example 907 |
| 915 | 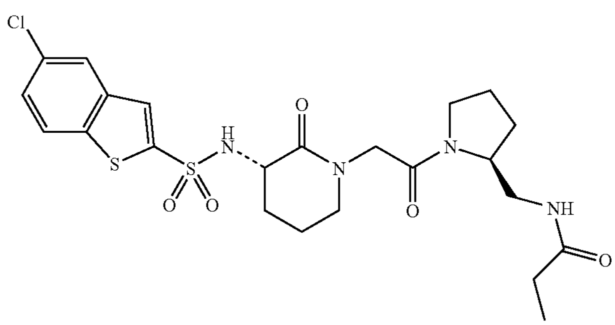 | HPLC (method 7) $t_R$ = 3.2 min LCMS (method 6) (ESI, pos. ion spectrum) m/z 541/543 (M + 1) | Prepared using the method described in Example 907 |
| 916 | 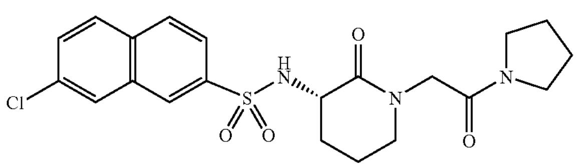 | HPLC (method 1) $t_R$ = 3.4 min LRMS (ESI, pos. ion spectrum) m/z 450/452 (M + H) | Prepared using the method described in Example 613 Part A and INT44 |
| 917 | 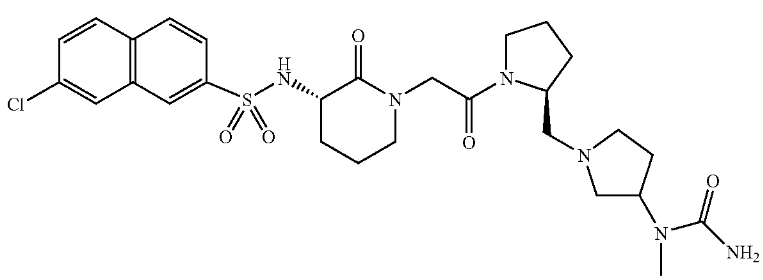 | HPLC (method 1) $t_R$ = 3.0 min LRMS (ESI, pos. ion spectrum) m/z 605/607 (M + H) | Prepared using the procedures described in Example 613 and Example 655 and using INT44 |

-continued

| Ex # | Structure | characterization | method |
|---|---|---|---|
| 918 | 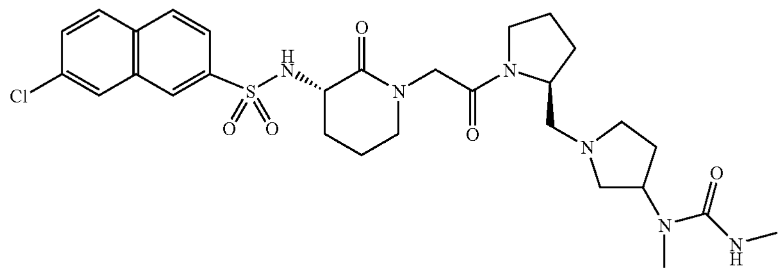 | HPLC (method 1) t_R = 3.1 min LRMS (ESI, pos. ion spectrum) m/z 619/621 (M + H) | Prepared using the procedures described in Example 613 and Example 655 and using INT44 |
| 919 | 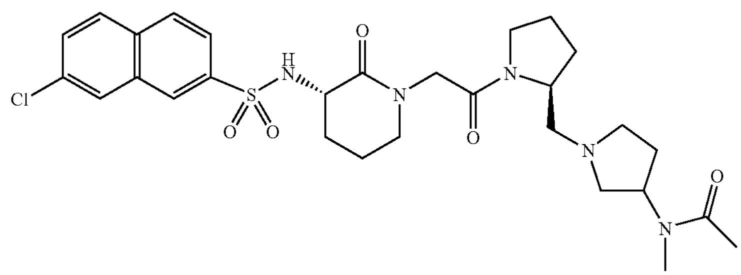 | HPLC (method 1) t_R = 3.1 min LRMS (ESI, pos. ion spectrum) m/z 604/606 (M + H) | Prepared using the procedures described in Example 613 and Example 788 and using INT44 |
| 920 | 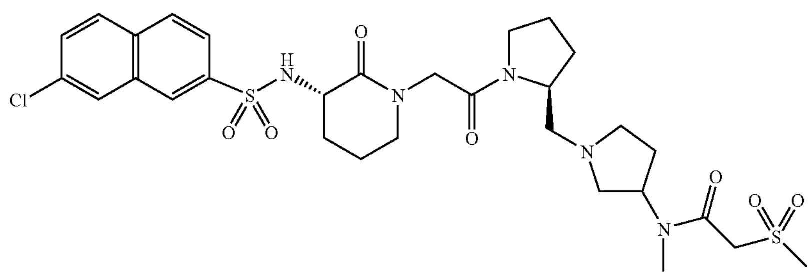 | HPLC (method 1) t_R = 3.0 min LRMS (ESI, pos. ion spectrum) m/z 682/684 (M + H) | Prepared using the procedures described in Example 613 and Example 788 and using INT44 |
| 921 | 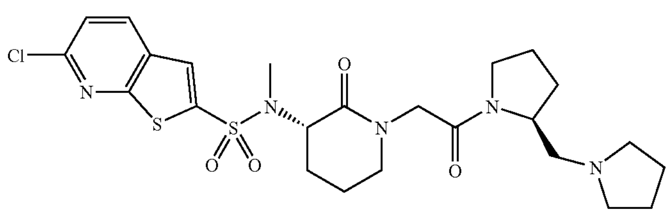 | HPLC (method 1) t_R = 2.2 min LRMS (ESI, pos. ion spectrum) m/z 554/556 (M + H) | Title compound of Example 921 |
| 922 | 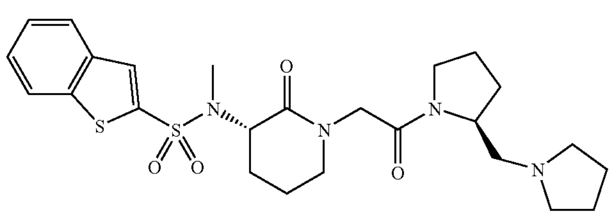 | HPLC (method 1) t_R = 2.2 min LRMS (ESI, pos. ion spectrum) m/z 519 (M + H) | Prepared using the method described in Example 921 |
| 923 | 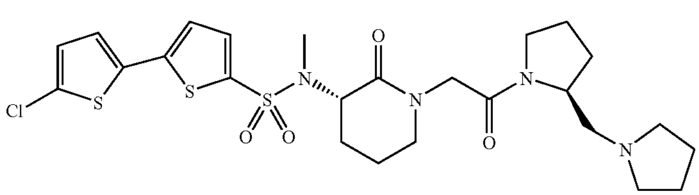 | HPLC (method 1) t_R = 3.0 min LRMS (ESI, pos. ion spectrum) m/z 585/587 | Prepared using the method described in Example 921 |

-continued

| Ex # | Structure | characterization | method |
|---|---|---|---|
| 924 | 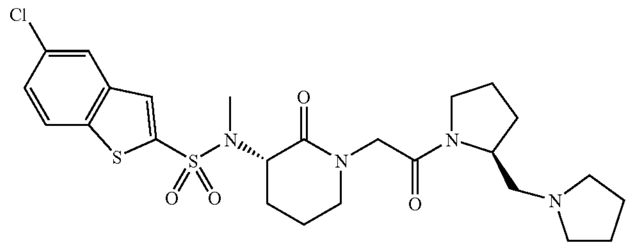 | HPLC (method 1) $t_R$ = 2.7 min LRMS (ESI, pos. ion spectrum) m/z 553/555 (M + H) | Prepared using the method described in Example 921 |
| 925 | 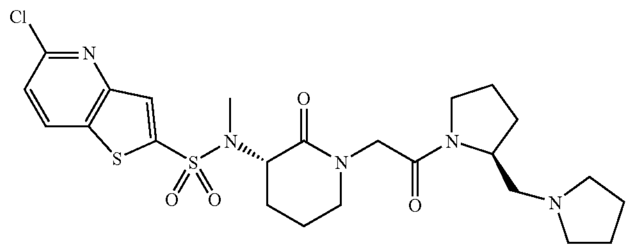 | HPLC (method 1) $t_R$ = 2.2 min LRMS (ESI, pos. ion spectrum) m/z 554/556 (M + H) | Prepared using the method described in Example 921 |
| 926 | 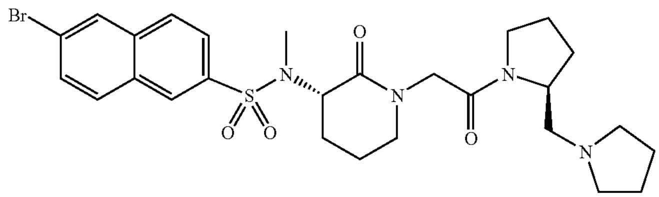 | HPLC (method 1) $t_R$ = 2.8 min LRMS (ESI, pos. ion spectrum) m/z 591/593 (M + H) | Prepared using the method described in Example 921 |
| 927 | 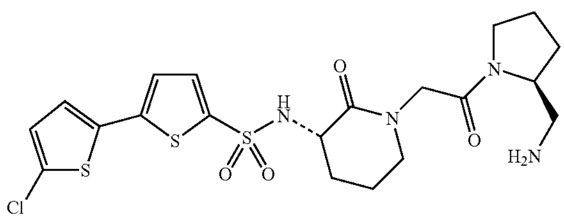 | HPLC (method 7) $t_R$ = 2.8 min LCMS (method 6) (ESI, pos. ion spectrum) m/z 517/519 (M + 1) | Title compound of Example 927 |
| 928 | 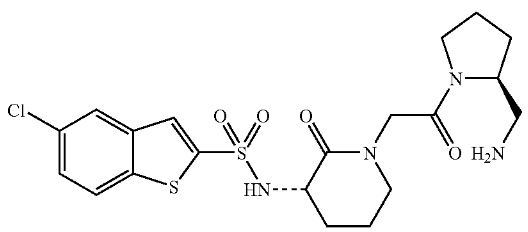 | HPLC (method 7) $t_R$ = 2.5 min LCMS (method 6) (ESI, pos. ion spectrum) m/z 485/487 (M + 1) | Title compound of Example 928 |
| 929 | 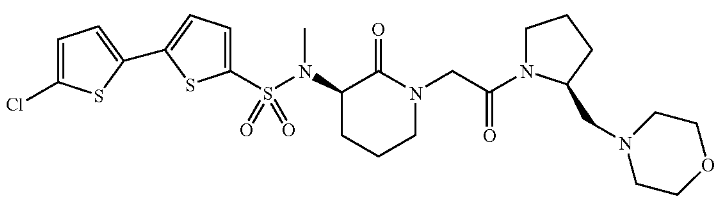 | LCMS (method 4) $t_R$ = 1.6 min (ESI, pos. ion spectrum) m/z 601/603 (M + 1) | prepared using the method described in Example 1 with INT8 |
| 930 | 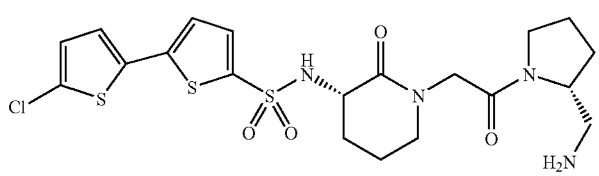 | HPLC (method 7) $t_R$ = 2.8 min LCMS (method 6) (ESI, pos. ion spectrum) m/z 517/519 (M + 1) | Title compound of Example 930 |

-continued

| Ex # | Structure | characterization | method |
|---|---|---|---|
| 931 | 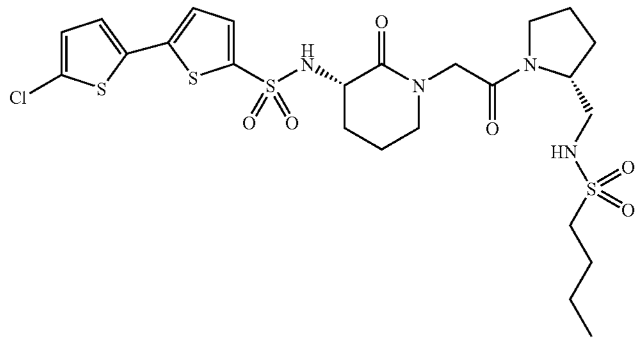 | HPLC (method 7) $t_R$ = 3.7 min LCMS (method 6) (ESI, pos. ion spectrum) m/z 637/639 (M + 1) | Title compound of Example 931 |
| 932 | 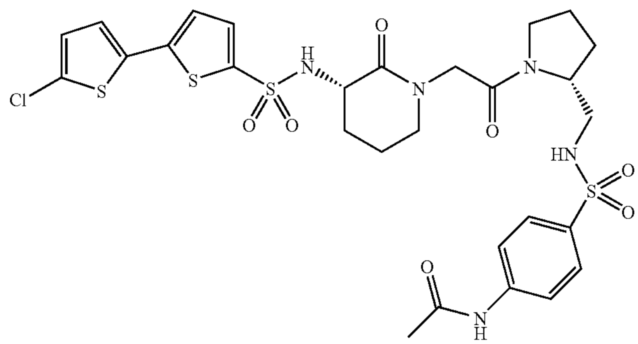 | HPLC (method 7) $t_R$ = 3.5 min LCMS (method 6) (ESI, pos. ion spectrum) m/z 714/716 (M + 1) | Prepared using the method described in Example 931 |
| 933 | 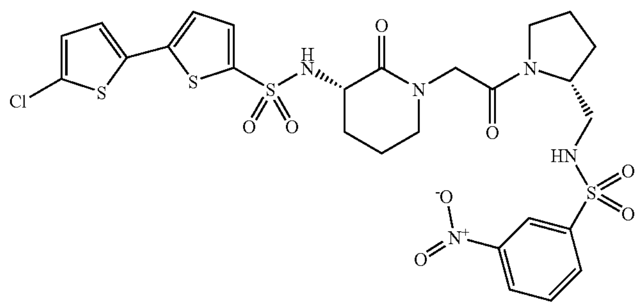 | HPLC (method 7) $t_R$ = 3.8 min LCMS (method 6) (ESI, pos. ion spectrum) m/z 702/704 (M + 1) | Prepared using the method described in Example 931 |
| 934 | 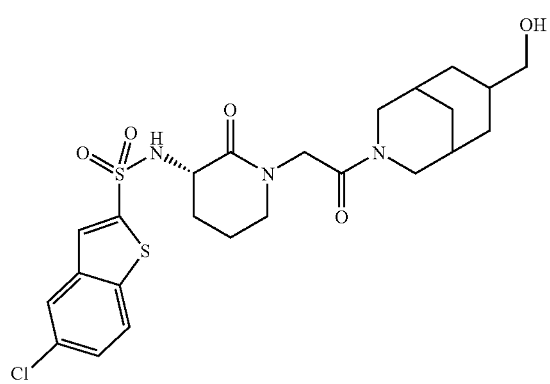 | HPLC (method 1) $t_R$ = 3.6 min LCMS (ESI, pos. ion spectrum) m/z 540/542 (M + 1) | Prepared using the method described in Example 48 using INT17 |
| 935 | 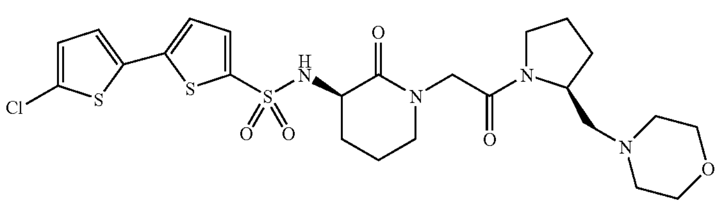 | HPLC (method 2) $t_R$ = 1.9 min LCMS (method 4) $t_R$ = 1.5 min (ESI, pos. ion spectrum) m/z 587/589 (M + 1) | prepared using the method described in Example 1 using INT7 |

-continued

| Ex # | Structure | characterization | method |
|---|---|---|---|
| 936 | 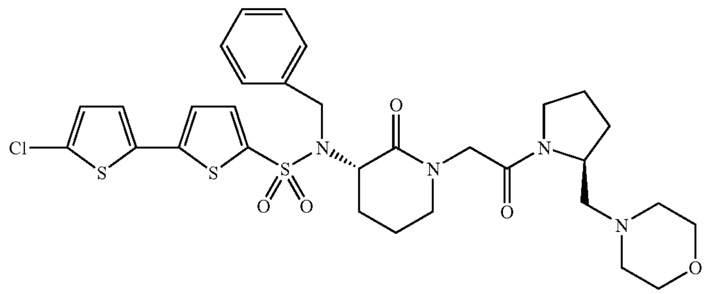 | HPLC (method 3) $t_R$ = 3.4 min LCMS (ESI, pos. ion spectrum) m/z 677/679 (M + 1) | Title compound of Example 936 |
| 937 | 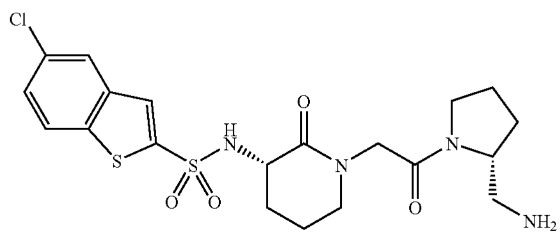 | HPLC (method 7) $t_R$ = 2.5 min LCMS (method 6) (ESI, pos. ion spectrum) m/z 485/487 (M + 1) | Prepared using the method described in Example 930 |
| 938 | 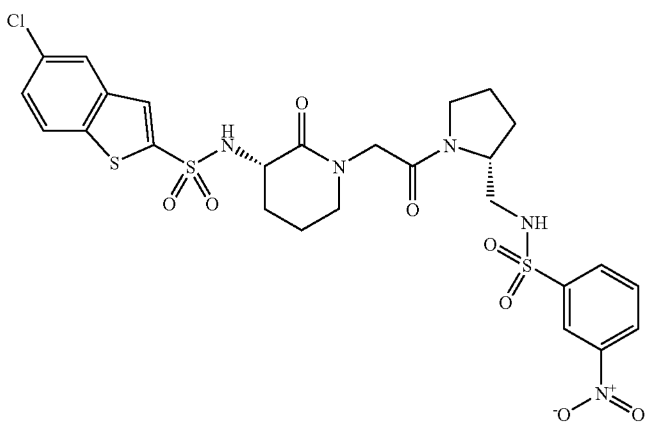 | HPLC (method 7) $t_R$ = 3.6 min LCMS (method 6) (ESI, pos. ion spectrum) m/z 670/672 (M + 1) | Prepared using the method described in Example 931 |
| 939 | 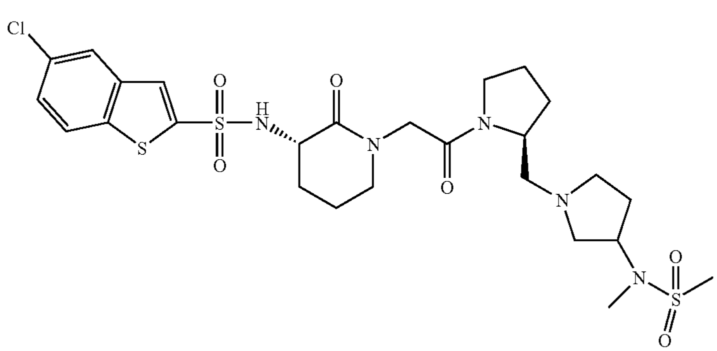 | HPLC (method 1) $t_R$ = 2.9 min LRMS (ESI, pos. ion spectrum) m/z 646/648 (M + H) | prepared using the methods described in Example 571 using the title compound of Example 615 |

-continued

| Ex # | Structure | characterization | method |
|---|---|---|---|
| 940 | 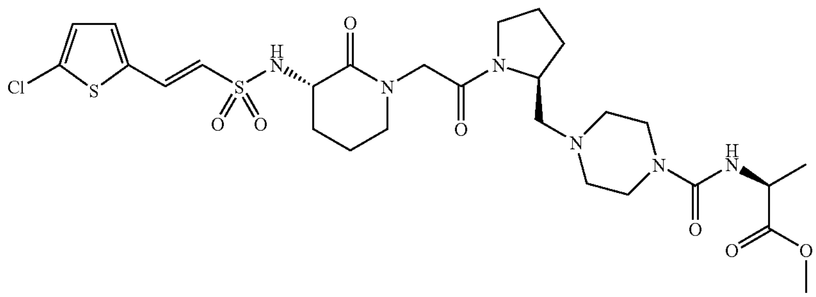 | HPLC (method 1) $t_R$ = 2.7 min LRMS (ESI, pos. ion spectrum) m/z 659/661 (M + H) | prepared using the methods described in Example 608 using the title compound of Example 612 |
| 941 | 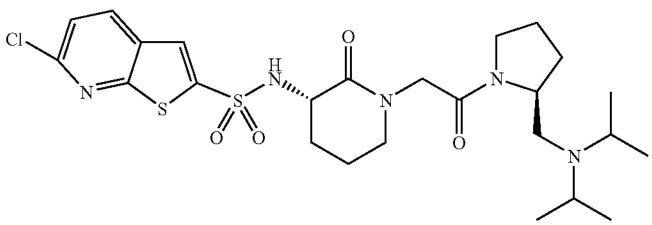 | HPLC (method 1) $t_R$ = 2.7 min LRMS (ESI, pos. ion spectrum) m/z 586/588 (M + H) | prepared using the methods described in Example 788 using the title compound of Example 612 |
| 942 | 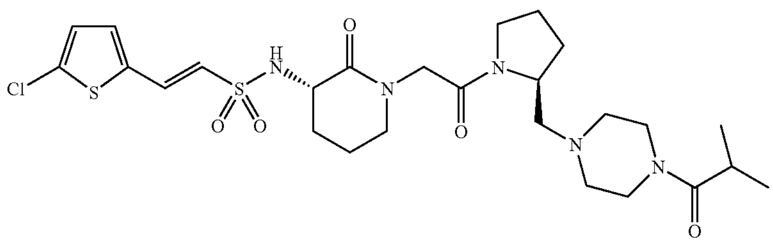 | HPLC (method 1) $t_R$ = 2.8 min LRMS (ESI, pos. ion spectrum) m/z 600/602 (M + H) | prepared using the methods described in Example 788 using the title compound of Example 612 |
| 943 | 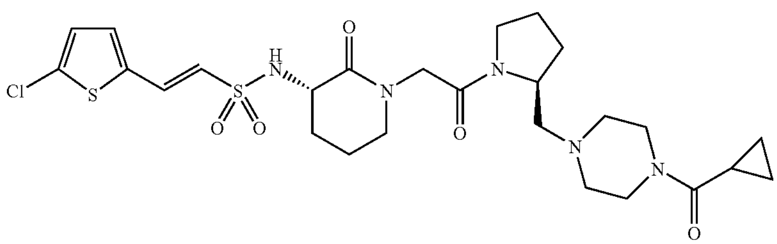 | HPLC (method 1) $t_R$ = 2.7 min LRMS (ESI, pos. ion spectrum) m/z 598/600 (M + H) | prepared using the methods described in Example 788 using the title compound of Example 612 |
| 944 | 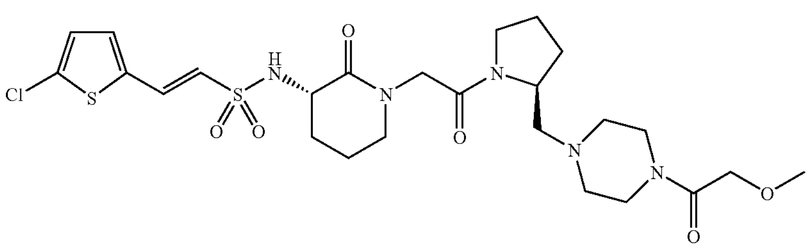 | HPLC (method 1) $t_R$ = 2.6 min LRMS (ESI, pos. ion spectrum) m/z 602/604 (M + H) | prepared using the methods described in Example 788 using the title compound of Example 612 |
| 945 | 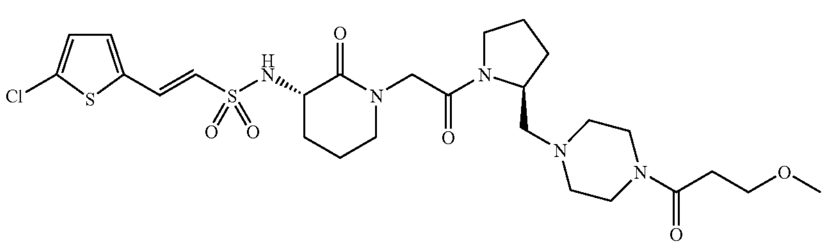 | HPLC (method 1) $t_R$ = 2.7 min LRMS (ESI, pos. ion spectrum) m/z 616/618 (M + H) | prepared using the methods described in Example 788 using the title compound of Example 612 |

| Ex # | Structure | characterization | method |
|---|---|---|---|
| 946 | 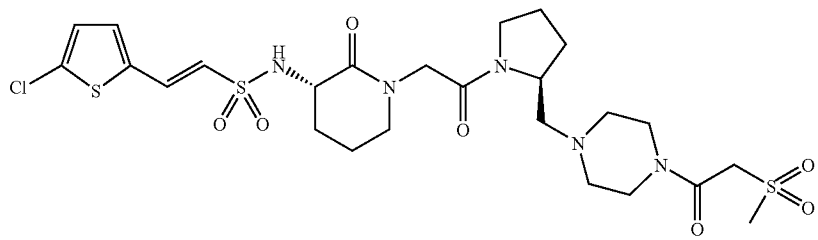 | HPLC (method 1) $t_R$ = 2.5 min LRMS (ESI, pos. ion spectrum) m/z 650/652 (M + H) | prepared using the methods described in Example 788 using the title compound of Example 612 |
| 947 | 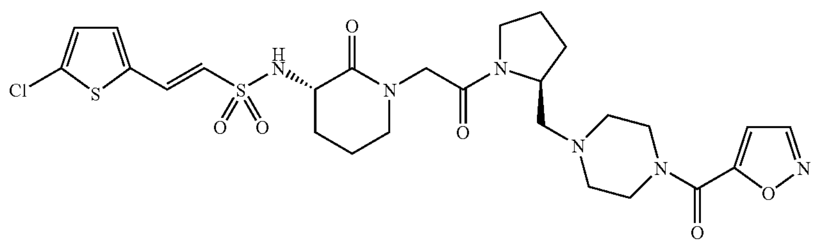 | HPLC (method 1) $t_R$ = 2.6 min LRMS (ESI, pos. ion spectrum) m/z 625/627 (M + H) | prepared using the methods described in Example 788 using the title compound of Example 612 |
| 948 | 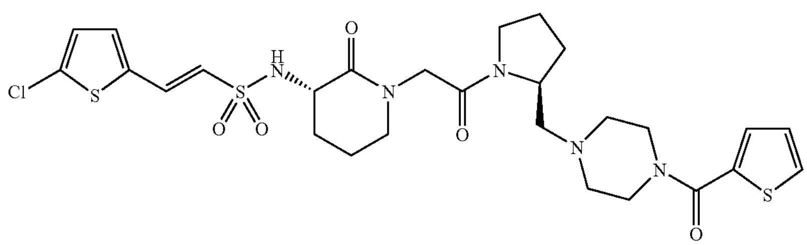 | HPLC (method 1) $t_R$ = 2.8 min LRMS (ESI, pos. ion spectrum) m/z 640/642 (M + H) | prepared using the methods described in Example 788 using the title compound of Example 612 |
| 949 | 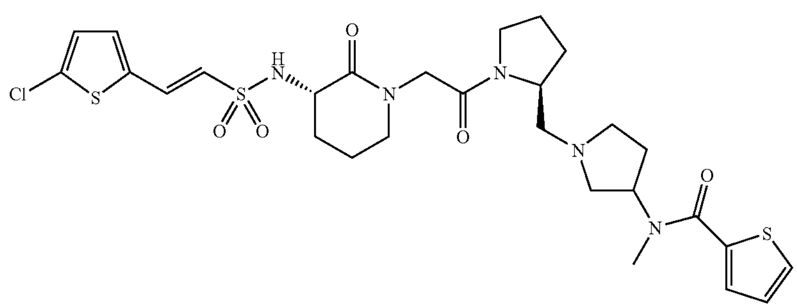 | HPLC (method 1) $t_R$ = 3.0 min LRMS (ESI, pos. ion spectrum) m/z 654/656 (M + H) | prepared using the methods described in Example 571 using the title compound of Example 613 |
| 950 | 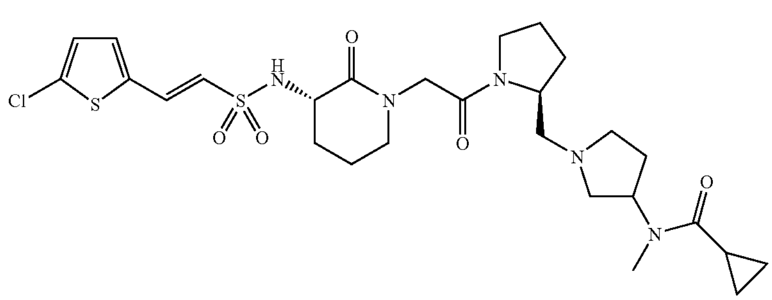 | HPLC (method 1) $t_R$ = 2.9 min LRMS (ESI, pos. ion spectrum) m/z 612/614 (M + H) | prepared using the methods described in Example 571 using the title compound of Example 613 |

| Ex # | Structure | characterization | method |
|---|---|---|---|
| 951 | 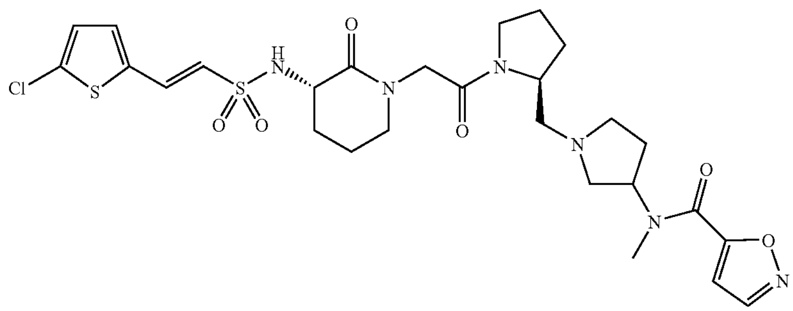 | HPLC (method 1) $t_R$ = 2.8 min LRMS (ESI, pos. ion spectrum) m/z 639/641 (M + H) | prepared using the methods described in Example 571 using the title compound of Example 613 |
| 952 | 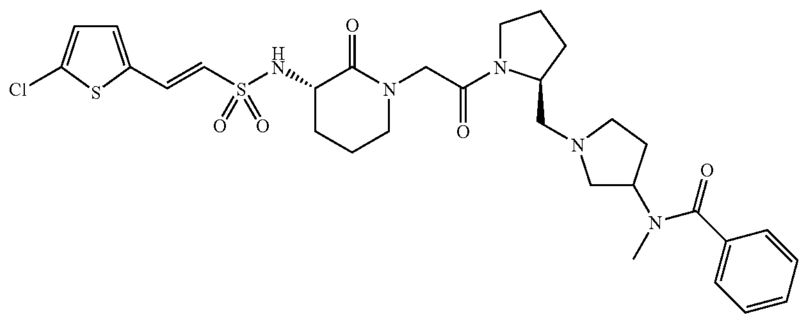 | HPLC (method 1) $t_R$ = 3.1 min LRMS (ESI, pos. ion spectrum) m/z 648/650 (M + H) | prepared using the methods described in Example 571 using the title compound of Example 613 |
| 953 | 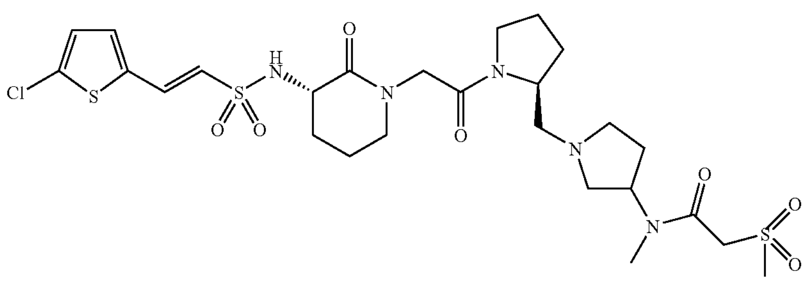 | HPLC (method 1) $t_R$ = 2.7 min LRMS (ESI, pos. ion spectrum) m/z 664/666 (M + H) | prepared using the methods described in Example 571 using the title compound of Example 613 |
| 954 | 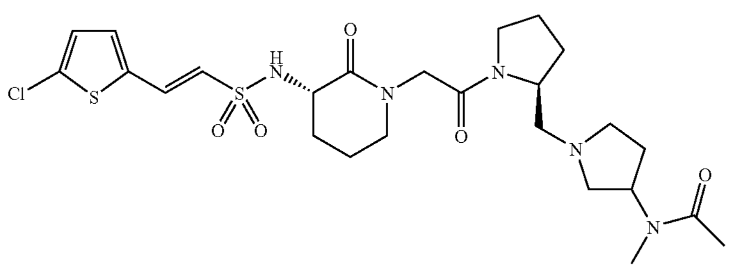 | HPLC (method 1) $t_R$ = 2.7 min LRMS (ESI, pos. ion spectrum) m/z 686/588 (M + H) | prepared using the methods described in Example 571 using the title compound of Example 613 |
| 955 | 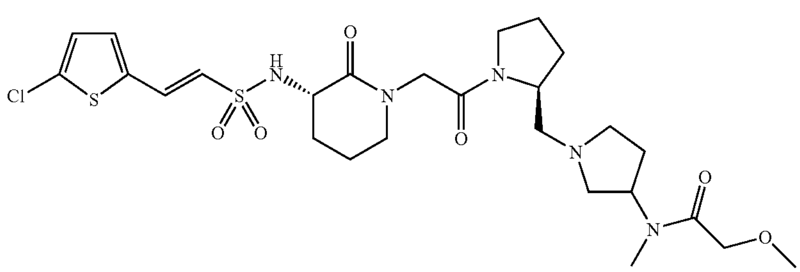 | HPLC (method 1) $t_R$ = 2.8 min LRMS (ESI, pos. ion spectrum) m/z 616/618 (M + H) | prepared using the methods described in Example 571 using the title compound of Example 613 |

-continued

| Ex # | Structure | characterization | method |
|---|---|---|---|
| 956 | 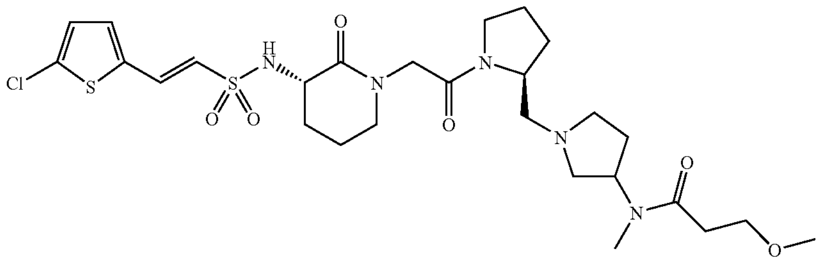 | HPLC (method 1) $t_R$ = 2.8 min LRMS (ESI, pos. ion spectrum) m/z 630/632 (M + H) | prepared using the methods described in Example 571 using the title compound of Example 613 |
| 957 | 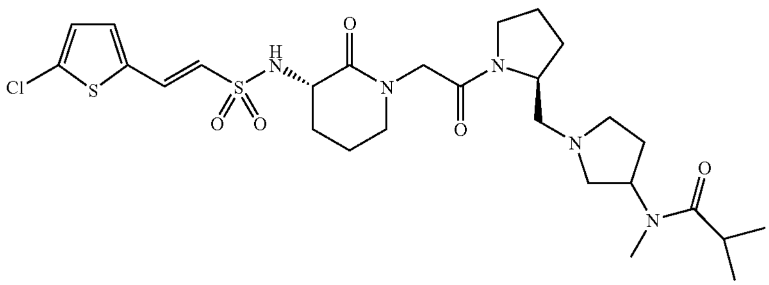 | HPLC (method 1) $t_R$ = 3.0 min LRMS (ESI, pos. ion spectrum) m/z 614/616 (M + H) | prepared using the methods described in Example 571 using the title compound of Example 613 |
| 958 | 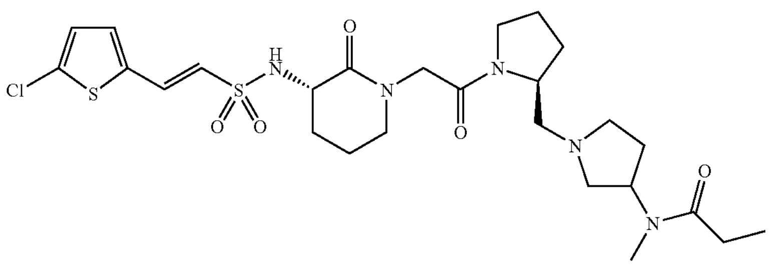 | HPLC (method 1) $t_R$ = 2.8 min LRMS (ESI, pos. ion spectrum) m/z 600/602 (M + H) | prepared using the methods described in Example 571 using the title compound of Example 613 |
| 959 | 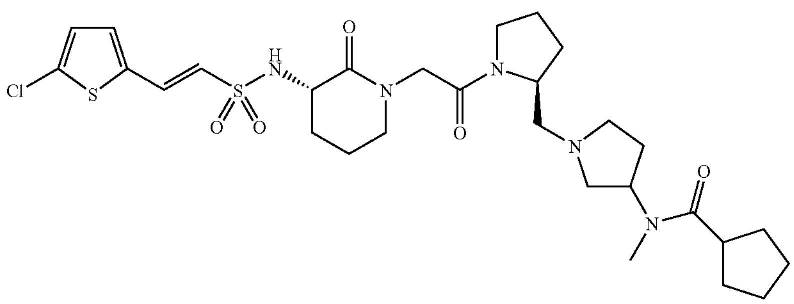 | HPLC (method 1) $t_R$ = 3.2 min LRMS (ESI, pos. ion spectrum) m/z 640/642 (M + H) | prepared using the methods described in Example 571 using the title compound of Example 613 |
| 960 | 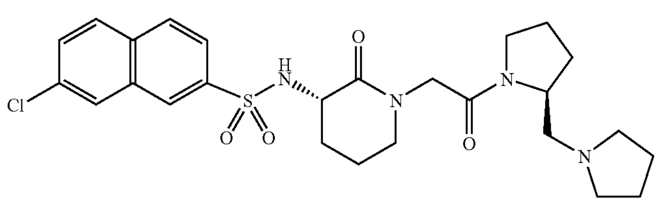 | HPLC (method 1) $t_R$ = 2.9 min LRMS (ESI, pos. ion spectrum) m/z 533/535 (M + H) | prepared using the methods described in Example 613 Part A using INT44 |
| 961 | 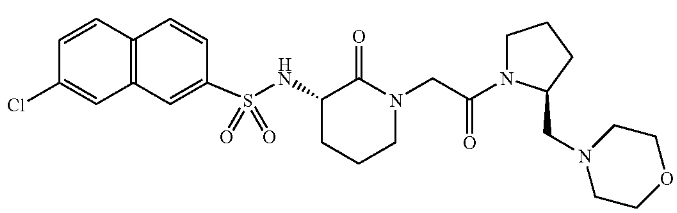 | HPLC (method 1) $t_R$ = 2.9 min LRMS (ESI, pos. ion spectrum) m/z 549/551 (M + H) | prepared using the methods described in Example 613 Part A-C using INT44 |

-continued

| Ex # | Structure | characterization | method |
|---|---|---|---|
| 962 | 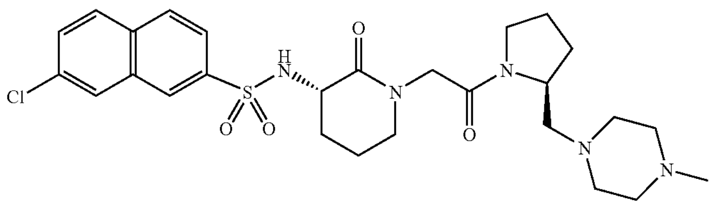 | HPLC (method 1) $t_R$ = 2.8 min LRMS (ESI, pos. ion spectrum) m/z 562/564 (M + H) | prepared using the methods described in Example 613 Part A-C using INT44 |
| 963 | 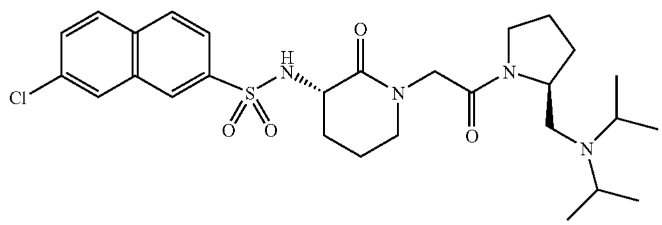 | HPLC (method 1) $t_R$ = 3.0 min LRMS (ESI, pos. ion spectrum) m/z 563/565 (M + H) | prepared using the methods described in Example 613 Part A-C using INT44 |
| 964 | 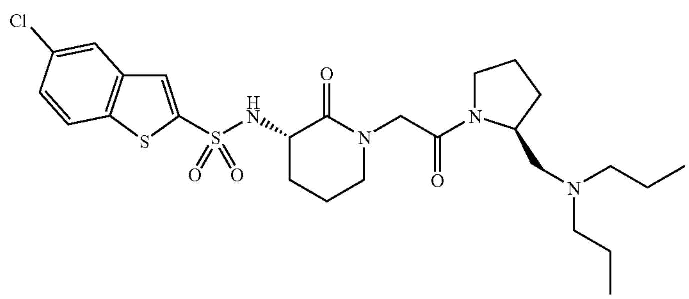 | HPLC (method 3) $t_R$ = 2.5 min LRMS (ESI, pos. ion spectrum) m/z 569/571 (M + H) | prepared using the method described in Example 130 using INT17 and INT68 |
| 965 | 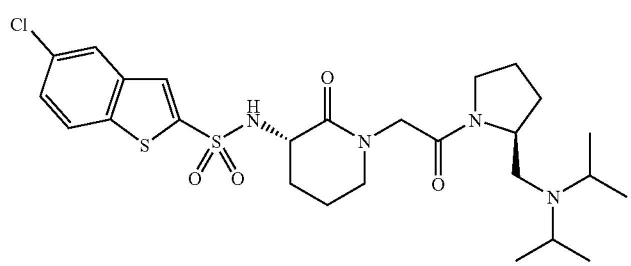 | HPLC (method 3) $t_R$ = 2.6 min LRMS (ESI, pos. ion spectrum) m/z 569/571 (M + H) | prepared using the method described in Example 130 using INT17 |
| 966 | 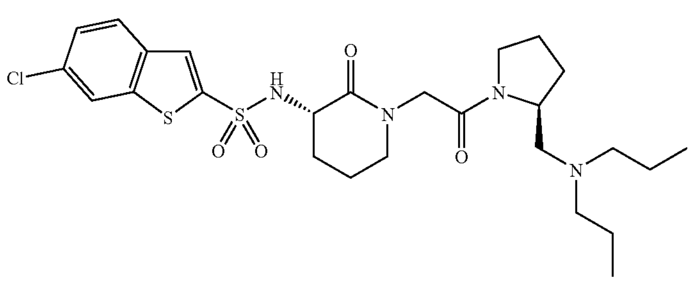 | HPLC (method 4) $t_R$ = 1.5 min LRMS (ESI, pos. ion spectrum) m/z 569/571 (M + H) | prepared using the method described in Example 130 using INT16 and INT68 |
| 967 | 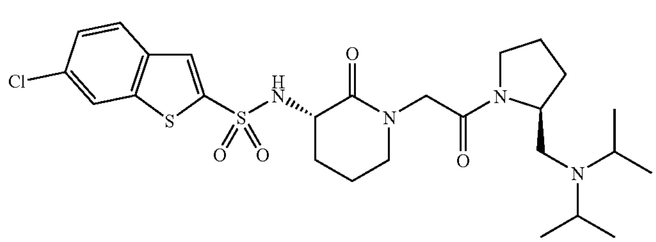 | HPLC (method 3) $t_R$ = 2.7 min LRMS (ESI, pos. ion spectrum) m/z 569/571 (M + H) | prepared using the method described in Example 130 using INT16 |

-continued

| Ex # | Structure | characterization | method |
|---|---|---|---|
| 968 | Chiral | HPLC (method 1) $t_R$ = 2.8 min LCMS (ESI, pos. ion spectrum) m/z 660/662 (M + 1) | Obtained as a co-product with the title compound of Example 429 |
| 969 | 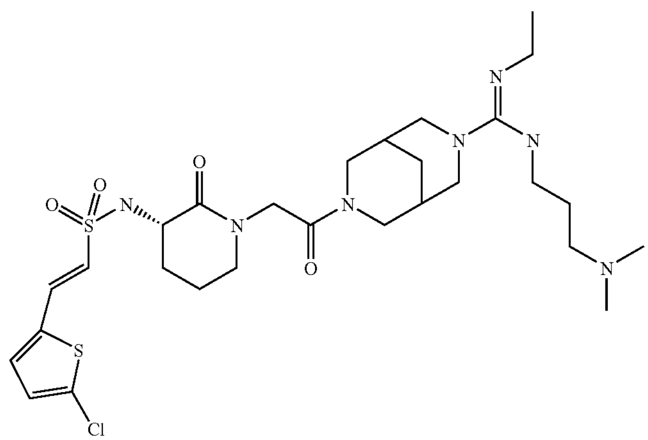 | HPLC (method 1) $t_R$ = 2.4 min LCMS (ESI, pos. ion spectrum) m/z 642/644 (M + 1) | Obtained as a co-product with the title compound of Example 457 |
| 970 | 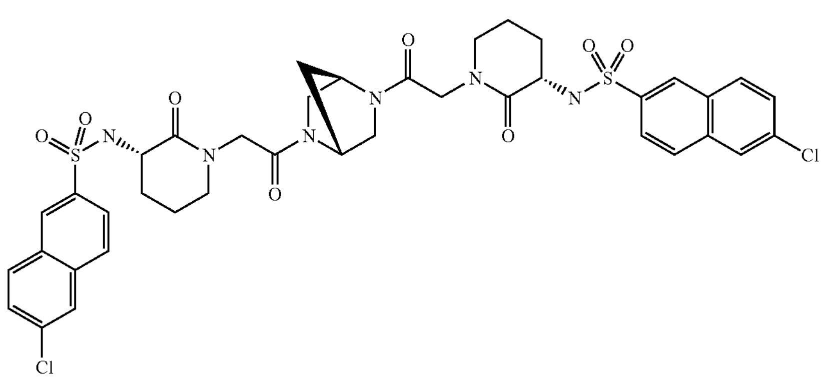 | HPLC (method 1) $t_R$ = 4.0 min LCMS (ESI, pos. ion spectrum) m/z 855/857/859 (M + 1) | Title compound of Example 970 |

| Ex # | Structure | characterization | method |
|---|---|---|---|
| 971 | 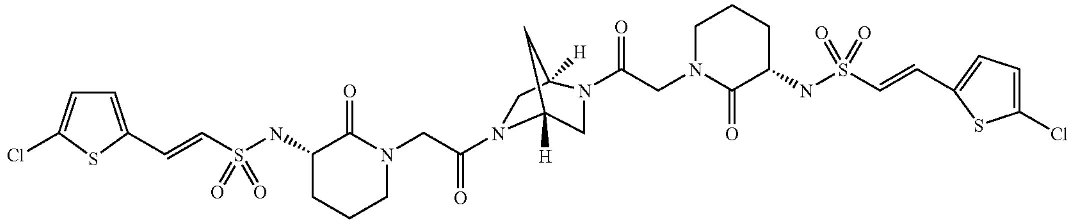 | LCMS (ESI, pos. ion spectrum) m/z 819/821/823 (M + 1) | Obtained as a co-product with the title compound of Example 575 Chiral |
| 972 | 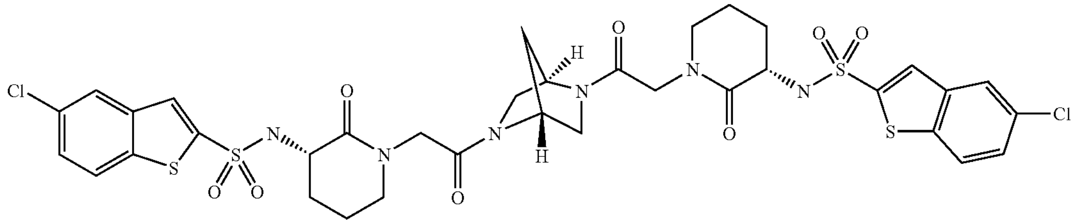 | LCMS (ESI, pos. ion spectrum) m/z 867/869/871 (M + 1) | Prepared using the method described in Example 575 |
| 973 | 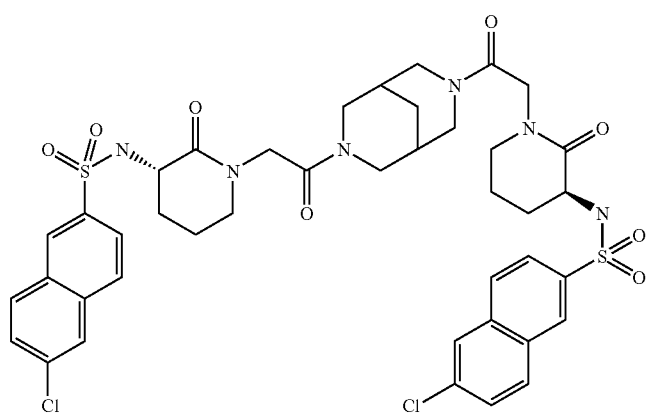 | HPLC (method 1) t$_R$ = 4.1 min LCMS (ESI, pos. ion spectrum) m/z 883/885/887 (M + 1) | Obtained as a co-product with the title compound of Example 429 |
| 974 | 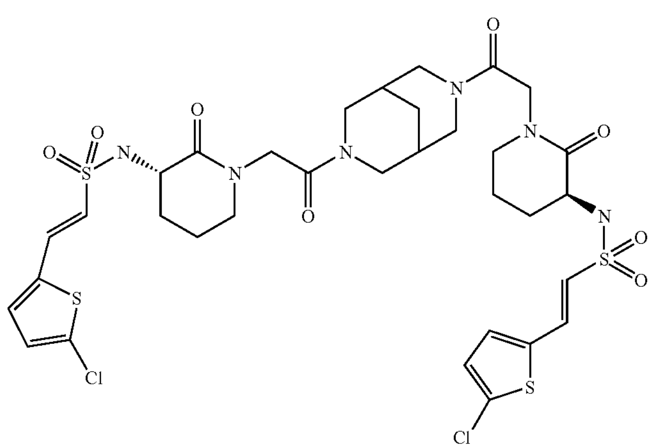 | HPLC (method 1) t$_R$ = 3.8 min LCMS (ESI, pos. ion spectrum) m/z 847/849/851 (M + 1) | Obtained as a co-product with the title compound of Example 457 |

EXAMPLE 1

A mixure of INT48 (45 mg, 0.20 mmol), naphthalene-2-sulfonyl chloride (68 mg, 0.30 mmol) and triethylamine (61 mg, 0.60 mmol) were dissolved in methylene chloride (1 mL). After stirring at room temperature for 0.5 h, the reaction mixture was diluted with 20 mL of ethyl acetate. The organic solution was washed with 0.1N HCl (10 mL) and saturated aqueous sodium bicarbonate (10 mL). The organic layer was collected and concentrated. The residue was purified by reverse phase chromatography to afford the title compound (51 mg, 66%): HPLC (method 1) $t_R$=2.7 min; LCMS (ESI, pos. ion spectrum) m/z 416 (M+H).

EXAMPLE 13

To the title compound of Example 3 (130 mg, 0.29 mmol) in 2 mL of DMF was added sodium hydride (14 mg, 0.35 mmol). The reaction mixture was stirred at room temperature for 10 min. Iodomethane (82 mg, 0.58 mmol) was added. The reaction mixture was stirred at room temperature for 1 h and quenched with 1 mL of water. Then the reaction mixture was extracted with 10 mL of methylene chloride. The organic layer was dried and concentrated. The residue was purified by reverse phase chromatography to give the title compound (15 mg, 11%): HPLC (method 1) $t_R$=3.2 min; LCMS (ESI, pos. ion spectrum) m/z 470/472 (M+H).

EXAMPLE 21

To a solution of INT48 (20 mg, 0.089 mmol) in dichloromethane (0.5 mL) was added triethylamine (0.013 mL, 0.089 mmol) and 6-chloronaphthalene-2-sulfonyl chloride (23 mg, 0.089 mmol). The reaction was stirred at room temperature for 1 h. The solvent was evaporated in vacuo to afford the crude product. Purification of the crude product over silica gel afforded the title compound (31 mg, 77%).

EXAMPLE 37

To 21 mL of a mixture of methanol and ethanol (1:2) was added the title compound of Example 36 (66 mg, 0.17 mmol), trifluoroacetic acid (0.3 mL) and 5 mg of 10% palladium on carbon. The reaction mixture was stirred under a hydrogen atmosphere (50 psi) for 24 h. The reaction mixture was filtered through CELITE and concentrated to provide the title compound (60 mg, 90%): HPLC (method 1) $t_R$=1.7 min; LCMS (ESI, pos. ion spectrum) m/z 395 (M+H).

EXAMPLE 41

To a solution of INT46 (47.4 mg, 0.20 mmol) in 2 mL of dichloromethane was added INT48 (47.8 mg, 0.20 mmol) and triethylamine (0.084 mL, 0.60 mmol). After stirring at room temperature for 1 h, the mixture was concentrated. The residue was purified by reverse phase chromatography. Product-containing fractions were combined, and concentrated and dried by lyophilization to provide the title compound (46 mg, 54%): LRMS (ESI, pos. ion spectrum) m/z 426/428 (M+H); HPLC (method 1) $t_R$=3.2 min

EXAMPLE 43

The title compound of Example 38 (43 mg, 0.074 mmol) was dissolved in 1.5 mL of THF and 1.5 mL of 1N sodium hydroxide solution. The reaction mixture was stirred at 60° C. for 9 h and then at room temperature overnight. The reaction mixture was extracted with 10 mL of ethyl acetate. The organic layer was washed with 10 mL of brine, dried and concentrated. The residue was purified by reverse phase chromatography to give the title compound (11 mg, 33%): HPLC (method 1) $t_R$=3.0 min; LCMS (ESI, pos. ion spectrum) m/z 439/441 (M+H).

EXAMPLE 48

To a solution of INT15 (85 mg, 0.22 mmol) in dichloromethane (2 mL) was added triethylamine (0.031 mL, 0.22 mmol), thiomorpholine (0.024 mL, 0.26 mmol), a catalytic amount of 4-dimethylaminopyridine, 1-hydroxy-7-azabenzotriazole (36 mg, 0.26 mmol) and EDCI (49 mg, 0.26 mmol) in that order. The reaction was stirred at room temperature for 2 h. The reaction was then quenched with water and extracted with methylene chloride (2×5 mL). The organic layers were combined, dried over magnesium sulfate, and evaporated in vacuo to afford the crude product. Purification of the crude product over silica gel afforded the title compound (85 mg, 80%).

EXAMPLE 49

To a solution of the title compound of Example 48 (80 mg, 0.17 mmol) in methylene chloride (2 mL) at −10° C. was added slowly 3-chloroperoxybenzoic acid (37 mg, 77% pure, 0.17 mmol). After stirring for 2 h, the reaction was quenched with saturated sodium thiosulfate solution. The mixture was extracted with methylene chloride (2×5 mL). The organic fractions were combined, dried over magnesium sulfate, and evaporated in vacuo to afford the crude product. RP-HPLC purification of the crude material afforded 40 mg (47%) of the title compound.

EXAMPLE 50

To a solution of the title compound of Example 49 (27 mg, 0.054 mmol) in methylene chloride (1 mL) was added 3-chloroperoxybenzoic acid (37 mg, 77% pure, 0.17 mmol). After stirring for 1 h, the reaction was quenched with saturated sodium thiosulfate solution, and extracted with methylene chloride (2×5 mL). The organic fractions were combined, washed with saturated sodium bicarbonate solution, dried over magnesium sulfate, and evaporated in vacuo to afford the the title compound (18 mg, 65%) as a white solid.

EXAMPLE 130

INT12, EDCI (29 mg, 0.15 mmol) and HOBT (14 mg, 0.10 mmol) were dissolved in 0.5 mL of acetonitrile and stirred at room temperature for 5 min. Then, N,N,N'-trimethylethane-1,2-diamine (15 mg, 0.15 mmol) was added and the reaction mixture was stirred at room temperature for an additional 30 min. The reaction mixture was quenched with 0.5 mL of water and purified by reverse phase chromatography to give the title compound (32 mg, 62%): HPLC (method 1) $t_R$=2.1 min; LCMS (ESI, pos. ion spectrum) m/z 506/508 (M$^+$).

EXAMPLE 148

Part A: The title compound of Example 299 (49 mg, 0.08 mmol) was dissolved in anhydrous DMF (0.4 mL). To this solution was added cesium carbonate (78 mg, 0.24 mmol), tetrabutylammonium iodide (89 mg, 0.24 mmol) and (2-bromoethoxy)-tert-butyldimethylsilane (0.052 mL, 0.24 mmol). The reaction mixture was warmed to 50° C. After 6 h the reaction mixture was partitioned between water and ethyl acetate. The organic phase was collected, and the aqueous phase extracted with ethyl acetate. The organic layers were combined, dried (sodium sulfate), and concentrated in vacuo to afford a semi-solid (75 mg).

Part B: The compound of part A was dissolved in THF (0.8 mL) and cooled to 0° C. A solution of tetrabutylammonium flouride in THF (1.0 M, 0.8 mL, 0.8 mmol) was added. After 1 h the reaction mixture was partitioned between aqueous 50% saturated ammonium chloride solution and ethyl acetate. The organic phase was collected, and the aqueous phase extracted with ethyl acetate. The organic layers were combined, dried (sodium sulfate), and concentrated in vacuo to afford a semi-solid. Purification by flash chromatography (silica, 5–10% methanol/dichloromethane) provided the title compound: 10 mg, 20%; HPLC (method 9) $t_R$=1.5 min; LRMS (ESI, pos. ion spectrum) 657/659 (M+H).

EXAMPLE 152

A solution of the title compound of Example 151 (17 mg, 0.027 mmol) and palladium activated carbon (10%, 5 mg) in methanol (0.5 mL) was stirred under one atmosphere of hydrogen at room temperature for 2 h. The reaction was diluted with methylene chloride (1 mL) and filtered through a pad of CELITE. The filtrate was evaporated in vacuo to afford the title compound 12 mg (99%).

EXAMPLE 177

Part A. Preparation of rel-(1R,2S,4S)-2-(((1,1-dimethylethyl)diphenylsilyl)oxymethyl)-7-aza-bicyclo[2.2.1]heptane. To a solution of ethyl rel-(1R,2S,4S)-2-(hydroxymethyl)-7-azabicyclo[2.2.1]heptane-7-carboxylate (386 mg, 1.94 mmol) in methylene chloride (3 mL) was added chloro (1,1-dimethylethyl)diphenylsilane (0.61 mL, 2.3 mmol) and triethylamine (0.33 mL, 2.3 mmol). The reaction was stirred overnight and concentrated in vacuo. The residue was dissolved in 4 mL of dry chloroform. To the solution was added dropwise iodotrimethylsilane (0.33 mL, 2.3 mmol) under argon at room temperature. The reaction was refluxed for 2 h and then quenched with methanol. The solvent was evaporated in vacuo. The residue was dissolved in ethyl acetate, washed with saturated sodium carbonate solution, dried over magnesium sulfate, and evaporated in vacuo to afford the crude product. RP-HPLC purification of the crude product afforded 200 mg (42%) of rel-(1R,2S,4S)-2-(((1,1-dimethylethyl)diphenylsilyl)oxymethyl)-7-aza-bicyclo [2.2.1]heptane.

Part B: N-((S)-1-{[rel-(1R,2S,4S)-2-(tert-butyldiphenyl-silanyloxymethyl)-7-aza-bicyclo[2.2.1]hept-7-yl]-2-oxoethyl}-2-oxopiperidin-3-yl) 6-chloronaphthalene-2-sulfonamide was prepared from part A compound and INT15 using the method described in Example 48.

Part C: To a solution of part B compound (2 mg, 0.003 mmol) in THF (0.1 mL) was added tetrabutylammonium fluoride (0.004 mL, 1M in THF). The reaction was stirred overnight, quenched with saturated ammonium chloride solution, and extracted with ethyl acetate (2×2 mL). The organic fractions were combined, dried over magnesium sulfate, and evaporated in vacuo. The crude product was purified by RP-HPLC to provide 1 mg (88%) of the title compound.

note: the rel-descriptor indicates that the substance is racemic but has the relative chirality indicated.

EXAMPLE 178

Part A. 1,1-dimethylethyl ((1-[2-[(3S)-3-(6-chloronaphthalene-2-sulfonylamino)-2-oxo-piperidin-1-yl]acetyl]piperidin-4-yl)methyl)carbamate was prepared using the method described in

EXAMPLE 48

Part B. To a solution of part A compound (21 mg, 0.036 mmol) in methylene chloride (0.5 mL) was added trifluoroacetic acid (TFA, 0.5 mL). After stirring for 1 h, the TFA and methylene chloride were evaporated in vacuo to afford 17 mg (97%) of the title compound.

EXAMPLE 183

A solution of INT15 (23 mg, 0.058 mmol) and triethylamine (0.016 mL, 0.12 mmol) in acetonitrile (0.2 mL) was added to 2-(4-nitrophenyl)thiazolidine (18 mg. 0.087 mmol) in a test tube. A solution of 1-hydroxy-7-azabenzotriazole (14 mg, 0.10 mmol) in DMF (0.1 mL) and a solution of EDCI (free base) (17 mg, 0.087 mmol) in DMF (0.1 mL) were added to above mixture in that order. The test tube was shaken overnight. The crude mixture was loaded onto a C-18 cartridge. The cartridge (2.5 g of C18 packing) had been previously pre-washed with 10 mL of MeOH and 10 mL of water and had the bulk solvent removed with air. The tube was rinsed with acetonitrile (0.1 mL) which was added to the top of the column. The cartridge was washed with water (30 mL), and 4% of acetonitrile in water (20 mL). The column was then eluted with acetonitrile (5 mL) to provide the title compound (26 mg, 77%).

EXAMPLE 292

To 0.2 mL of methanol containing 22 mg of 4 Å molecular sieves was added, sequentially, INT23 (25 mg, 0.05 mmol), dimethylamine (0.03 mL, 0.05 mmol) and borane-pyridine complex (ca. 8 M, 0.006 mL, 0.05 mmol). The reaction mixture was stirred at room temperature for 16 h. Then, 6N HCl (0.1 mL) was added. The reaction was stirred at room temperature for 1 h and was brought to pH 14 with 2N sodium hydroxide. The reaction mixtrue was extracted 3×1 mL with methylene chloride. The combined organic layers were dried and concentrated. The residue was purified by reverse phase chromatography to give the title compound (6 mg, 24%): HPLC (method 1) $t_R$=2.4 min; LCMS (ESI, pos. ion spectrum) m/z 513/515 (M+H).

EXAMPLE 311

Sodium metal (3 mg, 0.13 mmol) was added to ammonia (2 mL) at −33° C. and stirred for 10 min. A solution of the title compound of Example 298 (7 mg, 0.01 mmol) in dry THF (1 mL) was then added to the above solution. The reaction was stirred at −33° C. for 3 h, quenched with solid ammonium chloride, and stirred overnight at room temperature. The mixture was diluted with water (1 mL), and extracted with ethyl acetate (2×3 mL). The organic fractions were combined, dried over magnesium sulfate, and evaporated in vacuo to afford the crude product. Preparative HPLC purification over C18 silica gel afforded 1 mg (23%) of the title compound.

EXAMPLE 316

To a solution of the title compound of Example 301 (12 mg, 0.023 mmol) in methylene chloride (0.5 mL) was added triethylamine (0.007 mL, 0.05 mmol) and trimethylsilyl isocyanate (0.007 mL, 0.05 mmol). After stirring for 3 h, the reaction was concentrated. The residue was purified by RP-HPLC to afford 6 mg (47%) of the title compound.

EXAMPLE 317

To a solution of the title compound of Example 301 (10 mg, 0.019 mmol) in methylene chloride (0.5 mL) were added triethylamine (0.005 mL, 0.04 mmol) and 1-acetylimidazole (5 mg, 0.04 mmol). After stirring for 3 h, the reaction was concentrated. The residue was purified by RP-HPLC to afford 3 mg (27%) of the title compound.

EXAMPLE 331

A mixture of INT47 (1.5 g, 8.1 mmol), PS-MB-CHO resin (Argonaut Technologies Inc., 3.2 g, 1.26 mmol/g), and sodium triacetoxyborohydride (1.72 g, 8.1 mmol) in DMF-trimethyl orthoformate-acetic acid 49:49:2 (50 mL) was agitated at room temperature for 48 h. The mixture was filtered and the resin was subjected to 3 sequential washing cycles. In each cycle, the resin was washed sequentially with 6/3/1 THF/water/AcOH (3×), DMF (3×), methylene chloride (3×), and methanol (3×). The polymer supported amino ester (3.8 g) thus prepared was divided into 48 equal portions and each portion was suspended in methylene chloride (1.5 mL) and a sulfonyl chloride (1.5 equivalents based on the initial aldehyde resin is loading, chosen from INT45, 5-chlorobenzo[b]thiophene-2-sulfonyl chloride, 5-(1-methyl-5-trifluoromethyl-1H-pyrazol-3-yl)thiophene-2-sulfonyl chloride or 4-acetylamino-3-chloro-benzenesulfonyl chloride) and Hunig's base (3 equivalents) were added. The reactions were agitated for 3 h at room temperature. The reaction mixtures were individually filtered and washed with methylene chloride. A second coupling was performed as described above. The reaction mixtures were filtered. The resins were subjected to two sequential washing cycles. In each cycle, the resins were washed with methylene chloride (2×), methanol (2×), DMF (2×), and THF (2×). The resultant polymer supported sulfonylamino esters were treated, under agitation, with 2 N LiOH (1 mL) in THF (1 mL) for 36 h at room temperature. The resins were subjected to 3 sequential washing cycles. In each cycle, the resins were washed sequentially with 6/3/1 THF/water/AcOH (3 x), DMF (3×), methylene chloride (3×), and methanol (3×). The resins were then washed with THF. The polymer supported acids thus obtained were suspended in DMF (1 mL). Various commercially available amines (3 equivalents), PyBOP (3.4 equivalents) and N-methylmorpholine (0.3 mL) were added and the mixtures were agitated for 14 h at room temperature. The resins were subjected to two sequential washing cycles. In each cycle, the resins were washed with methylene chloride (2×), methanol (2×), DMF (2×), and THF (2×). In the final step the resins were agitated with a 1:1 mixture of methylene chloride-TFA (1.5 mL) for 30 min, filtered and washed with methylene chloride. Concentration of each of the individual combined filtrates afforded the title compounds.

EXAMPLE 372

The title compounds were prepared using the procedures described in Example 331 with the following modifications: a) only 4-acetylamino-3-chlorobenzenesulfonyl chloride was used in the sulfonylation step; b) before the final TFA cleavage step, the resins were agitated with acetyl chloride or cyclopropanecarbonyl chloride (3 equivalents, based on the initial loading of the aldehyde resin) in the presence of pyridine (5 equivalents) in methylene chloride (1.5 mL) for 15 min and then filtered and washed with methylene chloride.

EXAMPLE 391

A solution of (3-chlorophenyl)boronic acid (19 mg, 0.12 mmol) in ethanol (0.4 mL, sparged with argon for 30 min) was added to a stirring solution of the title compound of Example 363 (52 mg, 0.10 mmol) in toluene (0.8 mL, sparged with argon for 30 min). Sodium carbonate (23 mg, 0.20 mmol) in water (0.40 mL sparged with argon for 30 min) was then added followed by $Pd(PPh_3)_4$ (7 mg). After refluxing under argon for 2 h, the reaction was poured into brine and extracted with ethyl acetate (2×30 mL). The combined organic layers were dried over magnesium sulfate to afford 60 mg of crude product. Purification over C18 silica gel afforded 15 mg (27%) of the title compound.

EXAMPLE 400

A mixture of INT20 (78 mg, 0.15 mmol) and azepane (23 mg, 0.23 mmol) in 0.3 mL of 1,2-dichloroethane was stirred at room temperature for 10 min. To the reaction was added sodium triacetoxyborohydride (48 mg, 0.23 mmol). The reaction was stirred at room temperature for an additional 20 minutes. The volatiles were removed with a stream of nitrogen and the residue was purified by reverse phase chromatography to afford the title compound (62 mg, 69%): HPLC (method 1) $t_R$=3.0 min; LCMS (ESI, pos. ion spectrum) m/z 599/601 (M+H).

EXAMPLE 401

A mixture of the title compound of Example 363 (52 mg, 0.10 mmol), (3-methoxyphenyl)boronic acid (23 mg, 0.10 mmol), cesium carbonate (65 mg, 0.20 mmol), N,N'-dicyclohexyl-1,4-diaza-1,3-butadiene (0.66 mg), and palladium acetate (0.67 mg) in dioxane (1 mL) was stirred at 80° C. After 4.5 h, the reaction was transferred to a separators funnel with ethyl acetate/water and extracted with ethyl acetate (2×30 mL). The combined organic layers were dried over magnesium sulfate to afford 84 mg of crude product. Purification over silica gel afforded 45 mg (81%) of the title compound.

EXAMPLE 407

To a solution of the title compound of Example 301 (10 mg, 0.019 mmol) in 1,2-dichloroethane (0.3 mL) was added acetic acid (0.1 mL) and ethyl oxoacetate (10 mg, 0.1 mmol, 50% in toluene). After stirring for 30 min, sodium triacetoxyborohydride (8 mg, 0.037 mmol) was added. The reaction mixture was stirred for 2 h, quenched with saturated sodium bicarbonate solution, extracted with dichloromethane (2×1 mL). The organic fractions were combined, dried over magnesium sulfate, and evaporated in vacuo to afford the crude product. Preparative HPLC Purification afforded 7 mg (61%) of the title compound.

EXAMPLE 409

Part A. 4-(11,1-dimethyl)ethyl 1-(9H-fluoren-9-ylmethyl) 2-((1-pyrrolidinyl)carbonyl)piperazine-1,4-dicarboxylate was prepared from 1-(9H-fluoren-9-ylmethyl) 4-(1,1-dimethyl)ethyl 1,2,4-piperazinetricarboxylate and pyrrolidine according to the method described in Example 48.

Part B. Part A compound was treated with a solution (20% v/v) of piperazine in DMF for 10 min. The reaction was concentrated and purified over silica gel afford (1,1-dimethylethyl) 3-((1-pyrrolidinyl)carbonyl)-piperazine-1-carboxylate.

Part C. To a solution of lithium aluminum hydride (0.18 g, 4.7 mmol) in THF (2 mL) at 0° C. was added dropwise a solution of part B compound (0.88 g, 3 mmol) in THF (1 mL). The reaction was stirred for 3 h at room temperature and was quenched at 0° C. with 10 drops of MeOH. To the reaction were sequentially added NaOH solution (2 mL, 5%),THF (50 mL) and MeOH (10 mL) at 0° C. The mixture was stirred at room temperature for 1 h. Sodium sulfate was added to absorb water and mixture filtered through a plug of CELITE. The filtrate was concentrated and coevaporated with toluene three times to afford (1,1-dimethyl)ethyl 3-(pyrrolidin-1-ylmethyl)-piperazine-1-carboxylate (0.60 g, 74%) which was used immediately without further purification.

Part D. 4-{2-[(3S)-(6-Bromo-naphthalene-2-sulfonylamino)-2-oxo-piperidin-1-yl]-acetyl}-3-pyrrolidin-1-ylmethyl-piperazine-1-carboxylic acid tert-butyl ester was prepared from INT10 and part C compound using the method described in Example 48.

Part E. The title compound was prepared from part D compound using the method described in Example 178 part B.

EXAMPLE 410

Part A. To a solution of the title compound of Example 394 (100 mg, 0.21 mmol) in dichloromethane (1.5 mL) was added Dess-Martin reagent in dichloromethane (1.5 mL). After stirring at room temperature for 30 min, the mixture was concentrated and purified over silica gel afford 50 mg (50%) of N-[(S)-1-[2-(rel-(1S,2S,5R)-2-formyl-3-aza-bicyclo[3.1.0]hex-3-yl)-2-oxo-ethyl]-2-oxo-piperidin-3-yl] ((E)-2-(5-chloro-thiophen-2-yl)ethenesulfonamide).

Part B. The title compound was prepared from the part A aldehyde using the methods described in Example 407.

the rel-descriptor indicates that the bicyclic portion is racemic but has the relative stereochemistry shown.

EXAMPLE 412

Part A. A solution of the title compound of Example 390 (20 mg, 0.037 mmol) in methylene chloride (1 mL) was cooled to 0° C. 3-Chloroperoxybenzoic acid (10 mg, 57%, 0.026 mmol) was added. The mixture was allowed to warm to room temperature and was stirred overnight. The reaction was concentrated in vacuo to afford the crude product. Preparative HPLC purification over C18 silica gel afforded 4 mg (19%) of Example 390 title compound N-oxide: LCMS (method 4) $t_R$=0.84 min; LCMS (ESI, pos. ion spectrum) m/z 566 (M+1).

Part B. To part A compound (3 mg, 0.005 mmol) in dry pyridine (0.5 mL) at 0° C. was added p-toluenesulfonyl chloride (1.5 mg). The reaction was stirred at 0° C. for 2.5 h and the solvent was removed in vacuo. To the residue was added 2-aminoethanol (0.5 mL) and the mixture was stirred overnight. Preparative HPLC purification afforded 1 mg (39%) the title compound: LCMS (method 4) $t_R$=0.88 min; LCMS (ESI, pos. ion spectrum) m/z 565 (M+1).

EXAMPLE 414

Part A. INT9 (0.31 g, 1.0 mmol) and PS-MB-CHO (1.26 mmol/g, 0.40 g, 0.50 mmol) were suspended in 1/1 DMF/trimethylorthoformate containing 2% acetic acid (6.3 mL). Sodium triacetoxyborohydride (0.22 g, 1.0 mmol) was then added and the mixture was agitated at ambient temperature. After 2 days, the solid was filtered and subjected to 3 sequential washing cycles. In each cycle, the resin was washed sequentially with 6/3/1 THF/water/AcOH (3×), DMF (3×), methylene chloride (3×), and methanol (3×). The resin was then washed with THF (2×), and the solid was dried under vacuum to afford 0.41 g of resin-supported amine.

Part B. A portion of Part A amine resin (0.10 g, 0.12 mmol), diisopropylethylamine (48 mg, 0.38 mmol), and (4-bromophenyl)sulfonyl chloride (48 mg, 0.19 mmol) were suspended in methylene chloride (1.5 mL). The mixture was agitated at ambient temperature overnight. The resin was filtered and rinsed with methylene chloride. A second coupling was performed for 5 h. The resin was subjected to two sequential washing cycles. In each cycle, the resin was washed with methylene chloride (2×), methanol (2×), DMF (2×), and THF (2×). Finally, the resin was dried to provide part B resin-bound sulfonamide Part C: A portion of Part B sulfonamide resin (0.12 mmol theory) was suspended in dioxane (1.5 mL) (3-Methoxyphenyl)boronic acid (30 mg, 0.13 mmol), cesium carbonate (81 mg, 0.25 mmol), N,N'-dicyclohexyl-1,4-diaza-1,3-butadiene (0.80 mg), and palladium acetate (0.80 mg) were then added and the resultant mixture was agitated at 75° C. overnight. The solid was filtered and subjected to 3 sequential washing cycles and was dried. In each cycle, the resin was washed sequentially with methylene chloride (3×), methanol (3×), DMF (3×), and THF (3×). Methylene chloride (0.50 mL) and trifluoroacetic acid (0.50 mL) were added to the solid resin. After 15 min, the reaction was filtered and rinsed with methylene chloride. The combined filtrates were evaporated in vacuo to afford the crude product. Purification over C18 silica gel afforded 6 mg (9%) of Example 414 title compound BMS-525150.

EXAMPLE 415

The title compound (4 mg, 4%) was isolated from the product-containing fractions obtained during the purification of the title compound of Example 414.

EXAMPLE 421

A mixture of Example 397 title compound (48 mg, 0.10 mmol), (3-methoxyphenyl)boronic acid (25 mg, 0.12 mmol), 2 N potassium carbonate (0.14 mL, 0.28 mmol) in dimethoxyethane (1.0 mL) was sparged with argon for 20 min. Tetrakis(triphenylphosphine)palladium (6 mg) was added. After refluxing for 4 h, the reaction was transferred to a separatory funnel with ethyl acetate/water and extracted with ethyl acetate (2×30 mL).

The combined organic layers were washed with water and brine and dried over magnesium sulfate to afford 51 mg of crude product. Purification over silica gel afforded 23 mg (36%) of Example 421 title compound.

EXAMPLE 429

To a solution of INT15 (41 mg, 0.10 mmol) in acetonitrile (1 mL) were added diisopropylethylamine (0.036 mL, 0.21 mmol), 3,7-Diaza-bicyclo[3.3.1]nonane (13 mg, 0.10 mmol), a catalytic amount of 4-dimethylaminopyridine, 1-hydroxy-7-azabenzotriazole. (28 mg, 0.20 mmol) and EDCI (39 mg, 0.20 mmol) in that order. The reaction was stirred at room temperature overnight. Preparative HPLC purification afforded the title compound (11 mg, 22%).

EXAMPLE 431

Part A: To a solution of oxalyl chloride (1.3 mL, 15 mmol) in 20 mL of dichloromethane at −60° C. was added methyl sulfoxide dropwise over period of 10 min. After stirring at −60° C., a solution of 1,1-dimethylethyl 3-hydroxypyrrolidine-1-carboxylate (1.87 g, 10 mmol) in 20 mL of dichloromethane was added over 20 min. Then, diisopropylethylamine (8.8 mL, 50 mmol) was added over 5 min. The resulting mixture was stirred at −60° C. for 25 min, and at room temperature for 30 min. The reaction was diluted with dichloromethane (100 mL). The organic layer was washed sequentially with saturated sodium bisulfate solution (2×), saturated sodium bicarbonate solution, water, and brine; dried over sodium sulfate; and concentrated to afford 1.8 g (97%) of 1,1-dimethylethyl 3-oxo-pyrrolidine-1-carboxylate: $^1$H-NMR (CDCl$_3$) δ 3.75 (4H, m), 2.58 (2H, t, J=7.8 Hz), 1.49 (9H, s).

Part B: To a solution of part A compound (1.8 g, 9.7 mmol) in 2 mL of toluene was added a solution of (diethylamino)sulfur trifluoride (1.3 mL, 9.7 mmol) at 0° C. The mixture was stirred at 0° C. for 1 h and at room temperature for 22 h. The resulting mixture was then poured onto ice and extracted with ethyl acetate (3×). The organic layer was washed with saturated sodium bicarbonate aqueous solution, brine and dried over magnesium sulfate. The crude product was purified over silica gel to afford 1.1 g (54.7%) of 1,1-dimethylethyl 3,3-difluoropyrrolidine-1-carboxylate: $^1$H-NMR (CDCl$_3$, δ) 3.62 (4H, m), 2.34 (2H, m), 1.48 (9H, s).

Part C: To a solution of 1,1-dimethylethyl 3,3-difluoropyrrolidine-1-carboxylate (0.868 g, 4.19 mmol) in 1.5 mL of 1,4-dioxane was added a solution of hydrogen chloride in 1,4-dioxane (4 M, 11 mL, 44 mmol) at 0° C. The mixture was stirred at 0° C. for 40 min, at room temperature for 1 h and was then concentrated to afford 0.65 g (100%) of 3,3-difluoropyrrolidine hydrochloride: $^1$H-NMR (CD$_3$OD) δ 3.54 (2H, t, J=11.9 Hz), 3.43 (2H, t, J=7.8 Hz), 2.40 (2H, m).

Part D: The title compound was prepared using the procedures described in Example 613 Parts A–C employing part C compound and INT17.

EXAMPLE 494

The title compounds were prepared using the procedures described in Example 331 with the following modifications:
a) only (E)-2-(5-Chlorothien-2-yl)ethenesulfonyl chloride was used in the sulfonylation step; b) in the coupling step, the polymer supported acid was condensed with either D-proline methyl ester or L-proline methyl ester; c) the resulting polymer supported methyl esters were hydrolyzed by using lithium hydroxide as described in Example 331 and coupled (by using 5 equivalents PyBOP and 10 equivalents N-methylmorpholine) with 5 equivalents of various commercially available amines, anilines or aminoheterocyclic compounds as previously described.

EXAMPLE 532

Resin-supported sulfonamide Example 414 Part B (0.12 mmol) was suspended in dimethoxyethane (1.5 mL). (3-Chlorophenyl)boronic acid (23 mg, 0.15 mmol), 2 N potassium carbonate (0.10 mL, 0.20 mmol), and tetrakis (triphenylphosphine)palladium (4 mg) were then added and the resultant mixture was agitated at 80° C. overnight. The solid was filtered and subjected to 3 sequential washing cycles. In each cycle, the resin was washed sequentially with 6/3/1 THF/water/AcOH (3×), DMF (3×), methylene chloride (3×), and methanol (3×). The solid was subjected to 5 sequential washing cycles. In each cycle, the resin was washed sequentially with methanol (2×) and methylene chloride (2×). The resin was then washed with THF (3×). An aliquot of this resin was cleaved with 1/1 methylene chloride/TFA as described below. HPLC analysis of the residue indicated incomplete reaction, so the resin was resubmitted to the preceding reaction conditions and washing cycles. Methylene chloride (0.50 mL) and trifluoroacetic acid (0.50 mL) were added to the solid resin. After 30 min, the reaction was filtered and rinsed with methylene chloride and the combined filtrates were evaporated in vacuo to afford the crude product. Purification over C18 silica gel afforded 49 mg (58%) of Example 532 title compound.

EXAMPLE 534

The title compound of Example 439 (43 mg, 0.07 mmol) was dissolved in 0.4 mL of THF and cooled to 0° C. Then, 2 N lithium hydroxide (0.4 mL) was added. The reaction mixture was stirred at 0° C. for 30 min. The reaction mixture was neutralized with 6 N HCl and then was purified using reverse phase chromatography to give the title compound (36 mg, 86%): HPLC (method 1) $t_R$=2.8 min LCMS (ESI, pos. ion spectrum) m/z 589/591 (M+H).

EXAMPLE 570

To a solution of the title compound of Example 568 (95 mg, 0.17 mmol) in 1 mL of dichloromethane at 0° C. was added diisopropylethylamine (0.05 mL, 0.52 mmol) and 2-bromoethyl acetate (0.02 mL, 0.18 mmol). The mixture was stirred at room temperature for 2 h, heated at reflux for 2 h and cooled to room temperature. To the mixture were added additional portions of diisopropylethylamine, and 2-bromoethyl acetate as used above. The resulting mixture was heated at reflux for an additional 2 h. The solvent was exchanged for 1,2-dichloroethane and the mixture was heated at reflux for 2 h. The mixture was then diluted with dichloromethane (15 mL) and washed with saturated sodium bicarbonate solution and brine. The organic layer was dried over sodium sulfate and concentrated. The residue was purified over silica gel to afford 55 mg (50%) of the title compound: LRMS (ESI, pos. ion spectrum) m/z 640/642 (M+H); HPLC (method 1) $t_R$=2.9 min.

EXAMPLE 571

To a solution of the title compound of Example 568 (23 mg, 0.042 mmol) in dichloromethane (0.4 mL) was added, sequentially, diisopropylethylamine (0.010 mL, 0.058 mmol) and methanesulfonyl chloride (7 mg, 0.05 mmol). The mixture was shaken for 30 min and the volatiles were removed under a stream of nitrogen. The residue was purified by RP-HPLC chromatography to afford 6 mg (22%)

of the title compound: LRMS (ESI, pos. ion spectrum) m/z 632/634 (M+H); HPLC (method 1) $t_R$=2.7 min.

EXAMPLE 574

The title compounds were prepared using the procedures described in Example 331 with the following modifications:

a) in the coupling step, the resin supported acid (10 mg) was treated with tetramethylfluoroforamidinium hexafluorophosphate (TFFH, 20 mg) in the presence of triethylamine (0.1 mL) in 1:1 THF-acetonitrile (0.5 mL) for 1 minute prior to the addition of 2-aminopyridine hydrochloride (25 mg). The mixture was agitated at RT for 14 h, washed and subjected to the cleavage conditions as described in the general procedure Example 331.

EXAMPLE 575

The title compounds were prepared using the procedures described in Example 331 with the following modifications:

a) only E-2-(5-Chlorothien-2-yl)ethenesulfonyl chloride was used in the sulfonylation step; b) in the coupling step, the polymer supported acid was condensed only with tert-butyl (1S,4S)-(−)-2,5-diazabicyclo[2.2.1]heptane-2-carboxylate; c) the title compound of Example 575 was obtained by TFA cleavage of the above adduct; d) prior to the cleavage step, the resin was treated with trimethylsilyl triflate (0.1 mL) and 2,6-lutidine (0.1 mL) in methylene chloride (1 mL) for 3 h to remove the BOC protecting group. The resin was washed with methylene chloride, MeOH, DMF and acylated with acetyl chloride or benzoyl chloride as described in the general procedure Example 372 (Examples 115–116).

EXAMPLE 578

A mixture of INT20 (77 mg, 0.15 mmol), carbamic acid benzyl ester (68 mg, 0.45 mmol), triethylsilane (0.072 mL, 0.45 mmol) and trifluoroacetic acid (0.023 mL, 0.30 mmol) in 0.65 mL of acetonitrile was stirred at room temperature for 3 h. The reaction mixture was purified by reverse phase chromatography to give the title compound (59 mg, 60%): HPLC (method 1) $t_R$=4.0 min; LCMS (ESI, pos. ion spectrum) m/z 649/651 (M+H).

EXAMPLE 604

A mixture of Example 396 title compound (0.16 g, 0.30 mmol), 5-methylthiophene-2-boronic acid (48 mg, 0.34 mmol), and 2N potassium carbonate (0.45 mL, 0.90 mmol) in dimethoxyethane (4.5 mL) was sparged with argon for 20 min.

Bis(triphenylphosphine)palladium chloride (17 mg) was added. After refluxing for 5 h, the reaction was transferred to a separatory funnel with ethyl acetate/water and extracted with ethyl acetate (2×30 mL). The combined organic layers were washed with brine and dried over magnesium sulfate to afford 0.14 g of crude product. Sequential purification over silica gel and C18 silica gel afforded 18 mg (11%) of Example 604 title compound.

EXAMPLE 608

To a solution of the title compound of Example 615 (50 mg, 0.088 mmol) in 1 mL of 1,2-dichloroethane at 0° C. was added diisopropylethylamine (0.03 mL, 0.3 mmol), and 2-bromoethyl acetate (0.015 mL, 0.14 mmol). The mixture was stirred at room temperature for 2 h, at reflux for 4 h and was cooled to room temperature. To the reaction was added an additional portion of 2-bromoethyl acetate as used above. The resulting mixture was heated at reflux for additional 4 h; diluted with dichloromethane (15 mL); and washed with saturated sodium bicarbonate solution and brine. The organic layer was dried over sodium sulfate and concentrated. The residue was purified over silica gel to afford 22 mg (38%) of the title compound: LRMS (ESI, pos. ion spectrum) m/z 654/656 (M+H); HPLC (method 1) $t_R$=3.1 min.

EXAMPLE 613

Part A: A mixture of INT11 (2.26 g, 5.98 mmol), (S)-2-pyrrolidinylmethanol (0.89 mL, 8.97 mmol), WSC (1.72 g, 8.97 mmol), and 1-hydroxy-7-azabenzotriazole (0.81 g, 5.98 mmol) in 5 mL of DMF was stirred at room temperature overnight. The resulting mixture was diluted with ethyl acetate and then washed with brine. The organic layer was concentrated and purified over silica gel to provide 2.16 g (78%) of N-((S)-[1-[2-((2S)-2-(hydroxymethyl)pyrrolidin-1-yl)-2-oxoethyl]-2-oxopiperidin-3-yl]) ((E)-2-(5-chlorothiophen-2-yl)ethenesulfonamide): LRMS (ESI, pos. ion spectrum) m/z 462 (M+H); HPLC (method 1) $t_R$=2.5 min.

Part B: To a solution of part A compound (2.16 g, 4.68 mmol) in 10 mL of dichloromethane was added a suspension of Dess-Martin periodinane (3.77 g, 8.89 mmol) in 20 mL of dichloromethane. The mixture was stirred at room temperature for 30 min and diluted with ethyl ether (60 mL). The reaction was then quenched with a solution of sodium thiosulfate (8.13 g, 51.5 mmol) in saturated sodium bicarbonate. The resulting mixture was stirred at room temperature for 15 min and was then extracted with ethyl ether (3×). The aqueous layer was further extracted with dichloromethane (2×). The combined ether layers and combined methylene chloride layers were separately washed with brine, combined, dried over magnesium sulfate and concentrated. The crude product was purified over silica gel provide 1.7 g (79%) of INT22: LRMS (ESI, pos. ion spectrum) m/z 460/462 (M+H); HPLC (method 1) $t_R$=3.1 min.

Part C: A mixture of part B compound (1.00 g, 2.17 mmol) and 1,1-dimethylethyl methyl(3-pyrrolidinyl)carbamate (0.64 mL, 3.26 mmol) in 15 mL of 1,2-dichloroethane was stirred at room temperature for 10 min. To the reaction was added sodium triacetoxyborohydride (0.69 g, 3.3 mmol). The resulting mixture was stirred at room temperature for 30 min and concentrated. The crude product was purified over silica gel to afford 1.32 g (94%) of 1,1-dimethylethyl {1-[1-((2S)-2-{(3S)-3-[(E)-2-(5-Chloro-thiophen-2-yl)-ethenesulfonylamino]-2-oxo-piperidin-1-yl}-acetyl)-pyrrolidin-2-ylmethyl]-pyrrolidin-3-yl}-methyl-carbamate: HPLC (method 1) $t_R$=3.2 min.

Part D: To a solution of Part C compound (1.32 g, 2.05 mmol) in 5 mL of dichloromethane was added trifluoroacetic acid (2.0 mL). The mixture was stirred at room temperature for 1 h, and concentrated. The residue was then dissolved in ethyl acetate (40 mL), washed with saturated sodium bicarbonate and brine, dried over magnesium sulfate and concentrated to afford 0.92 g (84%) of the title compound: LRMS (ESI, pos. ion spectrum) m/z 544/546 (M+H); HPLC (method 1) $t_R$=2.1 min.

EXAMPLE 618–619

Part A: A One-third portion of Example 844 Part C resin was divided into 20 mg (ca. 0.022 mmol) portions. Each portion was shaken for 16 h to 28 h with Hunig's base (3 equivalents based on initial aldehyde loading) and an isocyanate (3 equivalents based on initial aldehyde loading) in dichloroethane or methylene chloride (1 mL). The resins were filtered and washed and then shaken with a solution of either TFA:methylene chloride or TFA:dichloroethane (1:1 mixture, 1.5 mL). The reactions were individually filtered and the individual filtrates were concentrated in vacuo to provide the title compounds. If the purity of the title compound was less than 90%, purification was performed (RP-HPLC [YMC Pack C18, 20 mm×100 mm; 20 mL/min; detection at 220 nm; 10–90% aqueous MeOH containing 0.1% TFA, 10.0 min linear gradient and then 2 min hold]). The title compound of Example 619 was prepared using this method and 3-ethylphenyl isocyanate.

Part B: A One-third portion of Example 844 Part D resin was divided into 20 mg (ca. 0.022 mmol) portions. Each portion was shaken for 16 h to 28 h with Hunig's base (3 equivalents) and an isocyanate (3 equivalents based on initial aldehyde loading) in dichloroethane or methylene chloride (1 mL). The resins were filtered and washed and then shaken with a solution of either TFA:methylene chloride or TFA: dichloroethane and (1:1 mixture, 1.5 mL). The reactions were filtered and the filtrates were concentrated in vacuo to provide the title compounds. If the purity of the title compound was less than 90%, purification was performed (RP-HPLC [YMC Pack C18, 20 mm×100 mm; 20 mL/min; detection at 220 nm; 10–90% aqueous MeOH containing 0.1% TFA, 10.0 min linear gradient and then 2 min hold]). The title compound of Example 618 was prepared using this method and 3-ethylphenyl isocyanate.

EXAMPLE 620–621

Part A: A One-third portion of Example 844 Part C resin was divided into 20 mg (ca. 0.022 mmol) portions. Each portion was shaken for 16 h to 28 h with pyridine (6 equivalents based on initial aldehyde loading) and a sulphonyl chloride (3 equivalents based on initial aldehyde loading) in either dichloroethane or methylene chloride (1 mL). The resins were filtered and washed and then shaken with a solution of either TFA:methylene chloride or TFA:dichloroethane (1:1 mixture, 1.55 mL). The reactions were filtered and the filtrates were concentrated in vacuo to provide the title compounds. If the purity of the title compound was less than 90%, purification was done as described in Example 618–619. The title compoun of Example 619 was prepared using this method and 3-chlorophenylsulfonyl chloride.

Part B: A One-third portion of Example 844 Part D resin was divided into 20 mg (ca. 0.022 mmol) portions. Each portion was shaken for 16 h to 28 h with pyridine (6 equivalents) and a sulphonyl chloride (3 equivalents based on initial aldehyde loading) in either dichloroethane or methylene chloride (1 mL). The resins were filtered and washed and then shaken with a solution of either TFA: methylene chloride or TFA:dichloroethane (1:1 mixture, 1.5 mL). The reactions were filtered and the filtrates were concentrated in vacuo to provide the title compounds. If the purity of the title compound was less than 90%, purification was done as described in Example 618–619. The title compoun of Example 620 was prepared using this method and 3-chlorophenylsulfonyl chloride.

EXAMPLE 622

A One-third portion of Example 844 Part D resin was divided into 20 mg (ca. 0.022 mmol) portions. Each portion was shaken for 16 h to 28 h with a carboxylic acid (3 equivalents based on initial aldehyde loading), PyBOP (3 equivalents based on initial aldehyde loading) and N-methylmorpholine (6 equivalents based on initial aldehyde loading) in either dichloroethane or methylene chloride (1 mL). The resins were filtered and washed and then shaken with a solution of either TFA:methylene chloride or TFA:dichloroethane (1:1 mixture, 1.5 mL). The reactions were filtered and the filtrates were concentrated in vacuo to provide the title compounds. If the purity of the title compund was less than 90%, purification was done as described in Example 618–619.

EXAMPLE 624

A One-third portion of Example 844 Part C resin was divided into 20 mg (ca. 0.022 mmol) portions. Each portion was shaken for 16 h to 28 h with a carboxylic acid (3 equivalents based on initial aldehyde loading), PyBOP (3 equivalents based on initial aldehyde loading) and N-methylmorpholine (6 equivalents based on initial aldehyde loading) in either dichloromethane or methylene chloride (1 mL). The resins were filtered and washed and then shaken with a solution of either TFA:methylene chloride or TFA: dichloroethane and (1:1 mixture, 1.5 mL). The reactions were filtered and the filtrates were concentrated in vacuo to provide the title compounds. If the purity of the title compound was less than 90%, purification was done as described in Example 618–619.

EXAMPLE 630

The title compound of Example 610 (19 mg, 0.034 mmol), triethylamine (5.0 mg, 0.040 mmol) and acetyl chloride (4.0 mg, 0.050 mmol) were dissolved in 0.5 mL of methylene chloride and stirred at room temperature for 1 h. Additional one equivalent-portions of acetyl chloride and triethylamine were added. The reaction mixture was stirred at room temperature overnight. The reaction mixture was concentrated and purified by reverse phase chromatography to provide the title compound (11 mg, 51%): HPLC (method 1) $t_R$=3.5 min; LCMS (ESI, pos. ion spectrum) m/z 601/603 (M+H).

EXAMPLE 655

To a solution of the title compound of Example 613 (20 mg, 0.037 mmol) in 0.1 mL of a mixture of acetonitrile and tetrahydrofuran (1:1) was added a solution of cyclopentylisocyanate (4.5 mg, 0.04 mmol) in 0.1 mL of acetonitrile and tetrahydrofuran (1:1). The resulting mixture was stirred at room temperature overnight. The solvent was removed on a Savant Speedvac® to afford 24 mg (99%) of the title compound: LRMS (ESI, pos. ion spectrum) m/z 655 (M+H); HPLC (method 1) $t_R$=3.2 min.

EXAMPLE 788

A solution of 1,1'-carbonyldiimidazole (8.2 mg, 0.051 mmol) in 0.2 mL of acetonitrile was added to acetic acid (3.3 mg, 0.055 mmol). The mixture was stirred at room temperature for 40 min. A solution of title compound of Example 569 (25 mg, 0.042 mmol) in 0.2 mL of dichloromethane was then added. The resulting mixture was stirred at room temperature for 2 d. The crude product was purified by C-18 chromatography to afford 21 mg (78%) of the title compound: LRMS (ESI, pos. ion spectrum) m/z 634/636 (M+H); HPLC (method 1) $t_R$=3.0 min.

EXAMPLE 836

To the title compound of Example 578 (56 mg, 0.086 mmol) was added 0.17 mL of 30% HBr in acetic acid. The mixture was stirred at room temperature for 1 hour and purified by reverse phase chromatography to give the title compound (9 mg, 20%): HPLC (method 1) $t_R$=3.3 min; LCMS (ESI, pos. ion spectrum) m/z 517/519 (M+H).

EXAMPLE 844

Part A. Preparation of resin-bound sulfonamide: A polymer-supported amino ester (2.4 g) was prepared using the procedures described in Example 331 from INT47 and PS-MB-CHO resin. The resin was shaken on a platform shaker for 16 h at room temperature with INT45 (1.3 equivalents based on the initial aldehyde resin loading) and Hunig's base (4 equivalents based on the initial aldehyde resin loading) in methylene chloride (25 mL). The resin filtered and washed repeatedly with, in sequence, methylene chloride, MeOH, DMF and THF and then dried. A total of 500 mL-1 L (approx.) of each solvent was used for the washing.

Part B. Preparation of resin-bound acid: The part A polymer-supported methyl ester was shaken for 2 h at room temperature with LiOH (10 equivalents based on the initial aldehyde resin loading) in a 1:1 THF:water mixture. The resin was filtered and was washed repeatedly with, in sequence, THF:water:acetic acid (6:3:1), DMF, methylene chloride, methanol and THF and then dried. A total of 500 ml-1 L (approx.) of each solvent was used for the washing.

Part C: One half of the part B polymer-supported acid was shaken for 16 h at room temperature with (R)-2-(azidomethyl)pyrrolidine (3 equivalents based on initial aldehyde loading), PyBOP (3 equivalents based on initial aldehyde loading) and N-methylmorpholine (6equivalents based on initial aldehyde loading) in DMF (15 mL). The resin was filtered and washed with THF:water:acetic acid (6:3:1), DMF, methylene chloride, methanol and THF and then dried. A total of 500 mL-1 L (approx.) of each solvent was used for the washing. The resultant resin was shaken for 72 h with triphenylphosphine (6 equivalents based on initial aldehyde loading) in THF:water (9:1, 20 mL). The resin was filtered and was washed repeatedly with, in sequence, methylene chloride, MeOH, DMF and THF and then dried. A total of 500 mL-1 L (approx.) of each solvent was used for the washing.

Part D: One half of the part B polymer supported acid was shaken for 16 h at room temperature with (S)-2-(azidomethyl)pyrrolidine (3 equivalents based on initial aldehyde loading), PyBOP (3 equivalents based on initial aldehyde loading) and N-methylmorpholine (6 equivalents based on initial aldehyde loading) in DMF (15 mL). The resin was filtered and washed with THF:water:acetic acid (6:3:1), DMF, methylene chloride, methanol and THF and then dried. A total of 500 mL-1 L (approx.) of each solvent was used for the washing. The resultant resin was shaken for 72 h with triphenylphosphine (6 equivalents based on initial aldehyde loading) in THF:water (9:1, 20 mL). The resin was filtered and was washed repeatedly with, in sequence, methylene chloride, MeOH, DMF and THF and then dried. A total of 500 mL-1 L (approx.) of each solvent was used for the washing.

Part E. the Part D resin (20 mg) was treated with a solution of methylene chloride and TFA (1:1 mixture, 1.5 mL) and filtered. The filtrate was concentrated in vacuo to provide the title compound.

EXAMPLE 845

The Example 844 Part C resin (20 mg) was treated with a solution of methylene chloride and TFA (1:1 mixture, 1.5 mL) and filtered. The filtrate was concentrated in vacuo to provide the title compound.

EXAMPLE 847

To a solution of the title compound of Example 840 (14 mg, 0.028 mmol) in methylene chloride (1 mL) was added triethylamine (0.007 mL, 0.055 mmol) and methyl chloroformate (0.005 mL, 0.055 mmol). After stirring at room temperature for 1 h, the mixture was concentrated and the residue was purified over C18 silica gel afforded 14 mg (80%) of the title compound.

EXAMPLE 848

A mixture of the title compound of Example 847 (10 mg, 0.016 mmol) and lithium hydroxide dihydrate (5 mg, 0.086 mmol) in 1 mL of THF-water (1:1) solution was stirred for 2 h. The mixture was extracted with ethyl acetate (2×3 mL). The organic fractions were combined, dried over magnesium sulfate, filtered and the filtrate evaporated in vacuo to afford the crude product. Preparative HPLC purification over C18 silica gel afforded 2.4 mg (23%) of the title compound.

EXAMPLE 850

Part A: (3S)-3-Amino-1-[2-oxo-2-((2S)-2-pyrrolidin-1-ylmethyl-1-pyrrolidinyl)ethyl]piperidine-2-one (5.4 g, 17 mmol) and PS-MB-CHO (1.26 mmol/g, 13 g, 16 mmol) were suspended in 1/1 DMF/trimethylorthoformate with 2% acetic acid (125 mL). Sodium triacetoxyborohydride (3.9 g, 18 mmol) was then added and the was filtered and subjected to 3 sequential washing cycles. In each cycle, the resin was washed sequentially with 6/3/1 THF/water/AcOH (3×), DMF (3×), methylene chloride (3×), and methanol (3×). The solid was subjected to 5 sequential washing cycles. In each cycle, the resin was washed sequentially with methylene chloride (2×) and methanol (2×). The isolated resin was is then resubmitted to the above reaction conditions and agitated for 3 days and washed again as above. After drying under vacuum 16 g of resin-supported amine was isolated.

Part B: Part A resin-bound amine (1.7 g, 1.7 mmol theory), diisopropylethylamine (0.88 mL, 5.1 mmol), and (4-bromophenyl)sulfonyl chloride (0.64 g, 2.5 mmol) were suspended in dichloroethane (17 mL). After agitating at ambient temperature for 4 d, the resin was filtered and rinsed with DMF (4×), methanol (3×), THF (3×) and methylene chloride (3×). The resin was again sulfonylated (3 d reaction time) and washed as described and dried.

Part C: A portion of Part B resin-bound sulfonamide (0.19 mmol theory) was suspended in dimethoxyethane (1.5 mL). (3,5-Dichlorophenyl)boronic acid (0.30 mmol), 2 N potassuim carbonate (0.30 mL, 0.60 mmol), and bis(triphenylphosphine)palladium chloride (5 mg) were then added and the resultant mixture was agitated at 75° C. overnight before the solid was filtered and washed with DMF (3×), methanol (3×), THF (3×) and methylene chloride. Methylene chloride (0.50 mL) and trifluoroacetic acid (0.50 mL) were added to the solid resin. After 30 min, the reaction was filtered and rinsed with methylene chloride and the combined filtrates were evaporated in vacuo to afford 32 mg (24%) of Example 850 BMS-543947 title compound. LCMS (method 4) $t_R$=1.7 min; LCMS (ESI, pos. ion specturm) m/z 593/595 (M+1).

EXAMPLE 892

The title compound was prepared using the procedures described in Example 620–621 using Example 927–928 part A resin.

EXAMPLE 895

The title compound was prepared using the procedures described in Example 620–621 using Example 927–928 part B resin.

EXAMPLE 898

The title compound was prepared using the procedures described in Example 622 using Example 927–928 part A resin.

EXAMPLE 907

The title compound was prepared using the procedures described in Example 622 using Example 927–928 part B resin.

EXAMPLE 921

INT58 (19.3 mg, 0.06 mmol) was dissolved in pyridine (0.6 mL) and cooled to 0° C. 6-Chloro-thieno[2,3-b]pyridine-2-sulfonyl chloride (24.1 mg, 0.09 mmol) was added, and the reaction mixture allowed to slowly warm to RT overnight without removal of the cooling bath. After 16 h the reaction mixture was concentrated in vacuo and the residue purified via preparative HPLC to afford the title compound as an off-white white solid (24.5 mg, 74%); HPLC (method 1), $t_4$=2.2 min., 90% pure; LRMS (ESI, pos. ion spectrum) m/z 554 (M+H).

EXAMPLE 927 and 928

Part A: The same procedure as Example 844 was followed using 5'-Chloro-[2,2']bithienyl-5-sulfonyl chloride in place of INT45 and (S)-2-(azidomethyl)pyrrolidine Part B: The same procedure as Example 844 was followed using 5-chlorobenzo[b]thiophene-2-sulphonyl chloride in place of INT45 and (S)-2-(azidomethyl)pyrrolidine

EXAMPLE 930

The title compound was prepared using the procedures described in Example 927–928 except that the reactions were carried out in solution phase. The isolation of product was done using prep HPLC as described earlier.

EXAMPLE 931

The title compound was prepared using the procedures described in Example 892 except that the reactions were carried out in solution phase. The isolation of product was done using prep HPLC as described earlier.

EXAMPLE 936

To a solution of the title compound of Example 425 (59 mg, 0.10 mmol) in DMF (0.3 mL) was added NaH as a 60% dispersion in oil (4.4 mg). After 15 minutes, benzyl bromide (17 mg, 0.10 mmol) was added. After 15 hours, the reaction was quenched with 3 drops of water and the solvent removed in vacuo. The residue was purified by reverse phase chromatography to provide 38 mg of the title compound: LCMS (method 3, ESI, pos. ion. spectrum), m/z 677/679.

EXAMPLE 970

To a solution of INT15 (30 mg, 0.08 mmol) in dichloromethane (1 mL) were added triethylamine (0.033 mL, 0.24 mmol), (1S, 4S)-(+)-2,5-diazabicyclo[2.2.1]heptane dihydrobromide (10 mg, 0.04 mmol), a catalytic amount of 4-(dimethylamino)pyridine, 1-hydroxy-7-azabenzotriazole (14 mg, 0.10 mmol) and WSC (23 mg, 0.12 mmol) in that order. The reaction was stirred at room temperature for 2 h, quenched with water, and extracted with methylene chloride (2×5 mL). The combined organic fractions were dried over magnesium sulfate and evaporated in vacuo. Purification of the residue over silica gel afforded the title compound: 42 mg (49%).

What is claimed is:

1. A compound of formula II

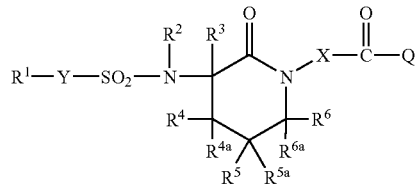

II pharmaceutically acceptable salts, stereoisomers, or prodrugs thereof, wherein Y is a bond, alkyl, alkenyl or alkynyl;

X is

—(CH$_2$)$_m$— where m is an integer between 1 and 3;

Q is

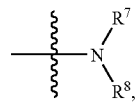

$R^1$ is aryl, heteroaryl, cycloalkyl or cycloheteroalkyl, any of which may be optionally substituted with one or more groups $Z^1$, $Z^2$ or $Z^3$;

$R^2$, $R^{2a}$, $R^3$ and $R^{3a}$ are independently selected from (1) hydrogen, alkyl, alkenyl, alkynyl, cycloalkyl, aryl, cycloheteroalkyl, or heteroaryl any of which may be optionally substituted with one or more groups $Z^{1a}$, $Z^{2a}$ or $Z^{3a}$; or (2) —C(O)$_r$H, or C(O)$_r$Z$^6$; or (3) -Z$^4$-NZ$^7$Z$^8$;

$R^4$, $R^{4a}$, $R^{4b}$, $R^{4c}$, $R^5$, $R^{5a}$, $R^{5b}$ and $R^{5c}$ are independently selected from hydrogen, alkyl, alkenyl, alkynyl, cycloalkyl, aryl, heteroaryl, cycloheteroalkyl, hydroxy, alkoxy,

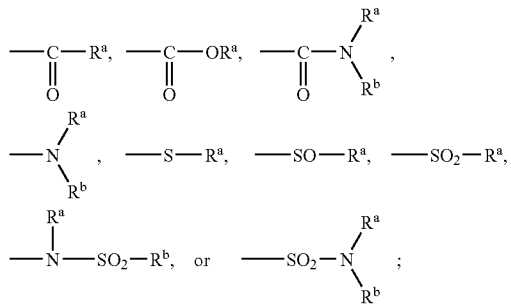

any of which may be optionally substituted with one or more groups $Z^{1b}$, $Z^{2b}$ or $Z^{3b}$;

$R^6$ and $R^{6a}$ are independently selected from hydrogen, alkyl, alkenyl, alkynyl, cycloalkyl, aryl, heteroaryl, or cycloheteroalkyl any of which may be optionally substituted with one or more groups $Z^{1c}$, $Z^{2c}$ or $Z^{3c}$;

$R^7$ and $R^8$ are independently chosen from optionally substituted cycloalkyl, optionally substituted cycloheteroalkyl or

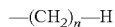

where n is an integer between 1 and 4 and wherein 1 to 4 of the methylene groups may be optionally mono- or di-substituted with alkyl, substituted alkyl, alkenyl, substituted alkenyl, alkynyl, substituted alkynyl, aryl, and heteroaryl, and which may be optionally substituted with 1 to 4 halogens except on a carbon that is directly bonded to a nitrogen;

$R^a$ and $R^b$ are the same or different and are independently selected from hydrogen, alkyl, alkenyl, alkynyl, aryl, heteroaryl, cycloheteroalkyl, cycloalkyl, alkylcarbonyl, arylcarbonyl, cycloalkylcarbonyl, cycloheteroalkylcarbonyl, heteroarylcarbonyl, aminocarbonyl, alkylaminocarbonyl, and dialkylaminocarbonyl, $Z^1$, $Z^{1a}$, $Z^{1b}$, $Z^{1c}$, $Z^2$, $Z^{2a}$, $Z^{2b}$, $Z^{2c}$, $Z^3$, $Z^{3a}$, $Z^{3b}$, $Z^{3c}$, $Z^{13}$ and $Z^{14}$ are each independently (1) hydrogen or $Z^6$, where $Z^6$ is
  (i) alkyl, hydroxyalkyl, alkoxyalkyl, alkenyl, alkynyl, cycloalkyl, cycloalkylalkyl, cycloalkenyl, cycloalkenylalkyl, aryl, arylalkyl, cycloheteroalkyl, cycloheteroalkylalkyl, heteroaryl or heteroarylalkyl;
  (ii) a group (i) which is itself substituted by one or more of the same or different groups (i); or
  (iii) a group (i) or (ii) which is independently substituted by one or more (preferably 1 to 3) of the following groups (2) to (13) of the definition of $Z^1$ through $Z^{3c}$,
(2) —OH or —O$Z^6$,
(3) —SH or —S$Z^6$,
(4) —C(O)$_t$H, —C(O)$_t Z^6$, or —O—C(O)$Z^6$,
(5) —SO$_3$H, —S(O)$_t Z^6$, or S(O)$_t$N($Z^9$)$Z^6$,
(6) halo,
(7) cyano,
(8) nitro,
(9) -$Z^4$-N$Z^7 Z^8$,
(10) -$Z^4$-N($Z^9$)-$Z^5$-N$Z^7 Z^8$,
(11) -$Z^4$-N($Z^{10}$)-$Z^5$-$Z^6$,
(12) -$Z^4$-N($Z^{10}$)-$Z^5$-H,
(13) oxo, $Z^4$ and $Z^5$ are each independently
(1) a single bond,
(2) -$Z^{11}$-S(O)$_t$-$Z^{12}$-,
(3) -$Z^{11}$-C(O)-$Z^{12}$-,
(4) -$Z^{11}$-C(S)-$Z^{12}$-,
(5) -$Z^{11}$-O-$Z^{12}$-,
(6) -$Z^{11}$-S-$Z^{12}$-,
(7) -$Z^{11}$-O—C(O)-$Z^{12}$-,
(8) -$Z^{11}$-C(O)—O-$Z^{12}$-,
(9) -$Z^{11}$-C(=N$Z^{9a}$)-$Z^{12}$-, or
(10) -$Z^{11}$-C(O)—C(O)-$Z^{12}$-, $Z^7$, $Z^8$, $Z^9$, $Z^{9a}$ and $Z^{10}$
(1) are each independently hydrogen or a group provided in the definition of $Z^6$,
(2) $Z^7$ and $Z^8$ may together be alkylene or alkenylene, completing a 3- to 8-membered saturated or unsaturated ring together with the atoms to which they are attached, which ring is unsubstituted or substituted with one or more groups provided in the defintion of $Z^1$ through $Z^3$,
(3) $Z^7$ or $Z^8$, together with $Z^9$, may be alkylene or alkenylene completing a 3- to 8-membered saturated or unsaturated ring together with the nitrogen atoms to which they are attached, which ring is unsubstituted or substituted with one or more groups provided in the defintion of $Z^1$ through $Z^3$, or
(4) $Z^7$ and $Z^8$ or $Z^9$ and $Z^{10}$ together with the nitrogen atom to which they are attached may combine to form a group —N=C$Z^{13}Z^{14}$;

$Z^{11}$ and $Z^{12}$ are each independently
(1) a single bond,
(2) alkylene,
(3) alkenylene, or
(4) alkynylene;

provided that said compound is other than
(a) a compound of structure X

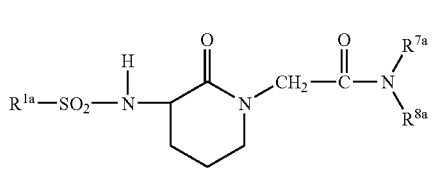

wherein $R^{1a}$ is selected from (i) or (ii)
  (i) cycloalkyl which may be optionally substituted with cycloalkyl, alkoxy, oxo, hydroxy, carboxy, —CF$_3$ or halogen;
  (ii) aryl provided that the total number of carbon atoms in $R^{1a}$ is $\geq 6$ and $\leq 14$ wherein said aryl may be optionally substituted with alkyl, cycloalkyl, alkoxy, hydroxy, carboxy, halo or —CF$_3$;

$R^{7a}$ is alkyl; and $R^{8a}$ is a group of the formula

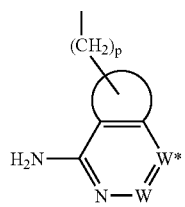

wherein the substructure

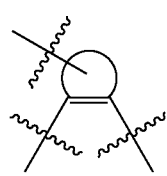

is a group selected from

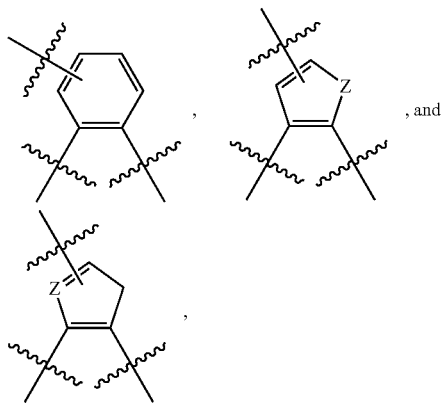

where Z is O or S;
p is 1, 2 or 3; and
W and W* are each independently CH or N;
(b) a compound of the structure XI

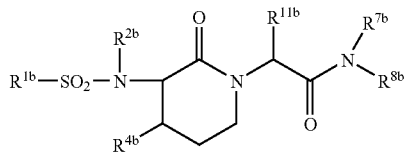

wherein
$R^{1b}$ is piperidino, morpholino, amino, alkylamino, phenyl or phenyl optionally substituted by up to three substituents independently selected from alkyl, dimethylamino, nitro, halo, or —$CF_3$;
$R^{2b}$ is hydrogen, alkyl, cycloalkyl, acyl, benzoyl or benzyl optionally substituted by up to three substituents independently selected from nitro, halo, —$CF_3$, alkyl, or alkoxy;
$R^{4b}$ is hydrogen or lower alkyl;
$R^{11b}$ is hydrogen or lower alkyl;
$R^{7b}$ is alkyl;
$R^{8b}$ is —CHB—CHD-CHE-CO—$(R^{12b})_u$-$(M)_x$-Q*;
B is hydrogen, alkyl, cycloalkyl, cycloalkylalkyl, or benzyl
D is hydrogen, acetoxy, hydroxy or alkoxy;
E is hydrogen or alkyl;
or B and E together are an alkylene bridge;
$R^{12b}$ is —$NR^{13b}$—CHG-CHK—CHL-CO, or a group of the formula

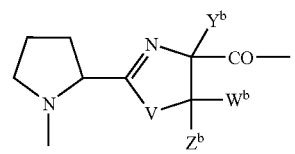

wherein
V is O or S;
$Y^b$ is hydrogen;
$Z^b$ is hydrogen or alkyl;
or $Y^b$ and $Z^b$ together form a bond;
$W^b$ is hydrogen, alkyl or phenyl; and
$R^{13b}$ is hydrogen or alkyl;
G is hydrogen, alkyl, cycloalkyl, cycloalkylalkyl or benzyl;
K is hydrogen, acetoxy, hydroxy or alkoxy;
L is hydrogen or alkyl;
or $R^{13b}$ and G together form an alkylene bridge optionally substituted with hydroxy;
M is selected from 1-aminopentyl-1 carbonyl, valyl, 2-tert-butylgylcyl, prolyl, hydroxyprolyl, isoleucyl, leucyl, 3-cyclohexylalanyl, phenylalanyl, tetrahydroisoquinolyl-2-carbonyl, 3-thiazolylalanyl, 3-thienylalanyl, histidyl, 2-aminoindyl-2-carbonyl, tyrosyl, 3-pryridylalanyl, 3-tert-butyalanyl, 2-cyclohexylglycyl or 3-napthylalanyl residues;
Q* is hydroxy, alkoxy, phenoxy, benyloxy, amino or substituted amino;
u and x are each independently 0 or 1; or
(d) a compound of structure XIV

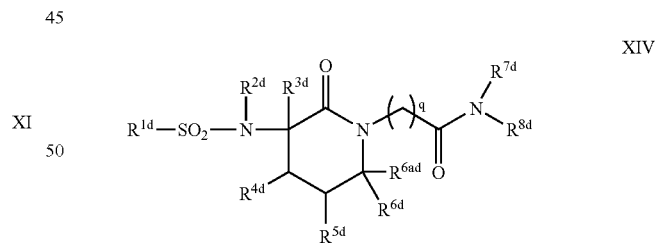

wherein
$R^{1d}$ is optionally substituted cycloalkyl, optionally substituted cycloheteroalkyl, optionally substituted aryl, optionally substituted heteroaryl, optionally substituted aralkyl, optionally substitued heteroaralkyl, optionally substituted aralkenyl, or optionally substituted heteroaralkenyl;
$R^{2d}$ is hydrogen, optionally substituted alkyl, optionally substituted alkenyl, optionally substituted aralkyl or optionally substituted heteroaralkyl;
$R^{3d}$ is hydrogen, optionally substituted alkyl, optionally substitued aralkyl or hydroxyalkyl;

R$^{4d}$ and R$^{5d}$ are hydrogen, hydroxy, optionally substituted alkyl, optionally substituted aryl, optionally substituted heteroaryl, optionally substituted aralkyl, or optionally substituted heteroaralkyl;

R$^{6d}$ and R$^{6ad}$ are independently selected from hydrogen, optionally substituted alkyl, optionally substituted aryl, optionally substituted aralkyl, optionally substituted heteroaryl, or optionally substituted heteroaralkyl;

R$^{7d}$ is optionally substituted alkyl, optionally substituted aralkyl, or optionally substituted heteroaralkyl;

R$^{8d}$ is —(CH$_2$)$_r$—Ar where Ar is an optionally substituted heteroaryl; and q and r are each independently 1 or 2.

2. A compound of claim 1 wherein Y is bond or alkenyl.

3. A compound of claim 2 wherein R$_1$ is aryl or heteroaryl either of which may be optionally substituted with one or more groups Z$^1$, Z$^2$ or Z$^3$.

4. A compound of claim 3 wherein

R$^2$ is H, alkyl, —C(O)$_r$H, —C(O)$_r$Z$^6$, -Z$^4$-NZ$^7$Z$^8$, -(alkyl)-C(O)$_r$H, -(alkyl)-C(O)$_r$Z$^6$, or -(alkyl)-Z$^4$-NZ$^7$Z$^8$; and R$^3$, R$^4$, R$^{4a}$, R$^5$, R$_{5a}$, R$^6$, and R$^{6a}$ are H.

5. A compound of claim 4 wherein R$^1$ is

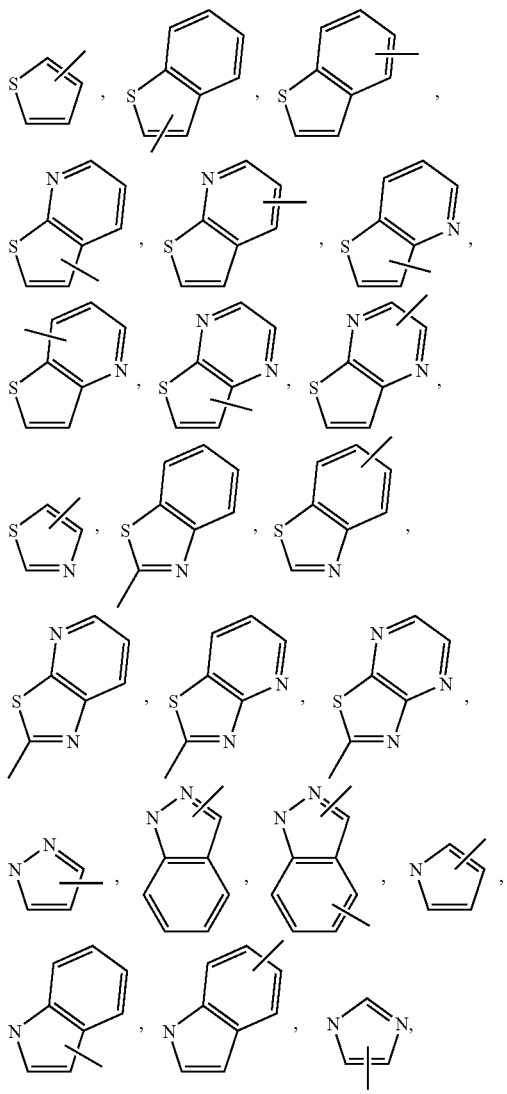

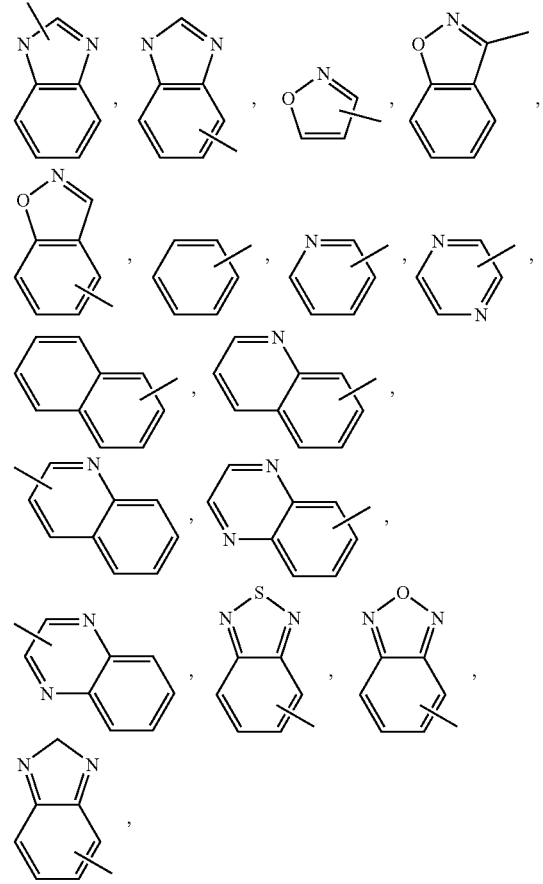

any of which may be optionally substituted with one or more Z$^1$, Z$^2$ or Z$^3$.

6. A pharmaceutical composition comprising at least one compound of claim 1 and a pharmaceutically acceptable vehicle or carrier therefor.

7. A pharmaceutical composition comprising at least one compound of claim 2 and a pharmaceutically acceptable vehicle or carrier therefor.

8. A pharmaceutical composition comprising at least one compound of claim 3 and a pharmaceutically acceptable vehicle or carrier therefor.

9. A pharmaceutical composition comprising at least one compound of claim 4 and a pharmaceutically acceptable vehicle or carrier therefor.

10. A pharmaceutical composition comprising at least one compound of claim 5 and a pharmaceutically acceptable vehicle or carrier therefor.

11. A method for treating thromboses, which comprises administering to a mammalian species in need thereof a therapeutically effective amount of at least one compound of claim 1.

12. A method for treating thromboses, which comprises administering to a mammalian species in need thereof a therapeutically effective amount of at least one compound of claim 2.

13. A method for treating thromboses, which comprises administering to a mammalian species in need thereof a therapeutically effective amount of at least one compound of claim 3.

14. A method for treating thromboses, which comprises administering to a mammalian species in need thereof a therapeutically effective amount of at least one compound of claim 4.

15. A method for treating thromboses, which comprises administering to a mammalian species in need thereof a therapeutically effective amount of at least one compound of claim 5.

* * * * *